US012522591B2

(12) United States Patent
Parham et al.

(10) Patent No.: US 12,522,591 B2
(45) Date of Patent: Jan. 13, 2026

(54) MATERIALS FOR ORGANIC ELECTROLUMINESCENT DEVICES

(71) Applicant: Merck Patent GmbH, Darmstadt (DE)

(72) Inventors: Amir Parham, Frankfurt am Main (DE); Jonas Kroeber, Frankfurt am Main (DE); Jens Engelhart, Darmstadt (DE); Christian Ehrenreich, Darmstadt (DE); Christian Eickhoff, Mannheim (DE)

(73) Assignee: Merck Patent GmbH, Darmstadt (DE)

( * ) Notice: Subject to any disclaimer, the term of this patent is extended or adjusted under 35 U.S.C. 154(b) by 963 days.

(21) Appl. No.: 17/637,832

(22) PCT Filed: Mar. 11, 2020

(86) PCT No.: PCT/EP2020/056437

§ 371 (c)(1),
(2) Date: Feb. 24, 2022

(87) PCT Pub. No.: WO2021/037401

PCT Pub. Date: Mar. 4, 2021

(65) Prior Publication Data

US 2022/0306613 A1 Sep. 29, 2022

(30) Foreign Application Priority Data

Aug. 26, 2019 (EP) .................................... 19193559

(51) Int. Cl.

| | |
|---|---|
| ***H01L 51/54*** | (2006.01) |
| ***C07D 209/82*** | (2006.01) |
| ***C07D 251/22*** | (2006.01) |
| ***C07D 251/24*** | (2006.01) |
| ***C07D 403/14*** | (2006.01) |
| ***C07D 405/04*** | (2006.01) |
| ***C07D 405/14*** | (2006.01) |
| ***C07D 409/14*** | (2006.01) |
| ***C07D 413/04*** | (2006.01) |
| ***C07D 417/04*** | (2006.01) |
| ***C07D 417/14*** | (2006.01) |
| ***C07D 421/14*** | (2006.01) |
| ***C07D 471/04*** | (2006.01) |
| ***C07D 471/14*** | (2006.01) |
| ***C07D 471/22*** | (2006.01) |
| ***C07D 487/04*** | (2006.01) |
| ***C07D 487/14*** | (2006.01) |
| ***C07D 491/048*** | (2006.01) |
| ***C07D 491/147*** | (2006.01) |
| ***C07D 495/14*** | (2006.01) |
| ***H10K 85/60*** | (2023.01) |
| *H10K 50/11* | (2023.01) |

(52) U.S. Cl.

CPC ......... *C07D 405/14* (2013.01); *C07D 209/82* (2013.01); *C07D 251/22* (2013.01); *C07D 251/24* (2013.01); *C07D 403/14* (2013.01); *C07D 405/04* (2013.01); *C07D 409/14* (2013.01); *C07D 413/04* (2013.01); *C07D 417/04* (2013.01); *C07D 417/14* (2013.01); *C07D 421/14* (2013.01); *C07D 471/04* (2013.01); *C07D 471/14* (2013.01); *C07D 471/22* (2013.01); *C07D 487/04* (2013.01); *C07D 487/14* (2013.01); *C07D 491/048* (2013.01); *C07D 491/147* (2013.01); *C07D 495/14* (2013.01); *H10K 85/622* (2023.02); *H10K 85/624* (2023.02); *H10K 85/625* (2023.02); *H10K 85/653* (2023.02); *H10K 85/654* (2023.02); *H10K 85/655* (2023.02); *H10K 85/656* (2023.02); *H10K 85/657* (2023.02); *H10K 85/6572* (2023.02); *H10K 85/6574* (2023.02); *H10K 85/6576* (2023.02); *H10K 85/658* (2023.02); *H10K 50/11* (2023.02)

(58) Field of Classification Search

None

See application file for complete search history.

(56) References Cited

U.S. PATENT DOCUMENTS

| | | | |
|---|---|---|---|
| 10,622,565 | B2 | 4/2020 | Parham et al. |
| 2017/0207399 | A1 | 7/2017 | Parham et al. |
| 2019/0047991 | A1 | 2/2019 | Jung et al. |
| 2021/0265572 | A1 | 8/2021 | Jung et al. |

FOREIGN PATENT DOCUMENTS

| | | | |
|---|---|---|---|
| CN | 106459018 | A | 2/2017 |
| CN | 108884086 | A | 11/2018 |
| CN | 111971281 | A | 11/2020 |
| JP | 2017-514878 | A | 6/2017 |
| JP | 2017-524707 | A | 8/2017 |
| JP | 2019-513131 | A | 5/2019 |
| JP | 2020-102627 | A | 7/2020 |
| KR | 10-1559431 | B1 | 10/2015 |

(Continued)

OTHER PUBLICATIONS

International Search Report and Written Opinion received for PCT Patent Application No. PCT/EP2020/056437, mailed on Apr. 17, 2020, 14 pages (6 pages of English Translation and 8 pages of Original Document).

*Primary Examiner* — Andrew K Bohaty

(74) *Attorney, Agent, or Firm* — Faegre Drinker Biddle & Reath LLP

(57) ABSTRACT

The present invention describes dibenzofuran derivatives substituted by electron-deficient heteroaryl groups, and electronic devices, especially organic electroluminescent devices, comprising these compounds as triplet matrix materials.

13 Claims, No Drawings

(56) References Cited

FOREIGN PATENT DOCUMENTS

| | | | |
|---|---|---|---|
| KR | 10-1849747 | B1 | 5/2018 |
| KR | 10-1856728 | B1 | 5/2018 |
| KR | 10-2018-0061076 | A | 6/2018 |
| KR | 10-1885899 | B1 | 8/2018 |
| KR | 10-2019-0008035 | A | 1/2019 |
| KR | 10-2019-0008073 | A | 1/2019 |
| WO | 2015/105251 | A1 | 7/2015 |
| WO | 2015/169412 | A1 | 11/2015 |
| WO | 2016/015810 | A1 | 2/2016 |
| WO | 2018/093080 | A1 | 5/2018 |
| WO | 2019/013435 | A1 | 1/2019 |
| WO | 2019/054833 | A1 | 3/2019 |
| WO | 2019/132374 | A1 | 7/2019 |

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2020/056437, filed Mar. 11, 2020, which claims benefit of European Application No. 19193559.2, filed Aug. 26, 2019, both of which are incorporated herein by reference in their entirety.

The present invention describes dibenzofuran derivatives substituted by electron-deficient heteroaromatic systems, and electronic devices comprising these compounds, especially organic electroluminescent devices comprising these compounds as triplet matrix materials.

Phosphorescent organometallic complexes are frequently used in organic electroluminescent devices (OLEDs). In general terms, there is still a need for improvement in OLEDs, for example with regard to efficiency, operating voltage and lifetime. The properties of phosphorescent OLEDs are not just determined by the triplet emitters used. More particularly, the other materials used, for example matrix materials, are also of particular significance here. Improvements to these materials can thus also lead to distinct improvements in the OLED properties.

According to prior art, carbazole derivatives, dibenzofuran derivatives, indenocarbazole derivatives and indolocarbazole derivatives, especially those substituted by electron-deficient heteroaromatic systems such as triazine, are among the matrix materials used for phosphorescent emitters. There is generally still a need for improvement in these materials for use as matrix materials. The problem addressed by the present invention is that of providing compounds which are especially suitable for use as matrix material in a phosphorescent OLED. More particularly, it is an object of the present invention to provide matrix materials that lead to an improved lifetime. This is especially true of the use of a low to moderate emitter concentration, i.e. emitter concentrations in the order of magnitude of 3% to 20%, especially of 3% to 15%, since, in particular, device lifetime is limited here.

It has been found that, surprisingly, electroluminescent devices containing compounds of the formula (1) below have improvements over the prior art, especially when the compounds are used as matrix material for phosphorescent dopants.

The invention therefore provides a compound of the following formula (1):

Formula (1)

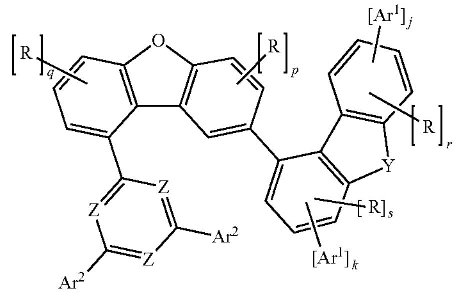

where the symbols used are as follows:

Y is O or S,

Z is the same or different at each instance and is CR or N, with the proviso that at least two Z are N;

$Ar^1$ is the same or different at each instance and is an aromatic ring system which has 6 to 40 aromatic ring atoms and may be substituted by one or more R radicals, or a heteroaromatic ring system which has 5 to 40 aromatic ring atoms and which is bonded to the dibenzofuran or dibenzothiophene via a nitrogen atom and which may be substituted by one or more R radicals, or a dibenzofuran or dibenzothiophene group which may be substituted by one or more R radicals;

$Ar^2$ is the same or different at each instance and is an aromatic or heteroaromatic ring system which has 5 to 40 aromatic ring atoms and may be substituted by one or more R radicals;

R is the same or different at each instance and is H, D, F, Cl, Br, I, $N(Ar')_2$, $N(R^1)_2$, OAr', SAr', CN, $NO_2$, $OR^1$, $SR^1$, $COOR^1$, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^1$ radicals, where one or more nonadjacent $CH_2$ groups may be replaced by $Si(R^1)_2$, C=O, $NR^1$, O, S or $CONR^1$, or an aromatic or heteroaromatic ring system which has 5 to 60 aromatic ring atoms, preferably 5 to 40 aromatic ring atoms, and may be substituted in each case by one or more $R^1$ radicals; at the same time, two R radicals together may also form a ring system;

Ar' is the same or different at each instance and is an aromatic or heteroaromatic ring system which has 5 to 40 aromatic ring atoms and may be substituted by one or more $R^1$ radicals; at the same time, two Ar' radicals bonded to the same nitrogen atom may also be bridged to one another by a single bond or a bridge selected from $N(R^1)$, $C(R^1)_2$, O and S, $R^1$ is the same or different at each instance and is H, D, F, Cl, Br, I, $N(R^2)_2$, CN, $NO_2$, $OR^2$, $SR^2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may each be substituted by one or more $R^2$ radicals, where one or more non-adjacent $CH_2$ groups may be replaced by $Si(R^2)_2$, C=O, $NR^2$, O, S or $CONR^2$ and where one or more hydrogen atoms in the alkyl, alkenyl or alkynyl group may be replaced by D, F, Cl, Br, I or CN, or an aromatic or heteroaromatic ring system which has 5 to 40 aromatic ring atoms and may be substituted in each case by one or more $R^2$ radicals; at the same time, two or more $R^1$ radicals together may form an aliphatic ring system;

$R^2$ is the same or different at each instance and is H, D, F, CN or an aliphatic, aromatic or heteroaromatic organic radical, especially a hydrocarbyl radical, having 1 to 20 carbon atoms, in which one or more hydrogen atoms may also be replaced by F;

p, q are the same or different at each instance and are 0, 1, 2 or 3;

r is 0, 1, 2, 3 or 4, with the proviso that r is not more than (4-j);

s is 0, 1, 2 or 3, with the proviso that s is not more than (3-k);

j, k are the same or different at each instance and are 0, 1, 2 or 3, with the proviso that j+k≥1.

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. Here, an aryl group or heteroaryl group is understood to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, etc. Aromatic systems joined to one another by a single bond, for example biphenyl, by contrast, are not referred to as an aryl or heteroaryl group but as an aromatic ring system.

An aromatic ring system in the context of this invention contains 6 to 60 carbon atoms, preferably 6 to 40 carbon atoms, in the ring system. A heteroaromatic ring system in the context of this invention contains 2 to 60 carbon atoms, preferably 2 to 40 carbon atoms, and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a nonaromatic unit, for example a carbon, nitrogen or oxygen atom. These shall likewise be understood to mean systems in which two or more aryl or heteroaryl groups are joined directly to one another, for example biphenyl, terphenyl, bipyridine or phenylpyridine. For example, systems such as fluorene, 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are joined, for example, by a short alkyl group. Preferred aromatic or heteroaromatic ring systems are simple aryl or heteroaryl groups and groups in which two or more aryl or heteroaryl groups are joined directly to one another, for example biphenyl or bipyridine, and also fluorene or spirobifluorene.

Alkyl groups in the context of the present invention also include cycloalkyl groups, and alkenyl groups in the context of the present invention also include cycloalkenyl groups. In the context of the present invention, an aliphatic hydrocarbyl radical or an alkyl group or an alkenyl or alkynyl group which may contain 1 to 40 carbon atoms and in which individual hydrogen atoms or $CH_2$ groups may also be substituted by the abovementioned groups is preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group OR' having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group SR' having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups according to the present invention may be straight-chain, branched or cyclic, where one or more nonadjacent $CH_2$ groups may be replaced by the abovementioned groups; in addition, it is also possible for one or more hydrogen atoms to be replaced by D, F, Cl, Br, I, CN or $NO_2$, preferably F, CI or CN, more preferably F or CN.

An aromatic or heteroaromatic ring system which has 5-60 aromatic ring atoms and may also be substituted in each case by the abovementioned $R^2$ radicals or a hydrocarbyl radical and which may be joined to the aromatic or heteroaromatic system via any desired positions is understood to mean especially groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or groups derived from a combination of these systems.

The wording that two or more radicals together may form a ring system is understood to mean the formation of an aliphatic, heteroaliphatic, aromatic or heteroaromatic ring system, and, in the context of the present description, should be understood to mean, inter alia, that the two radicals are joined to one another by a chemical bond with formal elimination of two hydrogen atoms. This is illustrated by the following scheme:

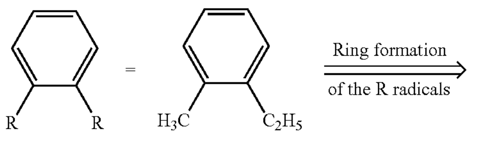

-continued

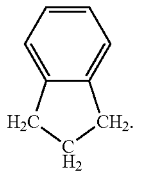

In addition, however, the abovementioned wording should also be understood to mean that, if one of the two radicals is hydrogen, the second radical binds to the position to which the hydrogen atom was bonded, forming a ring. This shall be illustrated by the following scheme:

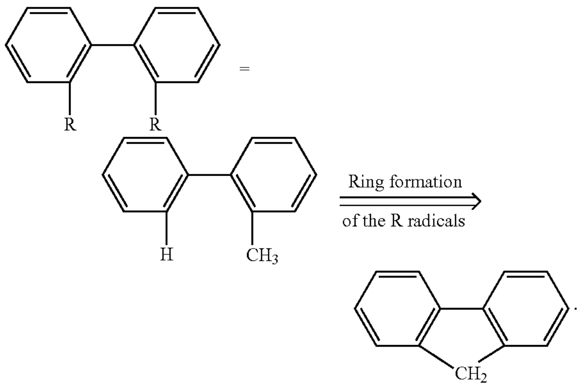

In a preferred embodiment of the invention, either all three Z groups are N, or two Z groups are N and the third Z group is CH. In a particularly preferred embodiment of the invention, all Z groups are N. The group is thus more preferably a diaryltriazine group.

In a preferred embodiment of the invention, the group

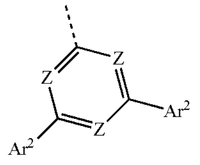

incorporated in formula (1) is therefore selected from the following groups (HetAr-1), (HetAr-2) and (HetAr-3):

(HetAr-1)

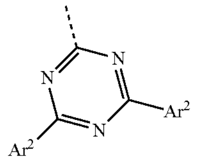

(HetAr-2)

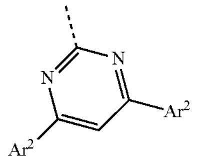

-continued (HetAr-3)

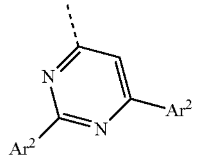

where $Ar^2$ has the definitions given above and the dotted bond indicates the linkage of this group.

Particular preference is given to (HetAr-1), and so the compound of the formula (1) is preferably a compound of the following formula (2):

Formula (2)

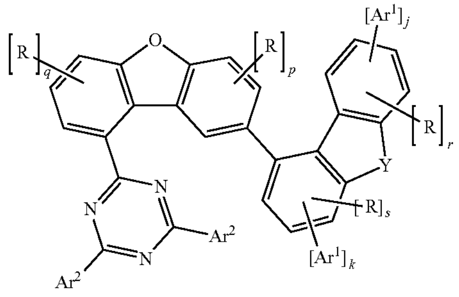

where the symbols and indices used have the definitions given above.

In a further preferred embodiment of the invention, Y is O, and so the compound is one of the following formula (3):

Formula (3)

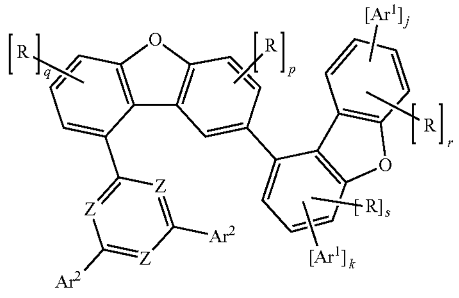

where the symbols and indices used have the definitions given above.

More preferably, all Z are N and, at the same time, Y is O, and so the compound is one of the following formula (4):

Formula (4)

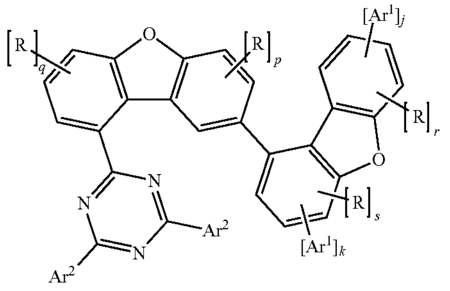

where the symbols and indices used have the definitions given above.

In a further preferred embodiment of the compounds of formulae (1), (2), (3) and (4), r and s are the same or different at each instance and are 0 or 1 and more preferably 0. In yet a further preferred embodiment of the compounds of formulae (1), (2), (3) and (4), p and q are the same or different at each instance and are 0, 1 or 2, more preferably 0 or 1, and most preferably 0. More preferably, the dibenzofuran groups thus do not bear any R radicals, and the compound is one of the following formula (5):

Formula (5)

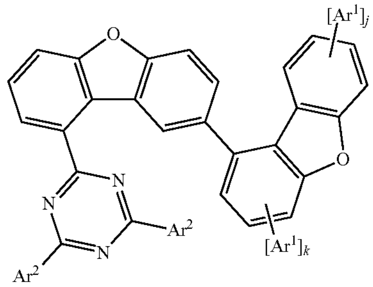

where the symbols and indices used have the definitions given above.

In a further preferred embodiment of the invention, j and k in the compounds of the formulae (1), (2), (3), (4) and (5) are the same or different at each instance and are 0, 1 or 2 and more preferably 0 or 1, with the proviso that $j+k \geq 1$. Most preferably, $j+k=1$, and so the compound has exactly one $Ar^1$ group. In one embodiment of the invention, $j=1$ and $k=0$, and, in a further embodiment, $j=0$ and $k=1$, particular preference being given to the $j=1$ and $k=0$ embodiment. Preference is thus given to the compounds of the following formulae (6a) and (6b):

Formula (6a)

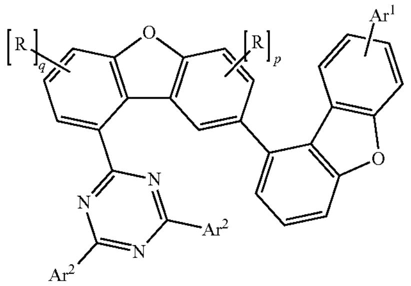

-continued

Formula (6b)

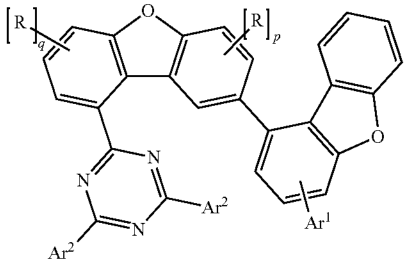

where the symbols and indices used have the definitions given above.

Particular preference is given to a compound of one of the following formulae (7a) and (7b):

Formula (7a)

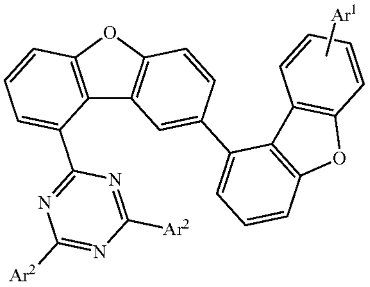

Formula (7b)

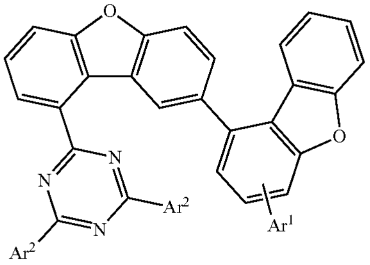

where the symbols used have the meanings given above.

When $j=1$, the $Ar^1$ group in the compounds of the formulae (1), (2), (3), (4), (5), (6a), (6b), (7a) and (7b) is preferably bonded in the 7 or 8 position of the dibenzofuran or dibenzothiophene, more preferably in the 8 position. Further preferably, when $k=1$, the $Ar^1$ group in the compounds of the formulae (1), (2), (3), (4), (5), (6a), (6b), (7a) and (7b) is preferably bonded in the 3 or 4 position of the dibenzofuran or dibenzothiophene, more preferably in the 4 position.

The numbering of dibenzofuran is shown in the scheme below, the numbering for dibenzothiophene being analogous:

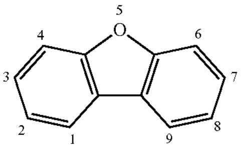

Very particular preference is given to a structure of the following formula (8a) or (8b):

Formula (8a)

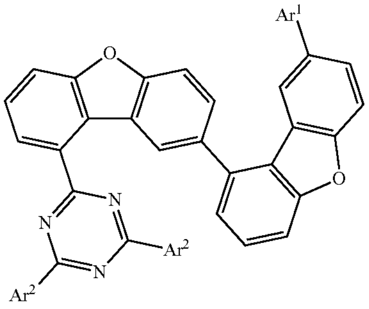

Formula (8b)

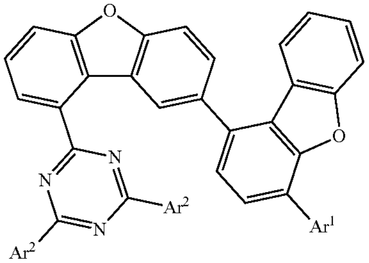

where the symbols used have the meanings given above.

In a preferred embodiment of the invention, $Ar^2$ is the same or different at each instance and is an aromatic or heteroaromatic ring system which has 6 to 30 aromatic ring atoms and may be substituted by one or more R radicals. More preferably, $Ar^2$ is the same or different at each instance and is an aromatic or heteroaromatic ring system, especially an aromatic ring system, which has 6 to 24 aromatic ring atoms, especially 6 to 13 aromatic ring atoms, and may be substituted by one or more, preferably nonaromatic, R radicals. When $Ar^2$ is a heteroaryl group, especially triazine, pyrimidine, quinazoline or carbazole, preference may also be given to aromatic or heteroaromatic substituents R on this heteroaryl group.

Suitable aromatic or heteroaromatic ring systems $Ar^2$ are the same or different at each instance and are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene which may be joined via the 1 or 2 position, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, phenanthrene, triphenylene or a combination of two or three of these groups, each of which may be substituted by one or more R radicals, preferably nonaromatic R radicals. When $Ar^2$ is a heteroaryl group, especially triazine, pyrimidine, quinazoline or carbazole, preference may also be given to aromatic or heteroaromatic R radicals on this heteroaryl group.

$Ar^2$ here is preferably the same or different at each instance and is selected from the groups of the following formulae Ar-1 to Ar-81:

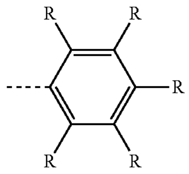

Ar-1

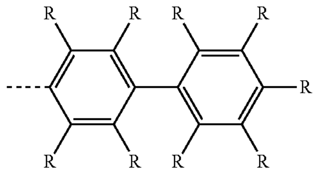

Ar-2

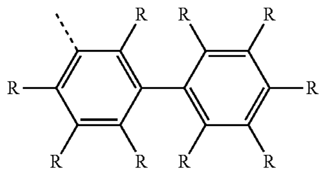

Ar-3

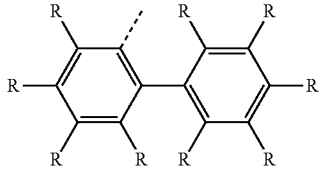

Ar-4

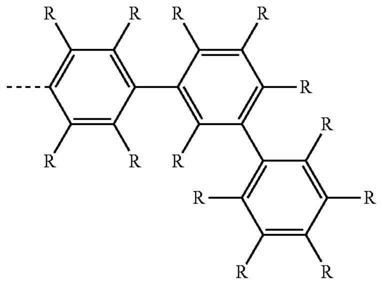

Ar-5

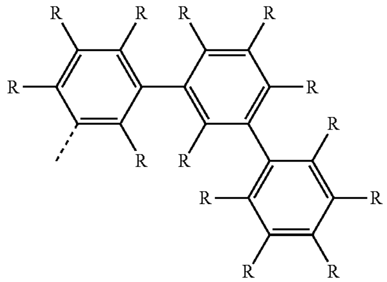

Ar-6

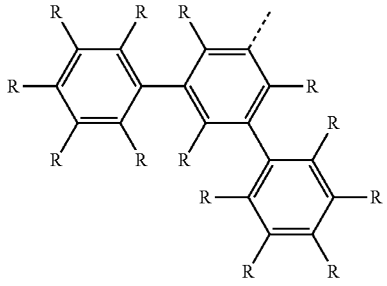

Ar-7

-continued
Ar-8
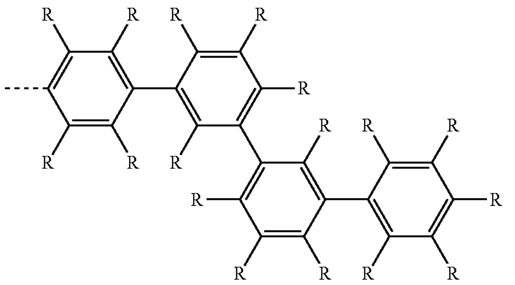
Ar-9
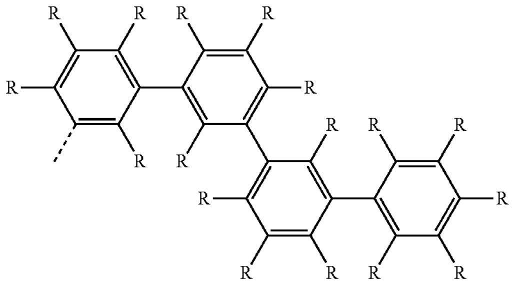
Ar-10
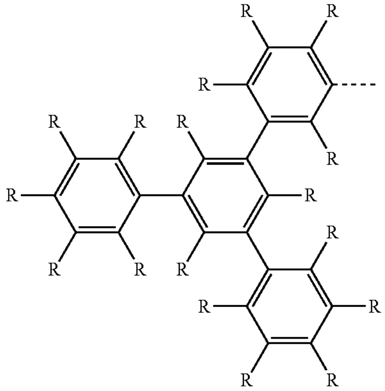
Ar-11
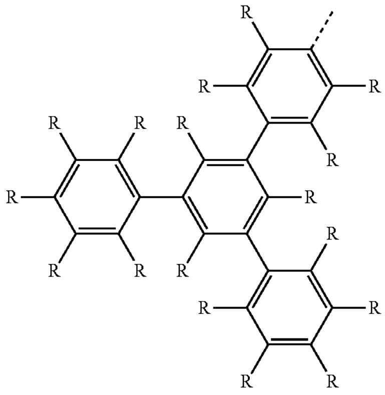
-continued
Ar-12
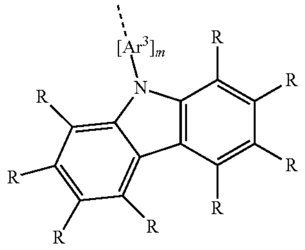
Ar-13
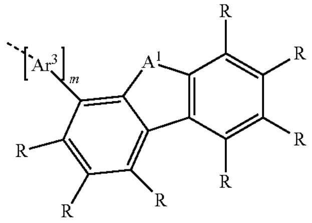
Ar-14
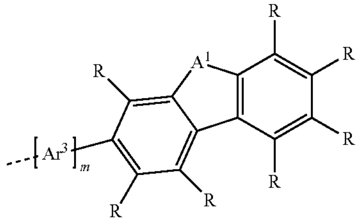
Ar-15
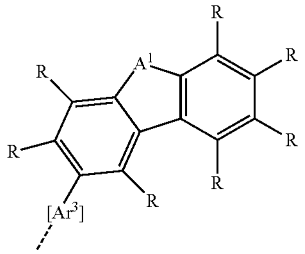
Ar-16
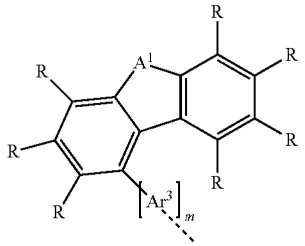
Ar-17
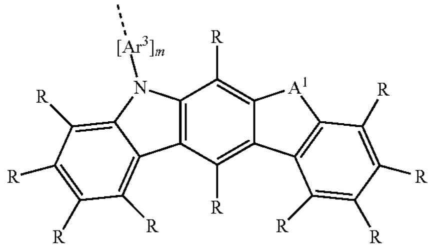

-continued
Ar-18
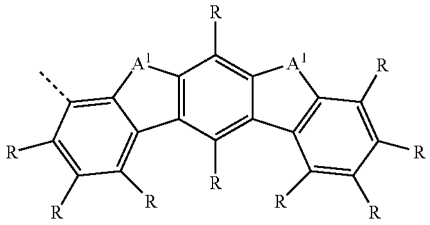
Ar-19
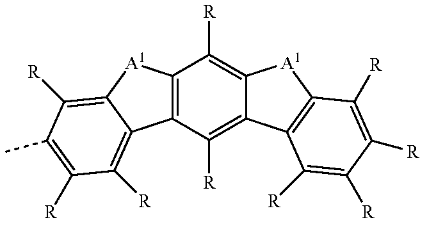
Ar-20
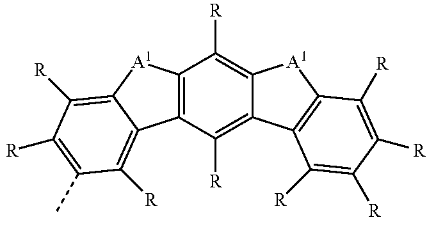
Ar-21
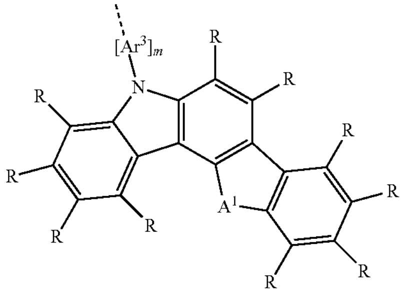
Ar-22
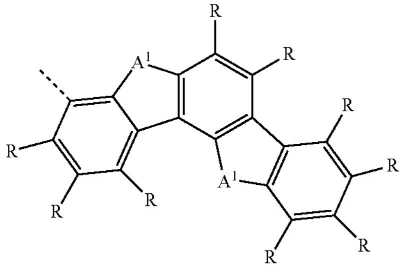
Ar-23
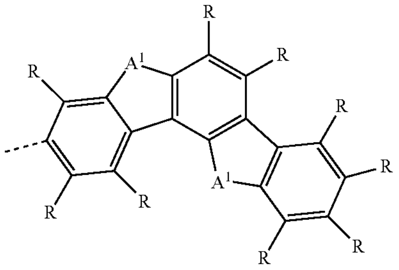
-continued
Ar-24
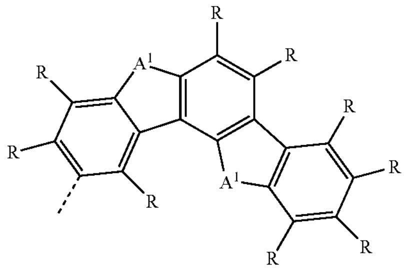
Ar-25
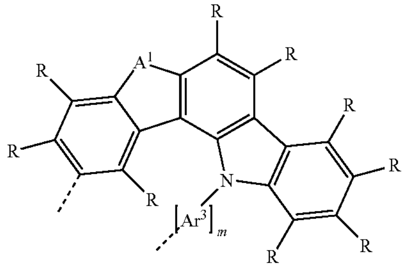
Ar-26
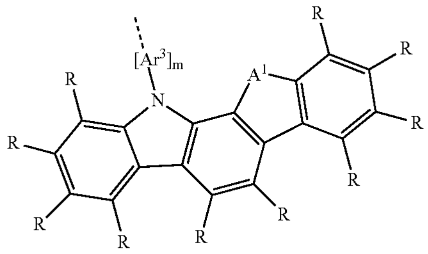
Ar-27
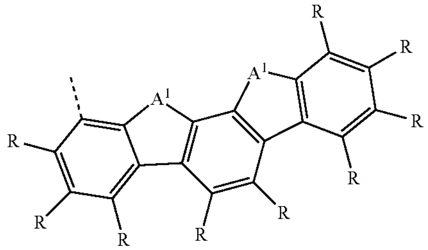
Ar-28
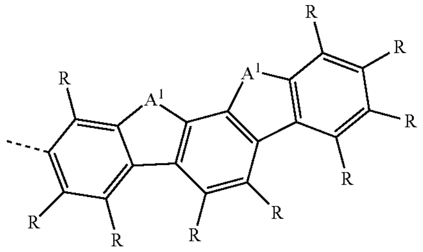
Ar-29
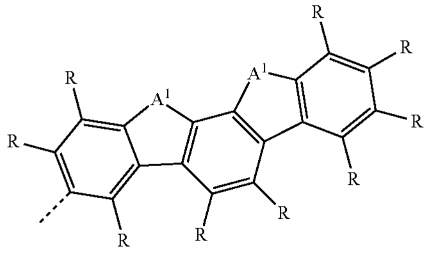

-continued
Ar-30
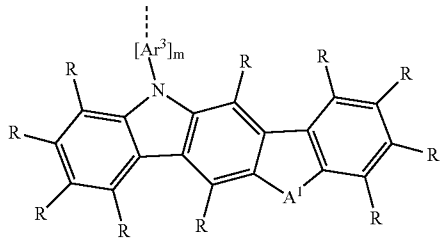
Ar-31
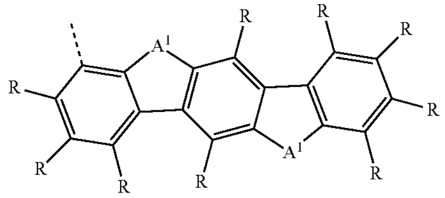
Ar-32
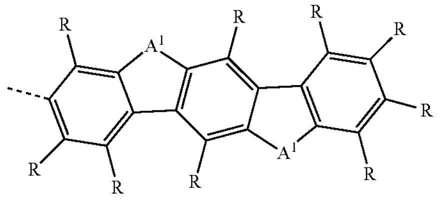
Ar-33
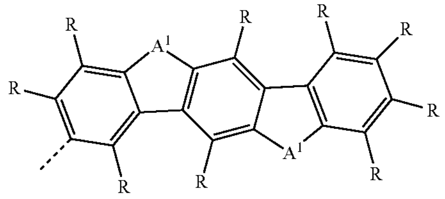
Ar-34
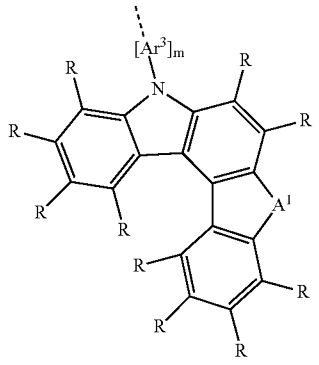
Ar-35
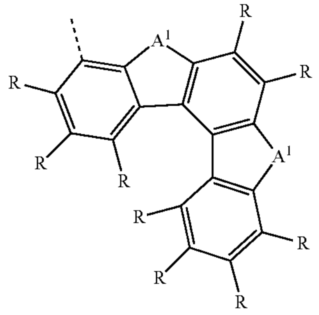
-continued
Ar-36
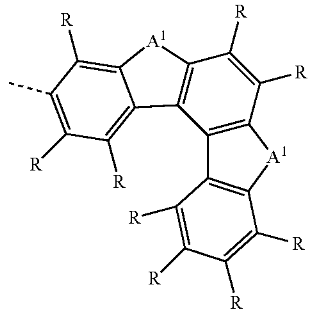
Ar-37
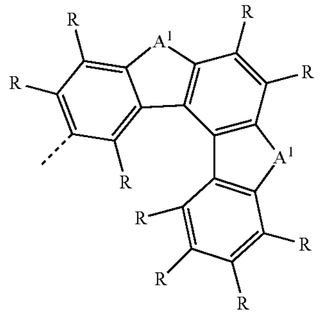
Ar-38
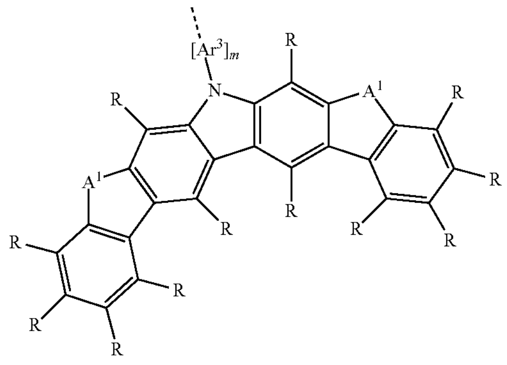
Ar-39
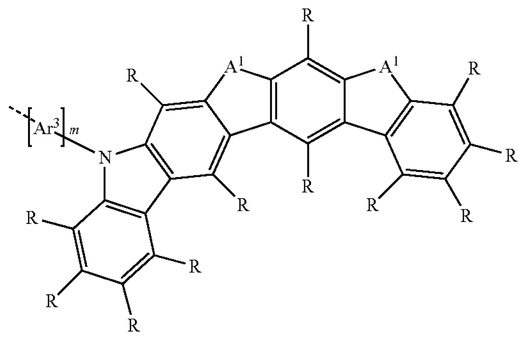

-continued
Ar-40
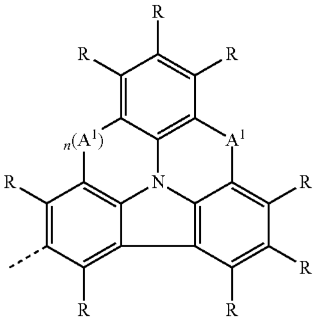
Ar-41
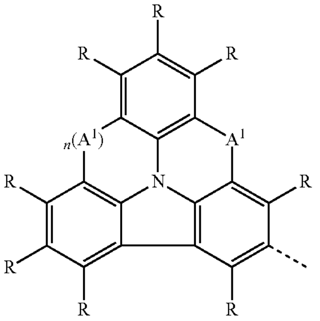
Ar-42
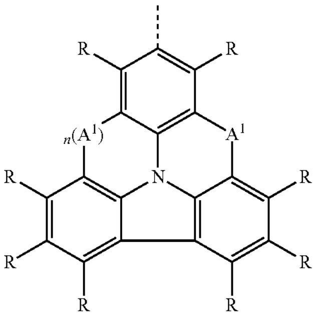
Ar-43
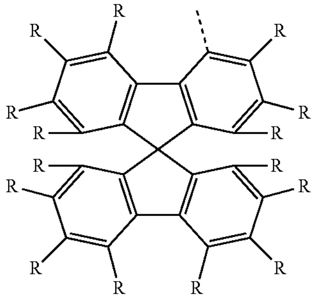
Ar-44
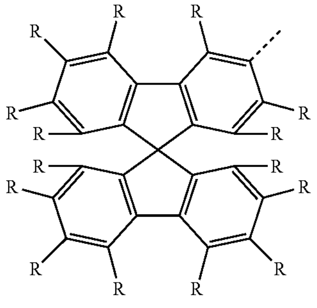
-continued
Ar-45
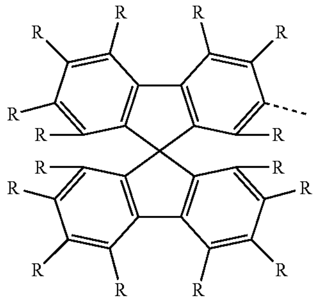
Ar-46
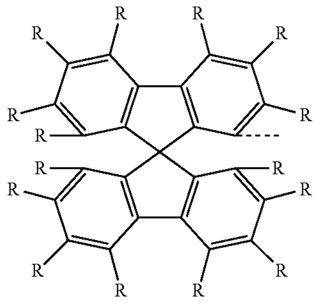
Ar-47
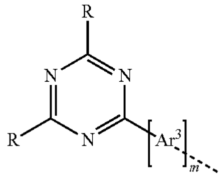
Ar-48
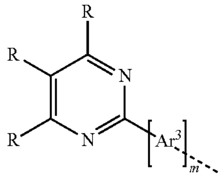
Ar-49
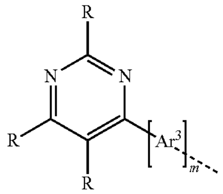
Ar-50
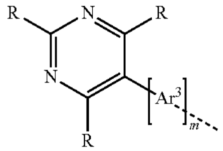
Ar-51
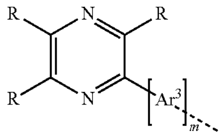

-continued
Ar-52
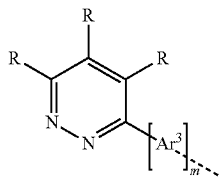
Ar-53
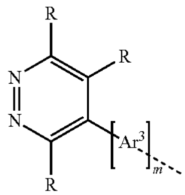
Ar-54
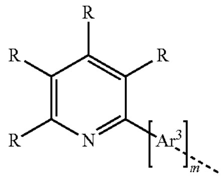
Ar-55
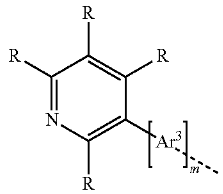
Ar-56
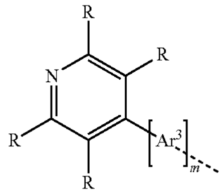
Ar-57
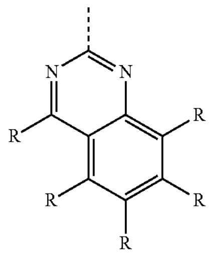
Ar-58
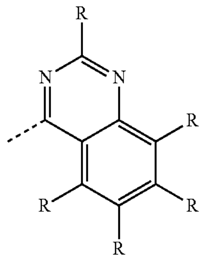
-continued
Ar-59
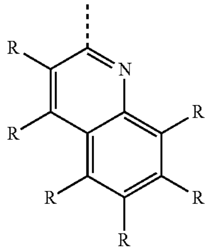
Ar-60
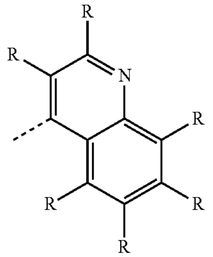
Ar-61
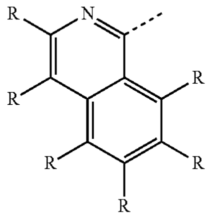
Ar-62
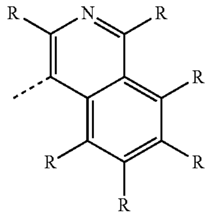
Ar-63
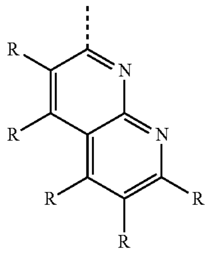
Ar-64
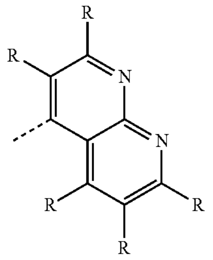

-continued
Ar-65
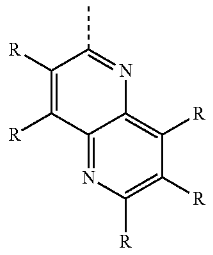
Ar-66
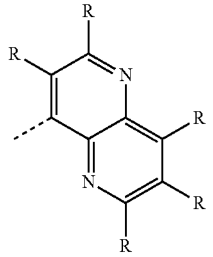
Ar-67
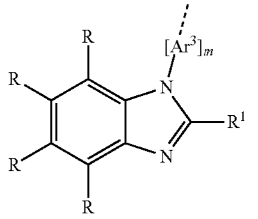
Ar-68
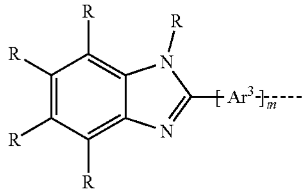
Ar-69
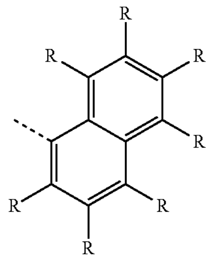
Ar-70
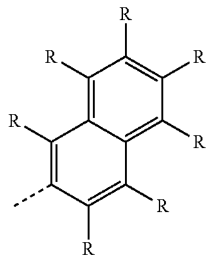
-continued
Ar-71
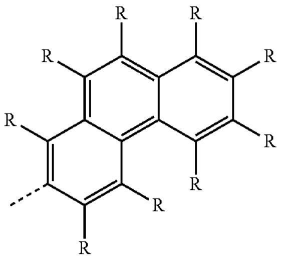
Ar-72
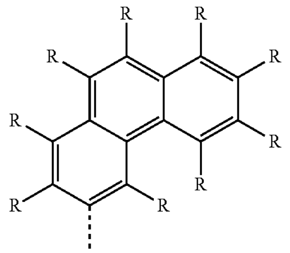
Ar-73
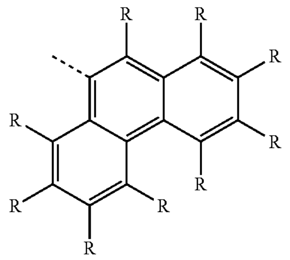
Ar-74
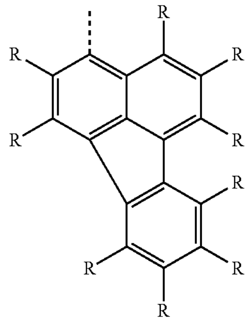
Ar-75
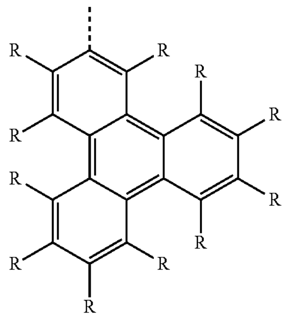

-continued

Ar-76

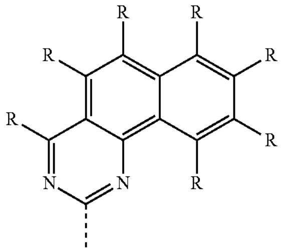

Ar-77

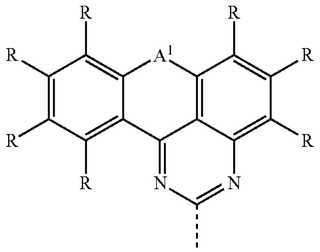

Ar-78

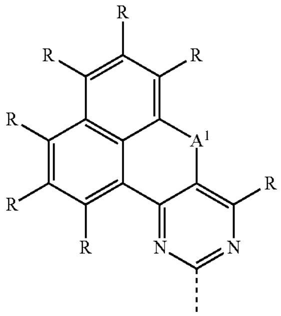

Ar-79

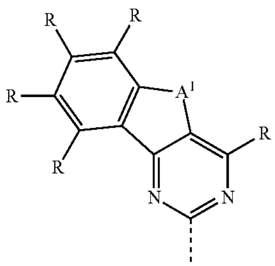

Ar-80

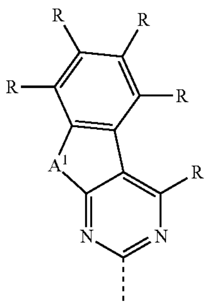

Ar-81

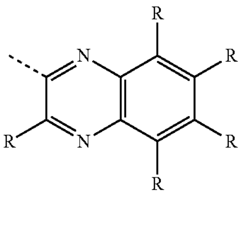

where R is as defined above, the dotted bond represents the bond to the heteroaryl group and, in addition:

$A^1$ is the same or different at each instance and is $CR_2$, NR, O or S;

$Ar^3$ is the same or different at each instance and is a bivalent aromatic or heteroaromatic ring system which has 6 to 18 aromatic ring atoms and may be substituted in each case by one or more R radicals;

n is 0 or 1, where n=0 means that no $A^1$ group is bonded at this position and R radicals are bonded to the corresponding carbon atoms instead;

m is 0 or 1, where m=0 means that the $Ar^3$ group is absent and that the corresponding aromatic or heteroaromatic group is bonded directly to the triazine or pyrimidine group in formula (1).

In a further preferred embodiment of the invention, $Ar^1$ is an aromatic ring system which has 6 to 30 aromatic ring atoms and may be substituted by one or more R radicals, or N-carbazolyl which may be substituted by one or more R radicals, or dibenzofuran or dibenzothiophene, each of which may be substituted by one or more R radicals. More preferably, $Ar^1$ is an aromatic ring system which has 6 to 24 aromatic ring atoms, especially 6 to 18 aromatic ring atoms, and may be substituted by one or more, preferably nonaromatic, R radicals, or a dibenzofuran group which may be substituted by one or more R radicals.

Suitable $Ar^1$ groups are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene which may be joined via the 1 or 2 position, N-carbazole, dibenzofuran which may be joined via the 1, 2, 3 or 4 position, dibenzothiophene which may be joined via the 1, 2, 3 or 4 position, phenanthrene, triphenylene or a combination of two or three of these groups, each of which may be substituted by one or more R radicals.

$Ar^1$ here is preferably the same or different at each instance and is selected from the groups of the following formulae Ar-1 to Ar-16, Ar-43 to Ar-46 and Ar-69 to Ar-75:

Ar-1

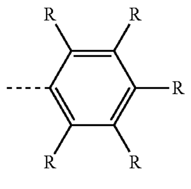

Ar-2

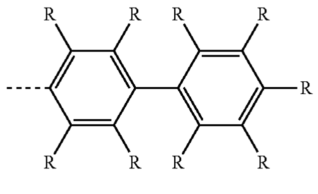

Ar-3

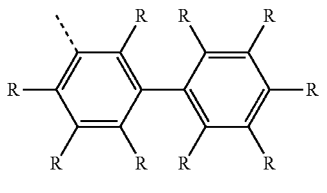

-continued
Ar-4
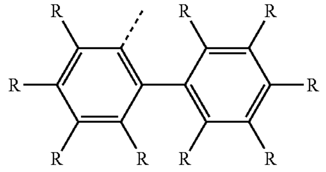
Ar-5
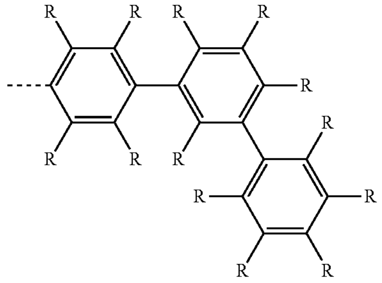
Ar-6
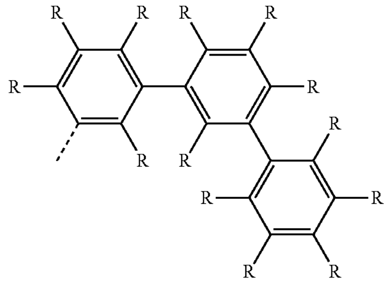
Ar-7
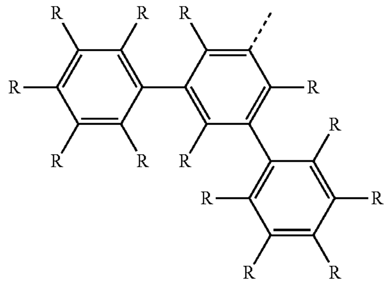
Ar-8
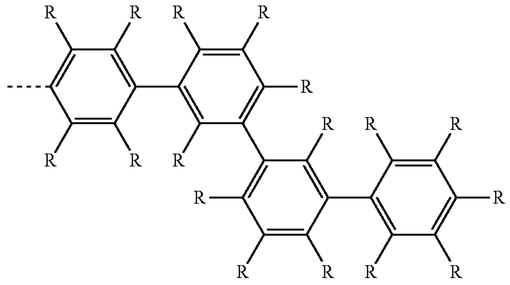
-continued
Ar-9
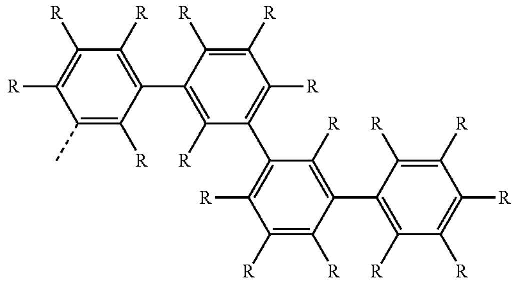
Ar-10
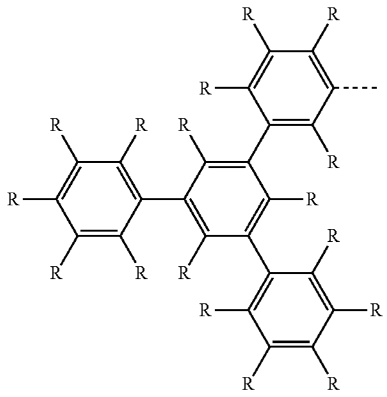
Ar-11
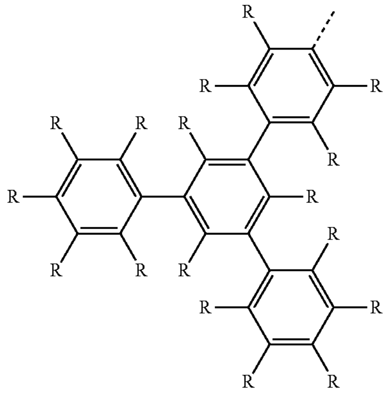
Ar-12
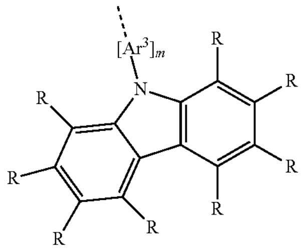
Ar-13
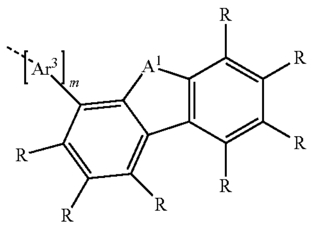

-continued
Ar-14
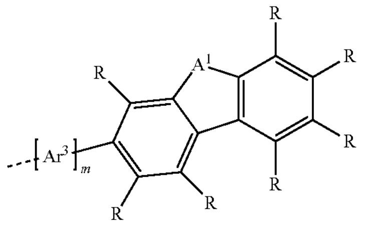
Ar-15
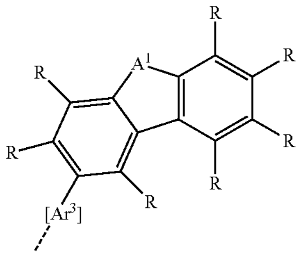
Ar-16
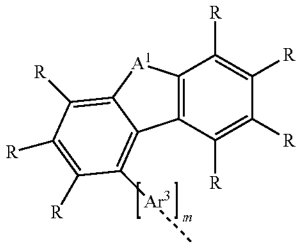
Ar-43
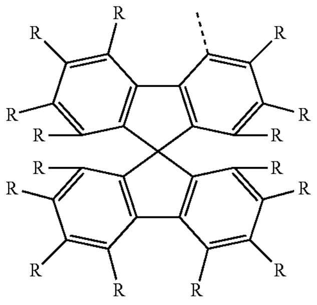
Ar-44
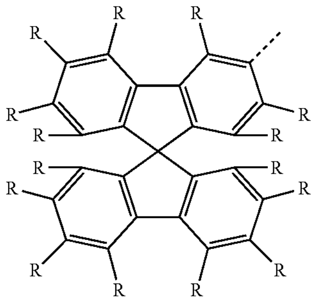
-continued
Ar-45
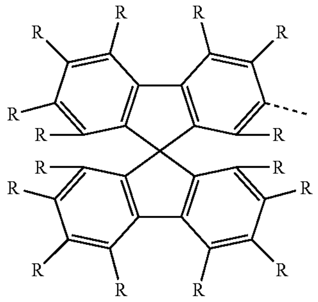
Ar-46
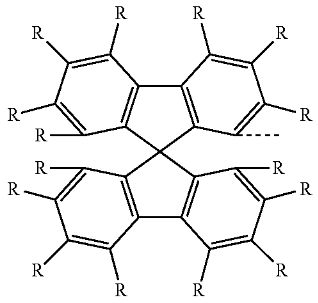
Ar-69
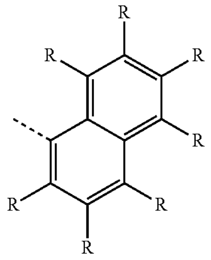
Ar-70
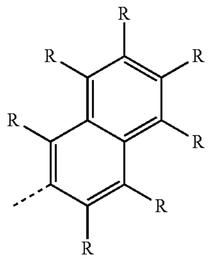
Ar-71
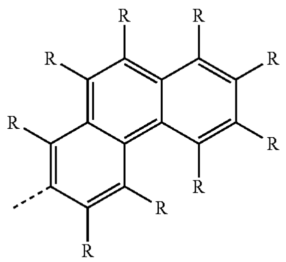

-continued

Ar-72

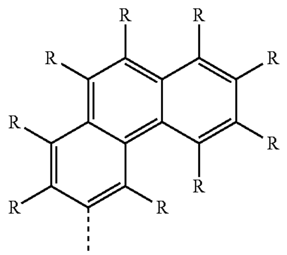

Ar-73

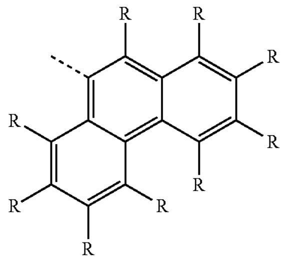

Ar-74

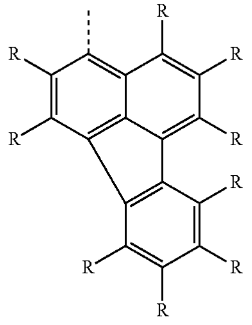

Ar-75

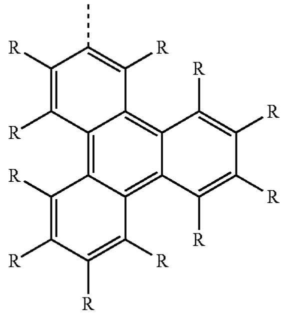

where R has the definitions given above, the dotted bond represents the bond to the dibenzofuran or dibenzothiophene and, in addition:

$A^1$ is the same or different at each instance and is $CR_2$, O or S;

$Ar^3$ is the same or different at each instance and is a bivalent aromatic ring system which has 6 to 18 aromatic ring atoms and may be substituted in each case by one or more R radicals;

n is 0 or 1;

m is 0 or 1, where m=0 means that the $Ar^3$ group is absent and that the corresponding aromatic or heteroaromatic group is bonded directly to the dibenzofuran or dibenzothiophene.

In a preferred embodiment of the invention, R is the same or different at each instance and is selected from the group consisting of H, D, F, $N(Ar)_2$, CN, $OR^1$, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may each be substituted by one or more $R^1$ radicals, but is preferably unsubstituted, and where one or more nonadjacent $CH_2$ groups may be replaced by O, or an aromatic or heteroaromatic ring system which has 6 to 30 aromatic ring atoms and may be substituted in each case by one or more $R^1$ radicals; at the same time, two R radicals together may also form an aliphatic, aromatic or heteroaromatic ring system. More preferably, R is the same or different at each instance and is selected from the group consisting of H, $N(Ar')_2$, a straight-chain alkyl group having 1 to 6 carbon atoms, especially having 1, 2, 3 or 4 carbon atoms, or a branched or cyclic alkyl group having 3 to 6 carbon atoms, where the alkyl group in each case may be substituted by one or more $R^1$ radicals, but is preferably unsubstituted, or an aromatic or heteroaromatic ring system which has 6 to 24 aromatic ring atoms and may be substituted in each case by one or more $R^1$ radicals, preferably nonaromatic $R^1$ radicals. Most preferably, R is the same or different at each instance and is selected from the group consisting of H or an aromatic or heteroaromatic ring system which has 6 to 24 aromatic ring atoms and may be substituted in each case by one or more $R^1$ radicals, preferably nonaromatic $R^1$ radicals.

In a further preferred embodiment of the invention, Ar' is an aromatic or heteroaromatic ring system which has 6 to 30 aromatic ring atoms and may be substituted by one or more $R^1$ radicals. In a particularly preferred embodiment of the invention, Ar' is an aromatic or heteroaromatic ring system which has 6 to 24 aromatic ring atoms, especially 6 to 13 aromatic ring atoms, and may be substituted by one or more, preferably nonaromatic, $R^1$ radicals.

Suitable aromatic or heteroaromatic ring systems R or Ar' are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene which may be joined via the 1 or 2 position, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, quinazoline, benzimidazole, phenanthrene, triphenylene or a combination of two or three of these groups, each of which may be substituted by one or more nonaromatic $R^1$ radicals. When R or Ar' is a heteroaryl group, especially triazine, pyrimidine or quinazoline, preference may also be given to aromatic or heteroaromatic $R^1$ radicals on this heteroaryl group.

The R groups here, when they are an aromatic or heteroaromatic ring system, or Ar' are preferably selected from the groups of the following formulae R-1 to R-81:

R-1

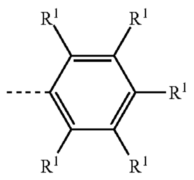

-continued
R-2
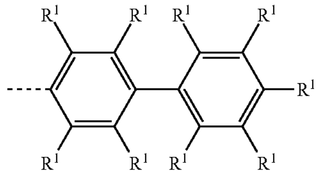
R-3
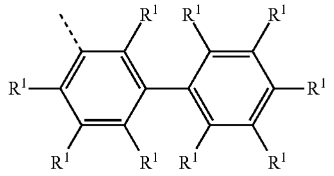
R-4
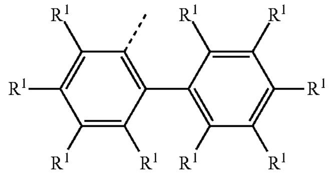
R-5
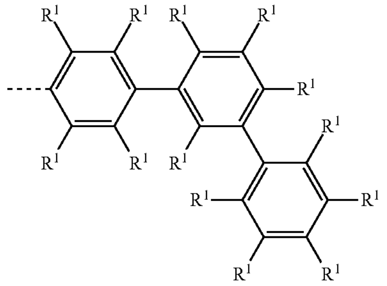
R-6
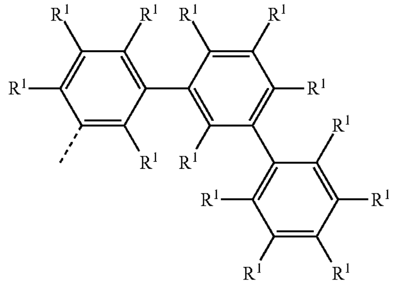
R-7
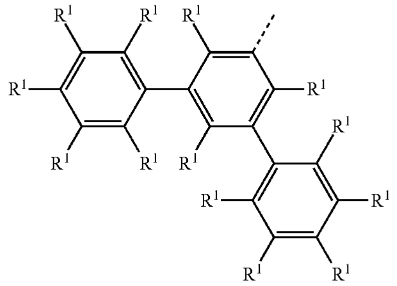
-continued
R-8
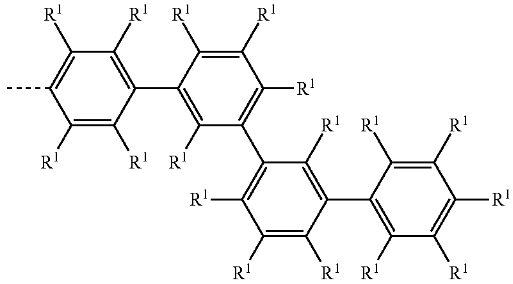
R-9
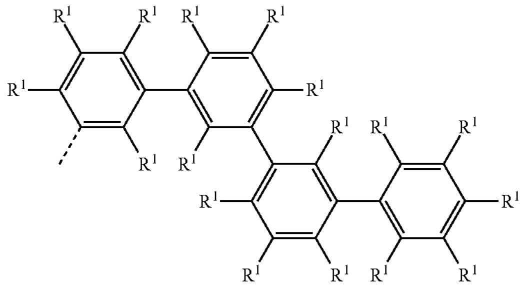
R-10
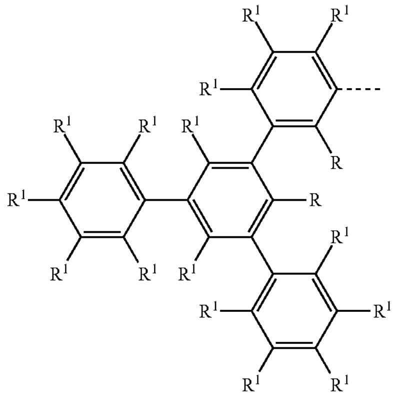
R-11
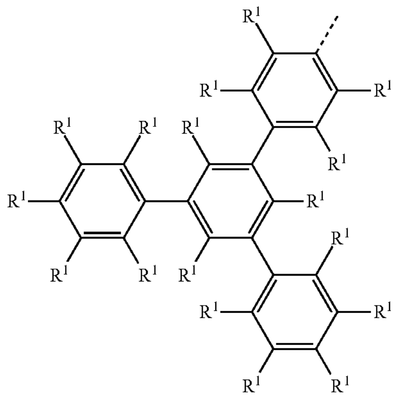

-continued
R-12
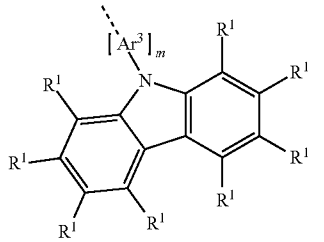
R-13
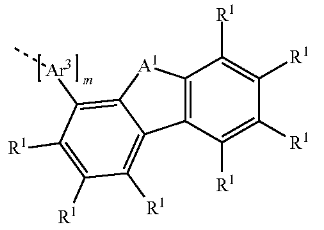
R-14
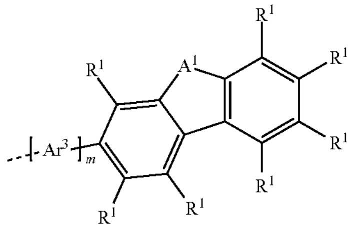
R-15
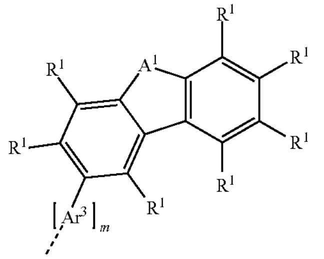
R-16
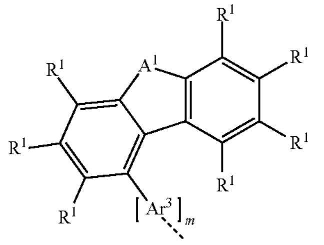
R-17
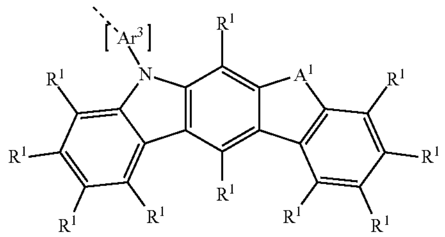
-continued
R-18
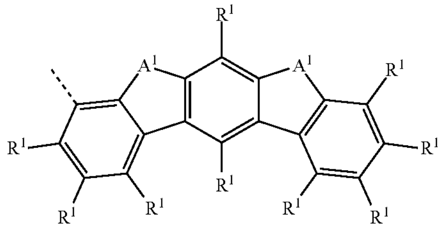
R-19
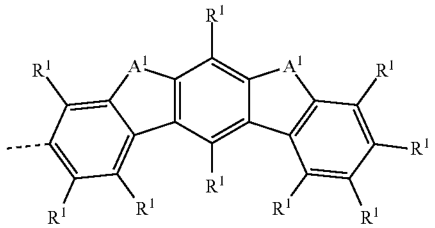
R-20
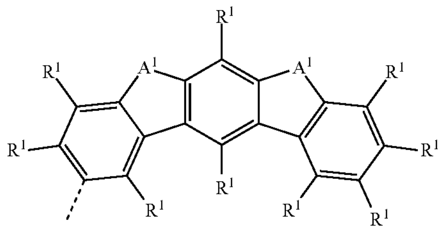
R-21
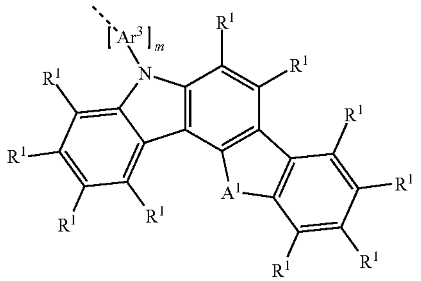
R-22
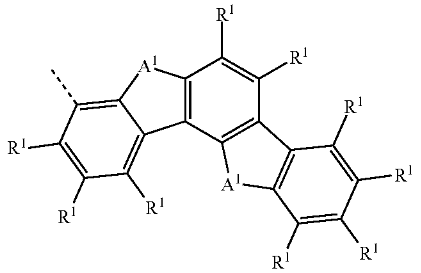
R-23
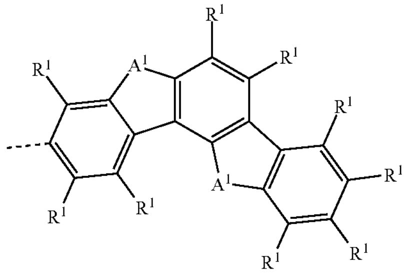

-continued
R-24
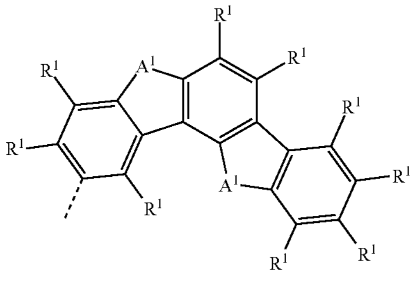
R-25
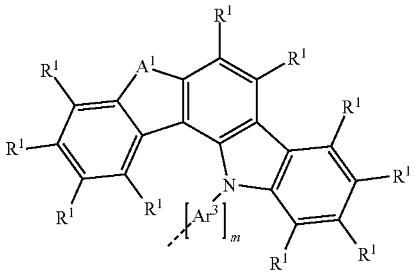
R-26
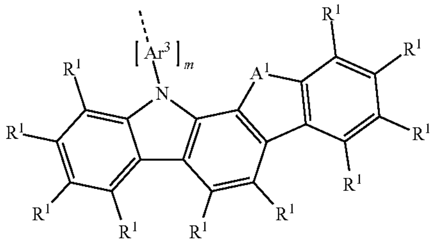
R-27
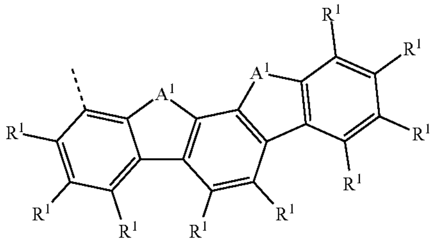
R-28
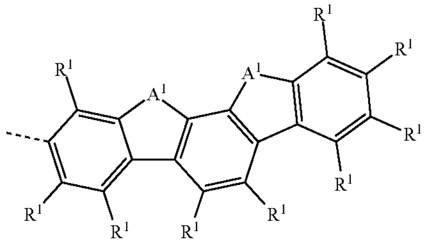
R-29
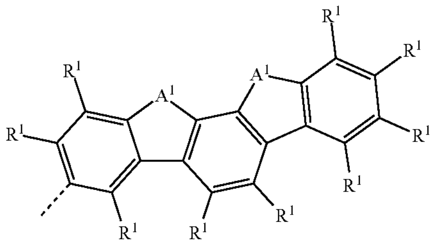
-continued
R-30
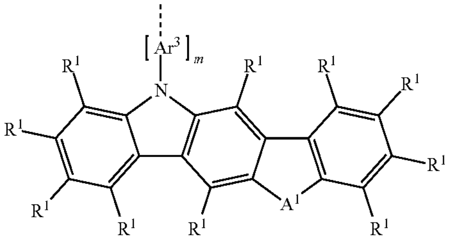
R-31
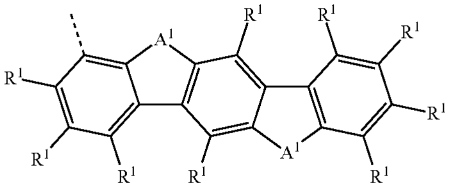
R-32
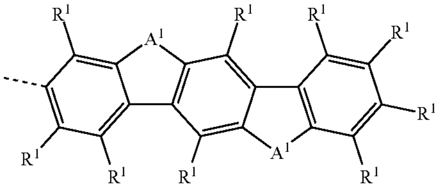
R-33
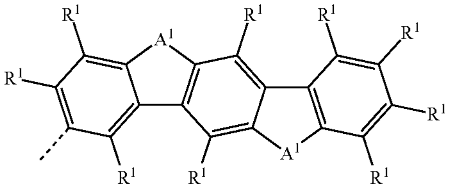
R-34
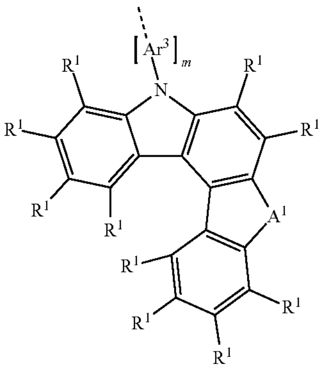
R-35
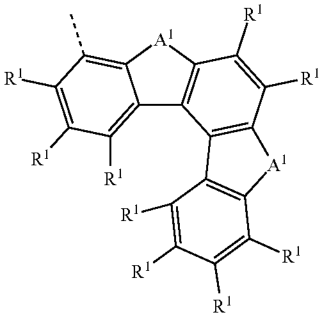

-continued
R-36
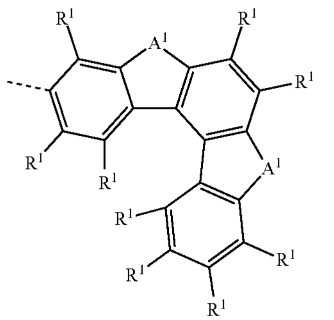
R-37
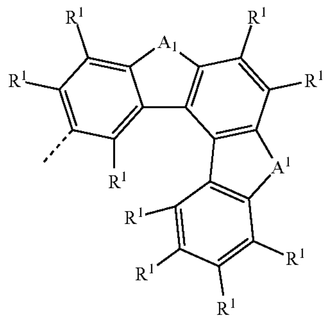
R-38
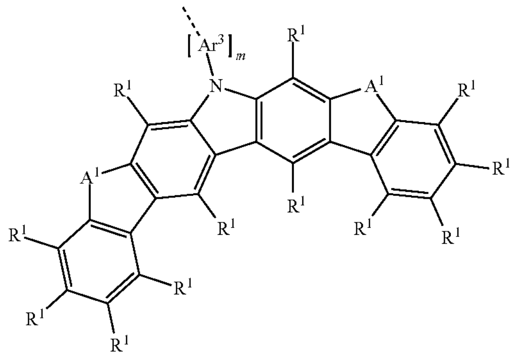
R-39
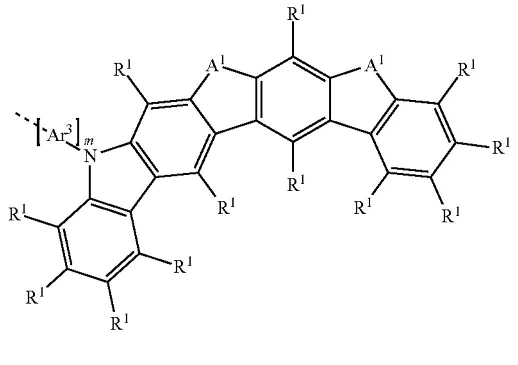
-continued
R-40
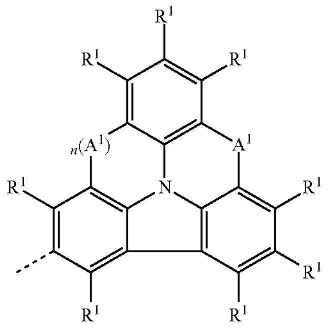
R-41
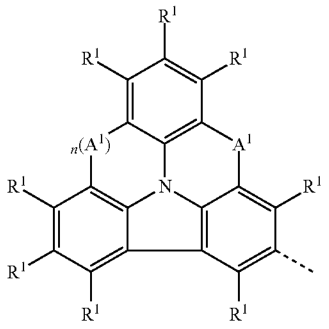
R-42
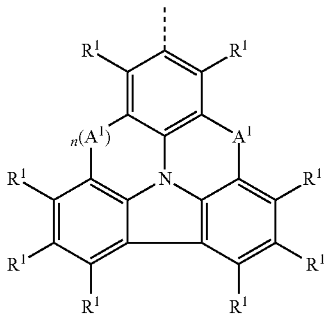
R-43
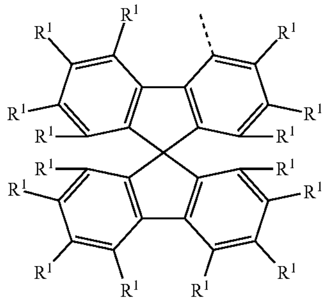
R-44
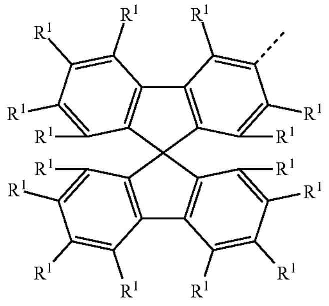

-continued
R-45
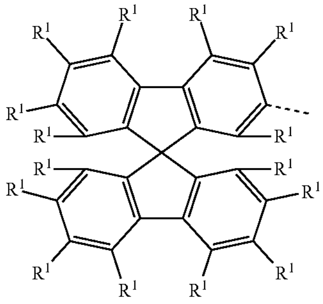
R-46
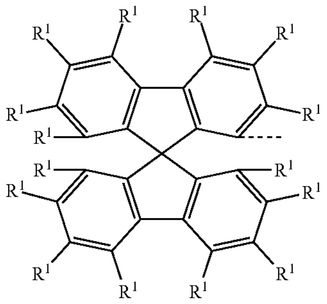
R-47
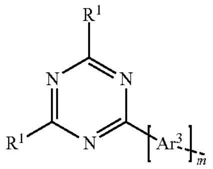
R-48
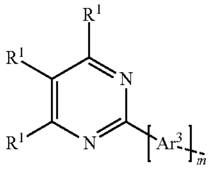
R-49
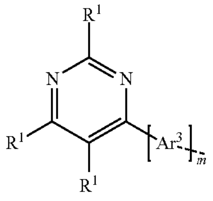
R-50
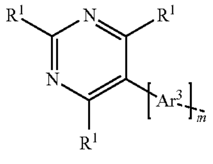
R-51
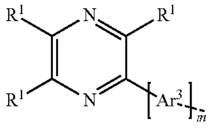
-continued
R-52
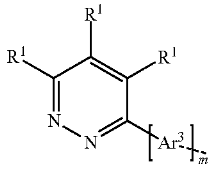
R-53
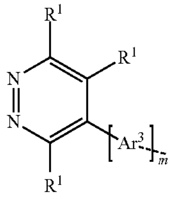
R-54
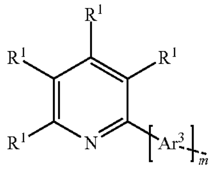
R-55
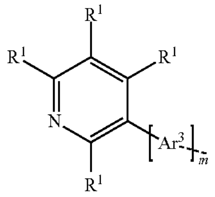
R-56
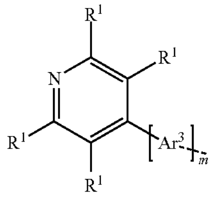
R-57
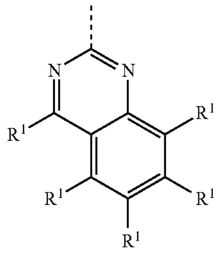
R-58
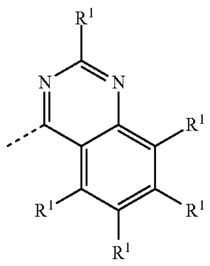

-continued
R-59
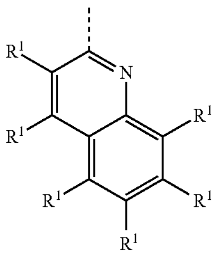
R-60
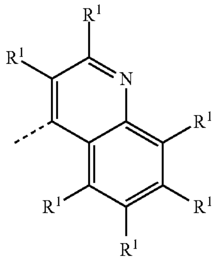
R-61
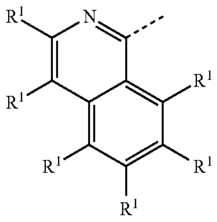
R-62
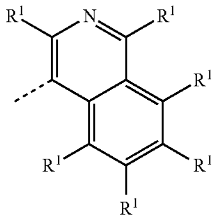
R-63
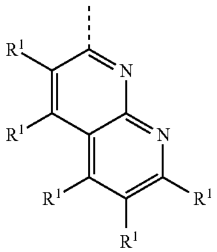
R-64
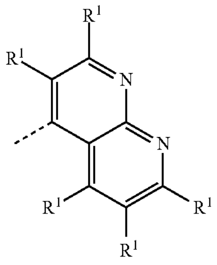
-continued
R-65
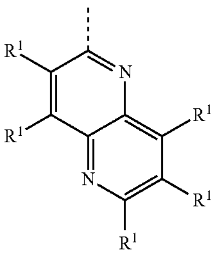
R-66
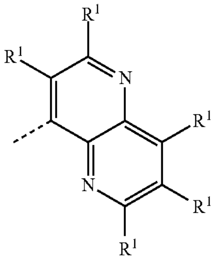
R-67
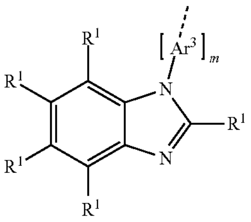
R-68
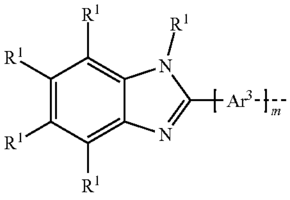
R-69
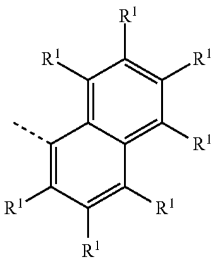
R-70
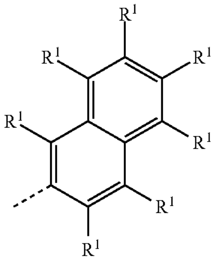

-continued
R-71
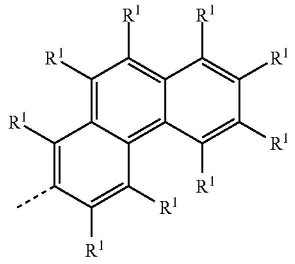
R-72
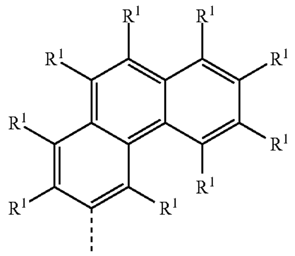
R-73
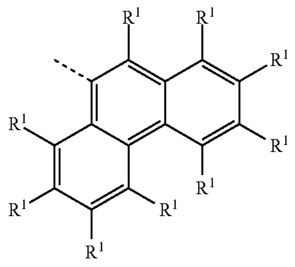
R-74
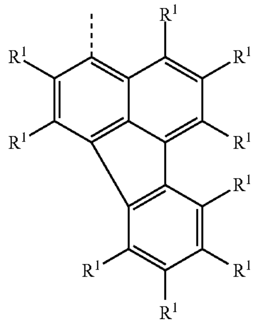
R-75
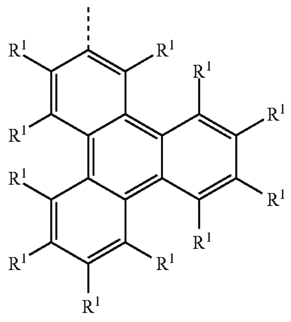
-continued
R-76
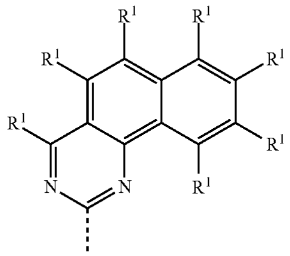
R-77
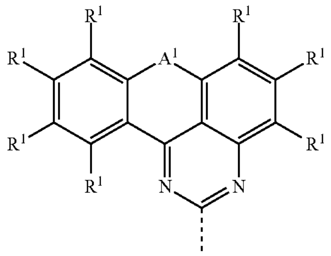
R-78
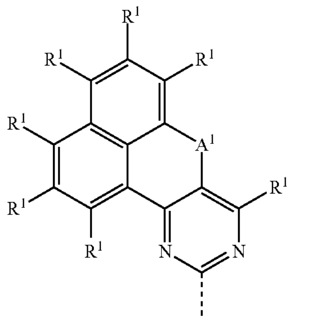
R-79
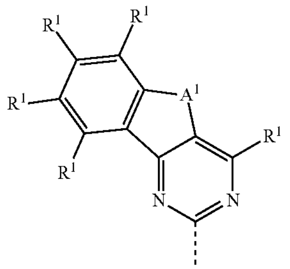
R-80
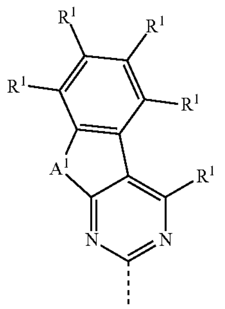

-continued

R-81

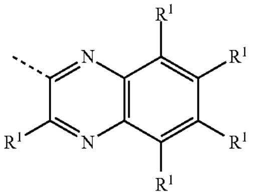

where $R^1$ has the definitions given above, the dotted bond represents the bond to a carbon atom of the base skeleton in formula (1) or in the preferred embodiments or the bond to $Ar^1$ or $Ar^2$ or to the nitrogen atom in the $N(Ar')_2$ group and, in addition:

- $Ar^3$ is the same or different at each instance and is a bivalent aromatic or heteroaromatic ring system which has 6 to 18 aromatic ring atoms and may be substituted in each case by one or more $R^1$ radicals;
- $A^1$ is the same or different at each instance and is $C(R^1)_2$, $NR^1$, 0 or S;
- n is 0 or 1, where n=0 means that no A group is bonded at this position and $R^1$ radicals are bonded to the corresponding carbon atoms instead;
- m is 0 or 1, where m=0 means that the $Ar^3$ group is absent and that the corresponding aromatic or heteroaromatic group is bonded directly to a carbon atom of the base skeleton in formula (1) or in the preferred embodiments, or to the nitrogen atom in the $N(Ar')_2$ group; with the proviso that m=1 for the structures (R-12), (R-17), (R-21), (R-25), (R-26), (R-30), (R-34), (R-38) and (R-39) when these groups are embodiments of Ar'.

When the abovementioned Ar-1 to Ar-81 groups for $Ar^1$ or $Ar^2$ or R-1 to R-81 groups for R or Ar have two or more $A^1$ groups, possible options for these include all combinations from the definition of $A^1$. Preferred embodiments in that case are those in which one $A^1$ group is NR or $NR^1$ and the other $A^1$ group is $C(R)_2$ or $C(R^1)_2$ or in which both $A^1$ groups are NR or $NR^1$ or in which both $A^1$ groups are O. In a particularly preferred embodiment of the invention, in $Ar^1$, $Ar^2$, R or Ar' groups having two or more $A^1$ groups, at least one $A^1$ group is $C(R)_2$ or $C(R^1)_2$ or is NR or $NR^1$.

When $A^1$ is NR or $NR^1$, the substituent R or $R^1$ bonded to the nitrogen atom is preferably an aromatic or heteroaromatic ring system which has 5 to 24 aromatic ring atoms and may also be substituted by one or more $R^1$ or $R^2$ radicals. In a particularly preferred embodiment, this R or $R^1$ substituent is the same or different at each instance and is an aromatic or heteroaromatic ring system which has 6 to 24 aromatic ring atoms, preferably 6 to 12 aromatic ring atoms, and which does not have any fused aryl groups or heteroaryl groups in which two or more aromatic or heteroaromatic 6-membered ring groups are fused directly to one another, and which may also be substituted in each case by one or more $R^1$ or $R^2$ radicals. Particular preference is given to phenyl, biphenyl, terphenyl and quaterphenyl having bonding patterns as listed above for Ar-1 to Ar-11 or R-1 to R-11, where these structures may be substituted by one or more $R^1$ or $R^2$ radicals, but are preferably unsubstituted.

When $A^1$ is $C(R)_2$ or $C(R^1)_2$, the substituents R or $R^1$ bonded to this carbon atom are preferably the same or different at each instance and are a linear alkyl group having 1 to 10 carbon atoms or a branched or cyclic alkyl group having 3 to 10 carbon atoms or an aromatic or heteroaromatic ring system which has 5 to 24 aromatic ring atoms and may also be substituted by one or more $R^1$ or $R^2$ radicals. Most preferably, R or $R^1$ is a methyl group or a phenyl group. In this case, the R or $R^1$ radicals together may also form a ring system, which leads to a spiro system.

In a further preferred embodiment of the invention, $R^1$ is the same or different at each instance and is selected from the group consisting of H, D, F, CN, $OR^2$, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may in each case be substituted by one or more $R^2$ radicals, and where one or more nonadjacent $CH_2$ groups may be replaced by O, or an aromatic or heteroaromatic ring system which has 6 to 30 aromatic ring atoms and may be substituted in each case by one or more $R^2$ radicals; at the same time, two or more $R^1$ radicals together may form an aliphatic ring system. In a particularly preferred embodiment of the invention, $R^1$ is the same or different at each instance and is selected from the group consisting of H, a straight-chain alkyl group having 1 to 6 carbon atoms, especially having 1, 2, 3 or 4 carbon atoms, or a branched or cyclic alkyl group having 3 to 6 carbon atoms, where the alkyl group may be substituted by one or more $R^2$ radicals, but is preferably unsubstituted, or an aromatic or heteroaromatic ring system which has 6 to 24 aromatic ring atoms and may be substituted in each case by one or more $R^2$ radicals, but is preferably unsubstituted.

In a further preferred embodiment of the invention, $R^2$ is the same or different at each instance and is H, F, an alkyl group having 1 to 4 carbon atoms or an aryl group having 6 to 10 carbon atoms, which may be substituted by an alkyl group having 1 to 4 carbon atoms, but is preferably unsubstituted.

The abovementioned preferences can occur individually or together. It is preferable when the abovementioned preferences occur together.

Examples of suitable compounds of the invention are the structures depicted below:

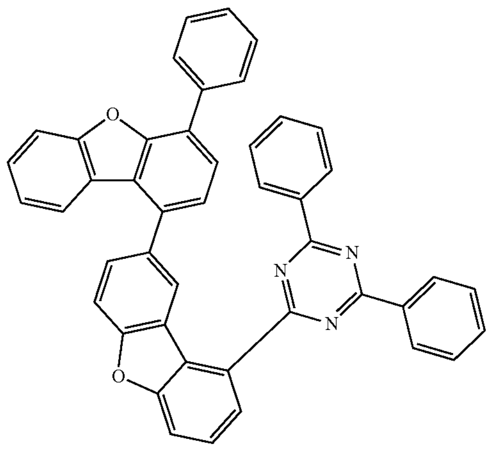

-continued
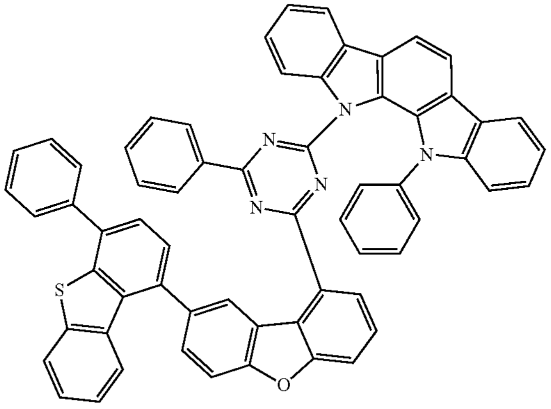
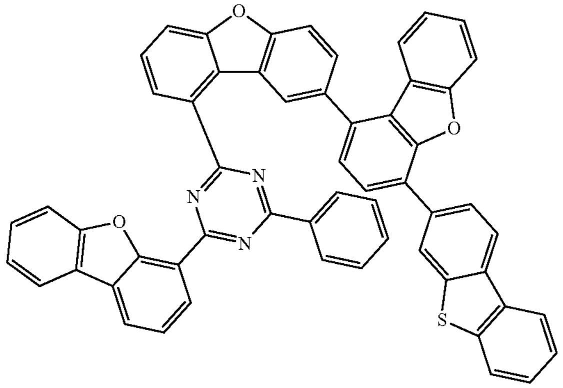
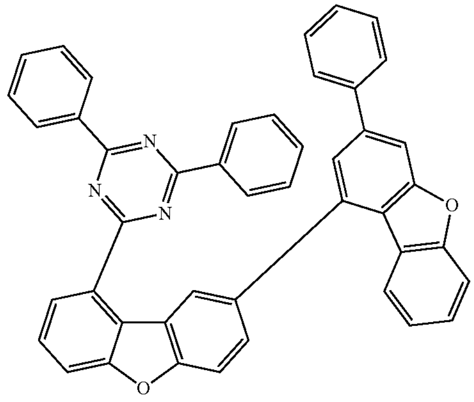
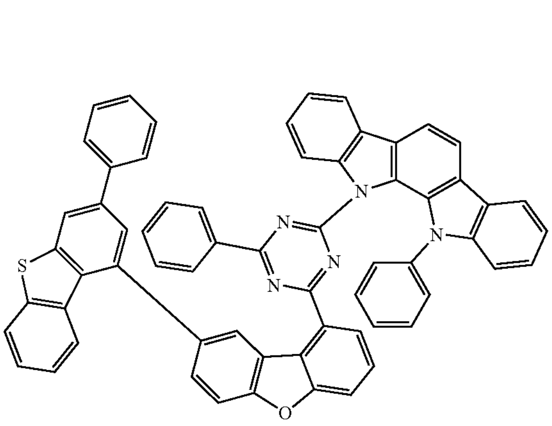
-continued
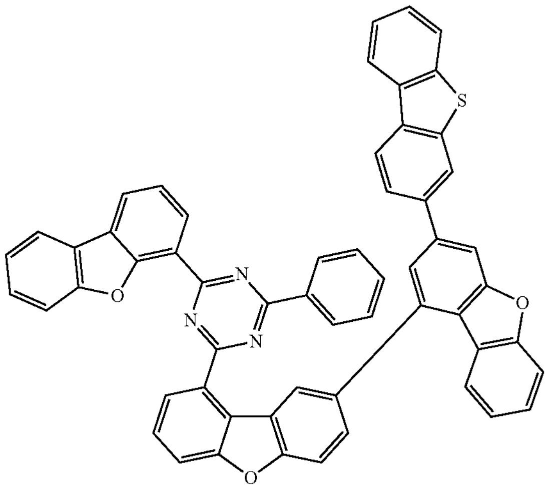
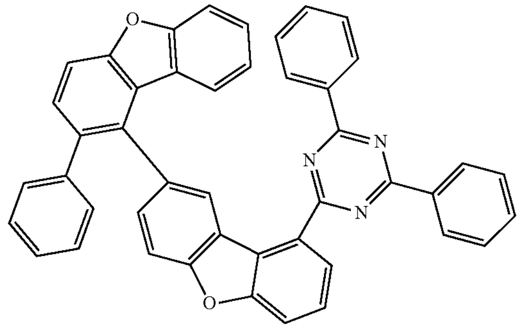
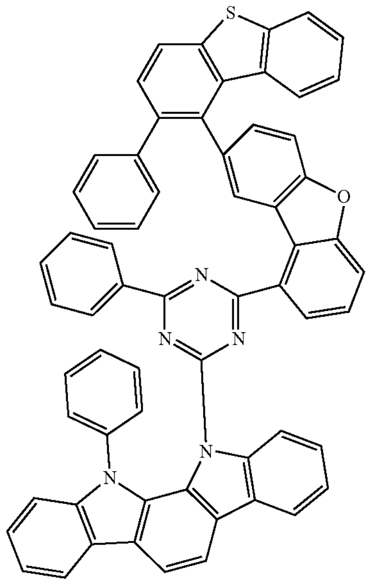

-continued
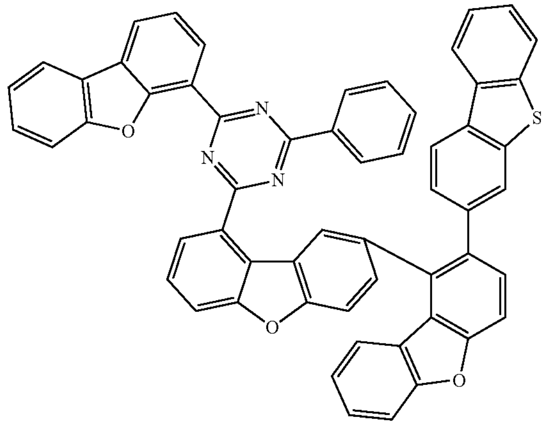
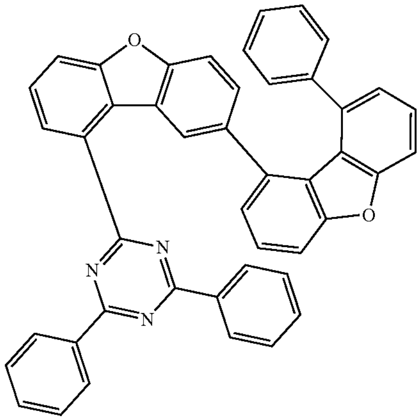
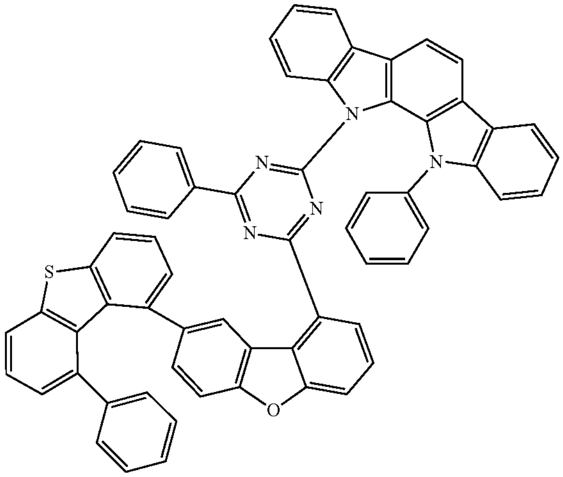
-continued
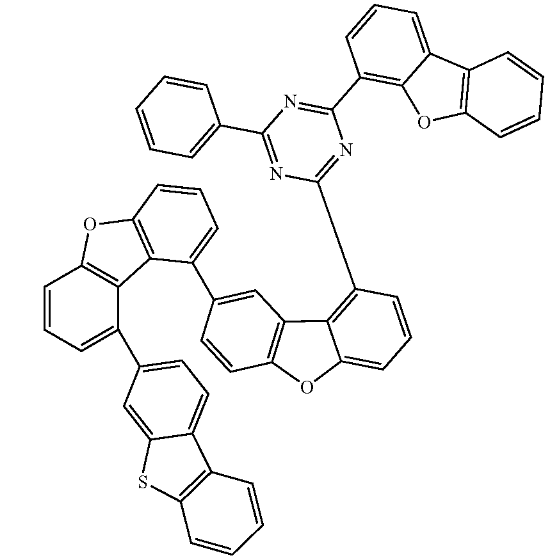
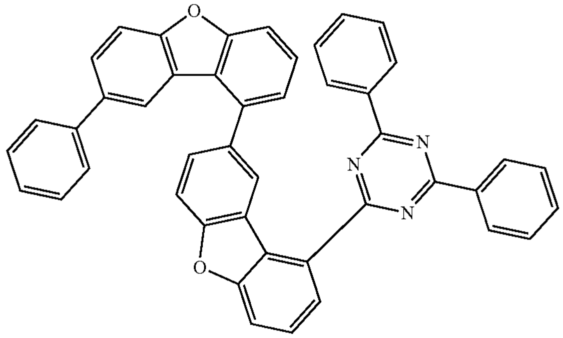
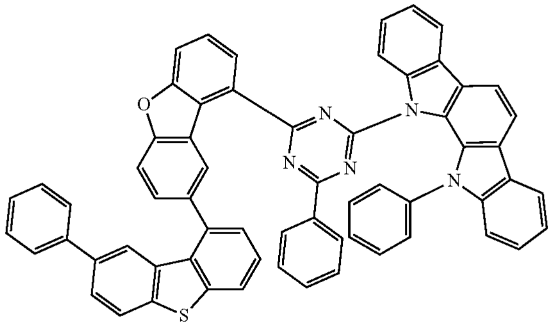
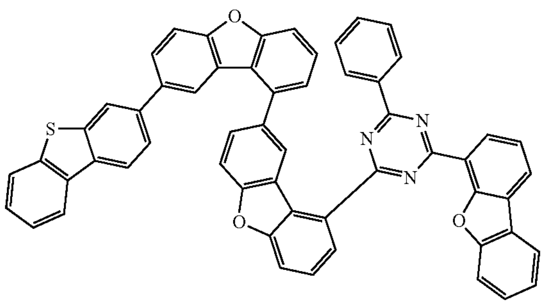

-continued
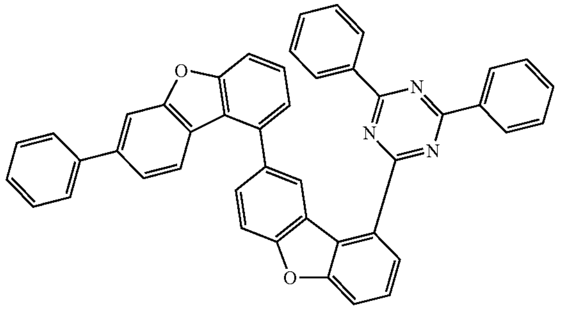
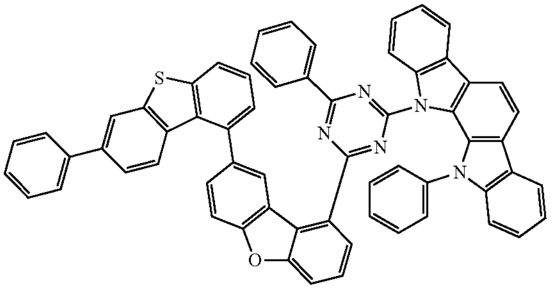
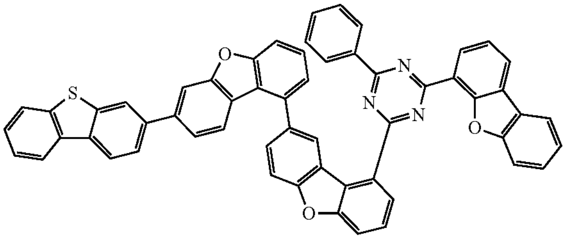
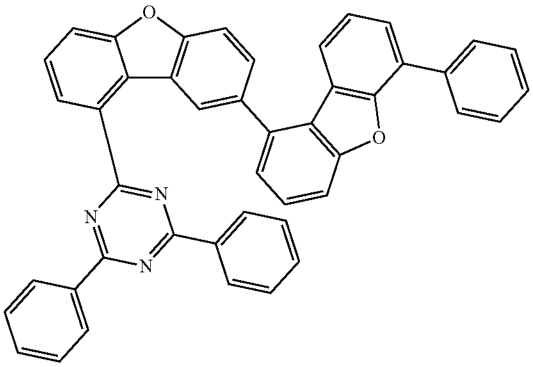
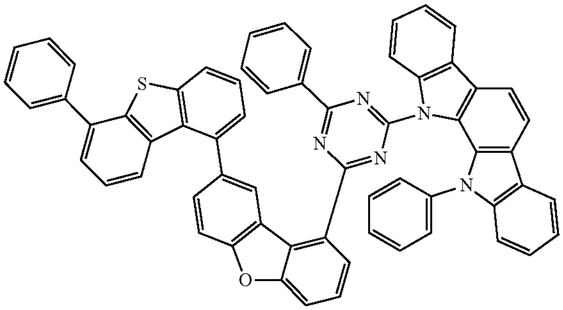
-continued
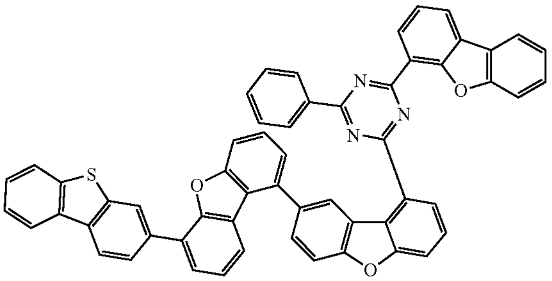
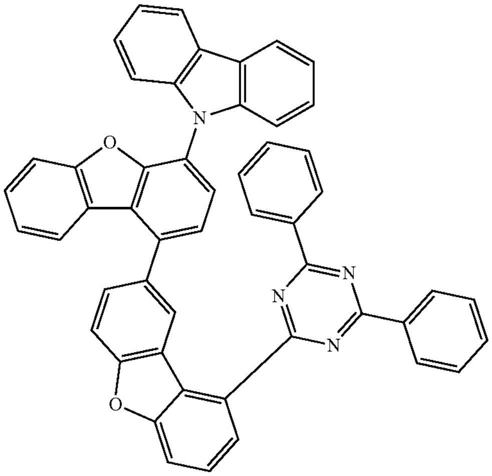
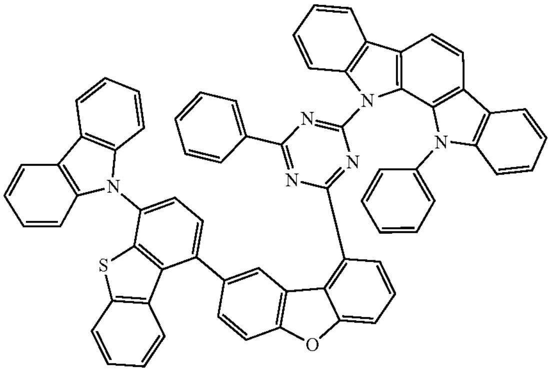
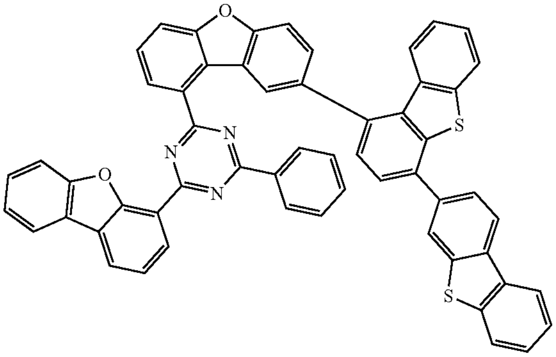

-continued
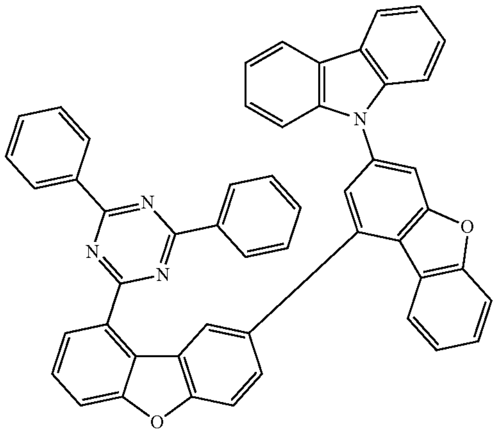
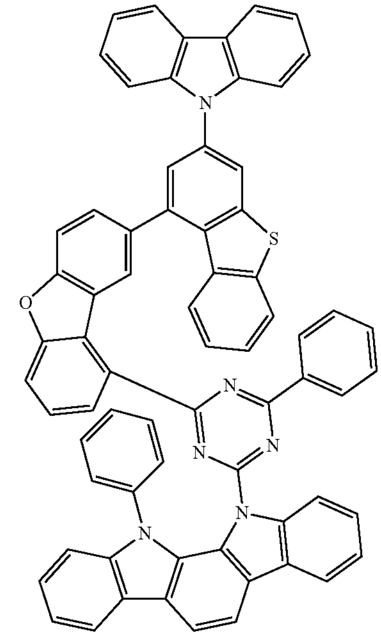
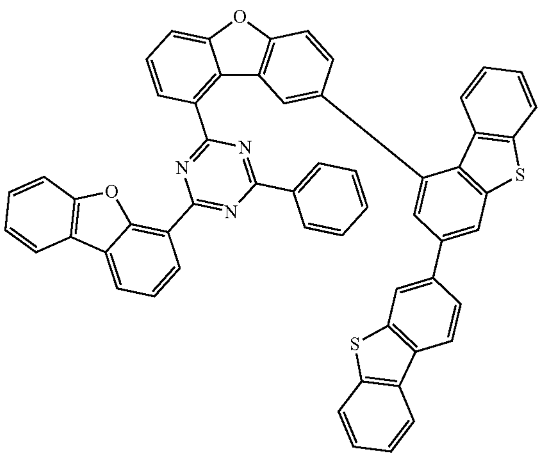
-continued
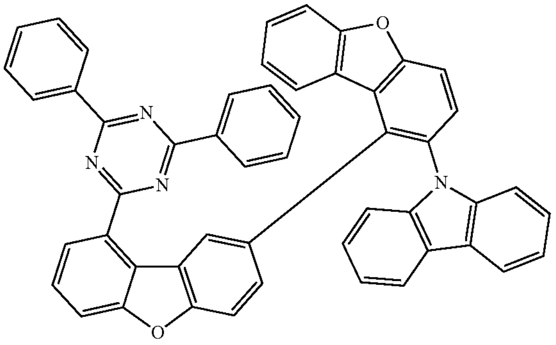
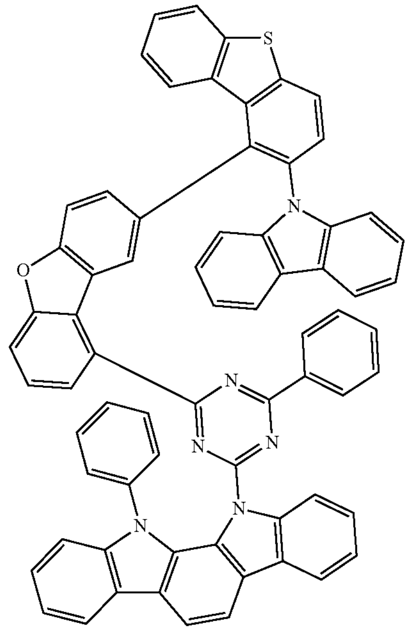
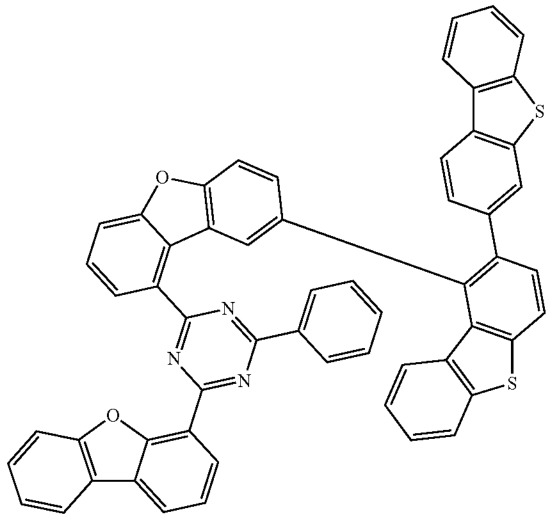

-continued
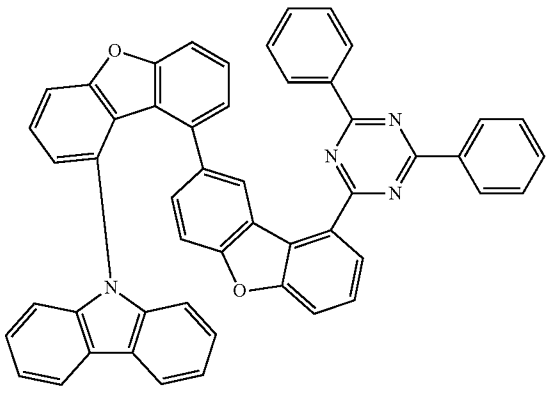
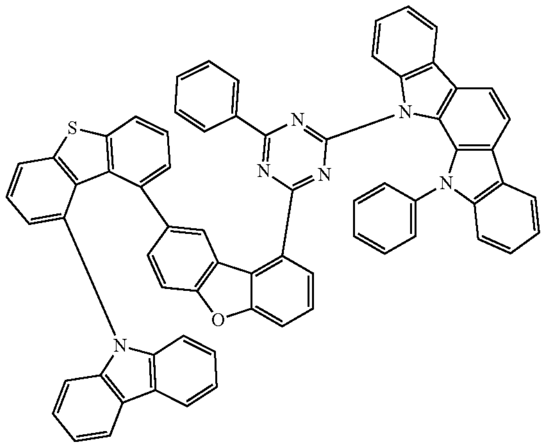
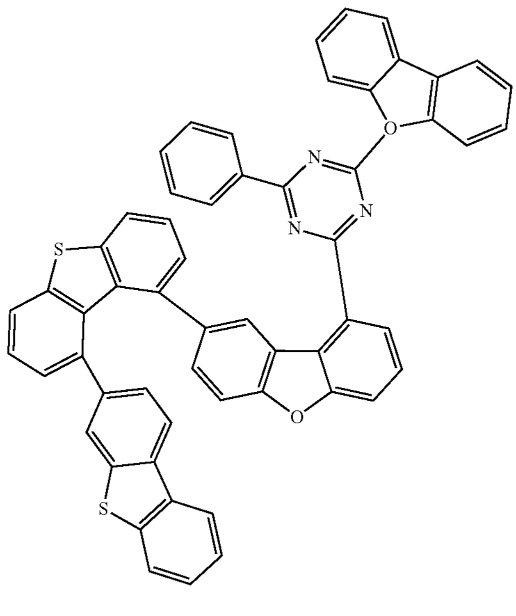
-continued
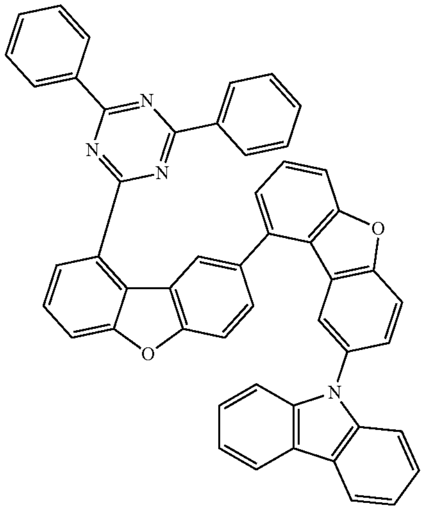
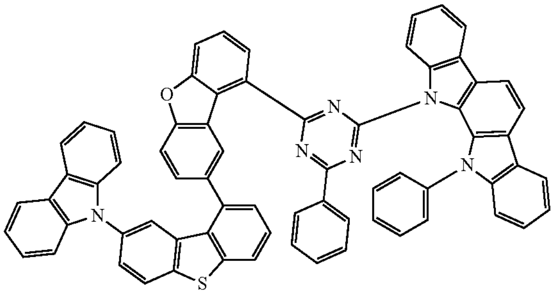
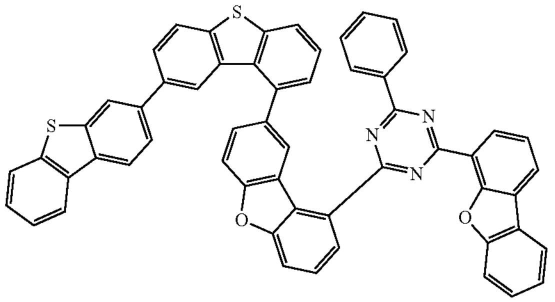
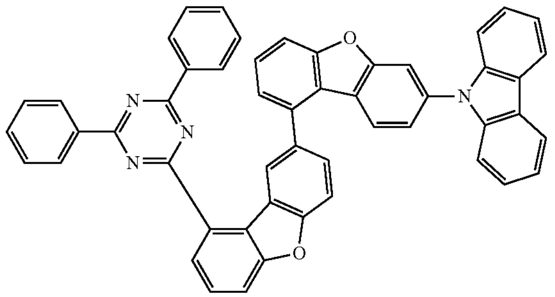
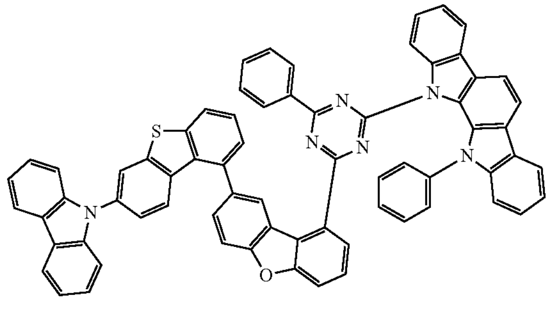

-continued
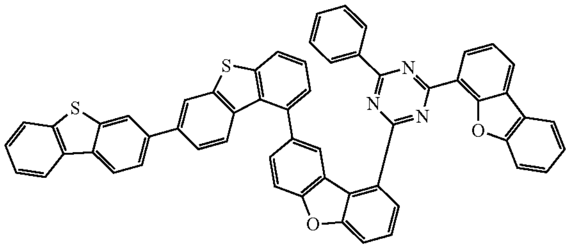
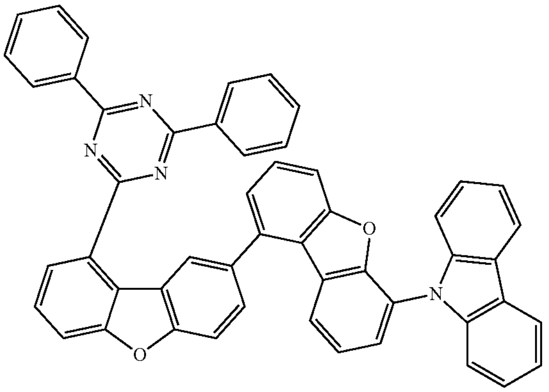
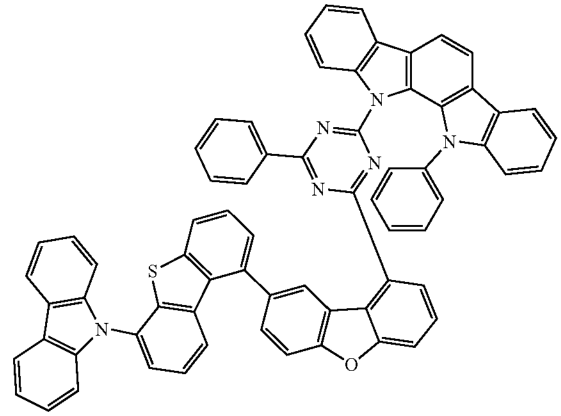
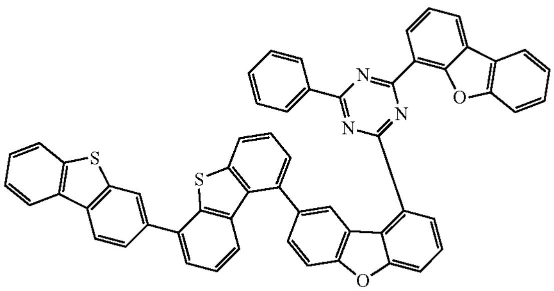
-continued
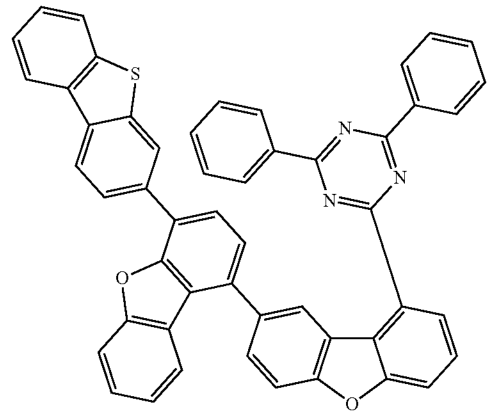
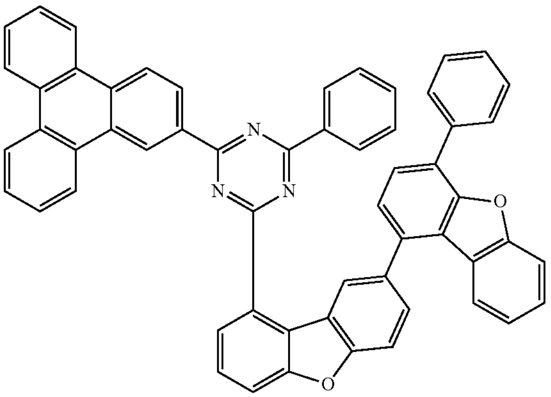
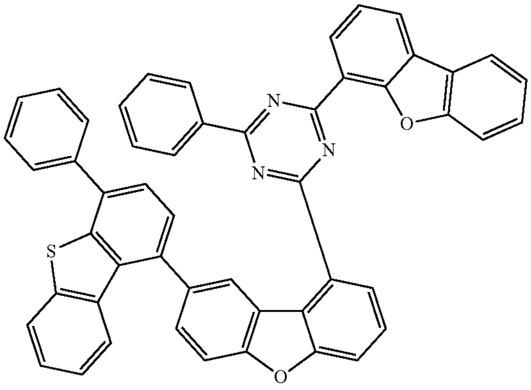
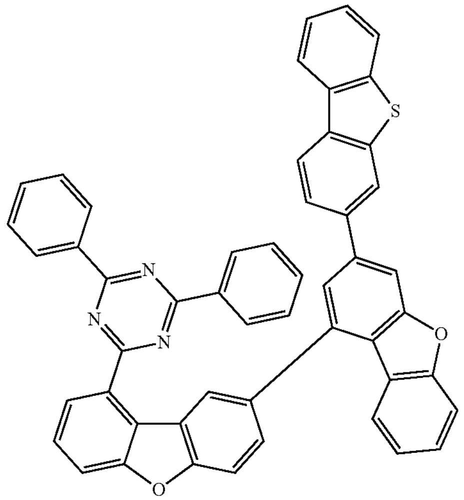

-continued
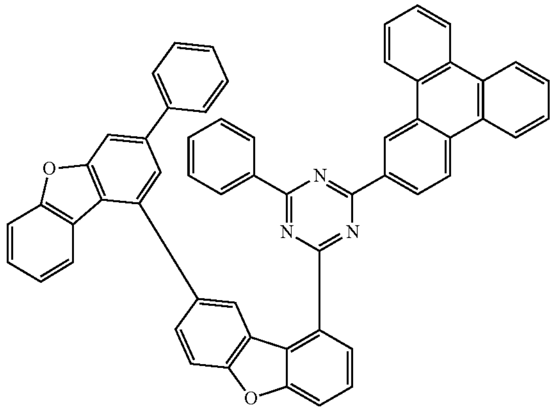
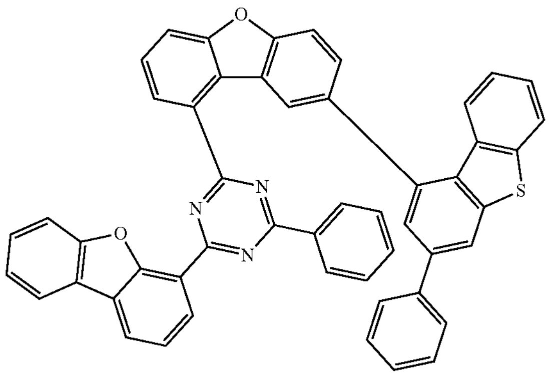
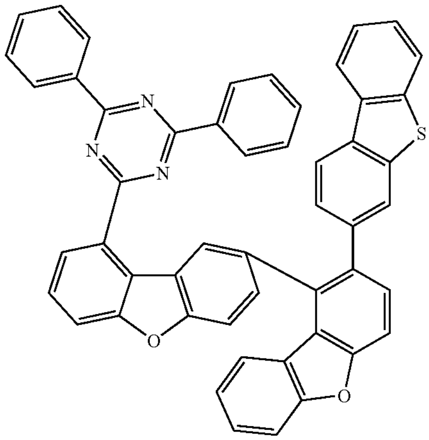
-continued
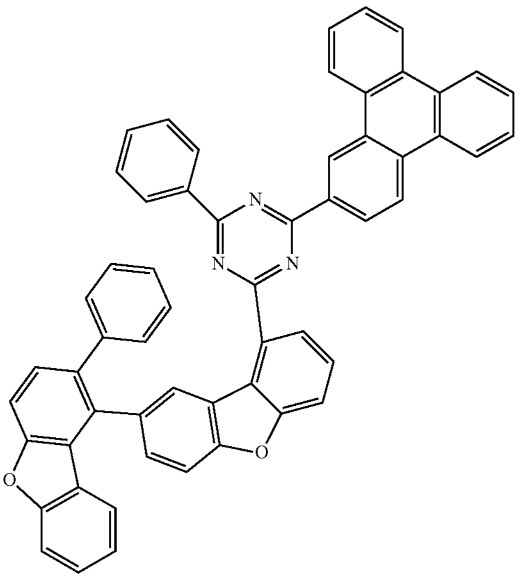
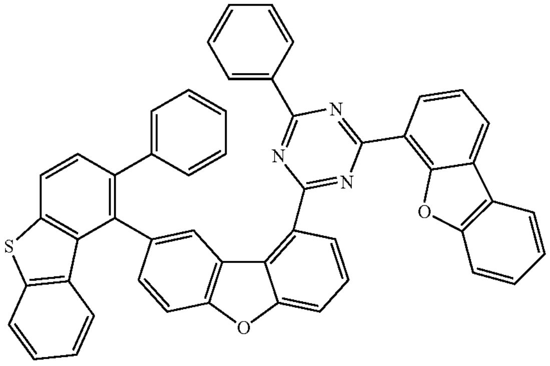
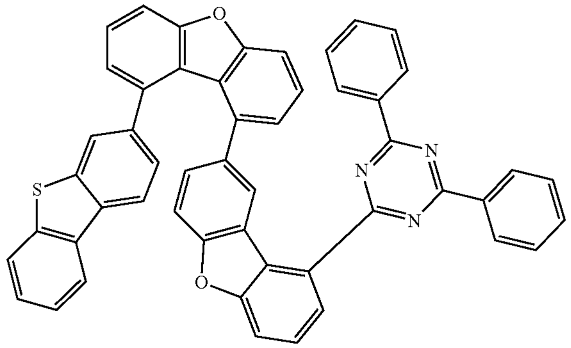
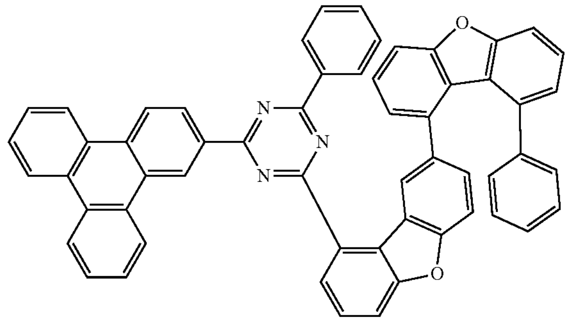

-continued
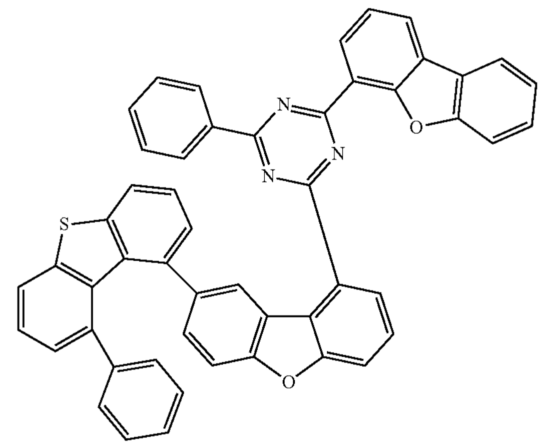
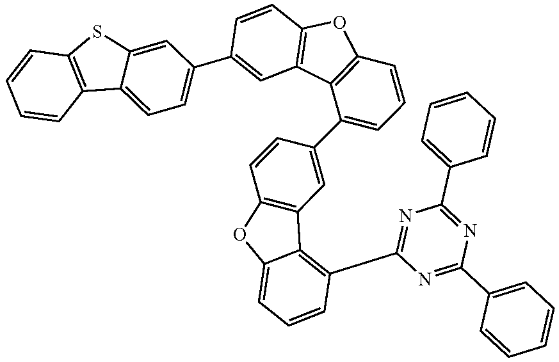
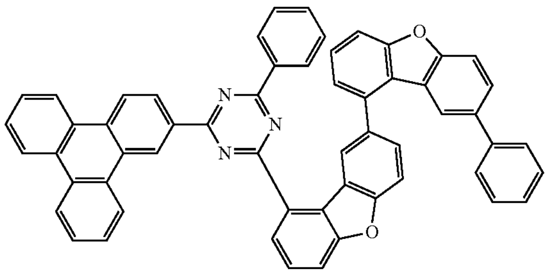
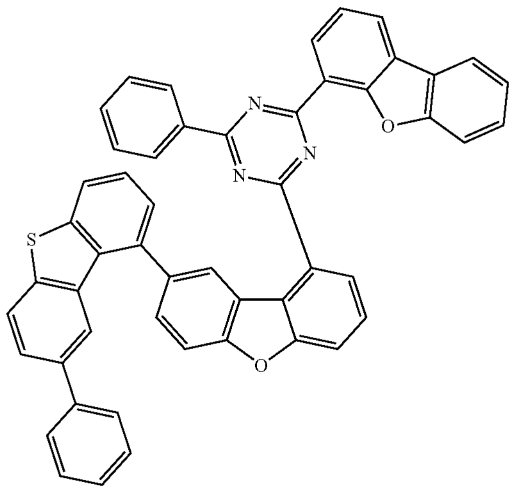
-continued
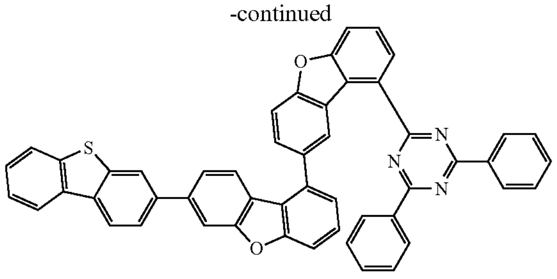
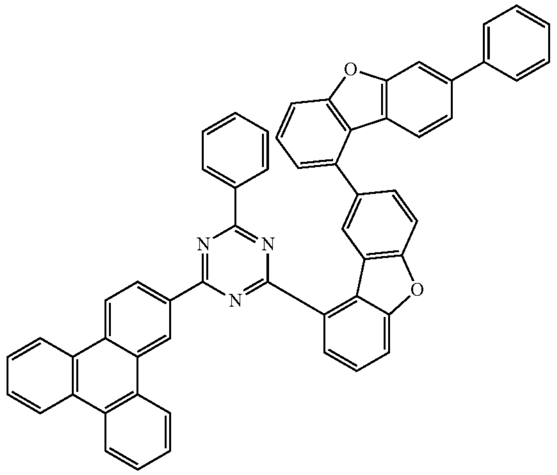
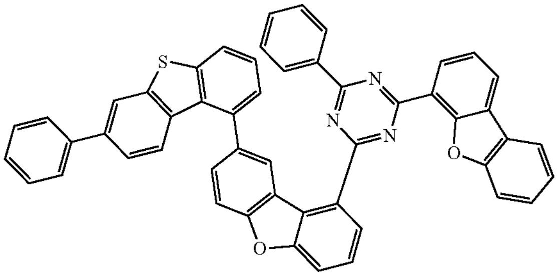
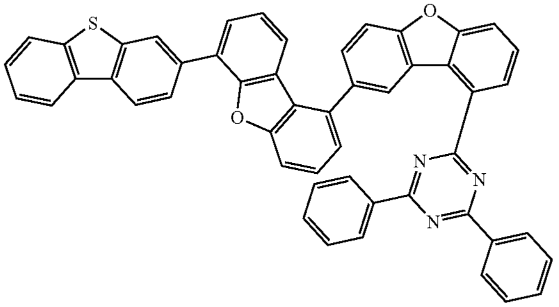

-continued
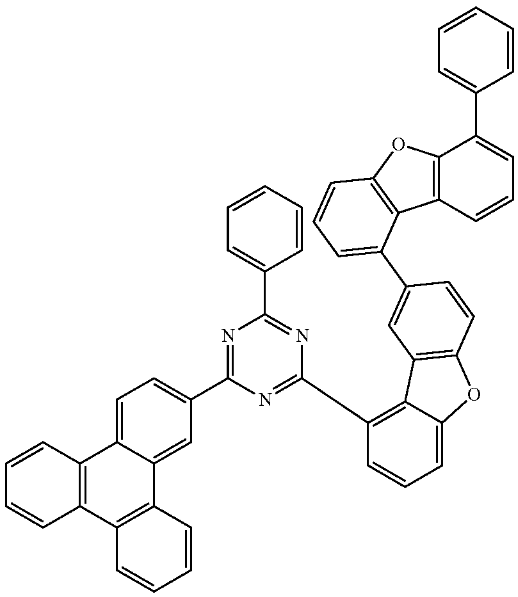
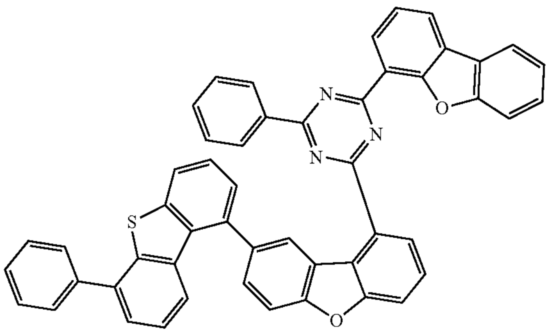
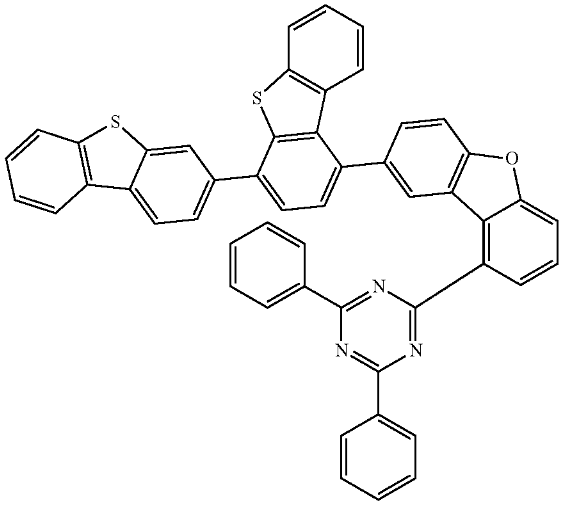
-continued
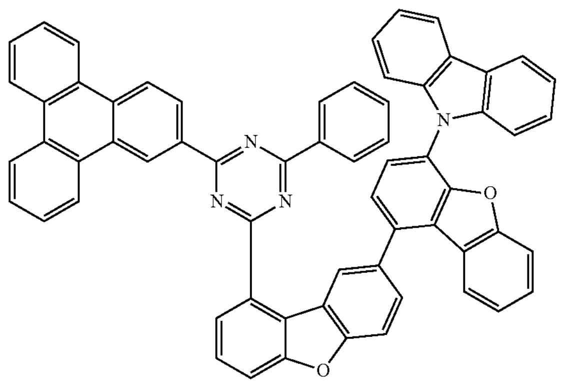
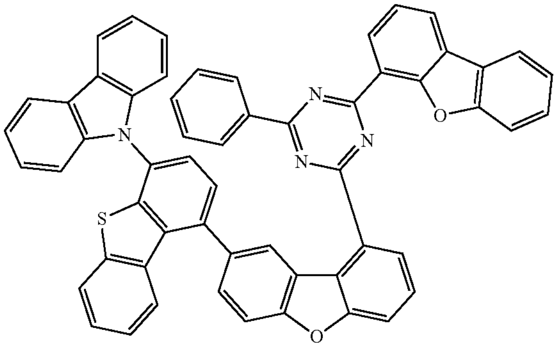
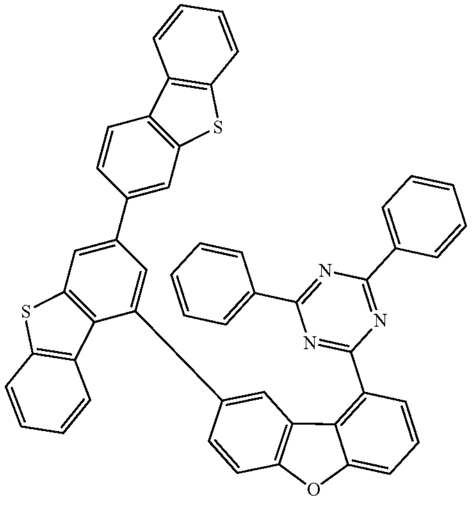
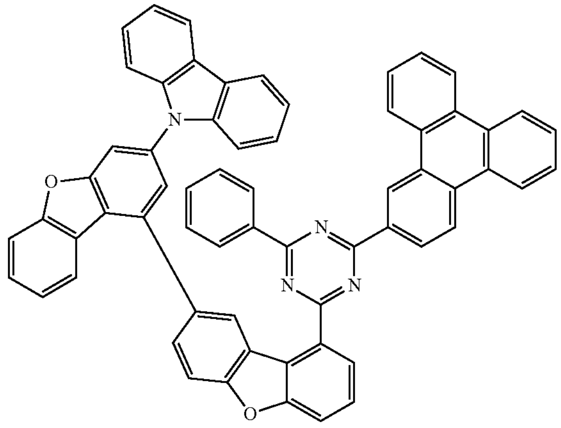

-continued
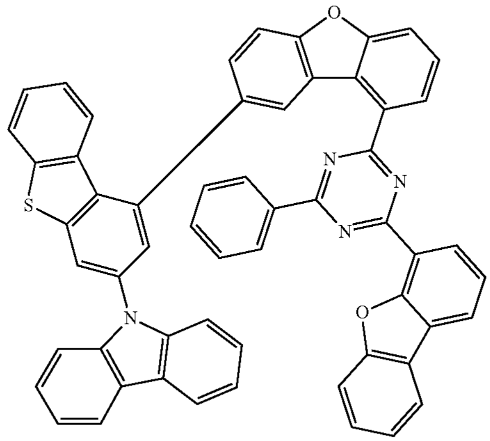
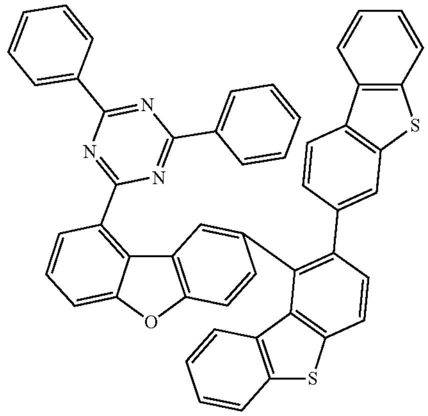
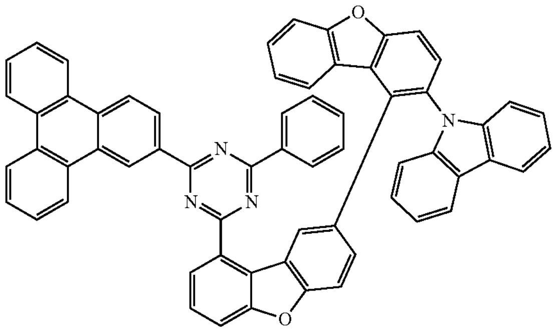
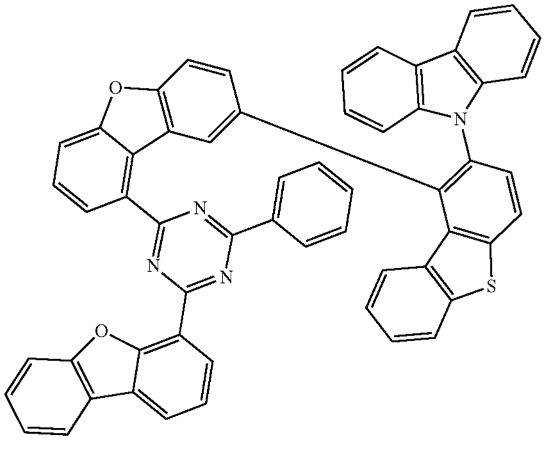
-continued
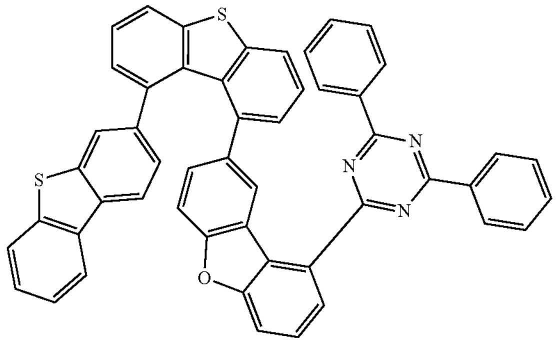
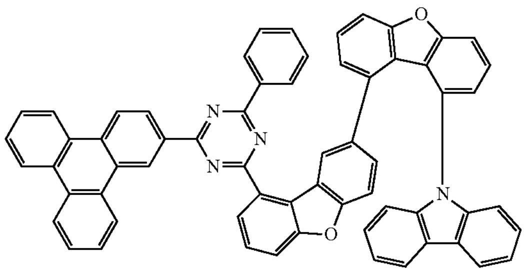
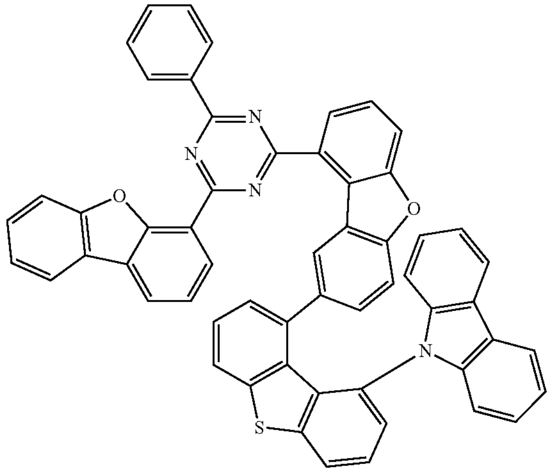
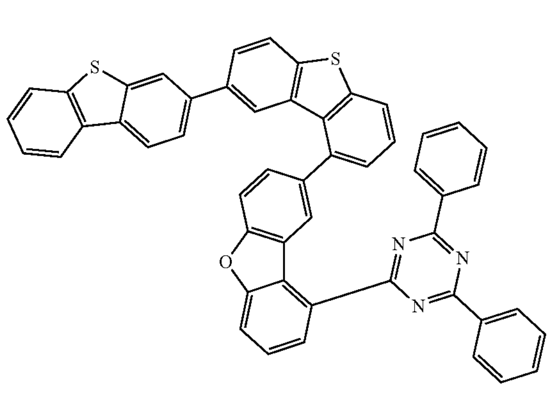

-continued
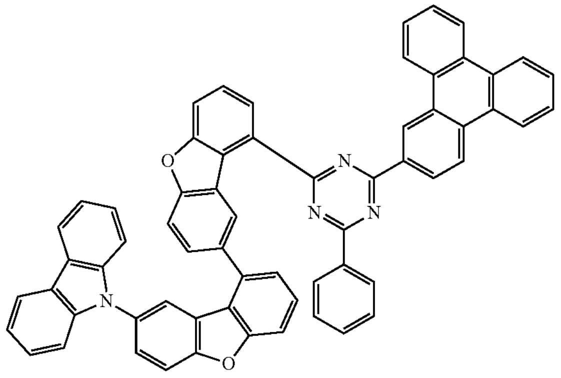
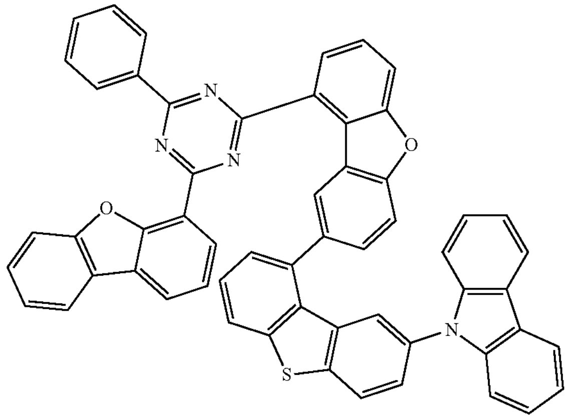
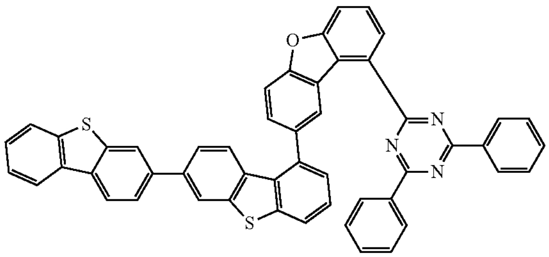
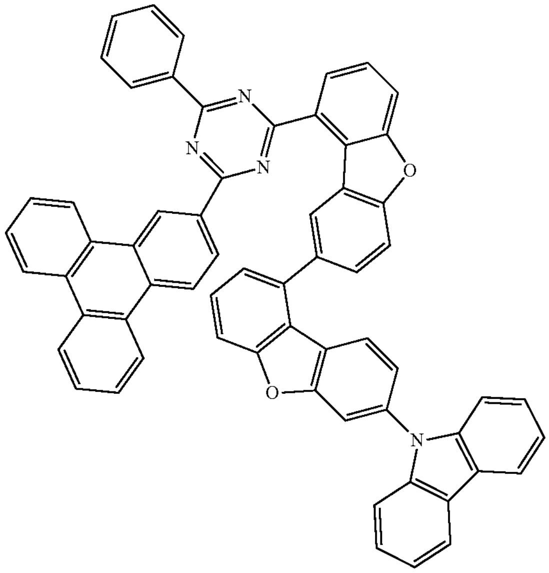
-continued
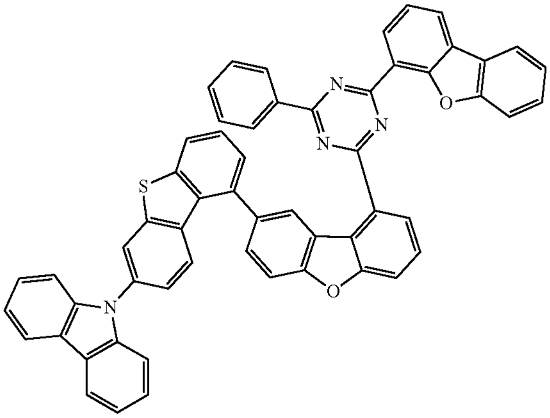
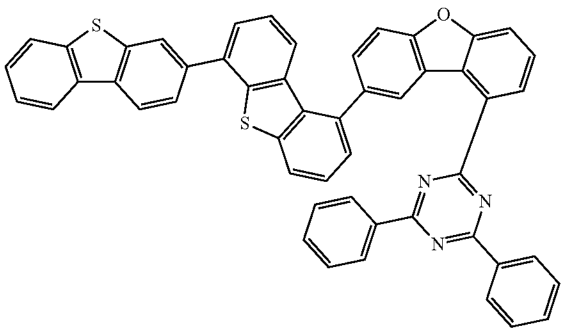
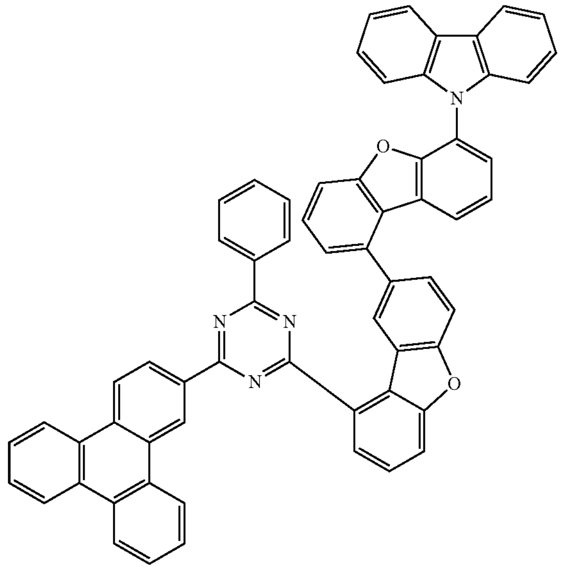
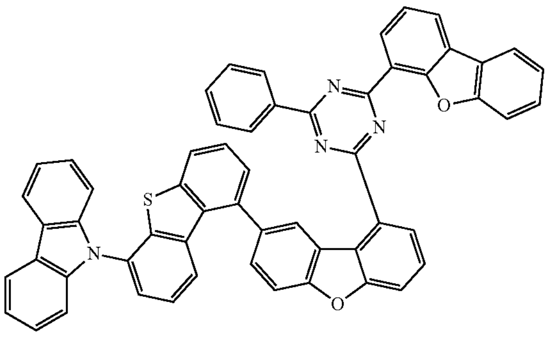

-continued
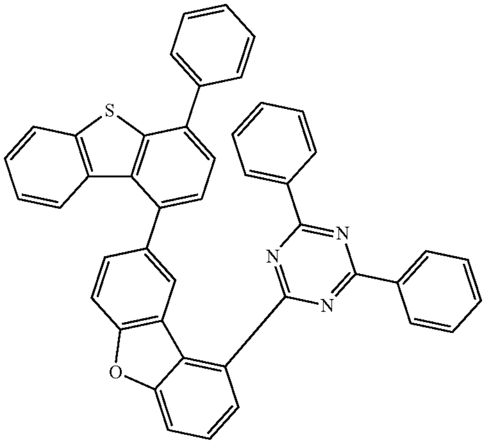
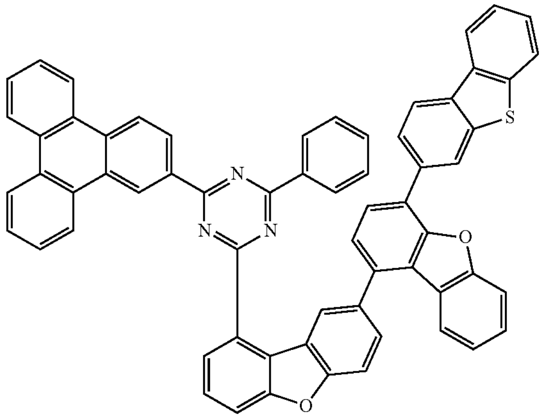
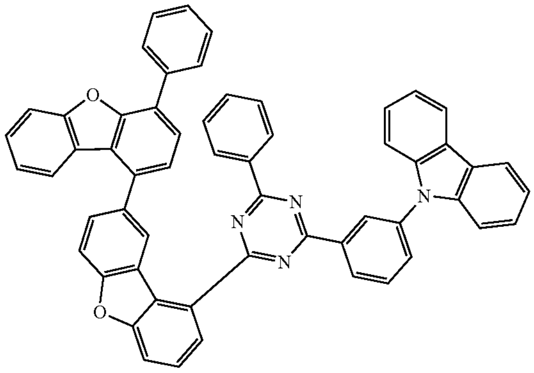
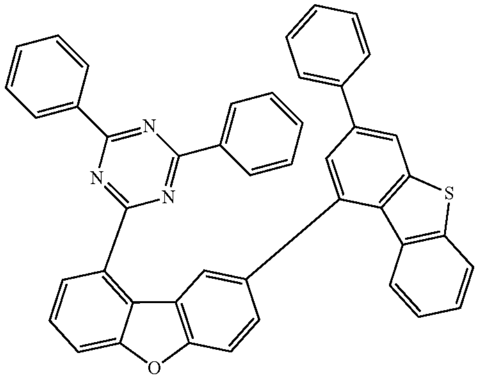
-continued
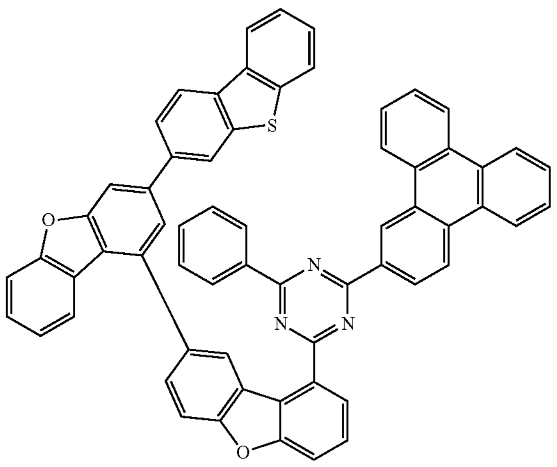
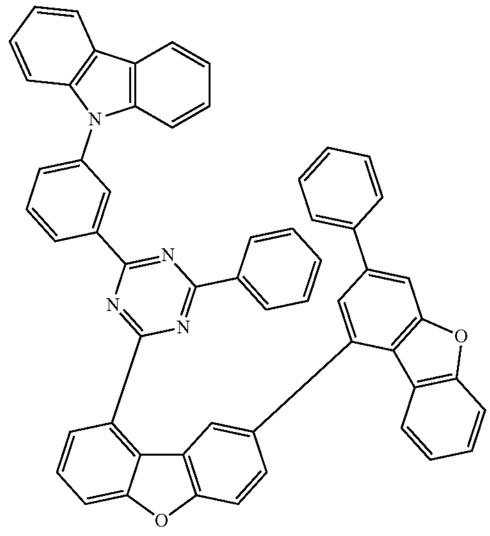
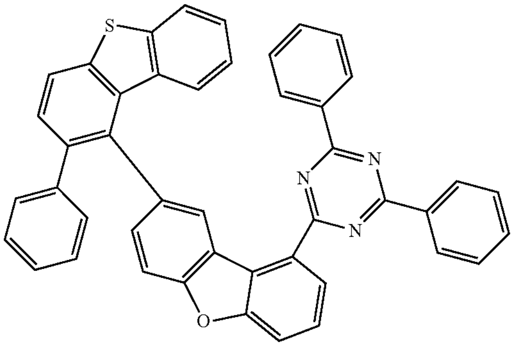

-continued
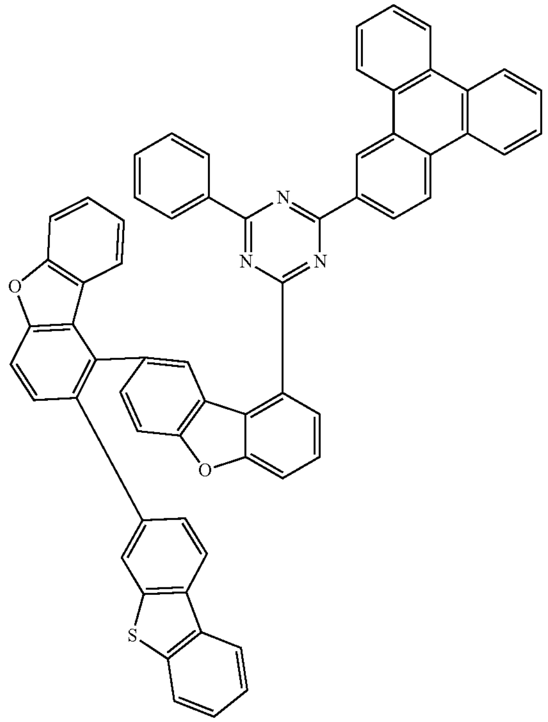
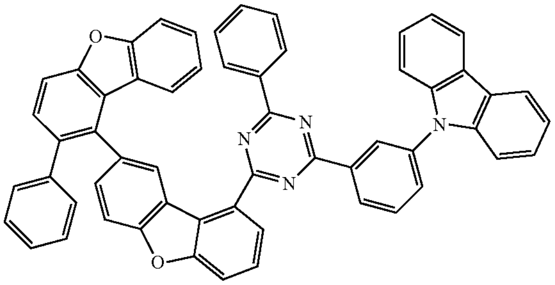
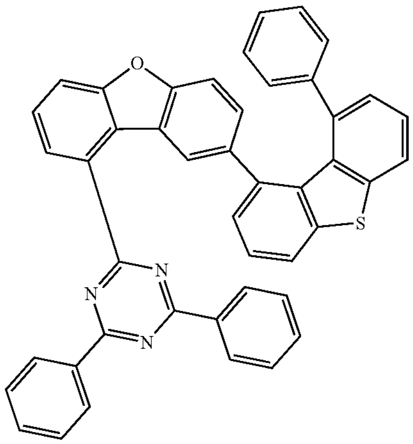
-continued
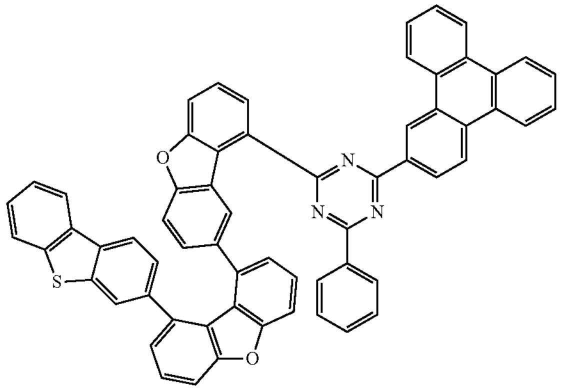
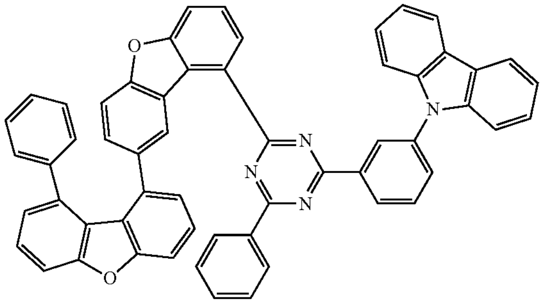
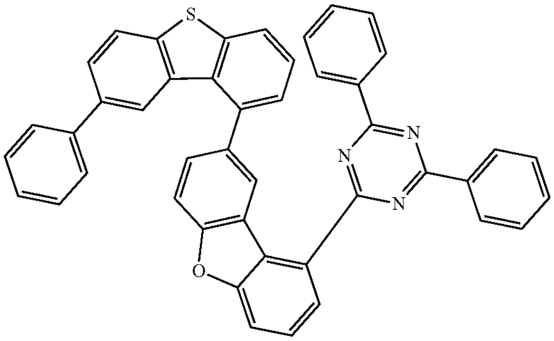
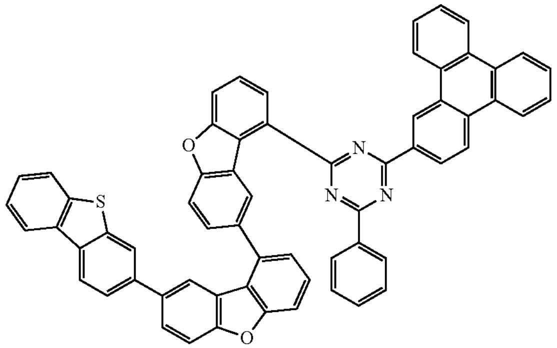
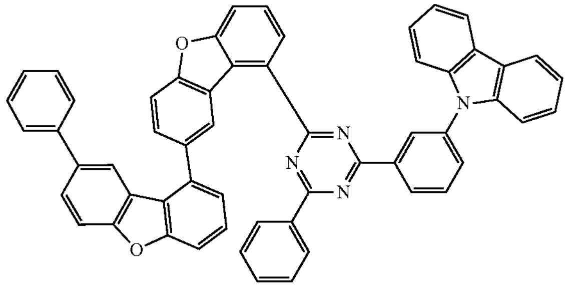

-continued
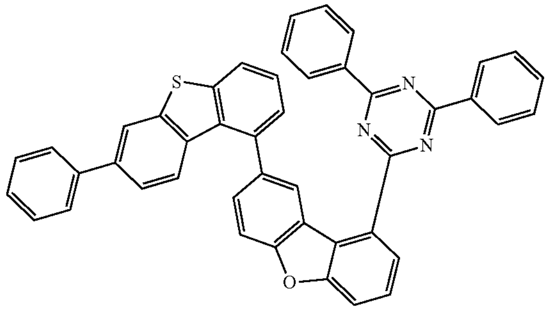
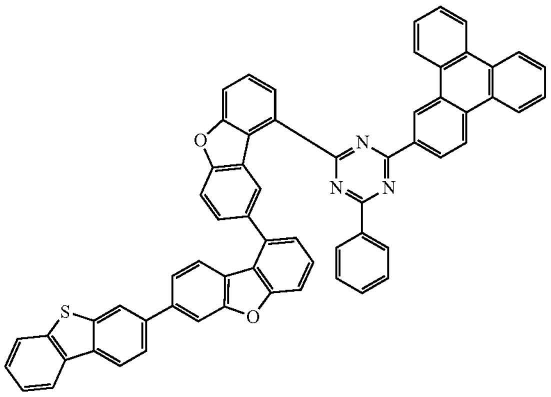
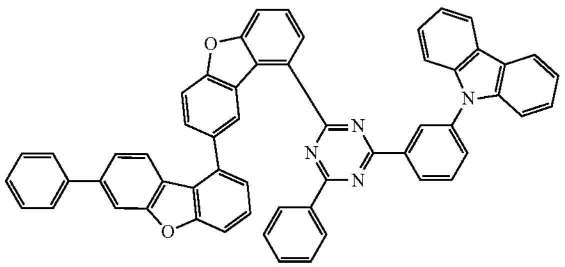
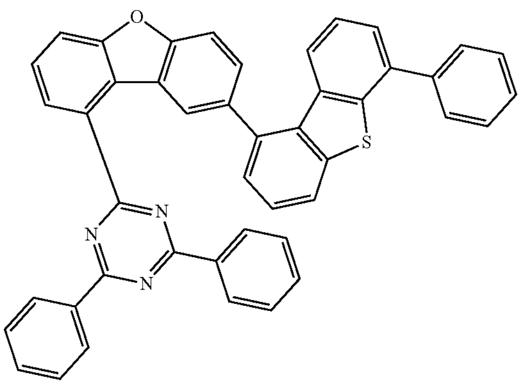
-continued
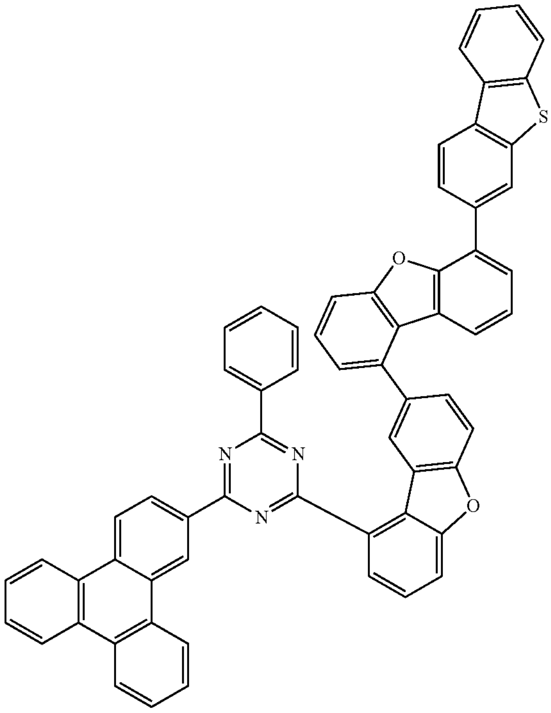
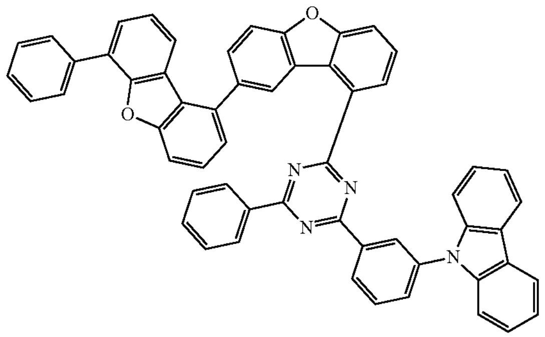
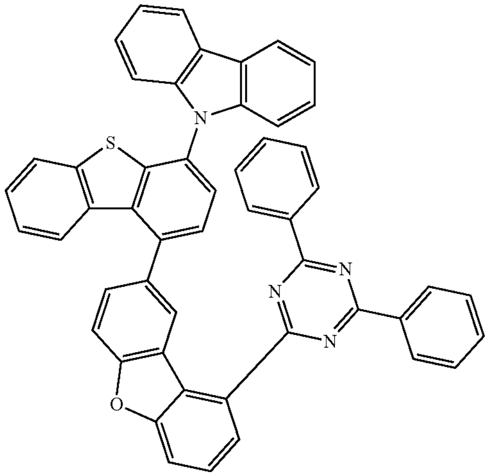

-continued
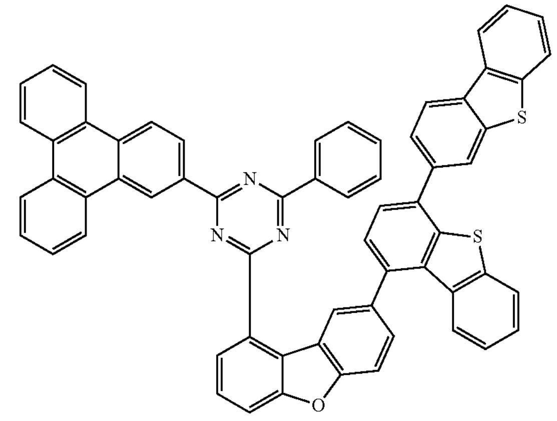
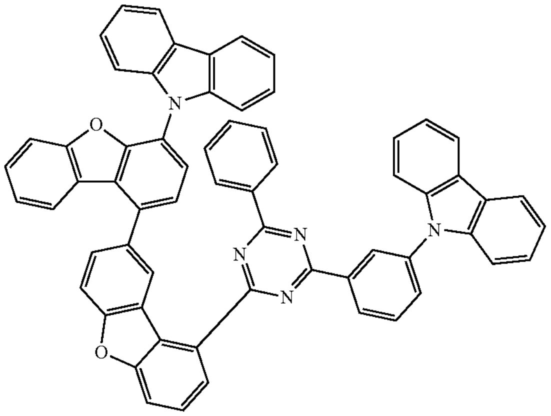
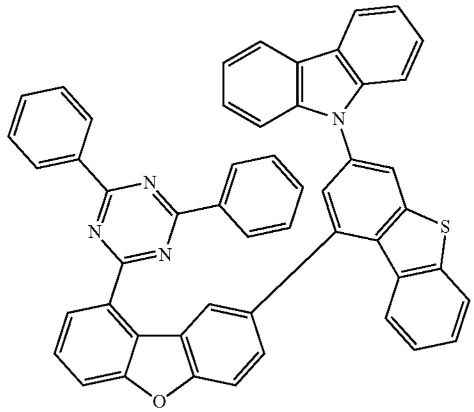
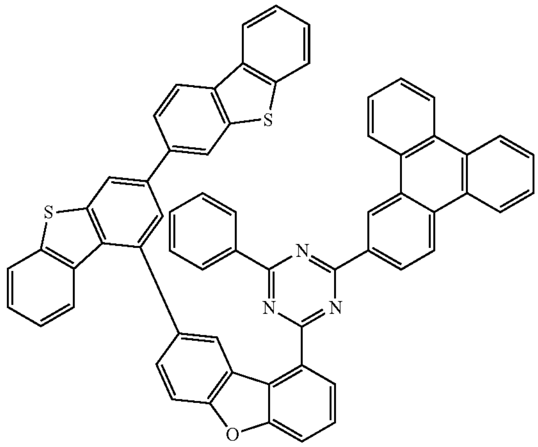
-continued
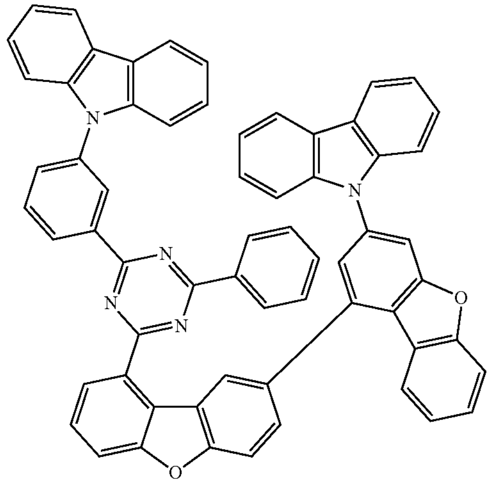
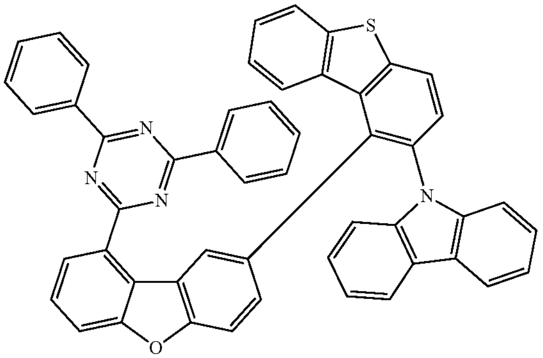
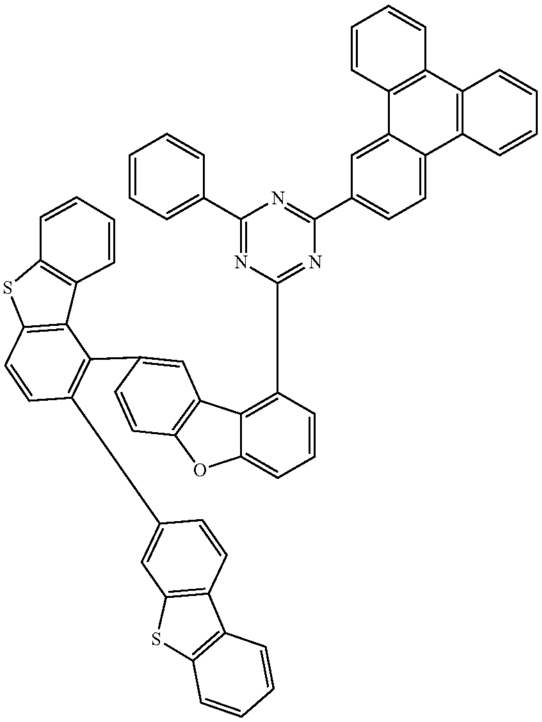

-continued
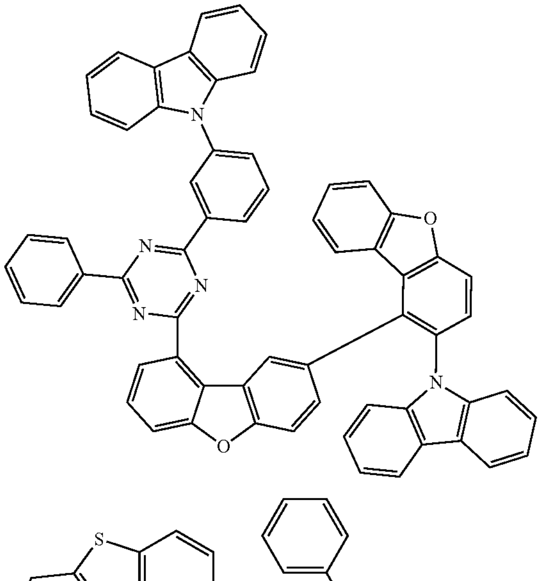
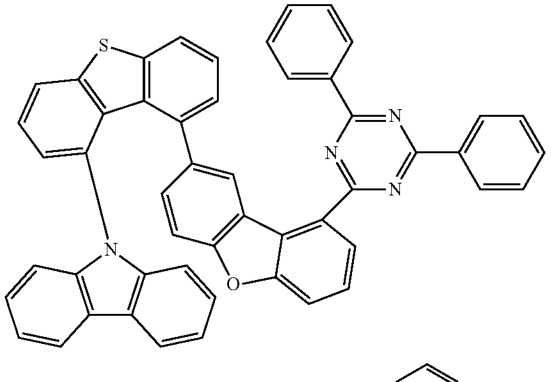
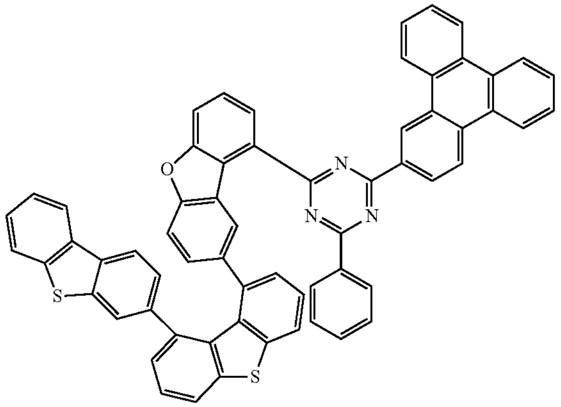
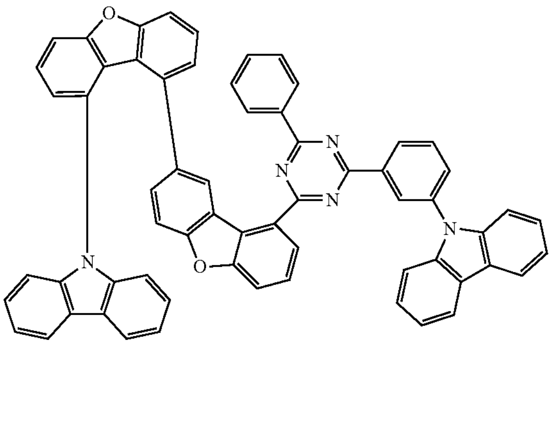
-continued
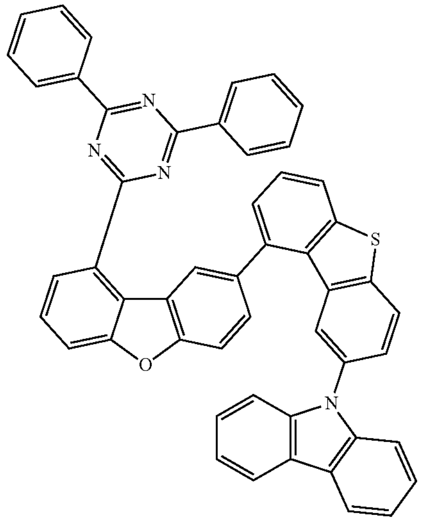
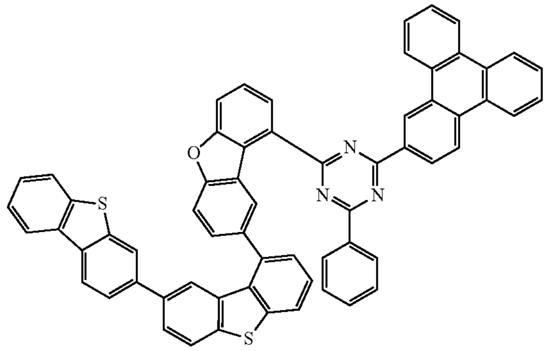
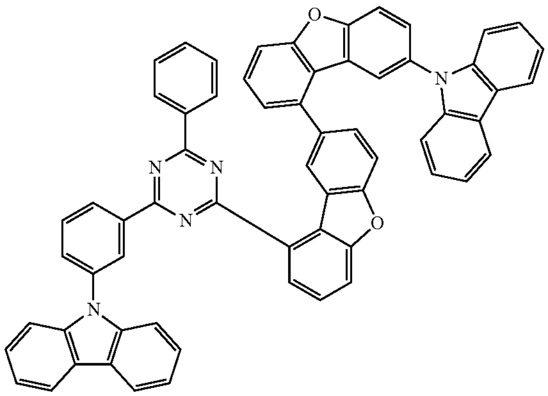
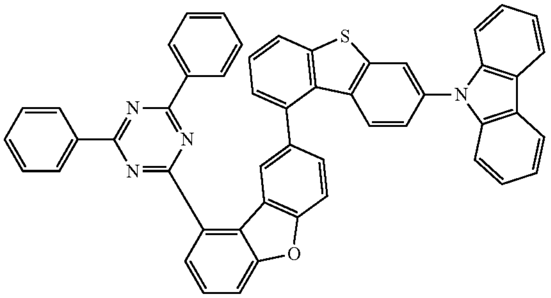

-continued
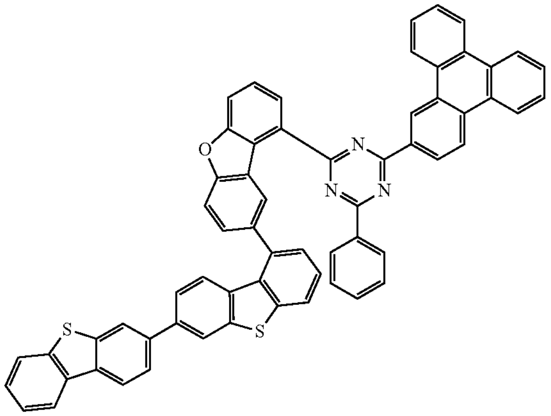
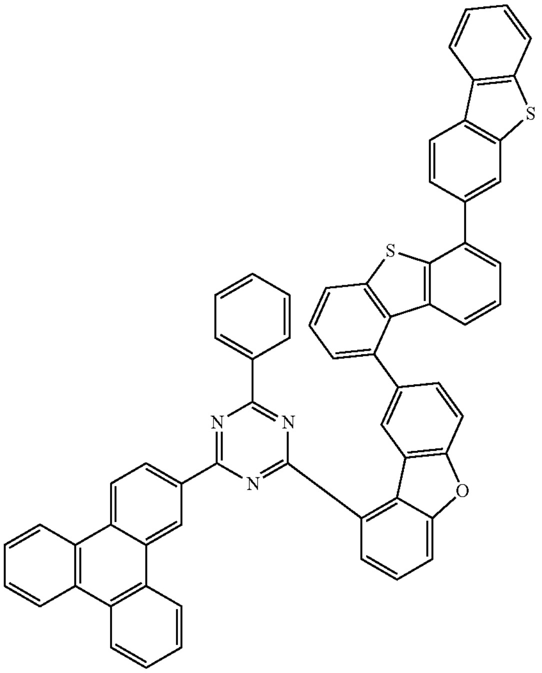
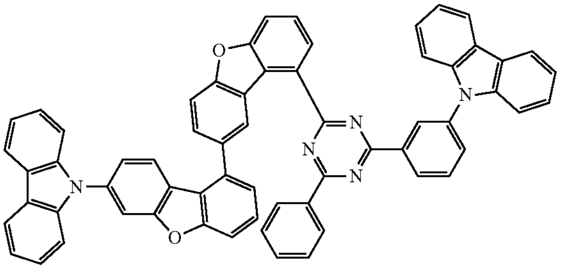
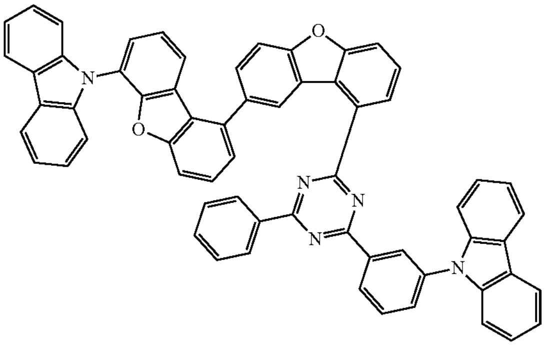
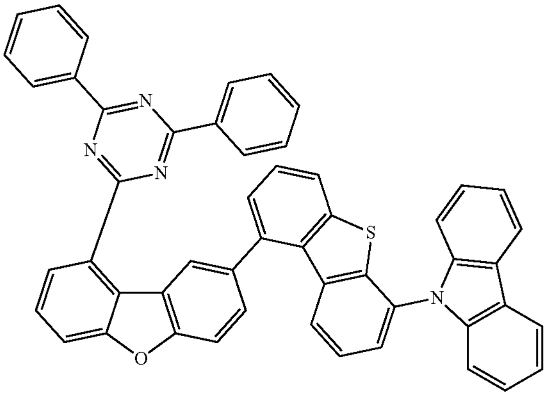
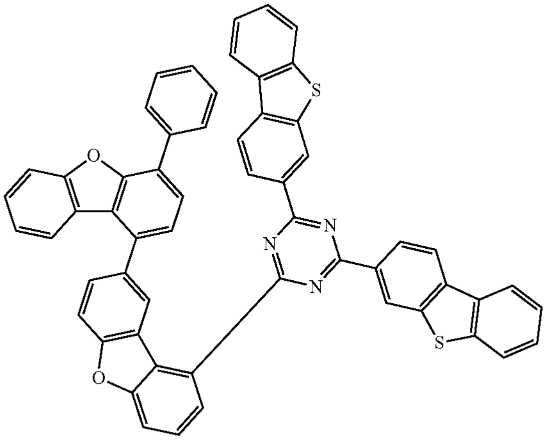
-continued -continued
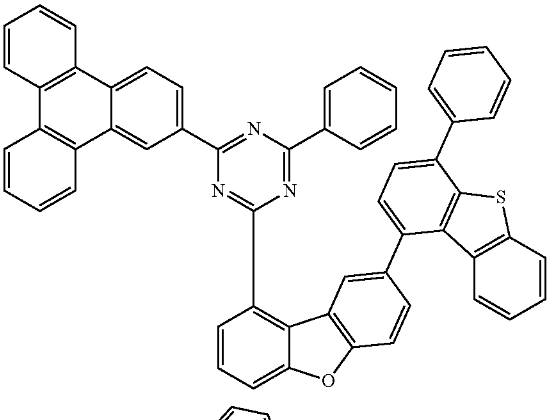
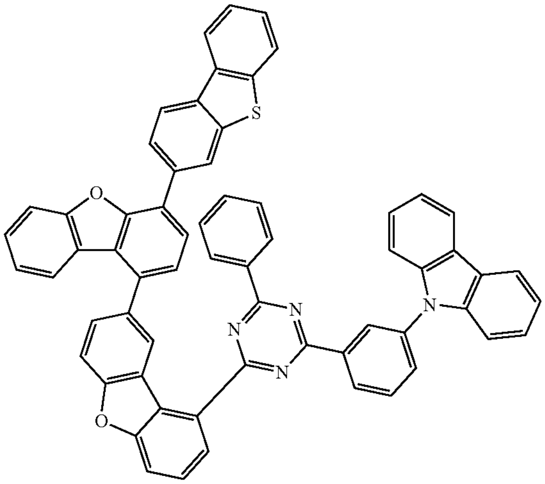
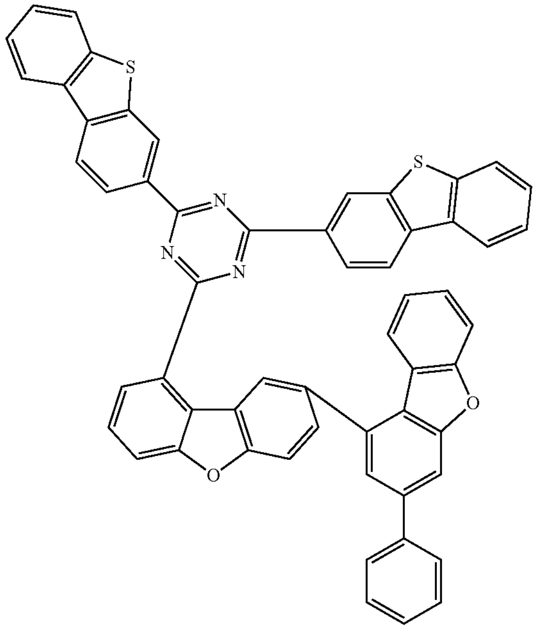
-continued
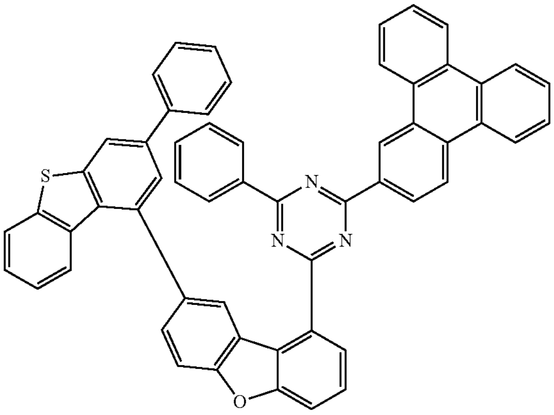
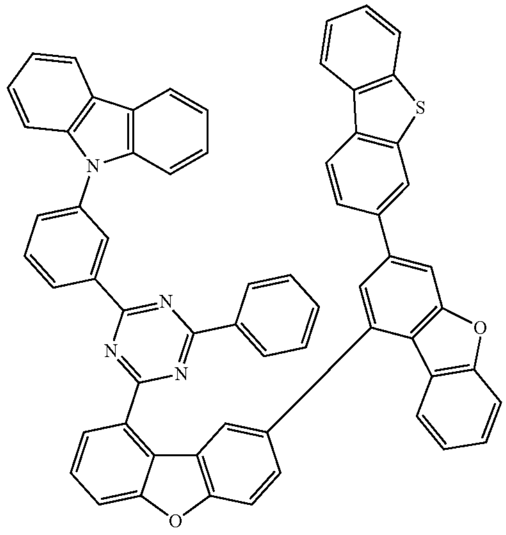
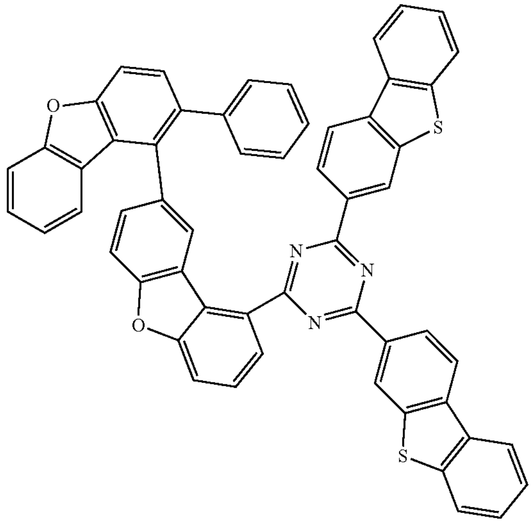

-continued
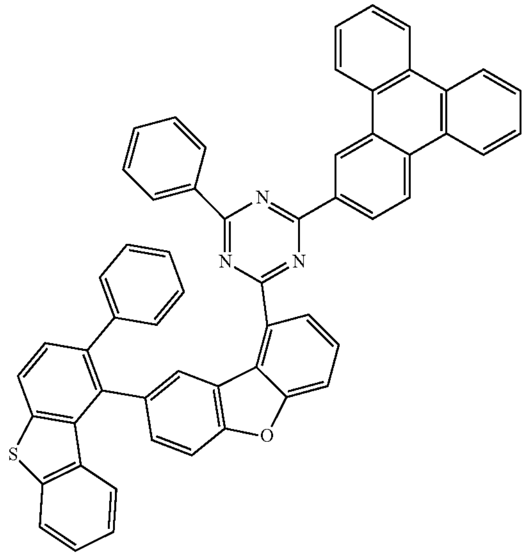
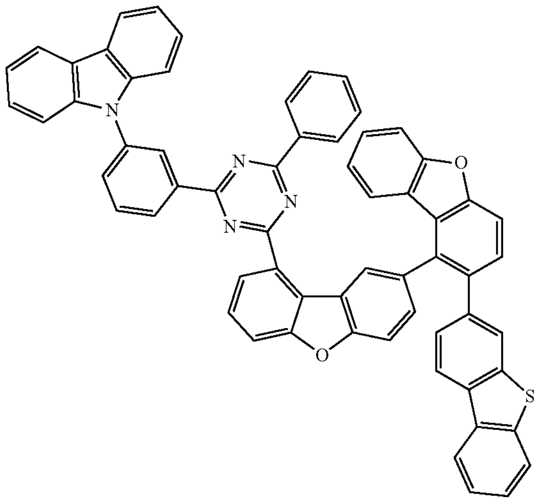
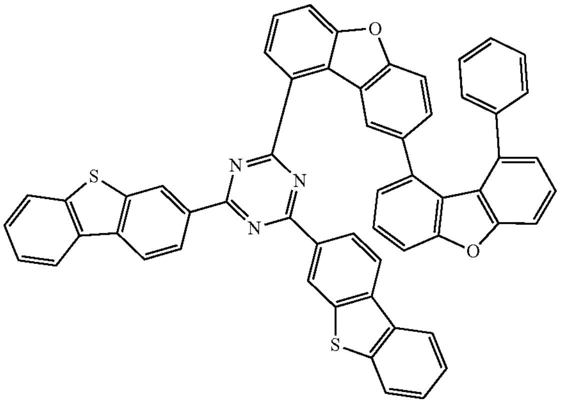
-continued
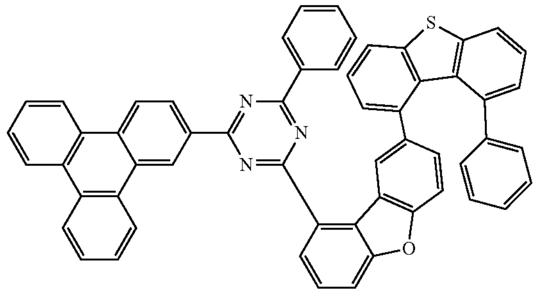
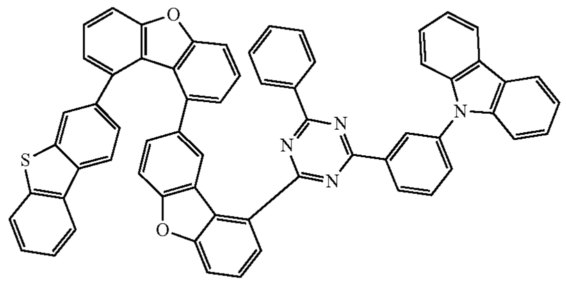
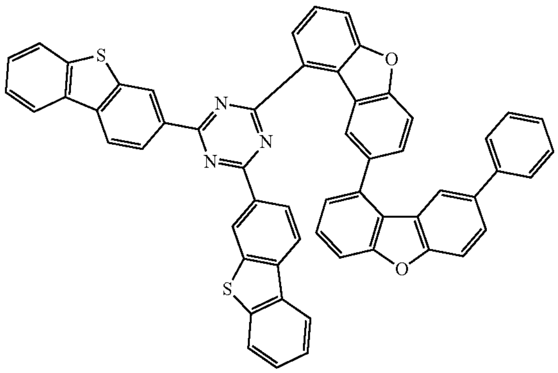
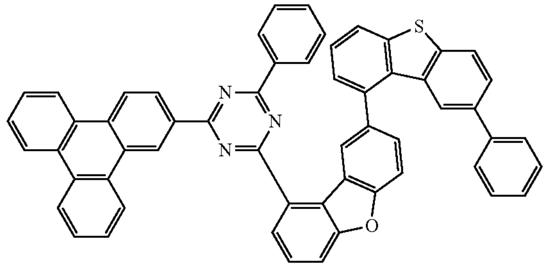
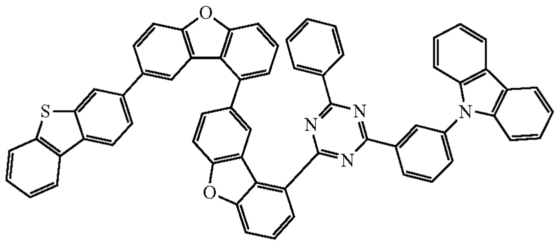

-continued
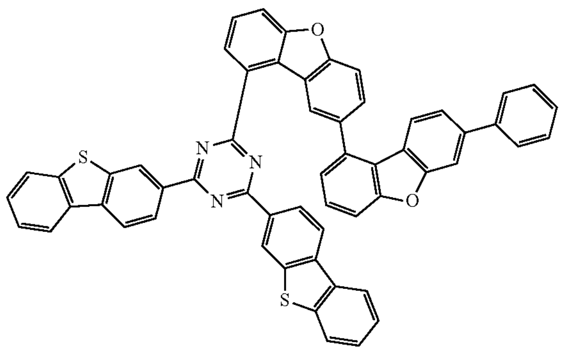
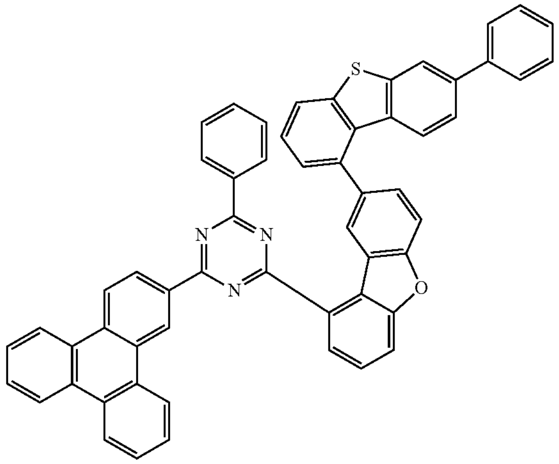
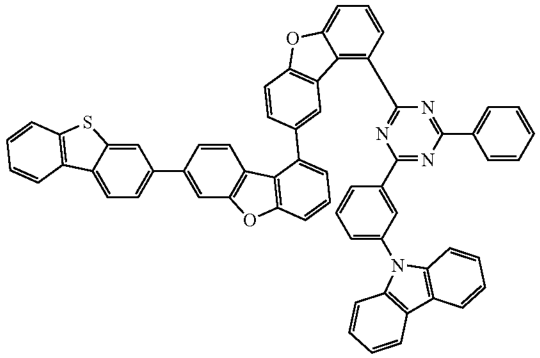
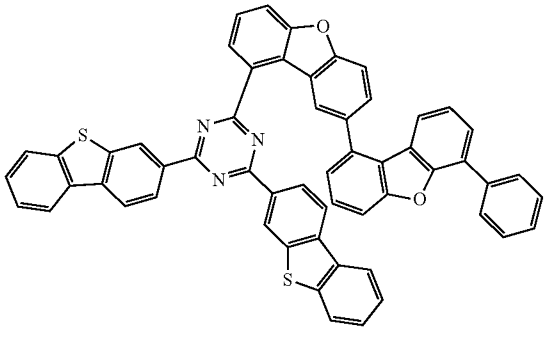
-continued
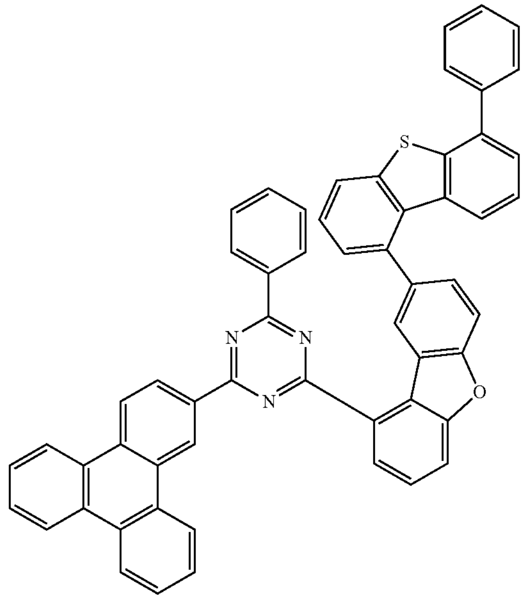
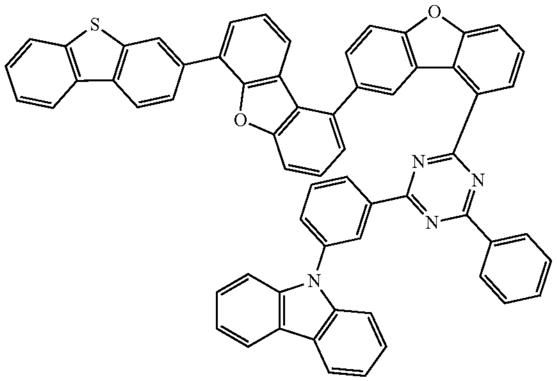
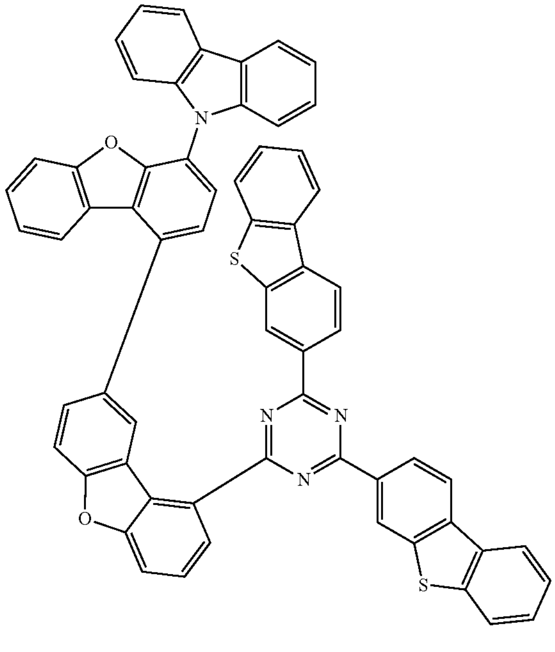

-continued
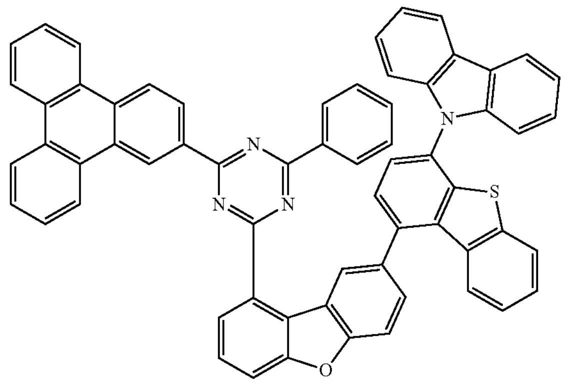
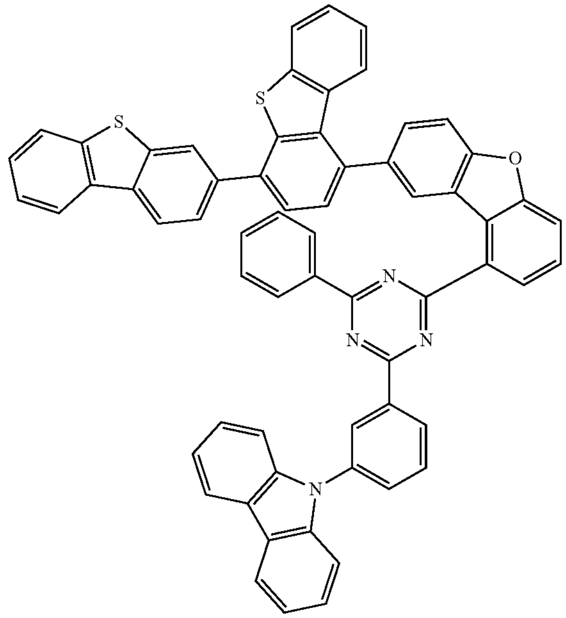
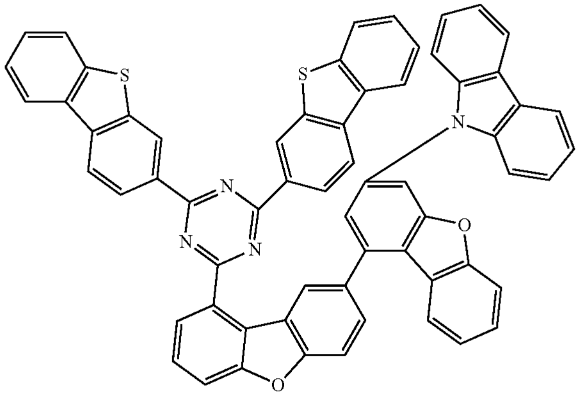
-continued
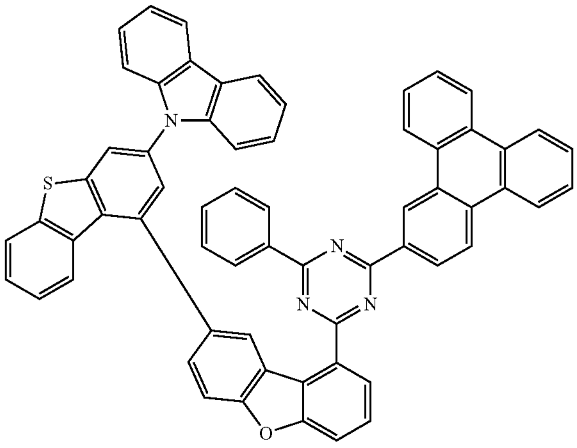
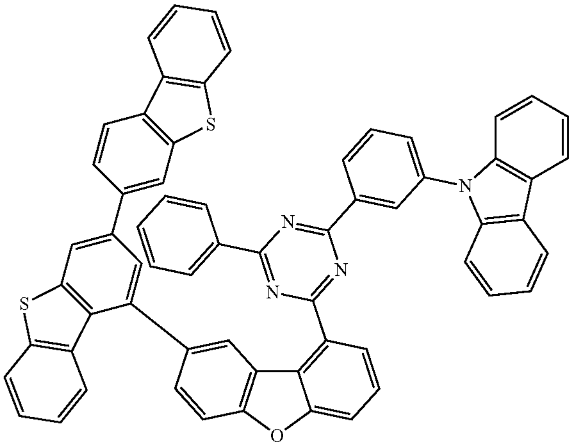
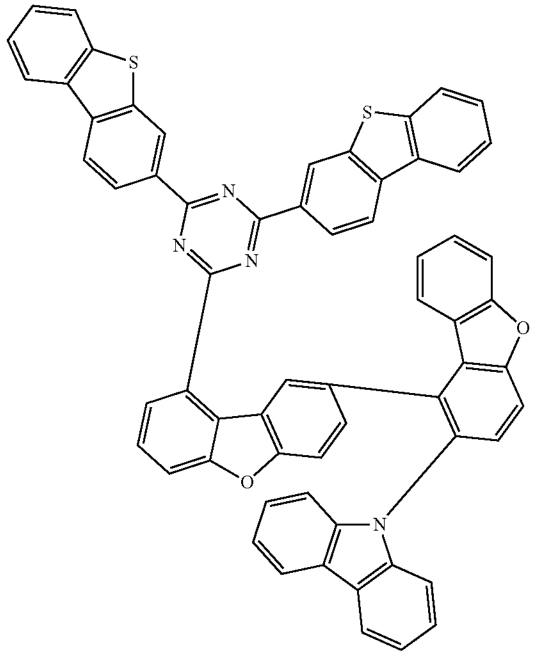

-continued
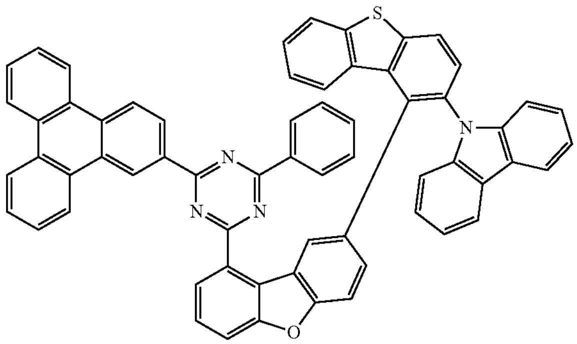
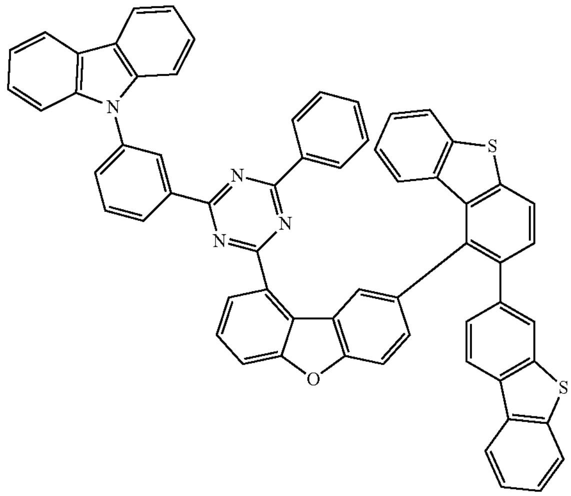
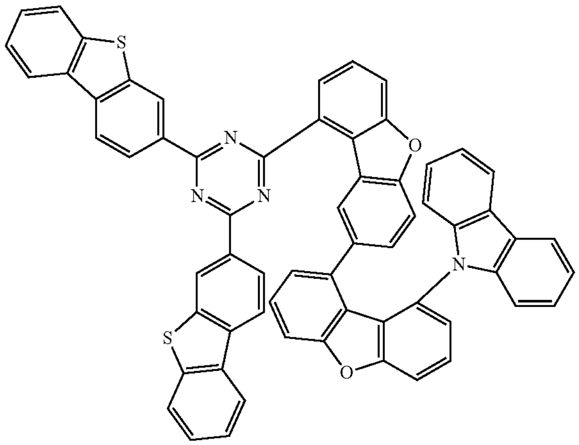
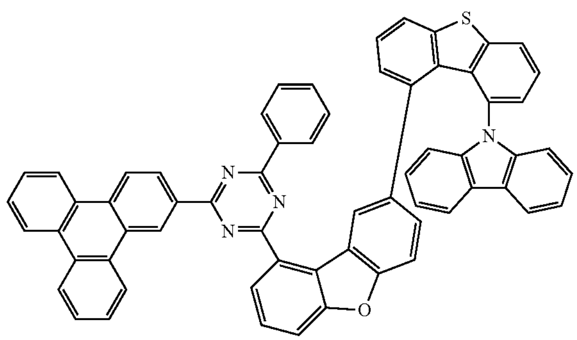
-continued
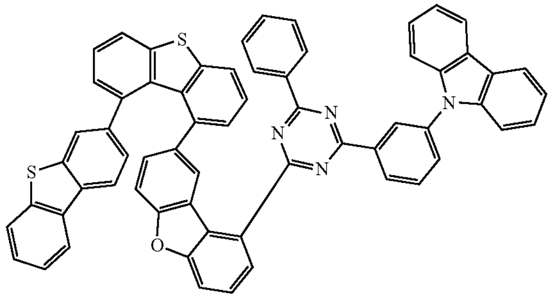 [SMILES: c1ccc(-c2nc(-c3cccc(-n4c5ccccc5c5ccccc54)c3)nc(-c3cccc4oc5ccc(-c6cccc7sc8cccc(-c9ccc%10c(c9)sc9ccccc9%10)c8c67)cc5c34)n2)cc1]
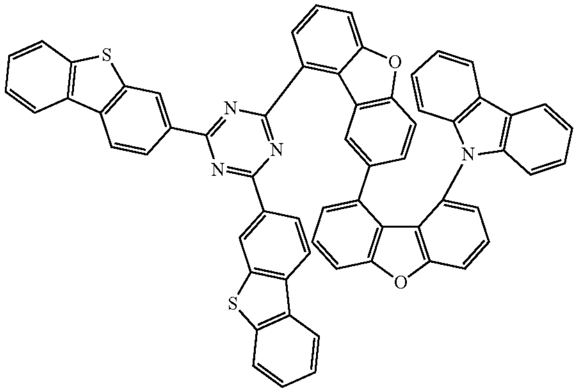
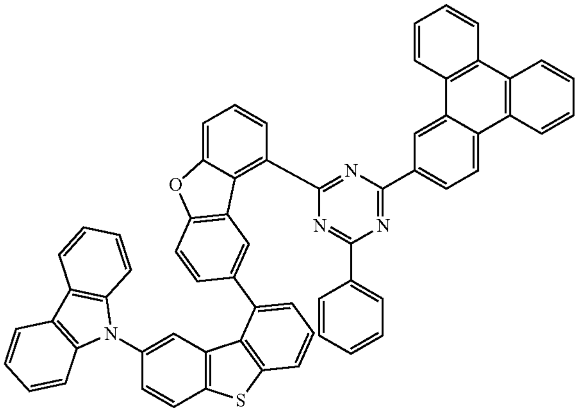
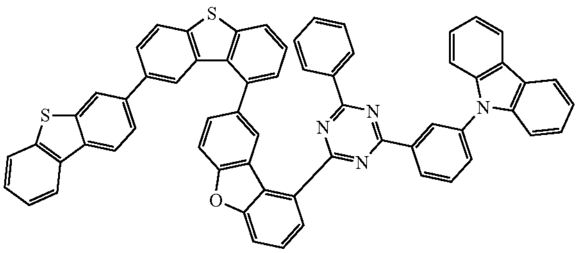
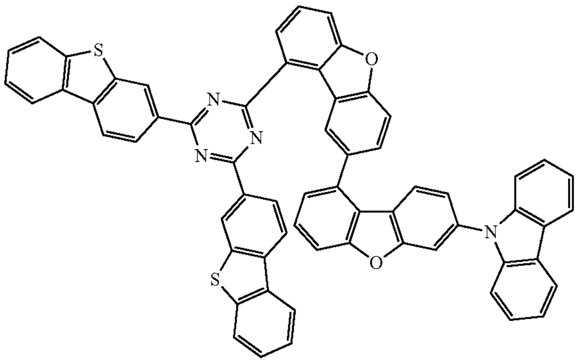

-continued
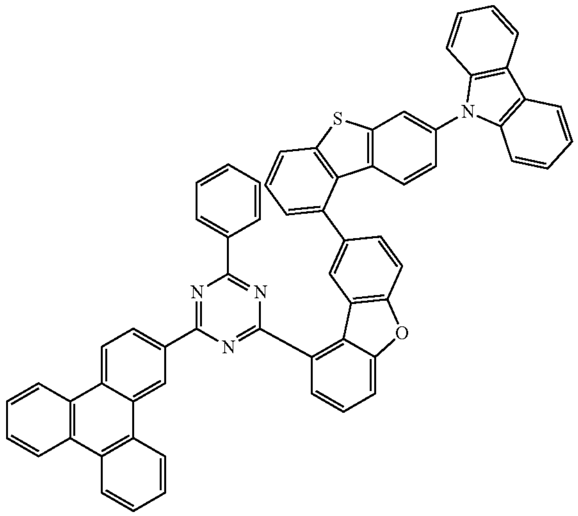
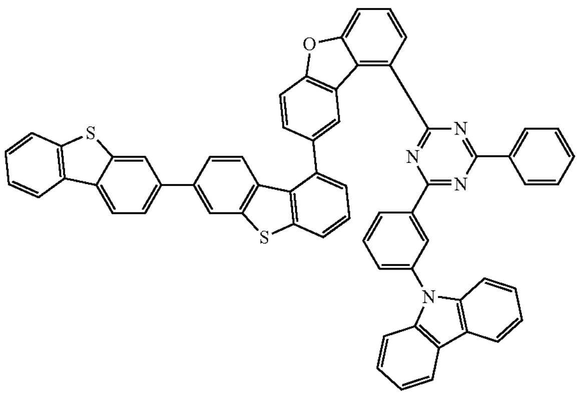
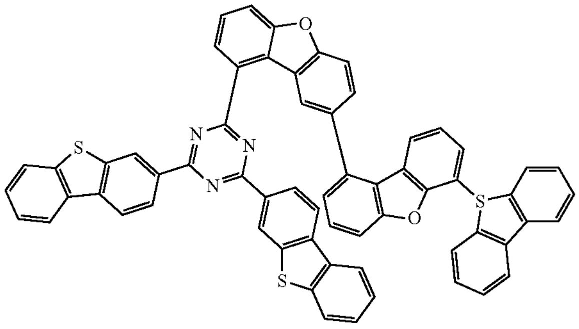
-continued
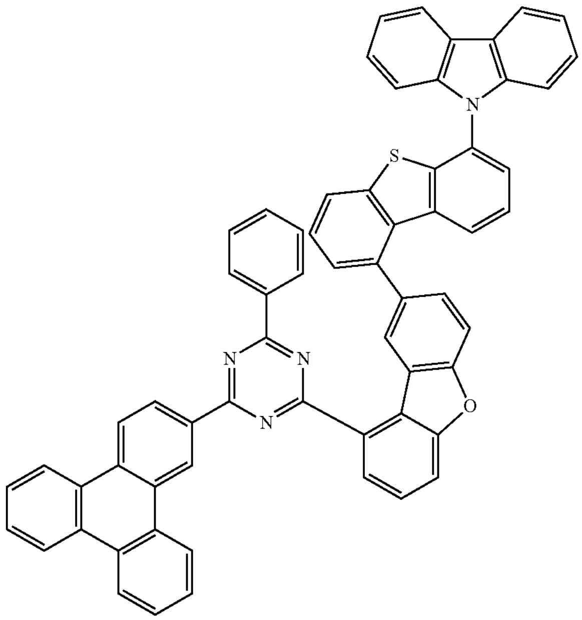
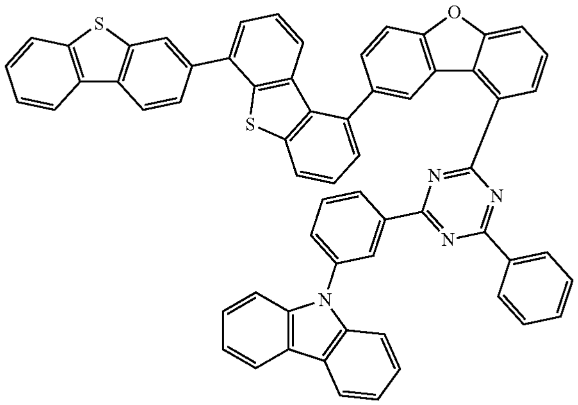
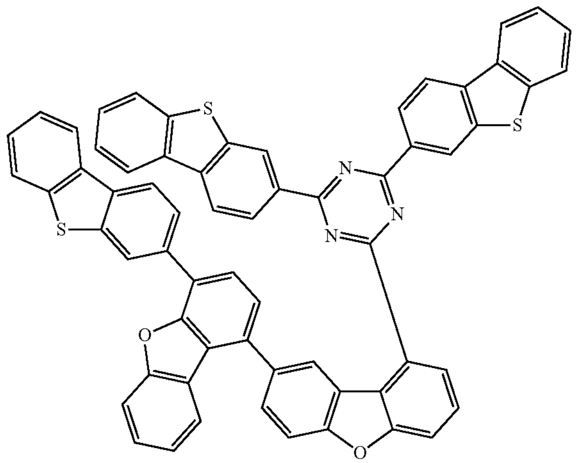

-continued
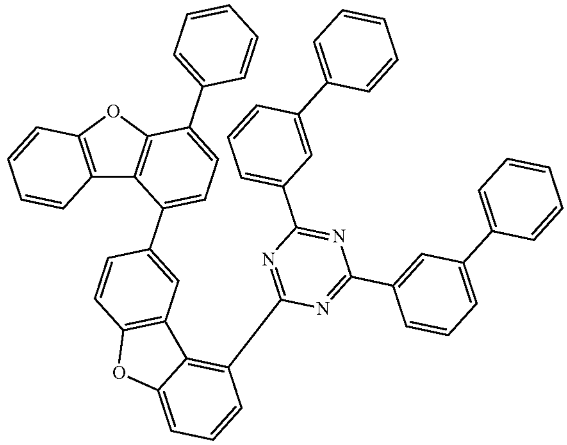
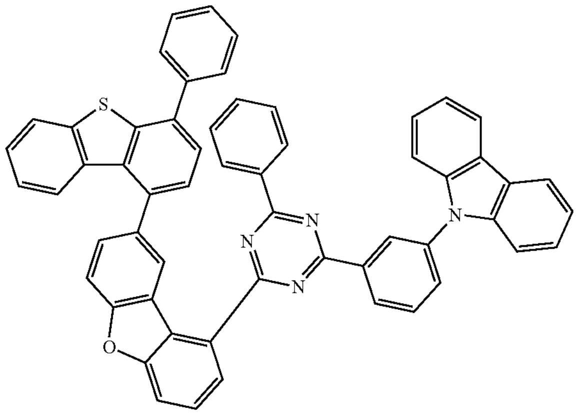
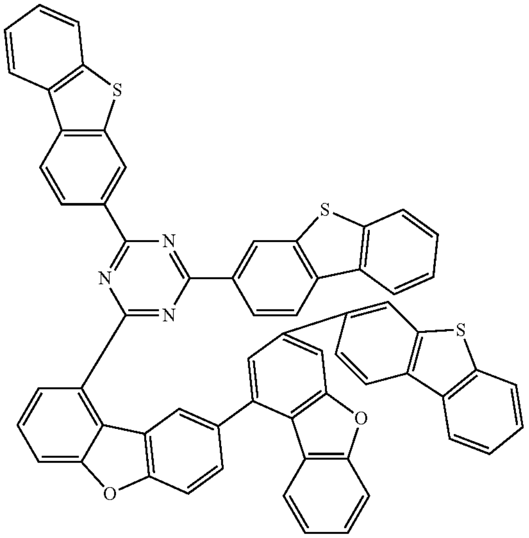
-continued
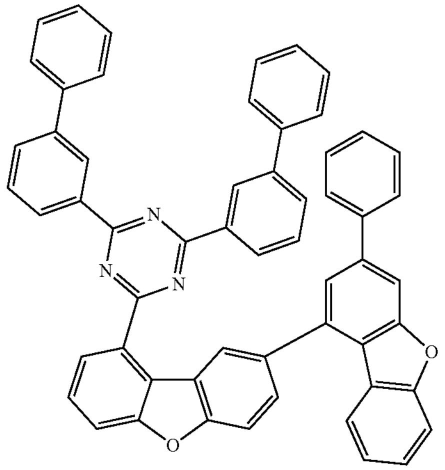
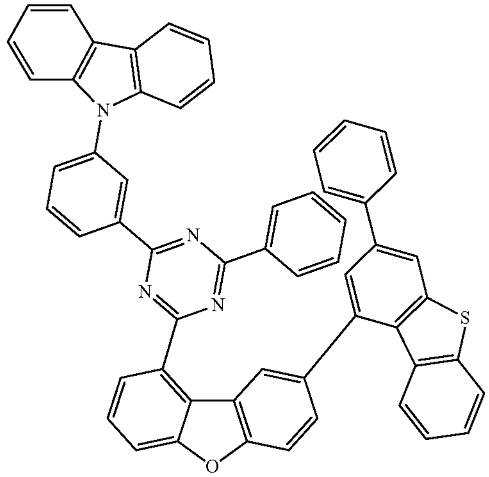
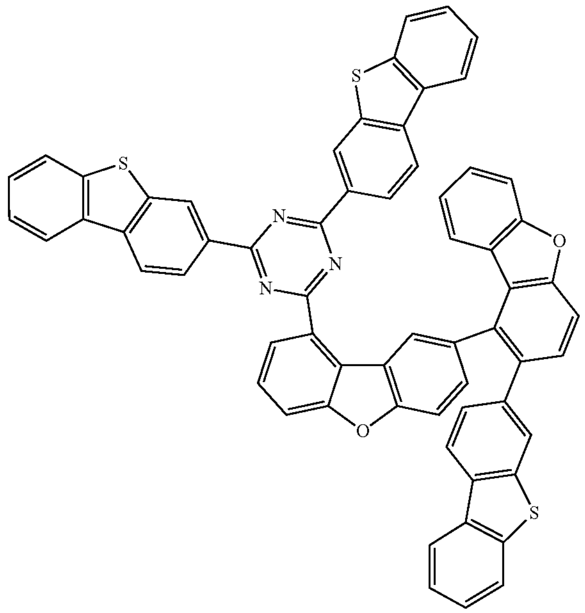

-continued
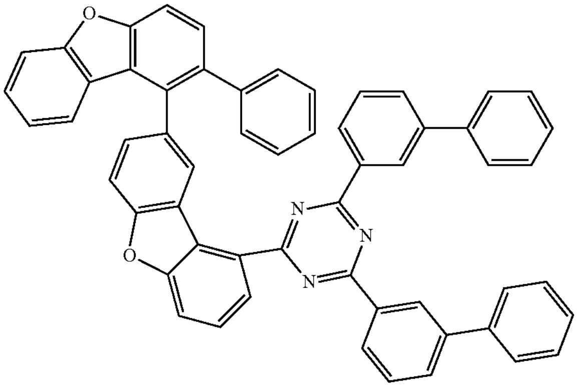
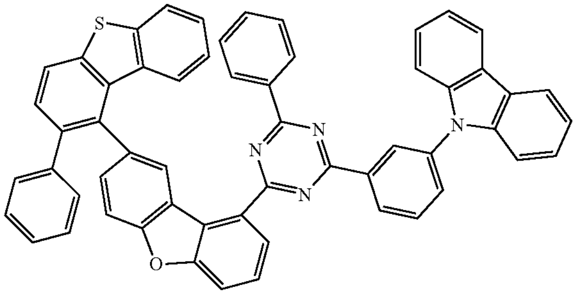
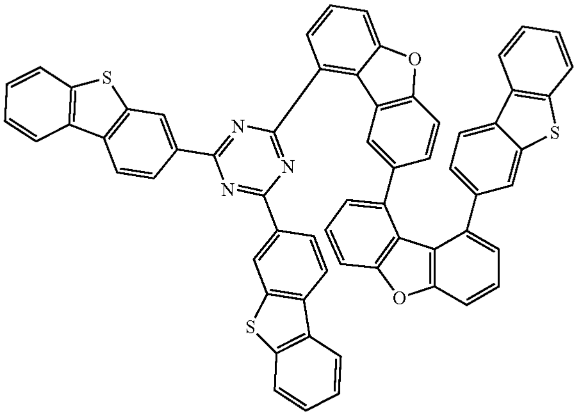
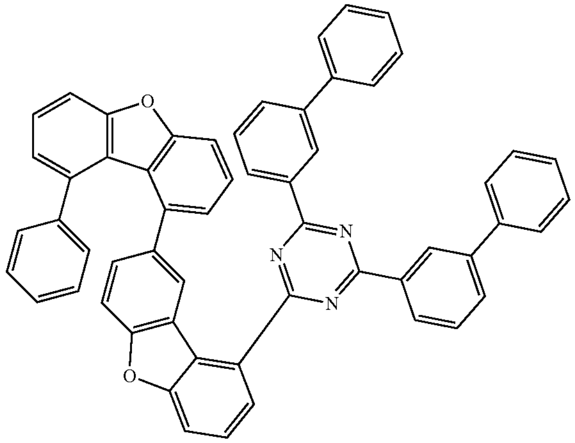
-continued
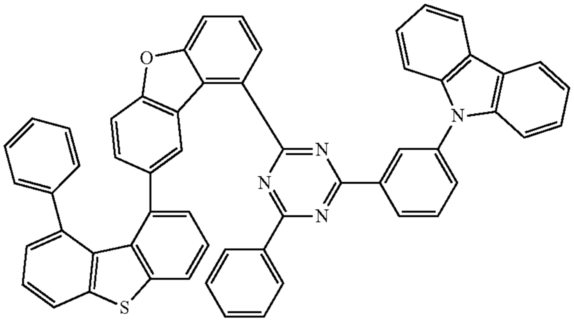
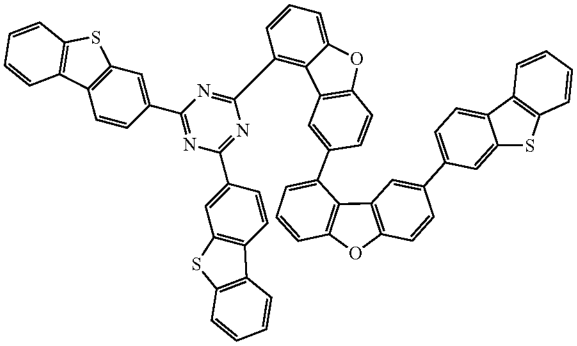
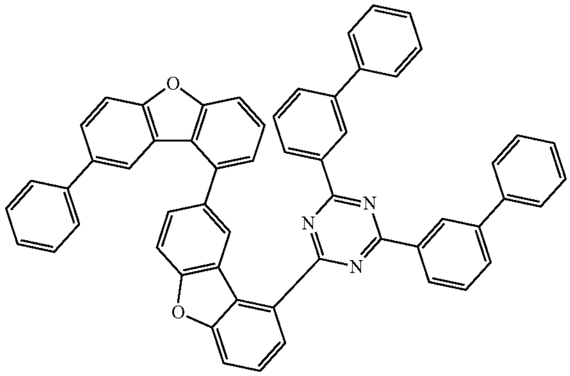
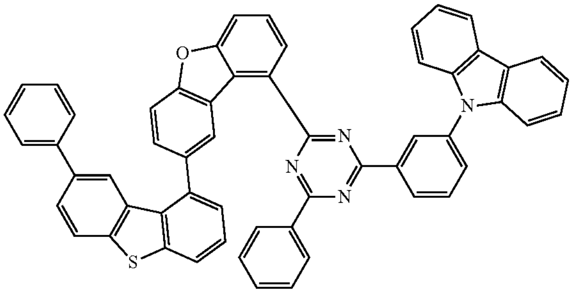
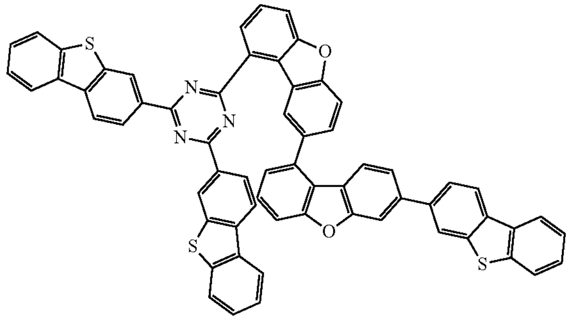

-continued
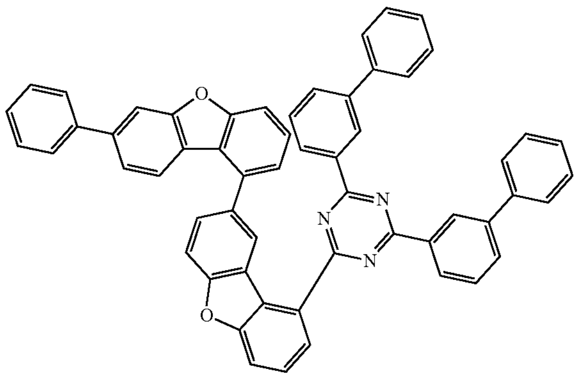
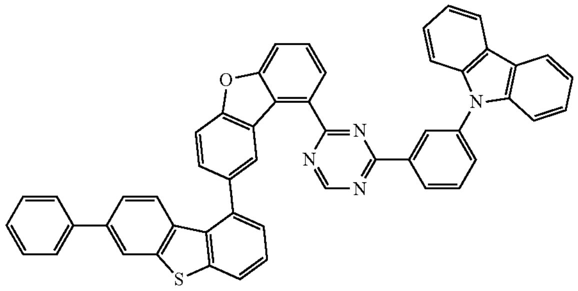
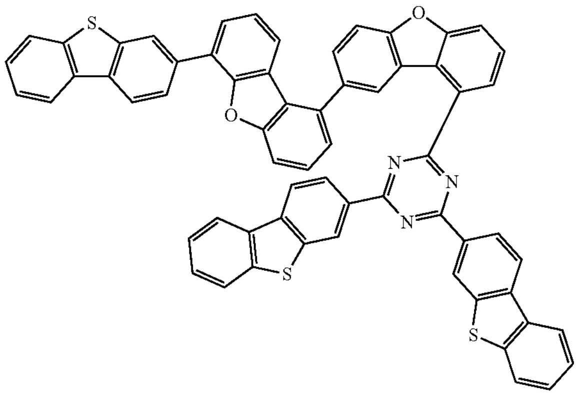
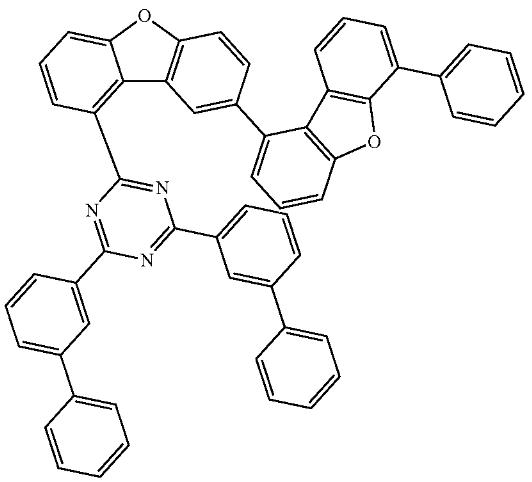
-continued
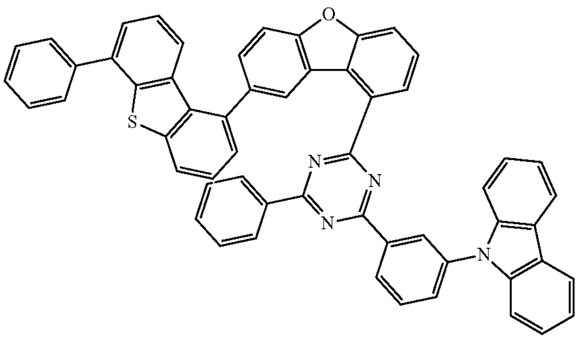
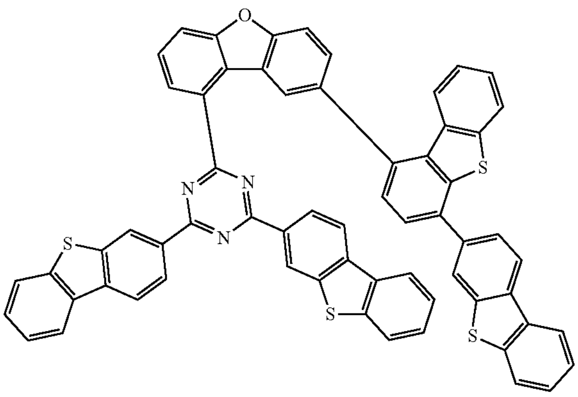
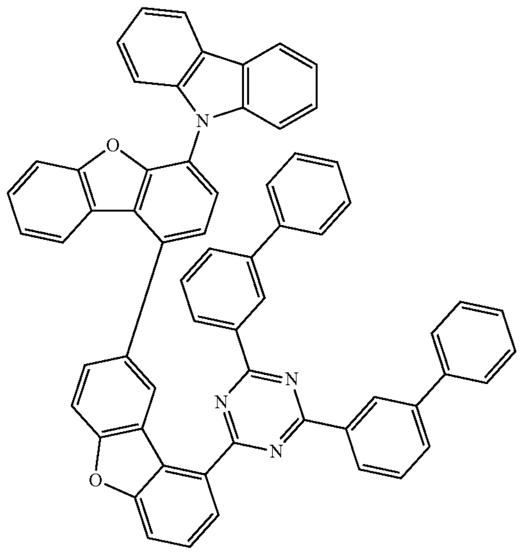

-continued
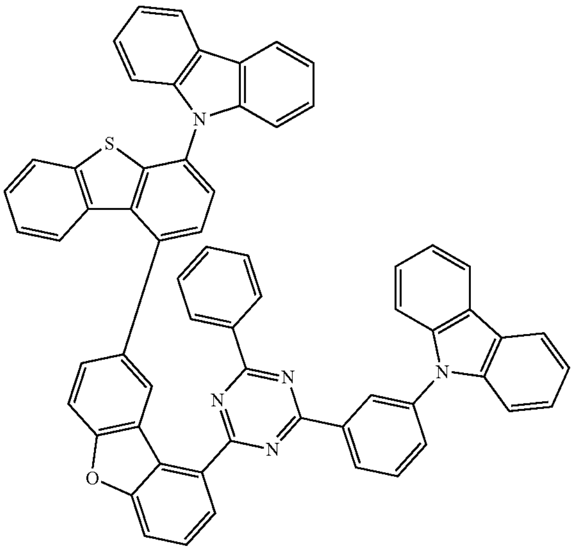
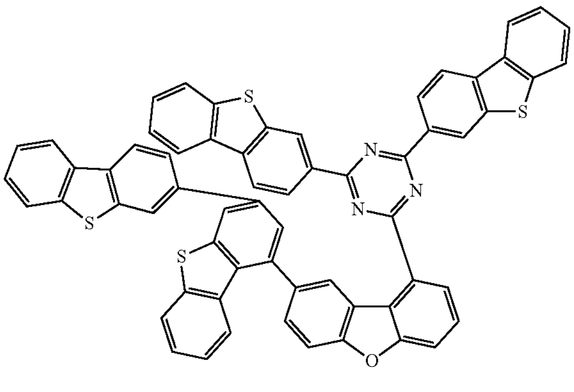
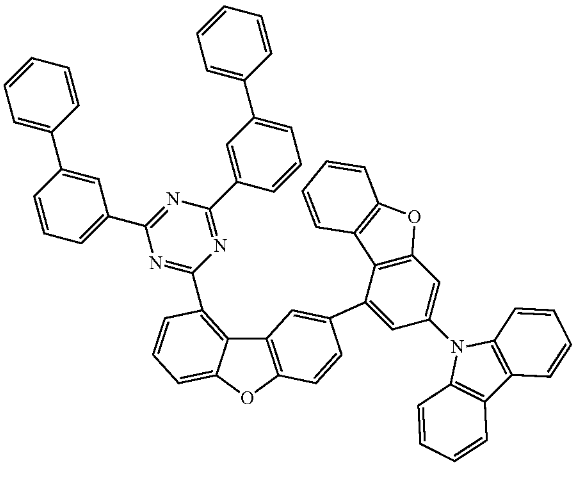
-continued
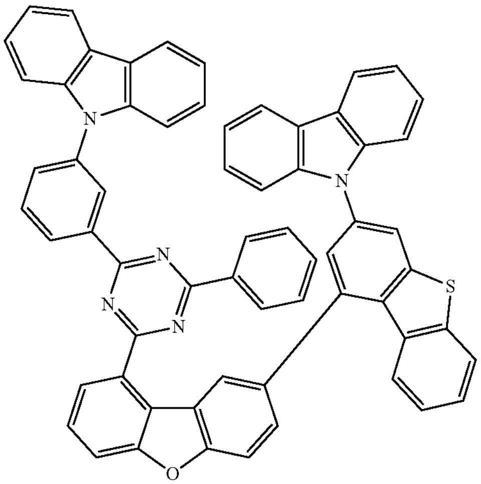
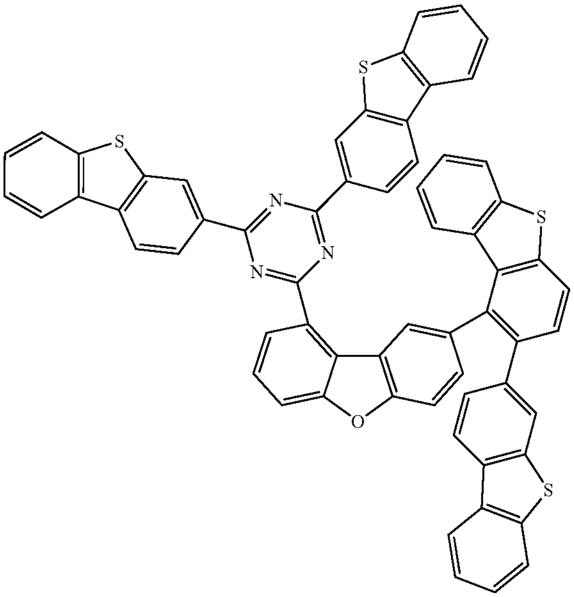
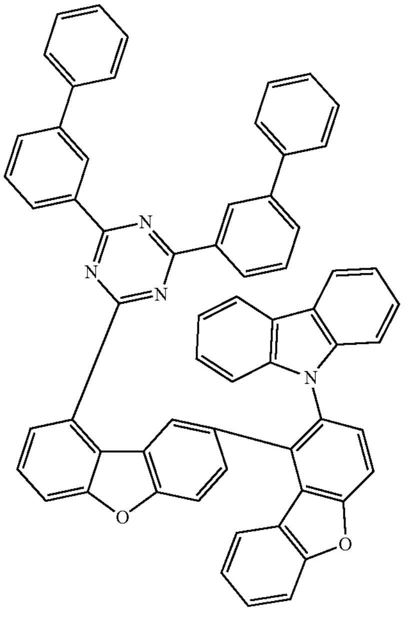

-continued
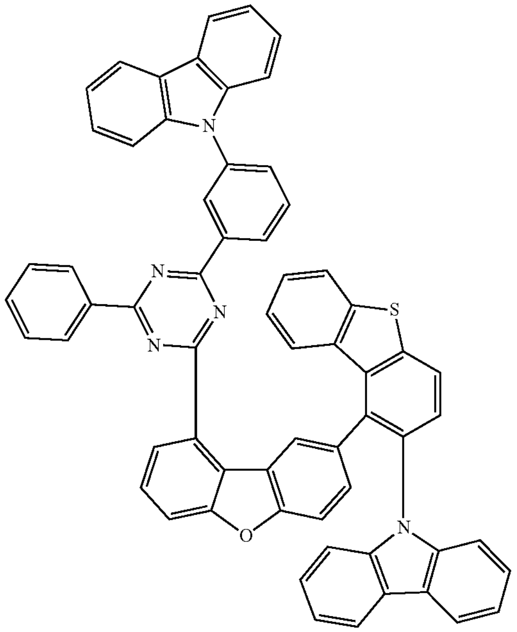
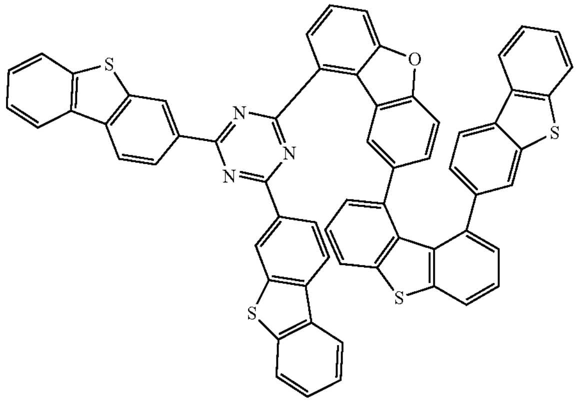
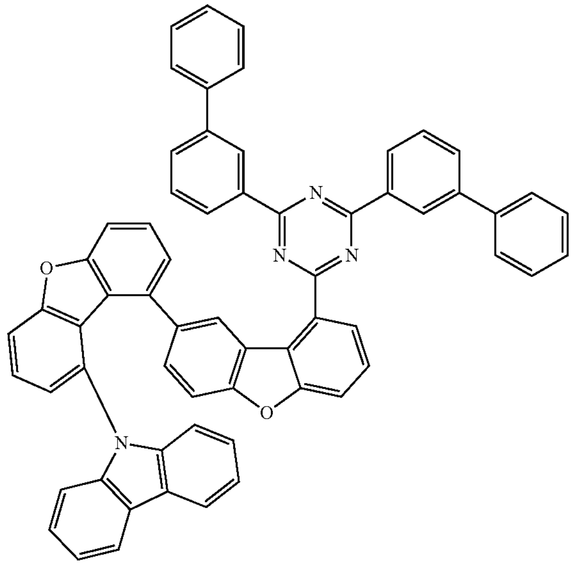
-continued
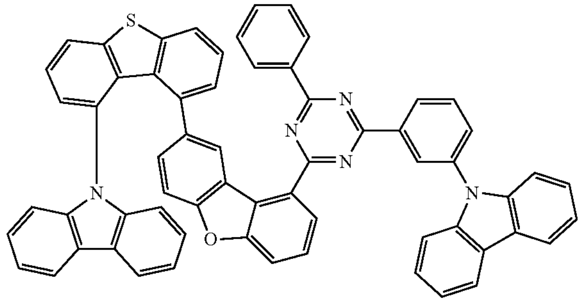
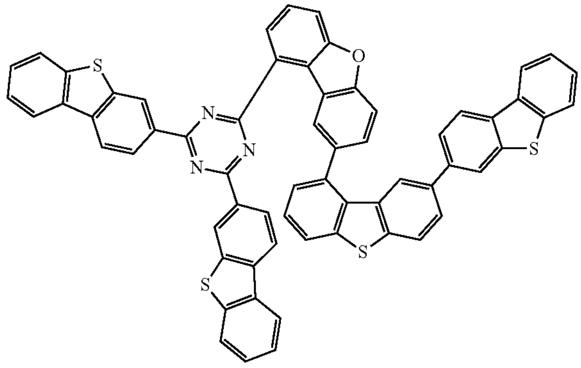
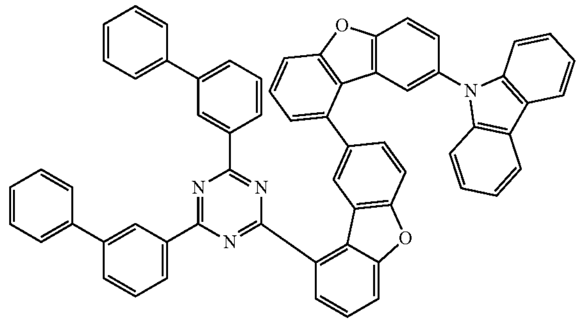
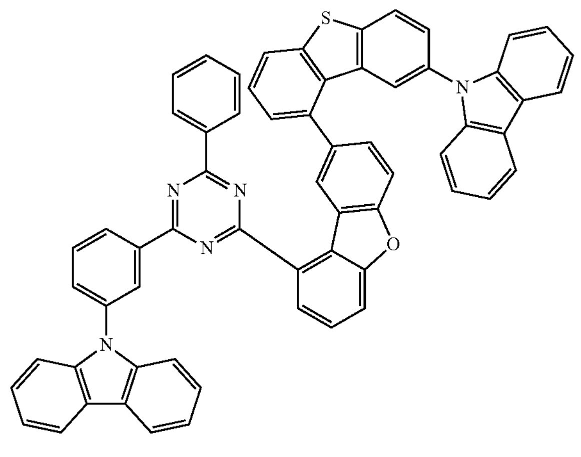

-continued
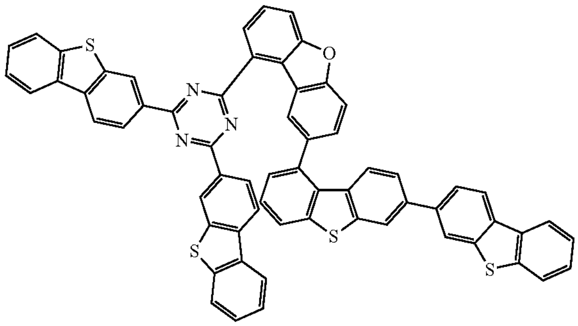
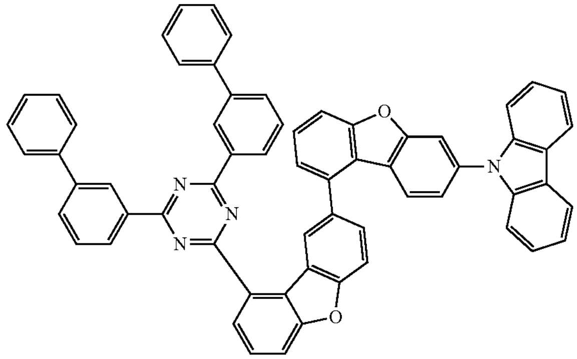
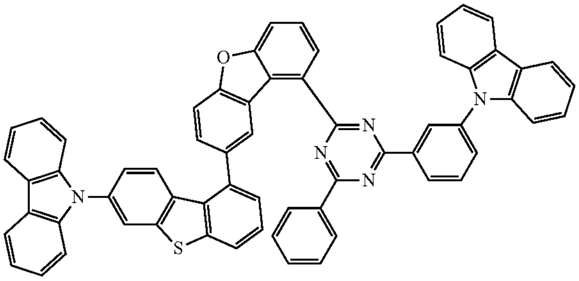
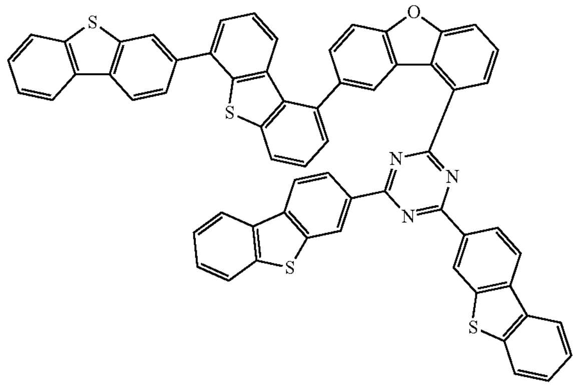
-continued
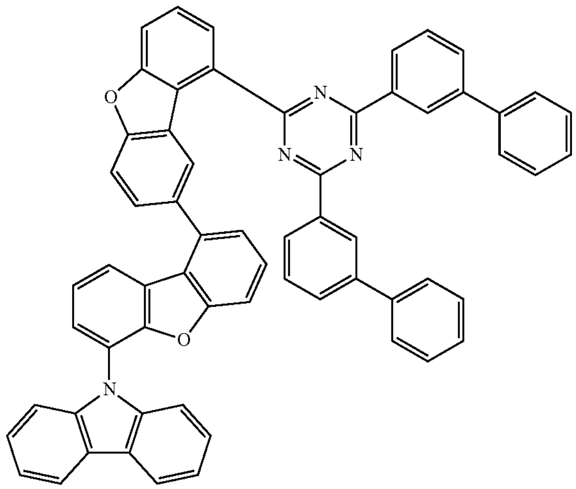
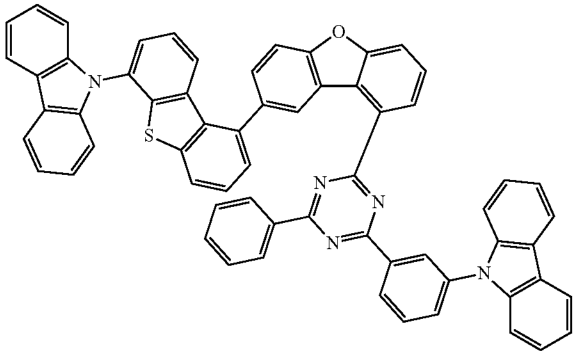
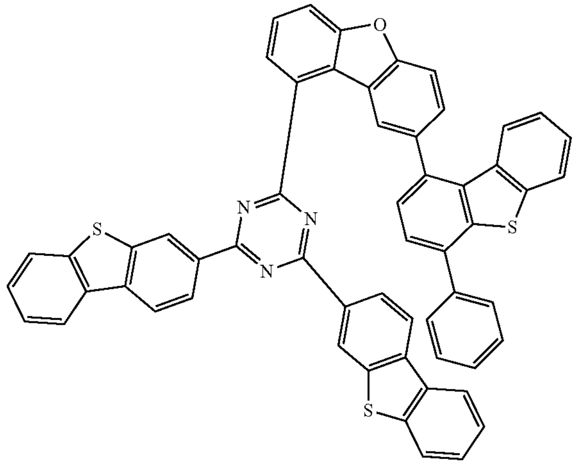

-continued
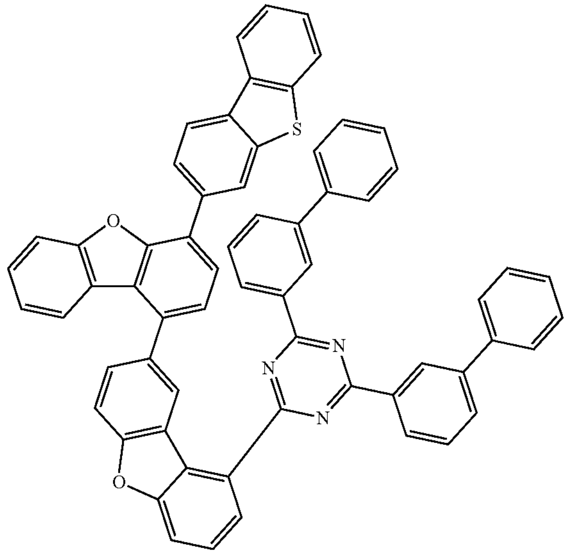
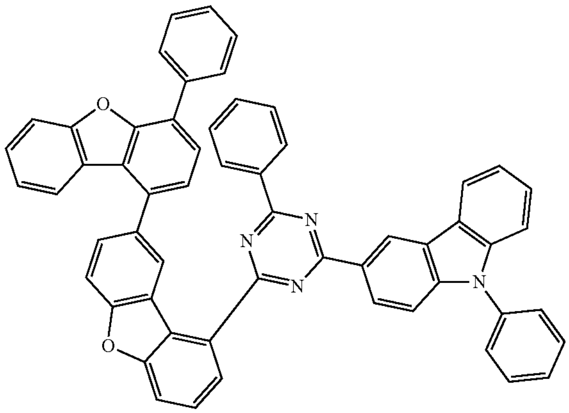
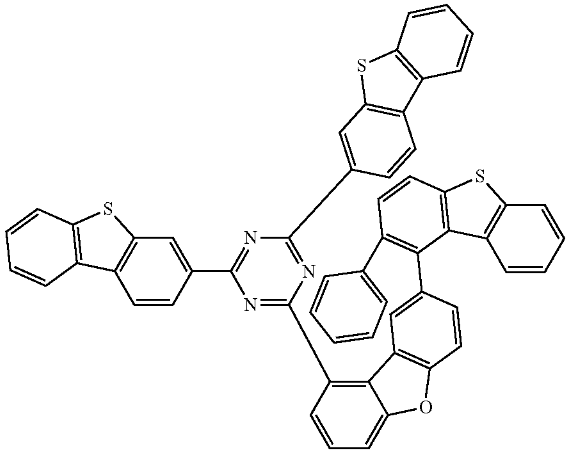
-continued
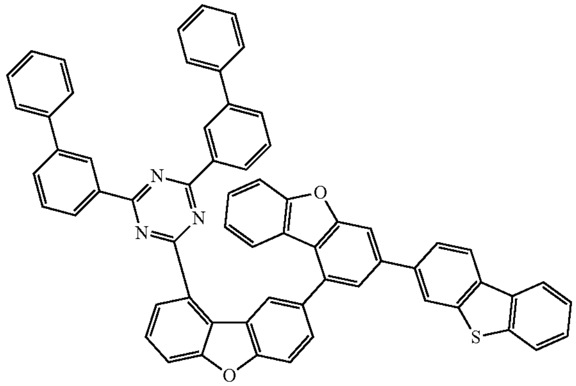
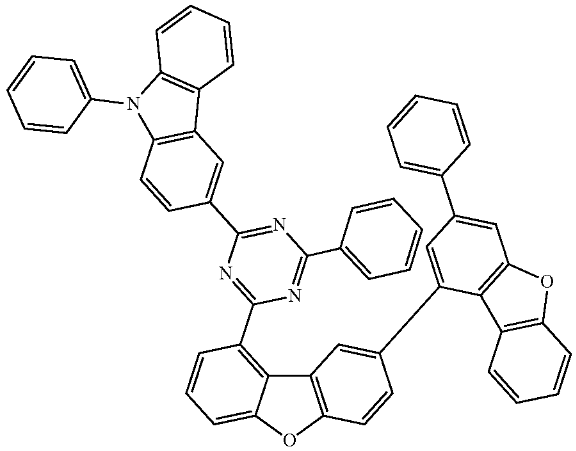
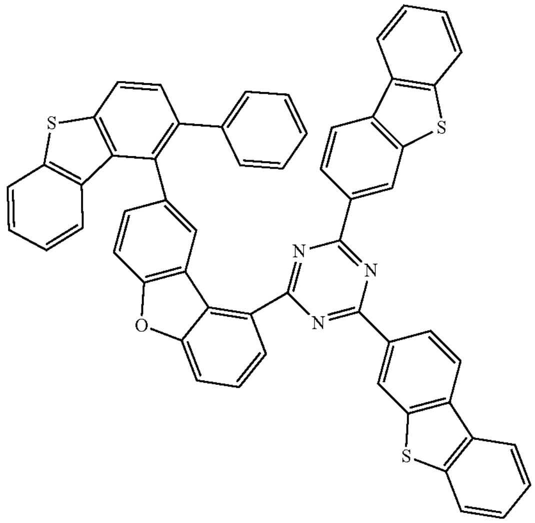

-continued
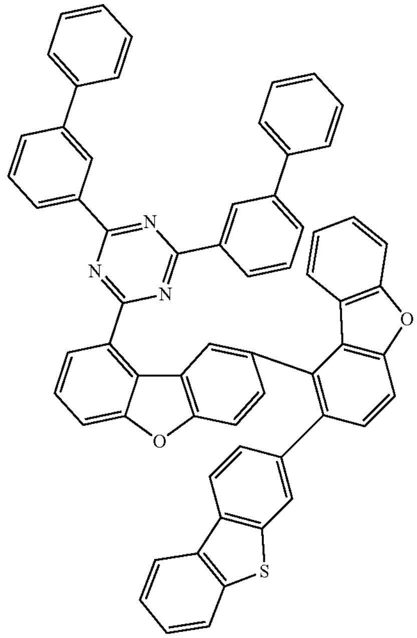
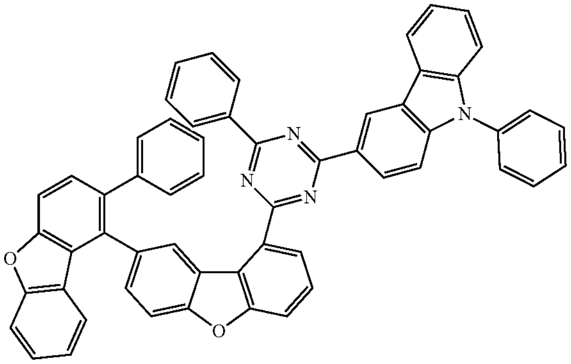
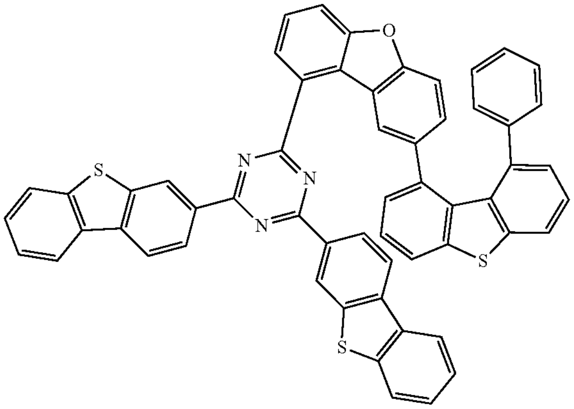
-continued
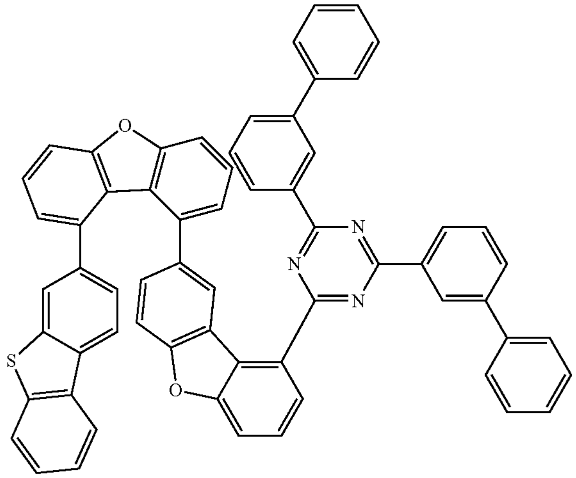
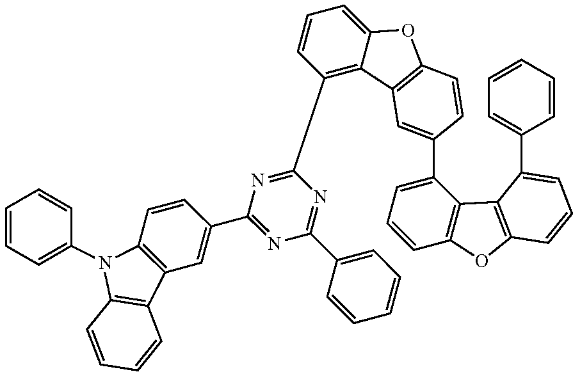
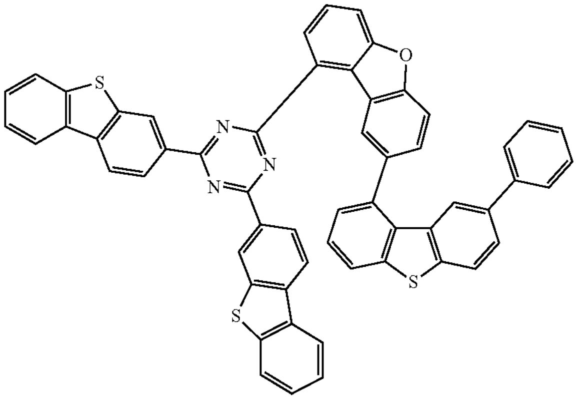
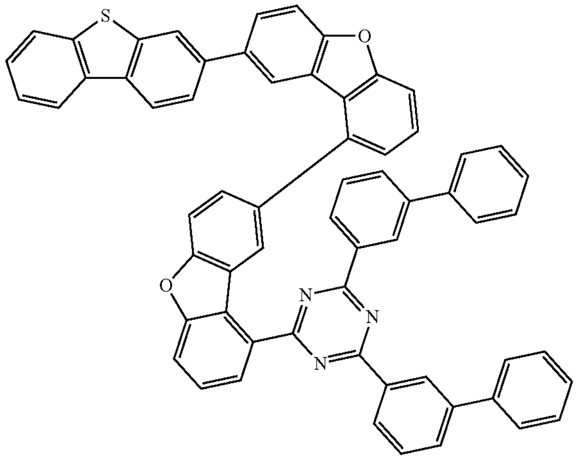

-continued
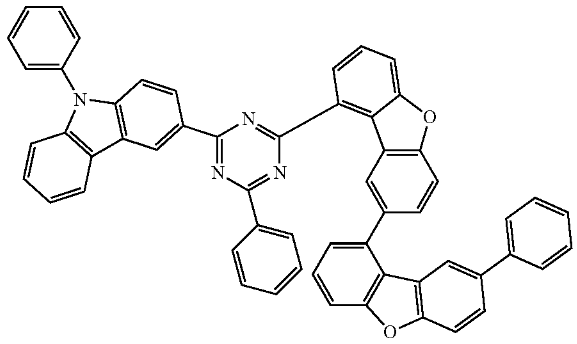
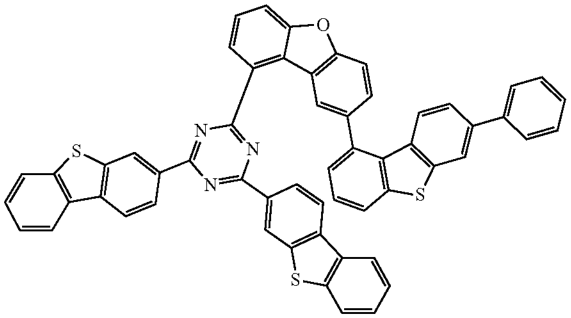
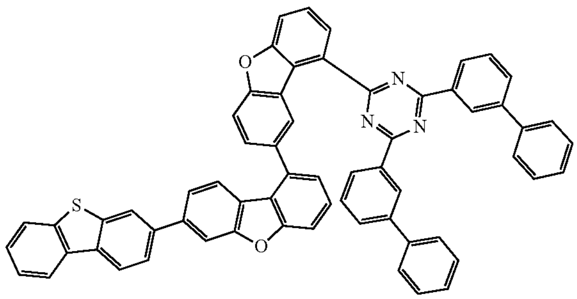
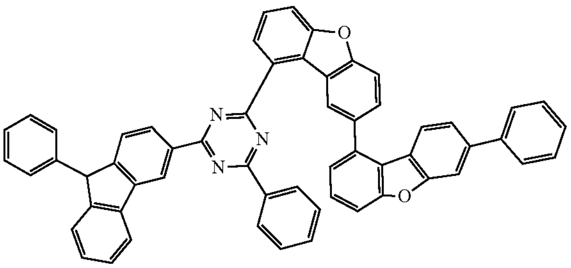
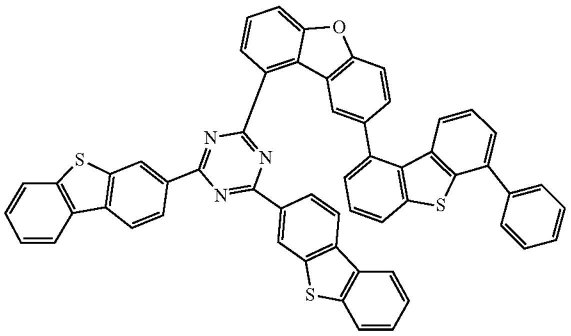
-continued
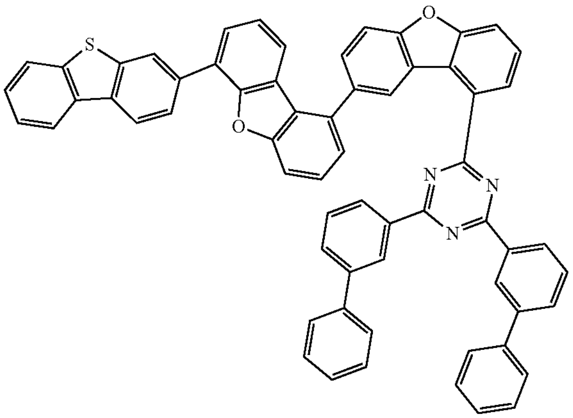
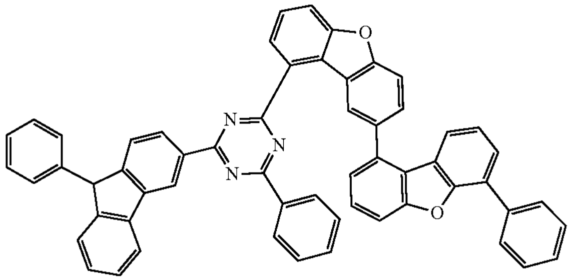
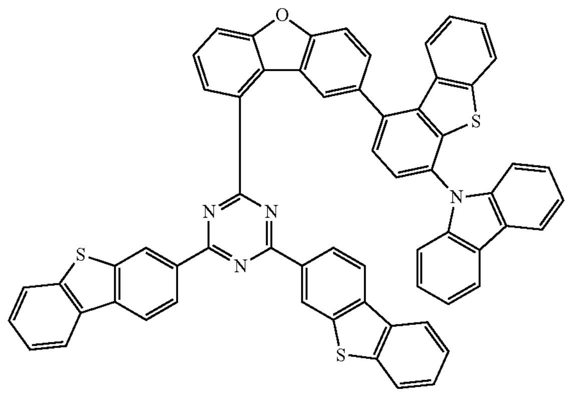
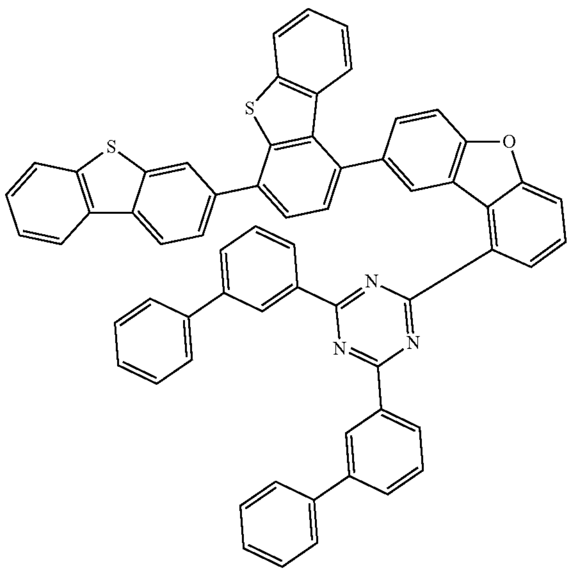

-continued
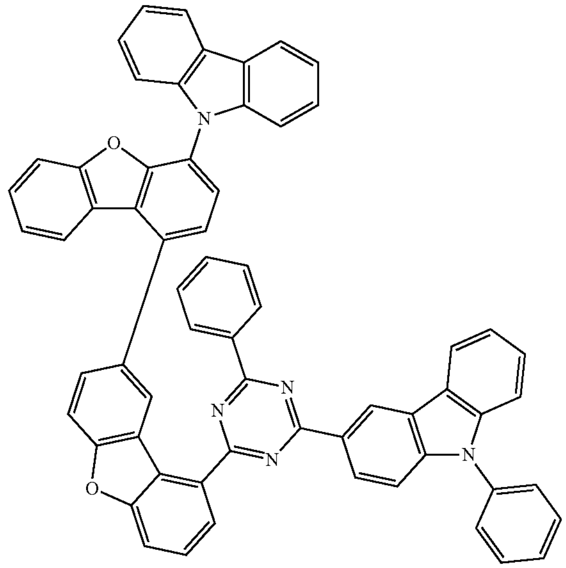
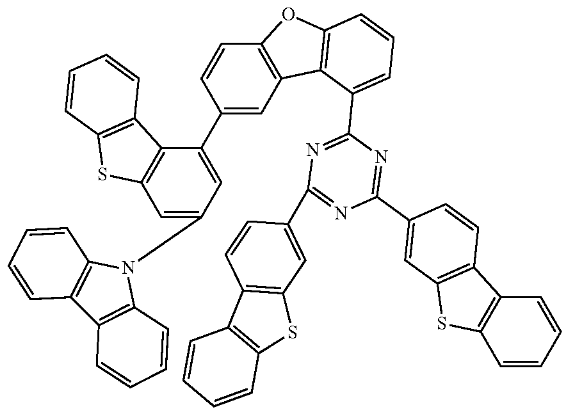
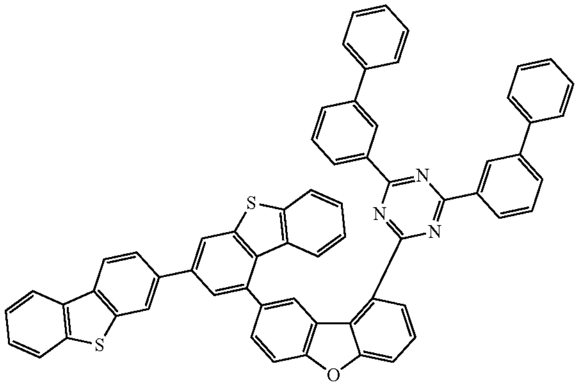
-continued
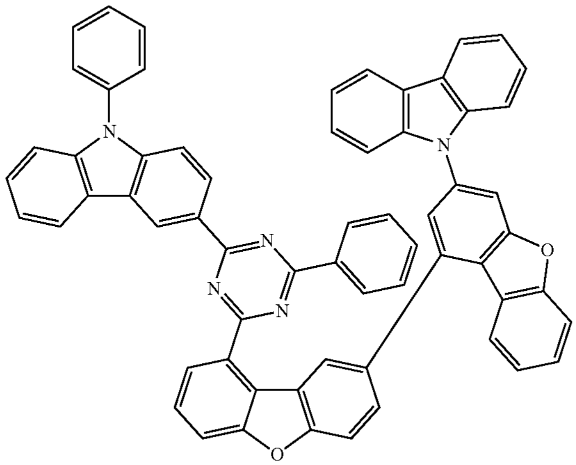
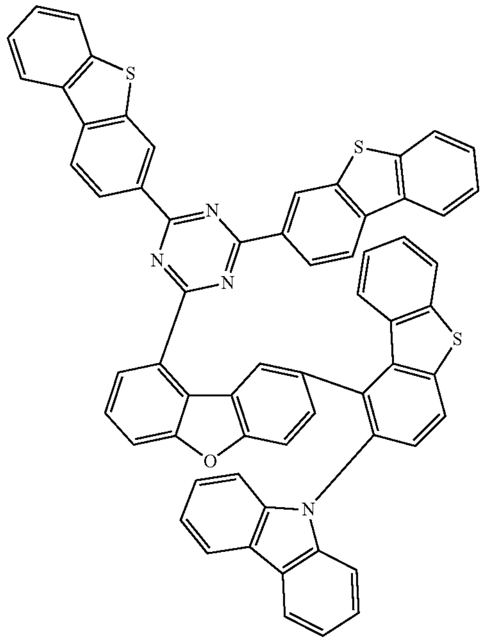

-continued
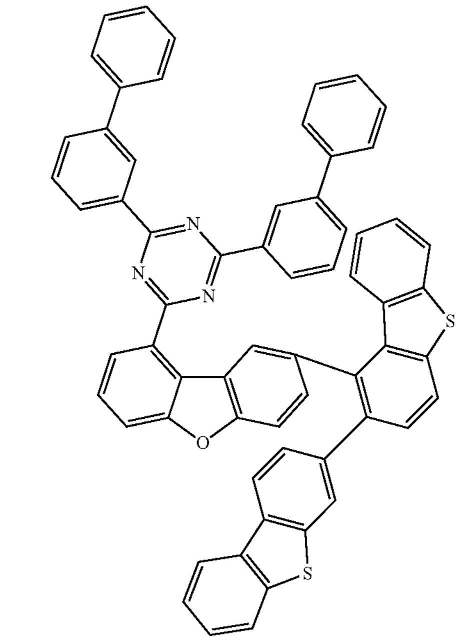
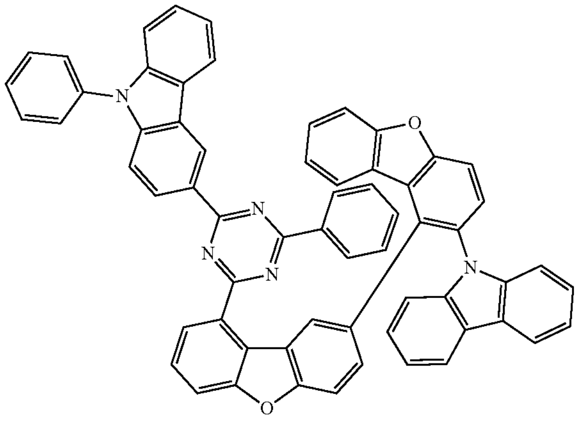
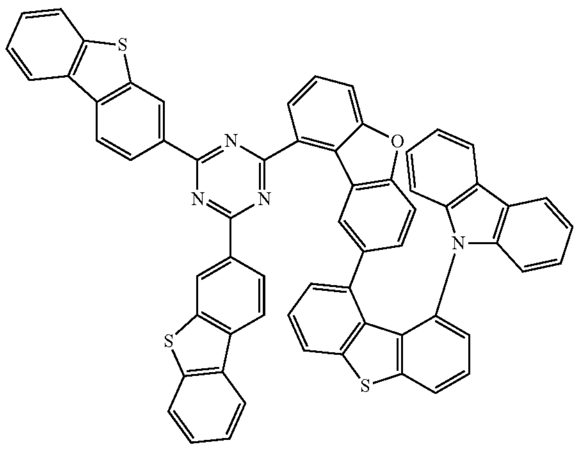
-continued
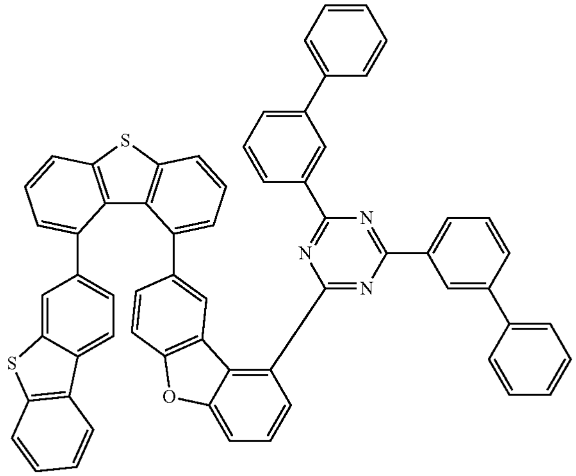
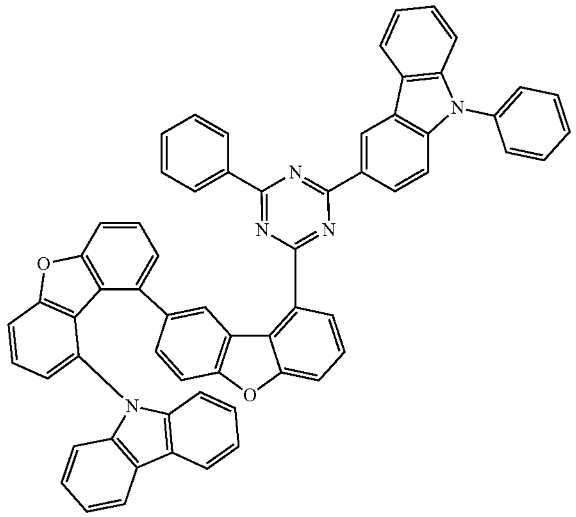
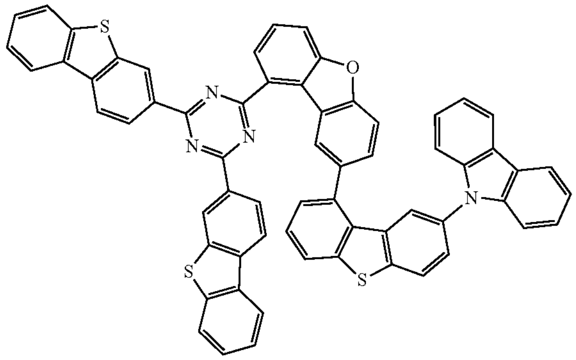

-continued
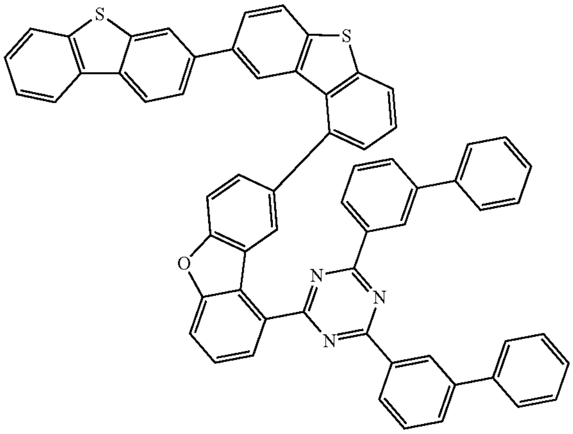
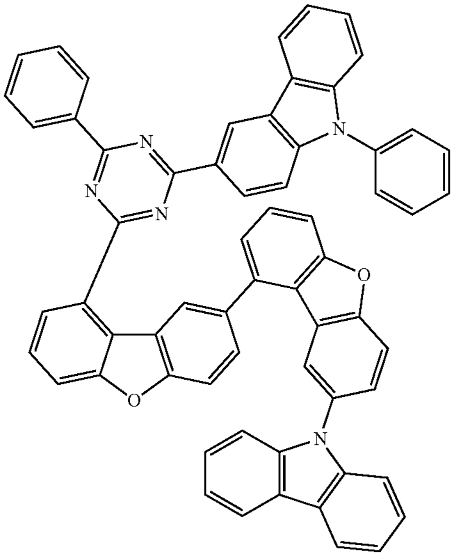
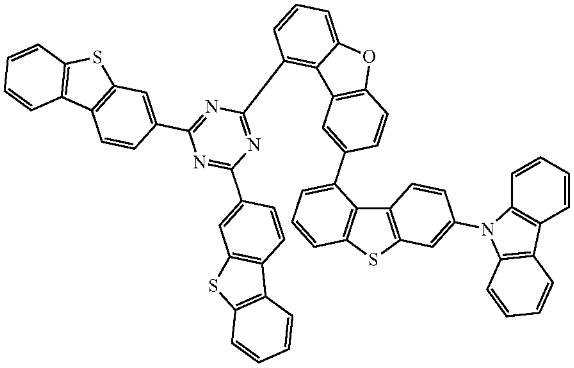
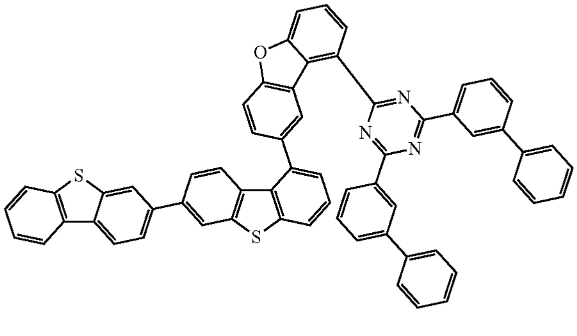
-continued
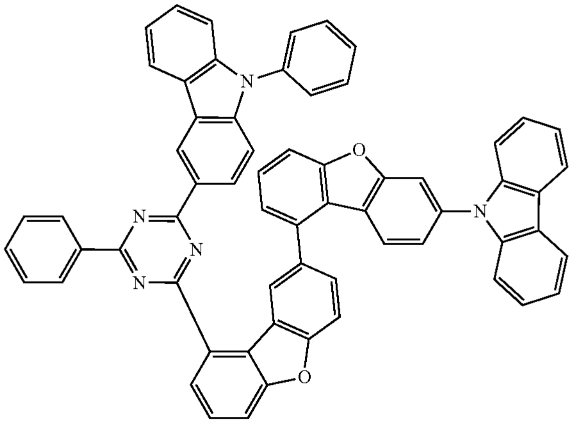
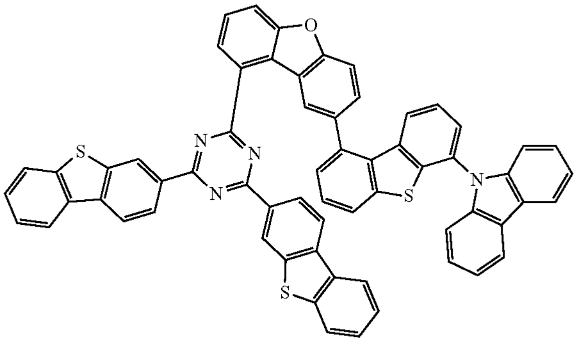
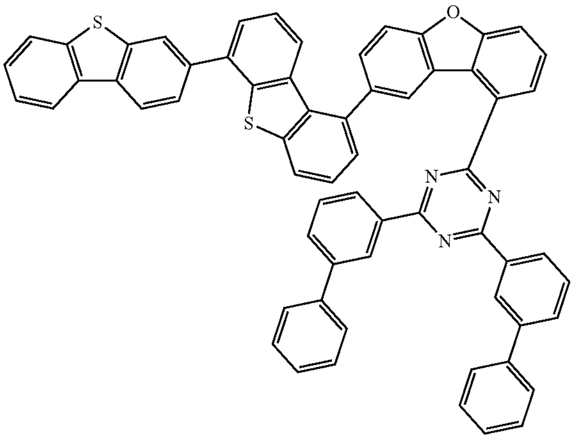
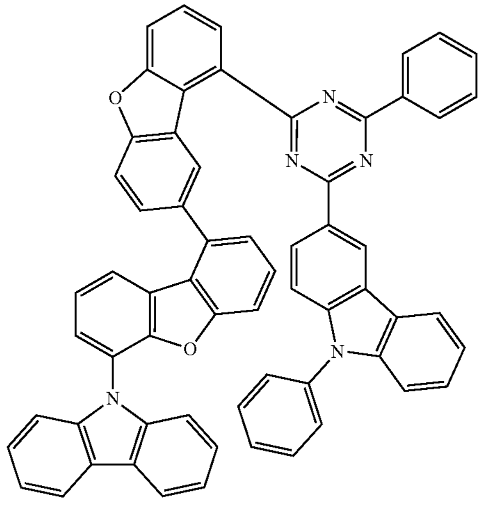

-continued
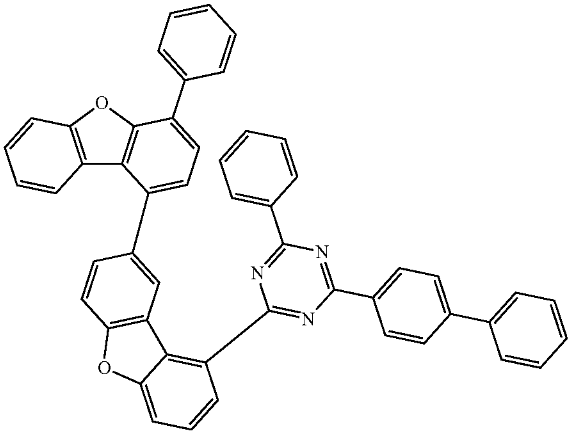
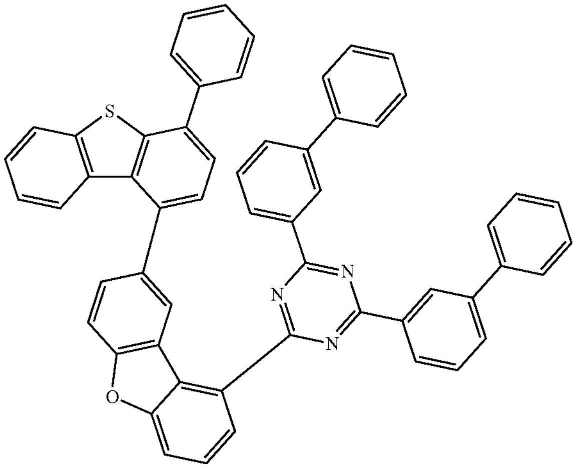
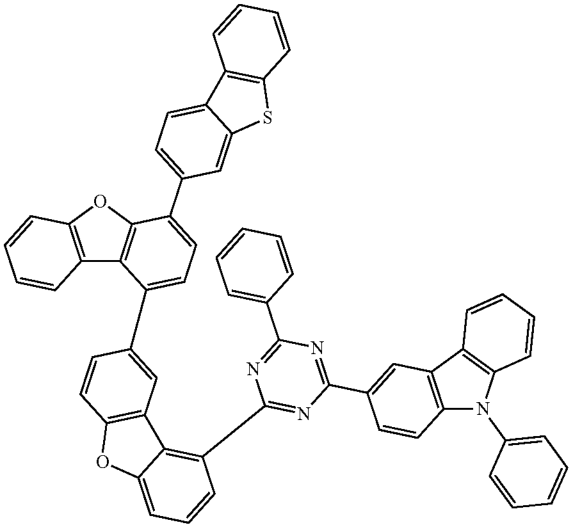
-continued
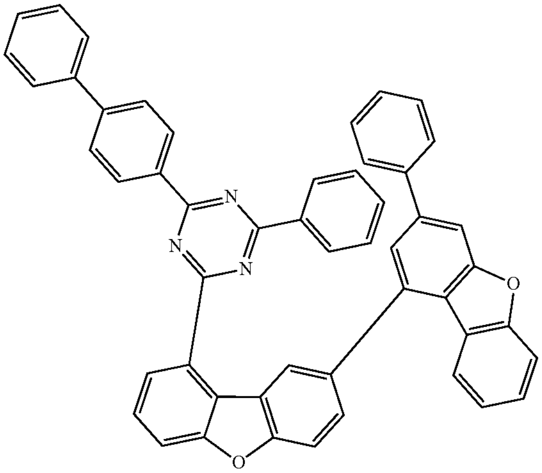
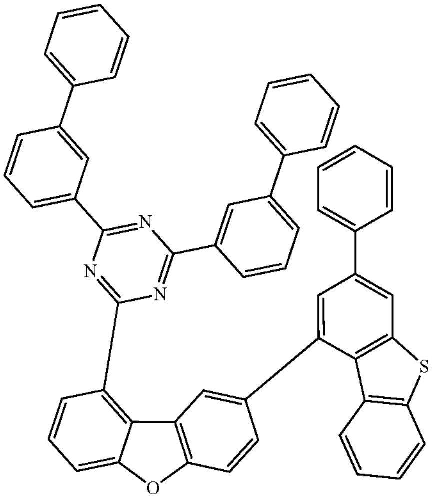
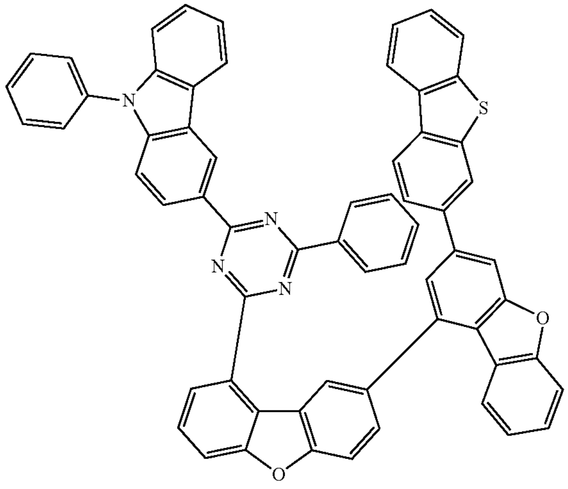

-continued
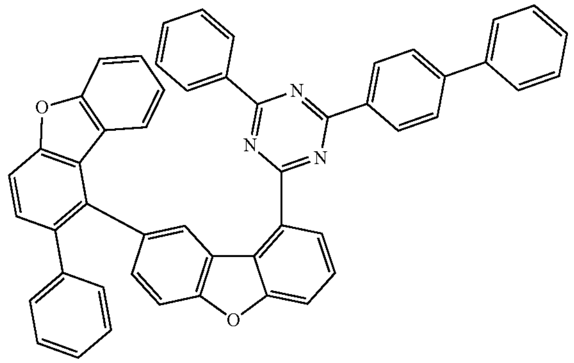
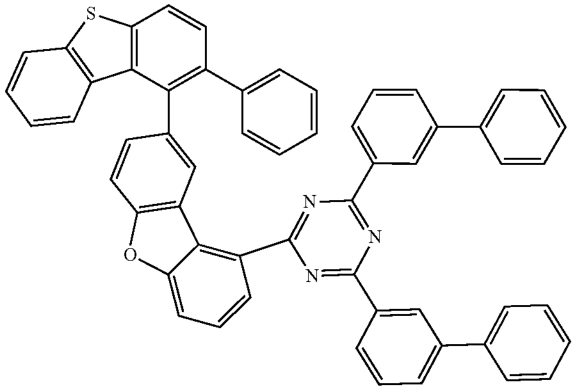
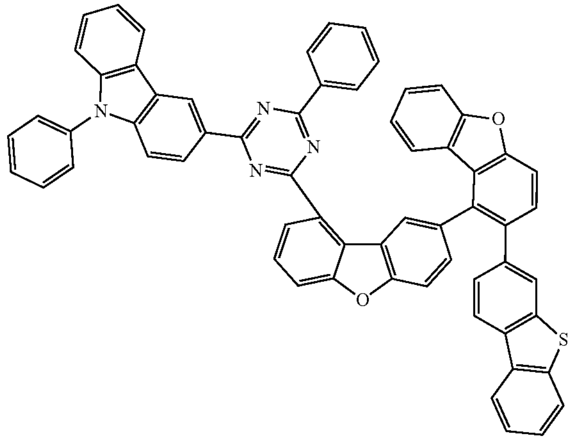
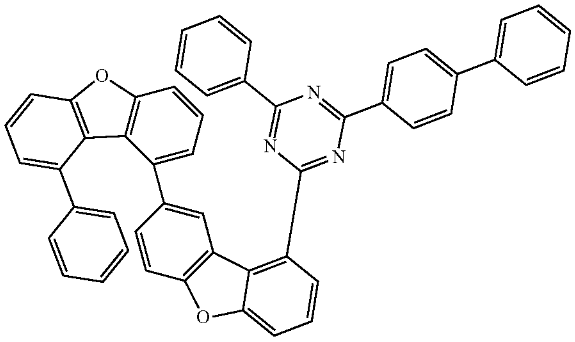
-continued
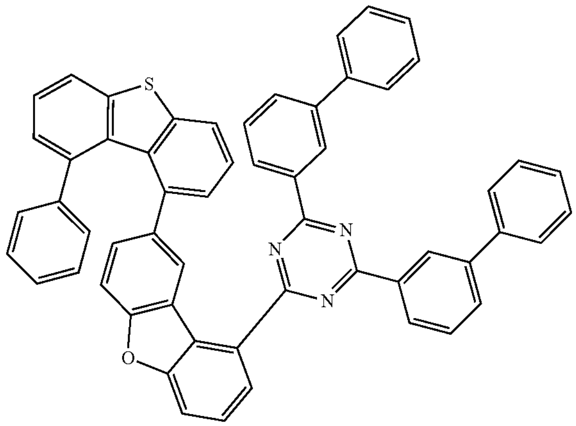
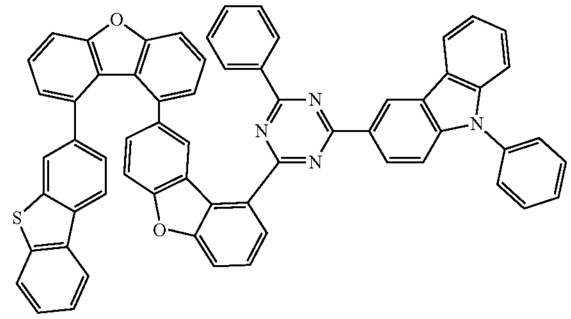
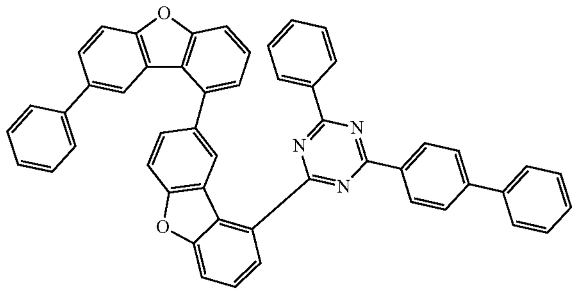
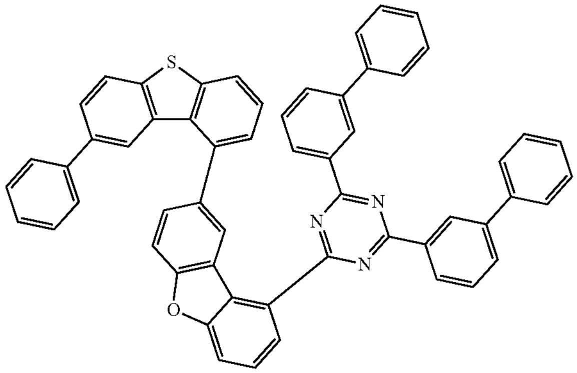
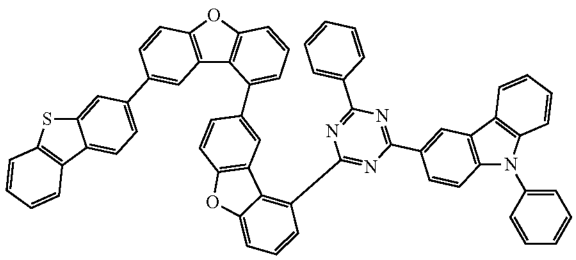

-continued
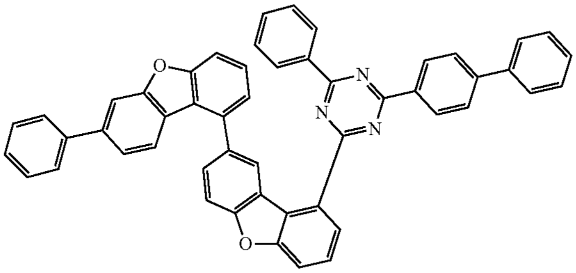
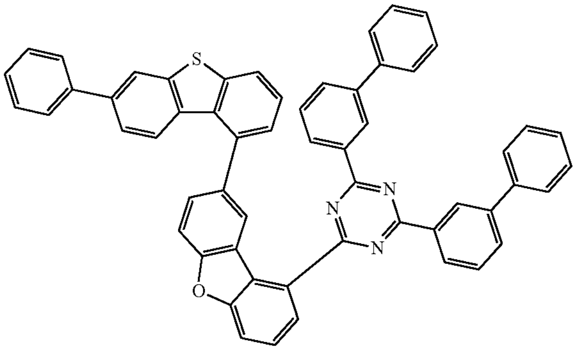
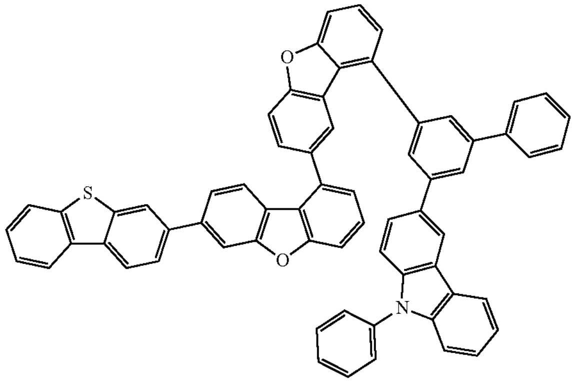
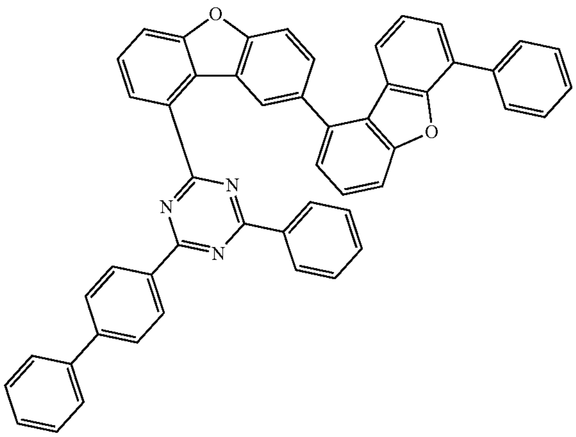
-continued
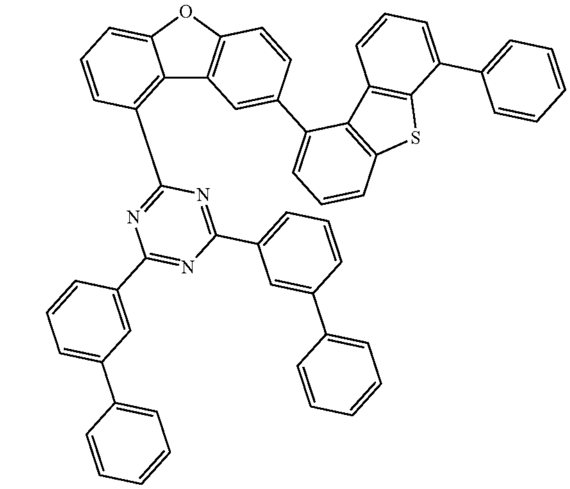
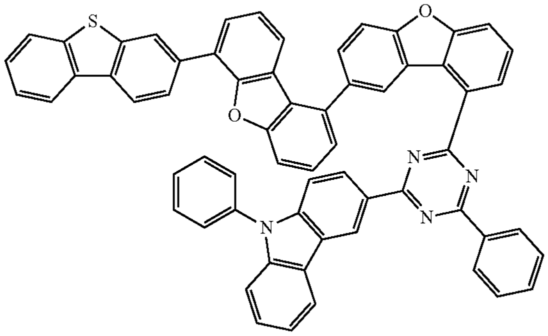
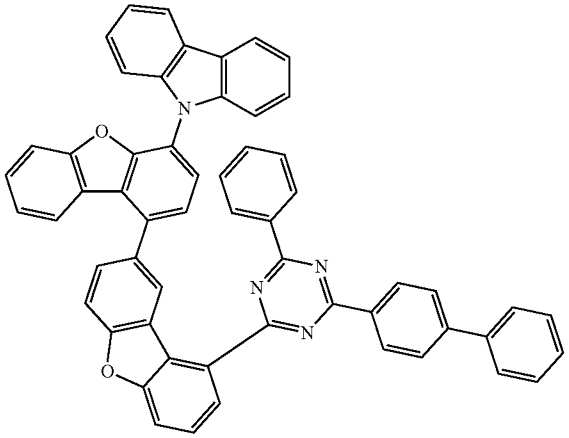
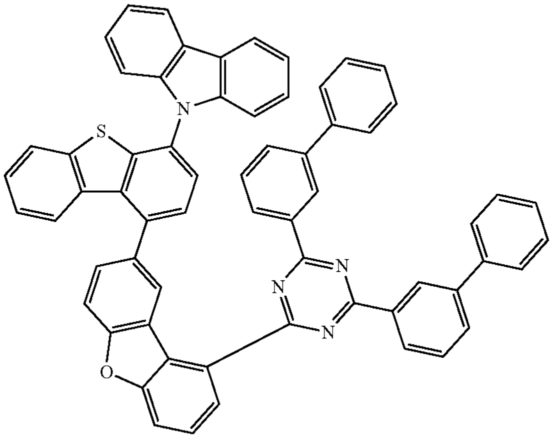

-continued
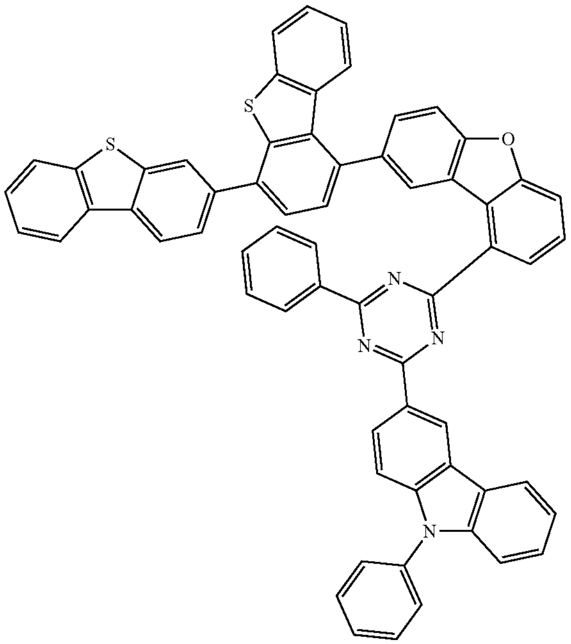
-continued
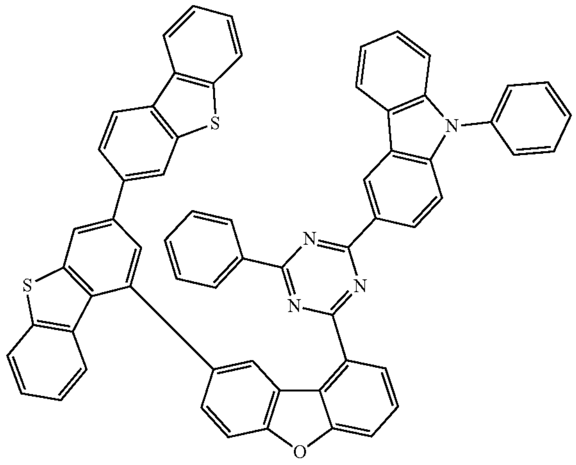
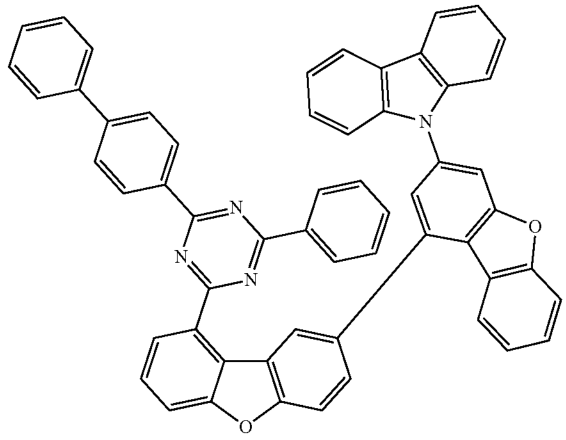
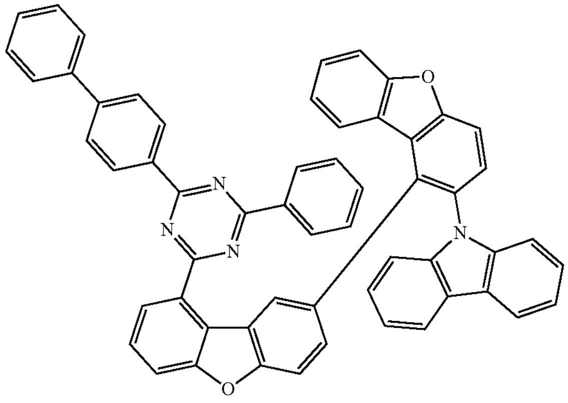
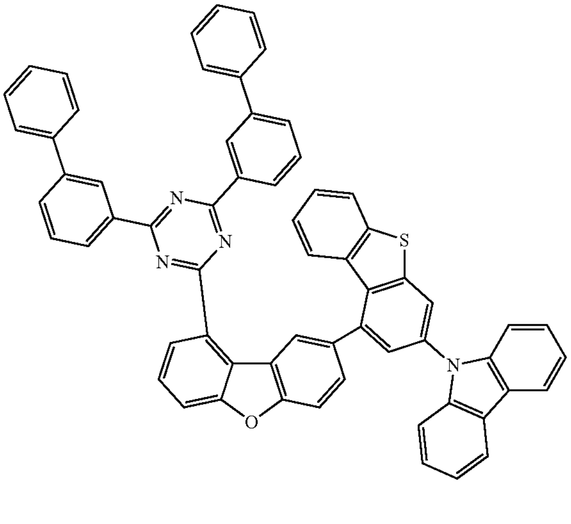
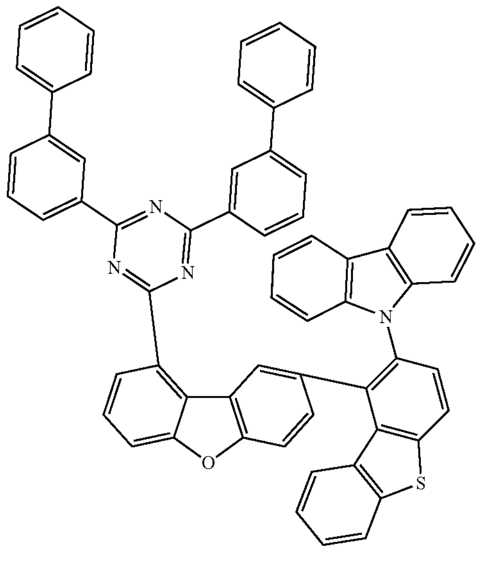

-continued
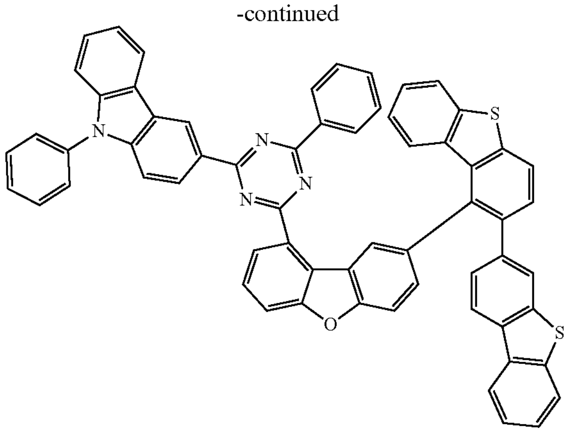
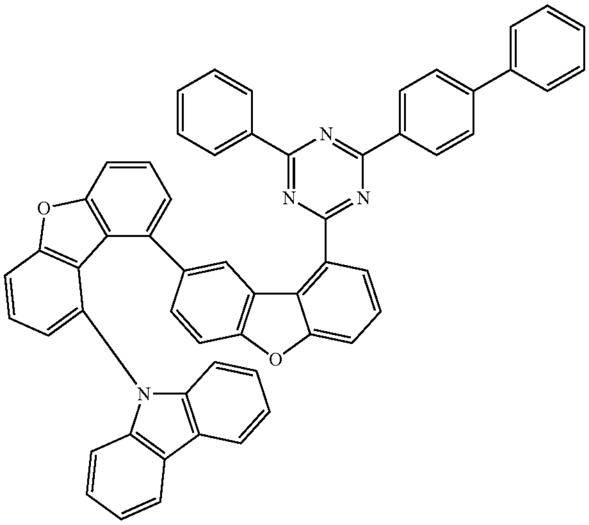
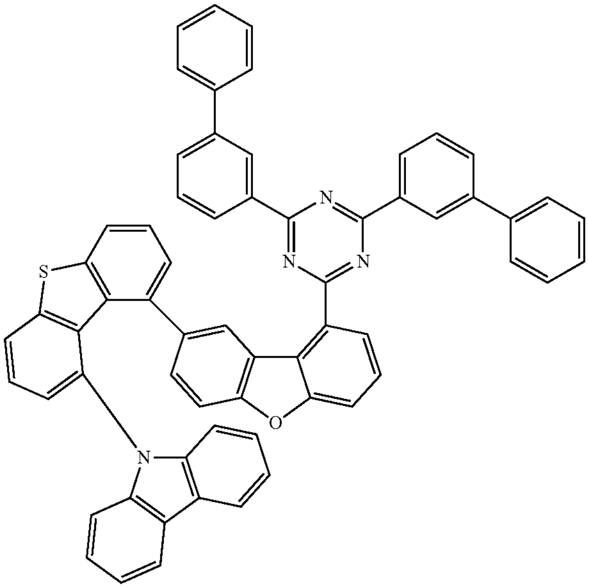

-continued
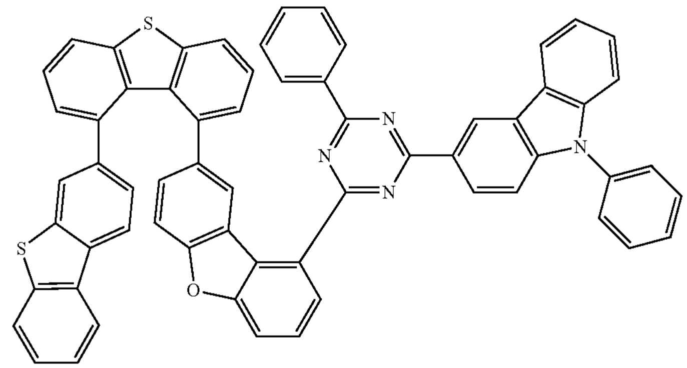
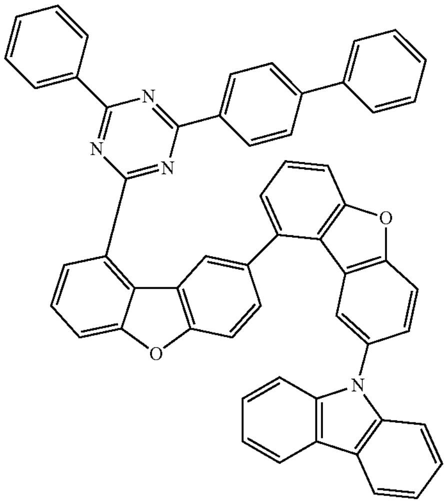
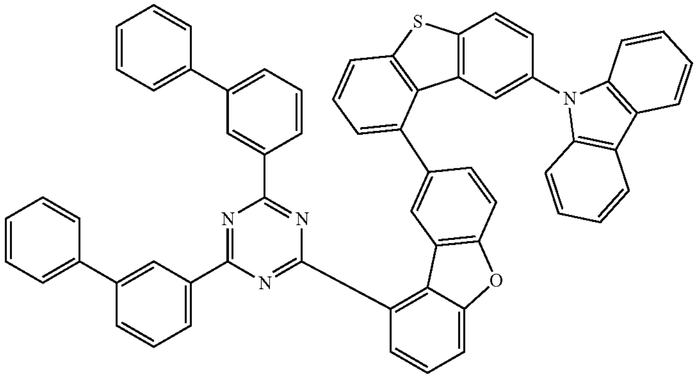
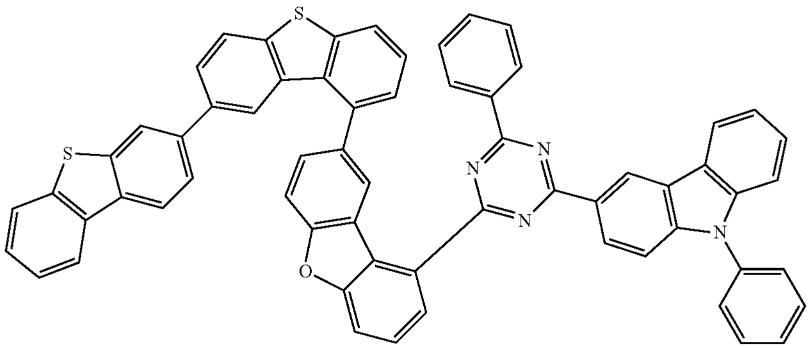
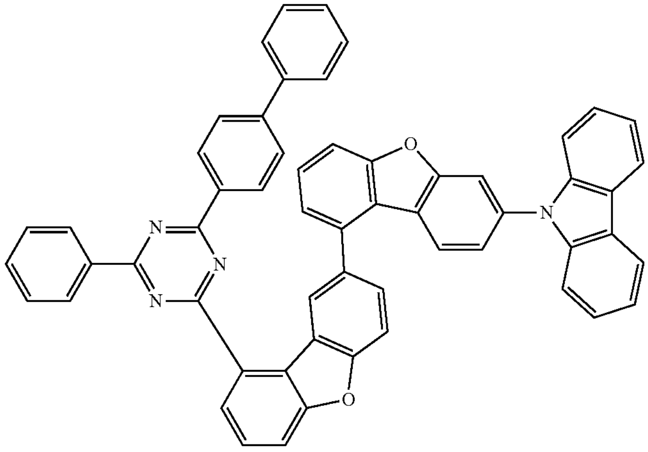

-continued
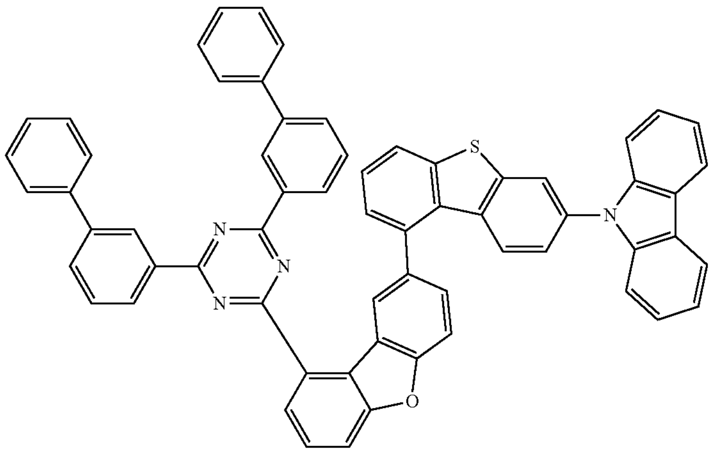
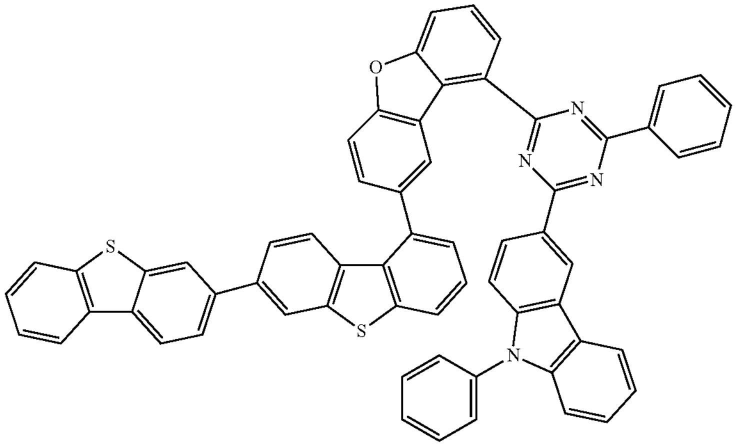
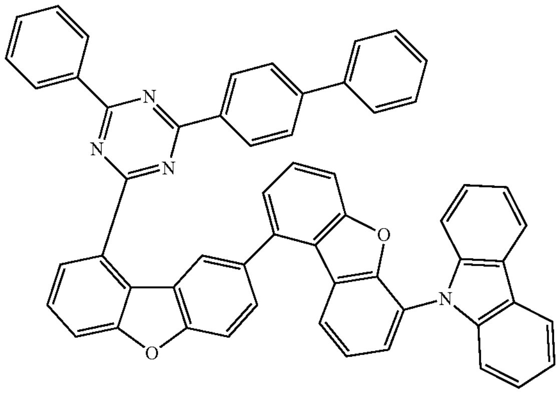
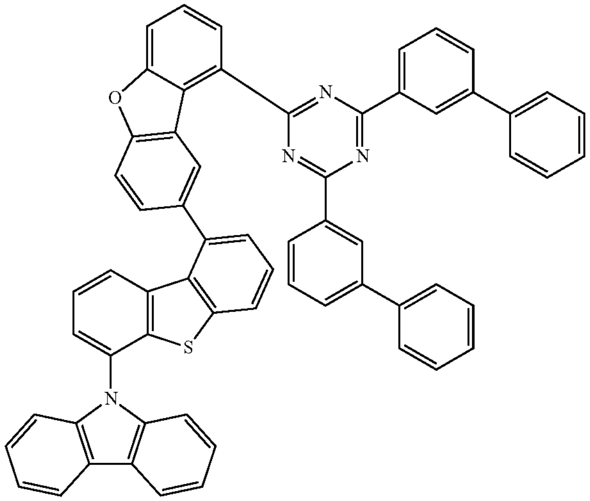

-continued
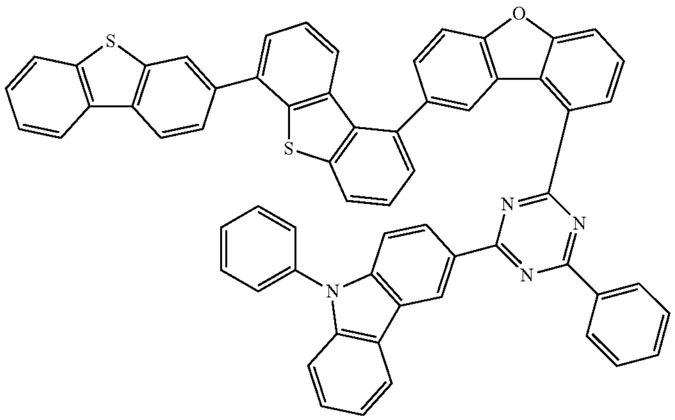
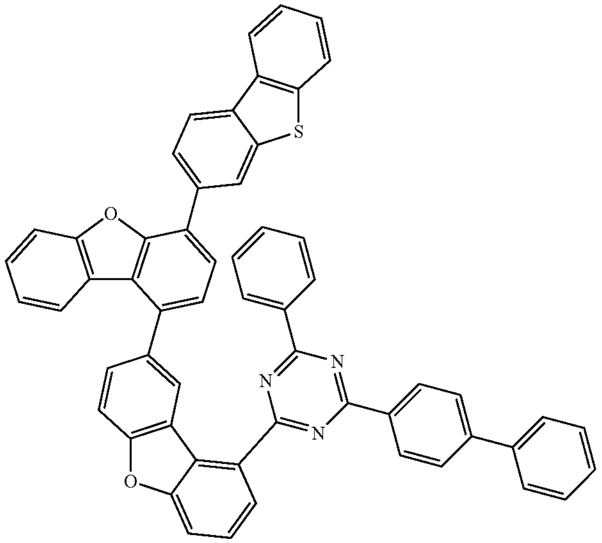
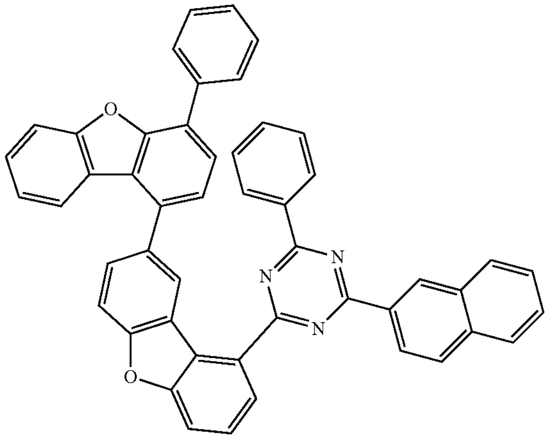
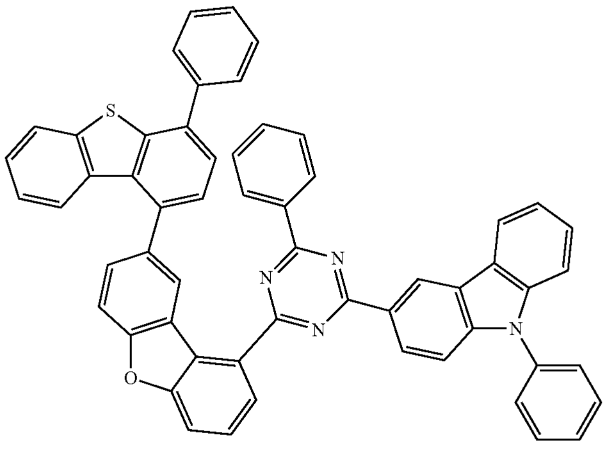

-continued
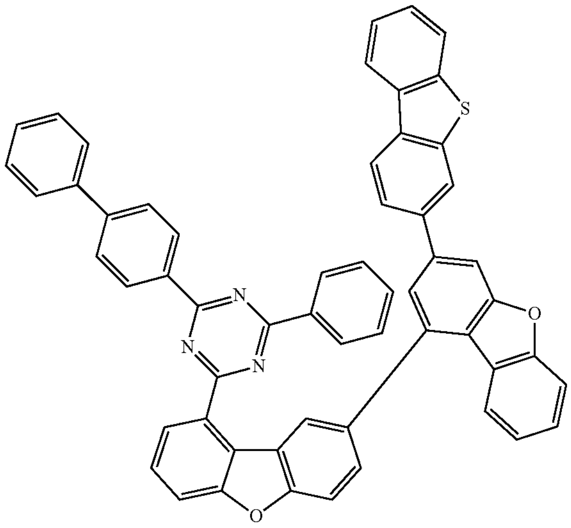
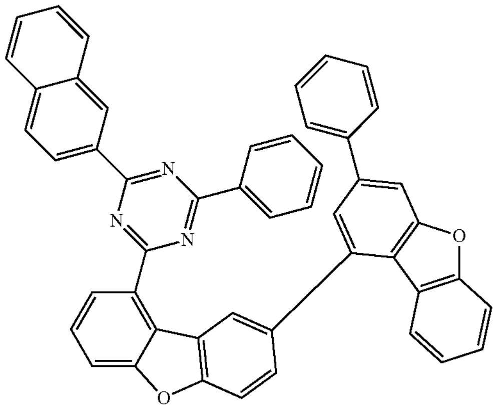
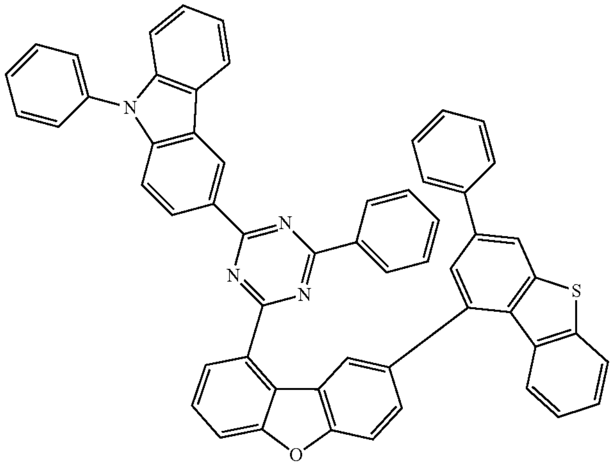
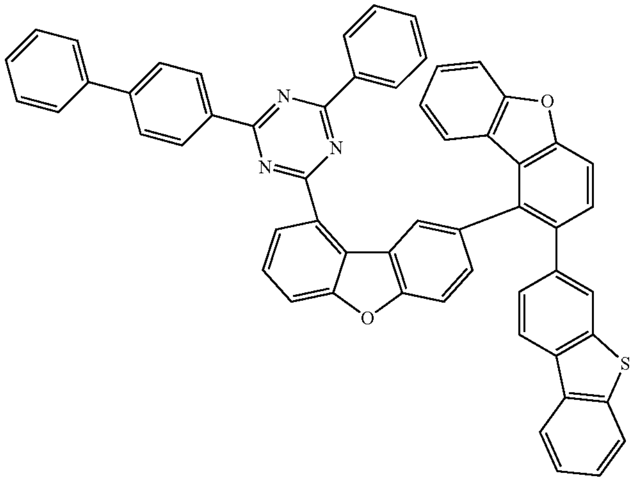

-continued
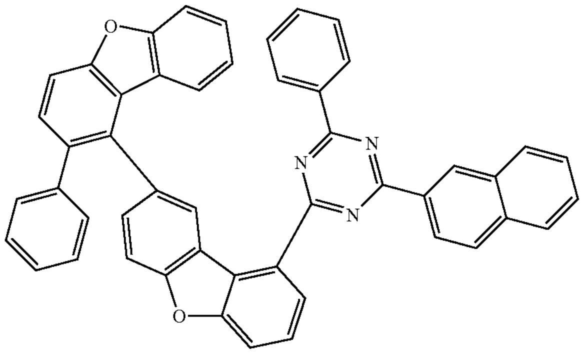
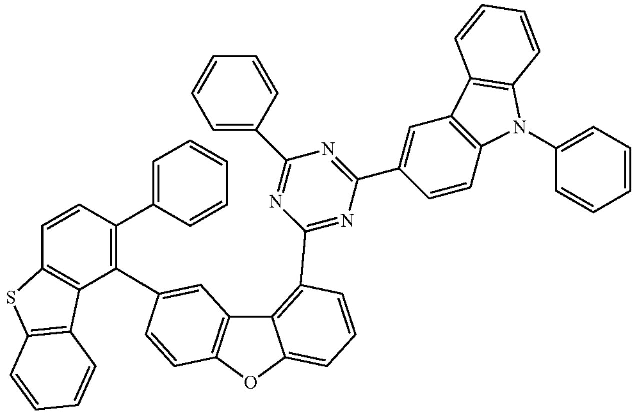
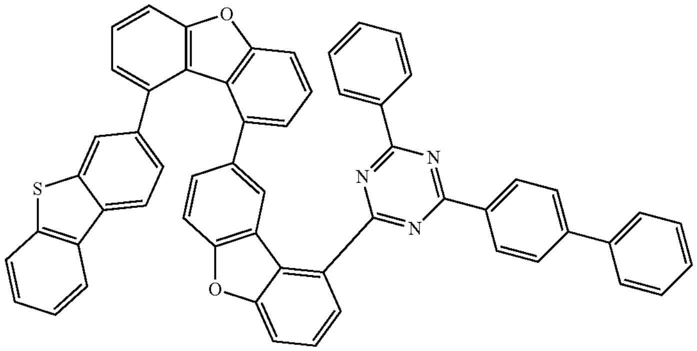
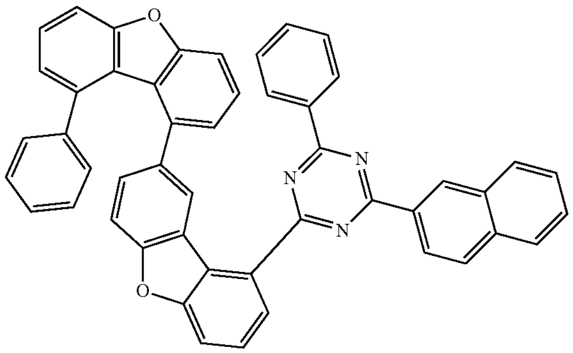

-continued
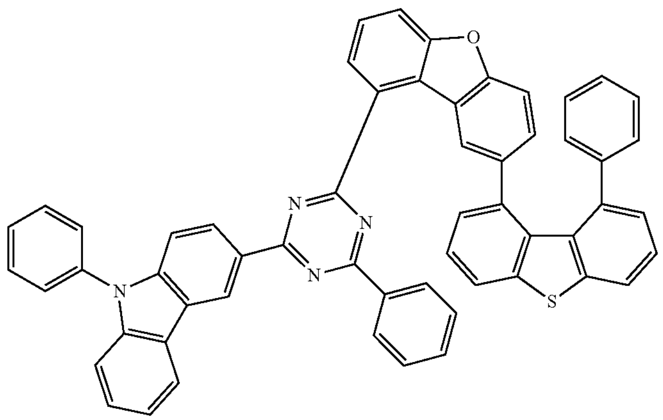
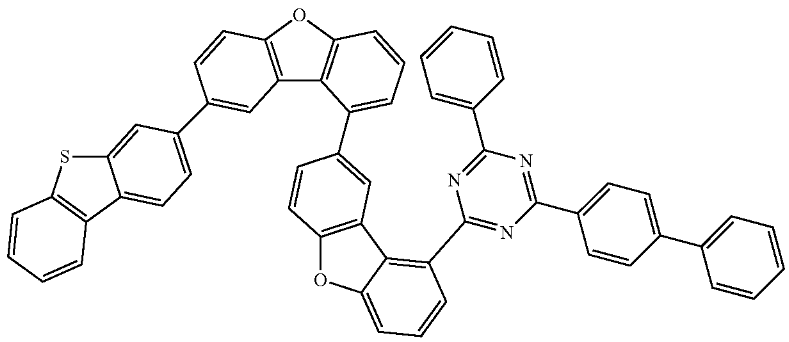
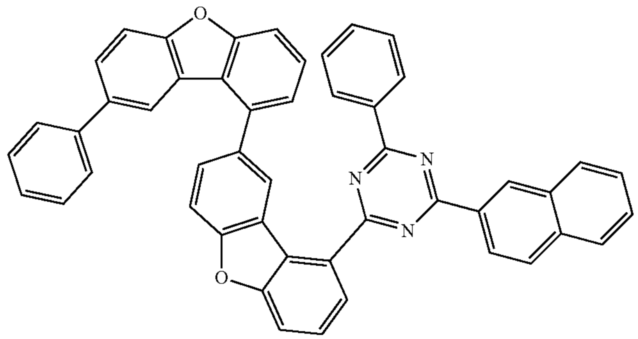
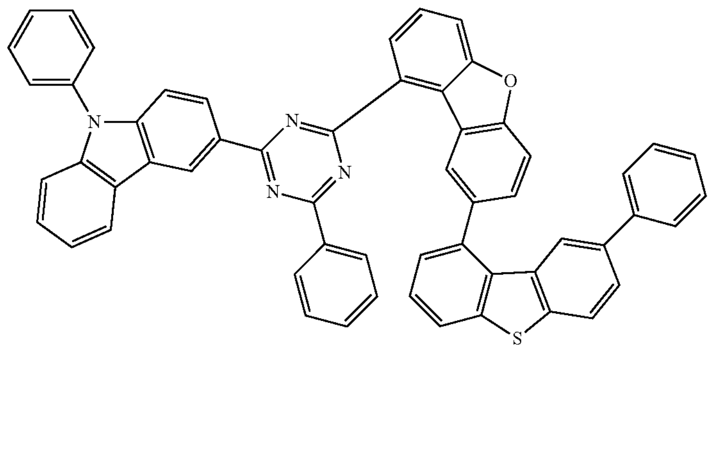

-continued
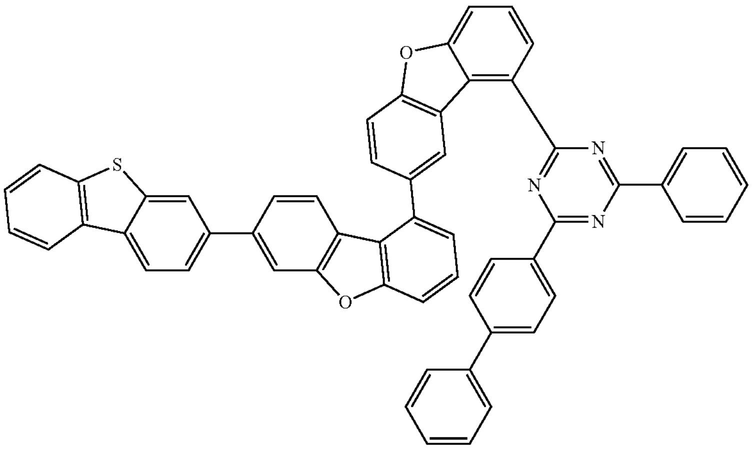
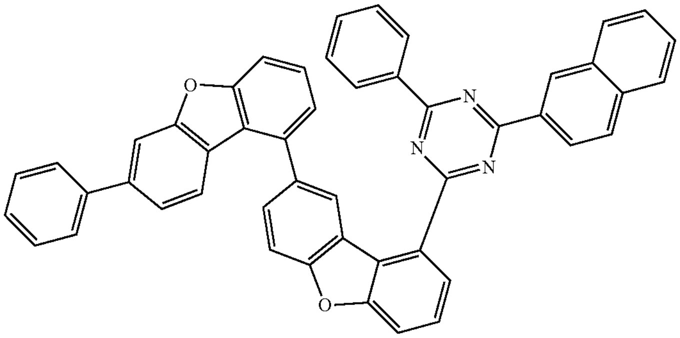
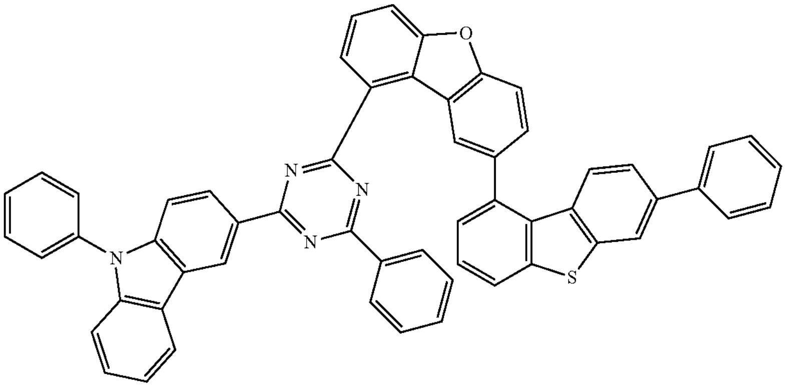
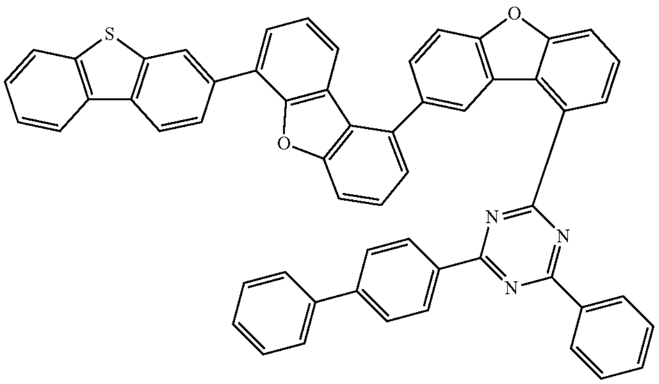

-continued
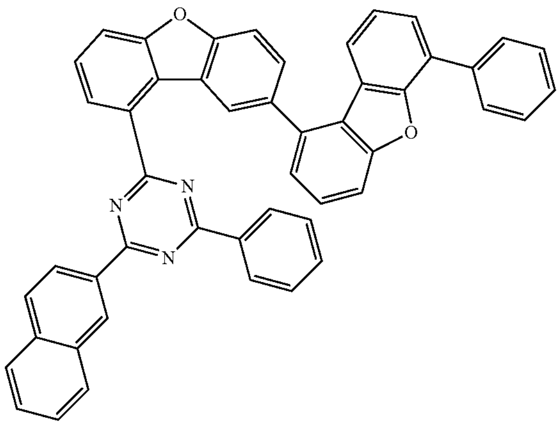
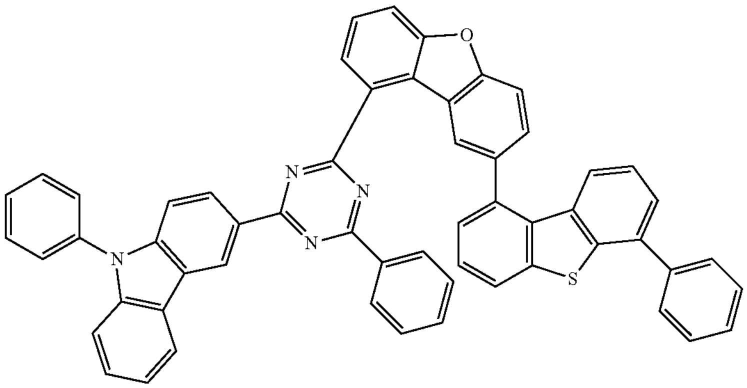
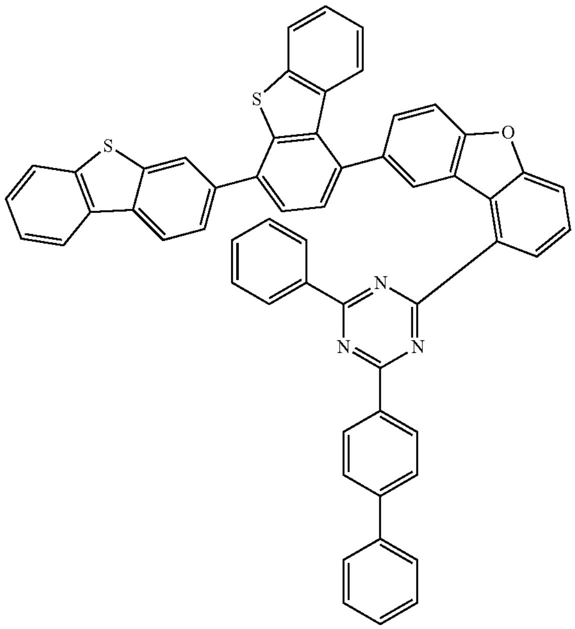
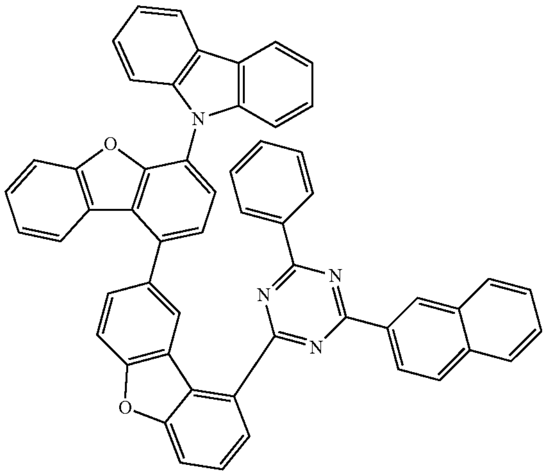

-continued
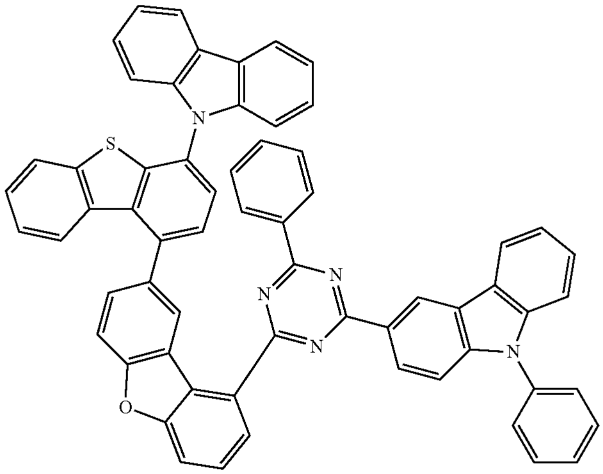
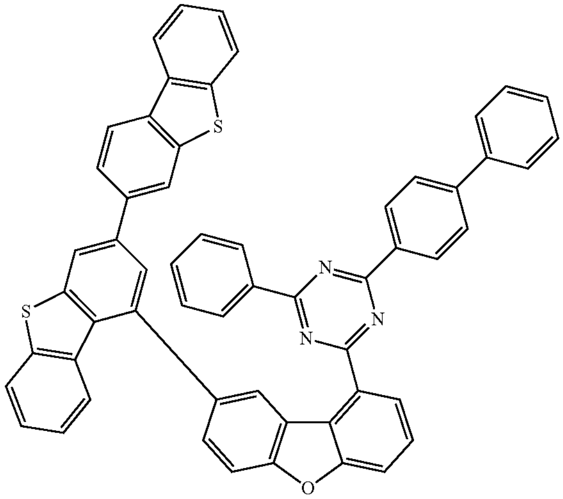
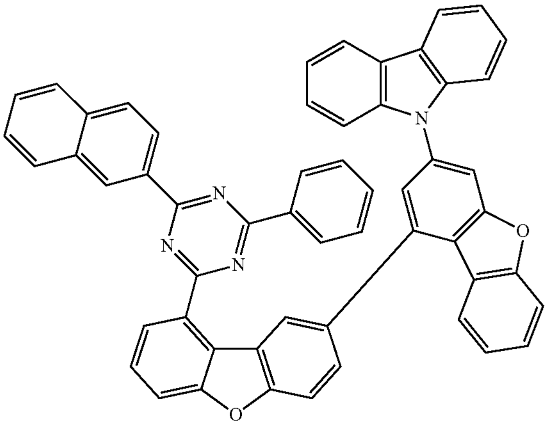
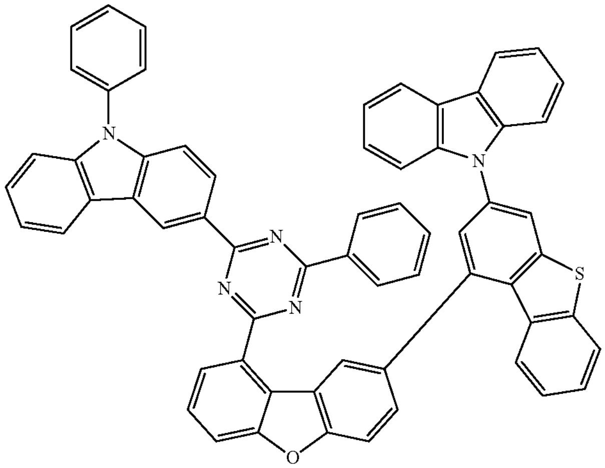

-continued
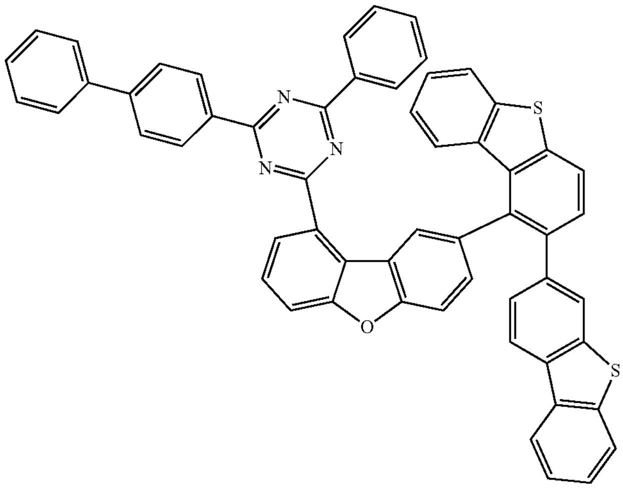
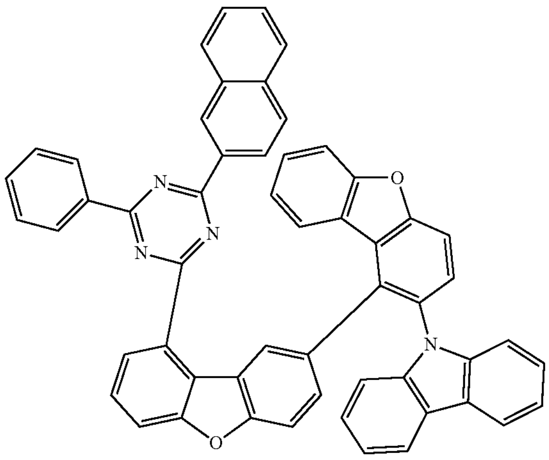
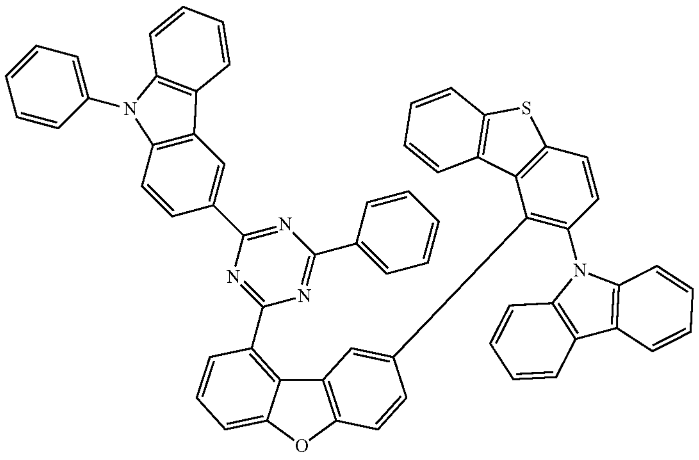

-continued
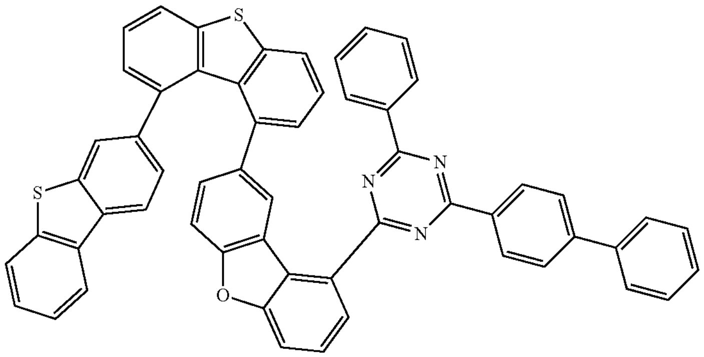
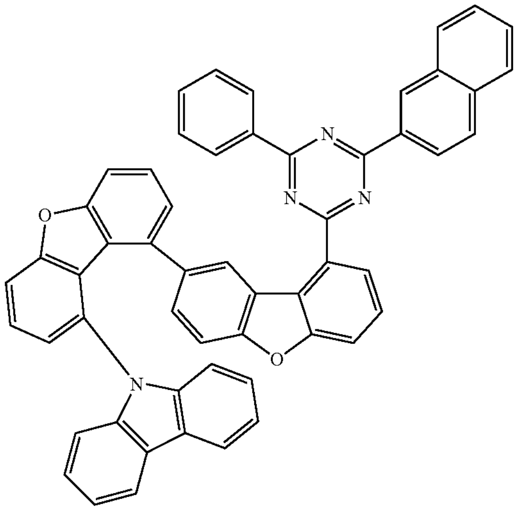
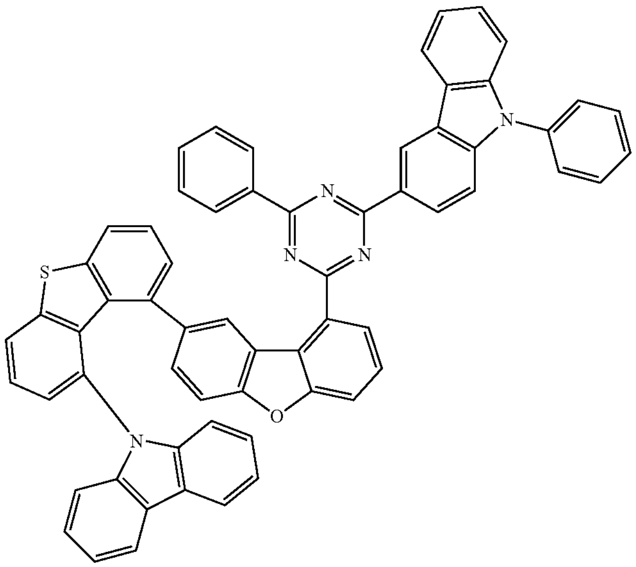

-continued
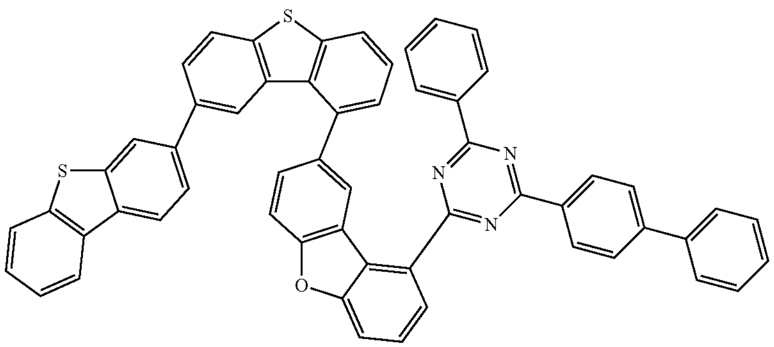
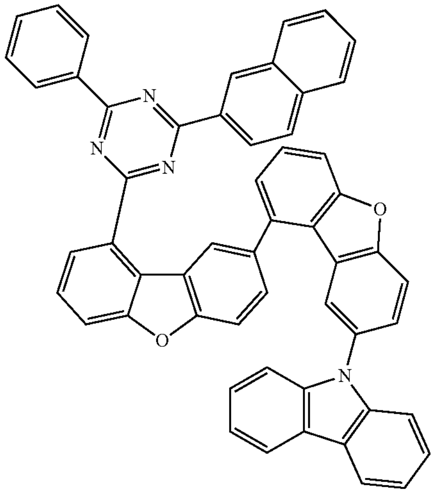
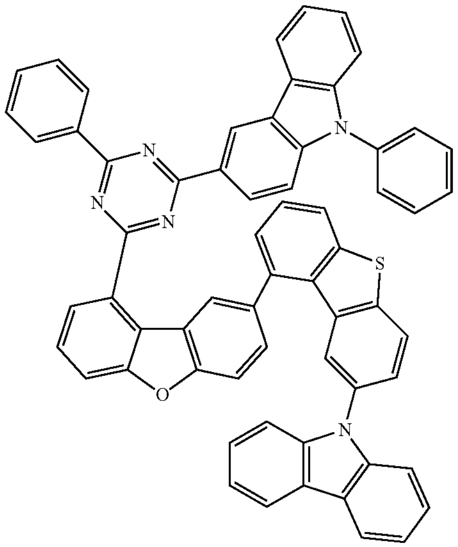
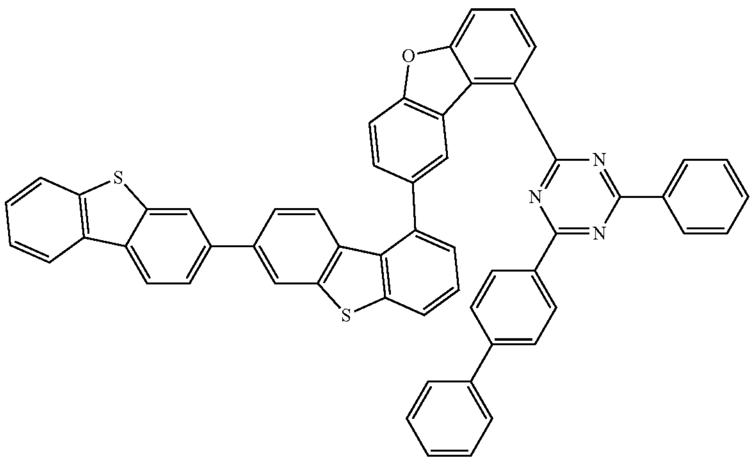

-continued
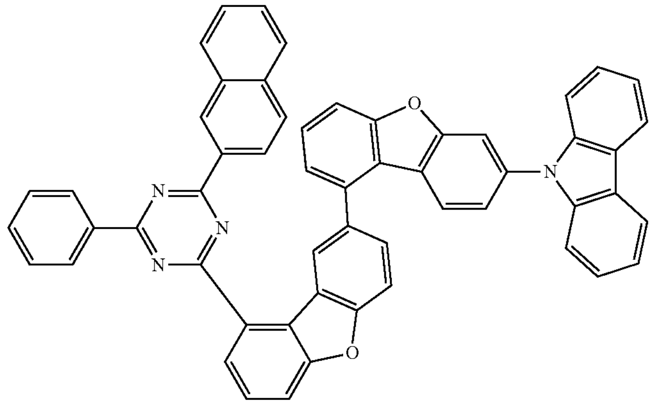
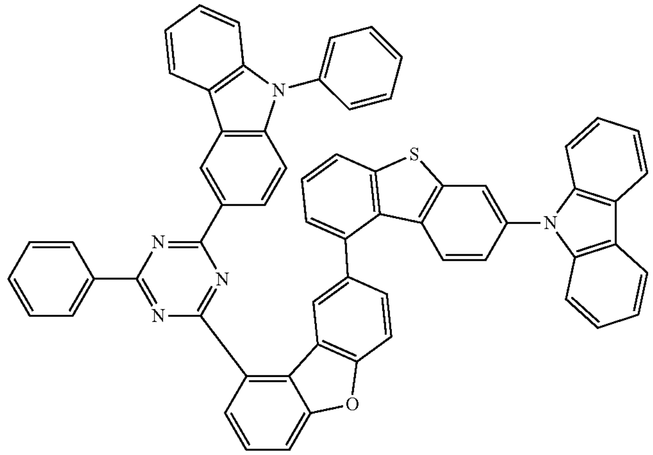
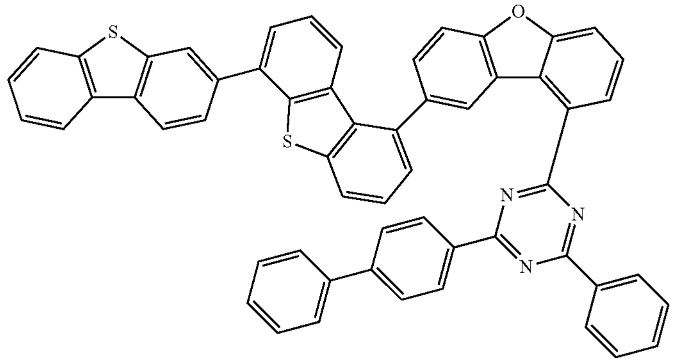
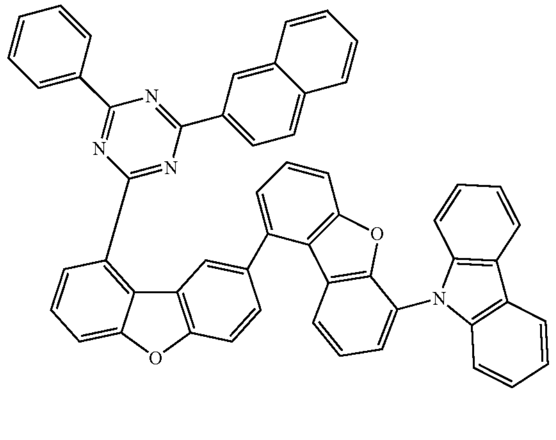
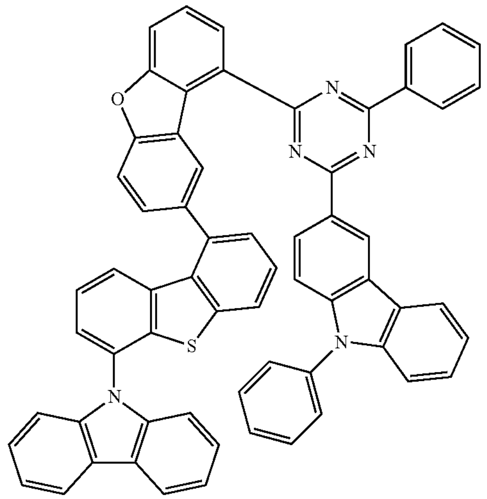

-continued
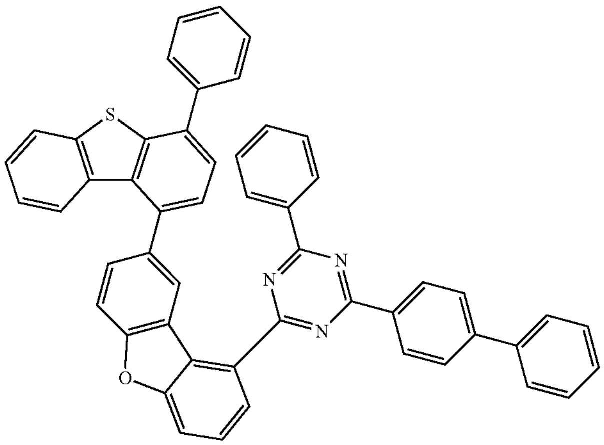
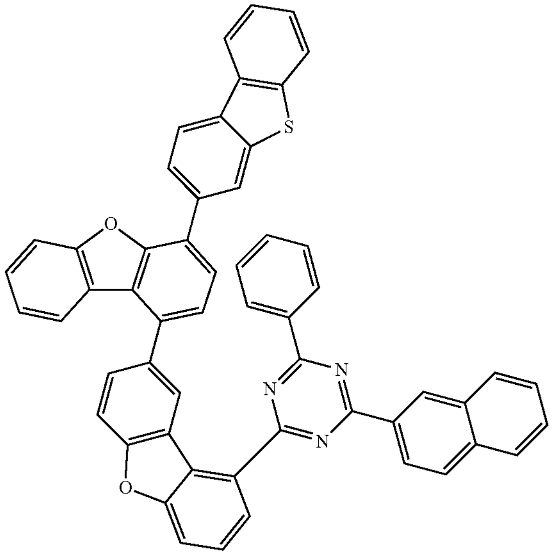
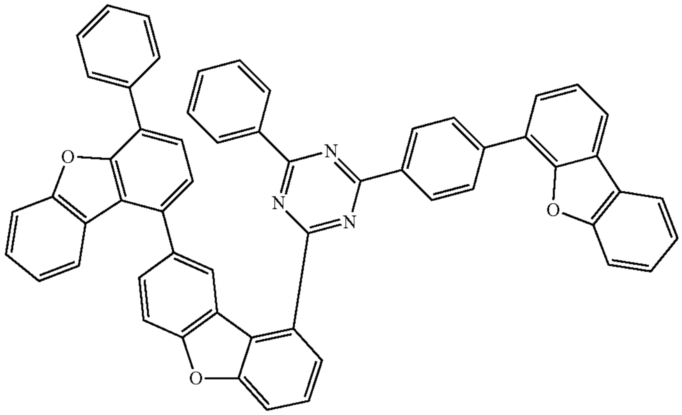

-continued
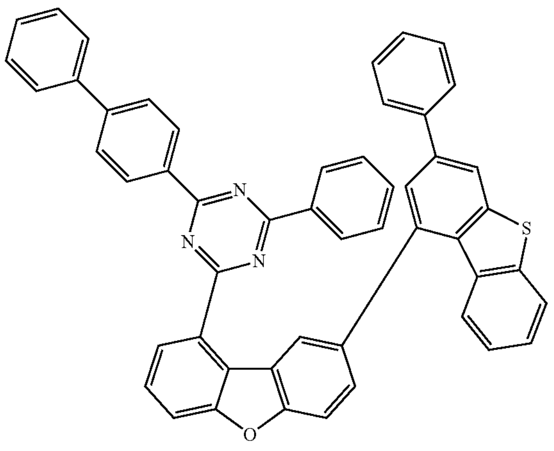
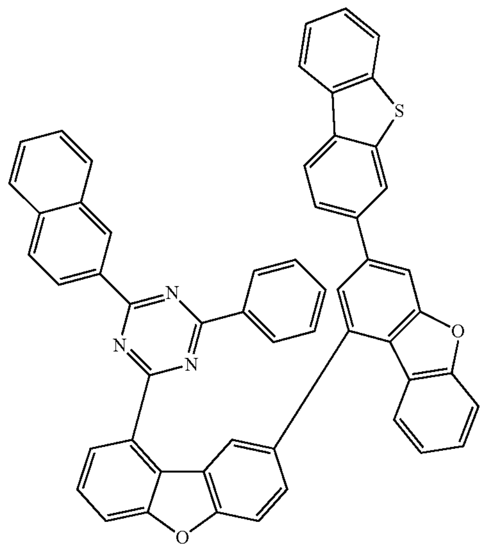
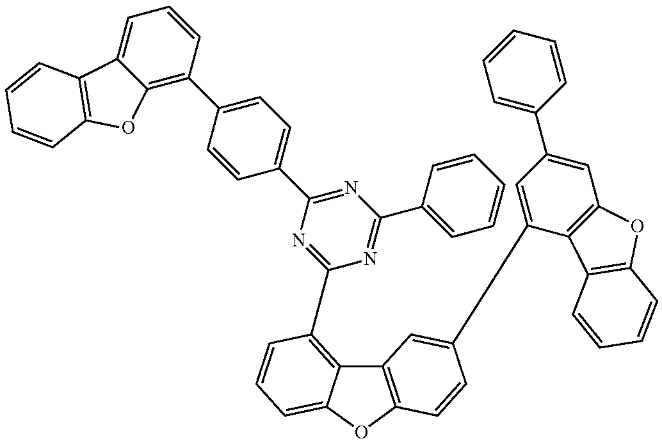
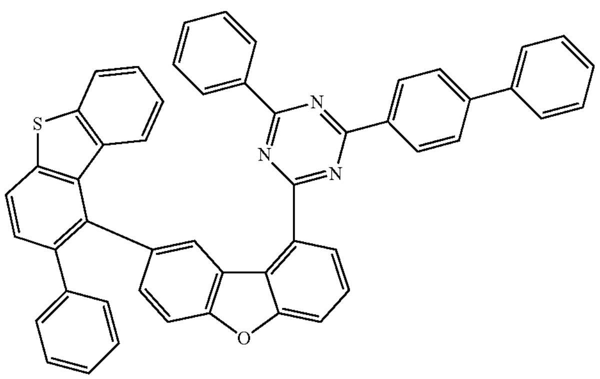
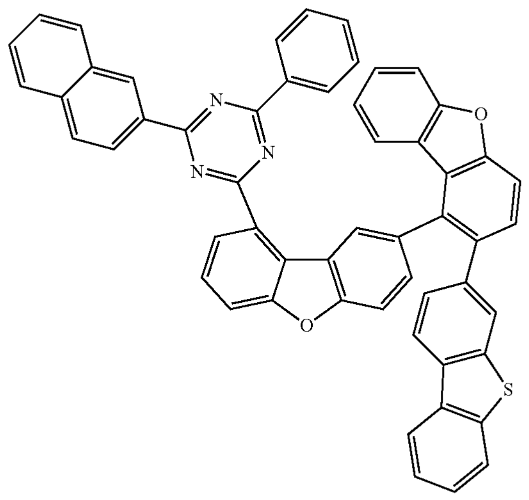

-continued
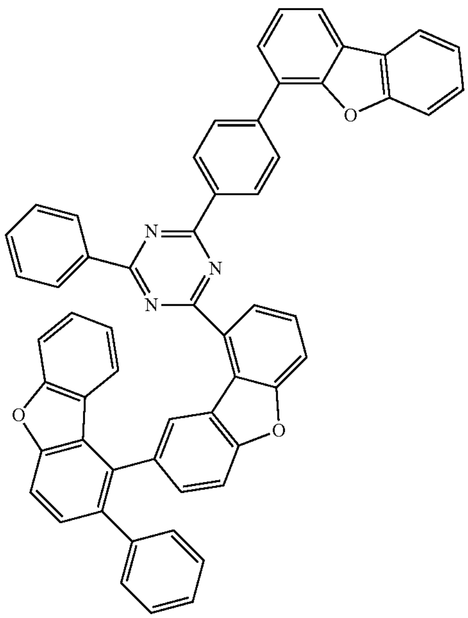
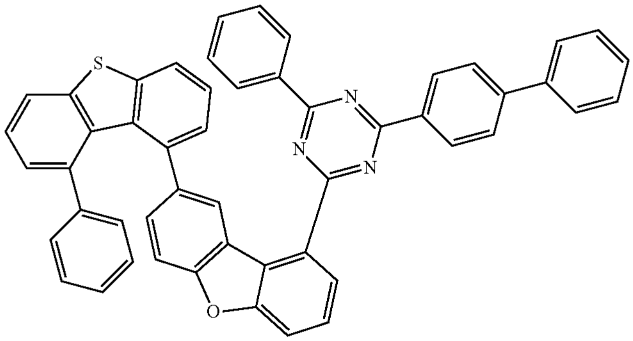
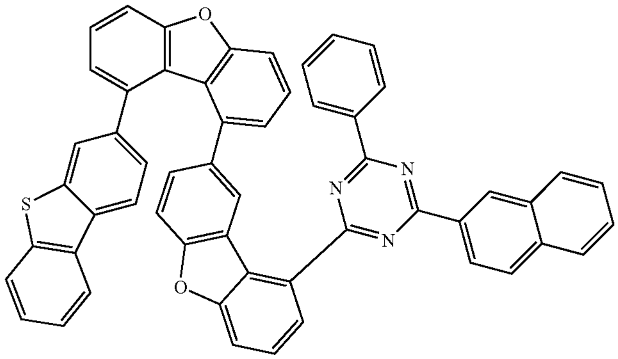
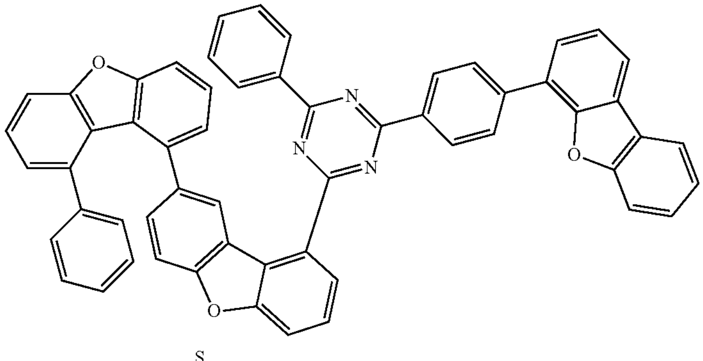
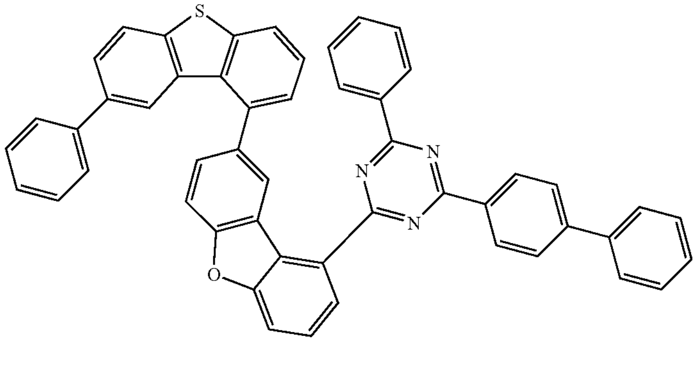

-continued
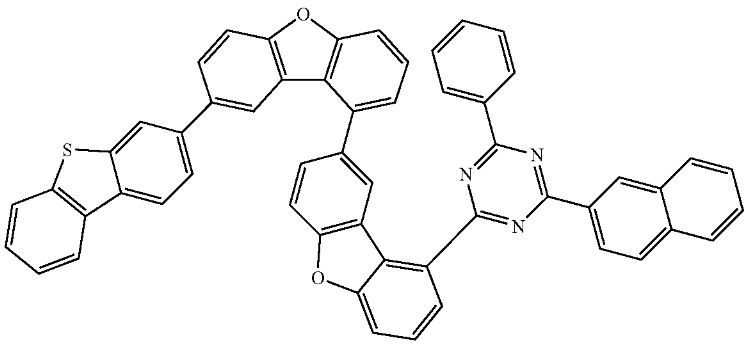
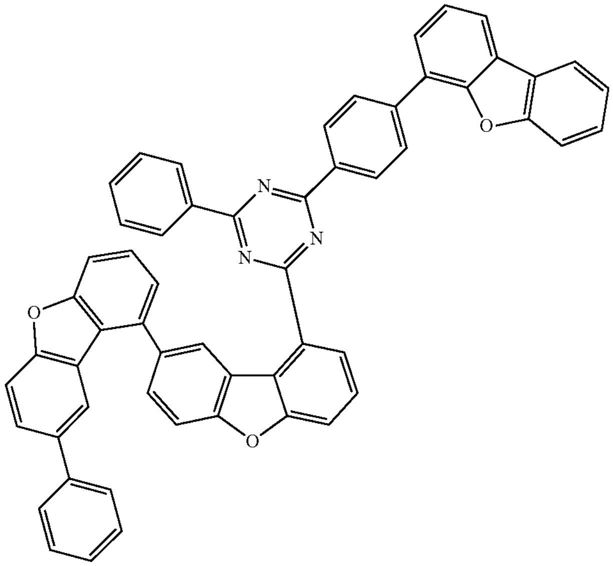
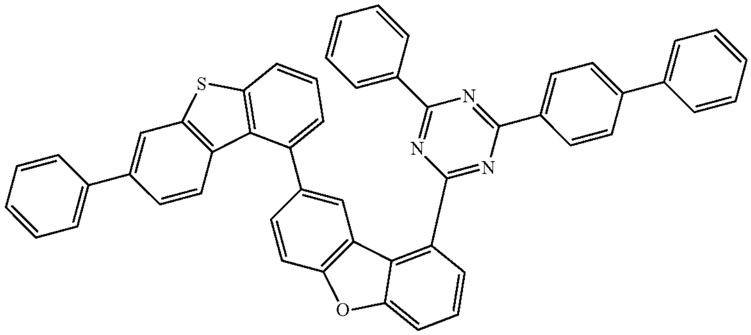
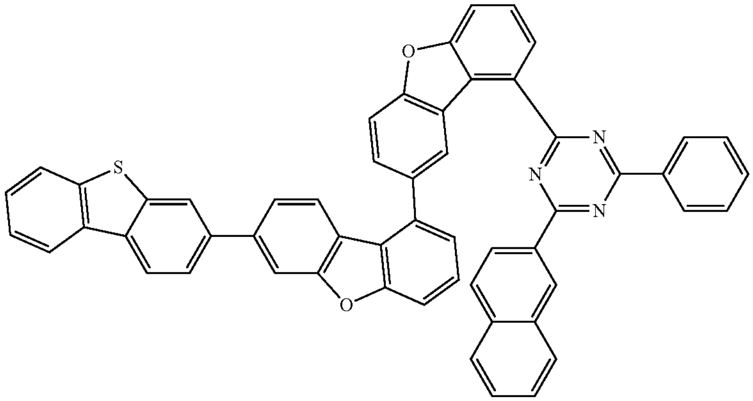

-continued
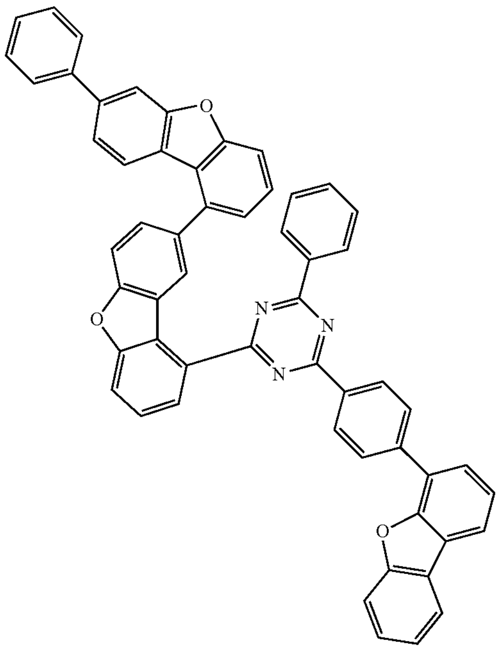
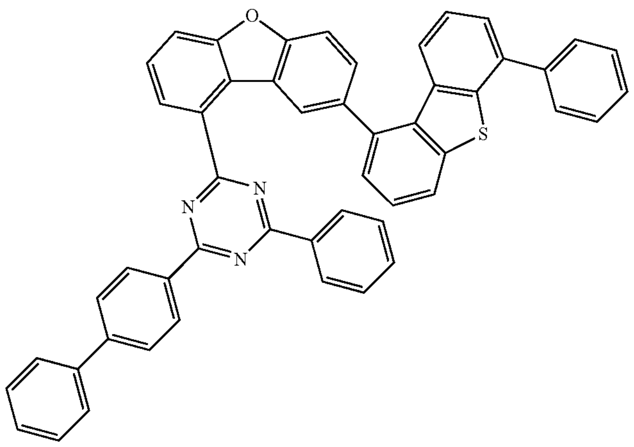
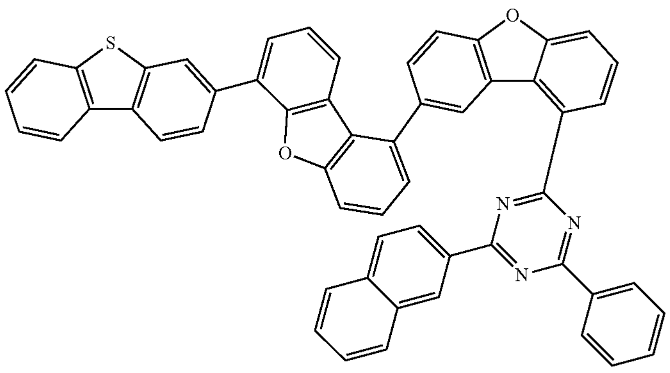
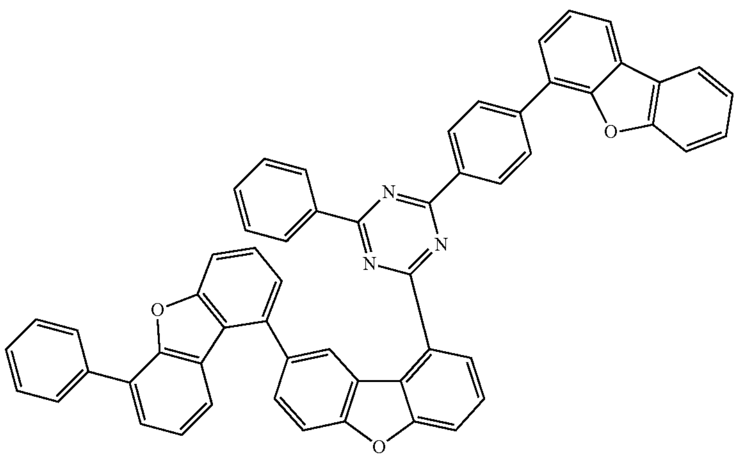

-continued
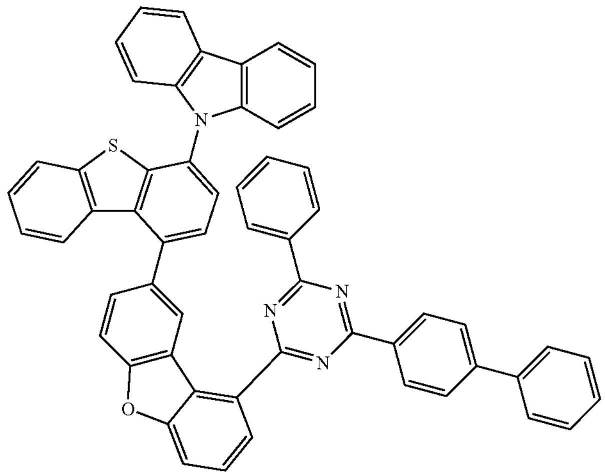
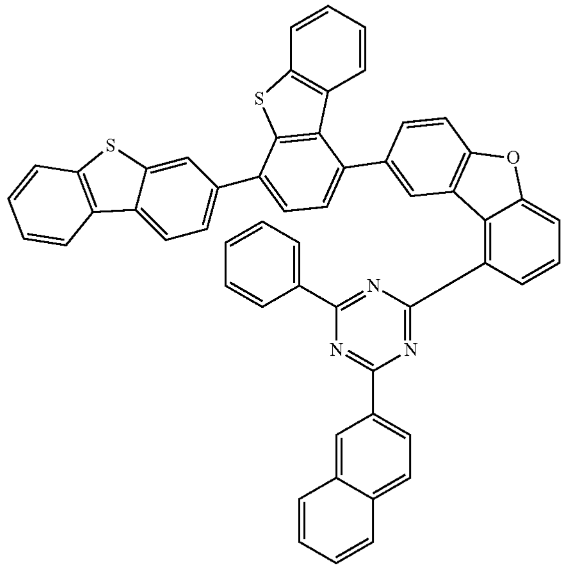
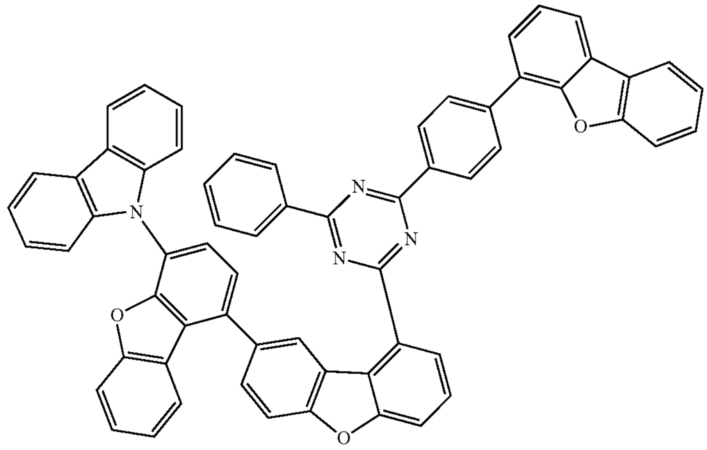

-continued
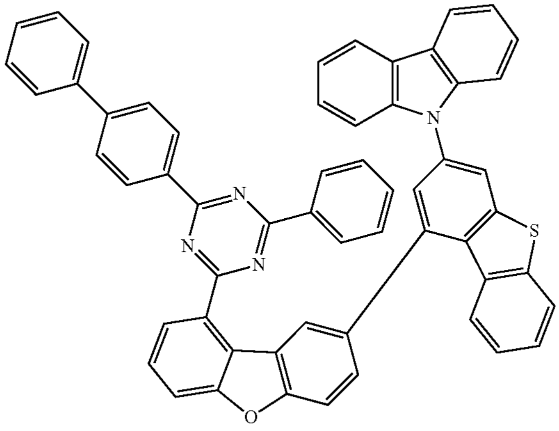
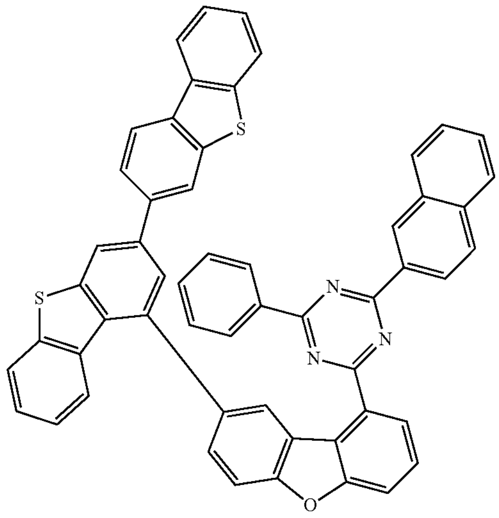
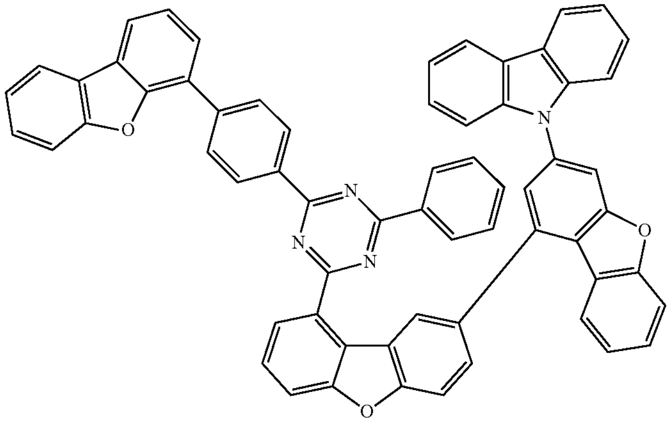
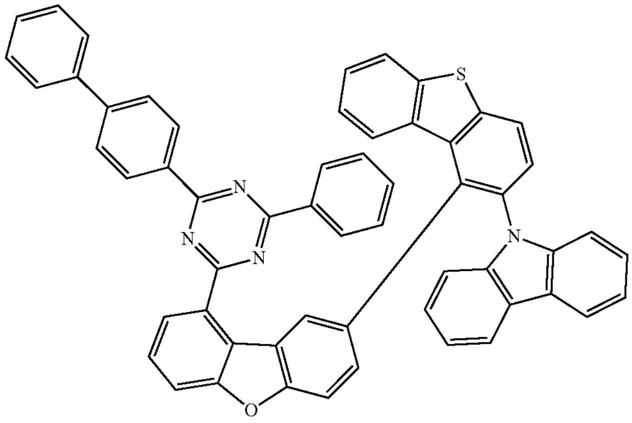

-continued
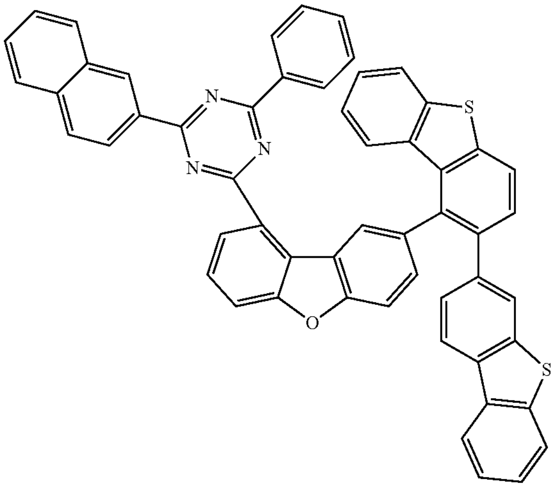
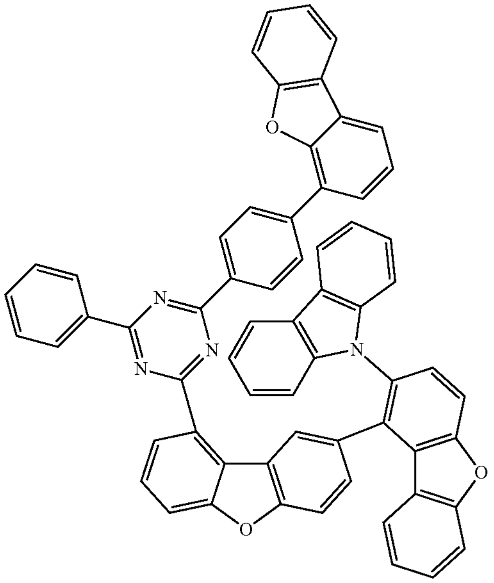
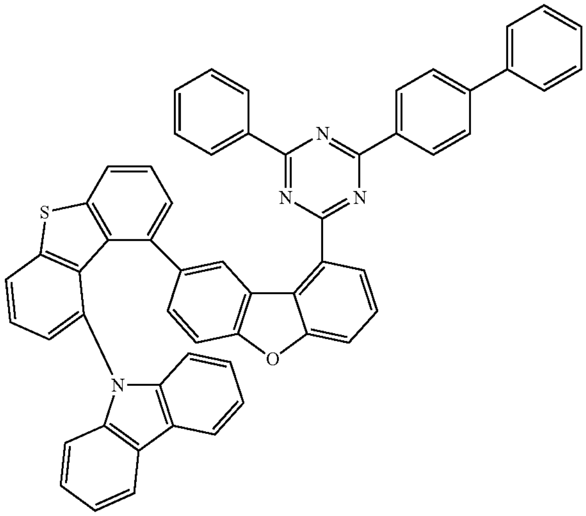
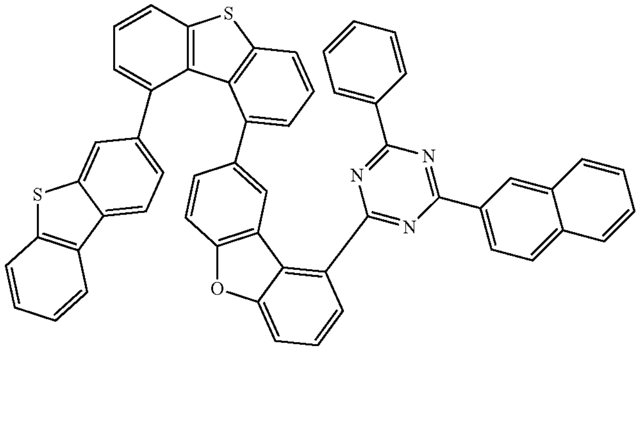

-continued
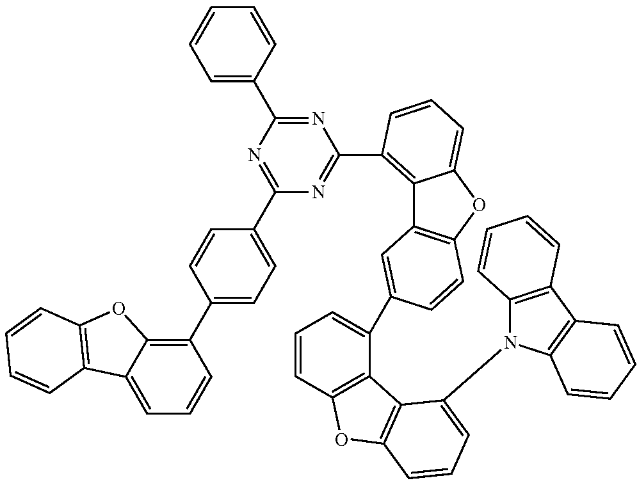
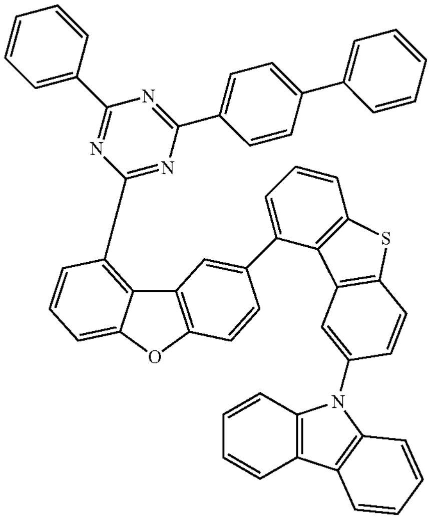
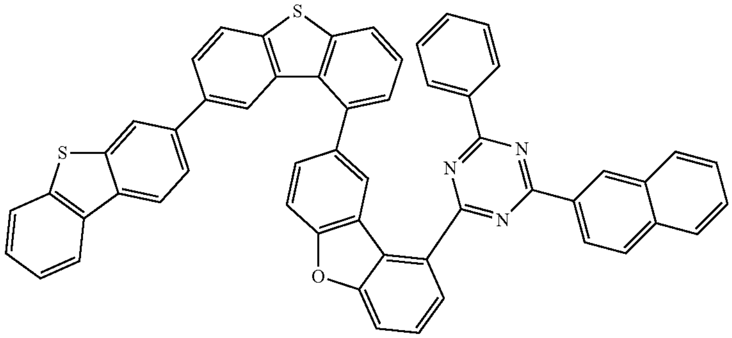
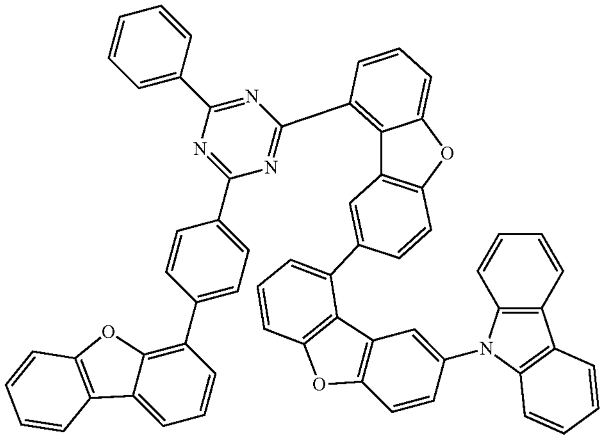
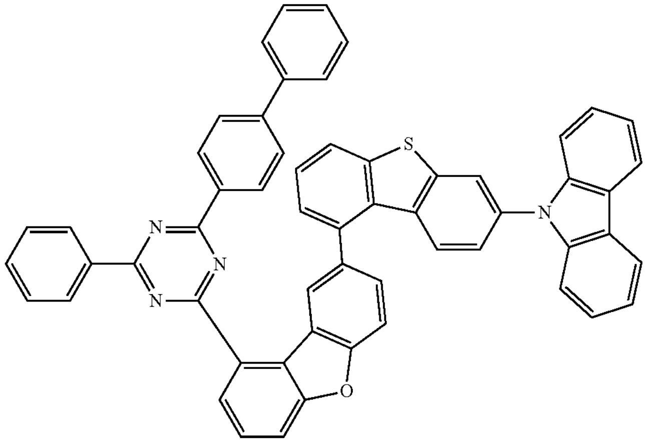

-continued
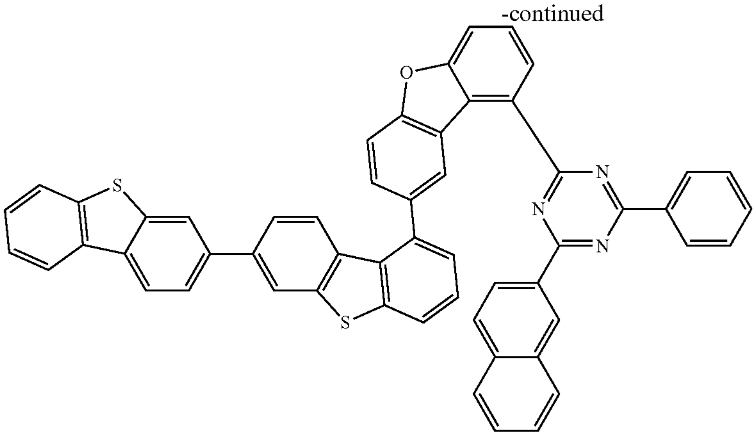
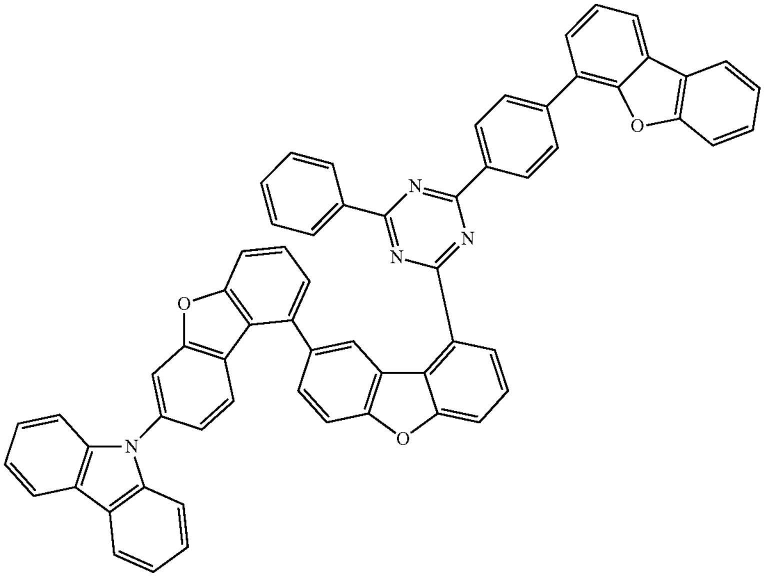
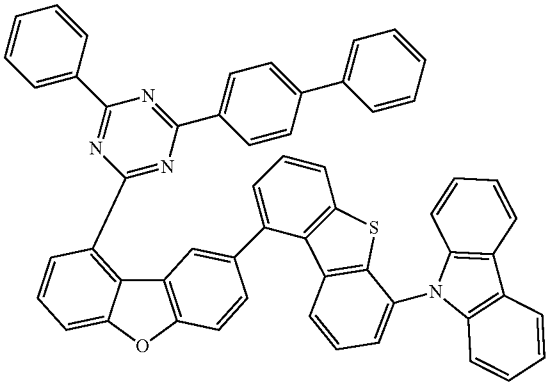
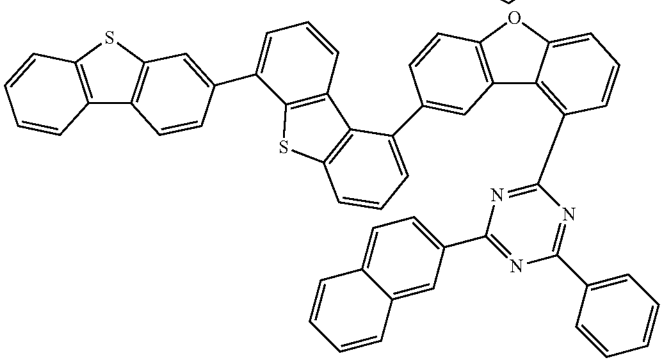

-continued
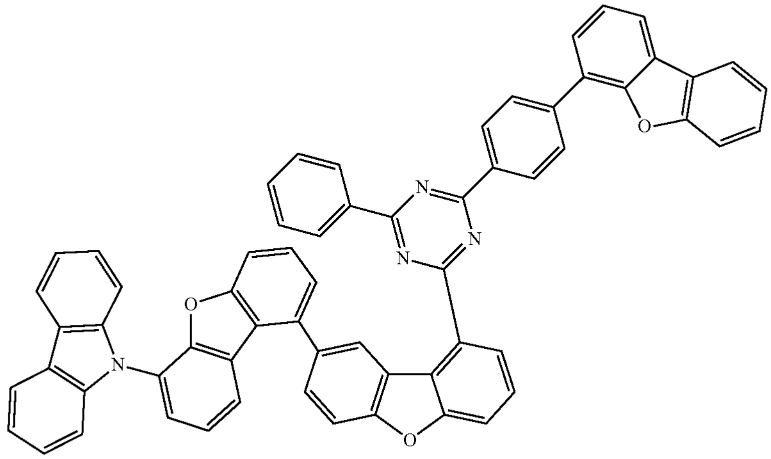
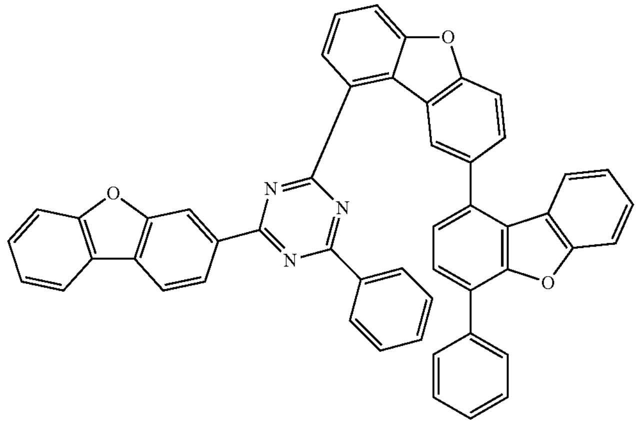
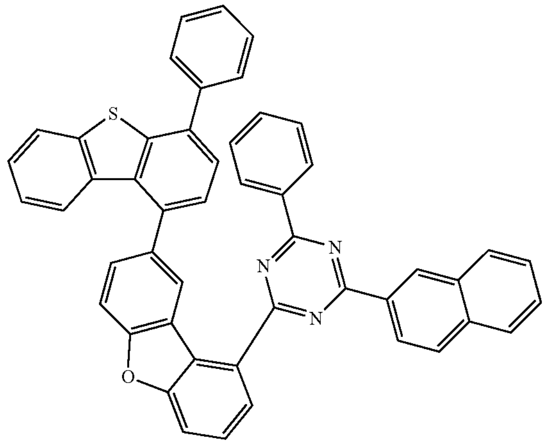

-continued
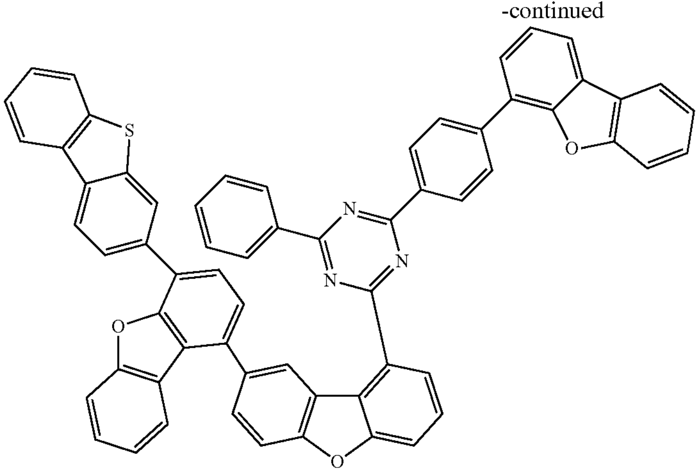
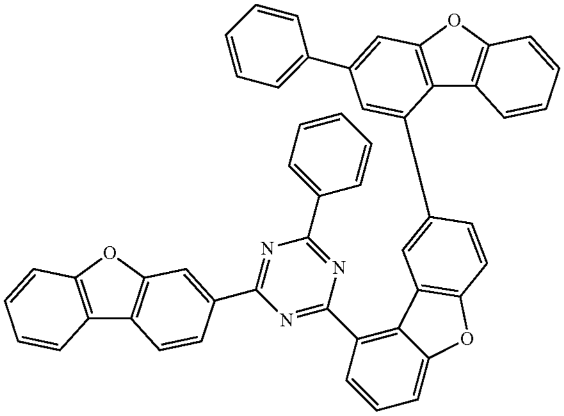
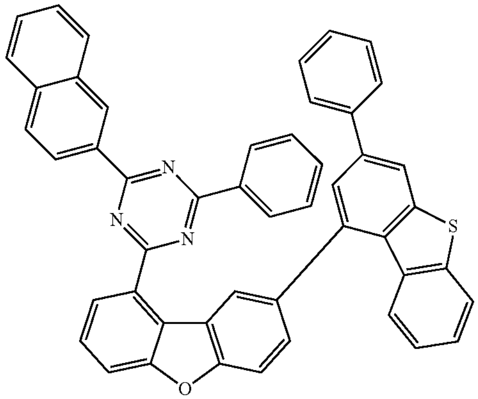
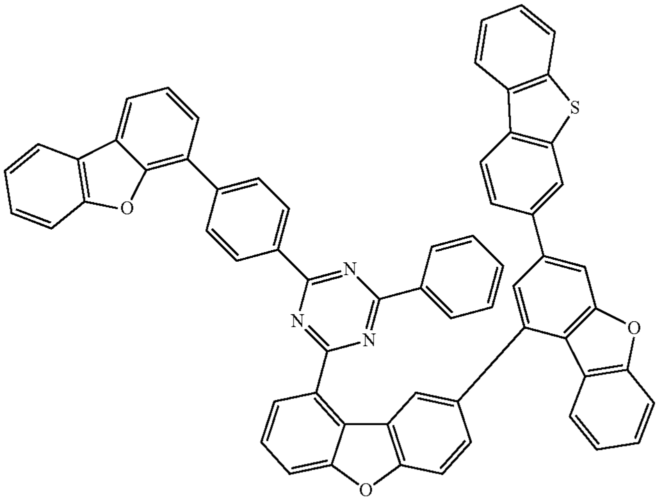
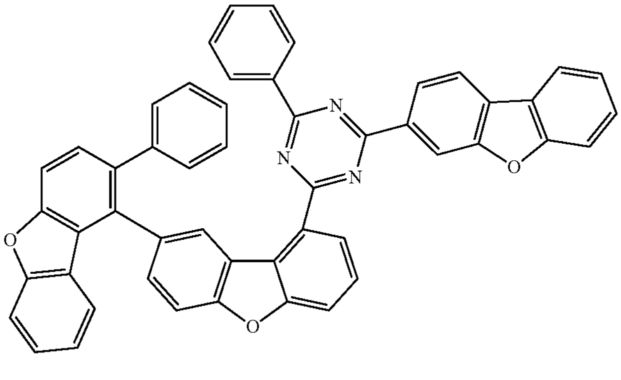

-continued
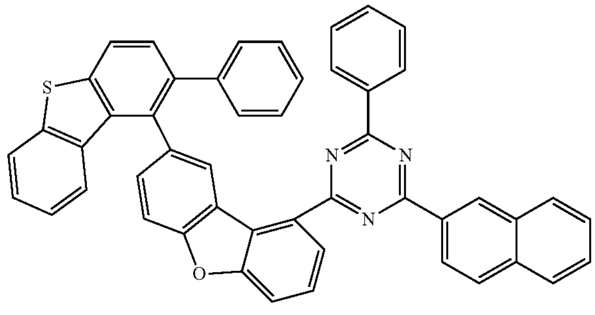
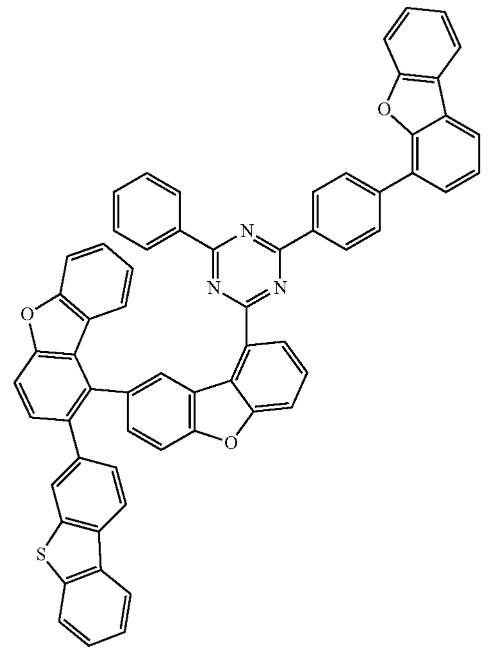
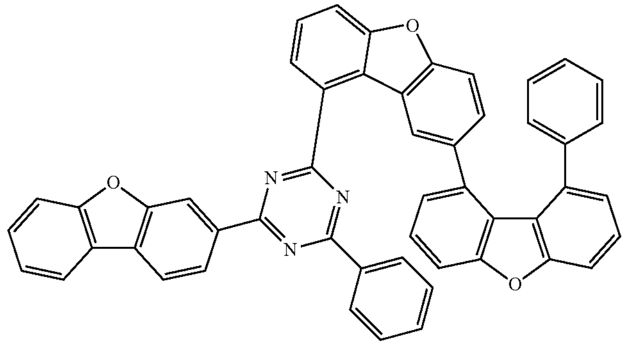
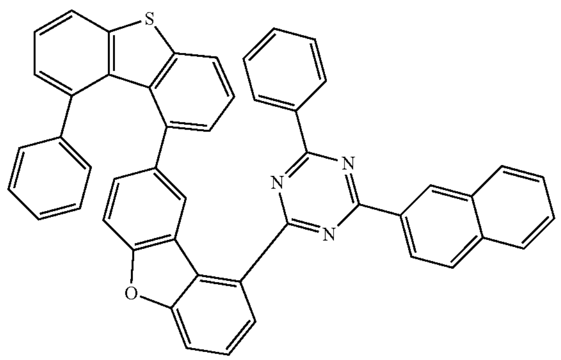

-continued
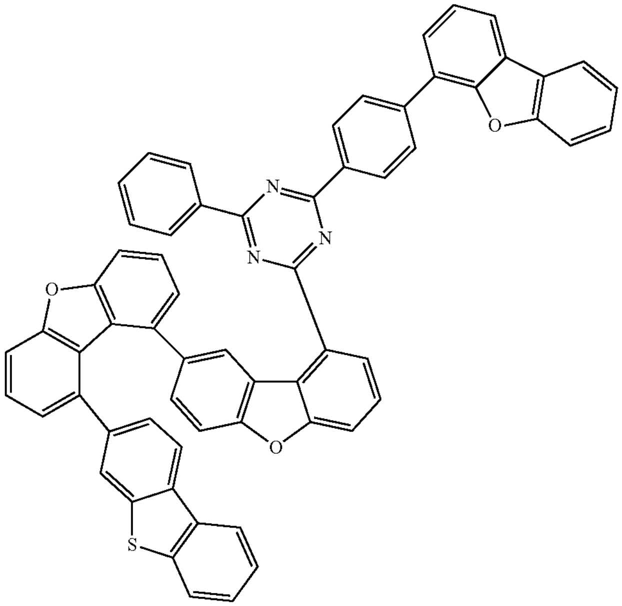
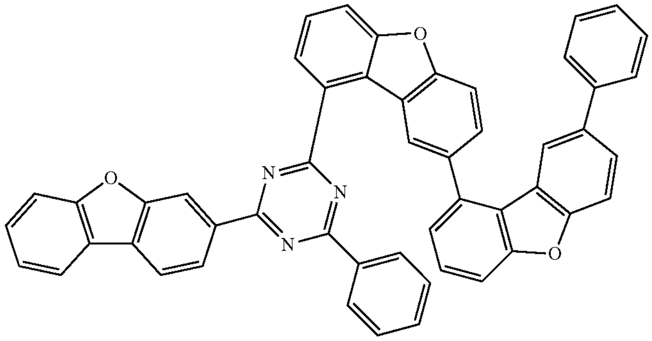
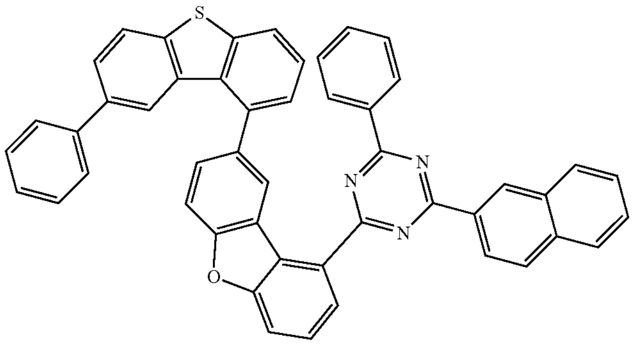
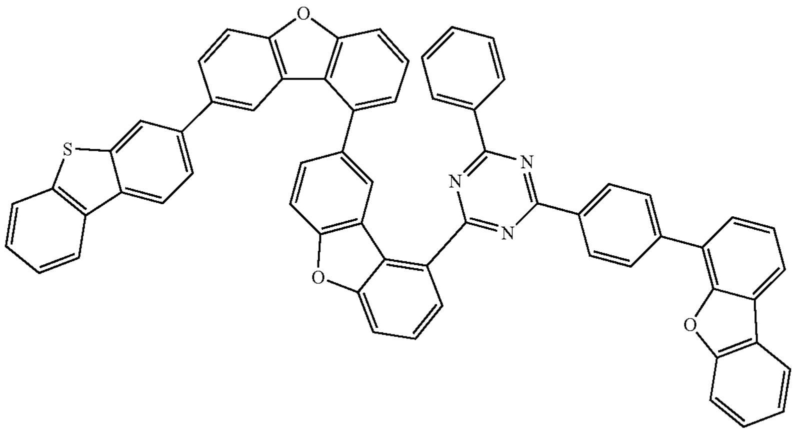

-continued
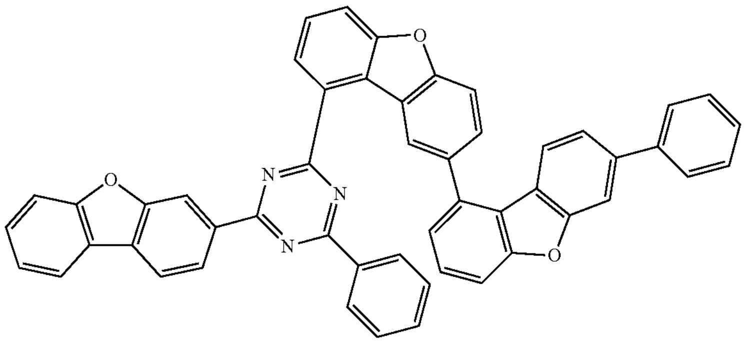
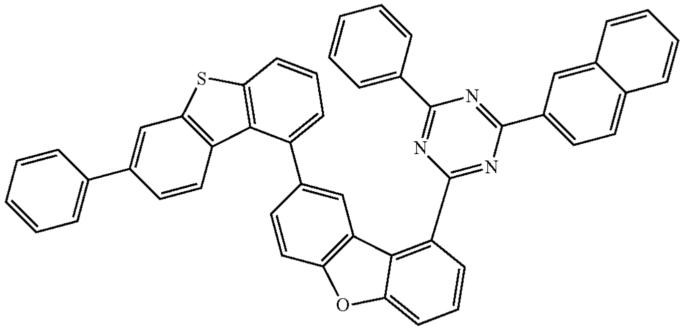
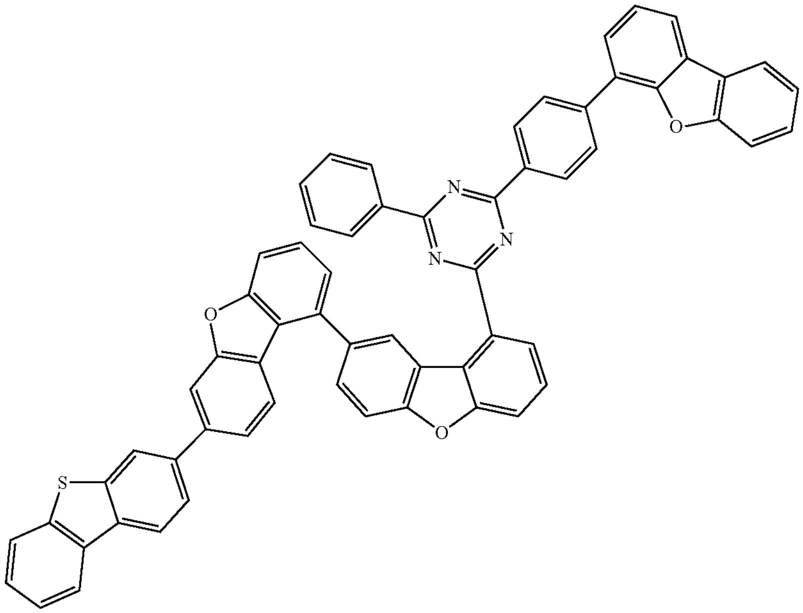
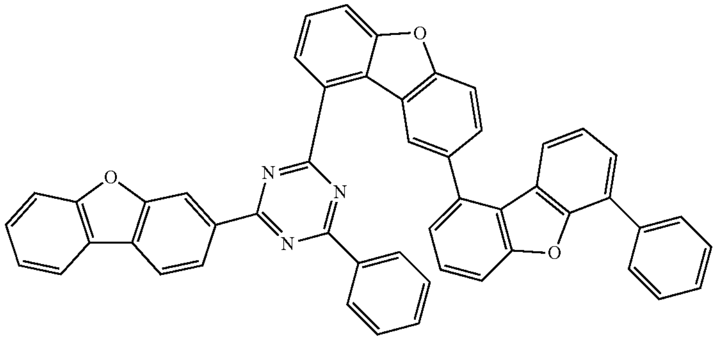

-continued
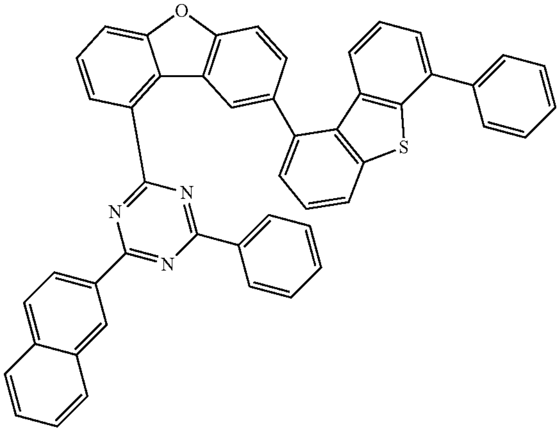
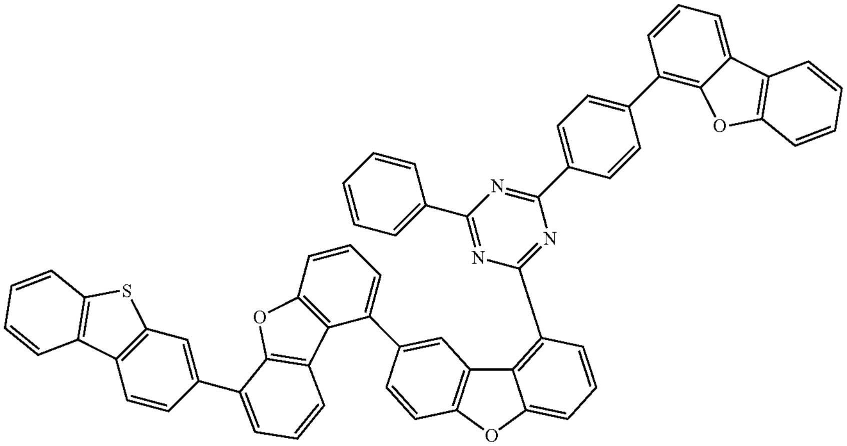
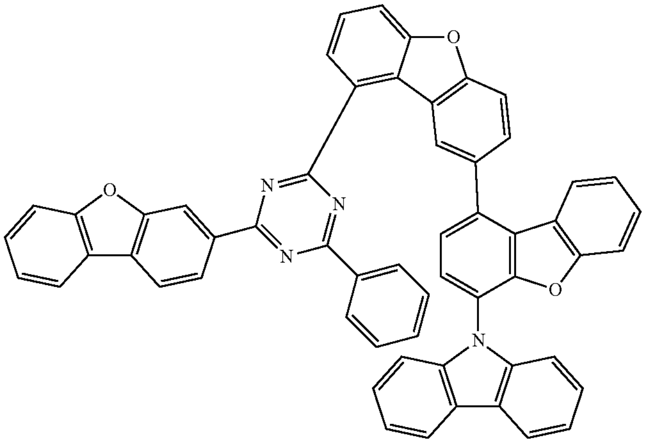

-continued
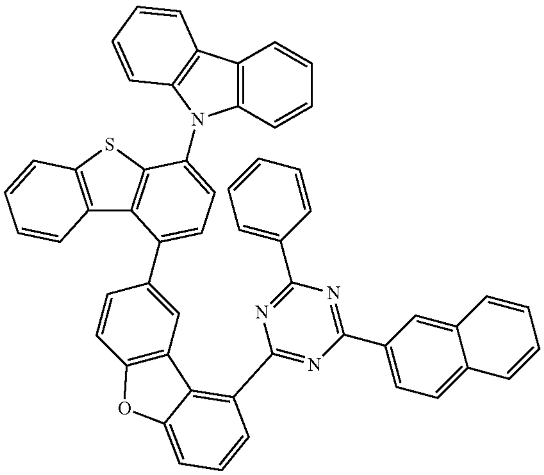
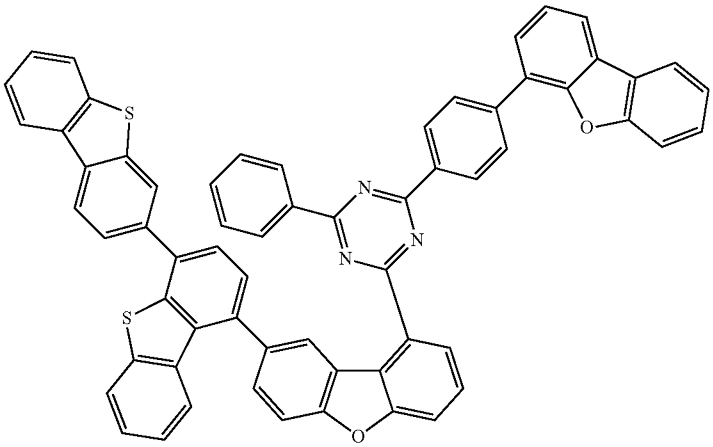
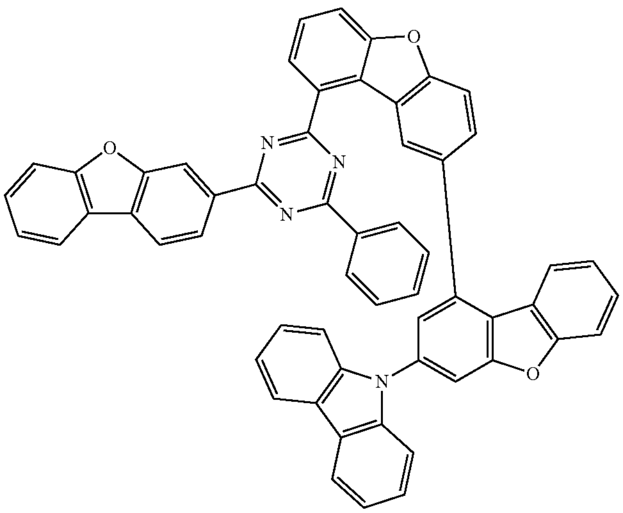

-continued
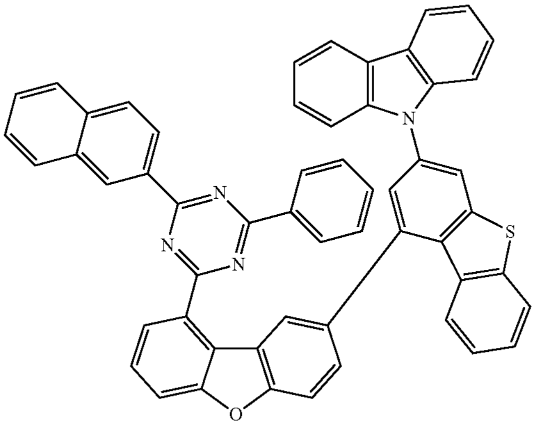
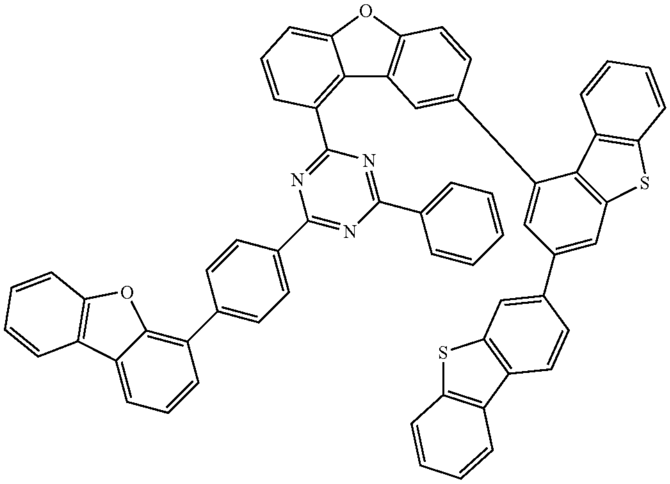
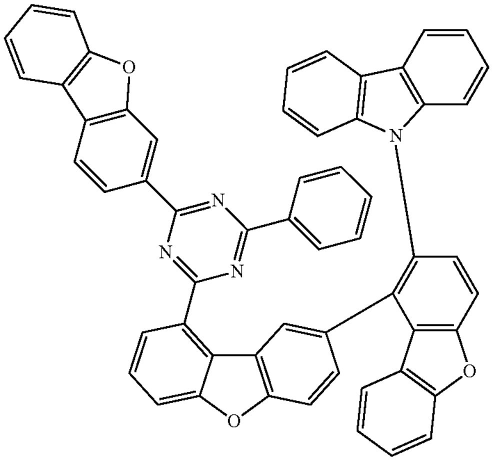
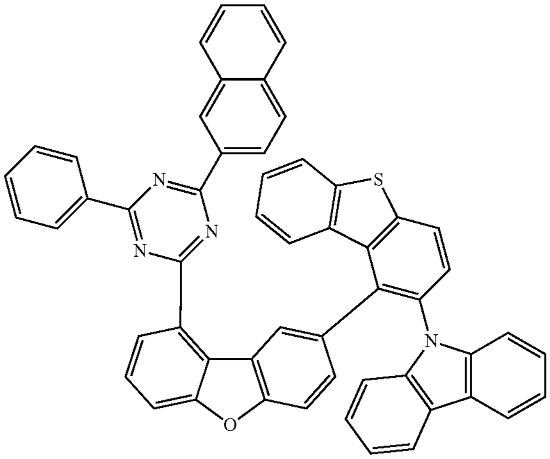

-continued
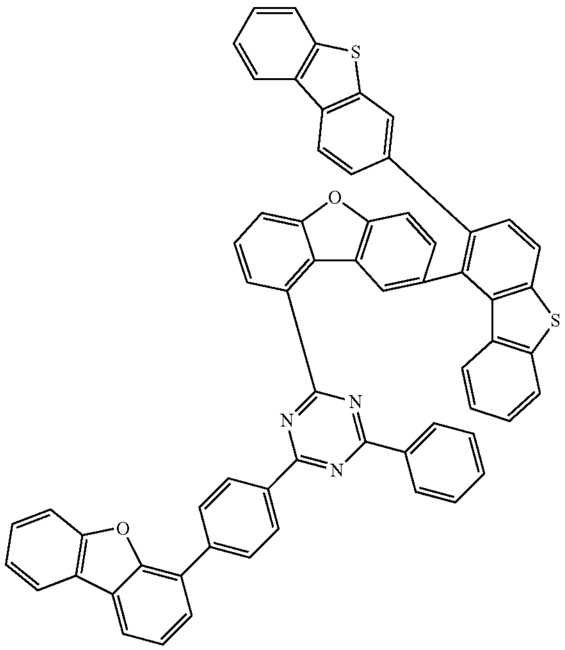
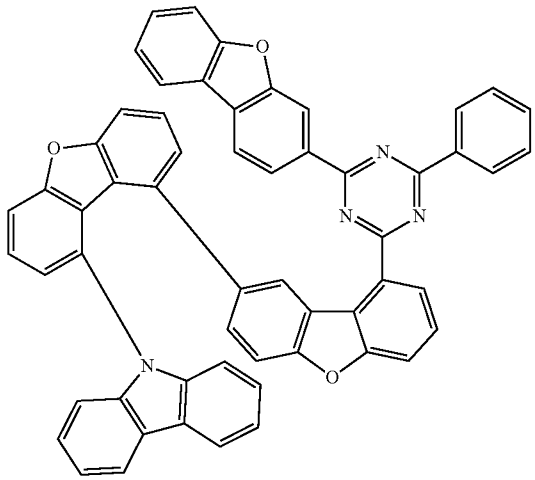
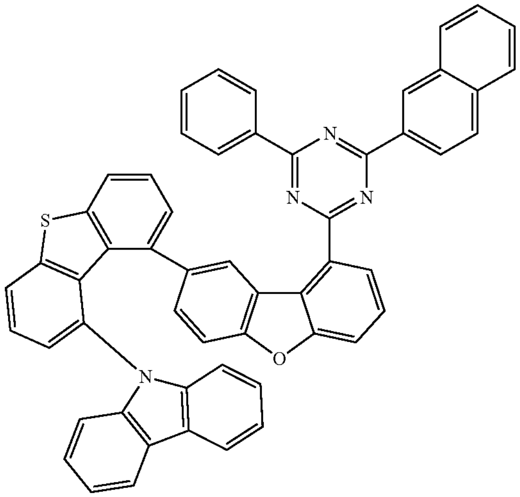
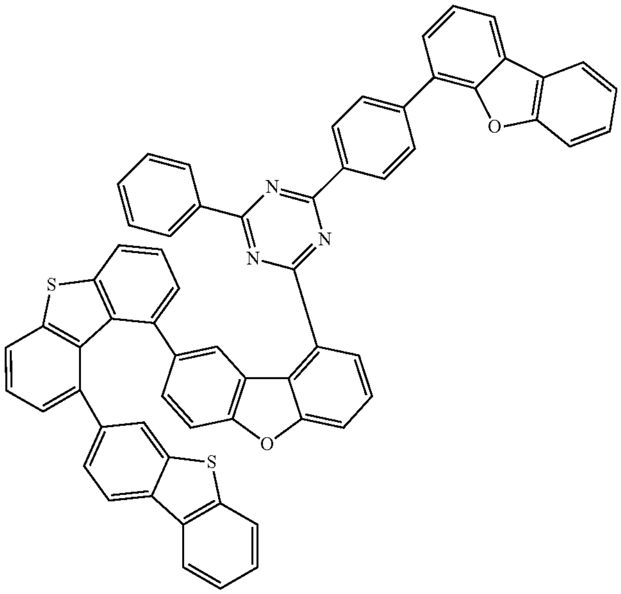

-continued
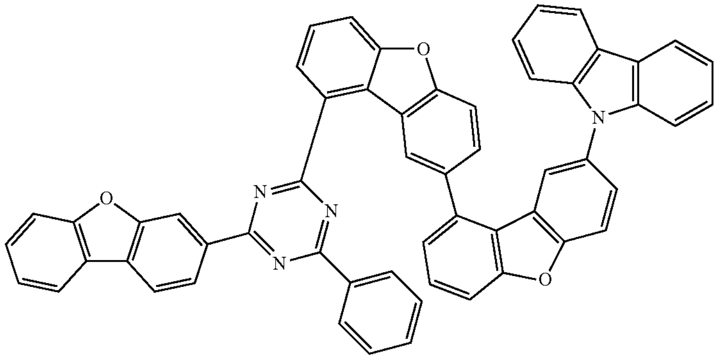
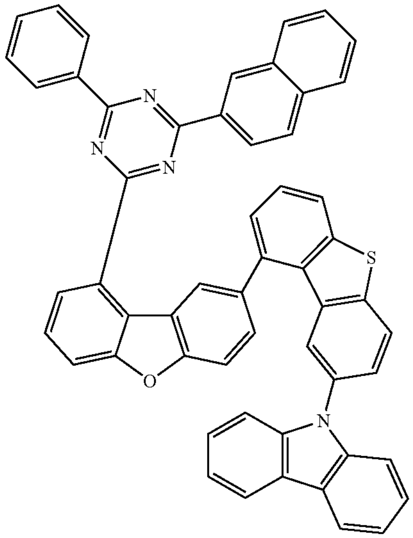
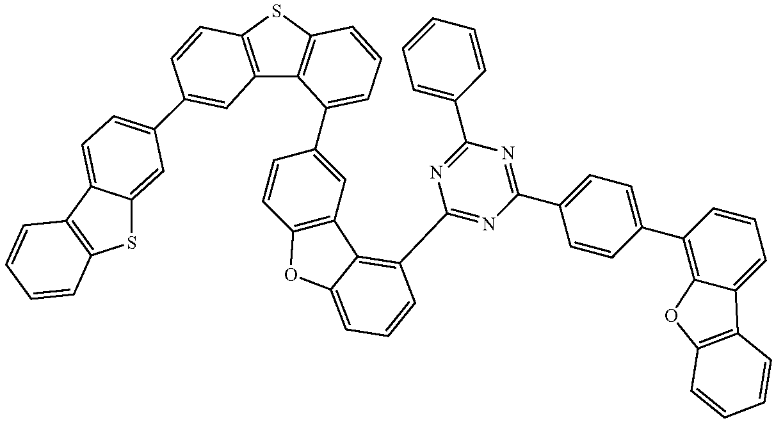
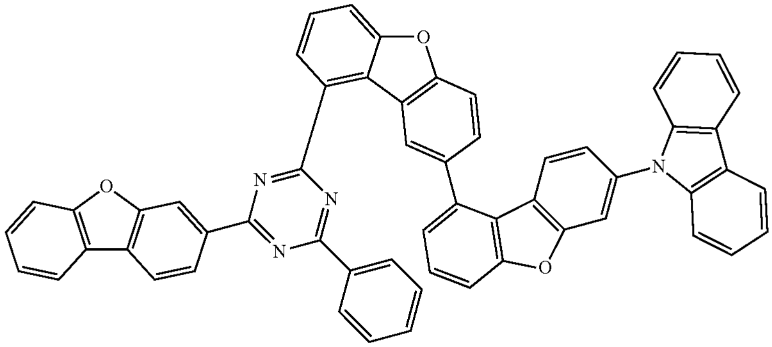
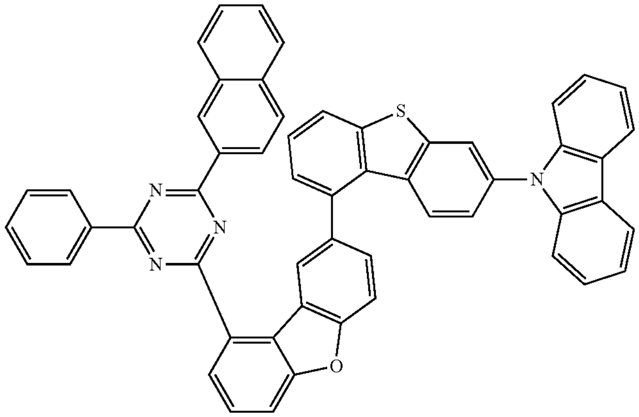

-continued
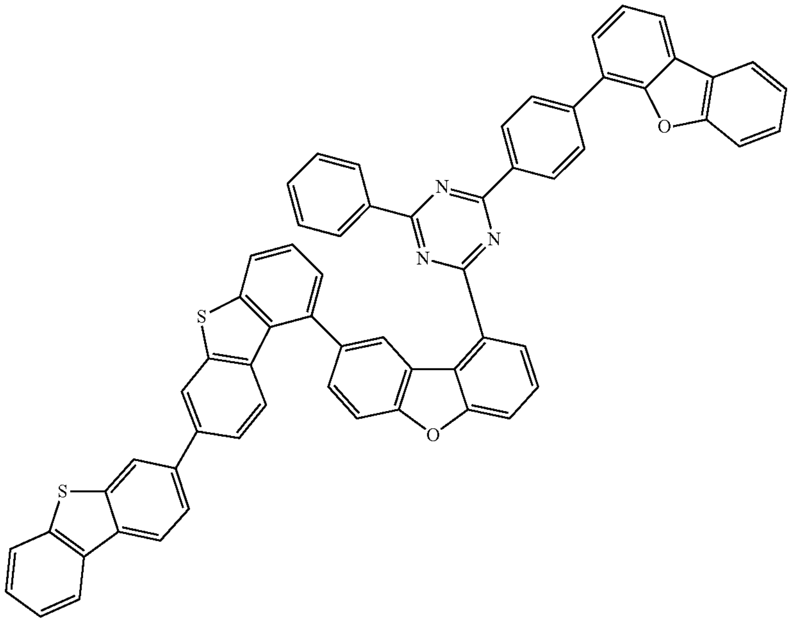
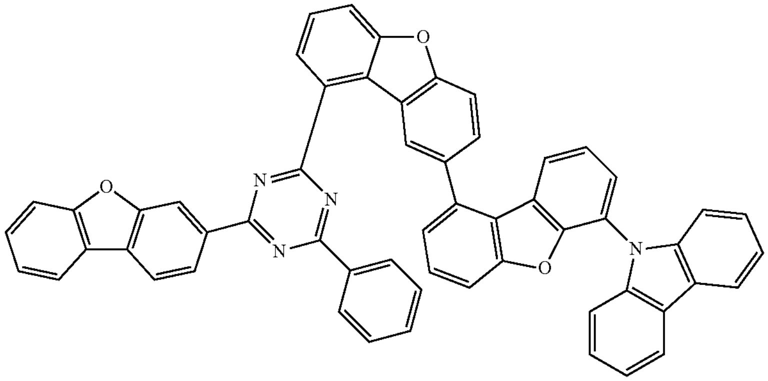
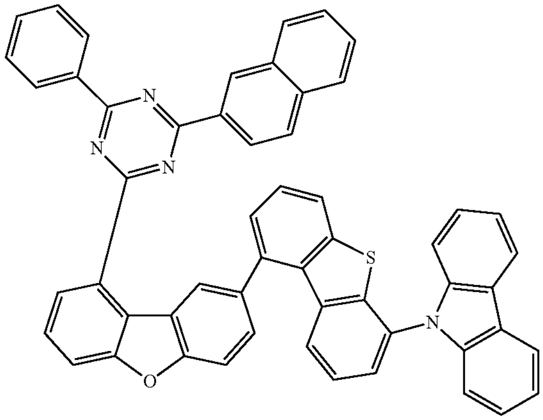

-continued
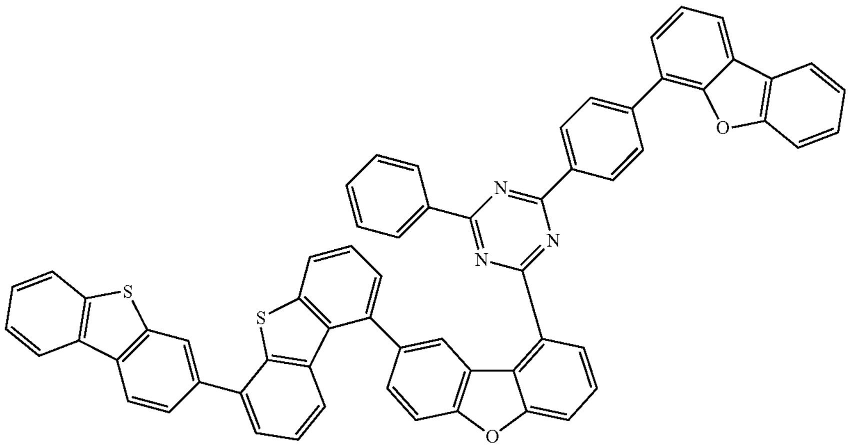
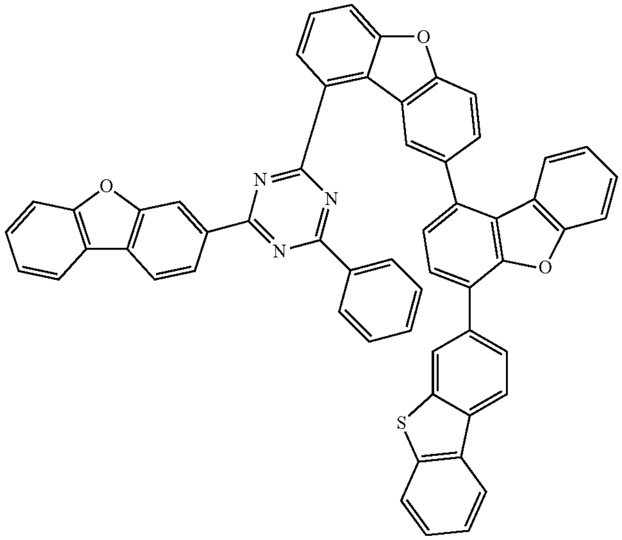
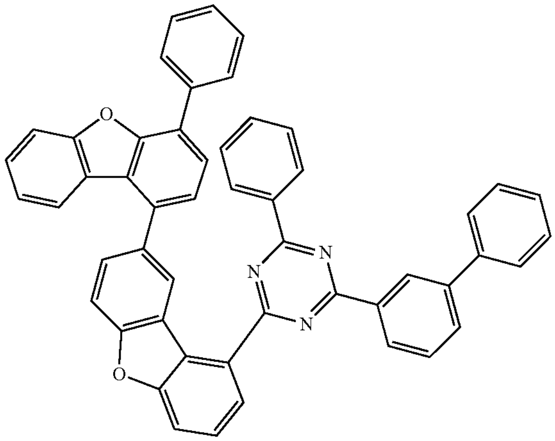

-continued
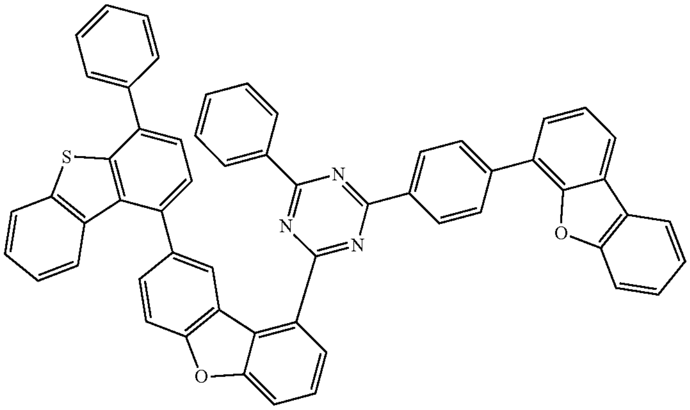
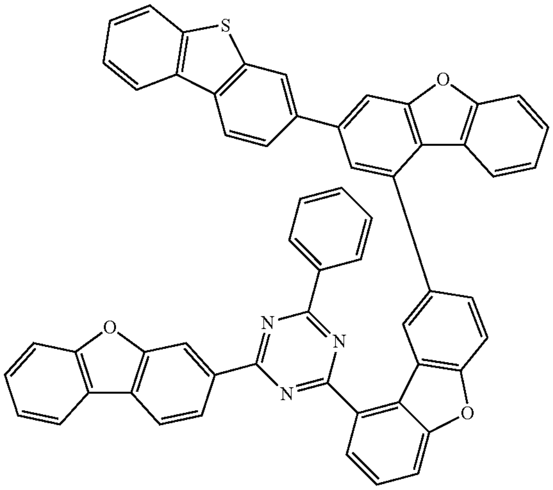
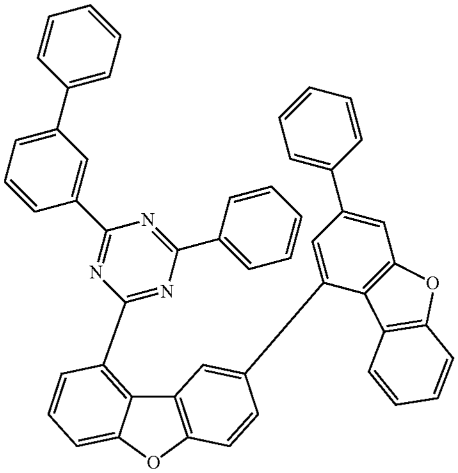
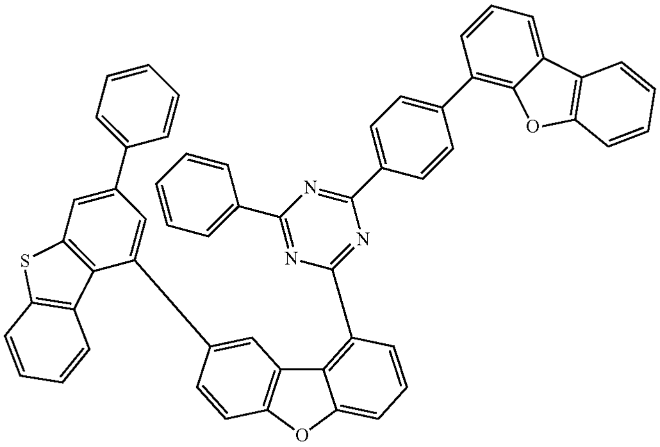

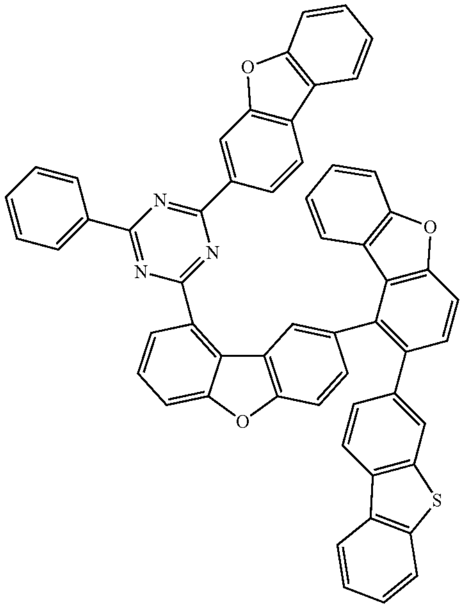
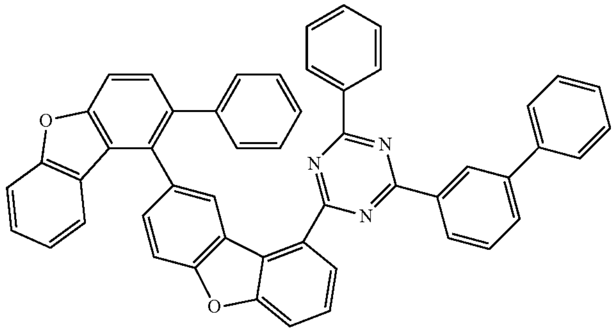
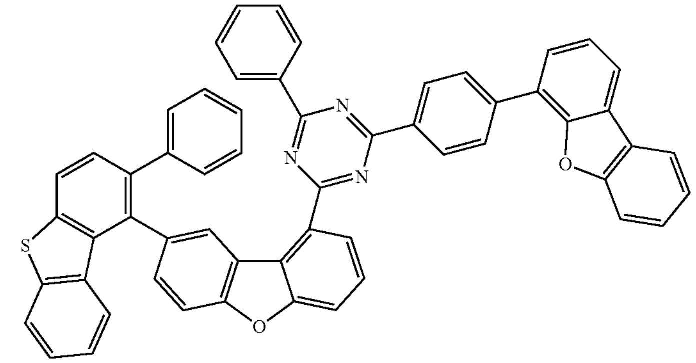
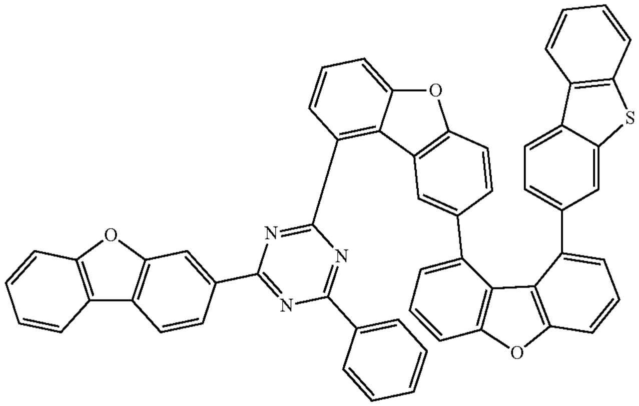
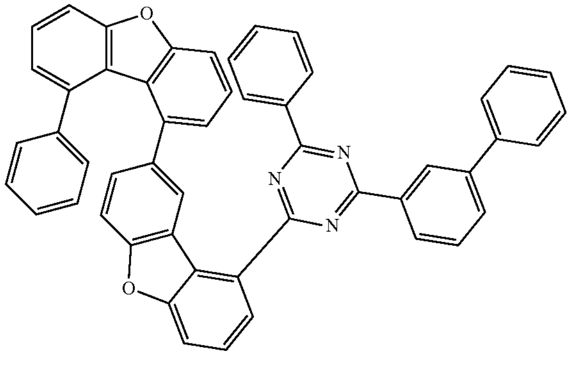

-continued
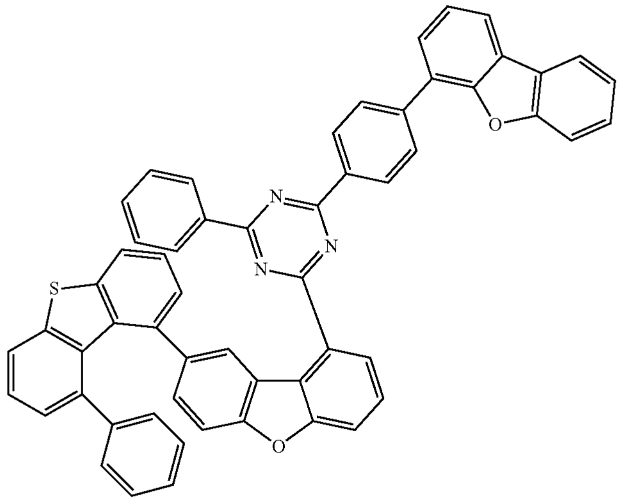
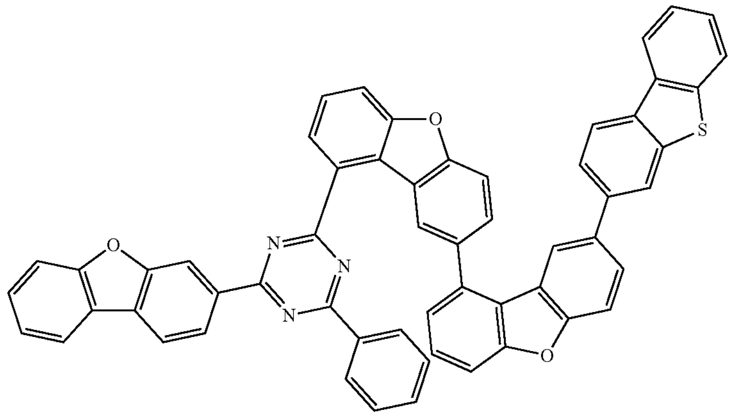
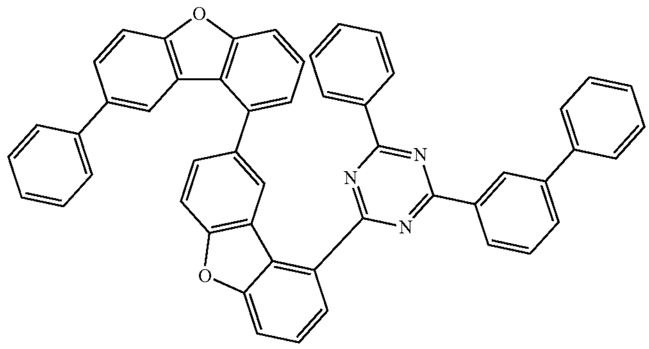

-continued
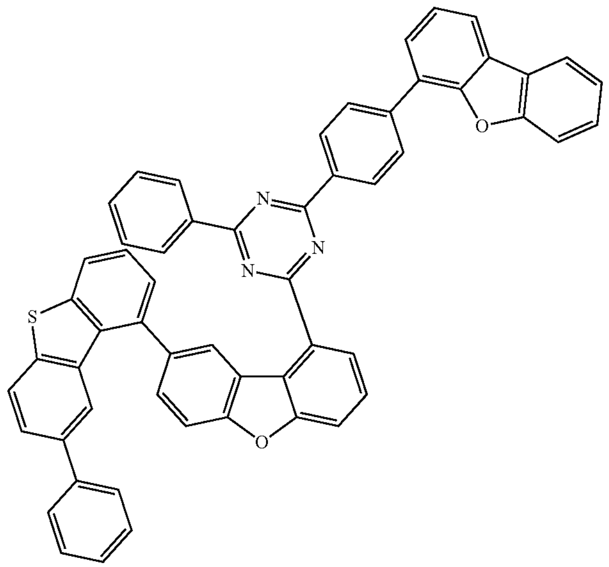
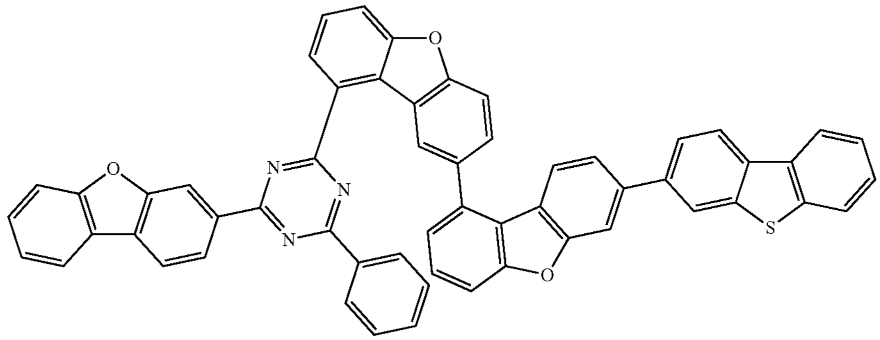
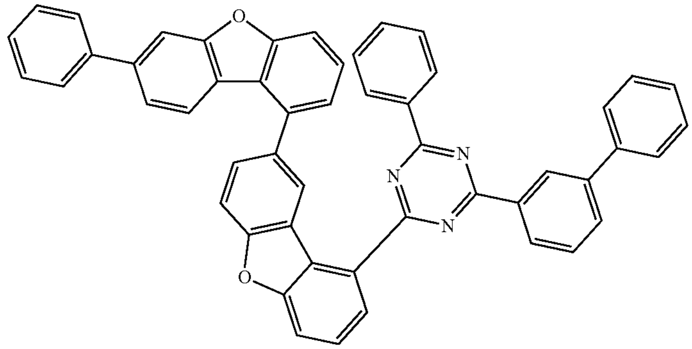
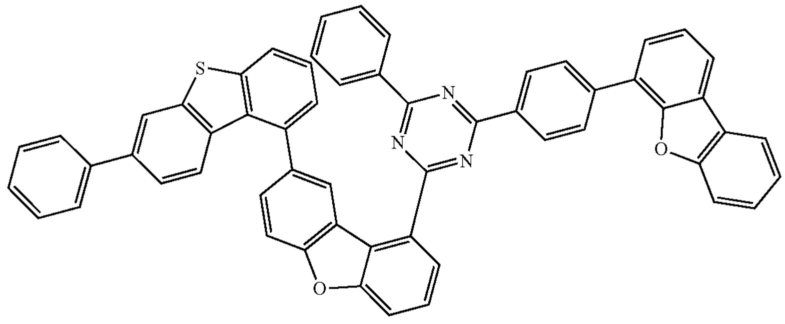

-continued
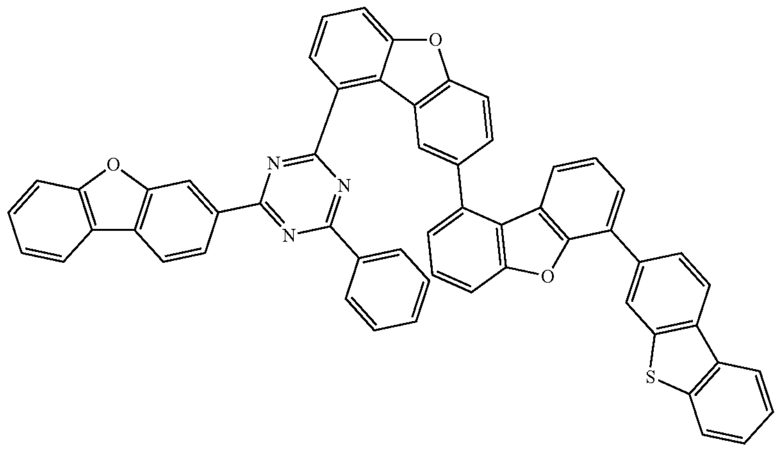
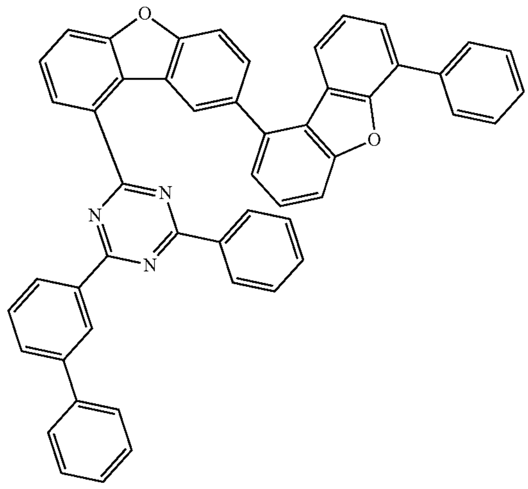 [SMILES: c1ccc(-c2cccc(-c3nc(-c4ccccc4)nc(-c4cccc5oc6ccc(-c7cccc8oc9c(-c%10ccccc%10)cccc9c78)cc6c45)n3)c2)cc1]
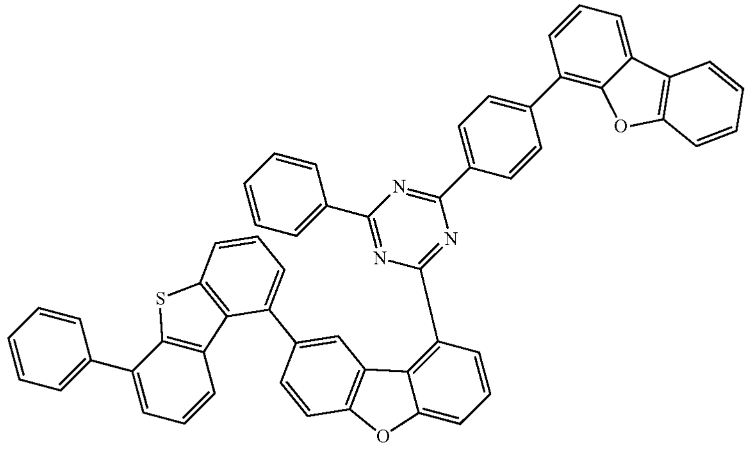

-continued
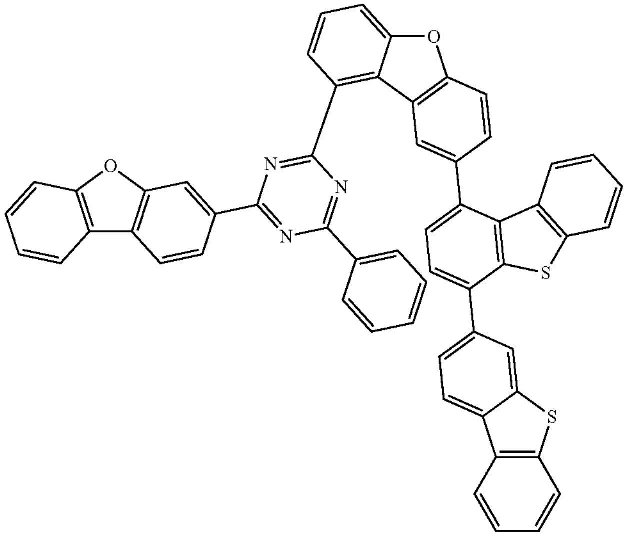
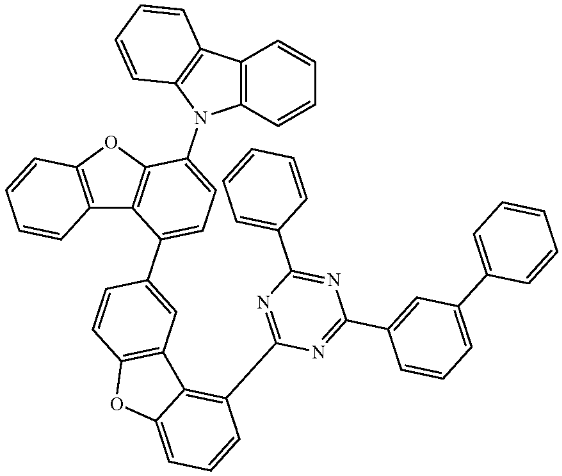
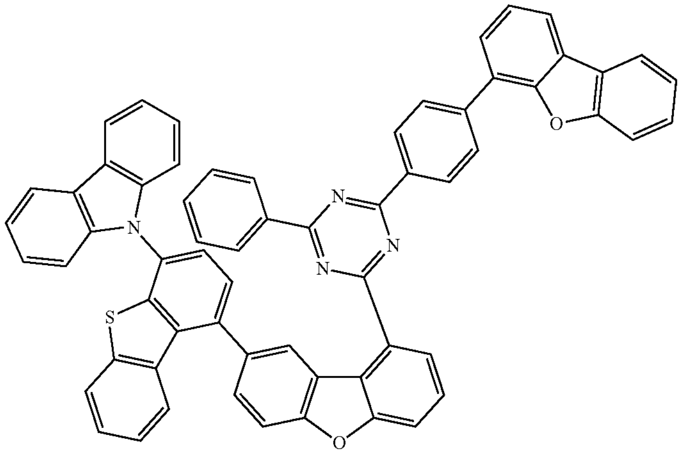

-continued
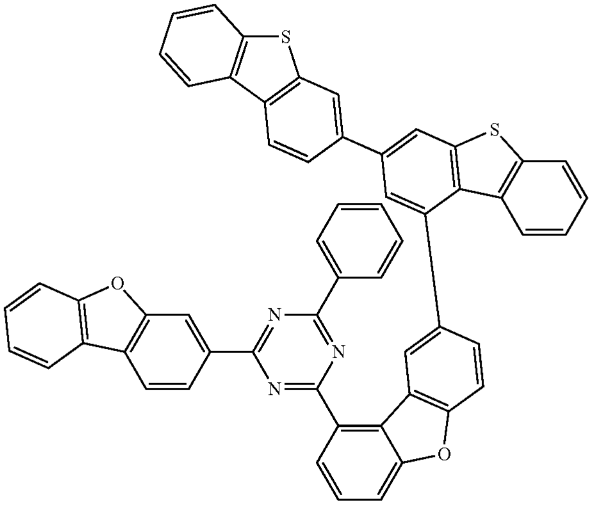
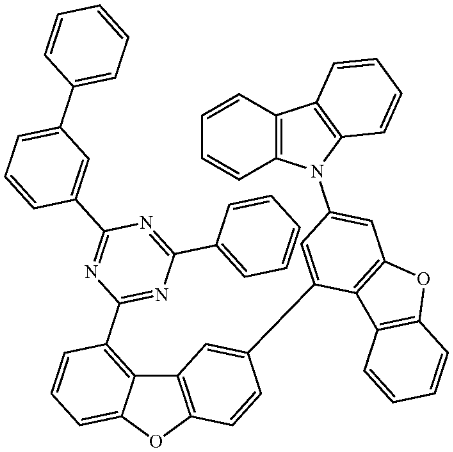
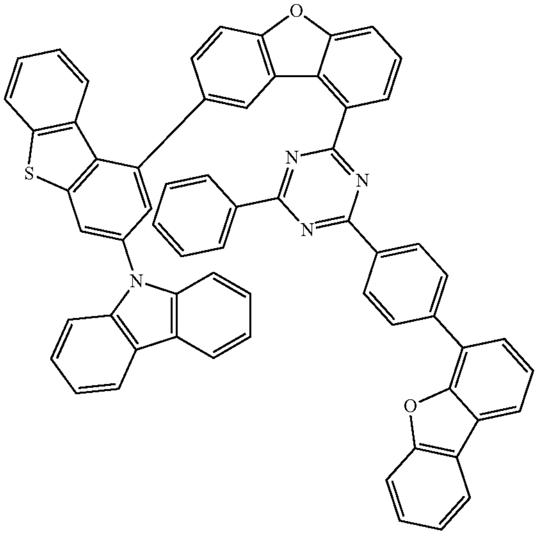
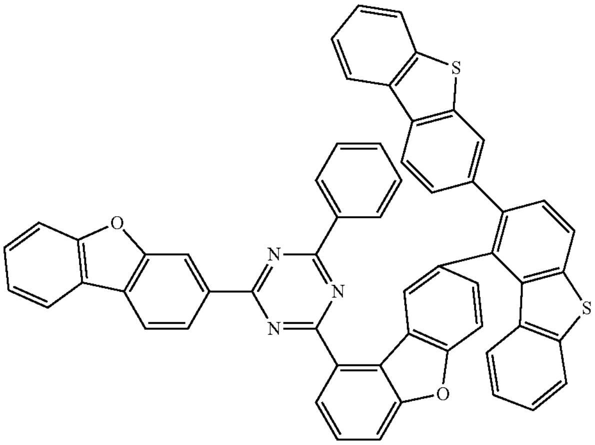
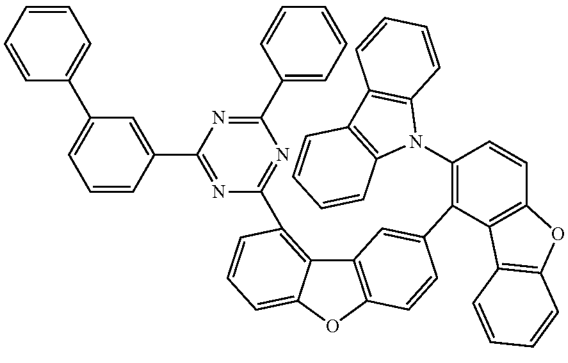

-continued
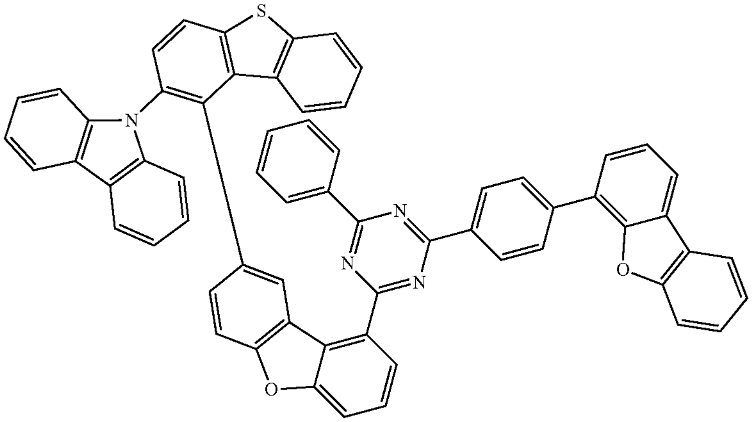
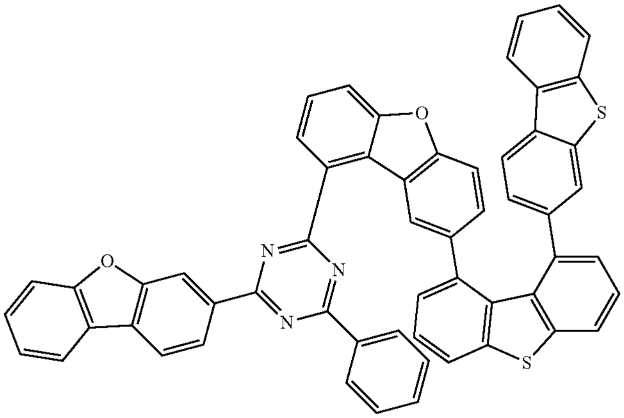
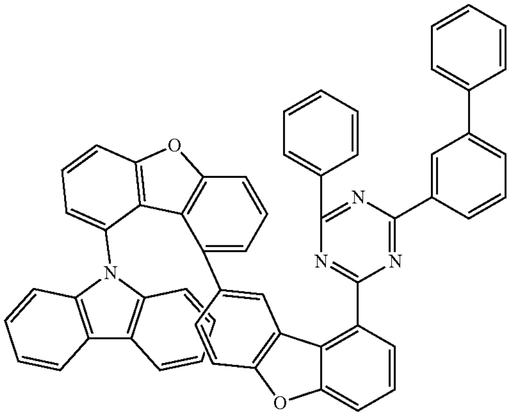
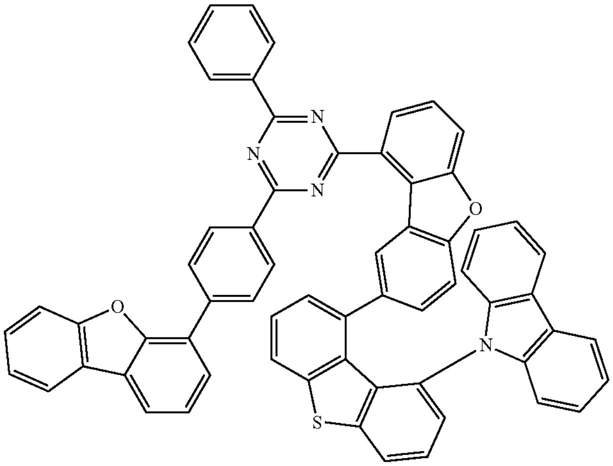

-continued
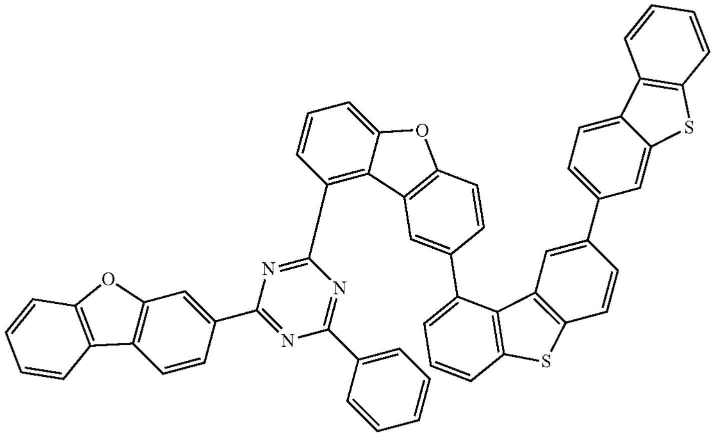
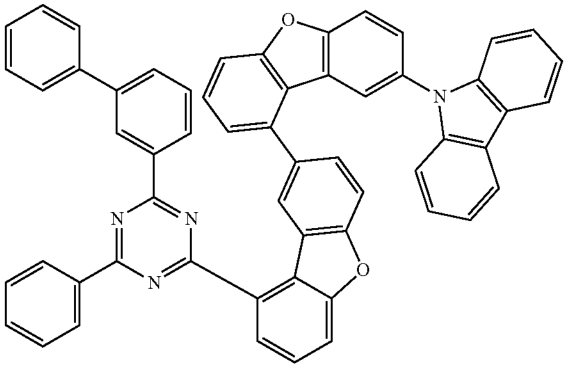
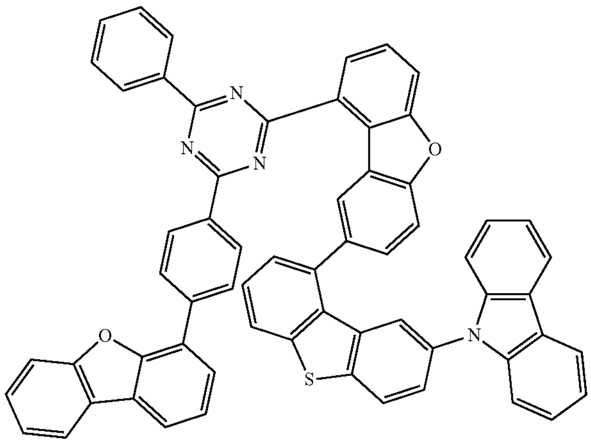
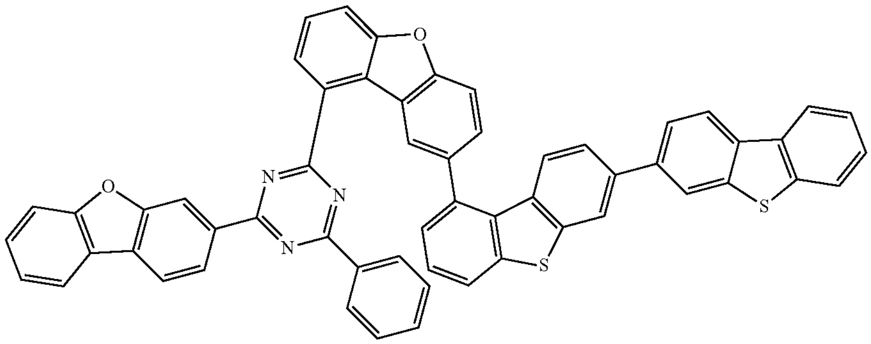

-continued
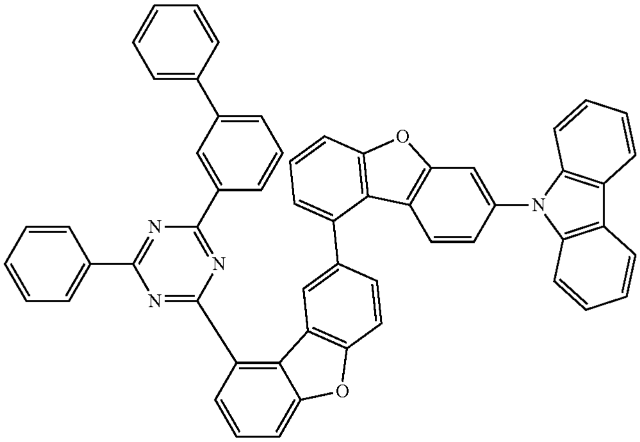
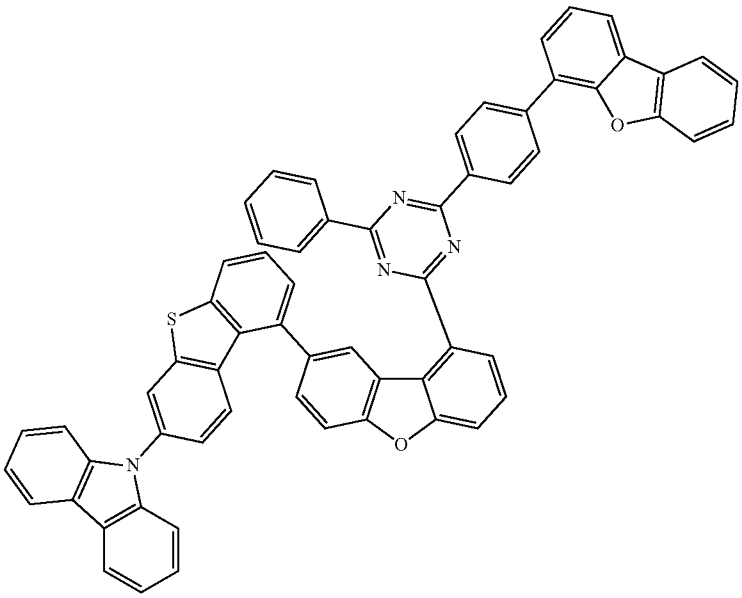
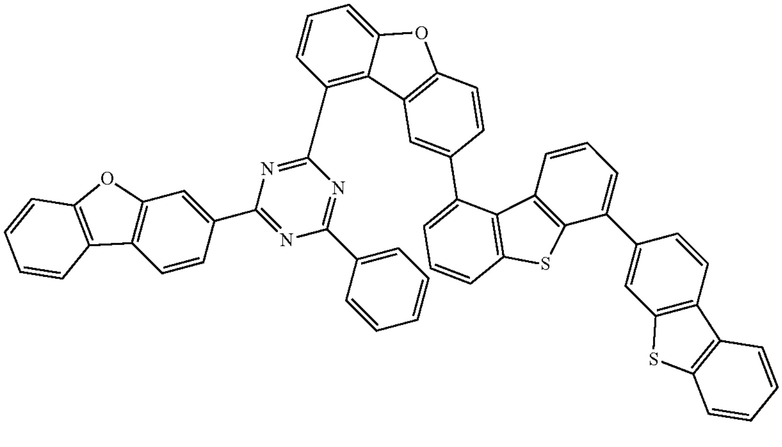

-continued
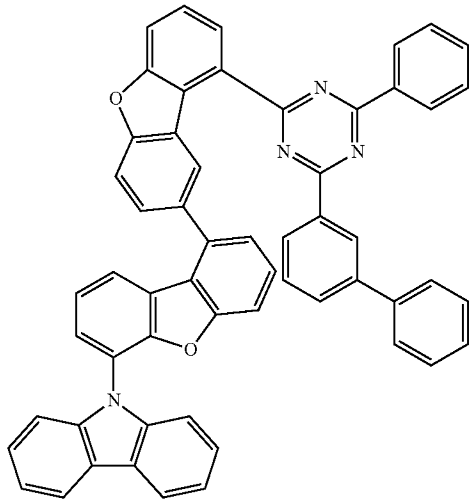
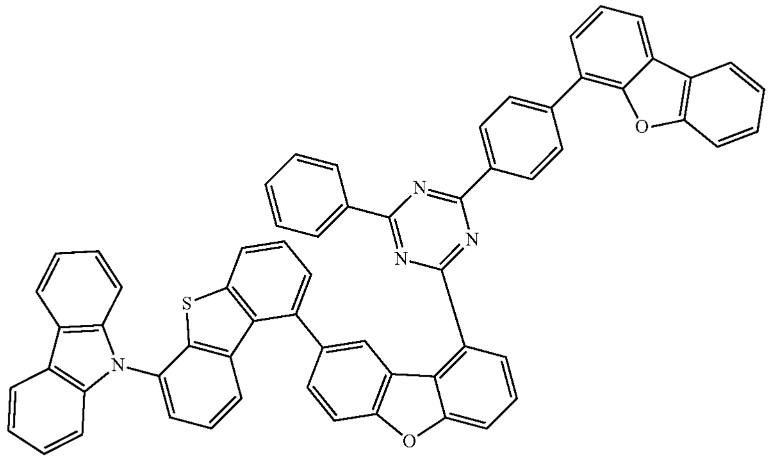
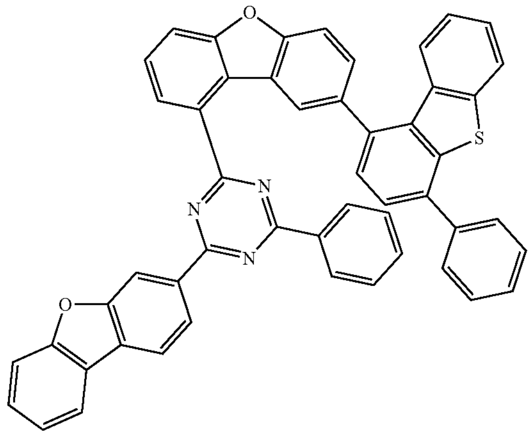
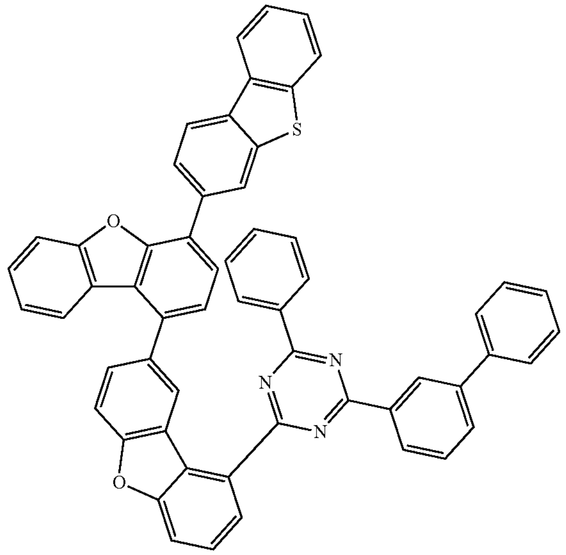

-continued
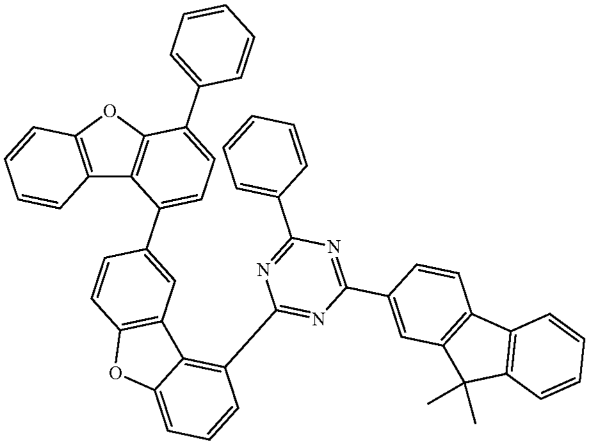
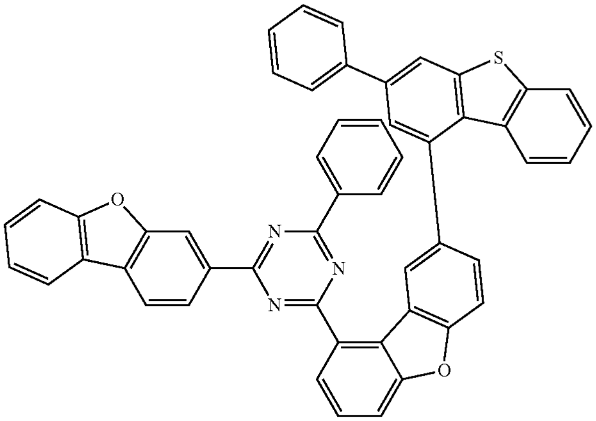
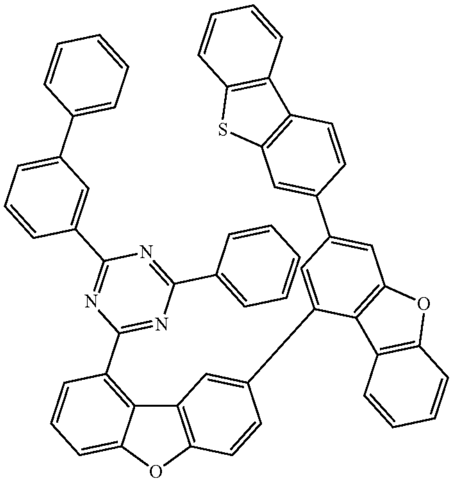
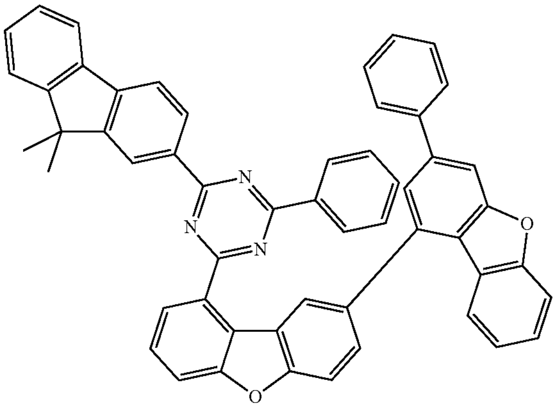
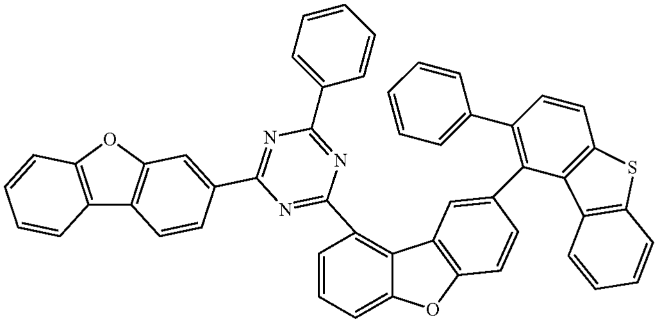

-continued
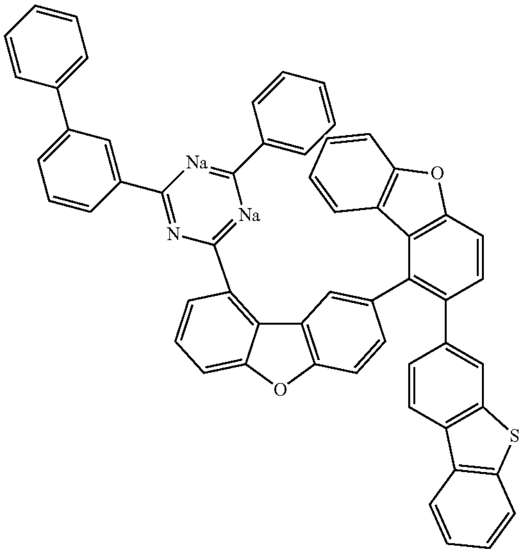
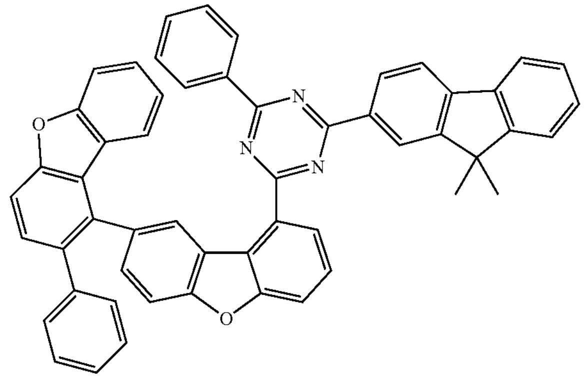
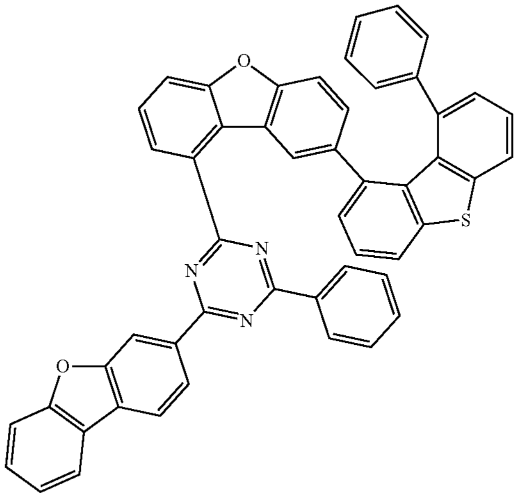
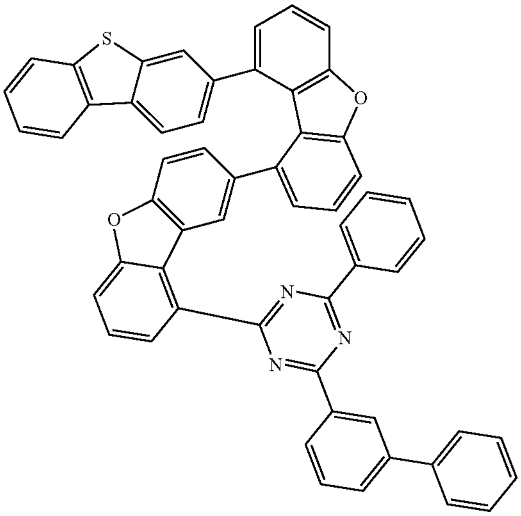
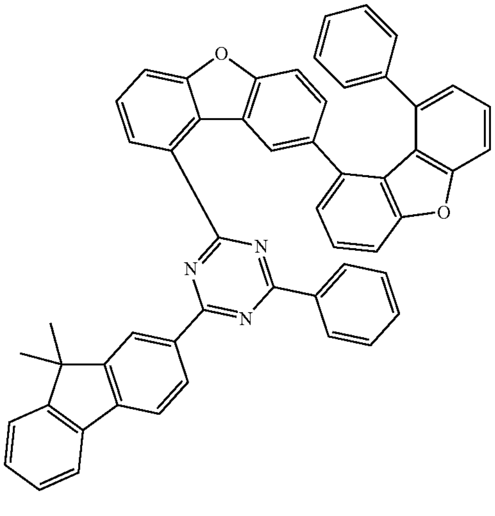
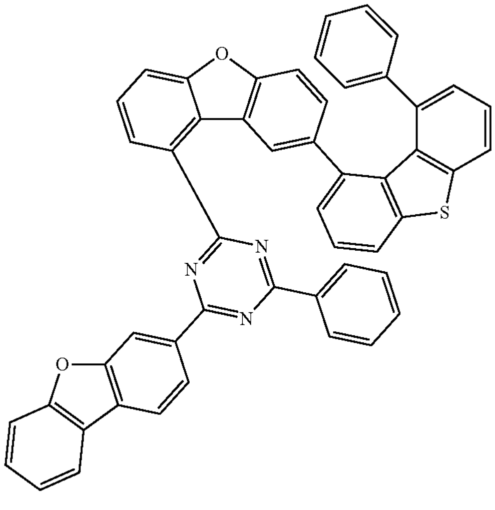

-continued
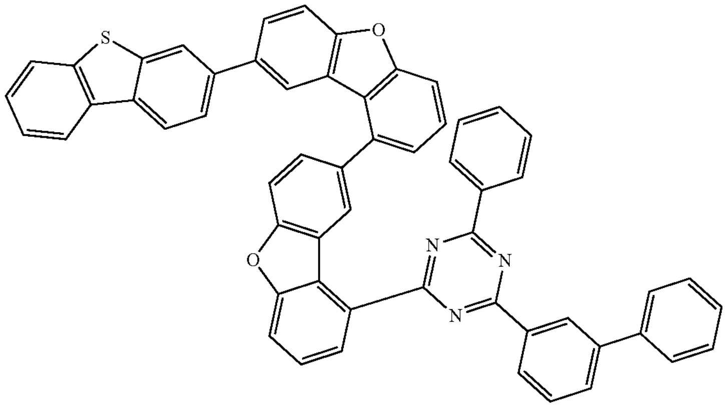
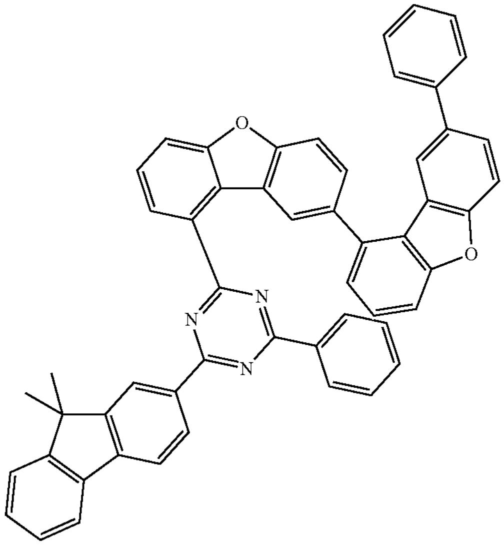
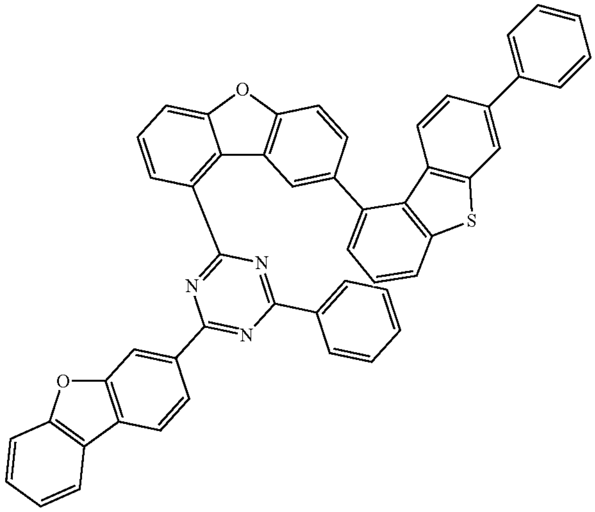
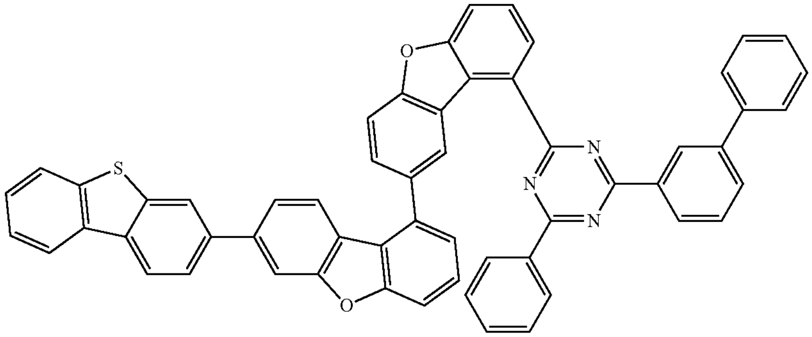

-continued
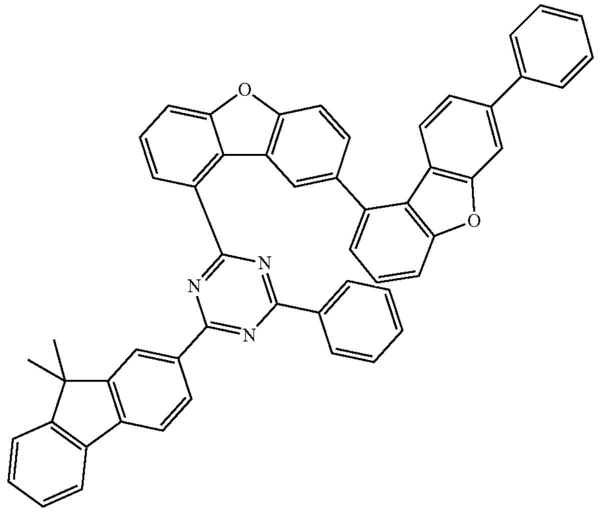
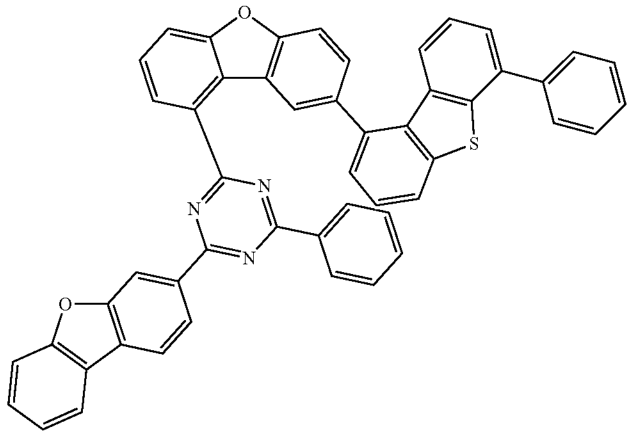
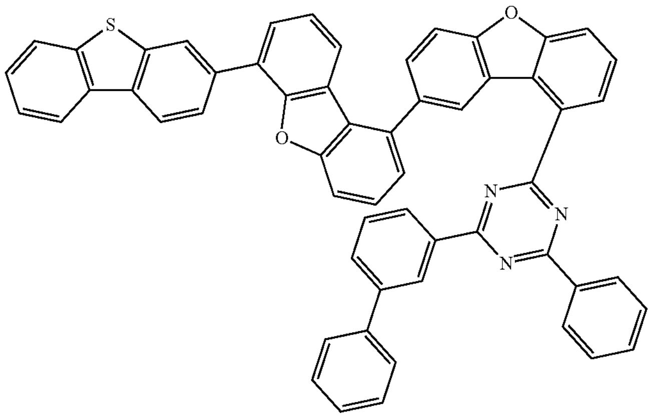

-continued
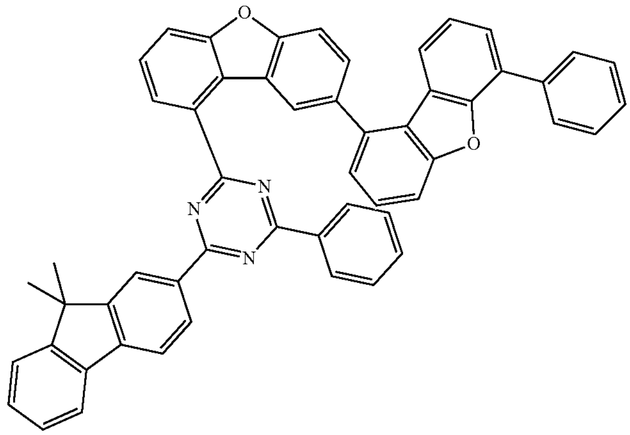
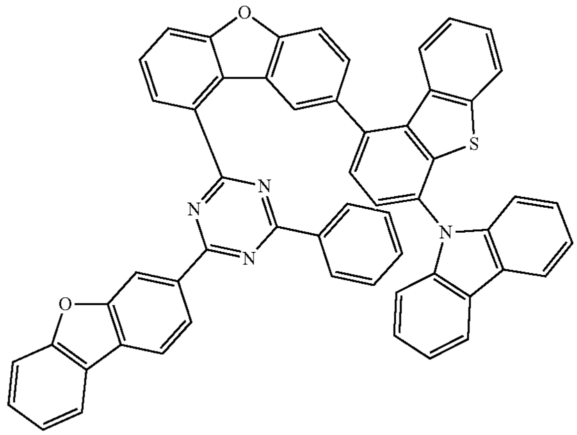
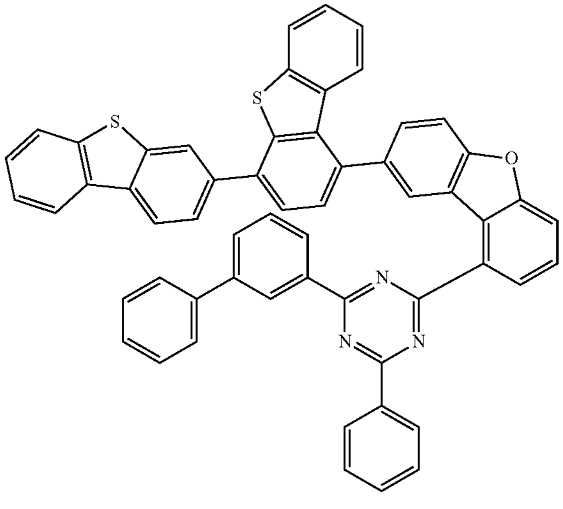
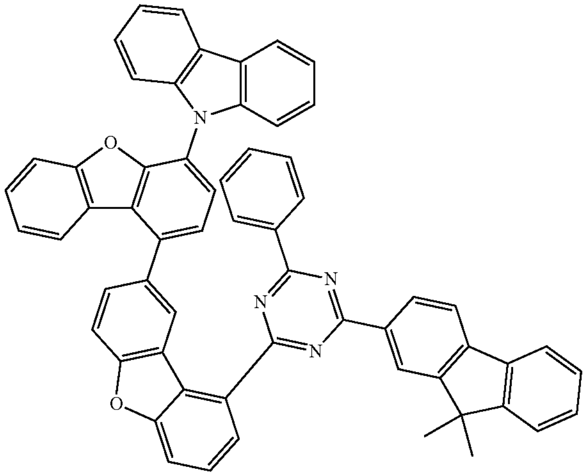

-continued
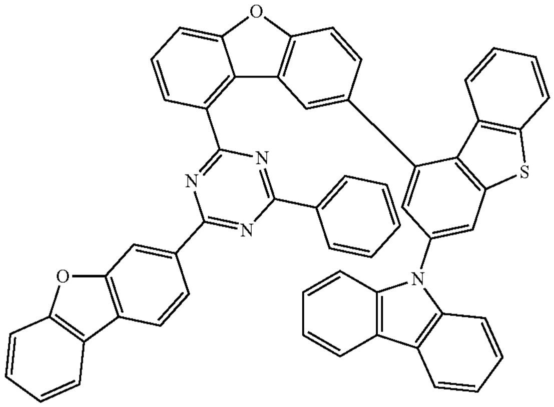
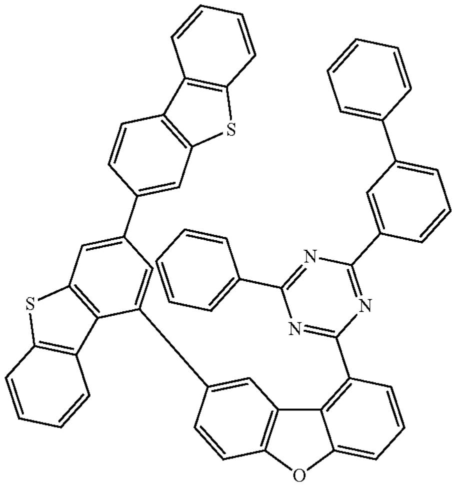
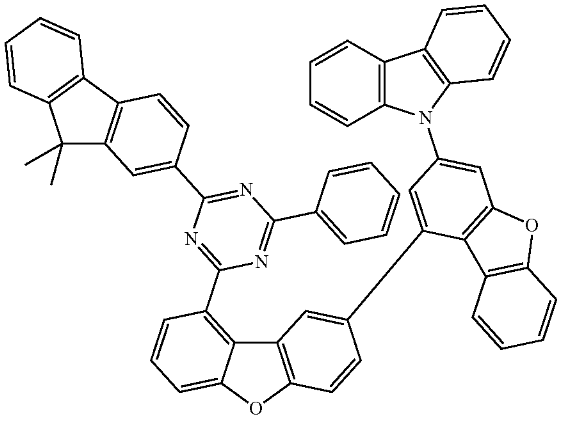
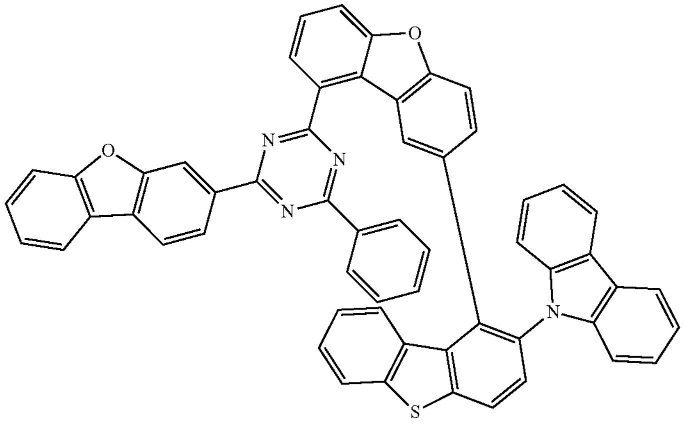

-continued
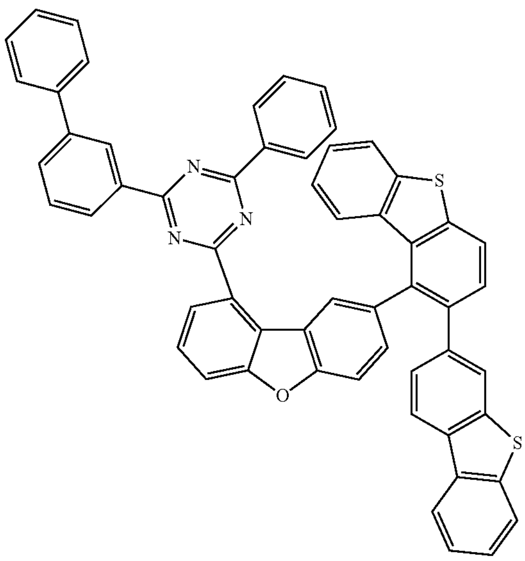
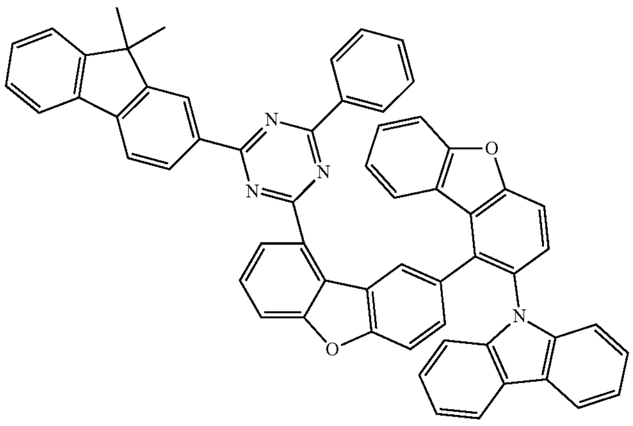
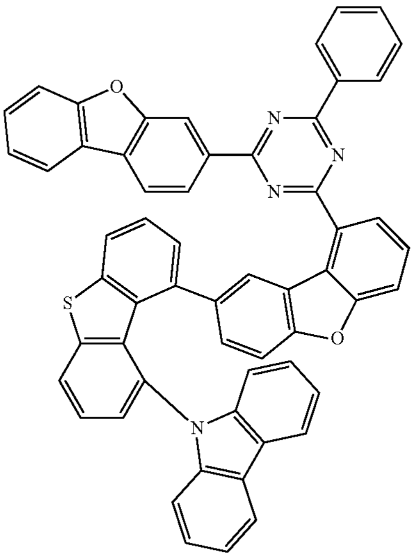
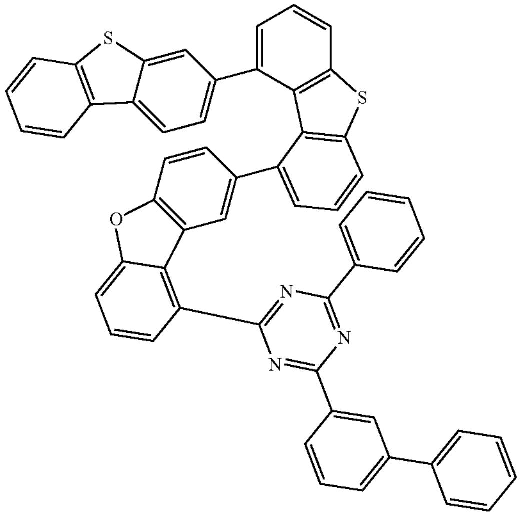
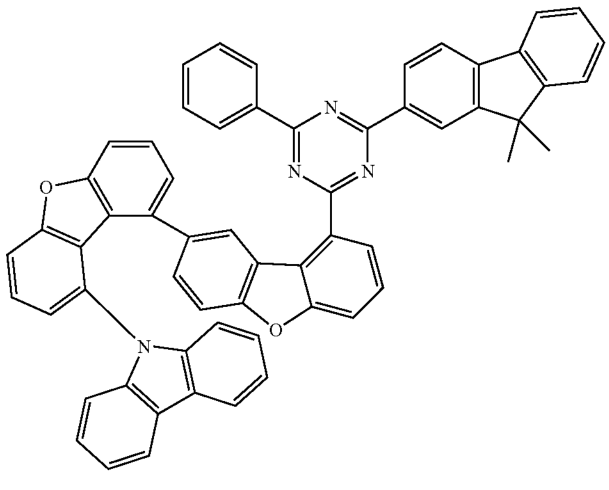

-continued
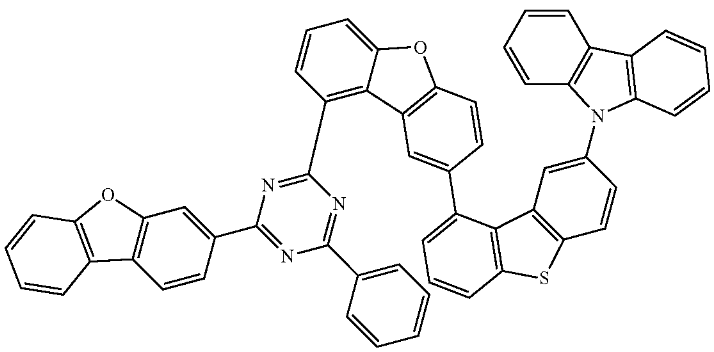
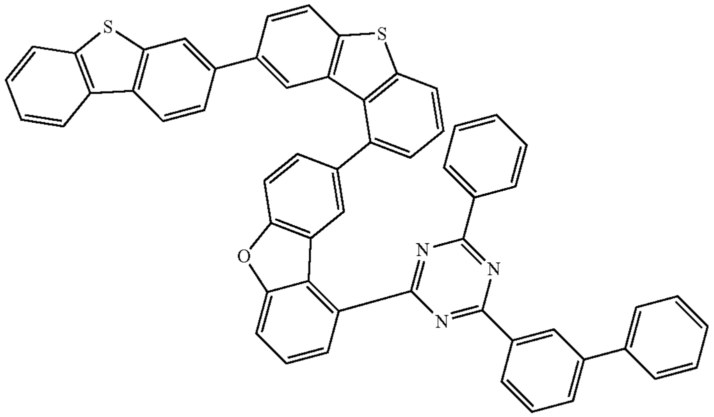
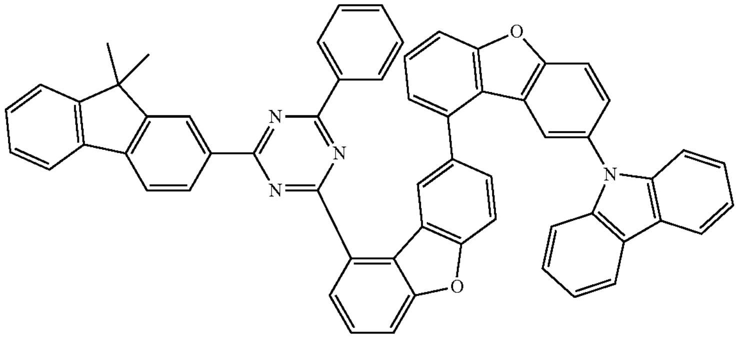
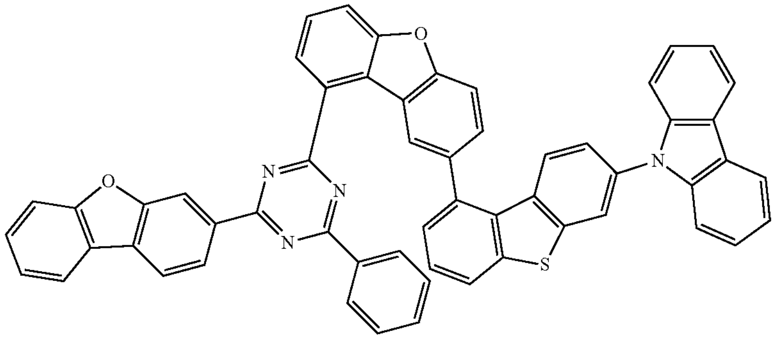

-continued
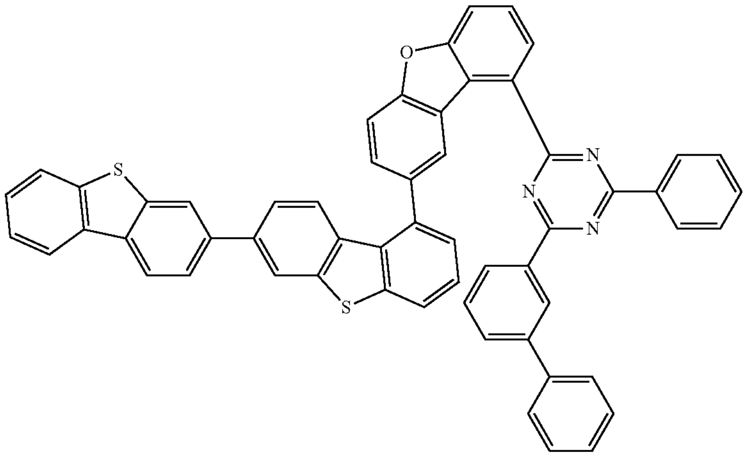
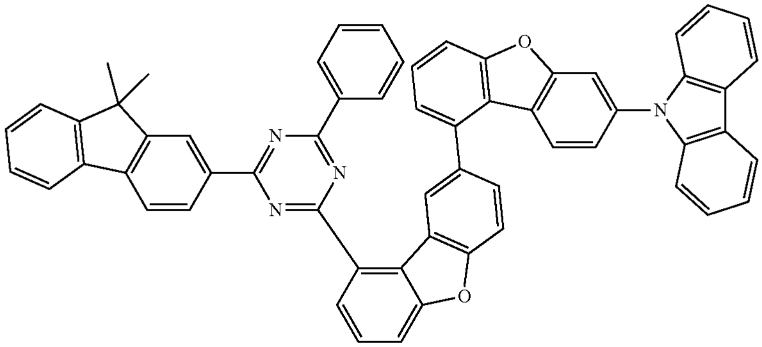
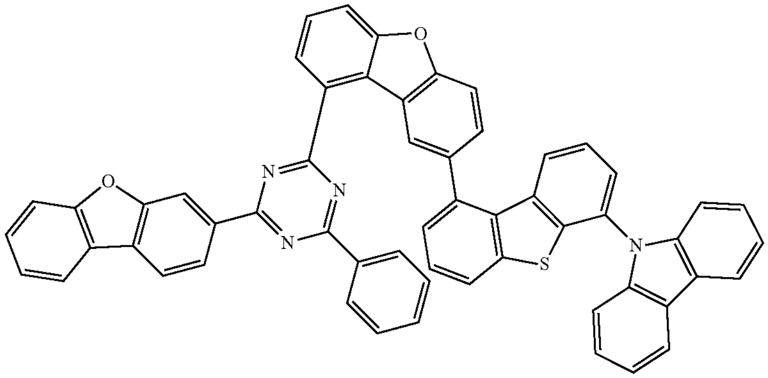
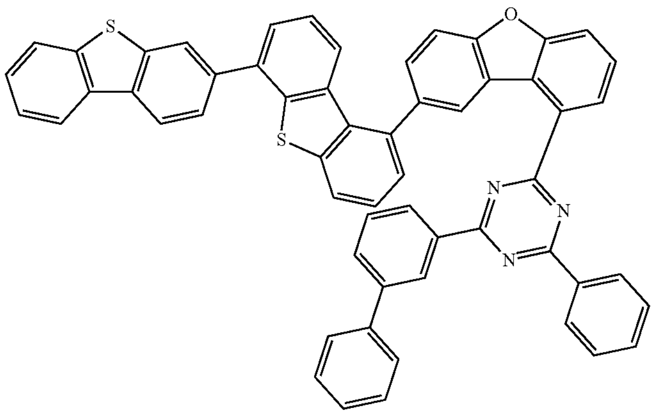

-continued
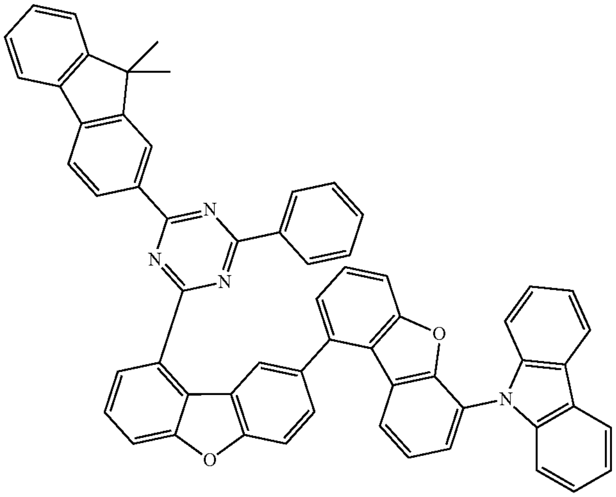
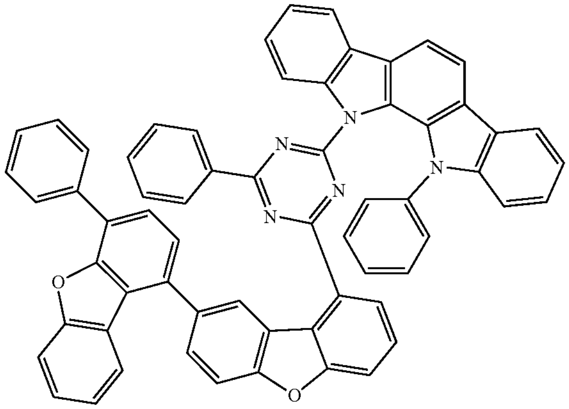
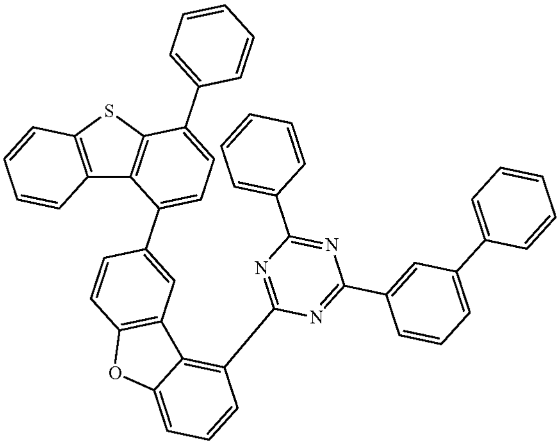
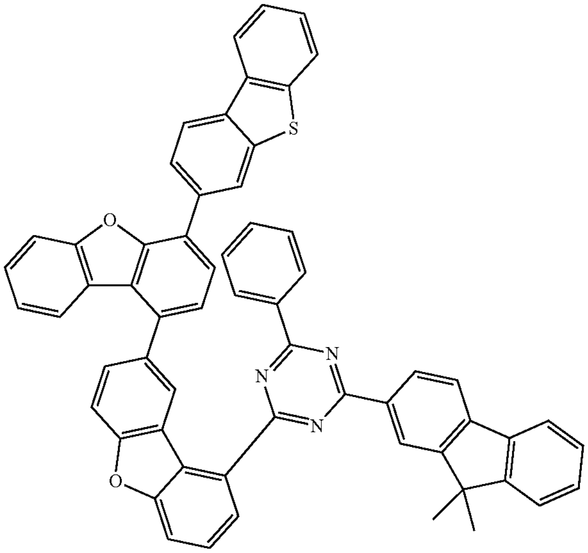

-continued
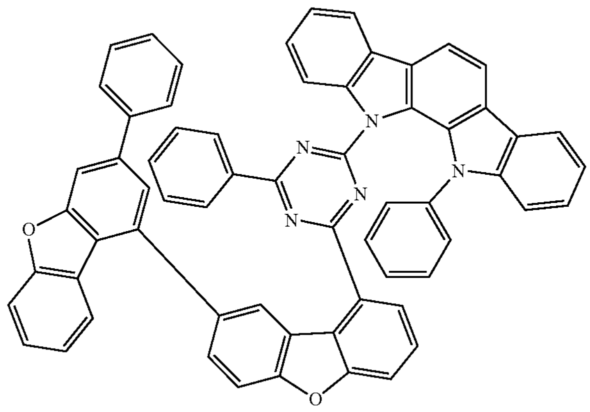
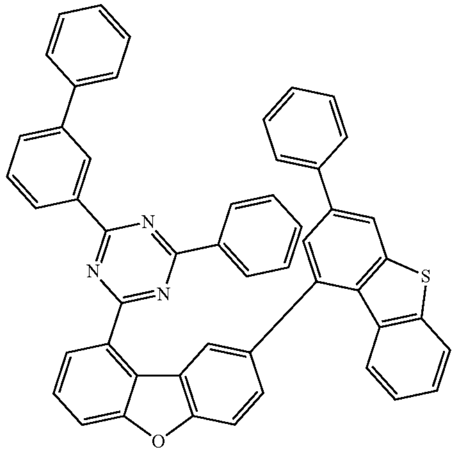
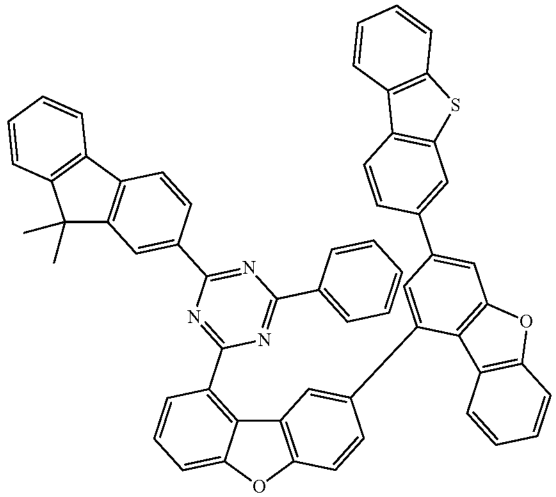
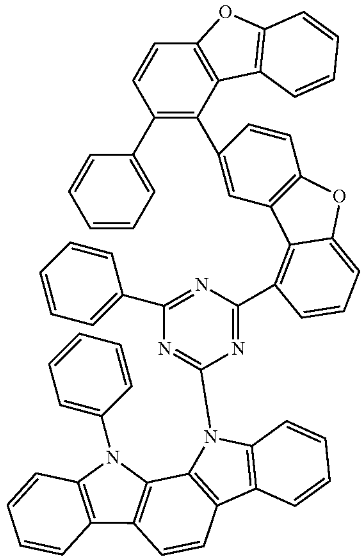
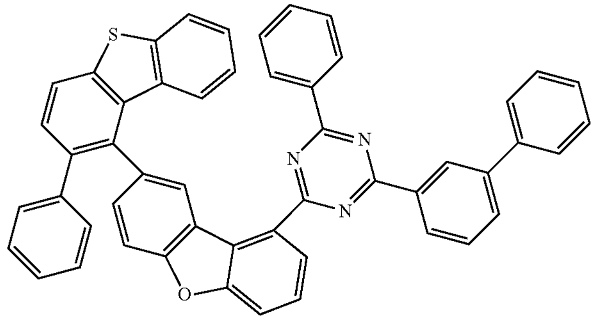
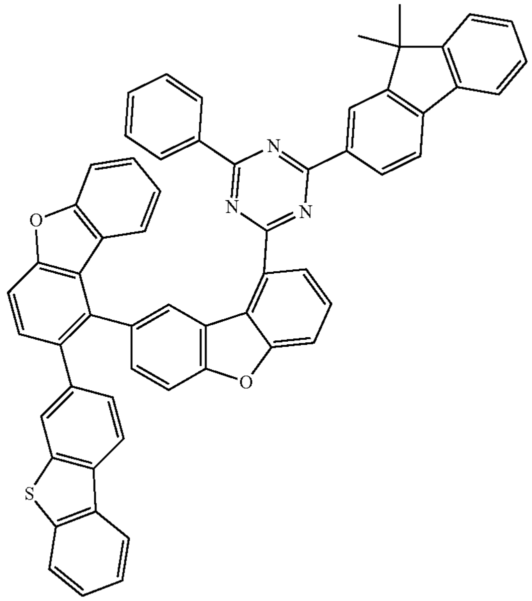

-continued
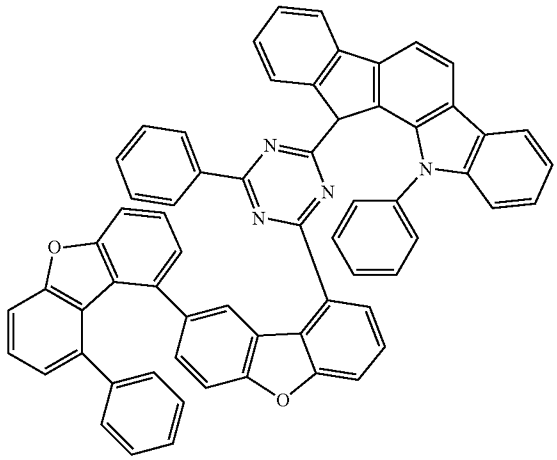
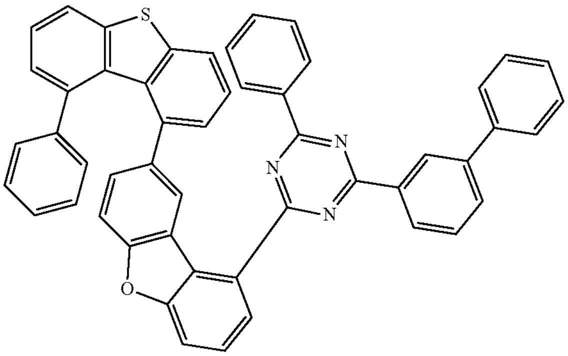
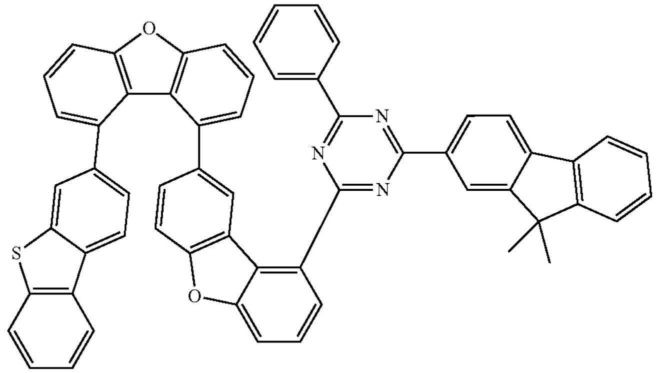
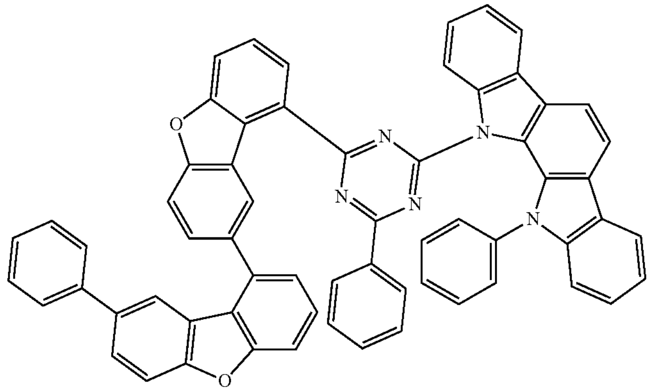
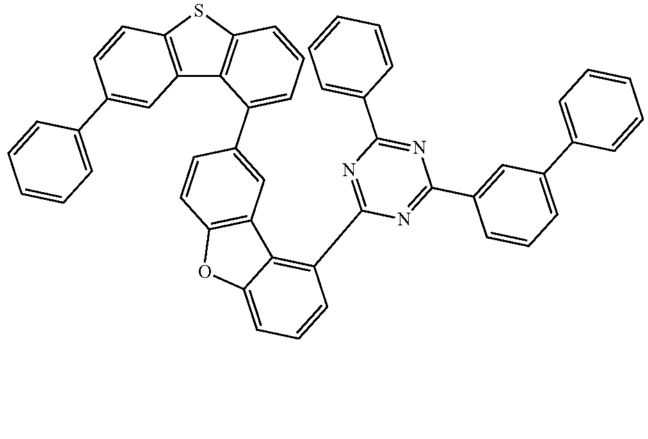

-continued
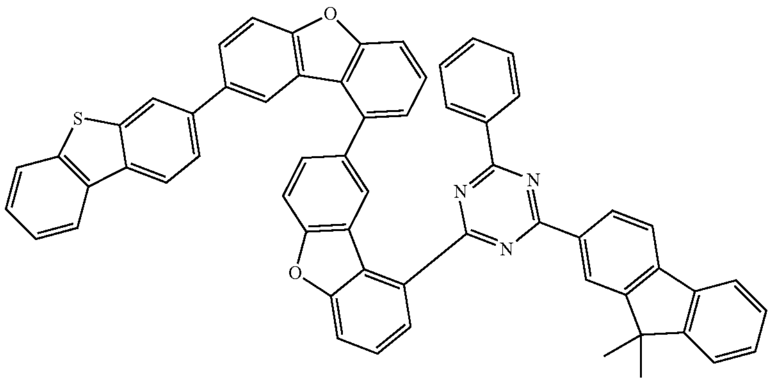
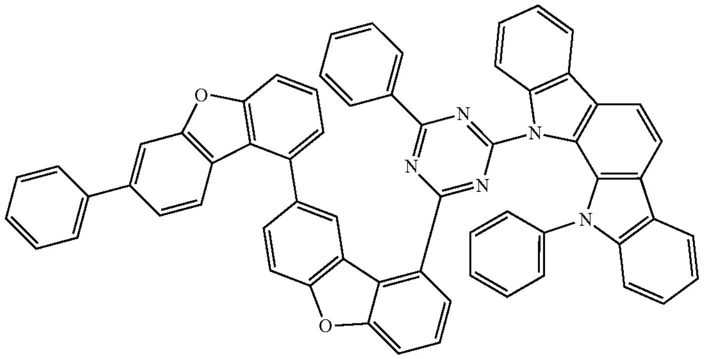
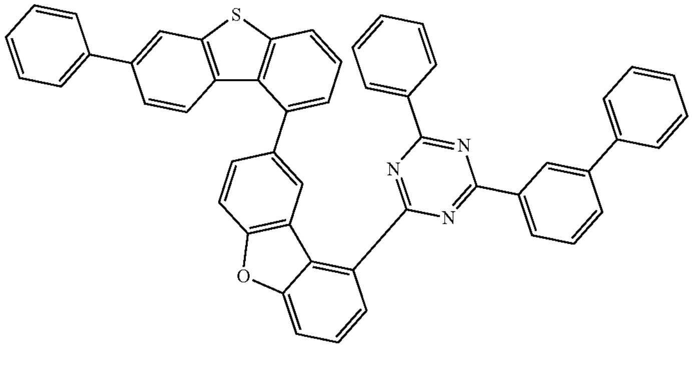
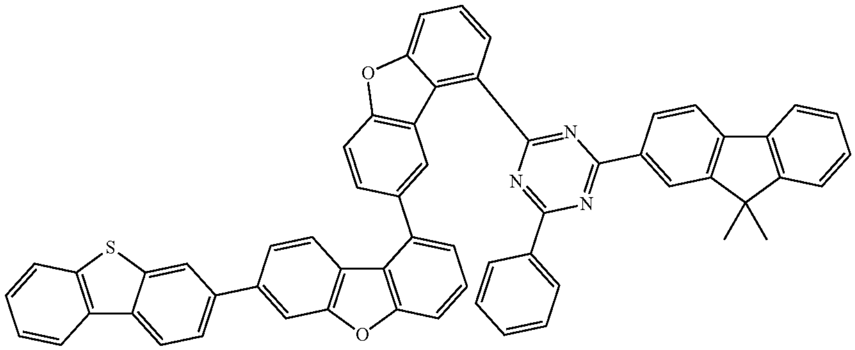

-continued
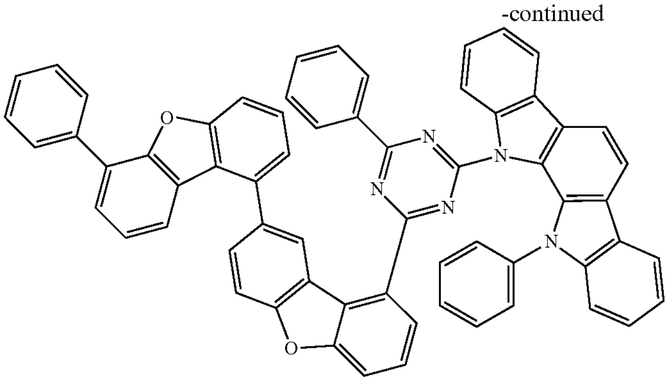
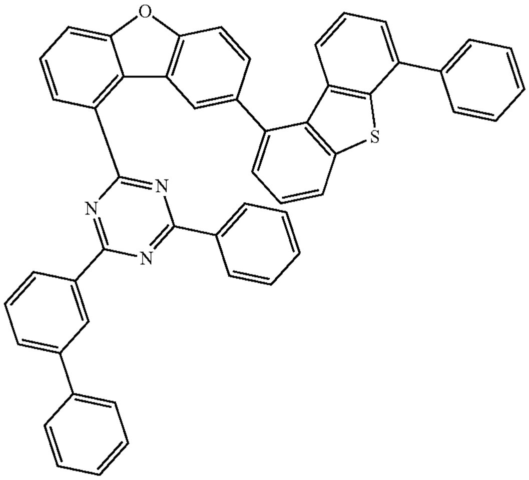
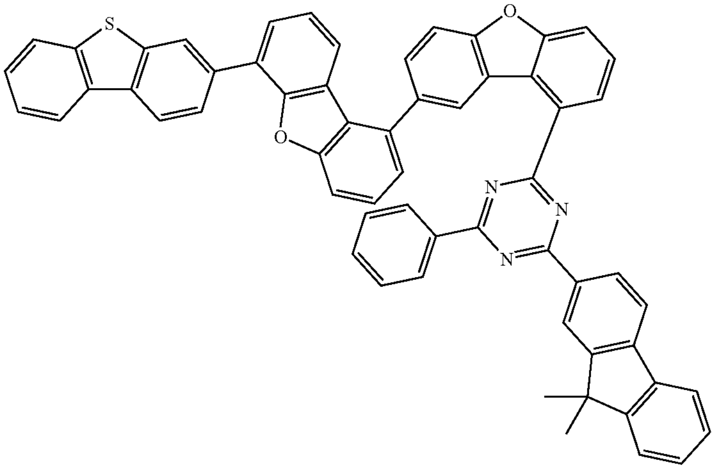
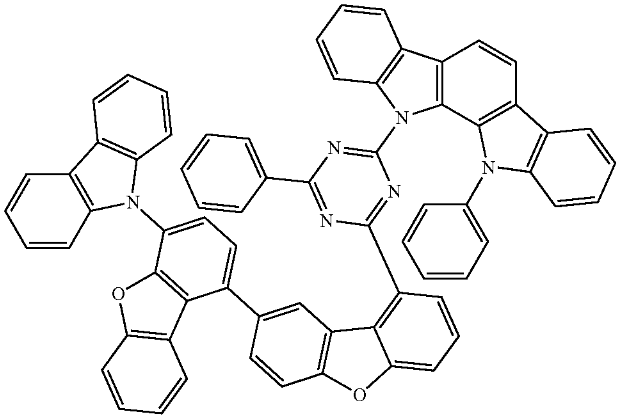

-continued
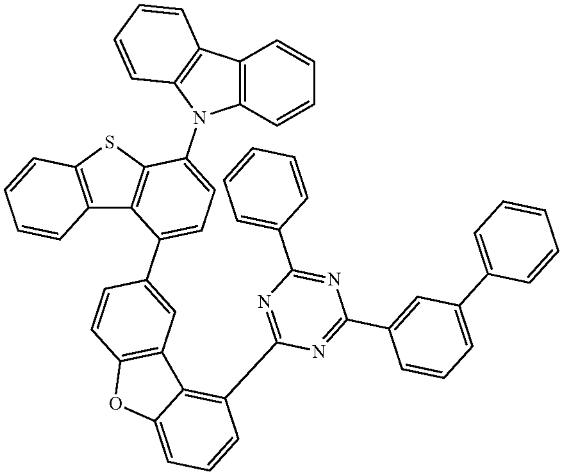
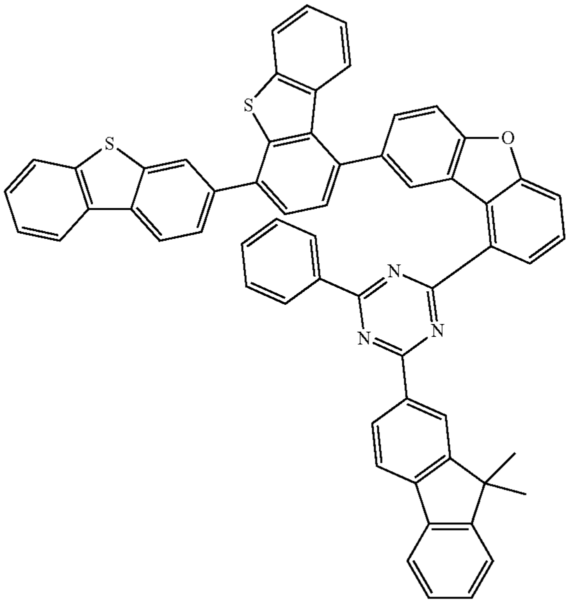
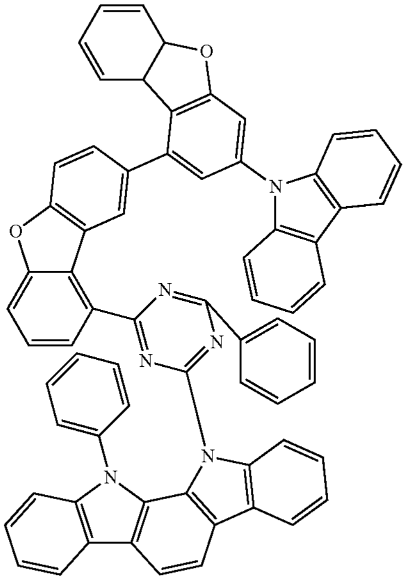
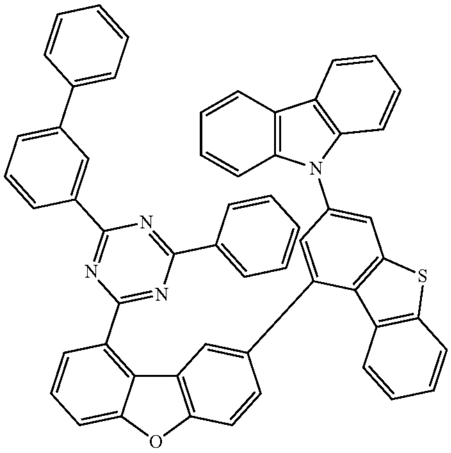
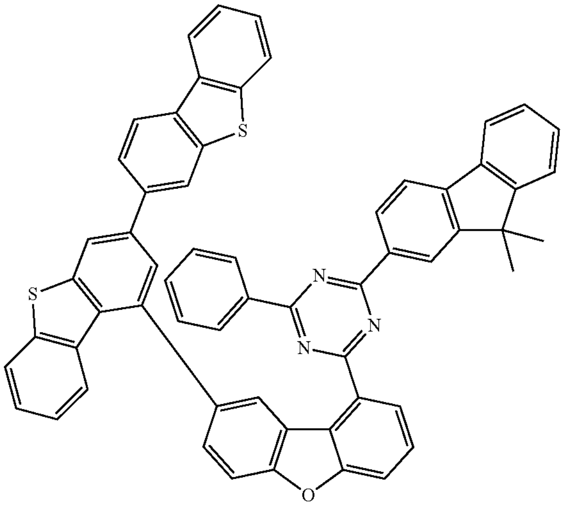

-continued
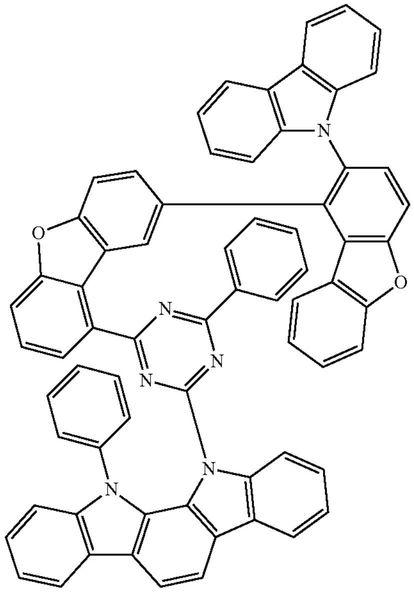
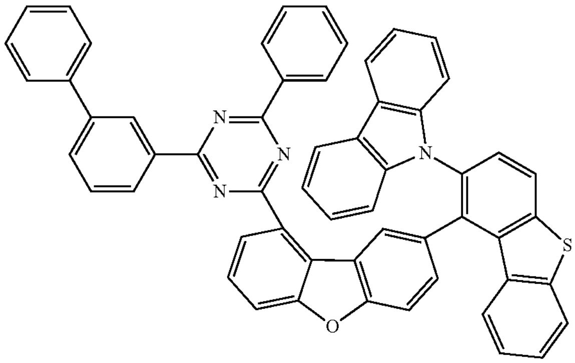
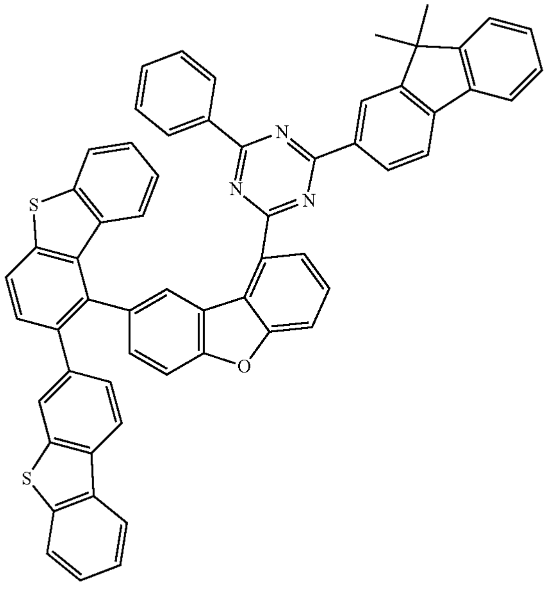
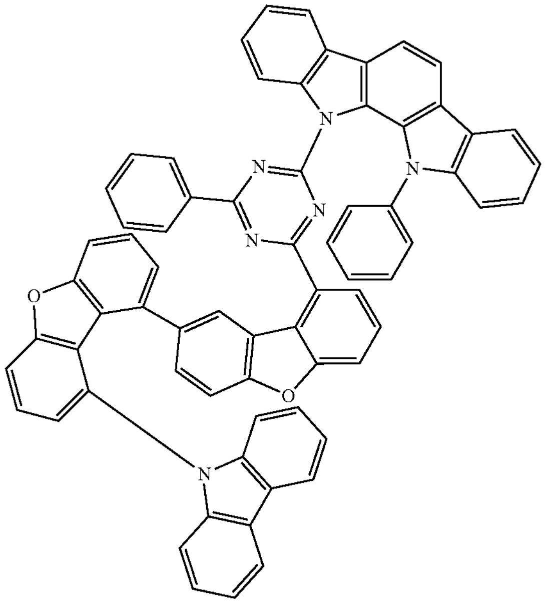

-continued
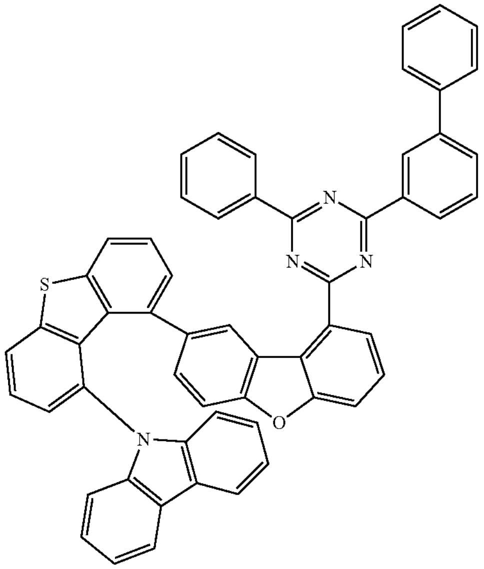
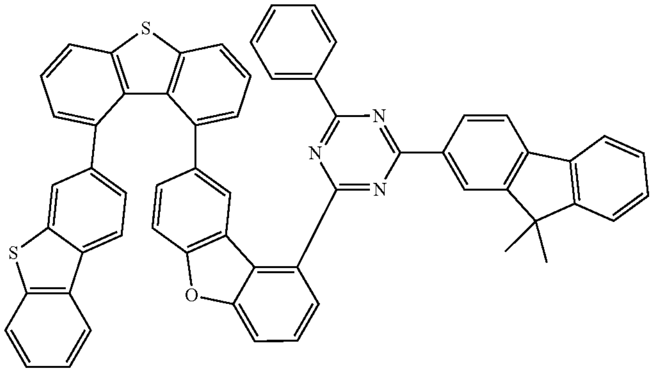
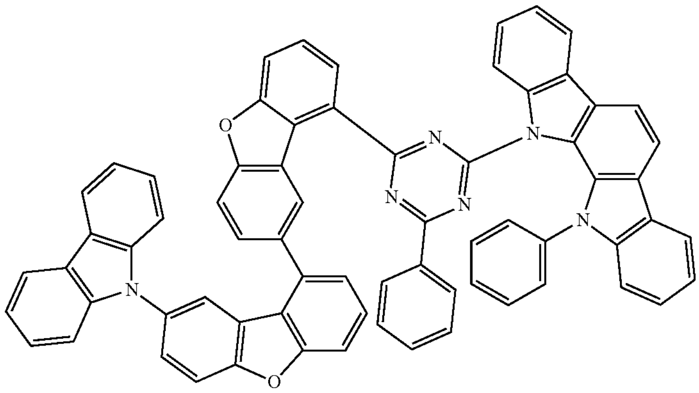
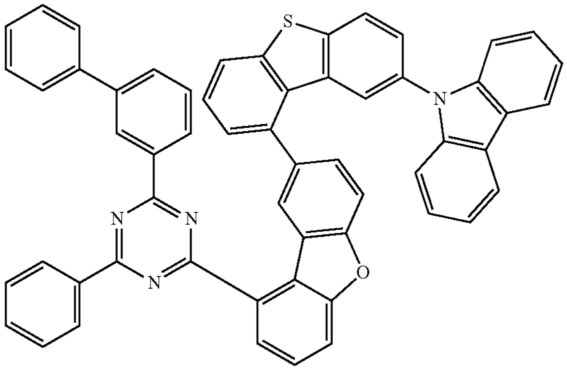
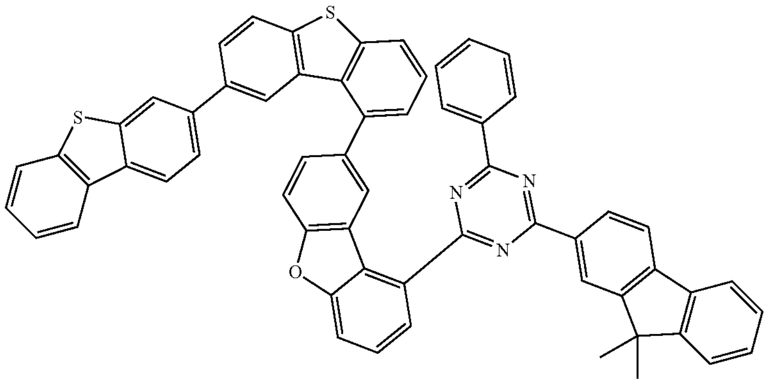

-continued
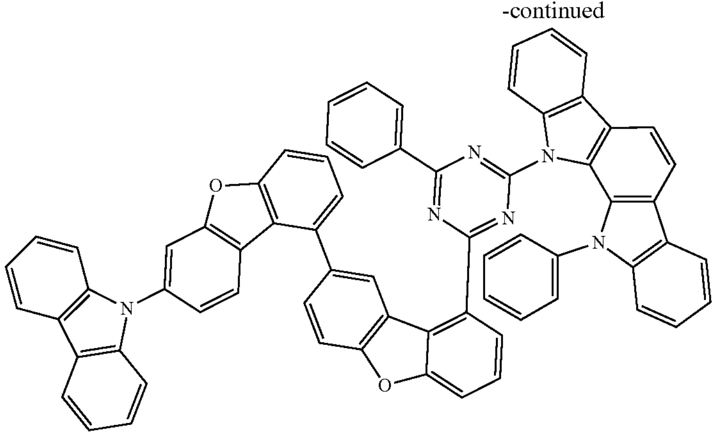
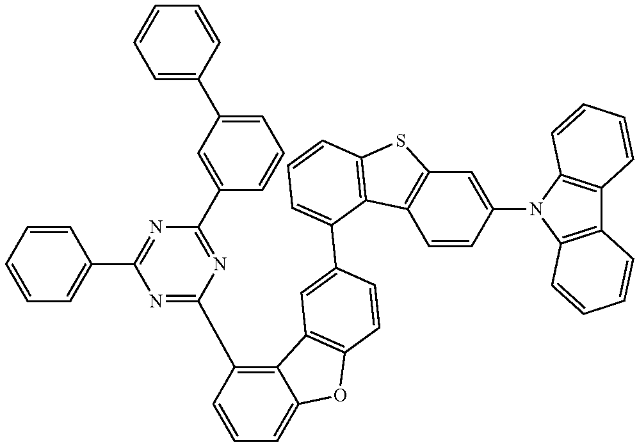
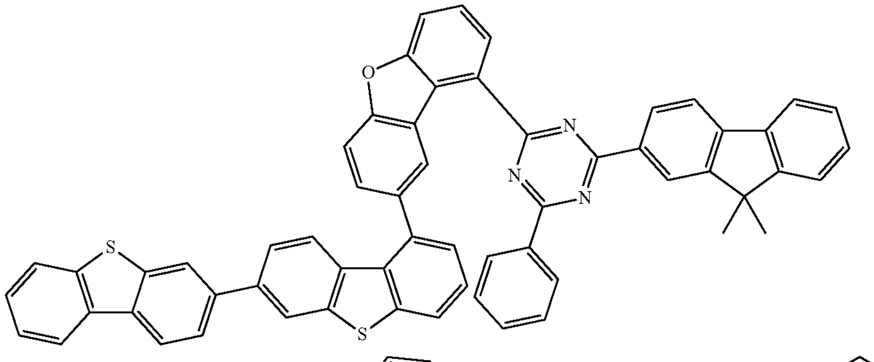
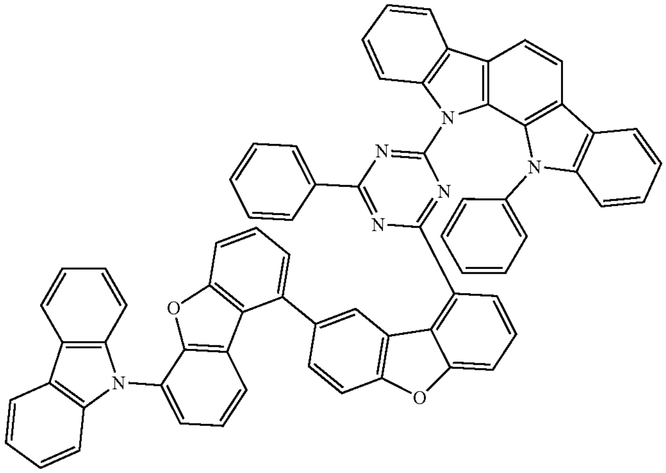
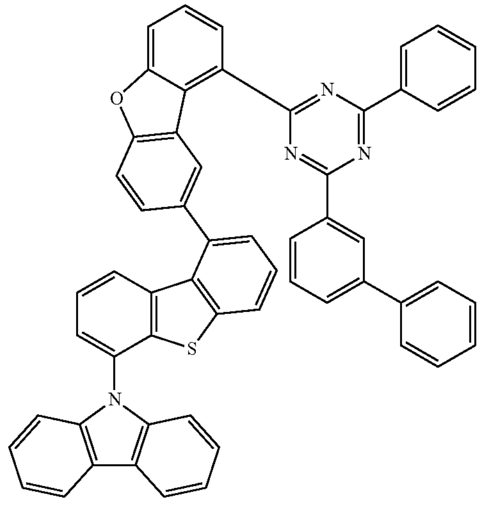

-continued
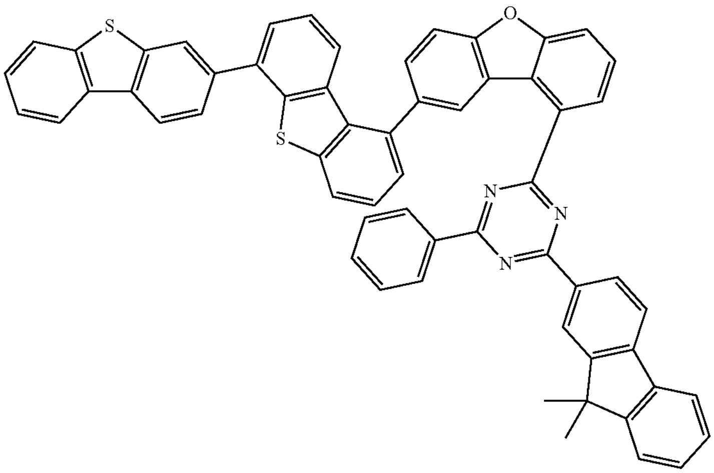
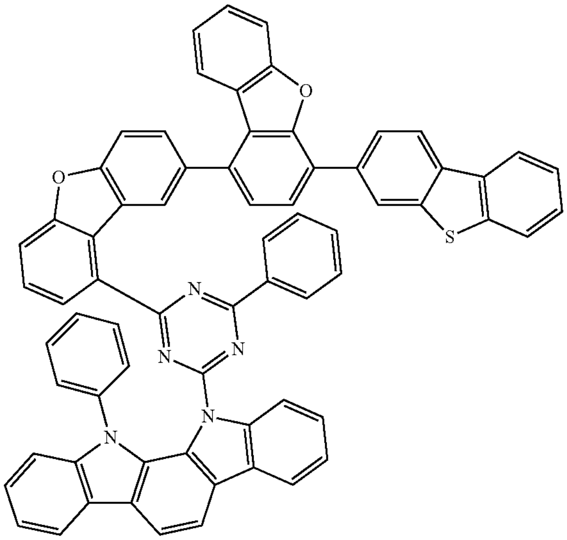
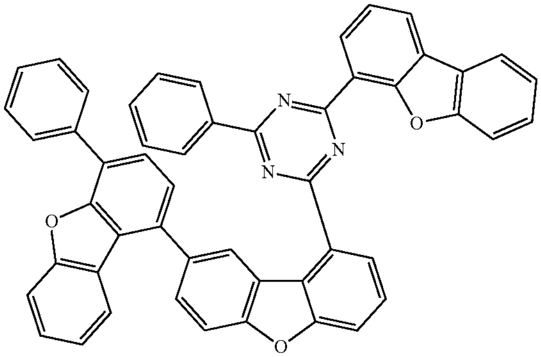
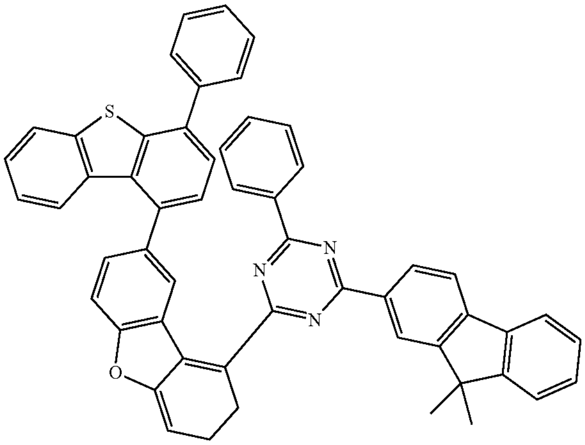
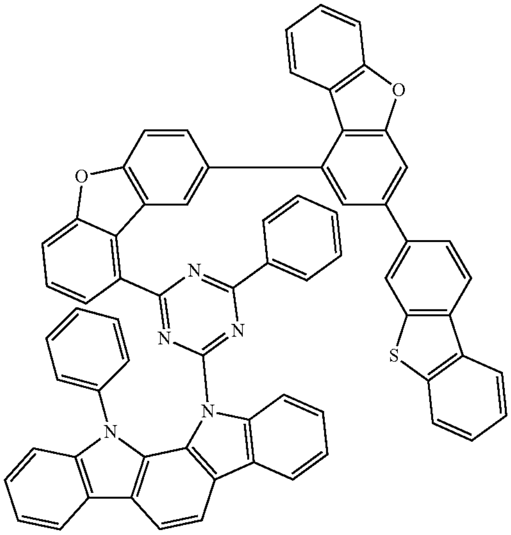

-continued
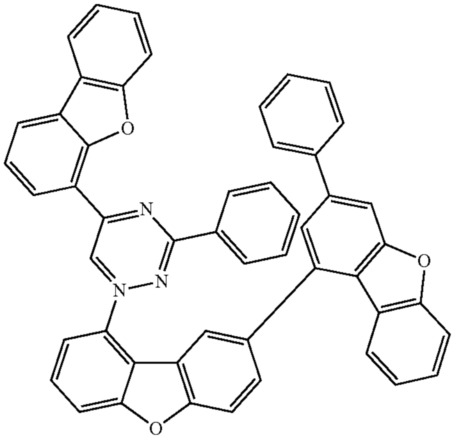
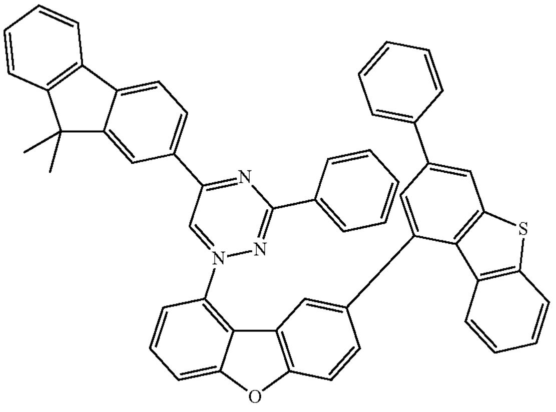
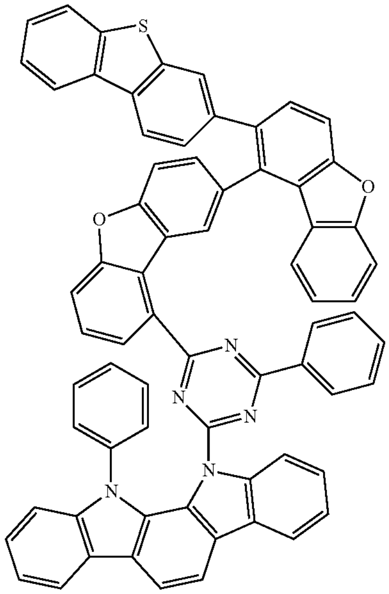
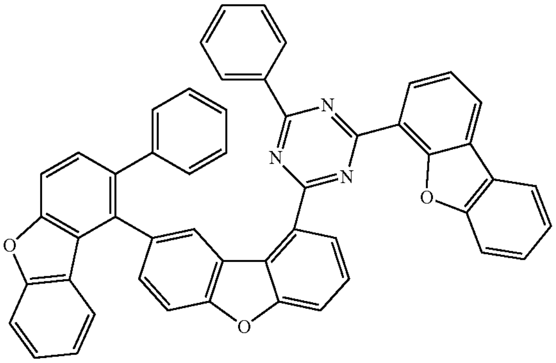
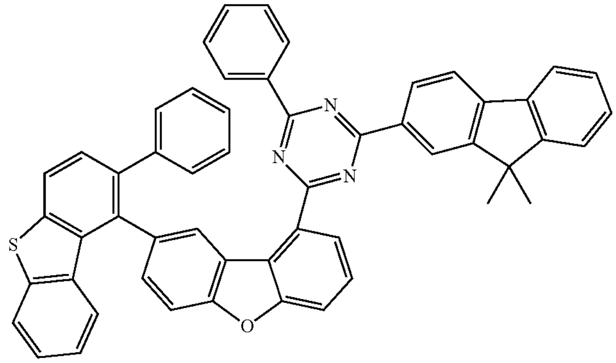
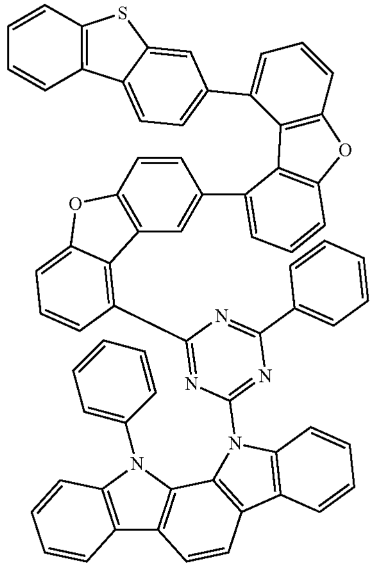

-continued
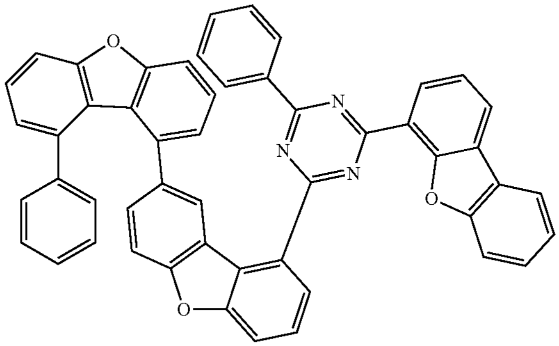
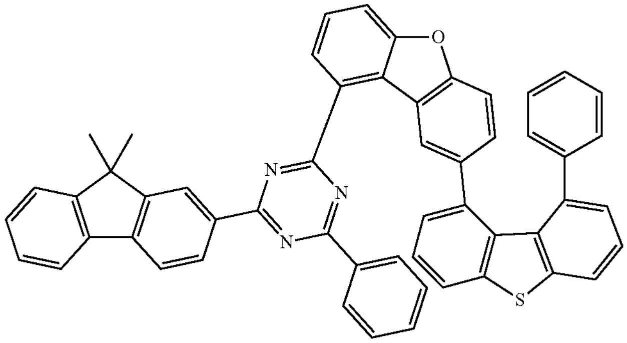
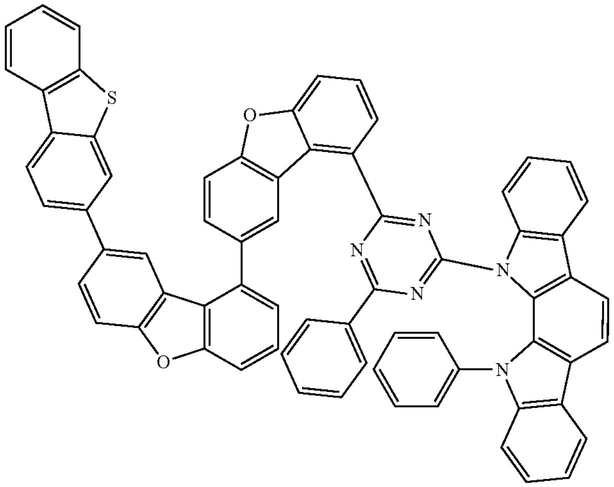
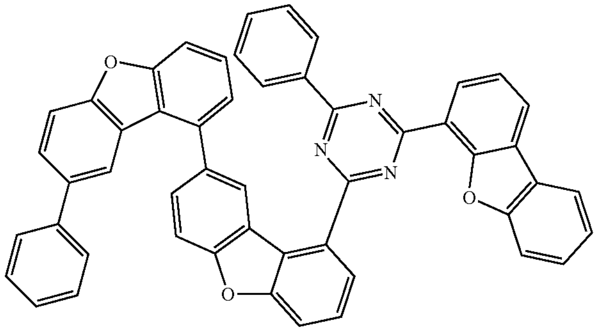

-continued
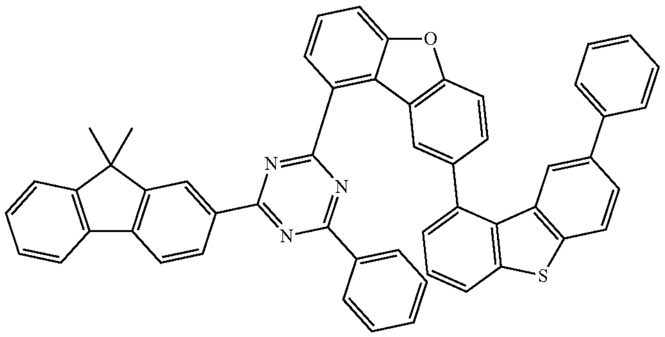
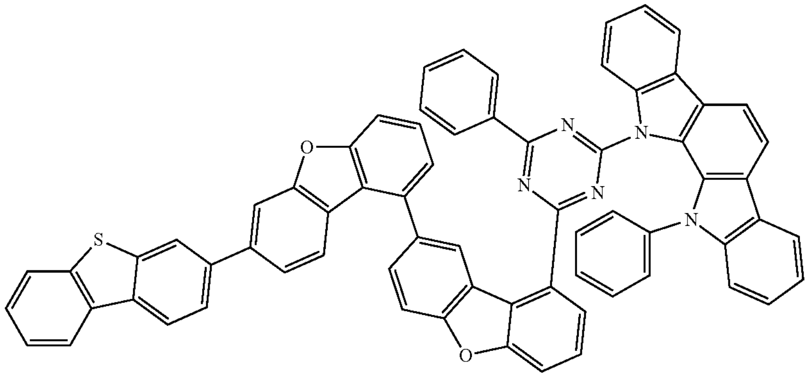
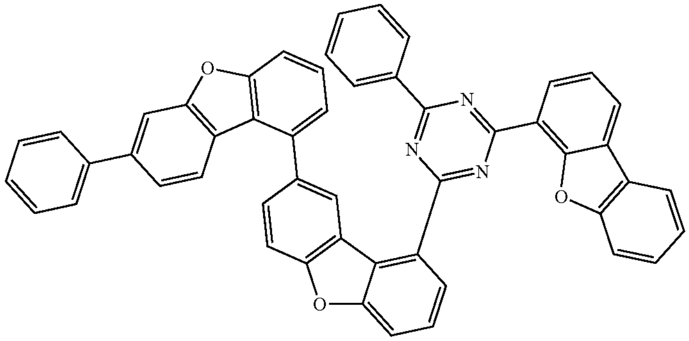
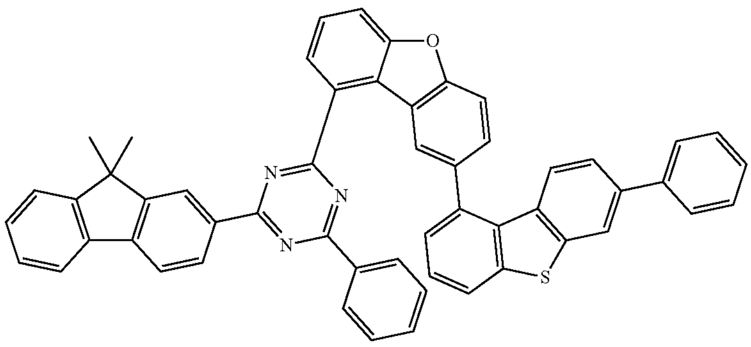

-continued
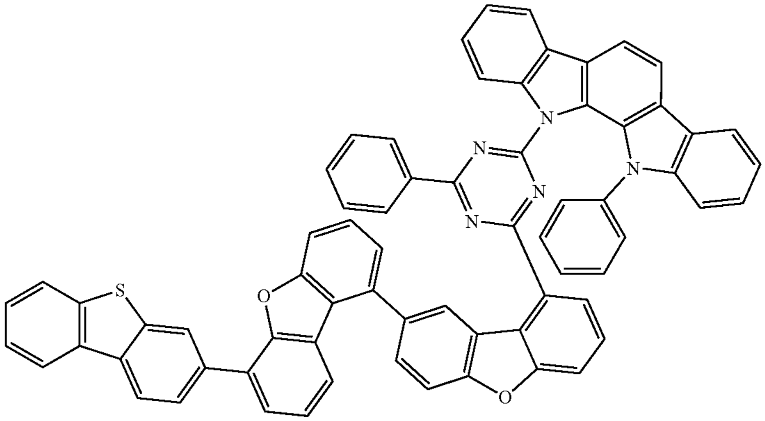
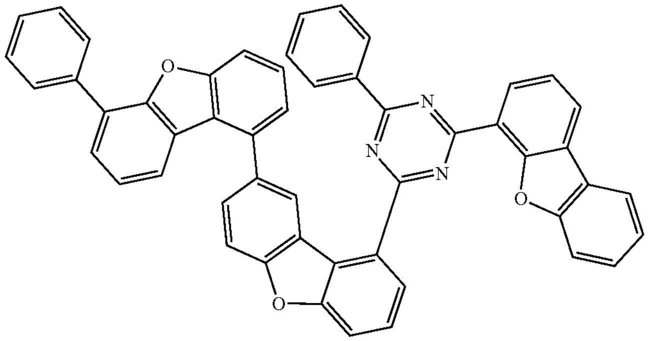
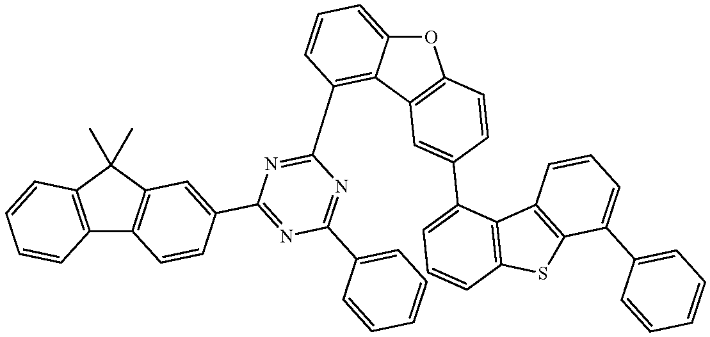
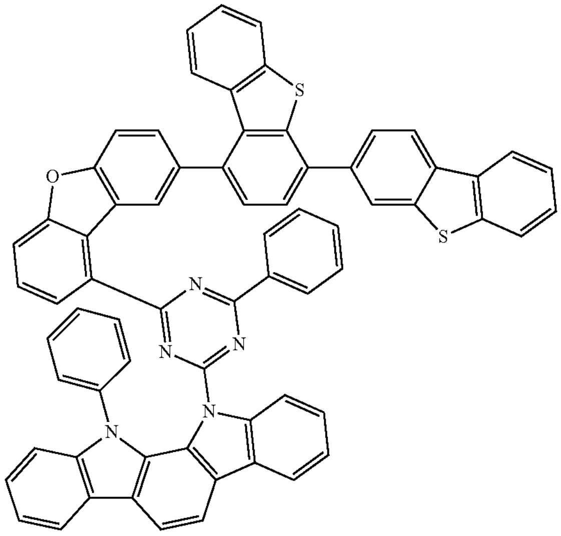

-continued
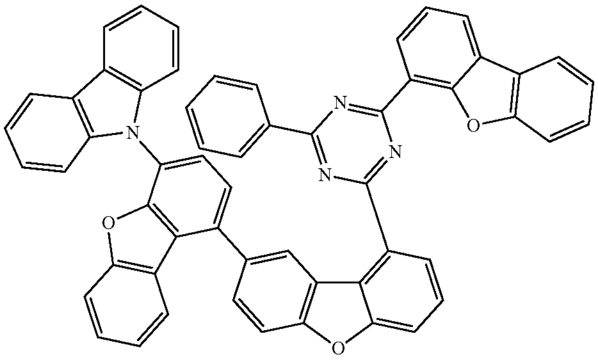
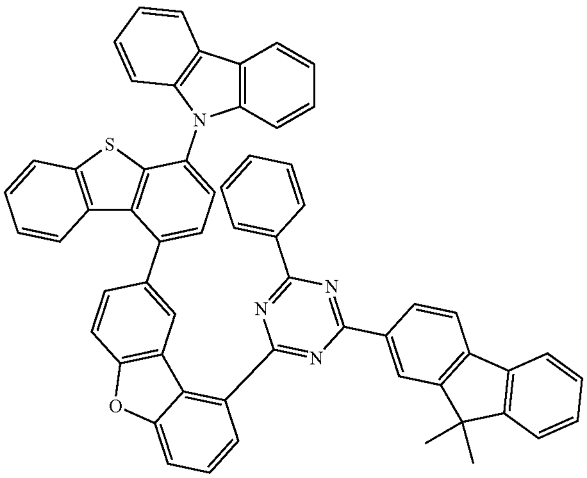
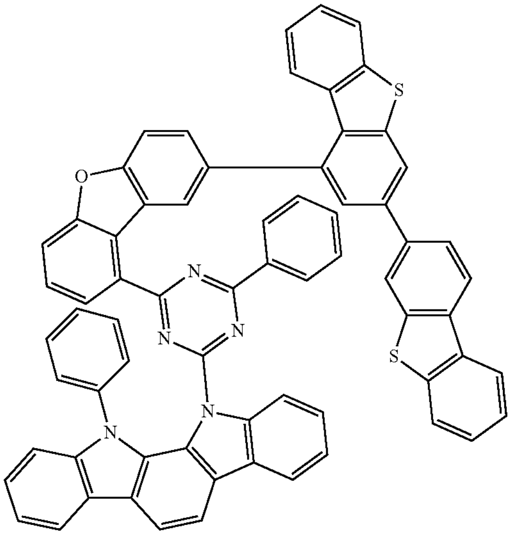
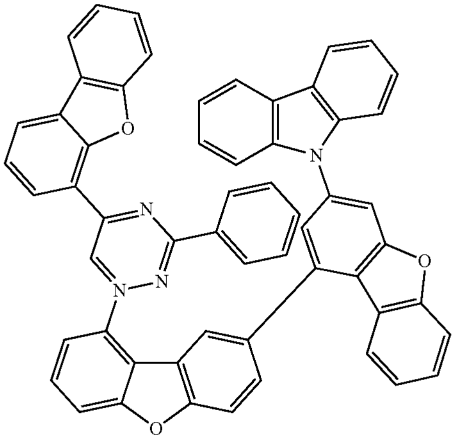
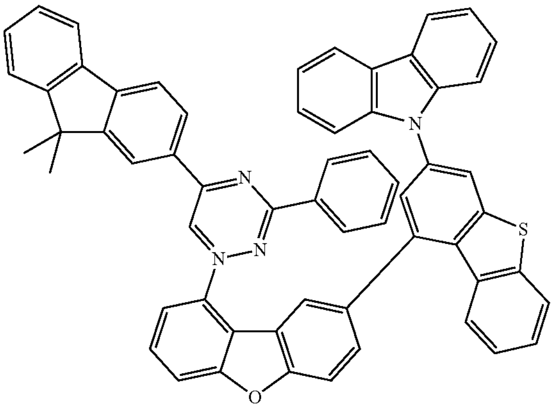

-continued
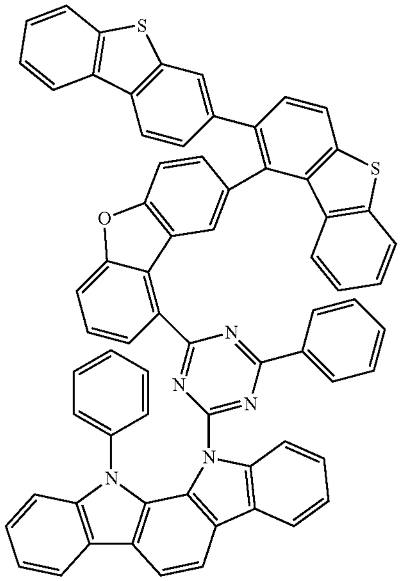
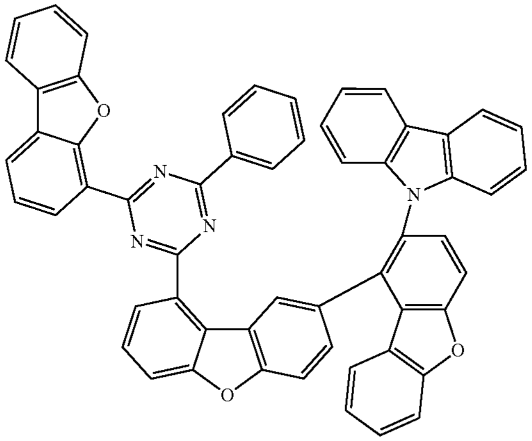
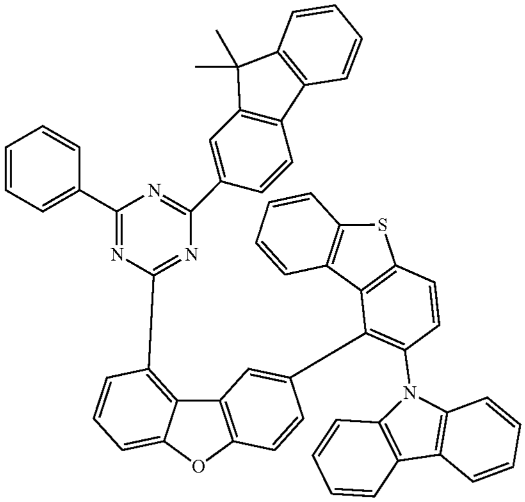
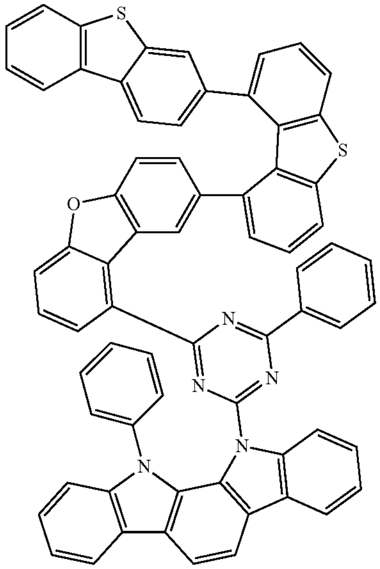
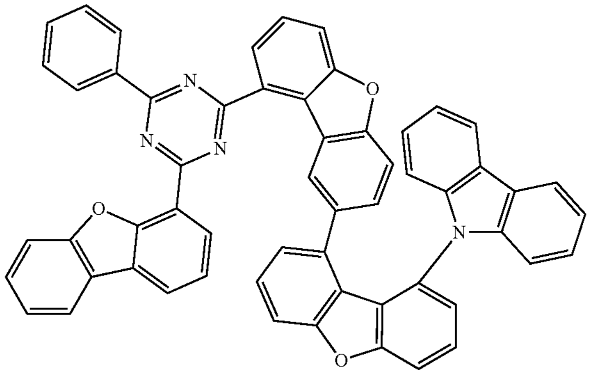

-continued
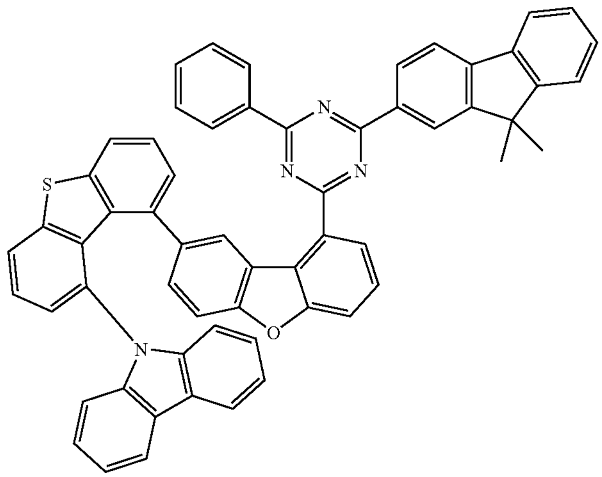
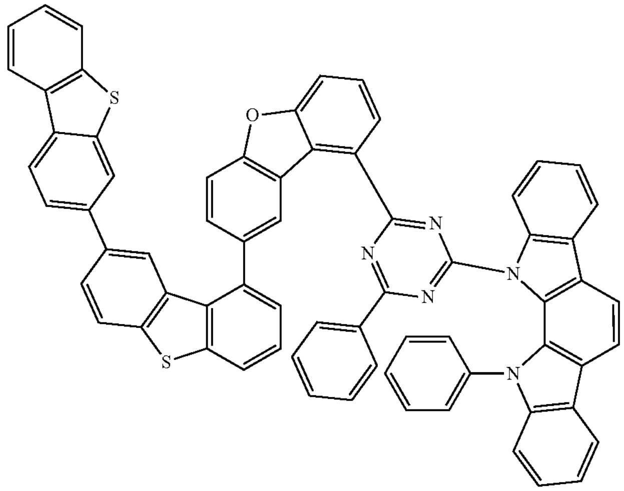
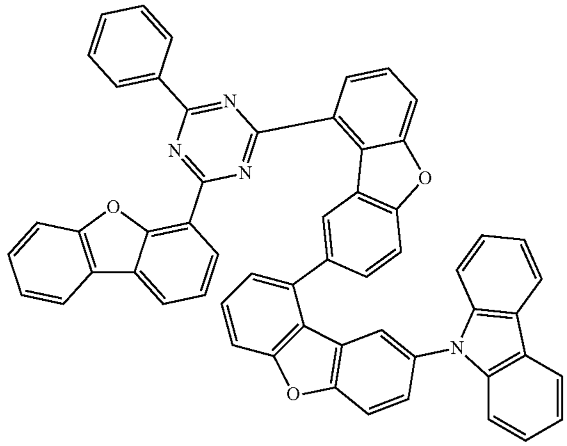

-continued
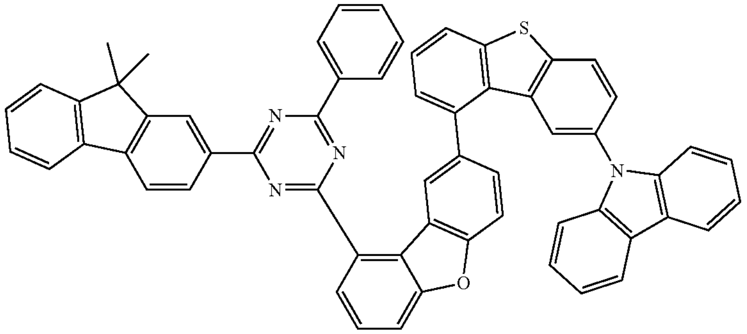
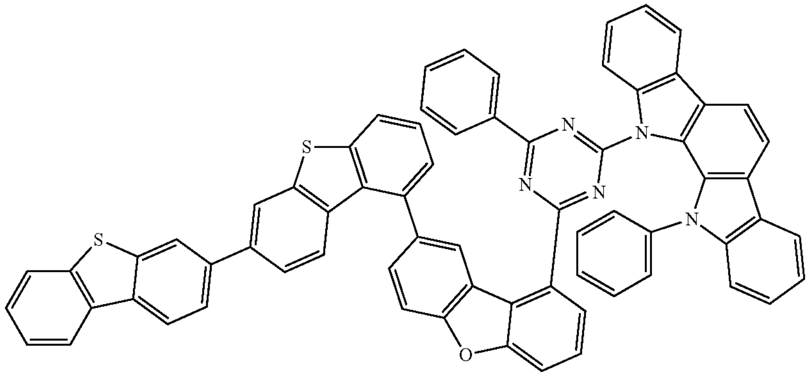
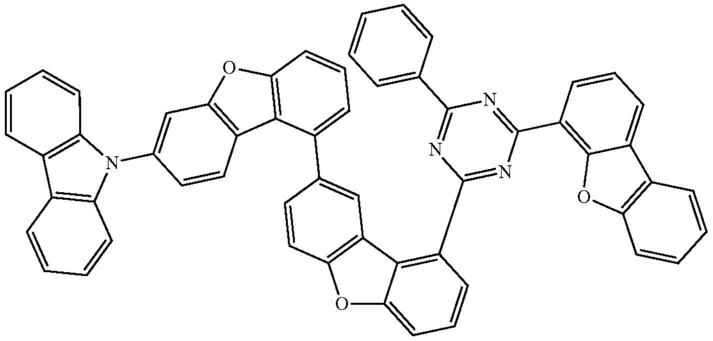
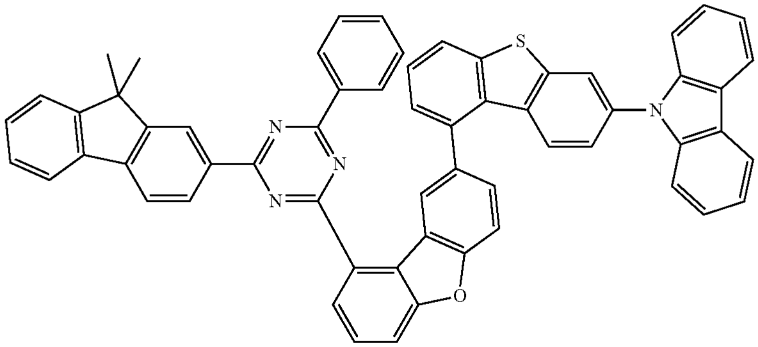

-continued
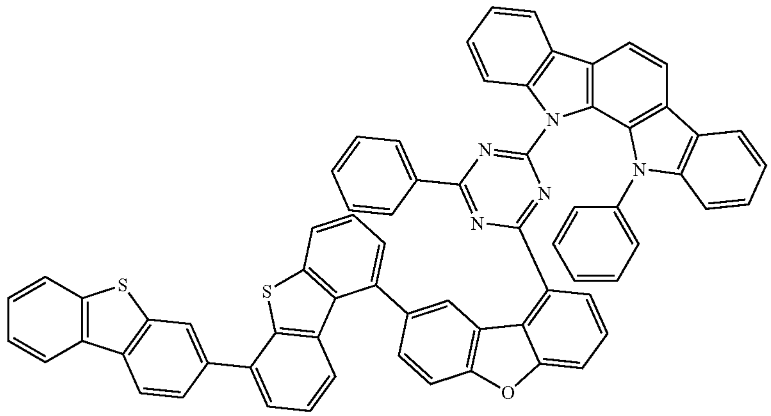
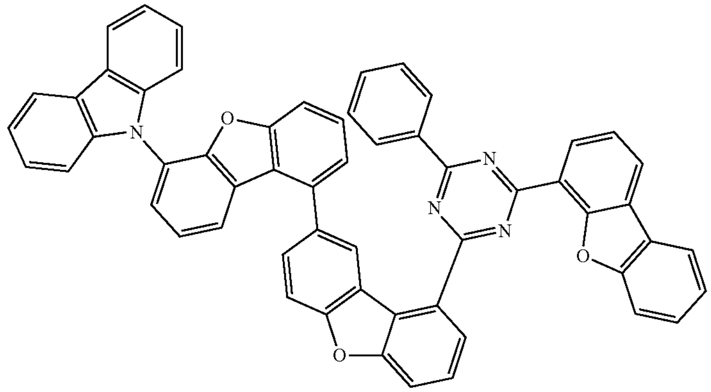
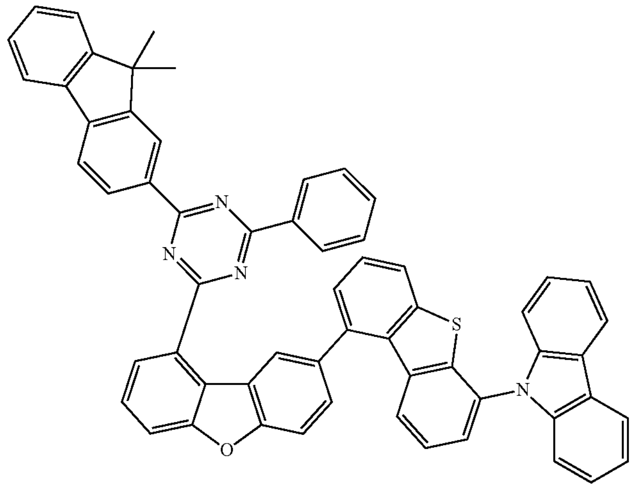

The compounds of the invention can be prepared by synthesis steps known to those skilled in the art, for example bromination, Suzuki coupling, Ullmann coupling, Hartwig-Buchwald coupling, etc. A suitable synthesis method is shown in general terms in Scheme 1 below, where the symbols and indices used have the definitions given above.

Scheme 1

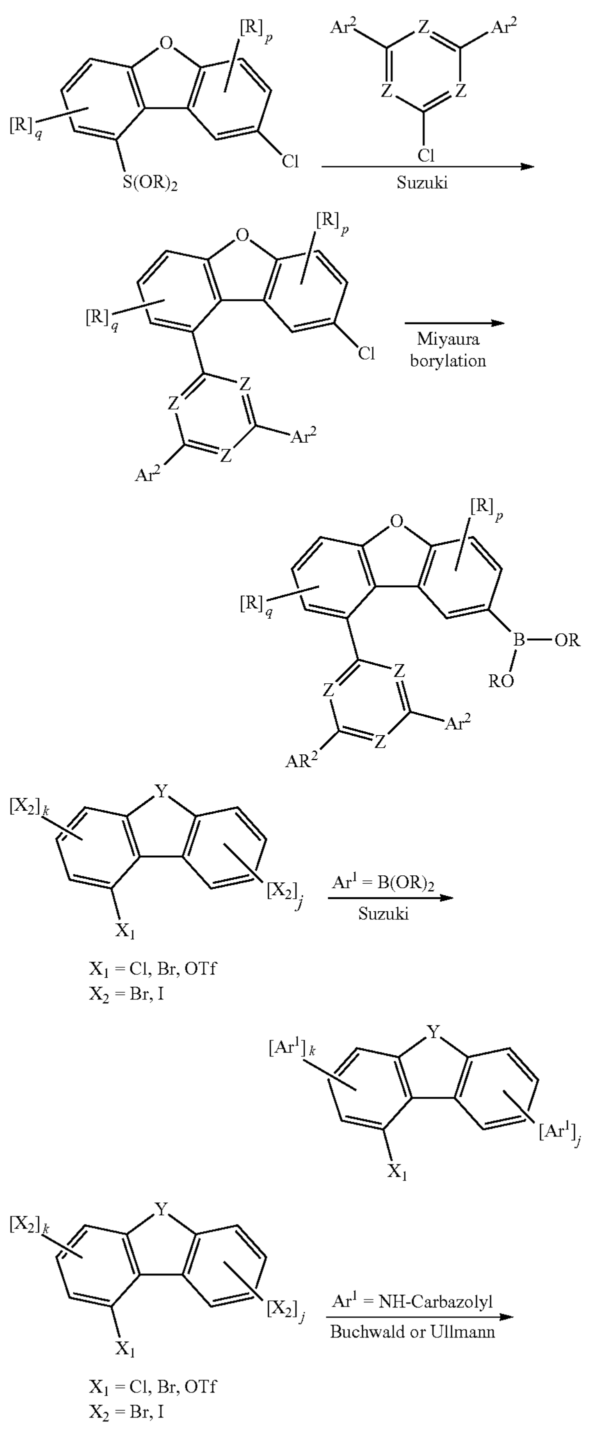

-continued

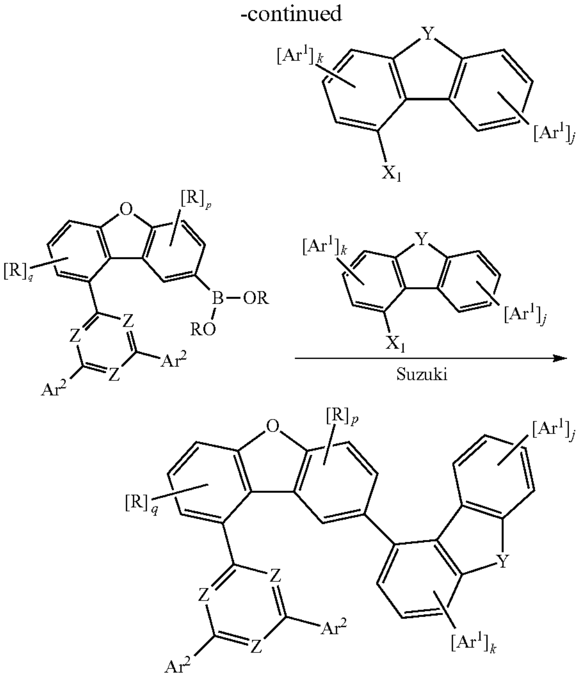

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, 2-methylbiphenyl, 3-methylbiphenyl, 1-methylnaphthalene, 1-ethylnaphthalene, ethyl octanoate, diethyl sebacate, octyl octanoate, heptylbenzene, menthyl isovalerate, cyclohexyl hexanoate or mixtures of these solvents.

The present invention therefore further provides a formulation comprising at least one compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound and/or a further matrix material. Suitable emitting compounds and further matrix materials are listed at the back in connection with the organic electroluminescent device. This further compound may also be polymeric.

The compounds of the invention are suitable for use in an electronic device, especially in an organic electroluminescent device. The present invention therefore further provides for the use of a compound of the invention in an electronic device, especially in an organic electroluminescent device.

The present invention still further provides an electronic device comprising at least one compound of the invention.

An electronic device in the context of the present invention is a device comprising at least one layer comprising at least one organic compound. This component may also comprise inorganic materials or else layers formed entirely from inorganic materials. The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), dye-sensitized organic solar cells (DSSCs), organic optical detectors, organic photoreceptors, organic field-quench devices (O-FQDs), light-emitting electrochemical cells (LECs), organic laser diodes (O-lasers) and organic plasmon emitting devices, but preferably organic electroluminescent devices (OLEDs), more preferably phosphorescent OLEDs.

The organic electroluminescent device comprises cathode, anode and at least one emitting layer. Apart from these layers, it may also comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers show blue, green and orange or red emission. The organic electroluminescent device of the invention may also be a tandem OLED, especially for white-emitting OLEDs.

The compound of the invention according to the above-detailed embodiments may be used in different layers, according to the exact structure. Preference is given to an organic electroluminescent device comprising a compound of formula (1) or the above-recited preferred embodiments in an emitting layer as matrix material for phosphorescent emitters or for emitters that exhibit TADF (thermally activated delayed fluorescence), especially for phosphorescent emitters. In this case, the organic electroluminescent device may contain an emitting layer, or it may contain a plurality of emitting layers, where at least one emitting layer contains at least one compound of the invention as matrix material. In addition, the compound of the invention may also be used in an electron transport layer and/or in a hole blocker layer.

When the compound of the invention is used as matrix material for a phosphorescent compound in an emitting layer, it is preferably used in combination with one or more phosphorescent materials (triplet emitters).

Phosphorescence in the context of this invention is understood to mean luminescence from an excited state having higher spin multiplicity, i.e. a spin state >1, especially from an excited triplet state. In the context of this application, all luminescent complexes with transition metals or lanthanides, especially all iridium, platinum and copper complexes, shall be regarded as phosphorescent compounds.

Examples of the emitters described above can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2017/032439, WO 2018/011186 and WO 2018/041769, WO 2019/020538, WO 2018/178001, WO 2019/115423 and WO 2019/158453. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Examples of phosphorescent dopants are adduced below.

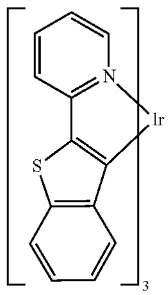
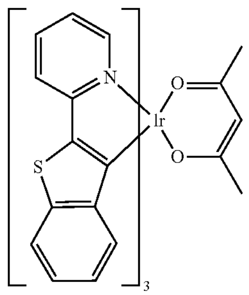
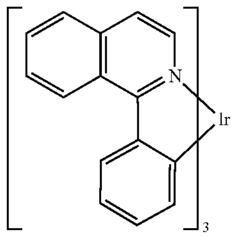
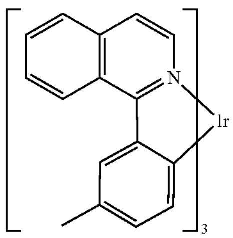
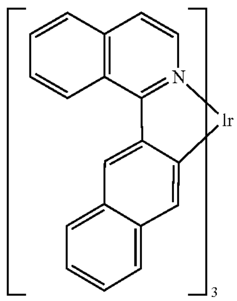
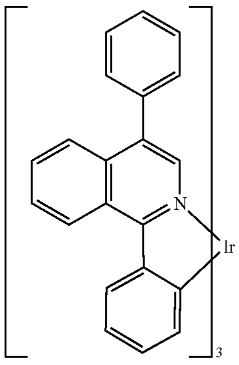

-continued
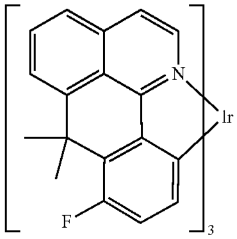
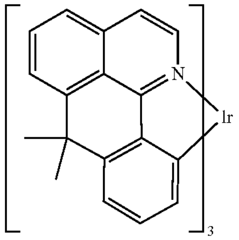
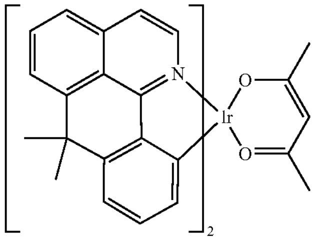
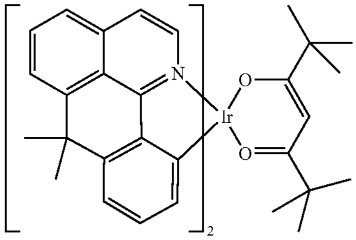
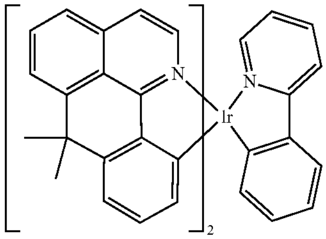
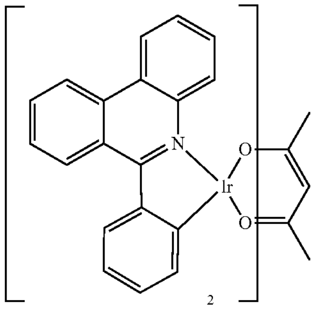
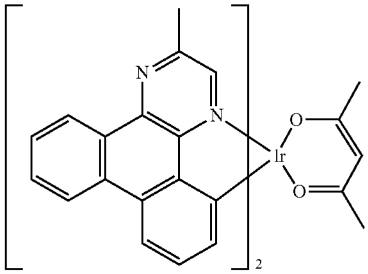
-continued
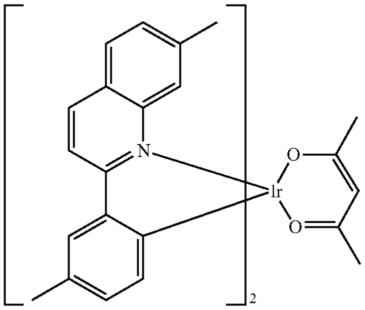
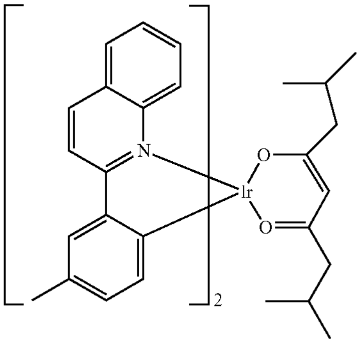
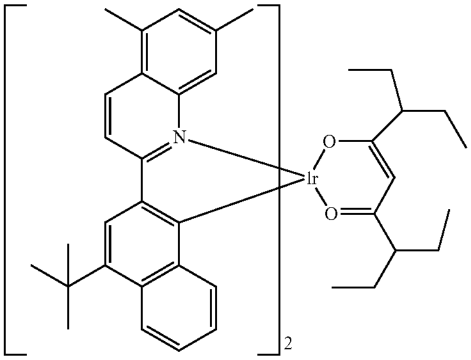
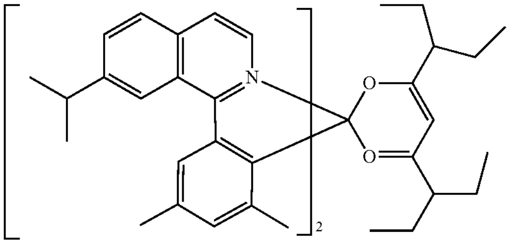
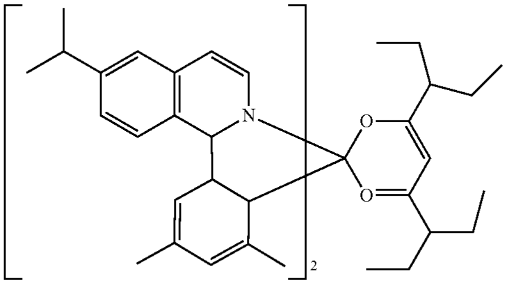

-continued
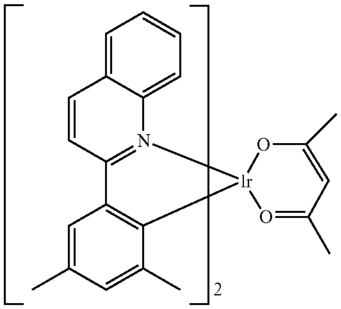
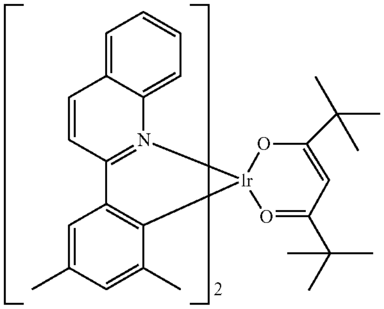
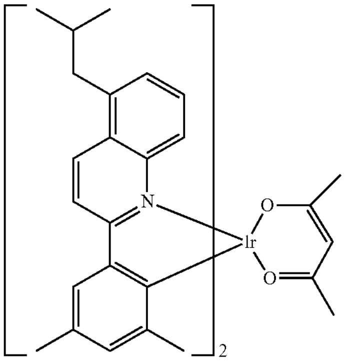
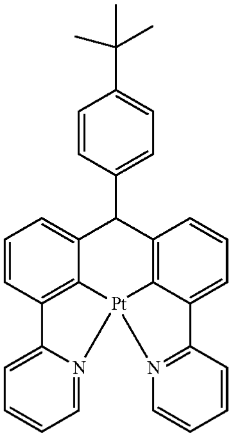
-continued
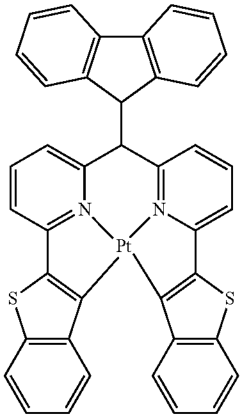
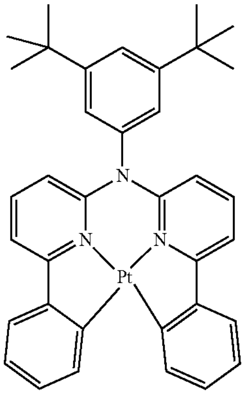
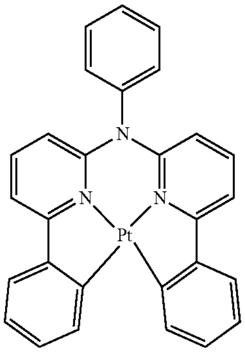
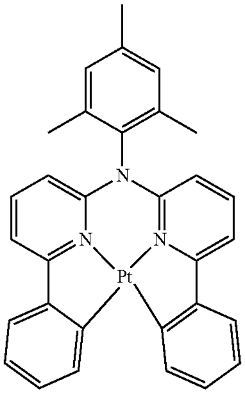

-continued
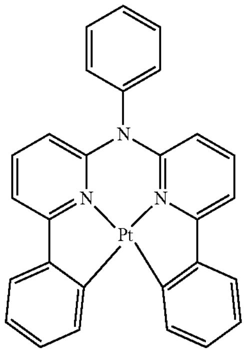
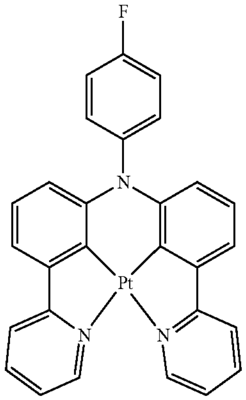
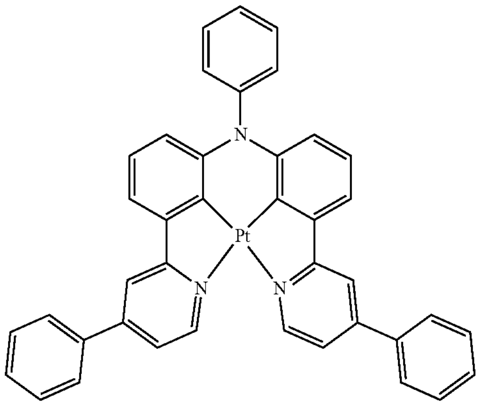
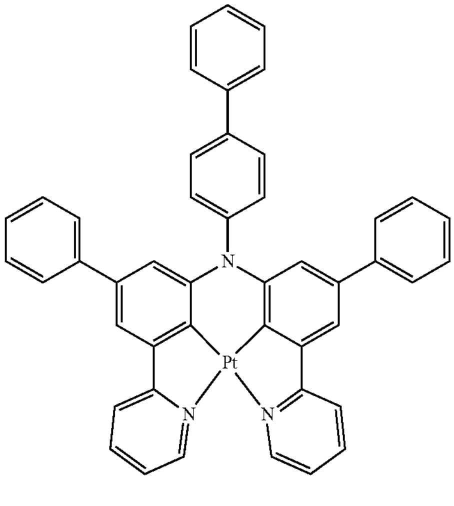
-continued
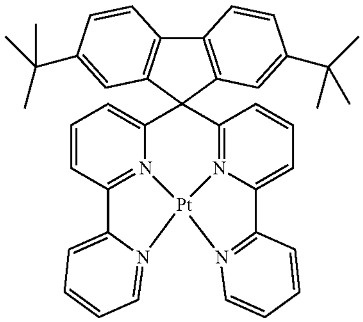
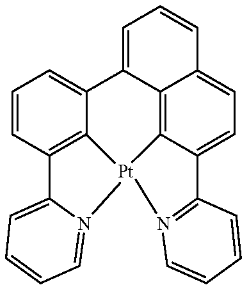
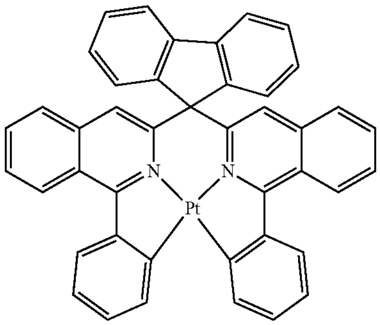
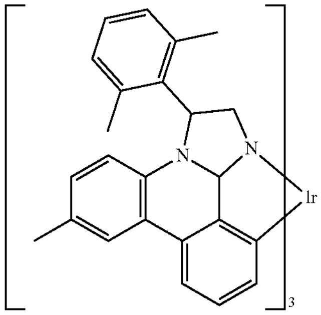
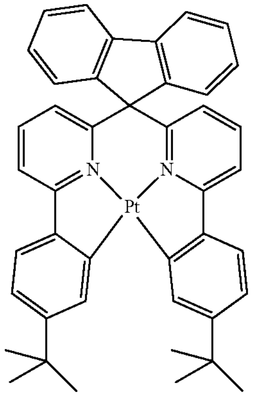

-continued
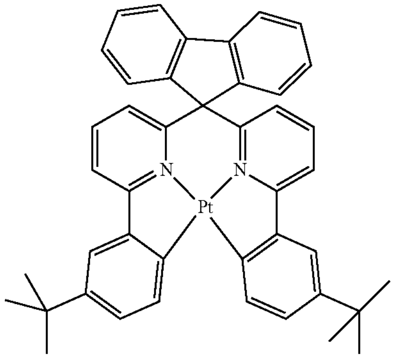
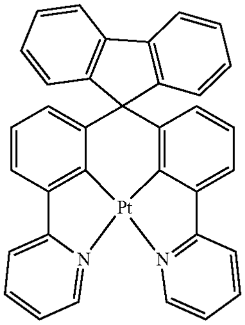
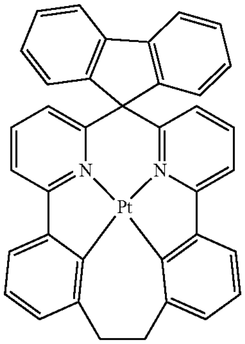
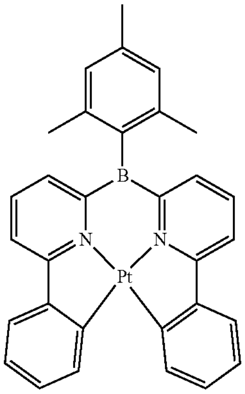
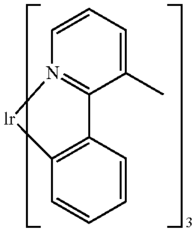
-continued
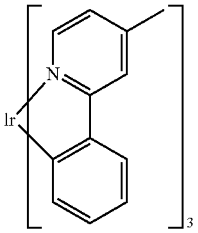
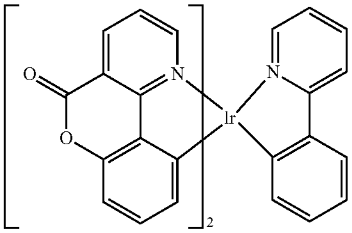
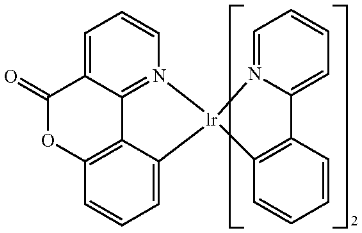
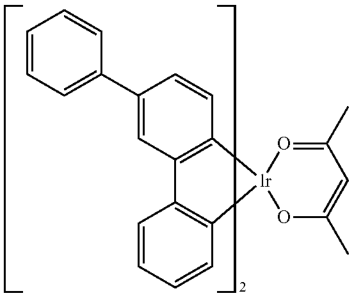
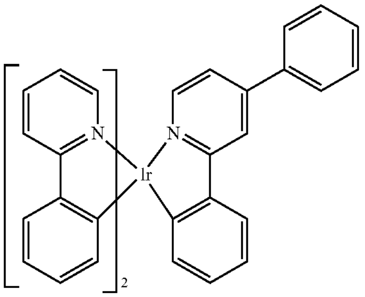
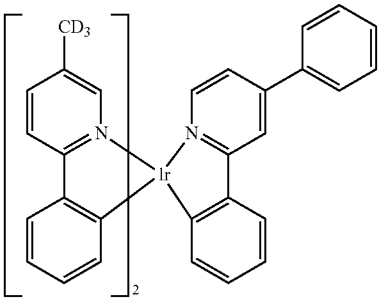

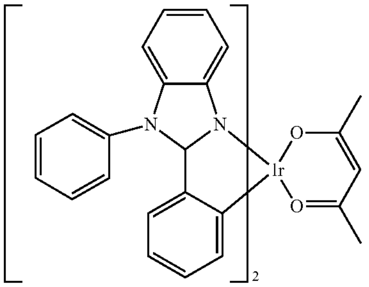
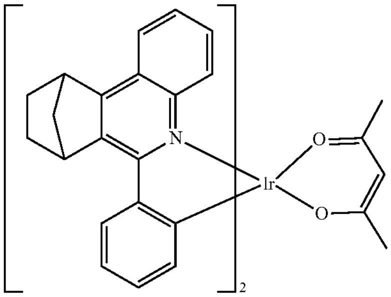
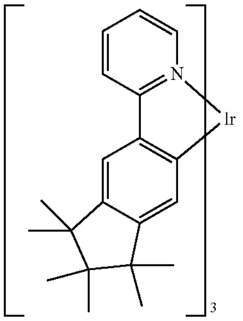
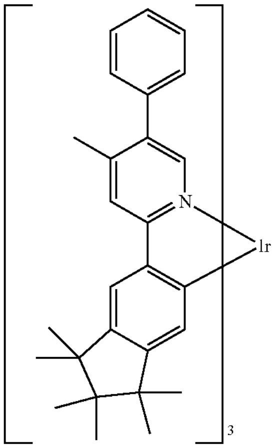
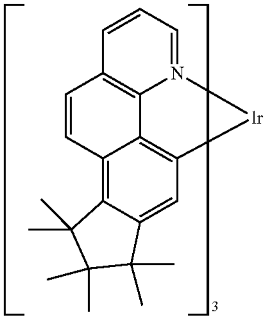
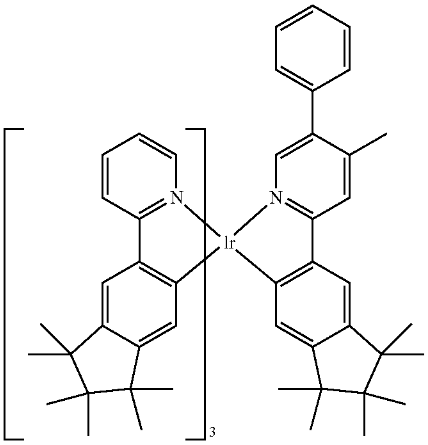
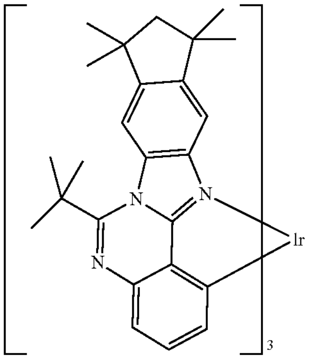
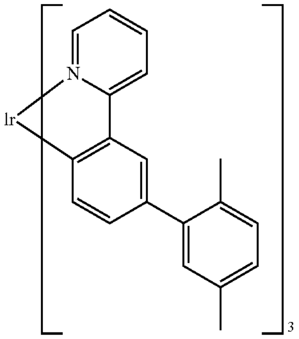
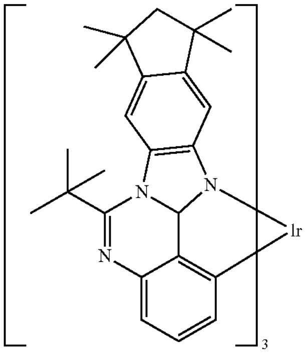

-continued
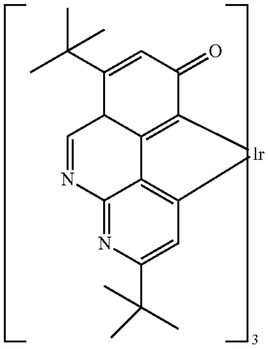
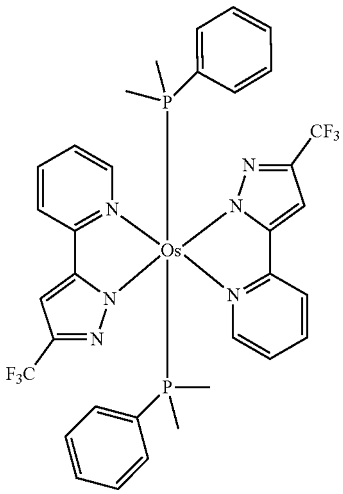
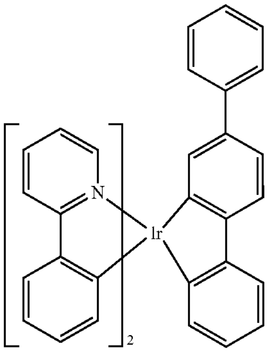
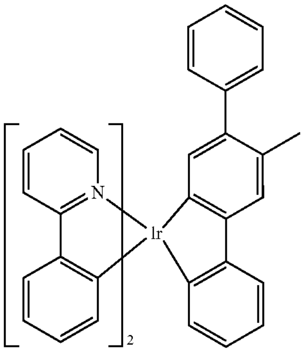
-continued
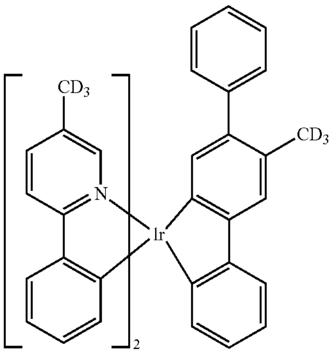
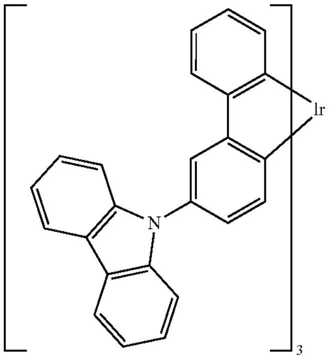
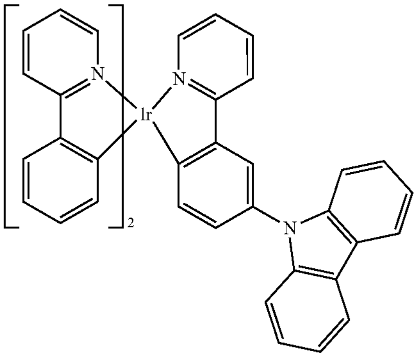
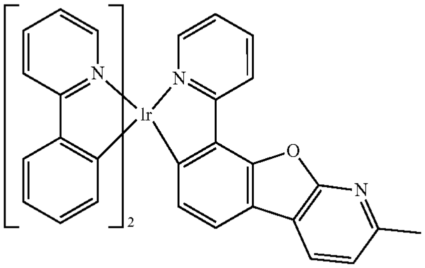
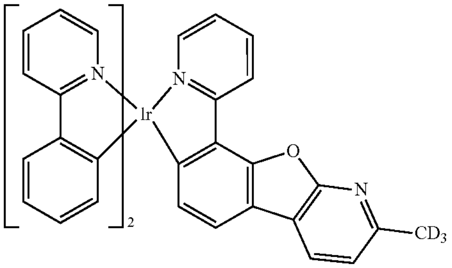

-continued
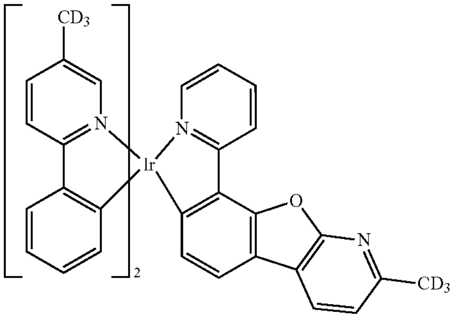
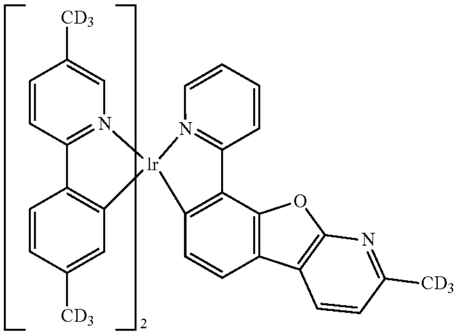
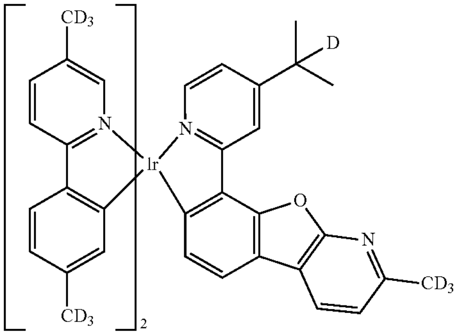
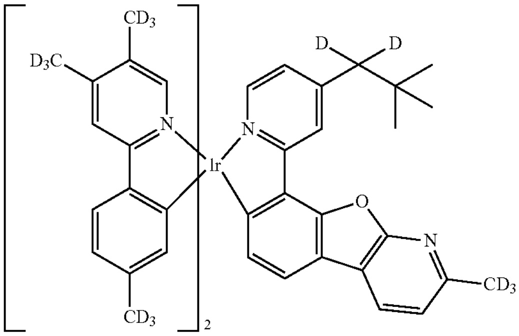
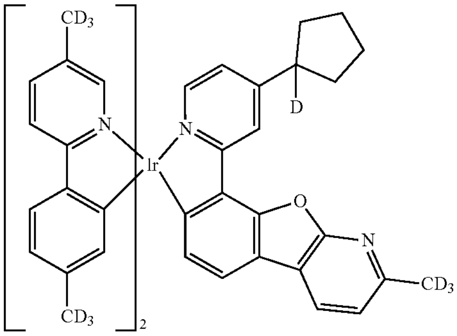
-continued
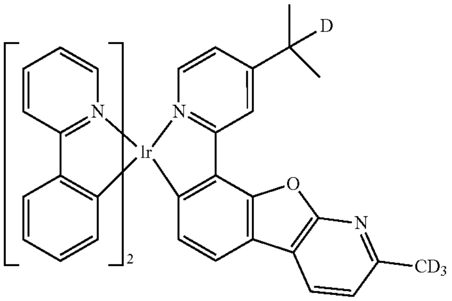
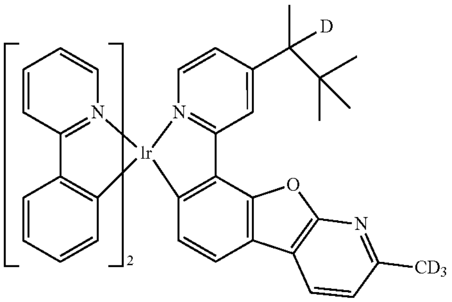
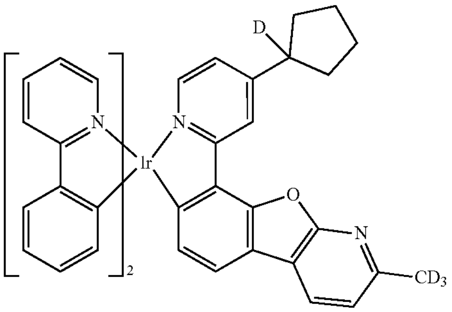
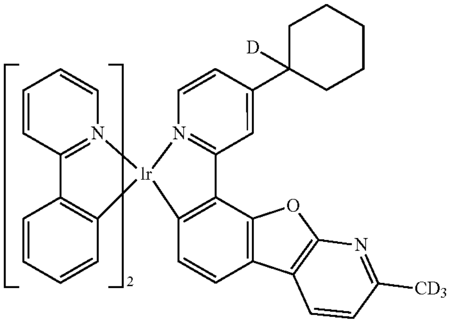
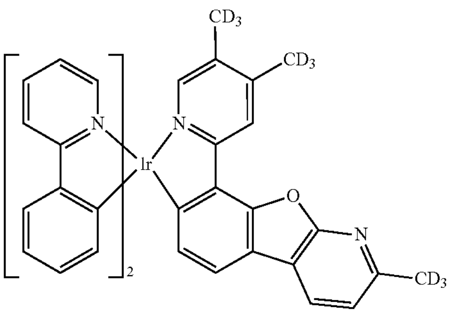

-continued
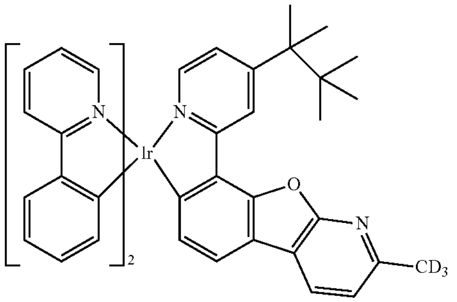
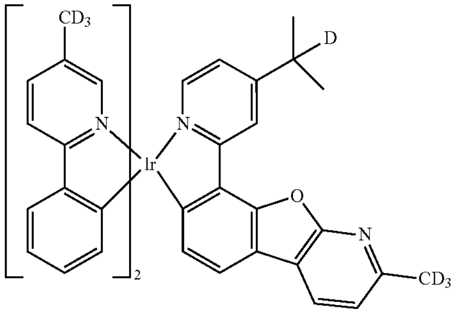
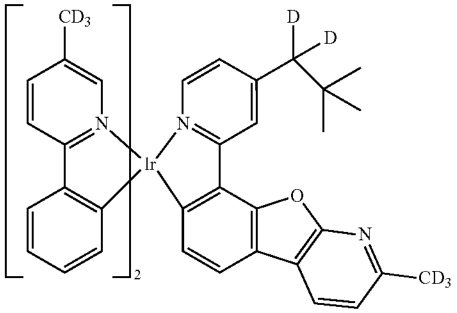
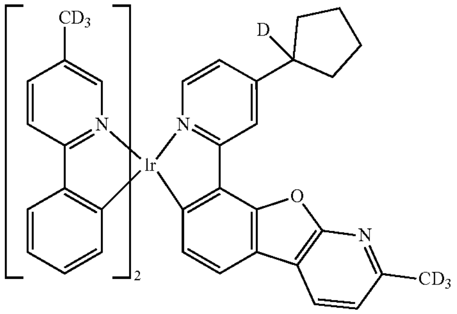
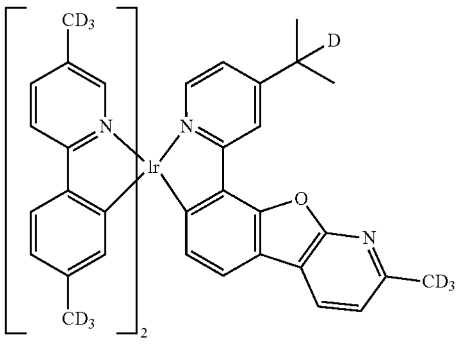
-continued
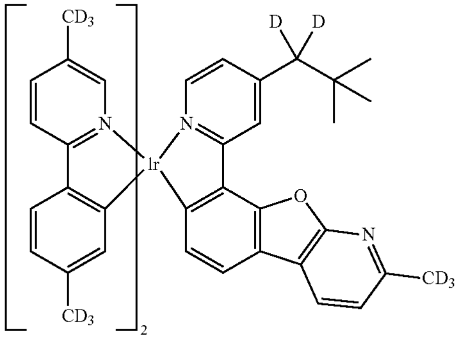
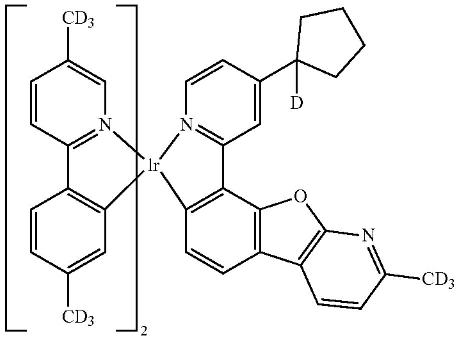
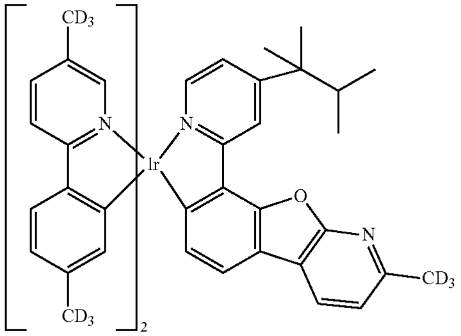
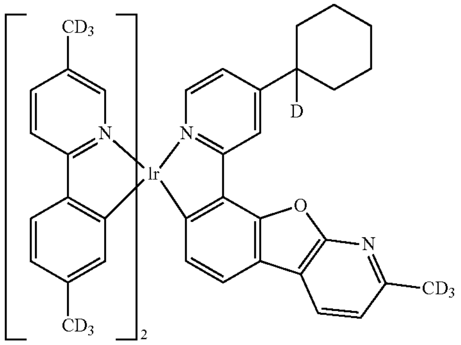
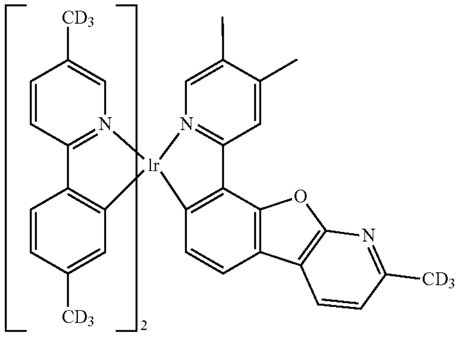

-continued
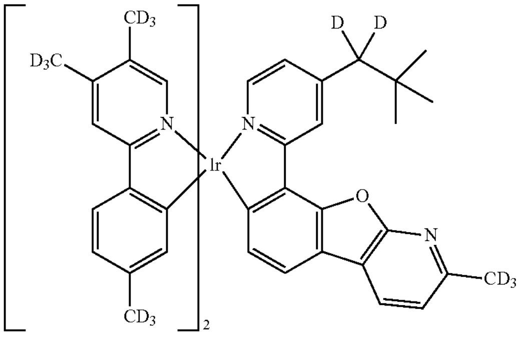
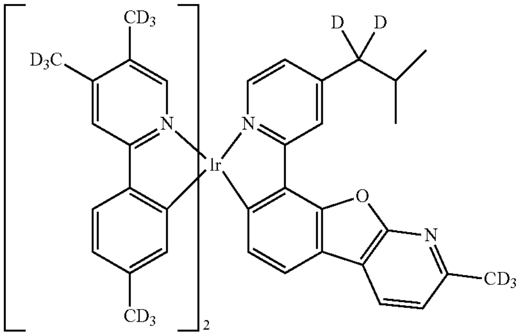
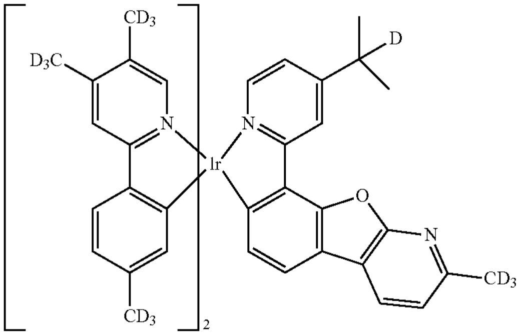
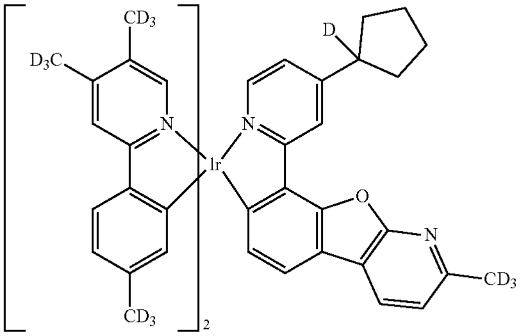
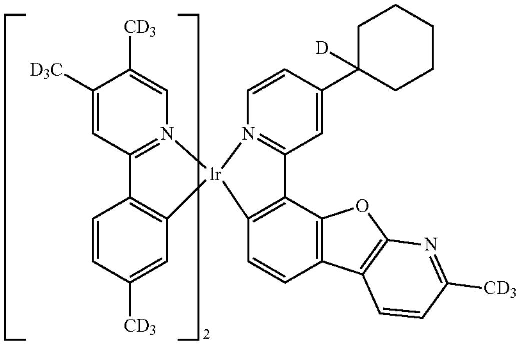
-continued
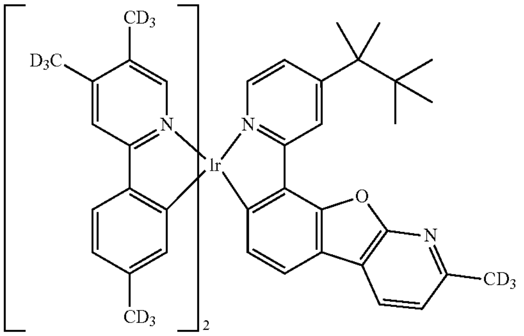
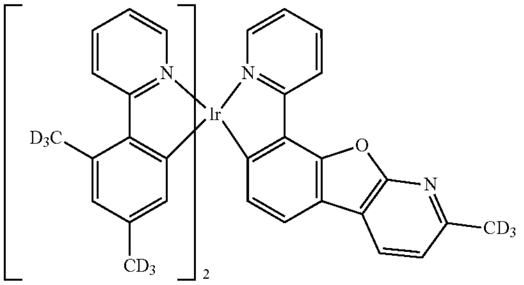
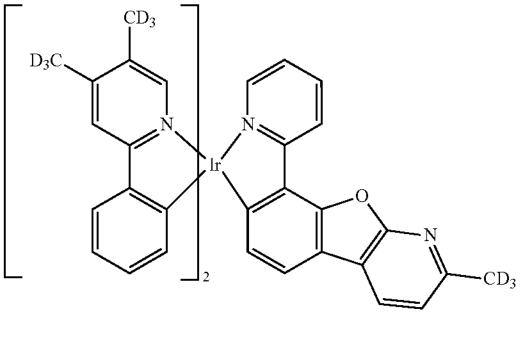
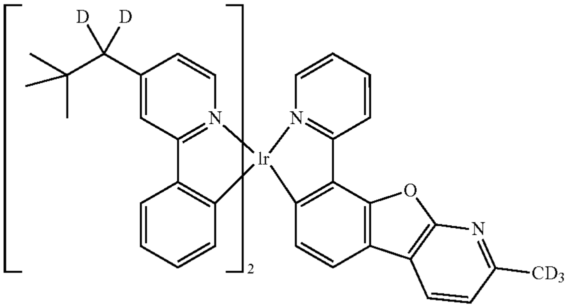
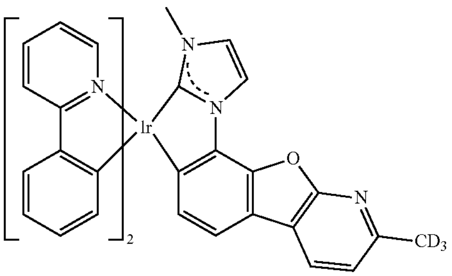

-continued
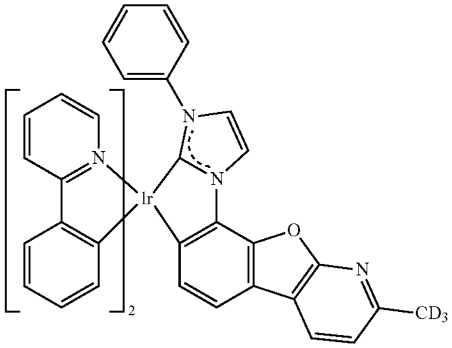
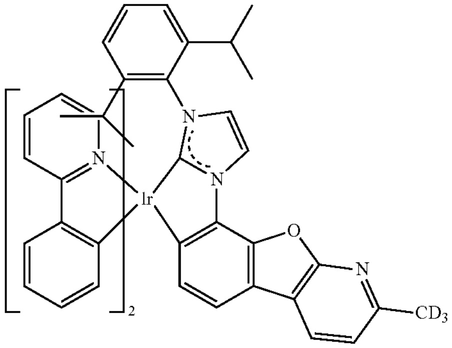
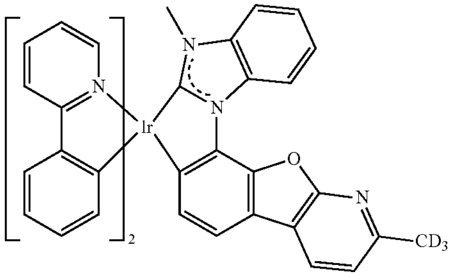
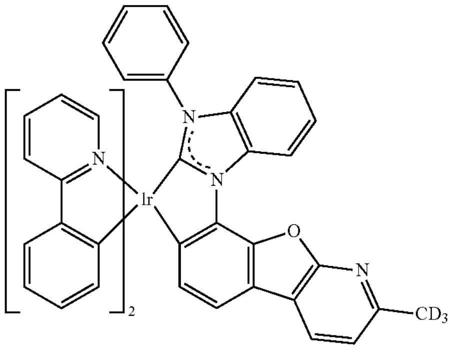
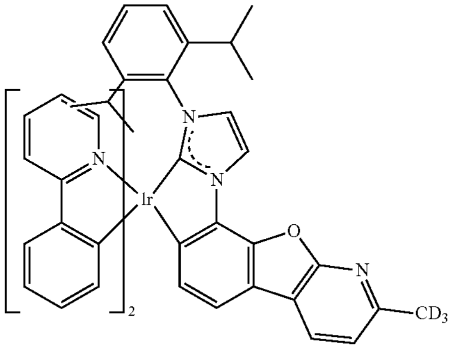
-continued
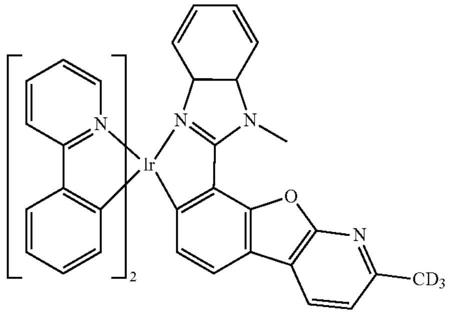
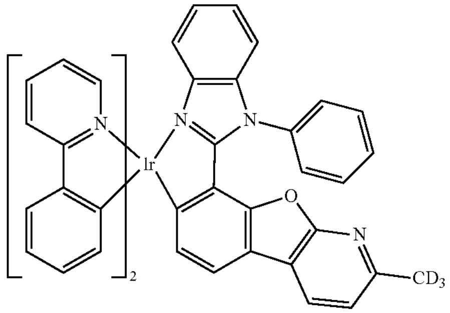
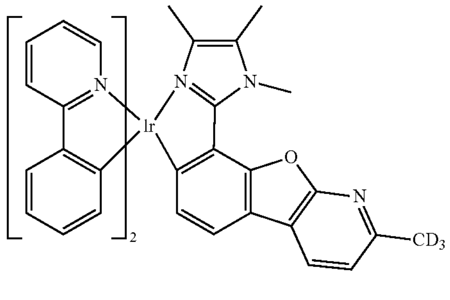
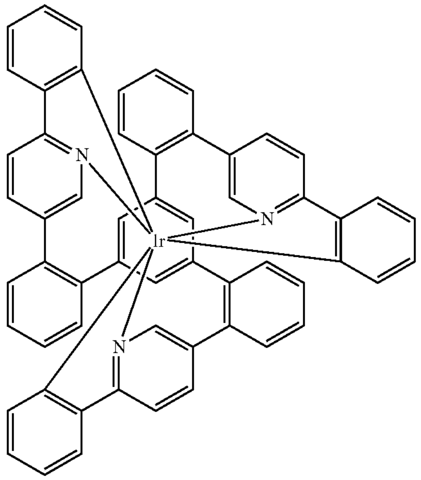

-continued
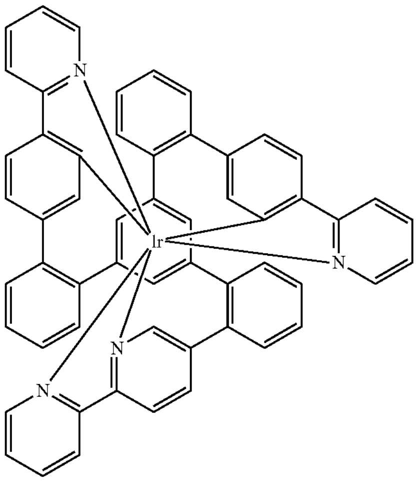
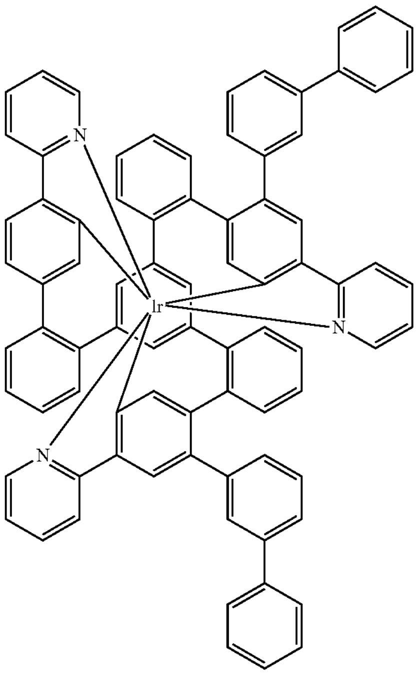
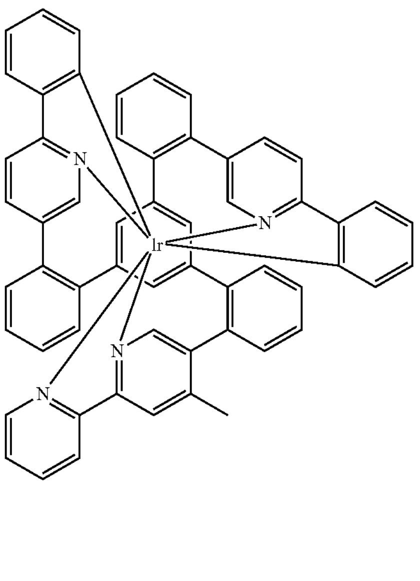
-continued
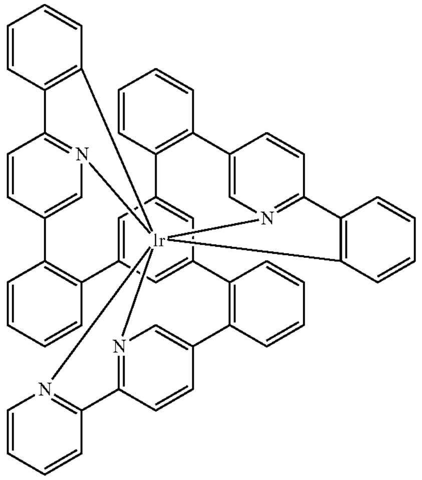
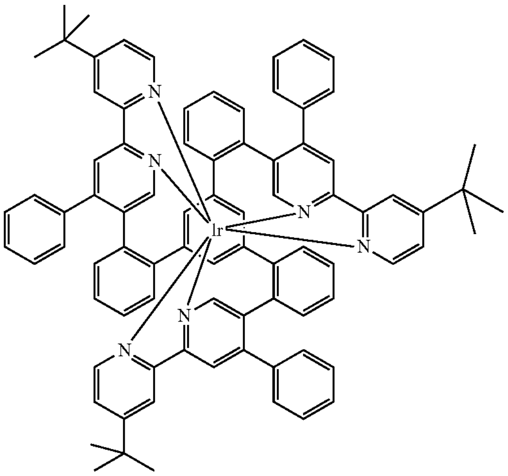
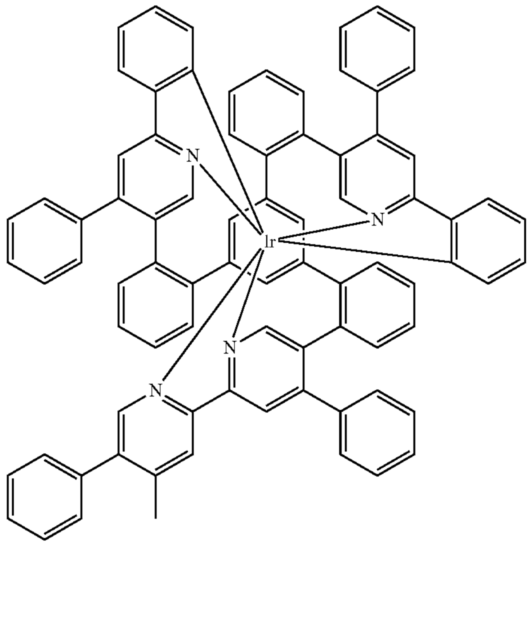

-continued
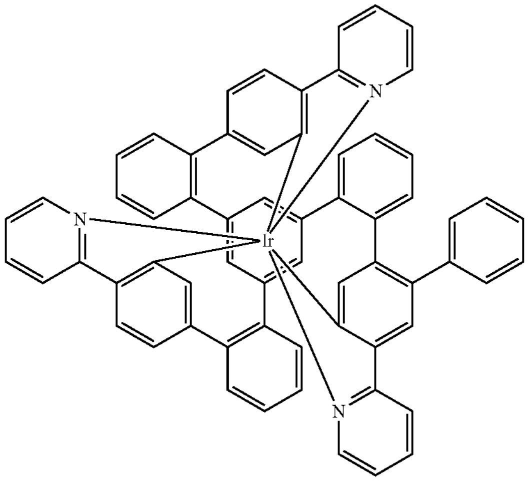
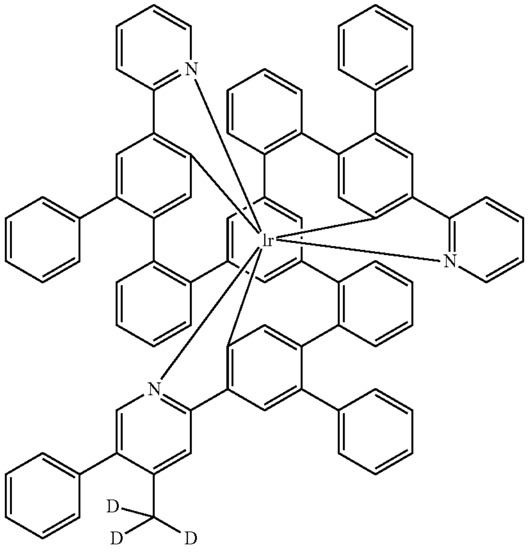
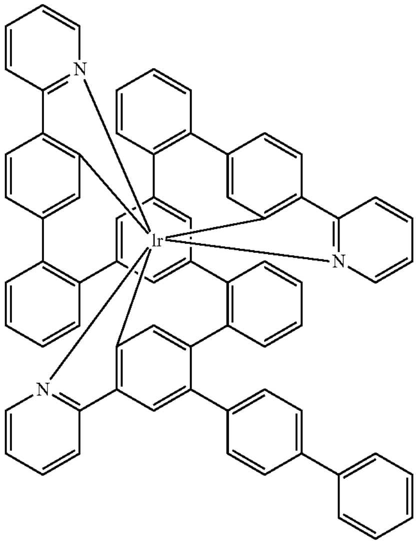
-continued
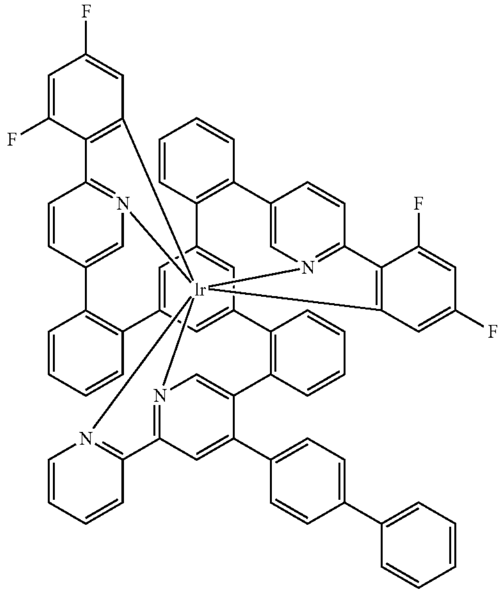
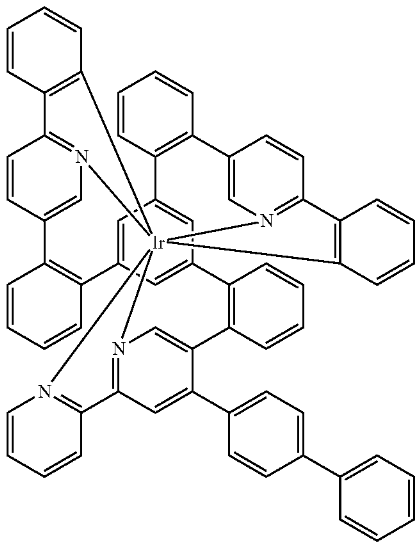

-continued
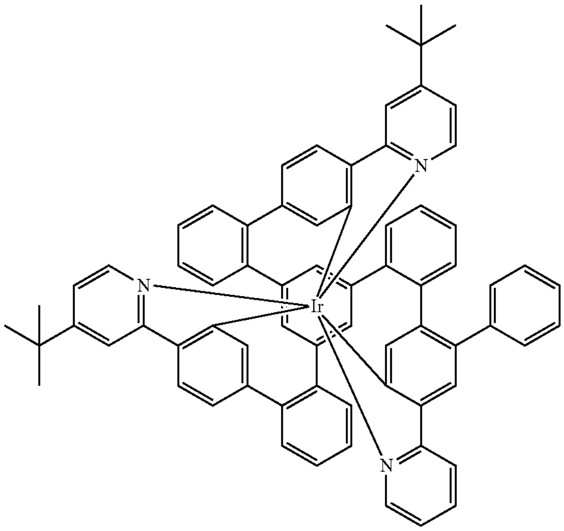
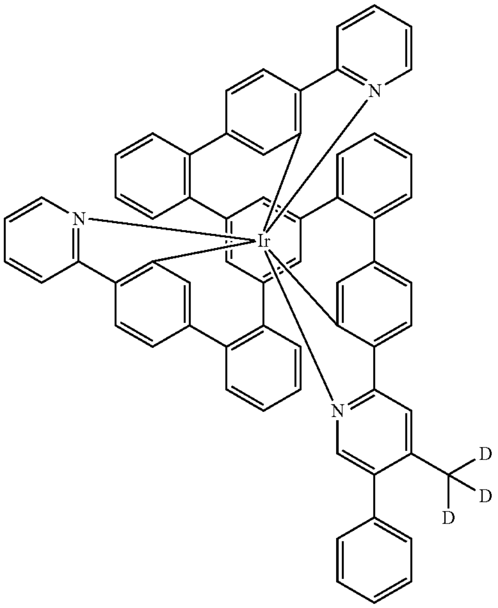
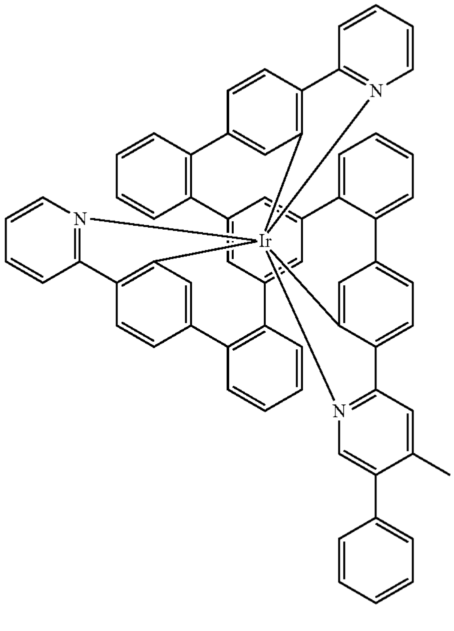
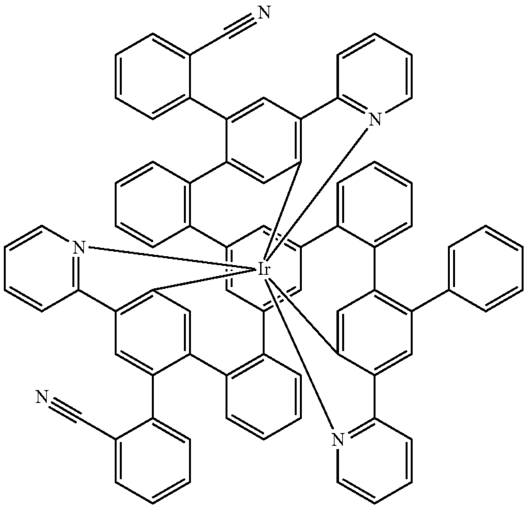

-continued
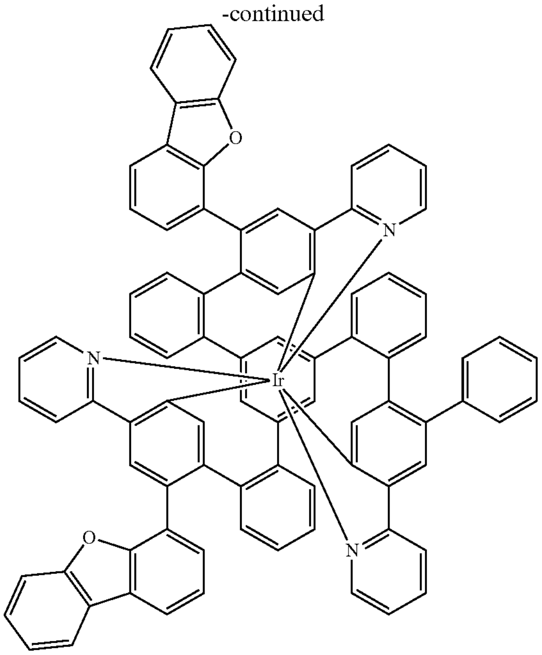
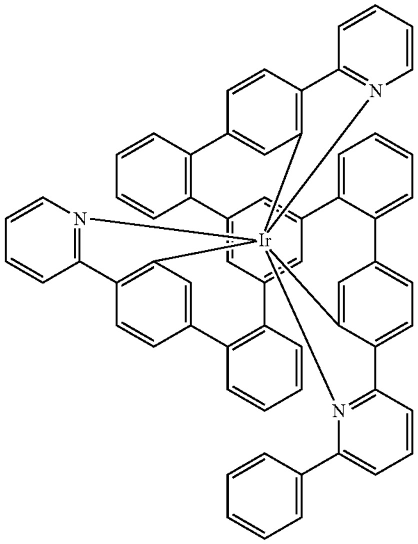
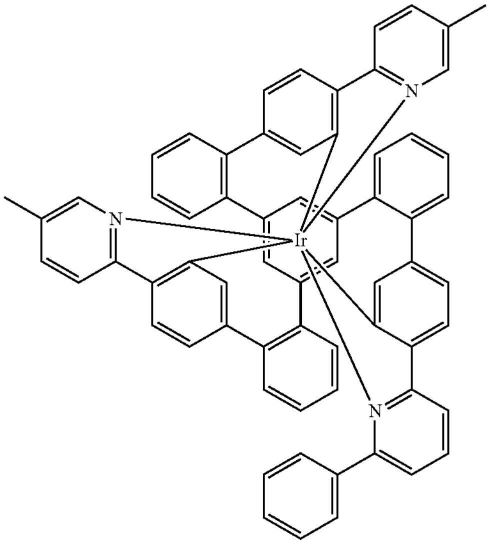
-continued
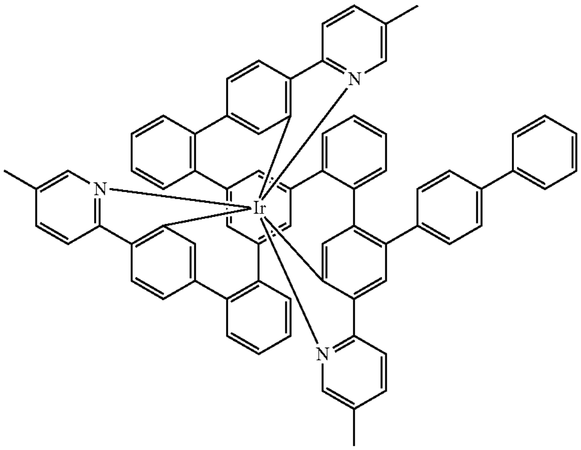
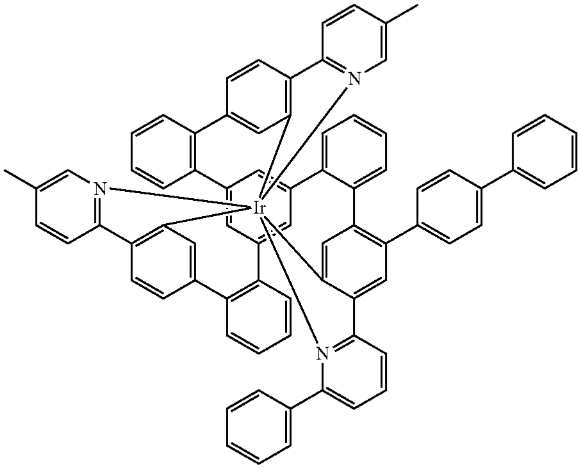
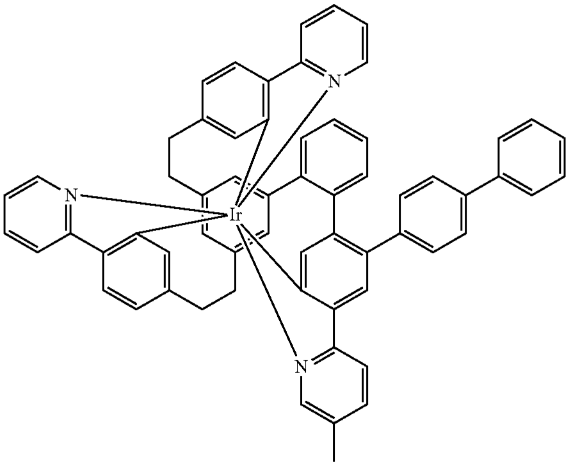

-continued
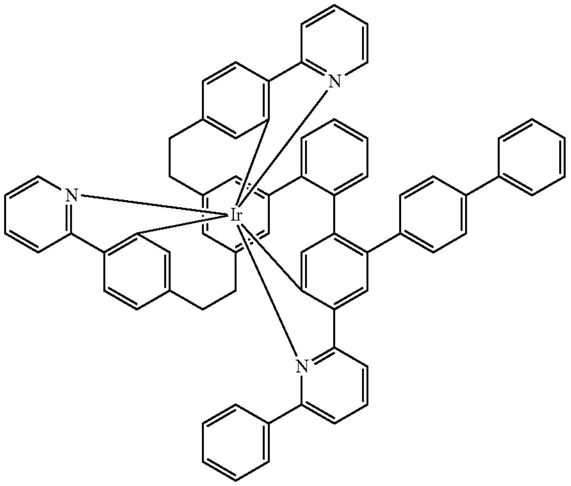
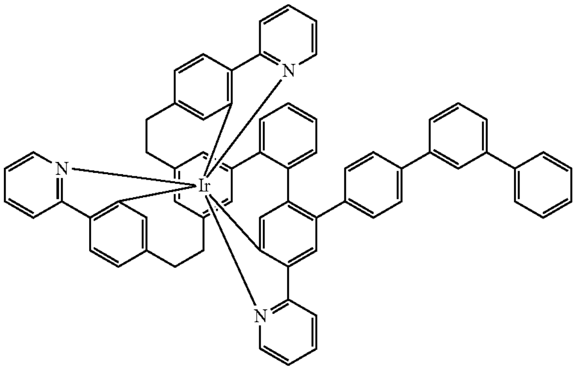
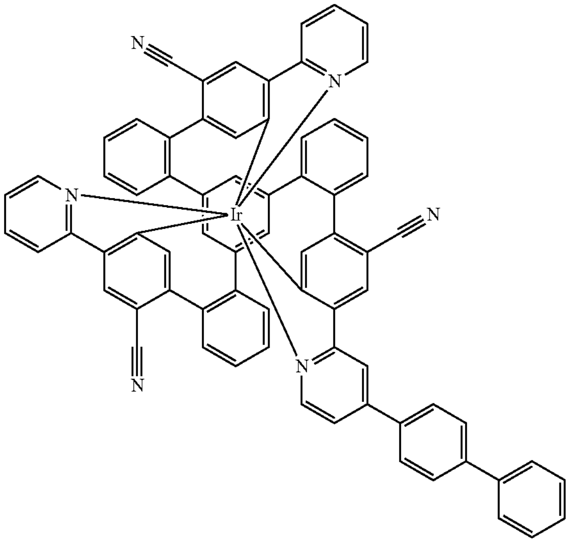
-continued
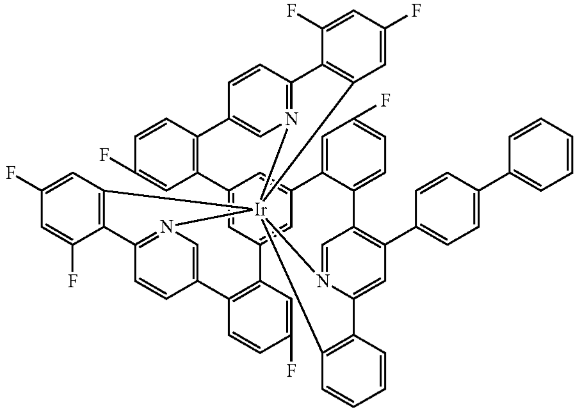
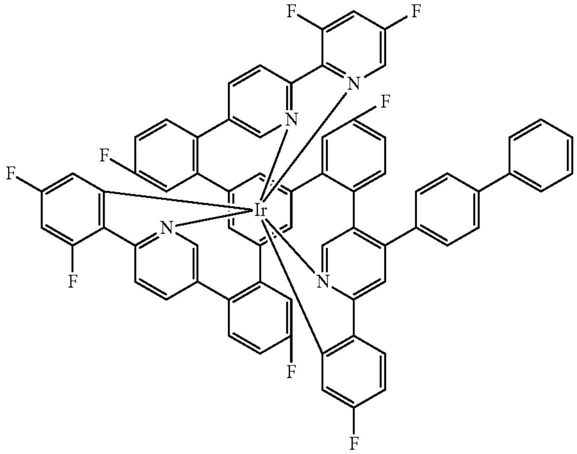
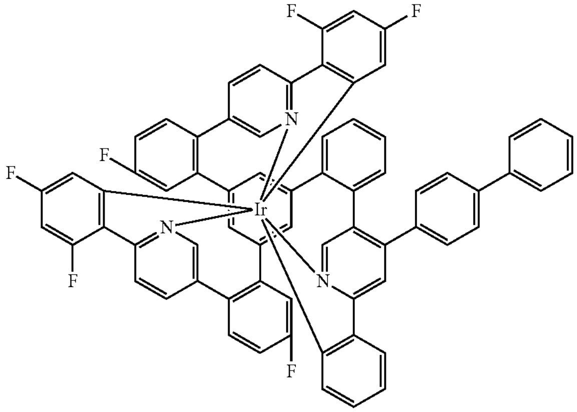
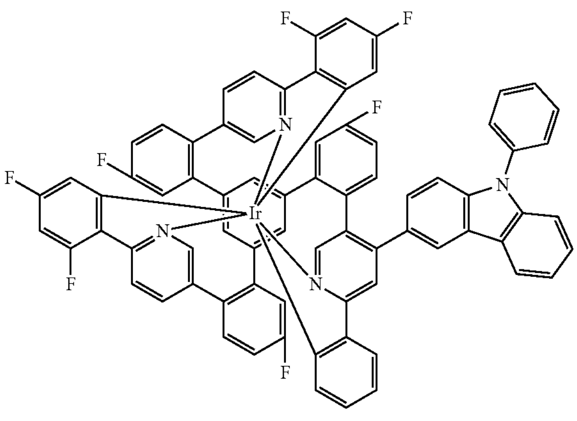

-continued
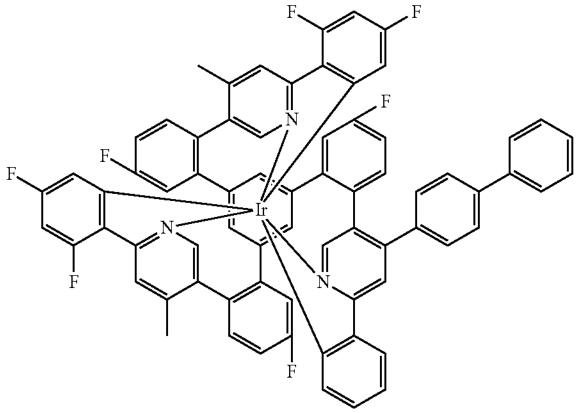
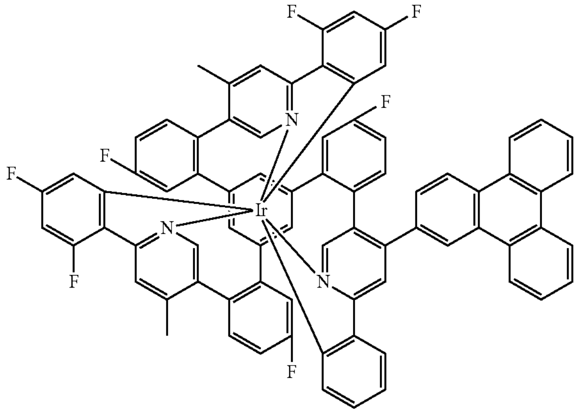
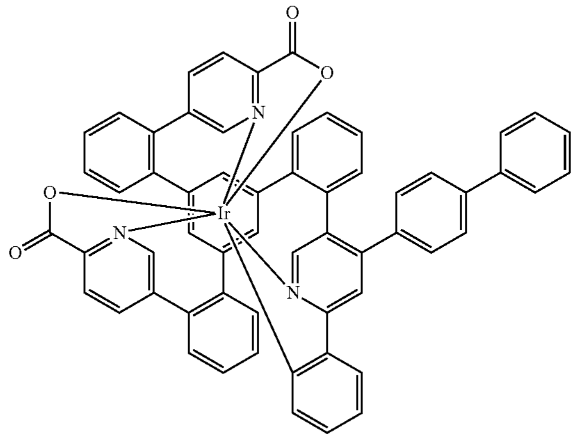
-continued
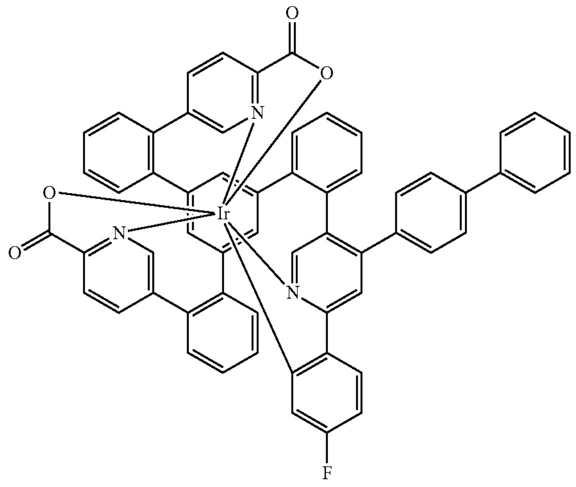
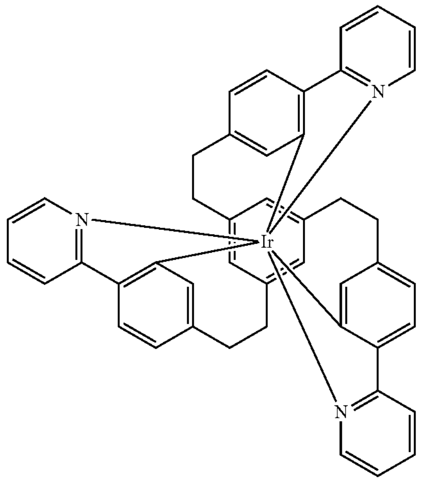
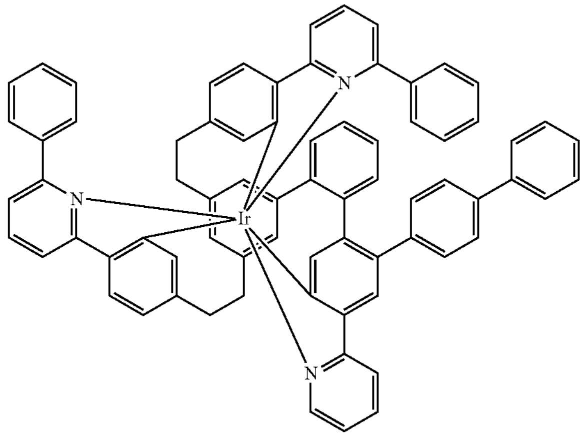

-continued
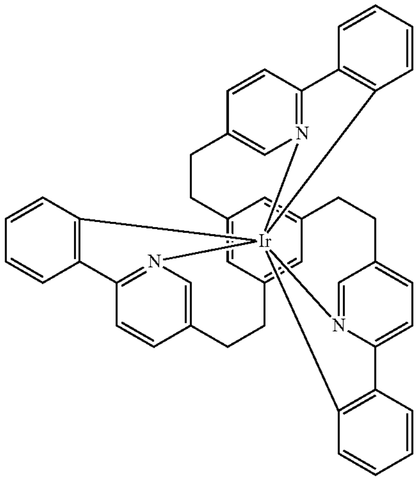
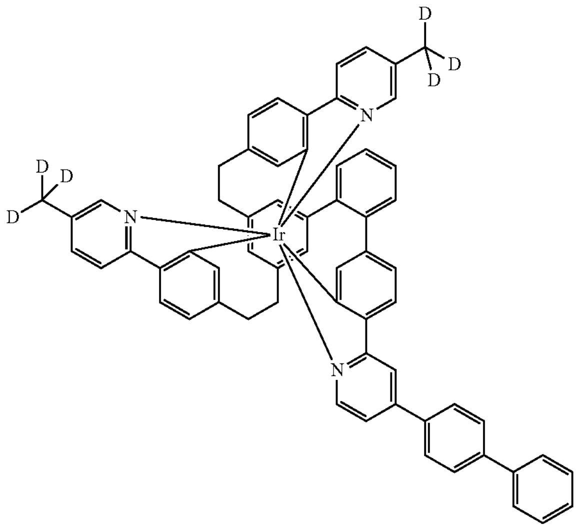
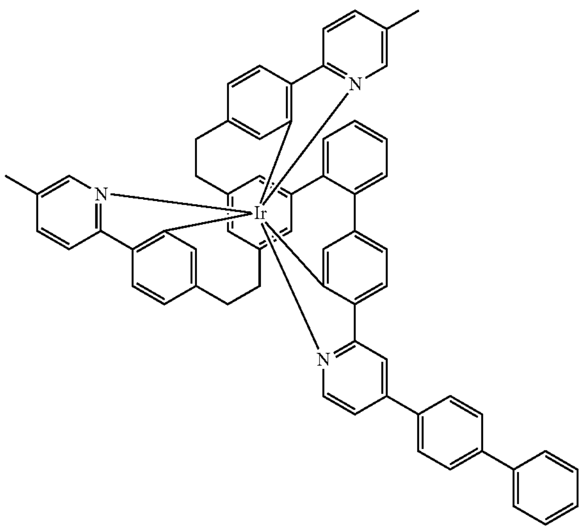
-continued
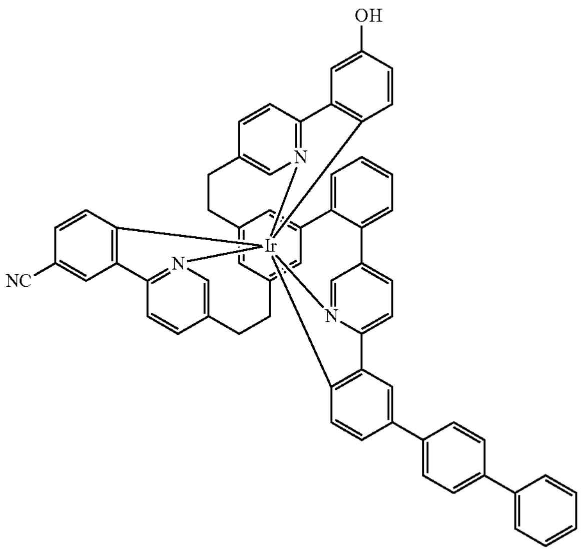
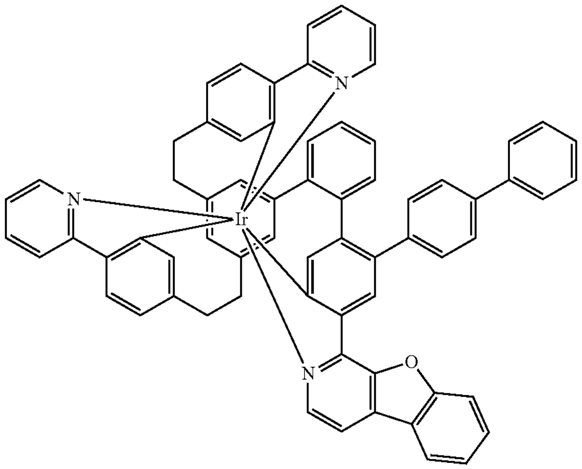
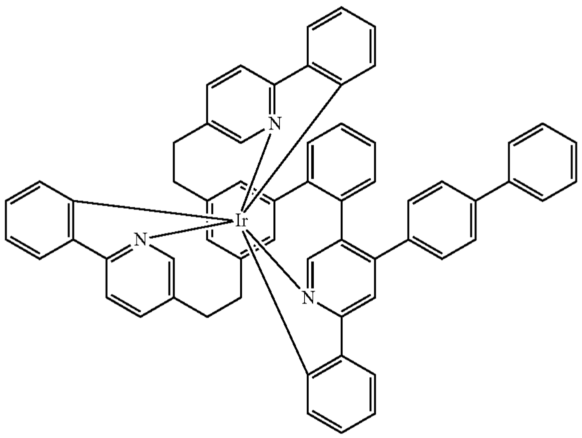

-continued
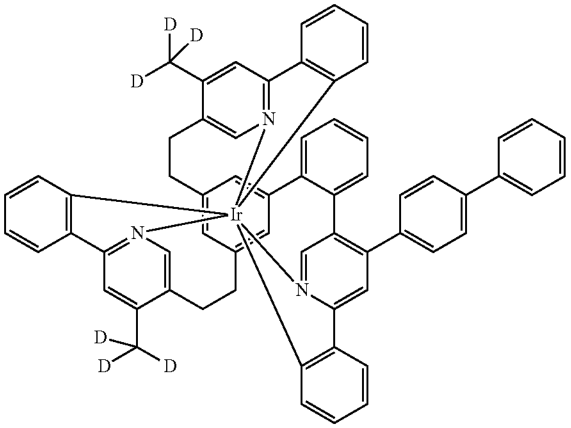
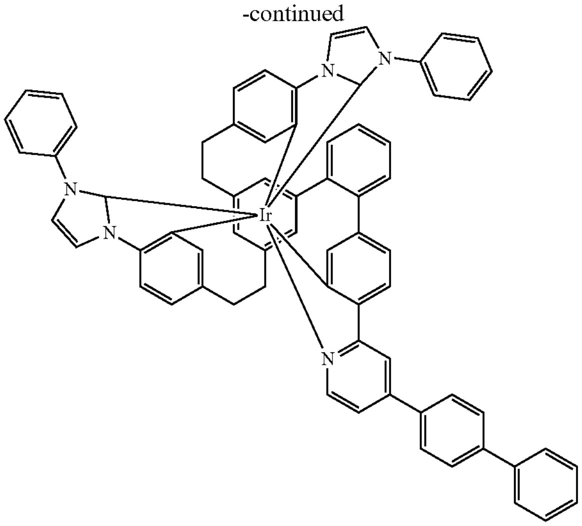
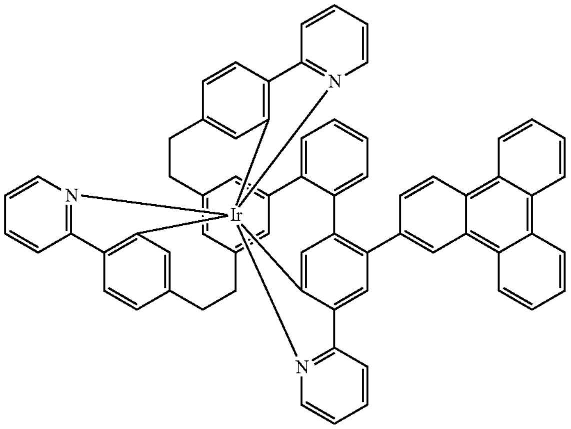
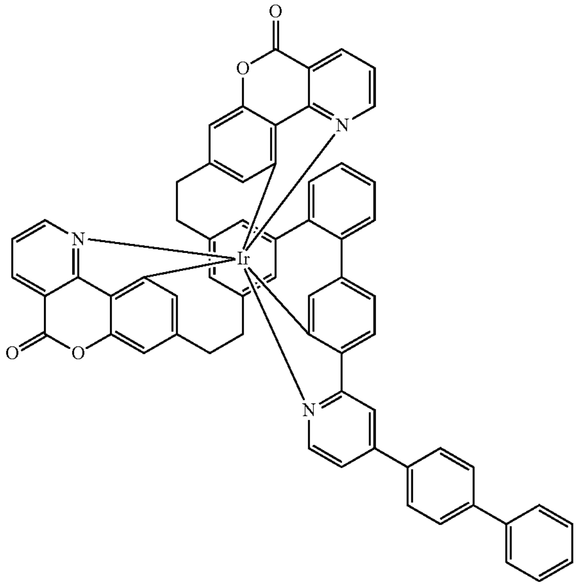
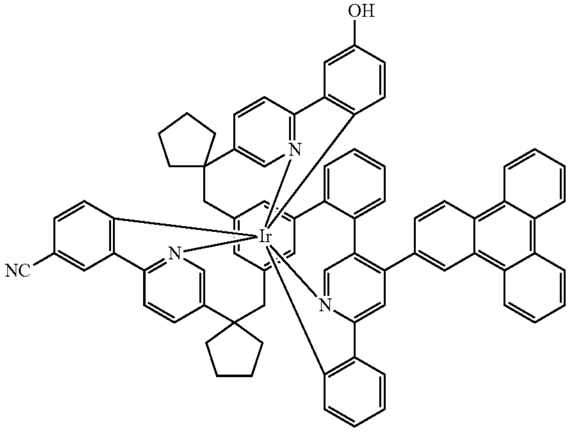
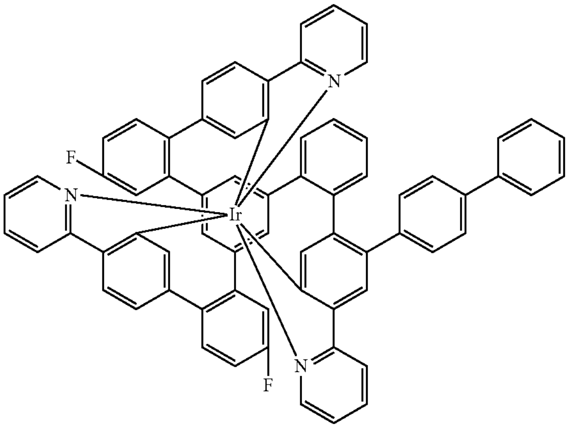
-continued -continued
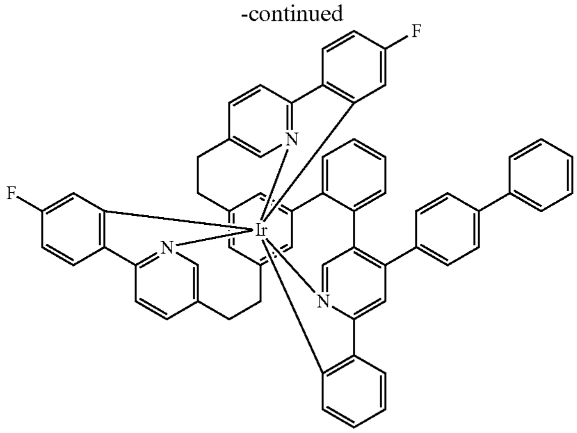
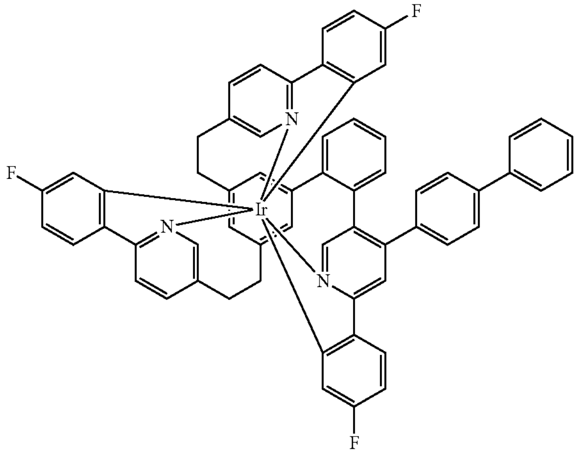
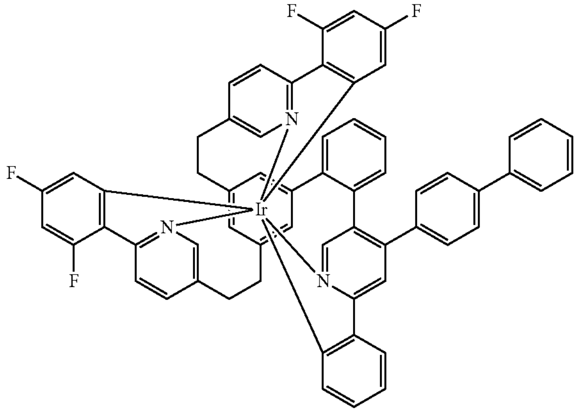
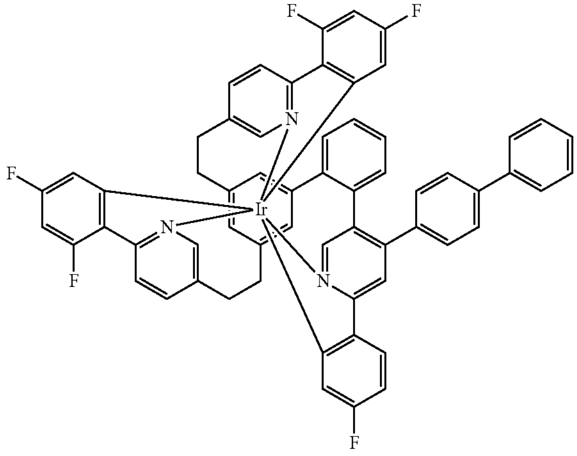
-continued
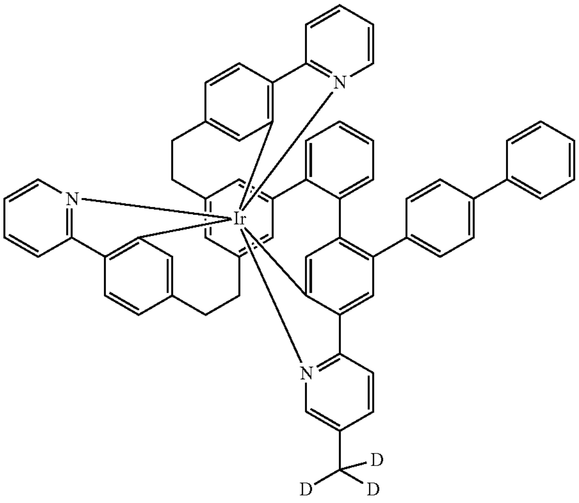
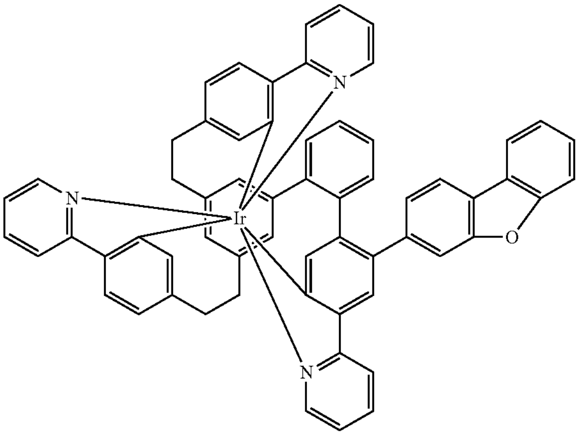
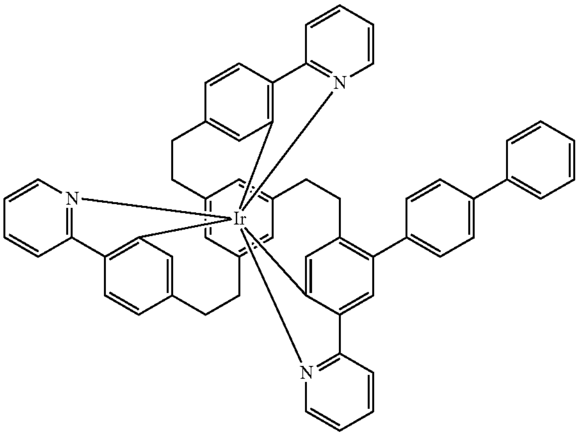

-continued
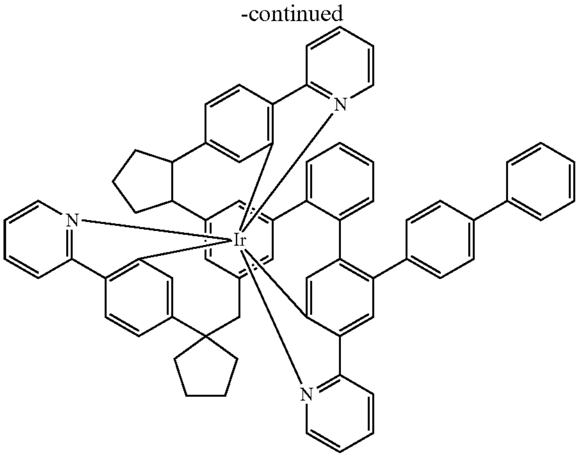
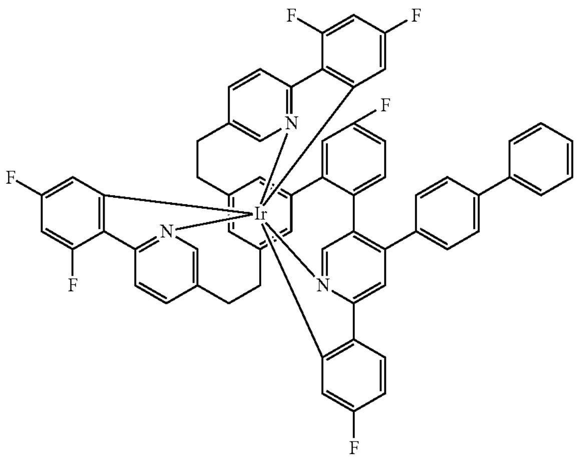
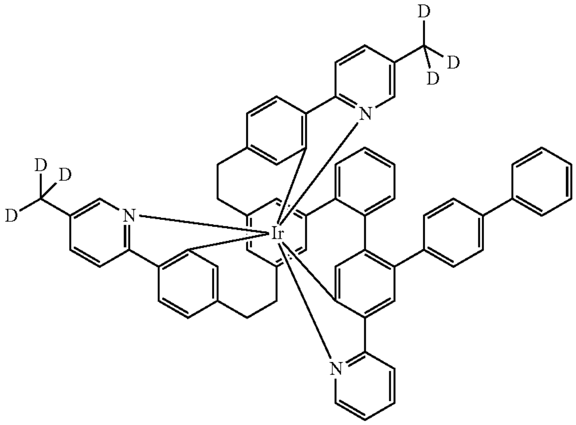
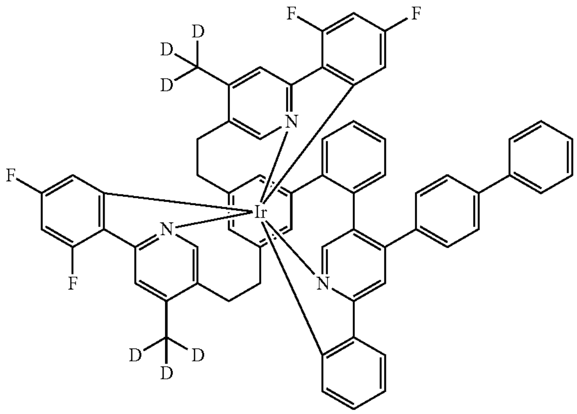
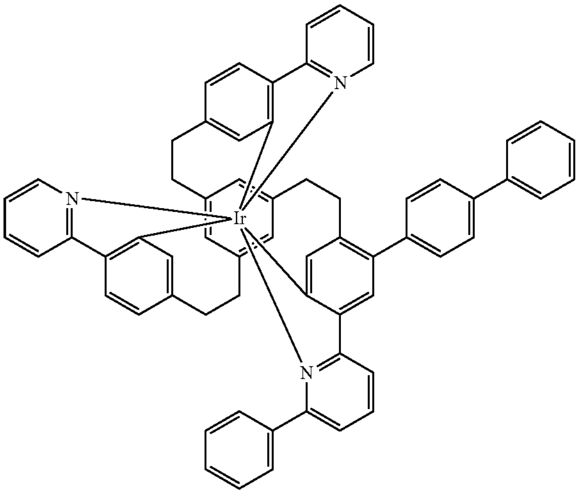
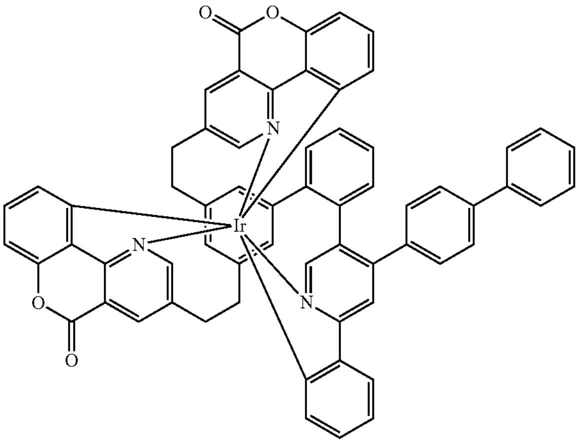

-continued
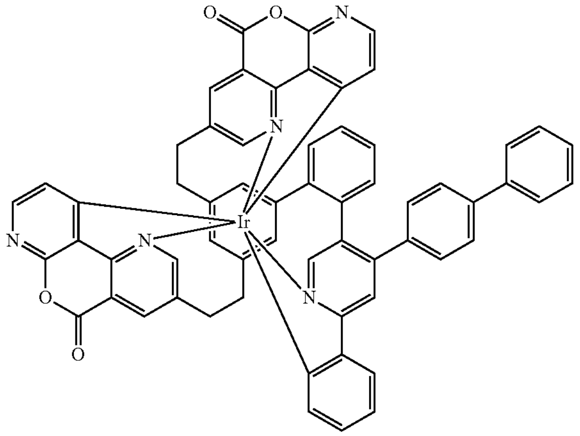
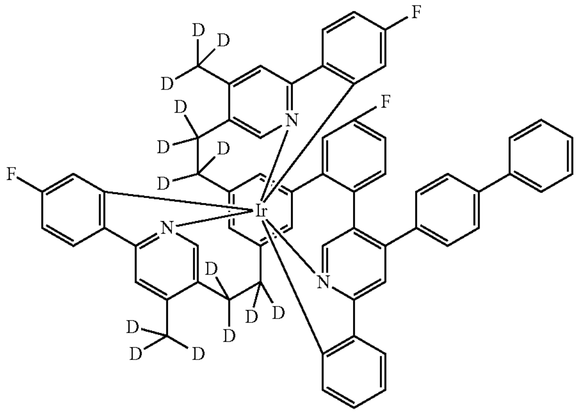
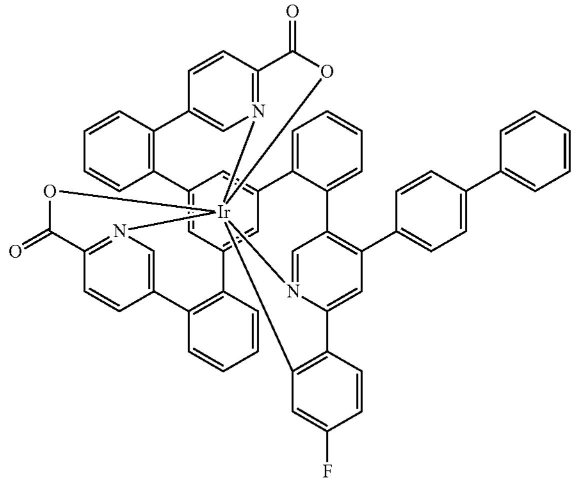
-continued
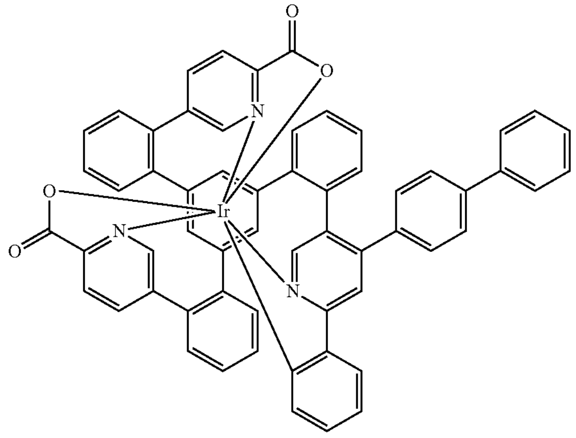
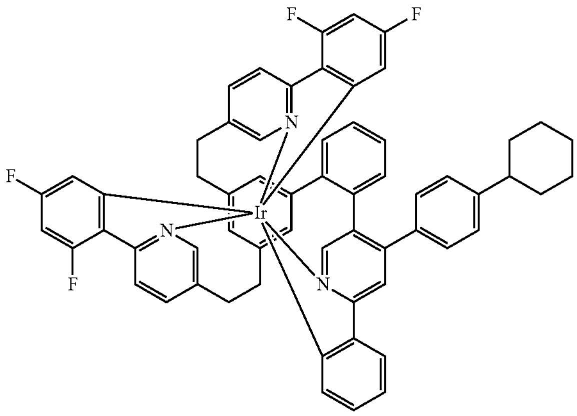
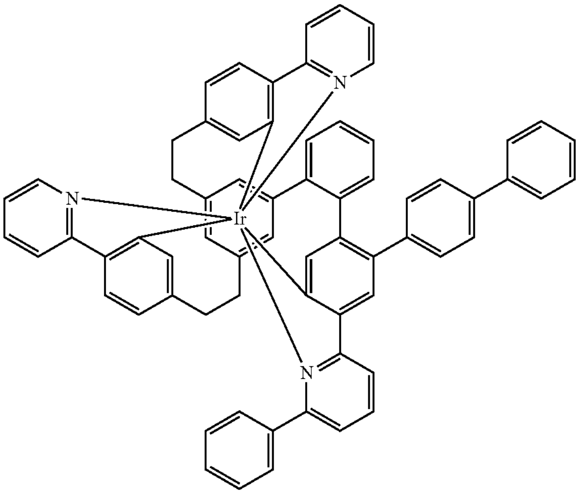

-continued
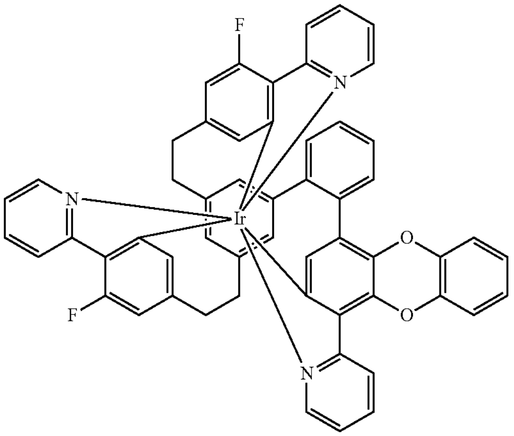
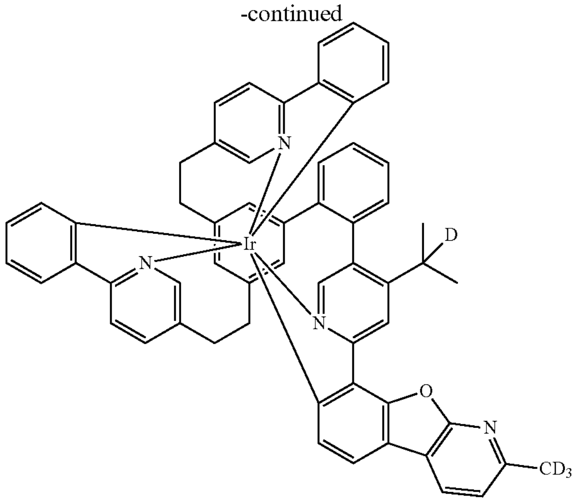
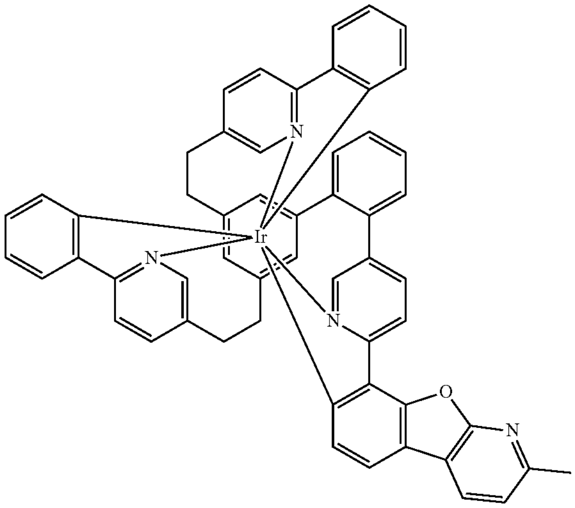
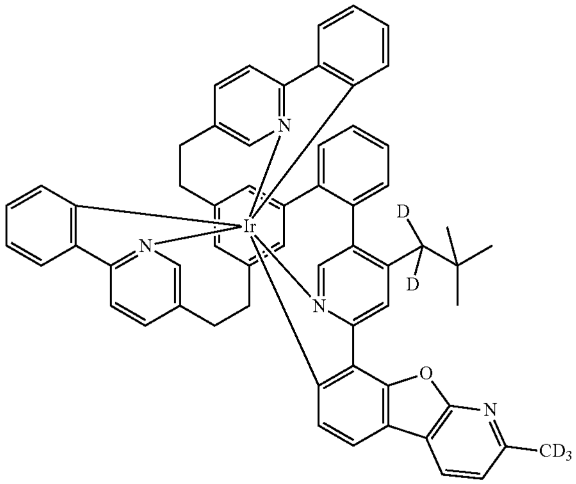
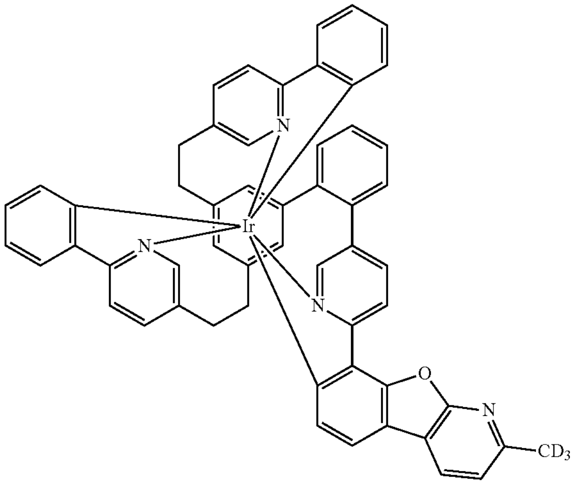
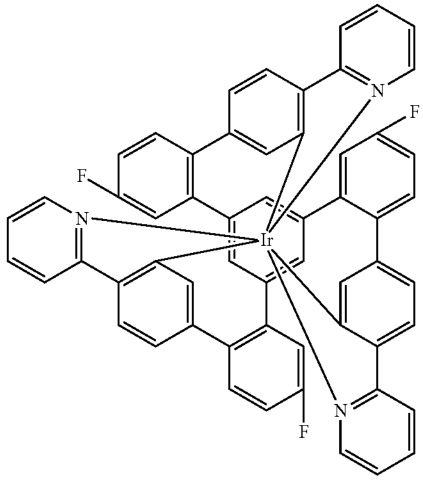

-continued
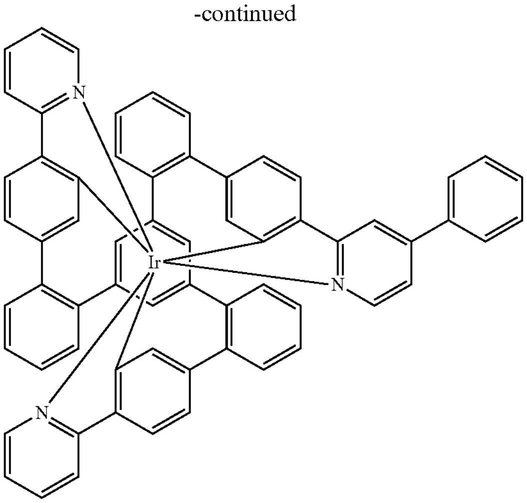
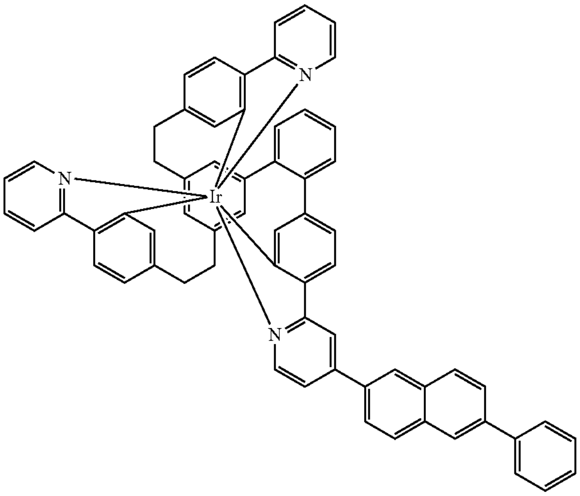
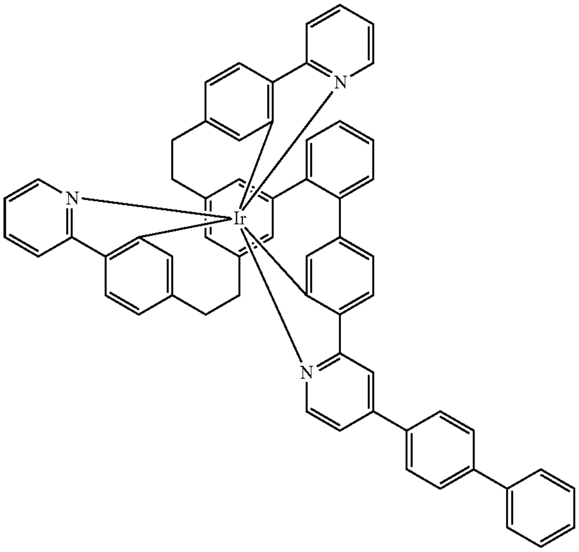
-continued
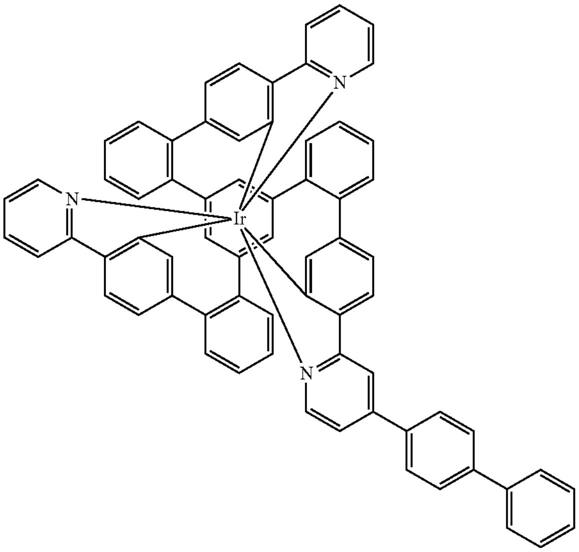
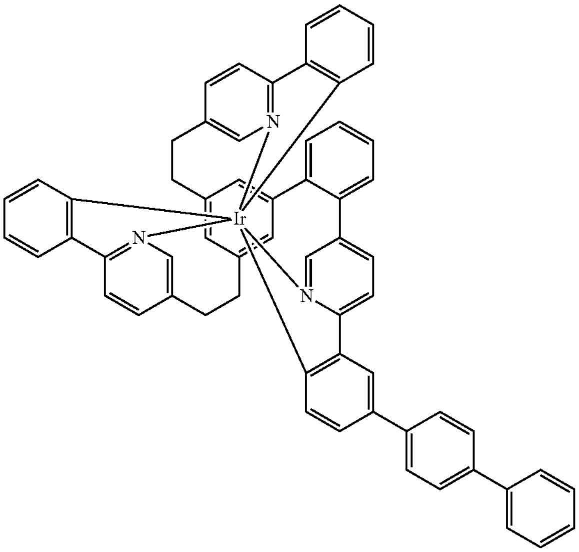
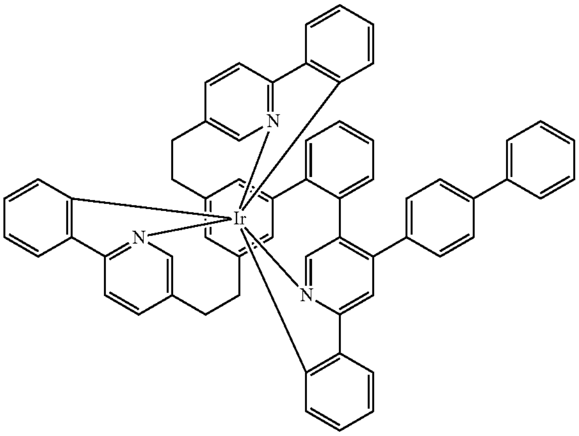

-continued

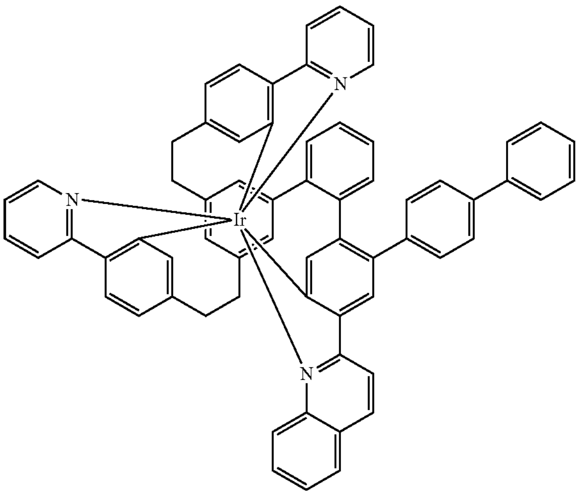

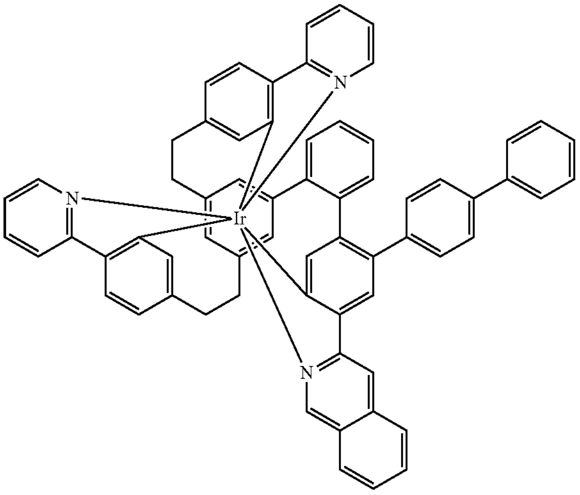

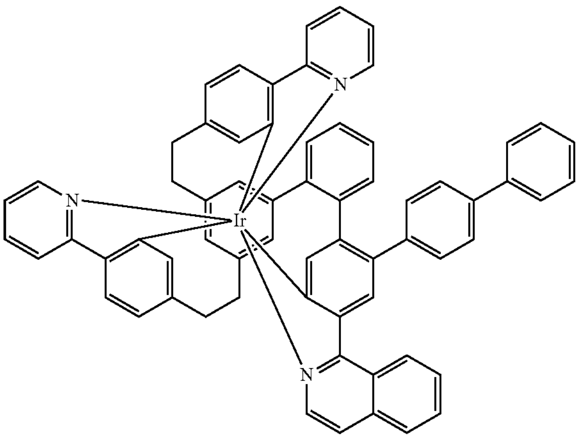

-continued

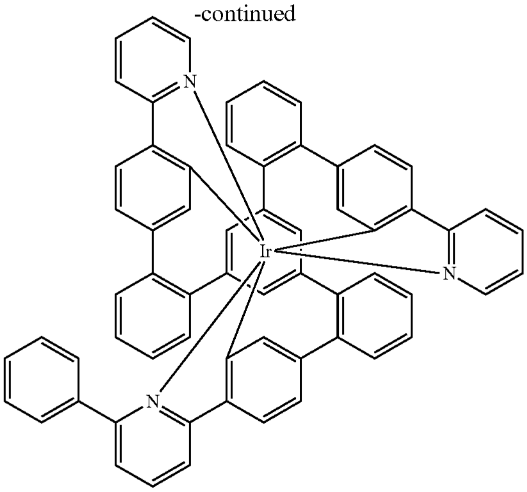

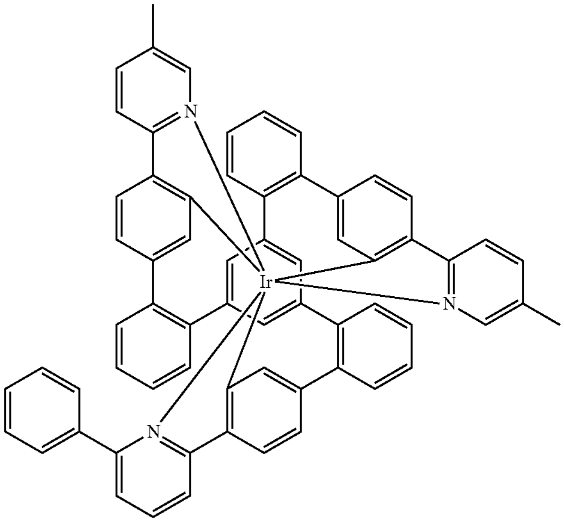

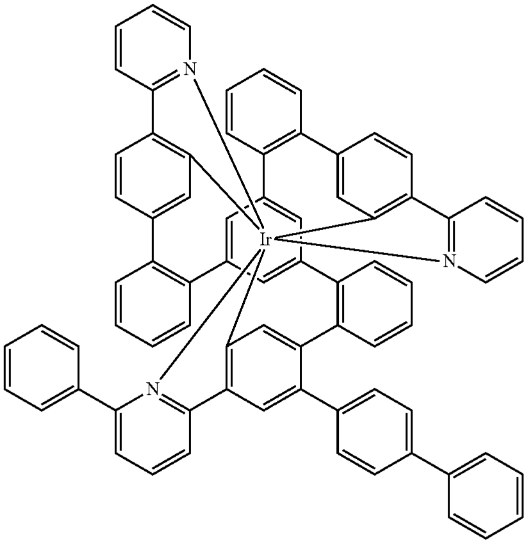

The mixture of the compound of the invention and the emitting compound contains between 99% and 1% by volume, preferably between 98% and 10% by volume, more preferably between 97% and 60% by volume and especially between 95% and 80% by volume of the compound of the invention, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

A further preferred embodiment of the present invention is the use of the compound of the invention as matrix material for a phosphorescent emitter in combination with a further matrix material. Suitable matrix materials which can be used in combination with the inventive compounds are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527, WO 2008/086851 or WO 2013/041176, indolocarbazole derivatives, for example according to WO 2007/063754 or WO 2008/056746, indenocarbazole derivatives, for example according to WO 2010/136109, WO 2011/000455, WO 2013/041176 or WO 2013/056776, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2007/063754, WO 2008/056746, WO 2010/015306, WO 2011/057706, WO 2011/060859 or WO 2011/060877, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to WO 2011/042107, WO 2011/060867, WO 2011/088877 and WO 2012/143080, triphenylene derivatives, for example according to WO 2012/048781, or dibenzofuran derivatives, for example according to WO 2015/169412, WO 2016/015810, WO 2016/023608, WO 2017/148564 or WO 2017/148565. It is likewise possible for a further phosphorescent emitter having shorter-wavelength emission than the actual emitter to be present as co-host in the mixture, or a compound not involved in charge transport to a significant extent, if at all, as described, for example, in WO 2010/108579.

In a preferred embodiment of the invention, the materials are used in combination with a further matrix material, especially with a hole-transporting matrix material. Preferred co-matrix materials are selected from the group of the carbazole and triarylamine derivatives, especially the biscarbazoles, the bridged carbazoles, the triarylamines, the dibenzofuran-carbazole derivatives or dibenzofuran-amine derivatives, and the carbazoleamines.

Preferred hole-transporting matrix materials are compounds of the following formula (9):

Formula (9)

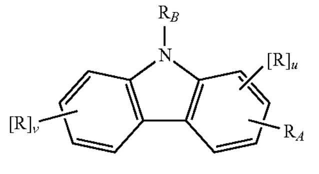

where R, $R^1$, $R^2$ and Ar' have the definitions detailed above and the further symbols and indices used are as follows:

$R_A$ is H, $-L^3-Ar^5$ or $-L^1-N(Ar)_2$, $R_B$ is $Ar^4$ or $-L^2-N(Ar')_2$;

$L^1$, $L^2$ are the same or different at each instance and are a single bond or an aromatic or heteroaromatic ring system which has 5 to 30 aromatic ring atoms and may be substituted by one or more $R^1$ radicals;

$L^3$ is a single bond or an aromatic or heteroaromatic ring system which has 5 to 30 aromatic ring atoms and may be substituted by one or more $R^2$ radicals, where one substituent $R^1$ may form a ring with a substituent R on the carbazole;

$Ar^4$ is an aromatic ring system having 6 to 40 aromatic ring atoms or a heteroaromatic ring system having 5 to 40 aromatic ring atoms, which may be substituted by one or more $R^1$ radicals;

$Ar^5$ is the same or different at each instance and is an unsubstituted or substituted 9-arylcarbazolyl or unsubstituted or substituted carbazol-9-yl, which may be substituted by one or more $R^1$ radicals, and where one or more instances each of two $R^1$ radicals or one $R^1$ radical together with one R radical may independently form a monocyclic or polycyclic, aliphatic, aromatic or heteroaromatic ring, where aryl is an aromatic or heteroaromatic ring system which has 5 to 30 aromatic ring atoms and may be substituted by $R^1$;

u at each instance is independently 0, 1, 2 or 3;

v at each instance is independently 0, 1, 2, 3 or 4.

Compounds of the formula (9) may be represented by the following formulae (9a), (9b), (9c) and (9d):

Formula (9a)

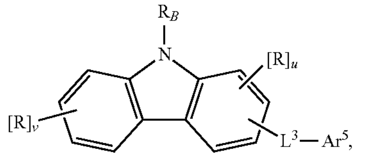

Formula (9b)

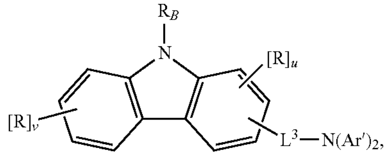

Formula (9c)

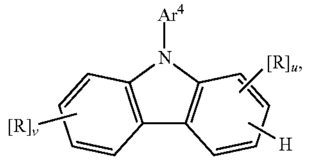

Formula (9d)

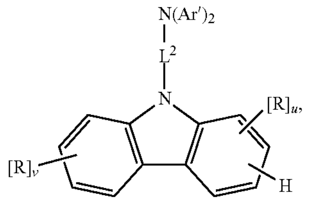

where $L^1$, $L^2$, $L^3$, Ar, $Ar^4$, $Ar^5$, R, u and v have the definition given above or hereinafter.

Preferred compounds of the formula (9) or (9a) are compounds of the formulae (9e), (9f), (9g), (9h) and (9i)

Formula (9e)

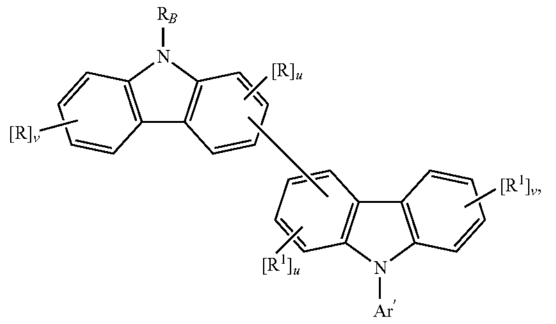

Formula (9f)

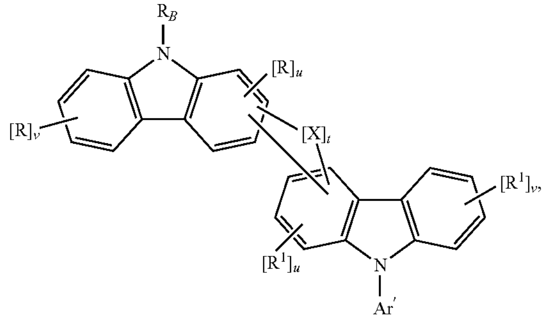

Formula (9g)

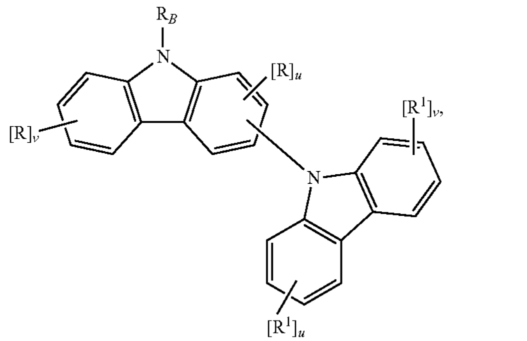

Formula (9h)

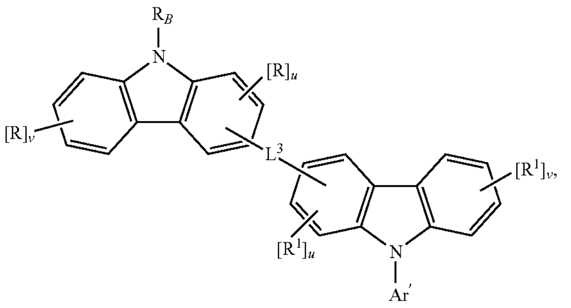

-continued

Formula (9i)

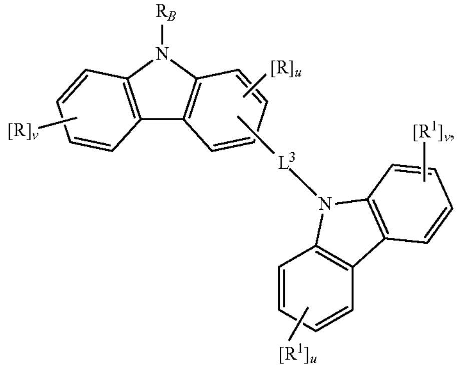

where $R_B$, Ar', R, $R^1$, $R^2$, u and v have the definitions given above or given hereinafter, $L^3$ in the formulae (9h) and (9i) is an aromatic or heteroaromatic ring system which has 5 to 30 aromatic ring atoms and may be substituted by one or more $R^1$ radicals, where one substituent R on the carbazole may form a ring with a substituent $R^1$, X=C($R^1$)$_2$, NAr', O or S and t=0 or 1.

In the compounds of the formulae (9), (9a), (9b), (9c), (9d), (9e), (9f), (9g), (9h) and (9i), one substituent R and one substituent $R^1$ may form a ring, for example also defined by $[X]_t$ in formula (9f), preferably forming the following rings X-1 to X-7, and where the dotted lines in each case represent the bond to the carbazoles:

X-1

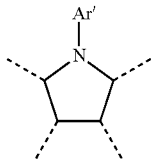

X-2

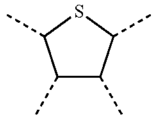

X-3

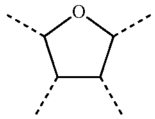

X-4

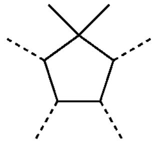

X-5

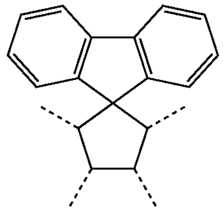

-continued

X-6

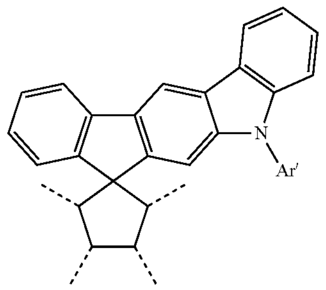

X-7

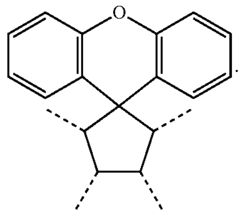

In the compounds of the formulae (9), (9a), (9b), (9c), (9d), (9e), (9f), (9g), (9h) and (9i), two substituents R in one or more instances may together form a ring or two substituents $R^1$ in one or more instances may together form a ring which is preferably selected from the following structures (Si) to (S9), where # and # represent the respective bonding site to the carbon atoms and the structures may each be substituted by one or more substituents $R^1$:

(S1)

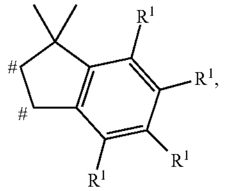

(S2)

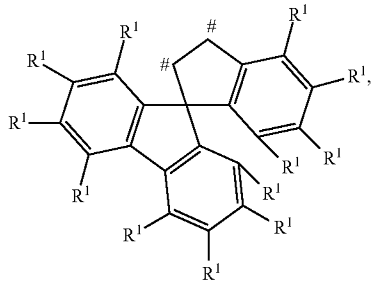

(S3)

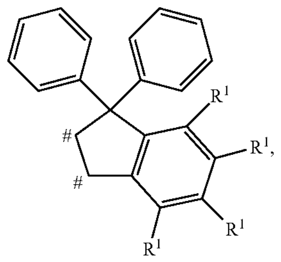

-continued (S4)

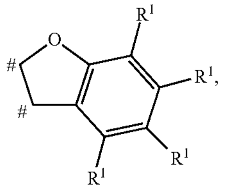

(S5)

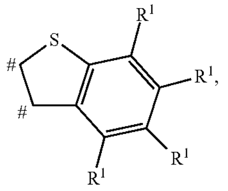

(S6)

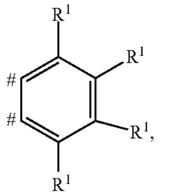

(S7)

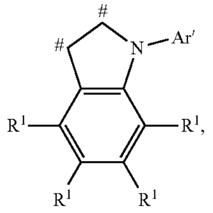

(S8)

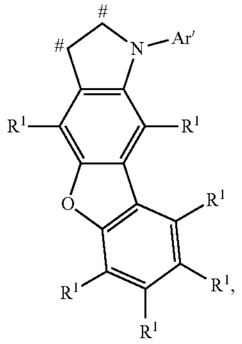

(S9)

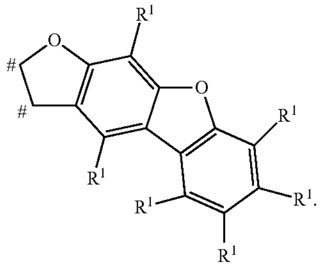

$R^1$ in the substructures (S1) to (S9) is preferably H or an aromatic or heteroaromatic ring system which has 5 to 40 ring atoms and may be substituted by $R^2$, preferably H or phenyl. When the structures (S1) to (S9) are structures that arise through ring formation by two substituents $R^1$, these structures are substituted by $R^2$ rather than by $R^1$.

In the compounds of the formulae (9), (9a), (9b), (9c), (9d), (9e), (9f), (9g), (9h) and (9i), the linkers $L^1$, $L^2$ and $L^3$, if they are not a single bond, are each independently selected from the linkers L-2.1 to L-2.33:
L-2.1
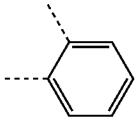
L-2.2
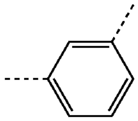
L-2.3
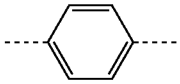
L-2.4
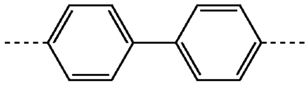
L-2.5
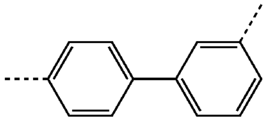
L-2.6
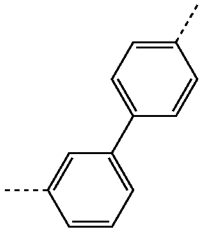
L-2.7
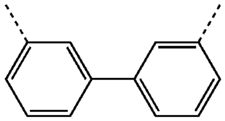
L-2.8
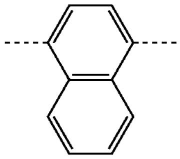
L-2.9
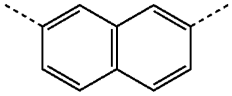
L-2.10
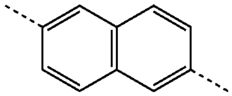
L-2.11
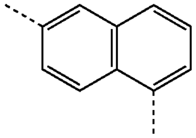
-continued
L-2.12
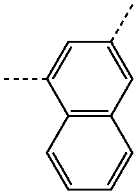
L-2.13
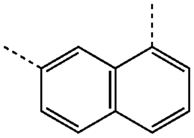
L-2.14
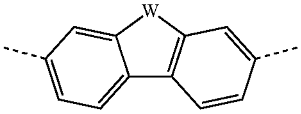
L-2.15
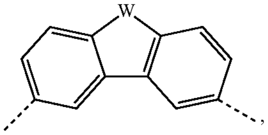
L-2.16
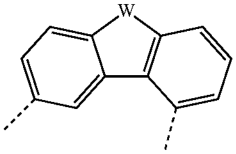
L-2.17
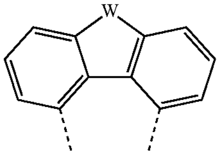
L-2.18
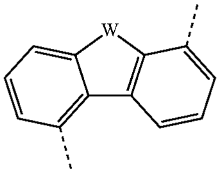
L-2.19
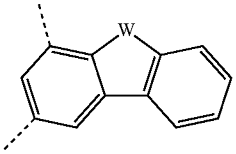
L-2.20
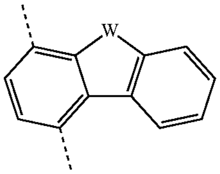
L-2.21
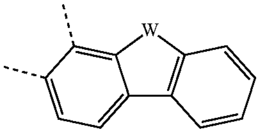

-continued

L-2.22

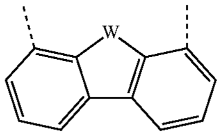

L-2.23

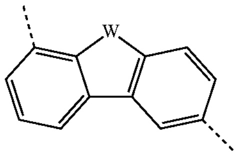

L-2.24

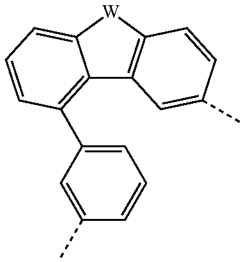

L-2.25

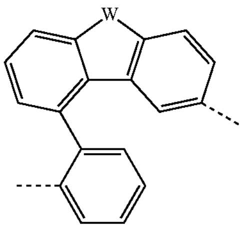

L-2.26

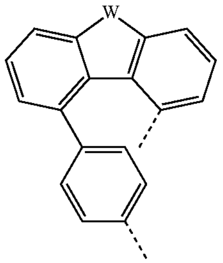

L-2.27

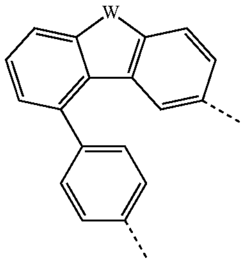

L-2.28

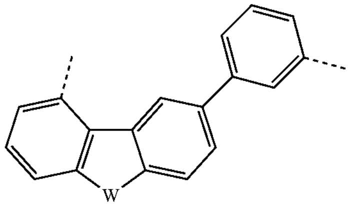

-continued

L-2.29

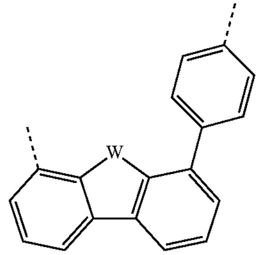

L-2.30

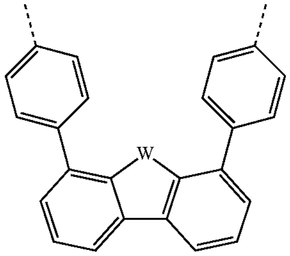

L-2.31

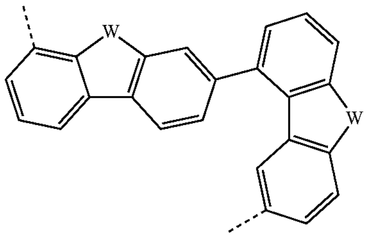

L-2.32

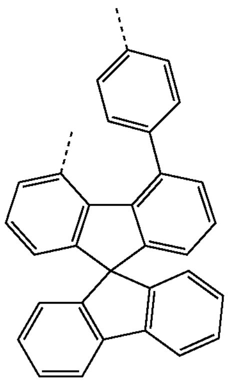

L-2.33

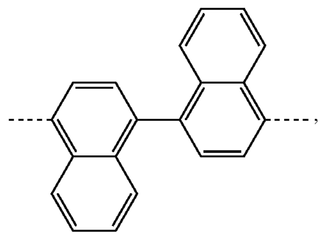

where W is NAr', O, S or $C(CH_3)_2$, Ar' has a definition given above, the linkers L-2.1 to L-2.33 may be substituted by one or more $R^1$ radicals and the dotted lines denote the attachment to the carbazoles. For the linker $L^3$, an $R^1$ radical on one of the linkers L-2.1 to L-2.33 may form a ring with an R radical of the carbazole.

Preferably, the linkers L-2.1 to L-2.33 are unsubstituted or substituted by a phenyl.

Preferred linkers for $L^1$ are selected from the structures L-2.1 to L-2.33 in which W is defined as S or O, more preferably defined as O.

Preferred linkers for $L^3$ are selected from the structures L-2.1 to L-2.33 in which W is defined as O, S or NAr', more preferably defined as O or NAr'.

In a preferred embodiment of the compounds of the formulae (9), (9a), (9b), (9c), (9d), (9e), (9f), (9g), (9h) and (9i), the two carbazoles are joined to one another, each in the 3 position.

In compounds of the formulae (9), (9a), (9b), (9c), (9d), (9e), (9f), (9g), (9h) and (9i), u is preferably 0, 1 or 2, where R has a definition given above or a definition given below. More preferably, u=0 or 1. Most preferably, u=0.

When, in compounds of the formulae (9), (9a), (9b), (9c), (9d), (9e), (9f), (9g), (9h) and (9i), u is greater than 0, the substituent R is the same or different at each instance and is preferably selected from the group consisting of D, F, an alkyl group having 1 to 10 carbon atoms or an aromatic or heteroaromatic ring system which has 6 to 24 aromatic ring atoms and may be substituted by one or more $R^1$ radicals. The aromatic or heteroaromatic ring system having 6 to 24 aromatic ring atoms in this R is preferably derived from benzene, dibenzofuran, dibenzothiophene, 9-phenylcarbazole, biphenyl and terphenyl, which may be substituted by one or more $R^1$ radicals. The preferred position of the substituent(s) $[R]_u$ is position 1, 2, 3 or 4 or the combinations of positions 1 and 4 and 1 and 3, more preferably 1 and 3, 2 or 3, most preferably 3, where R has one of the preferred definitions given above and u is greater than 0. Particularly preferred substituents R in $[R]_u$ are carbazol-9-yl, biphenyl, terphenyl and dibenzofuranyl.

In compounds of the formulae (9), (9a), (9b), (9c), (9d), (9e), (9f), (9g), (9h) and (9i), v is preferably 0, 1 or 2, where R has a definition given above or hereinafter. More preferably, v=0 or 1, most preferably 0.

When, in compounds of the formulae (9), (9a), (9b), (9c), (9d), (9e), (9f), (9g), (9h) and (9i), v is greater than 0, the substituent R is the same or different at each instance and is preferably selected from the group consisting of D, F, an alkyl group having 1 to 10 carbon atoms or an aromatic or heteroaromatic ring system having 5 to 30 aromatic ring atoms, in which one or more hydrogen atoms may be replaced by D, F, CI, Br, I, a straight-chain or branched alkyl group having 1 to 4 carbon atoms or CN. It is possible here for two or more adjacent R substituents together to form a mono- or polycyclic ring system. The aromatic or heteroaromatic ring system having 5 to 30 aromatic ring atoms in this R is preferably derived from benzene, dibenzofuran, dibenzothiophene, 9-phenylcarbazole, biphenyl, terphenyl and triphenylene.

The preferred position of the substituent(s) $[R]_v$ is position 1, 2 or 3, more preferably 3, where R has one of the preferred definitions given above and v is greater than 0.

Ar' in $N(Ar')_2$ is preferably derived from benzene, dibenzofuran, fluorene, spirobifluorene, dibenzothiophene, 9-phenylcarbazole, biphenyl and terphenyl which may be substituted by one or more substituents $R^1$. Ar' here is preferably unsubstituted.

Preferred substituents R and $R^1$ are the same as already detailed above as preferred for the compounds of the formula (1).

In compounds of the formulae (9), (9a), (9b), (9c), (9d), (9e), (9f), (9g), (9h) and (9i), as described above, $Ar^4$ is in each case independently an aromatic ring system having 6 to 30 aromatic ring atoms or a heteroaromatic ring system having 10 to 30 aromatic ring atoms which may be substituted by one or more $R^1$ radicals. $Ar^4$ is preferably derived from benzene, dibenzofuran, fluorene, spirobifluorene, dibenzothiophene, 9-phenylcarbazole, biphenyl and terphenyl, which may be substituted by one or more substituents $R^1$, where $R^1$ has a definition given above.

In the case of the heteroaromatic ring systems which have 10 to 40 carbon atoms and may be substituted by one or more of the substituents $R^1$, particular preference is given to electron-rich ring systems, where the optionally $R^1$-substituted ring system preferably contains just one nitrogen atom in its entirety or the optionally $R^1$-substituted ring system contains one or more oxygen and/or sulfur atoms in its entirety.

In compounds of the formulae (9), (9a), (9b), (9c), (9d), (9e), (9f), (9g), (9h) and (9i), Ar' and $Ar^4$, independently at each instance, are preferably selected from the same groups as listed above as structures R-1 to R-81.

Examples of suitable compounds of the formulae (9), (9a), (9b), (9c), (9d), (9e), (9f), (9g), (9h) and (9i) are the structures depicted in the table below.

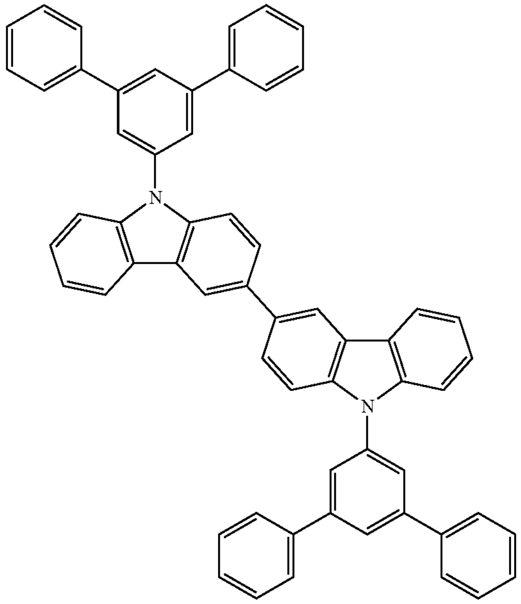

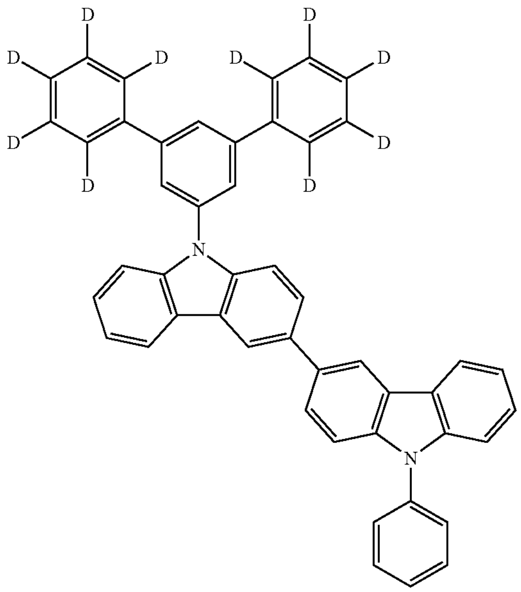

-continued
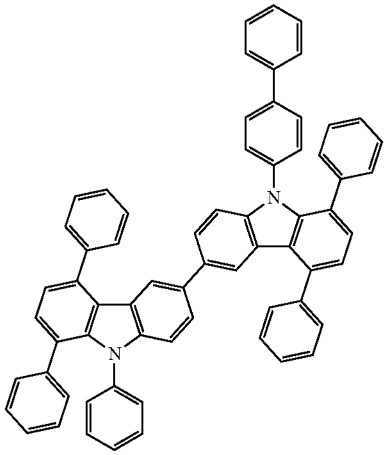
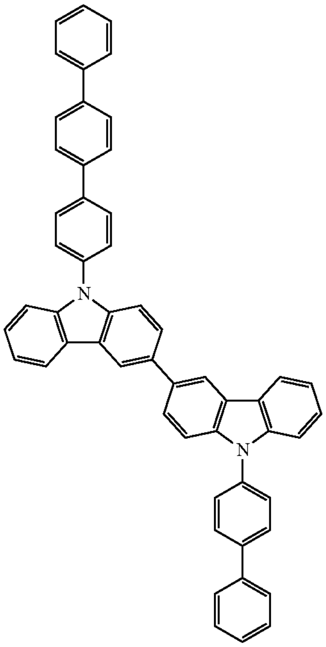
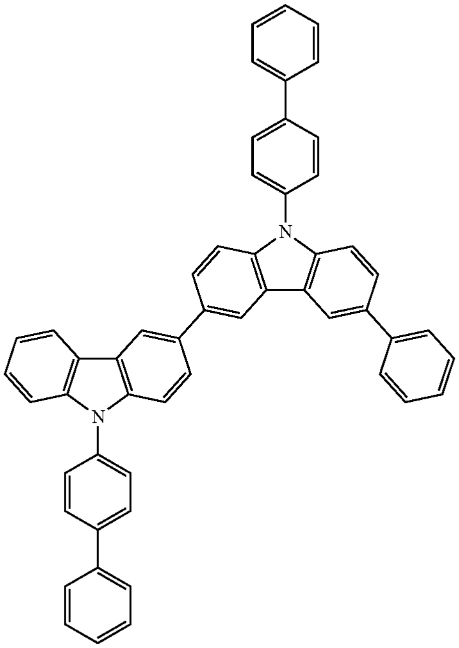
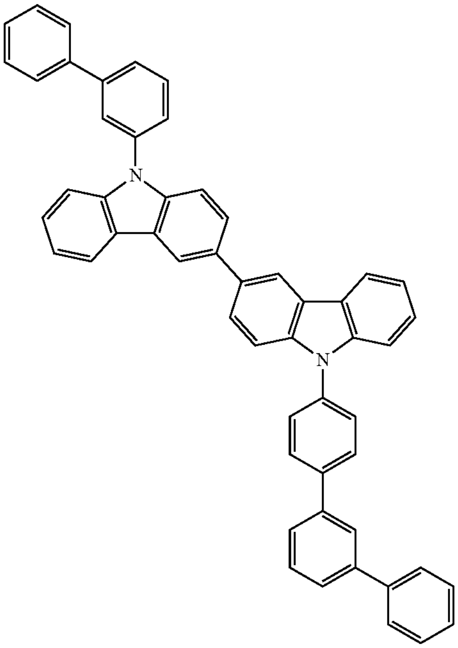

-continued
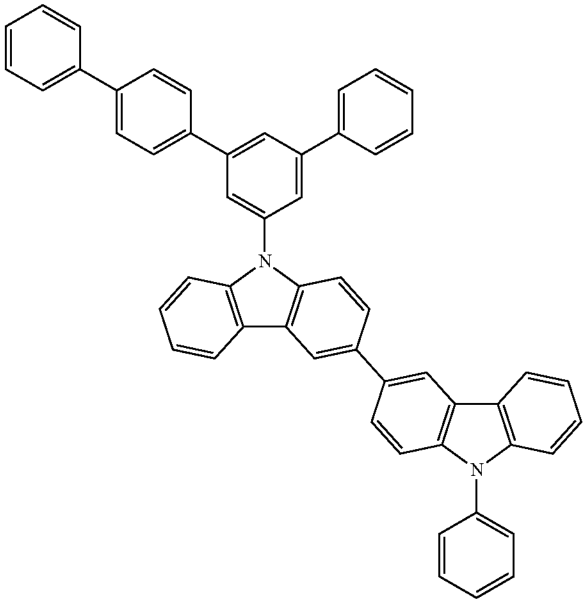
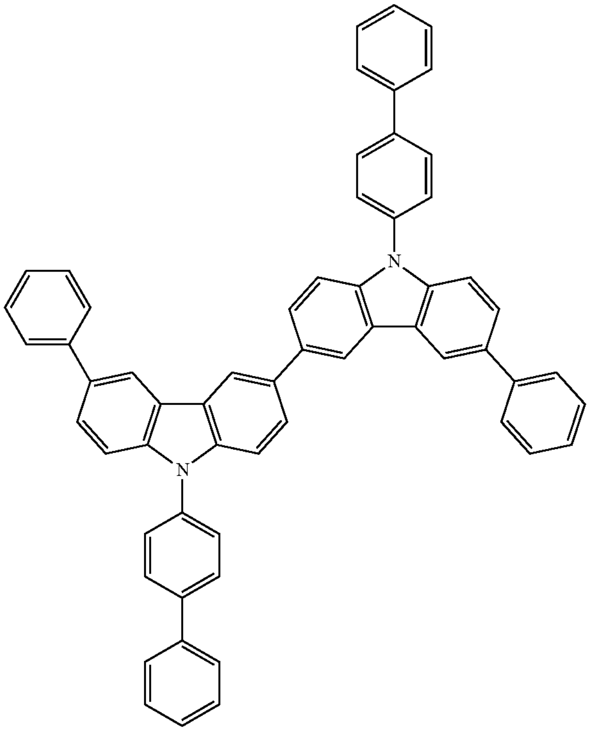
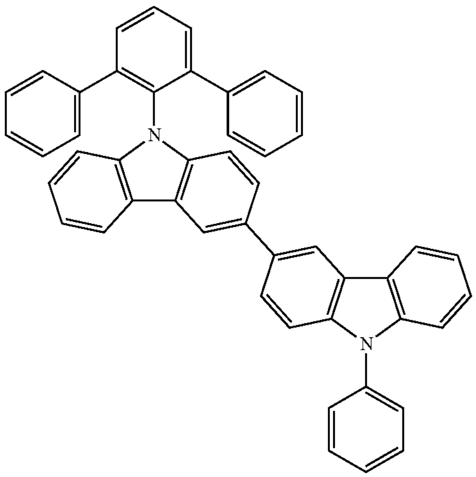
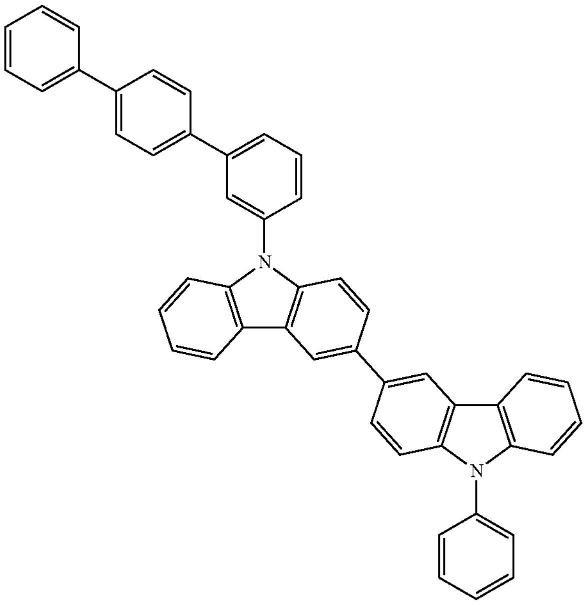

-continued
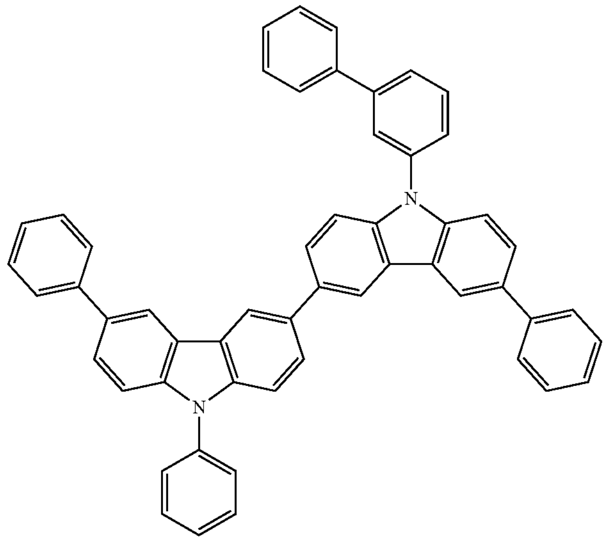
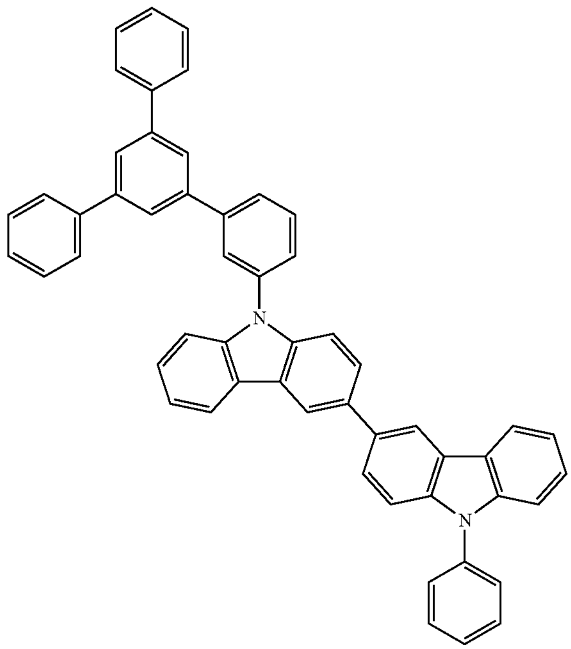
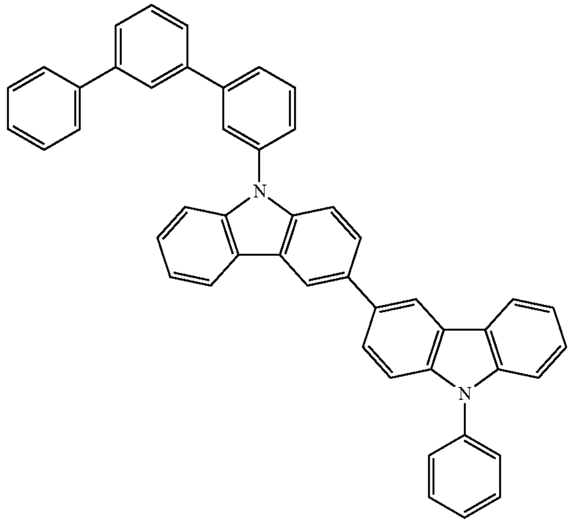

-continued
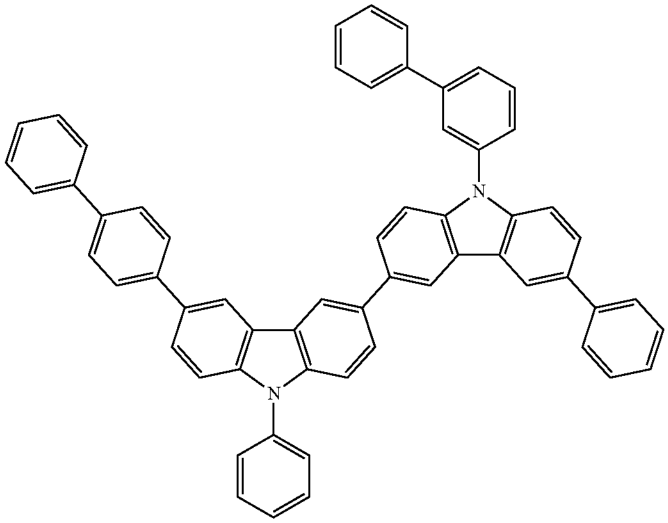
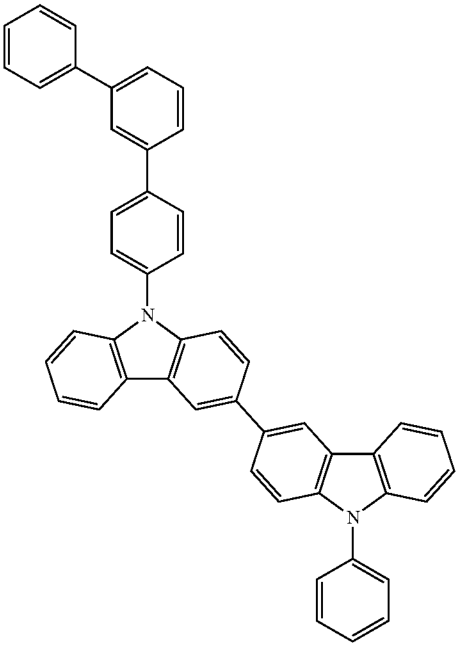
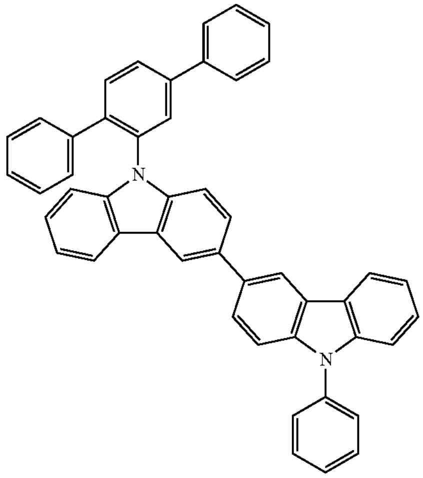
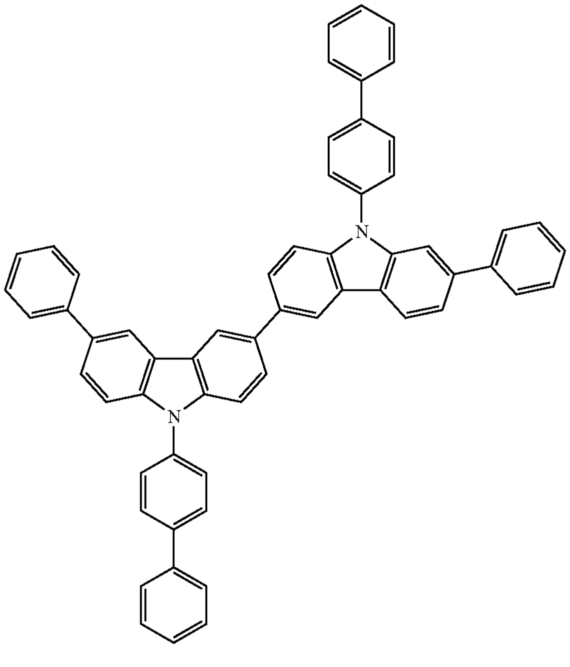

-continued
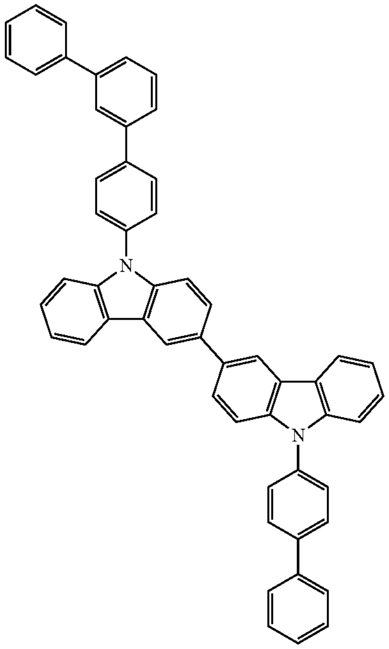
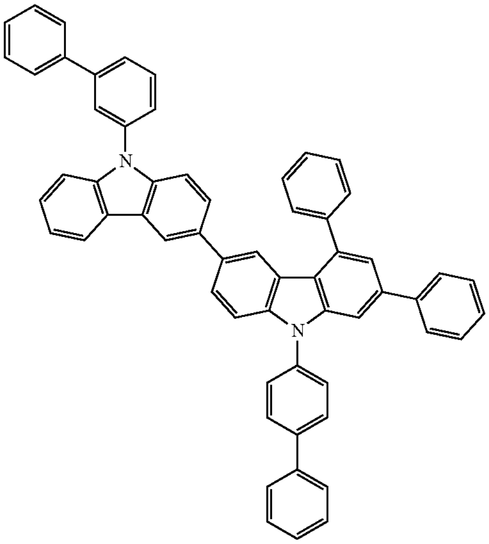
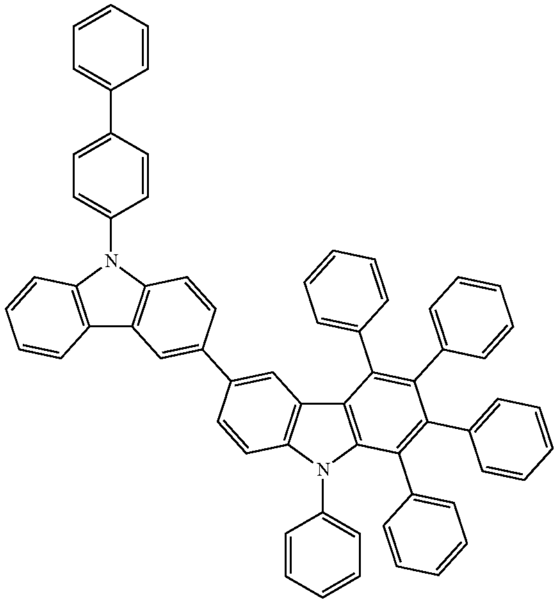
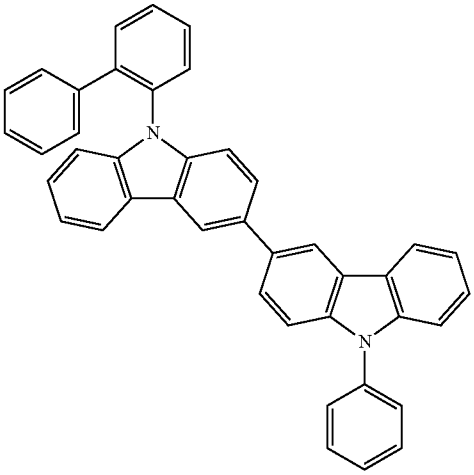

-continued
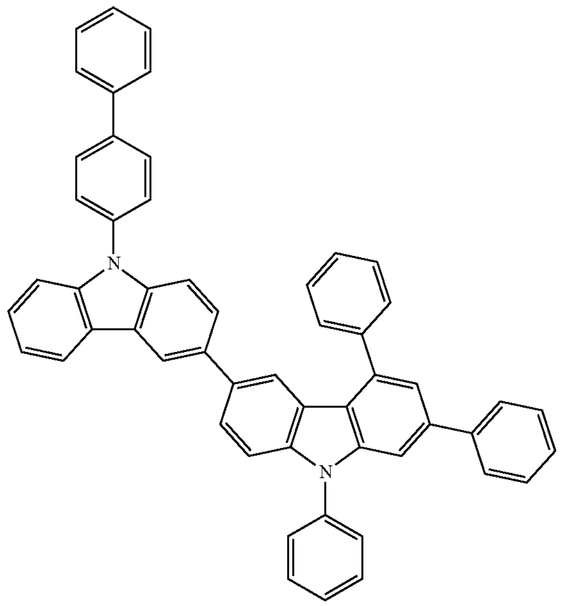
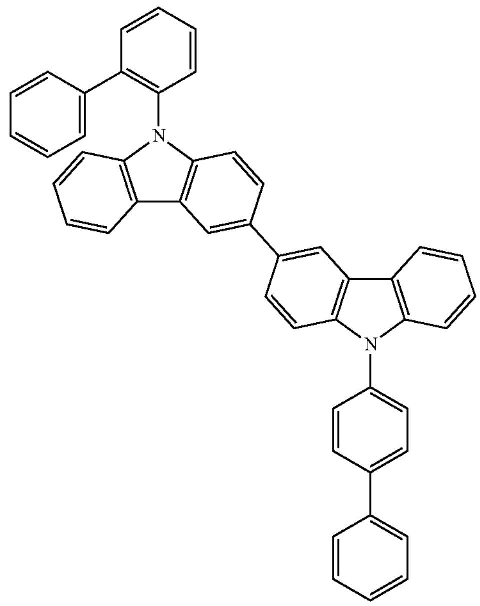
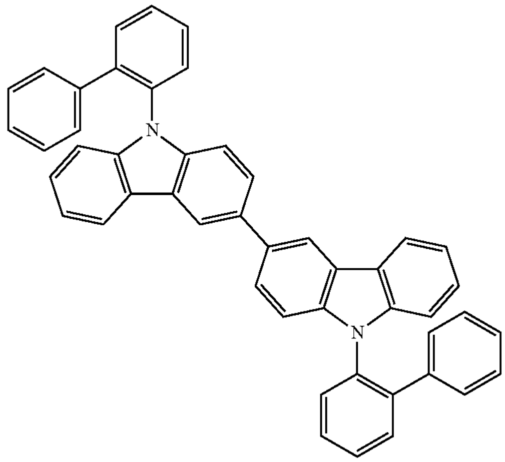
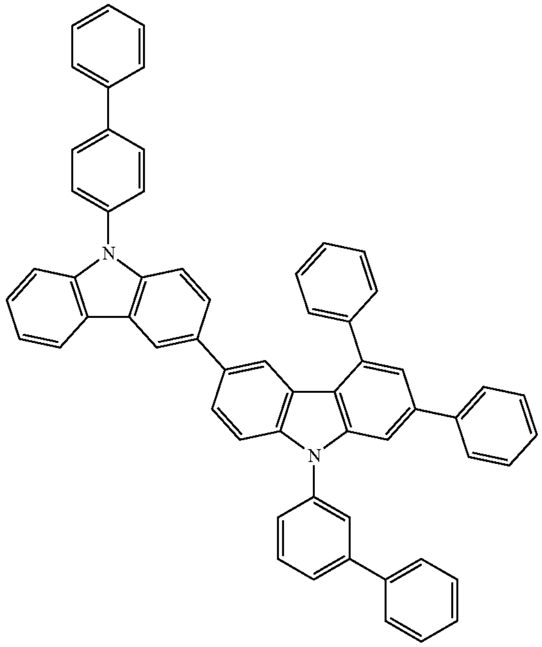

-continued
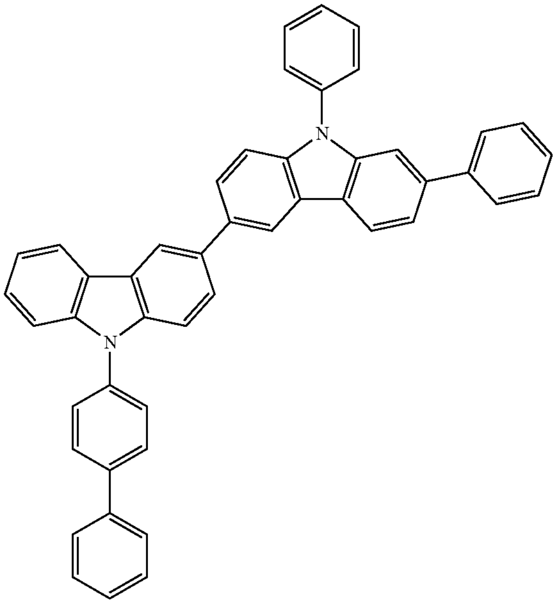
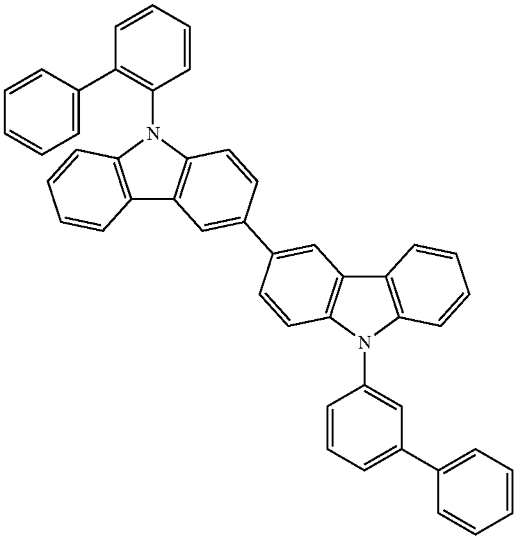
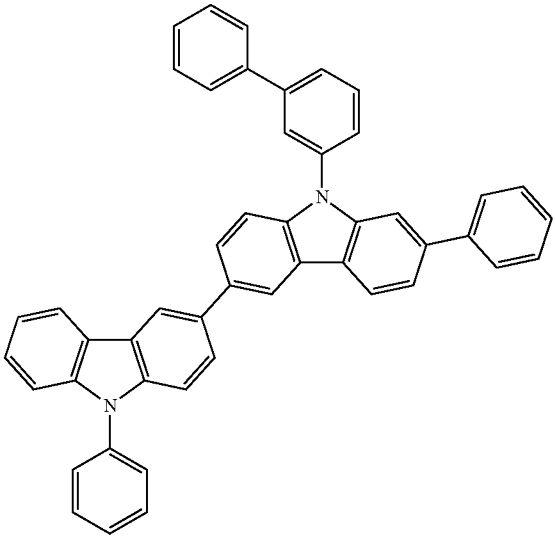
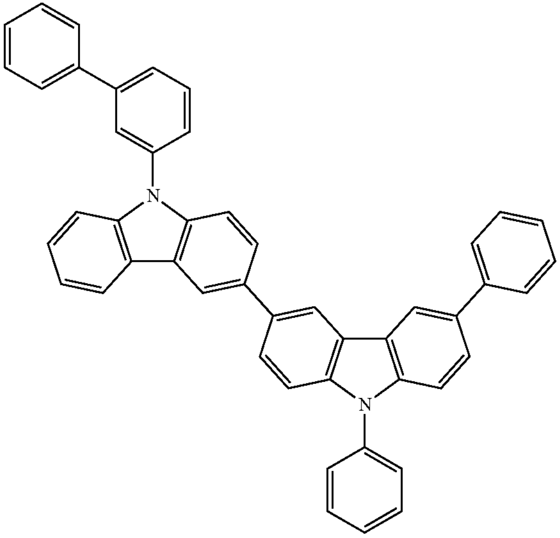
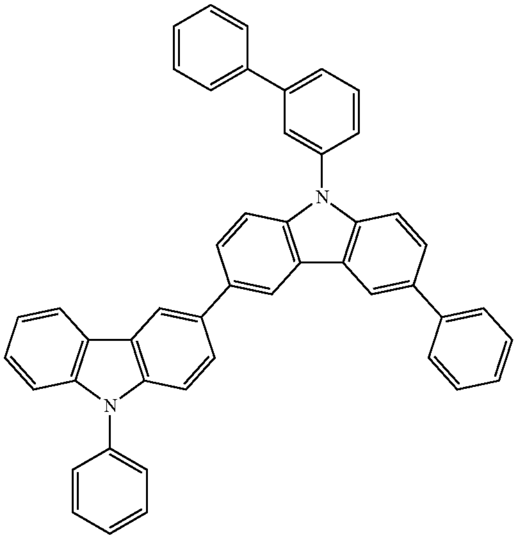
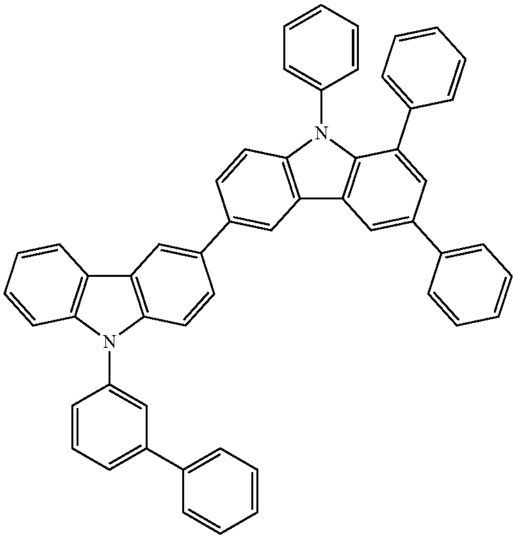

-continued
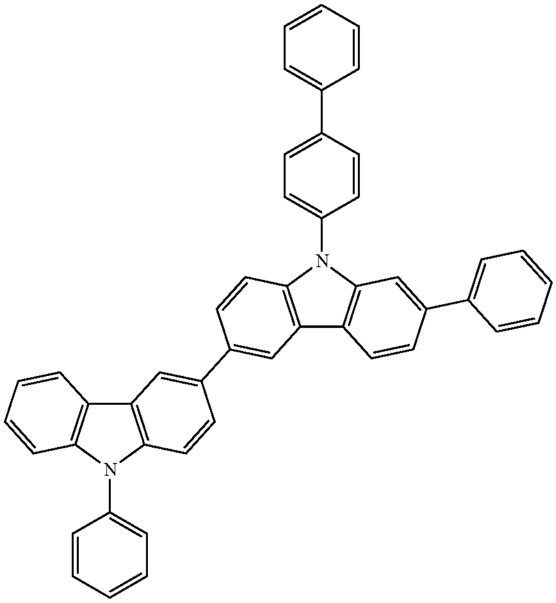
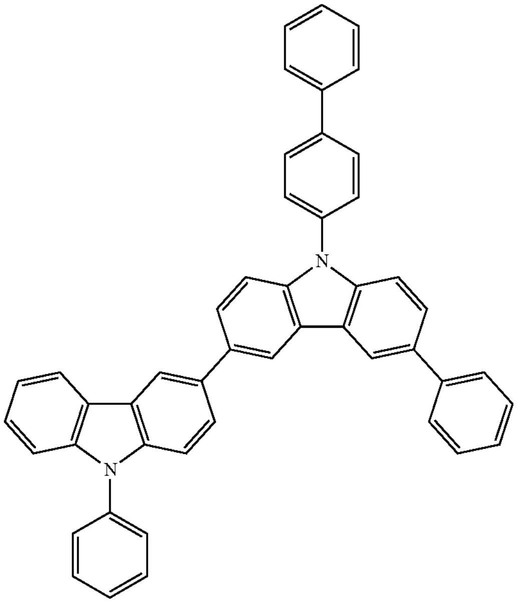
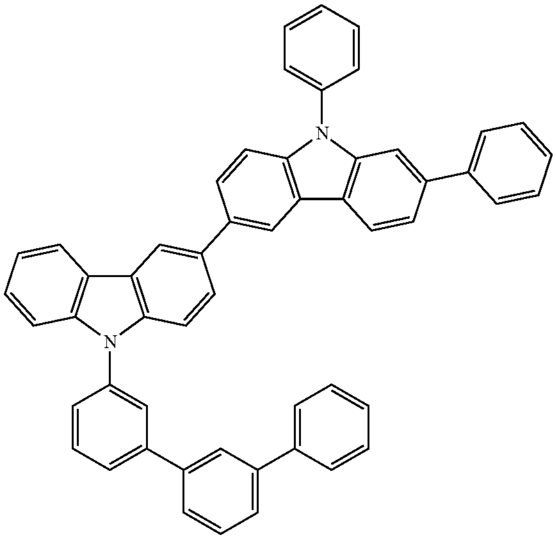
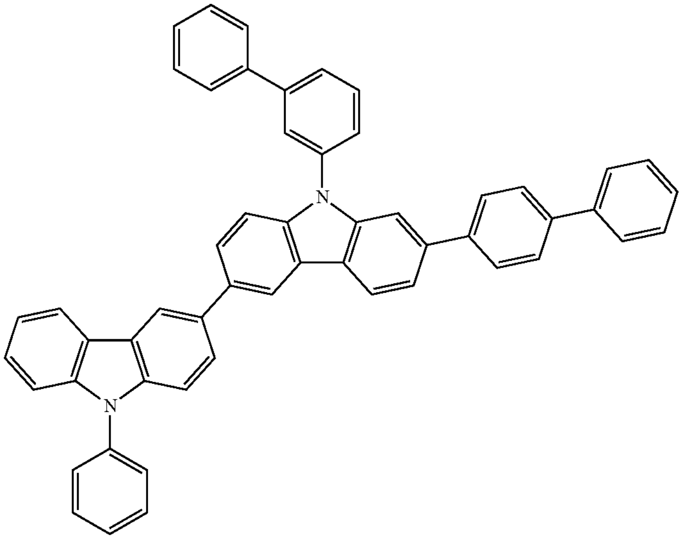

-continued
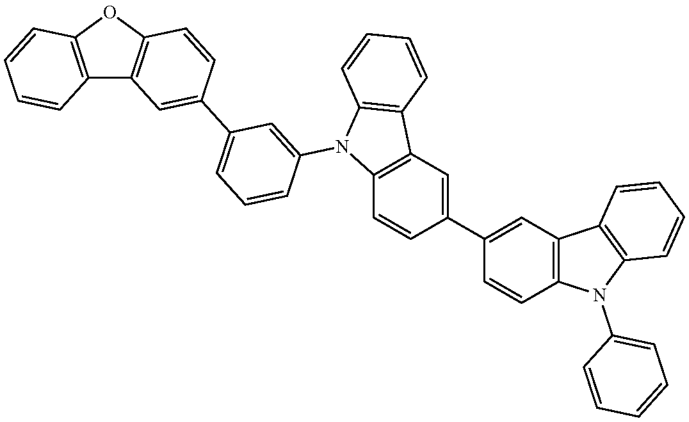
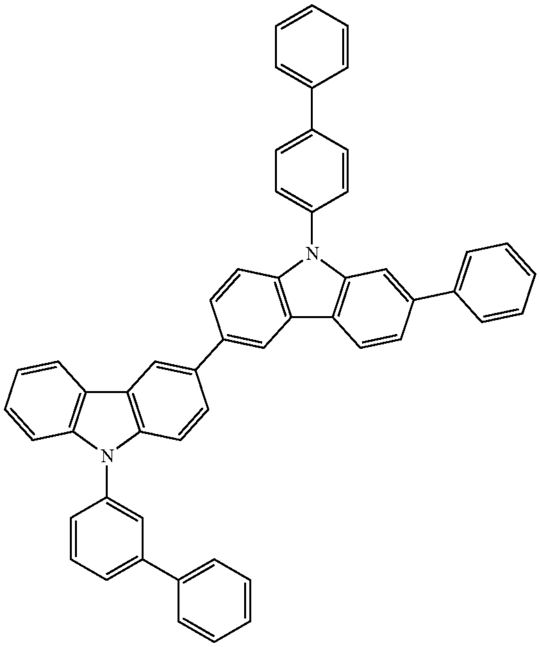
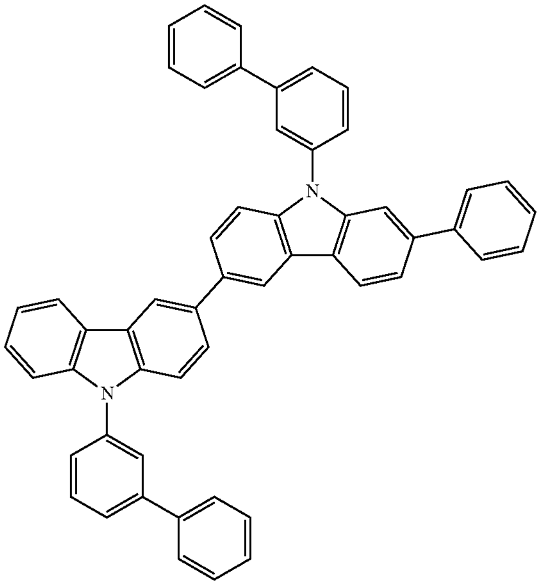
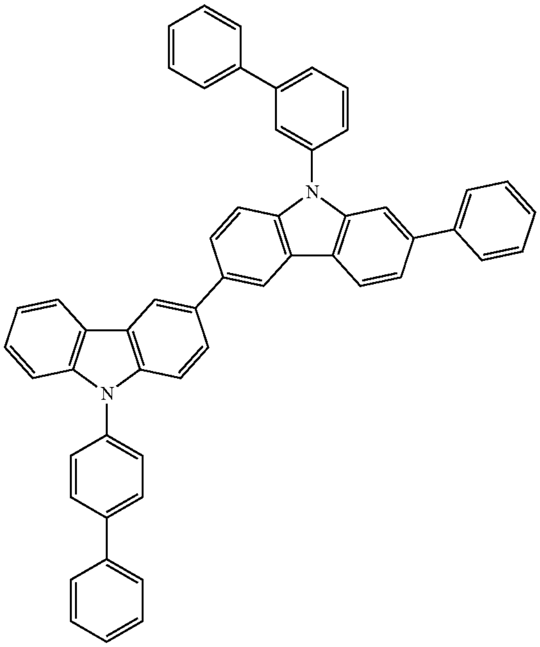

-continued
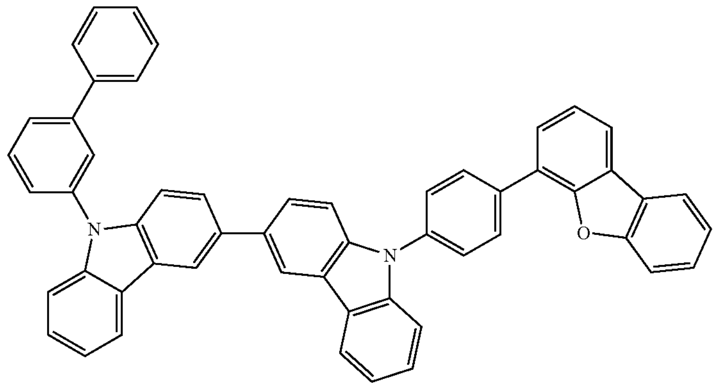
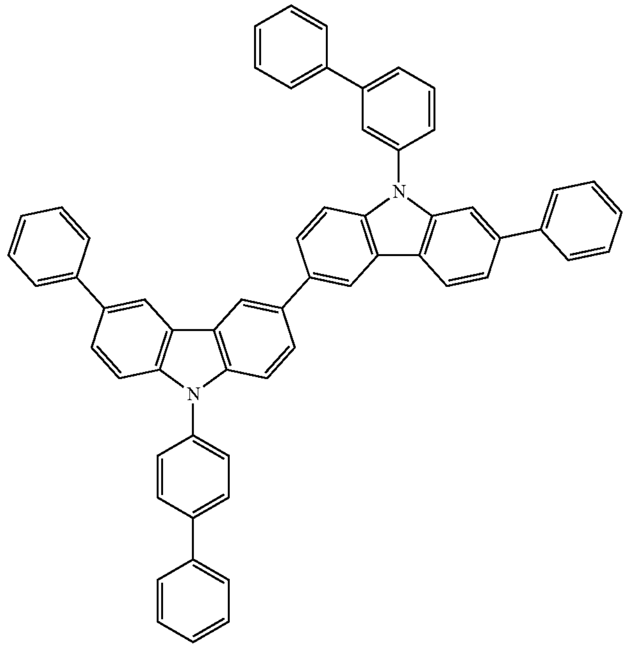
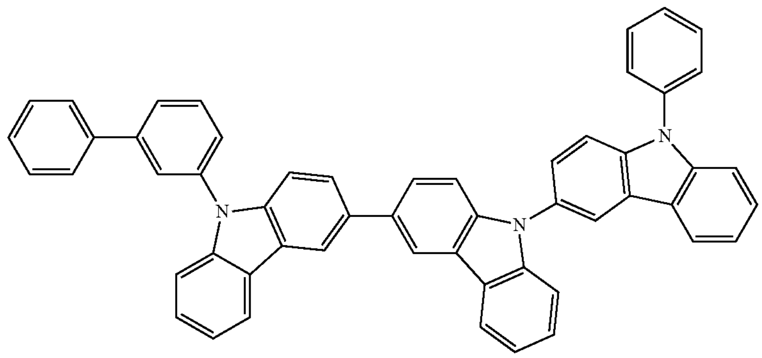

-continued
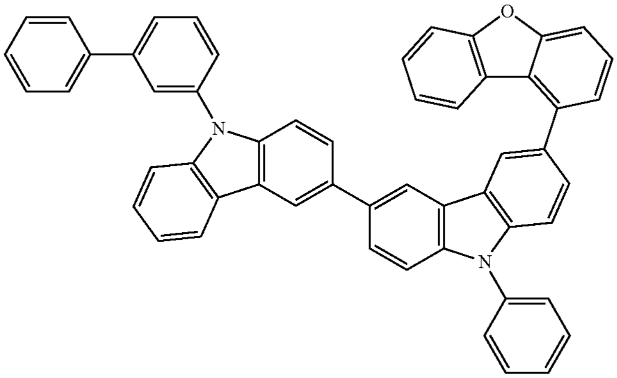
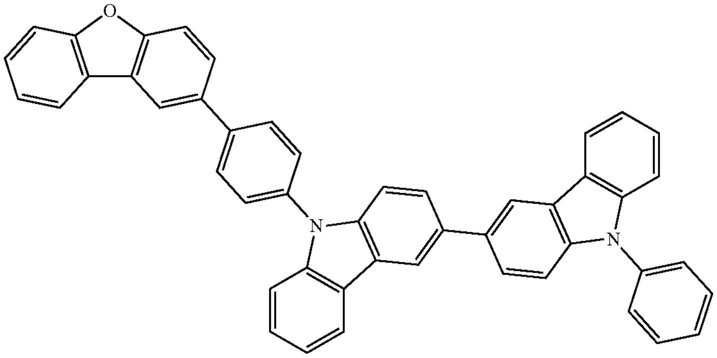
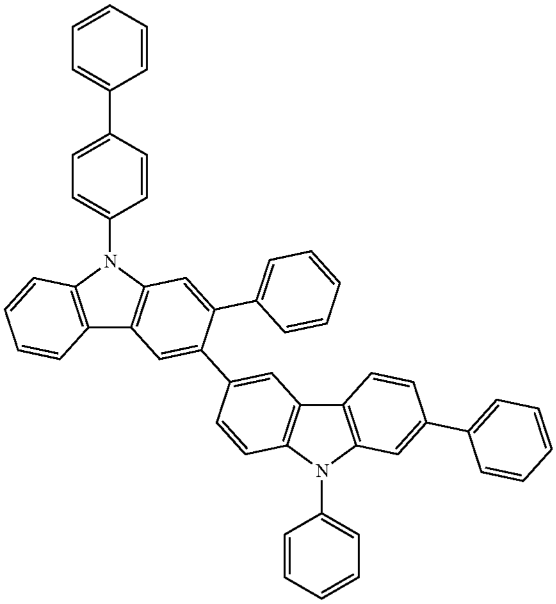
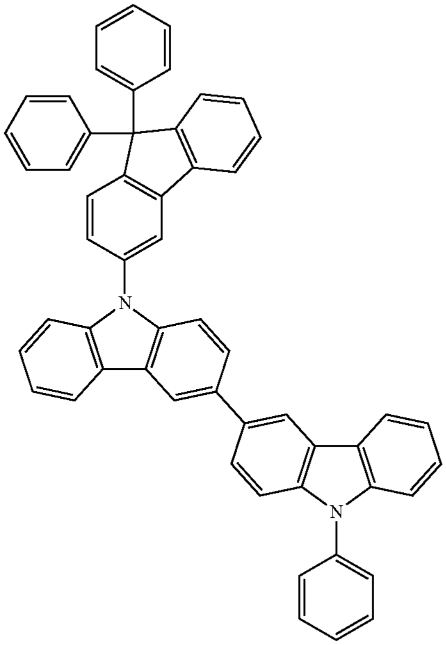

-continued
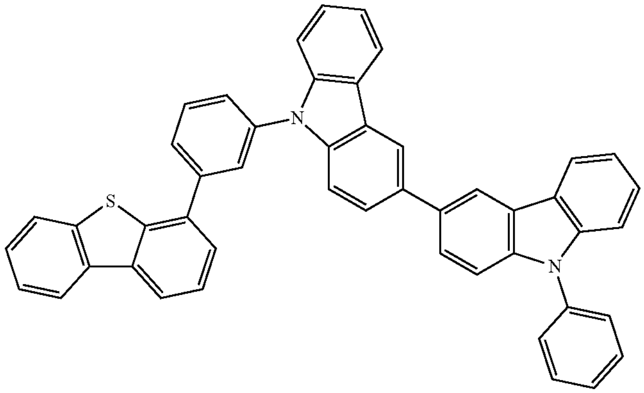
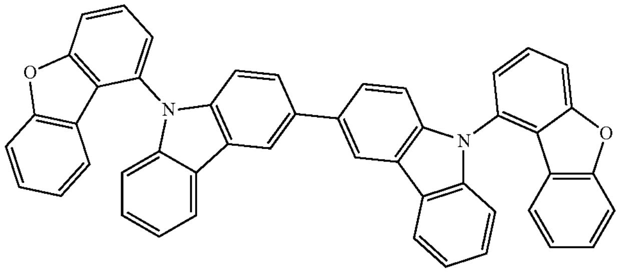
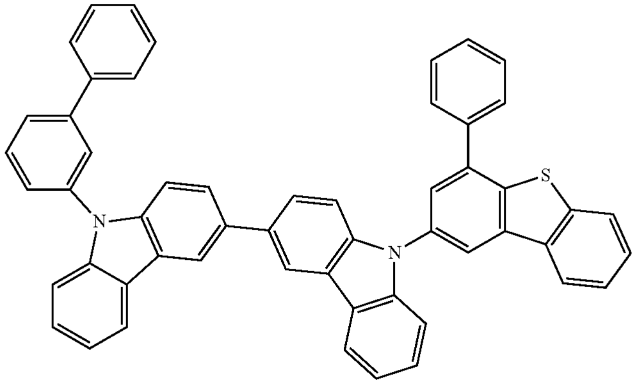
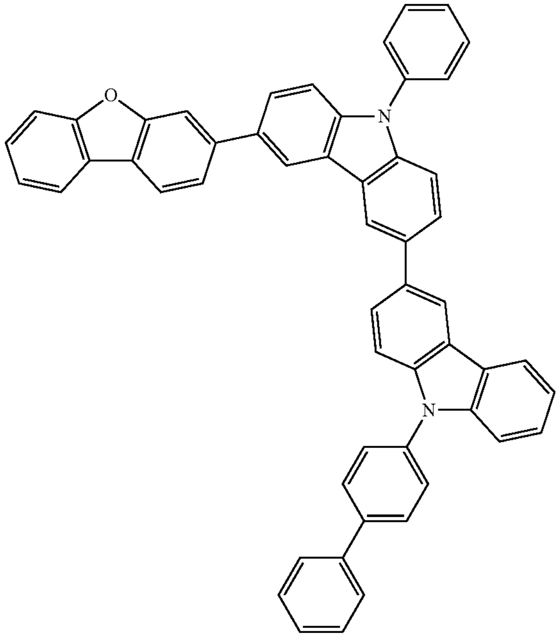

-continued
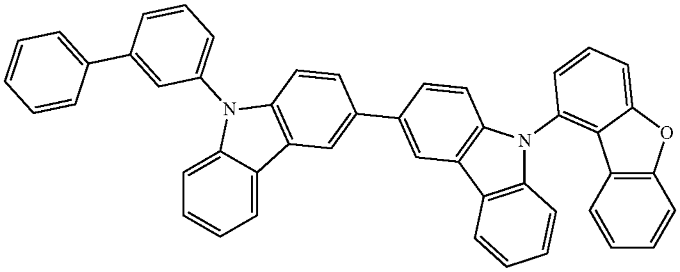
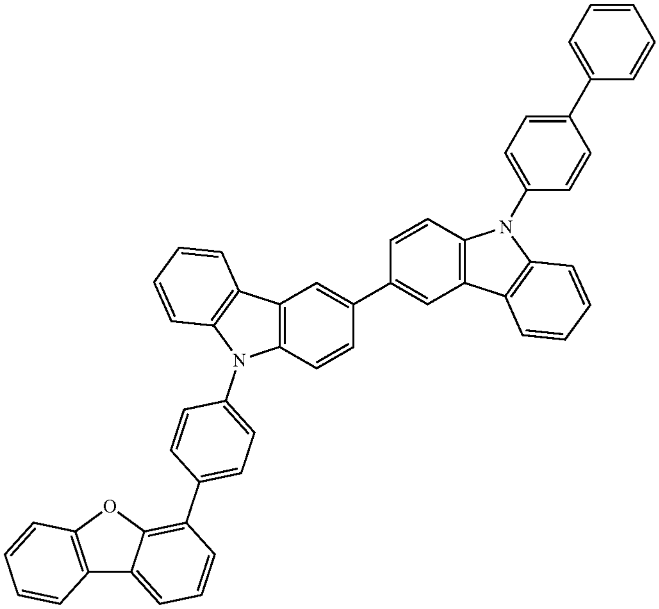
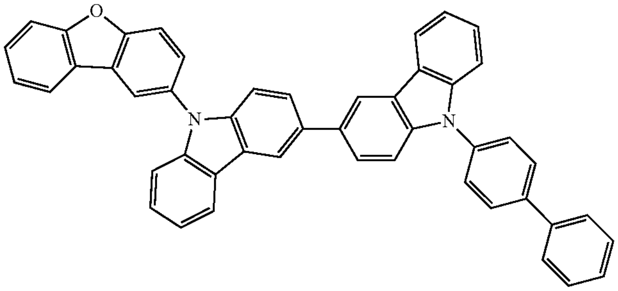
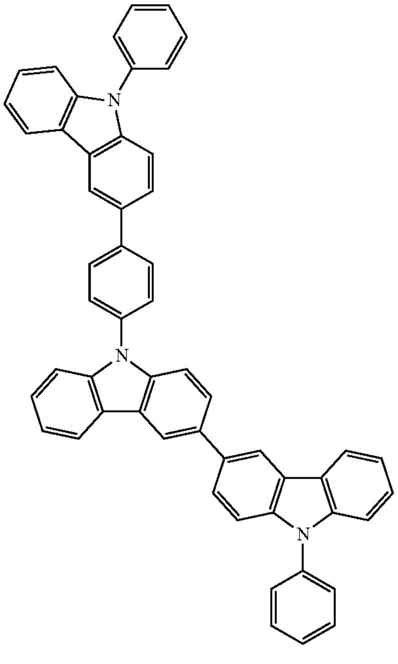

-continued
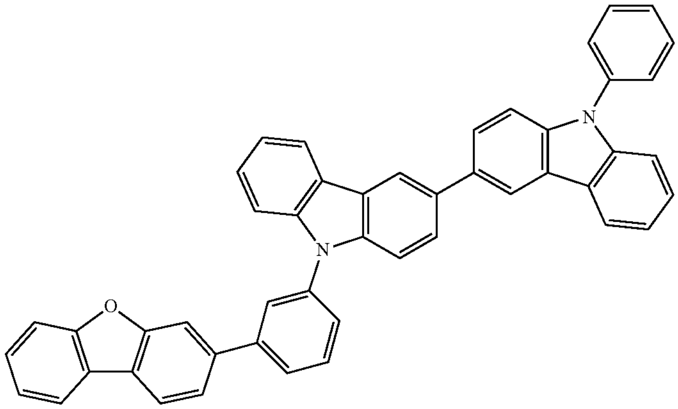
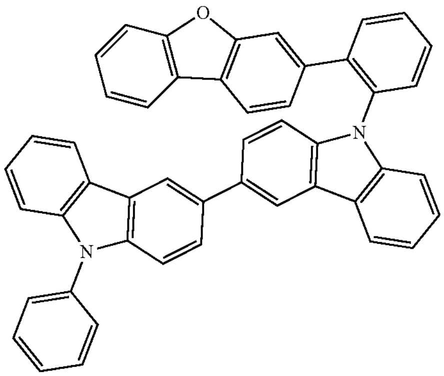
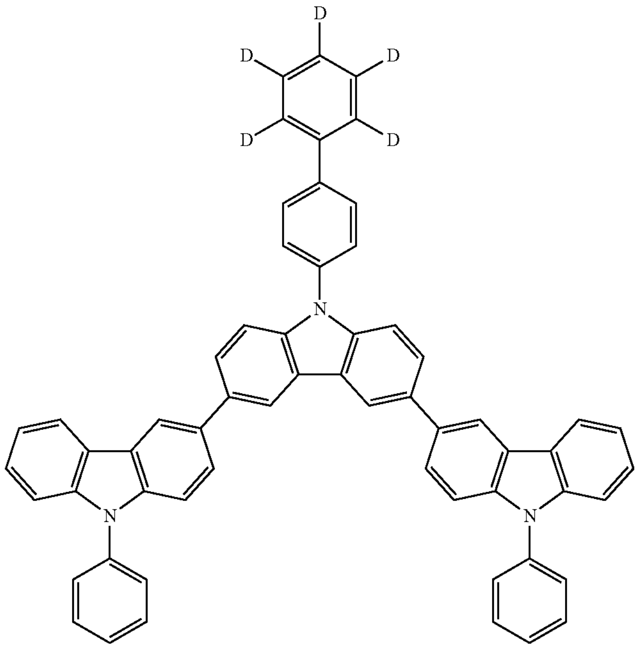
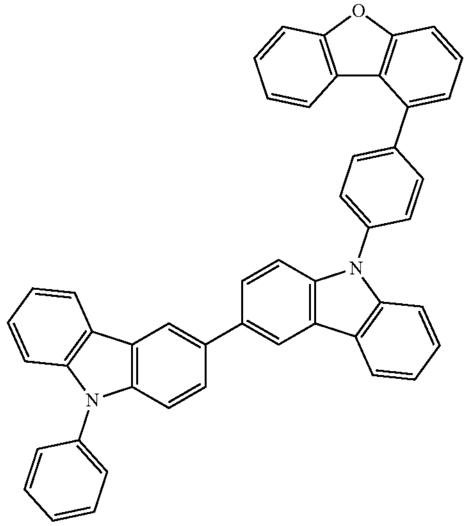
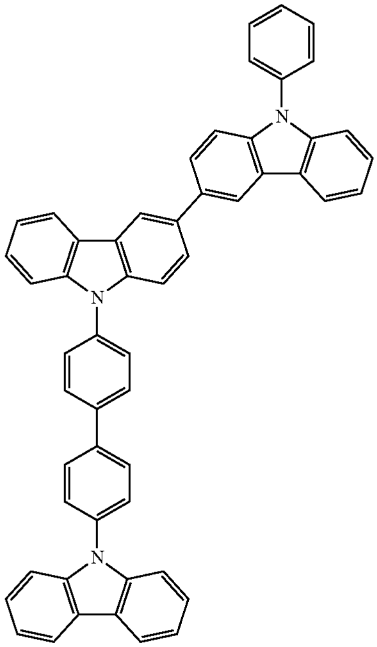
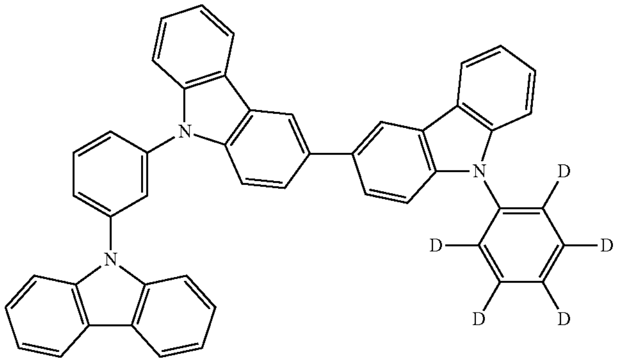

-continued
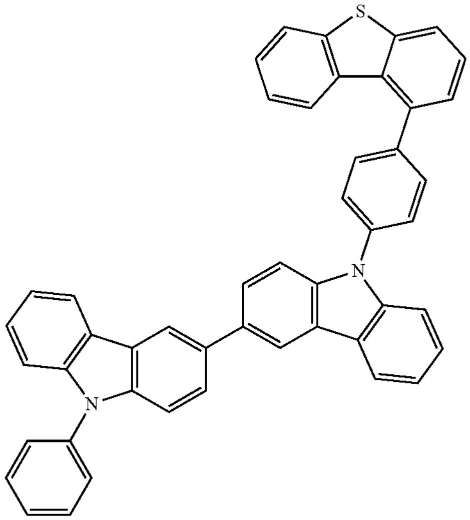
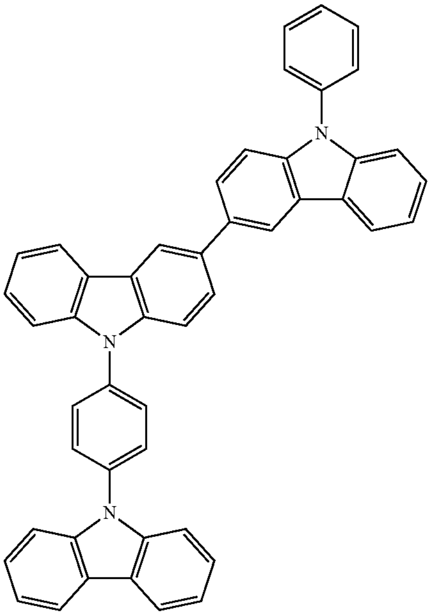
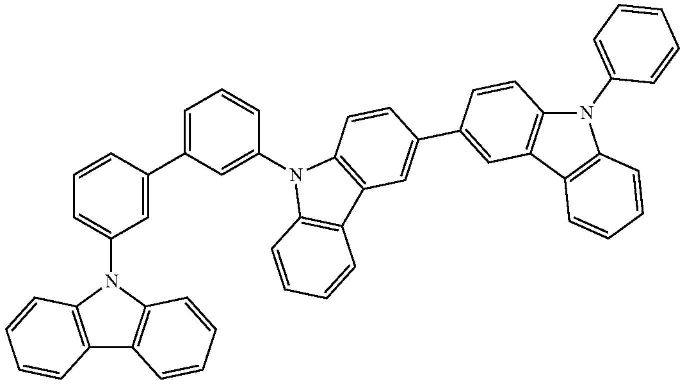
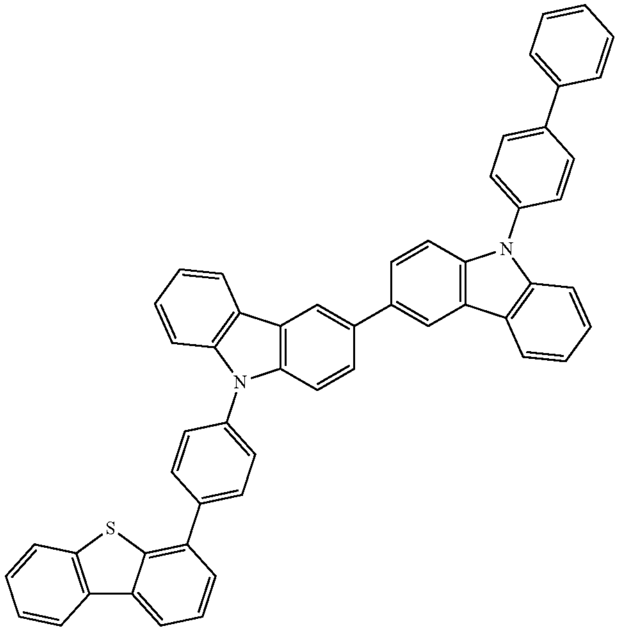

-continued
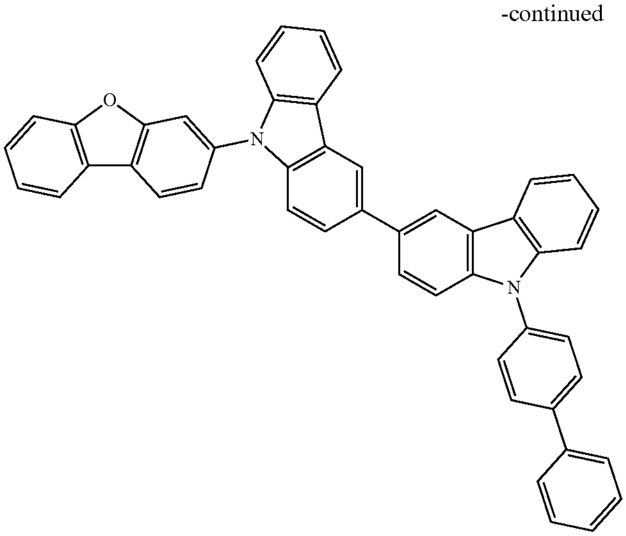
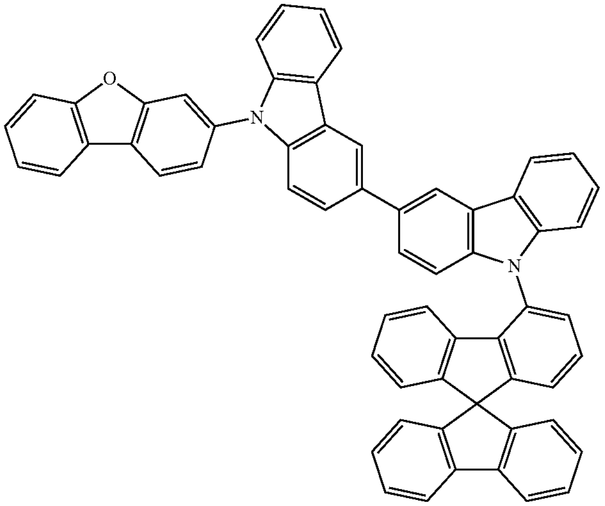
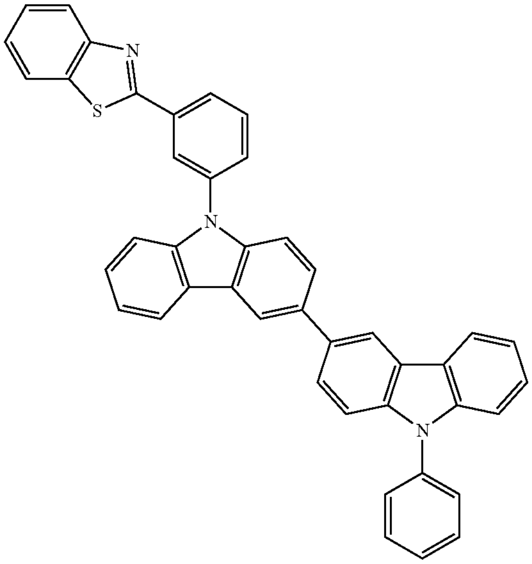
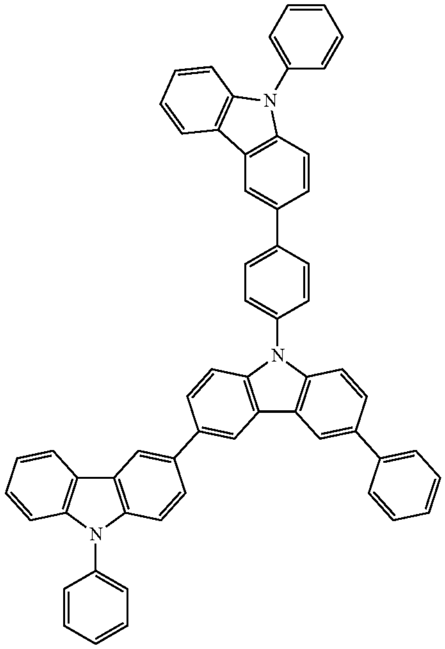
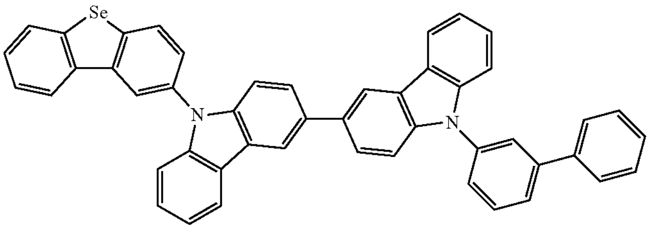

-continued
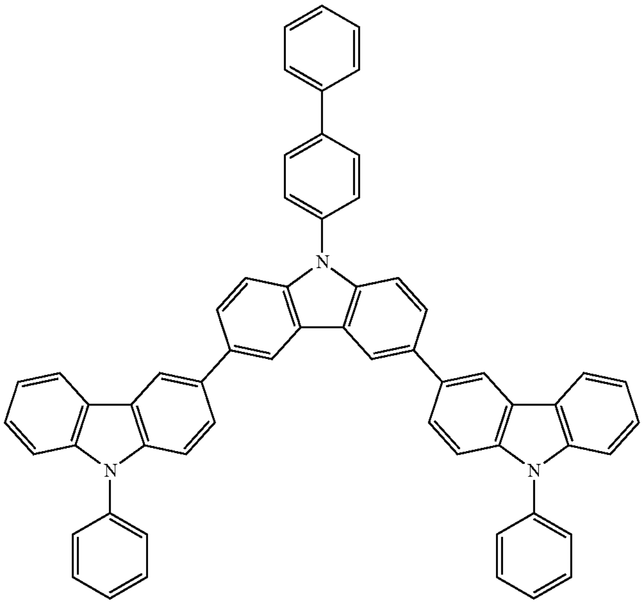
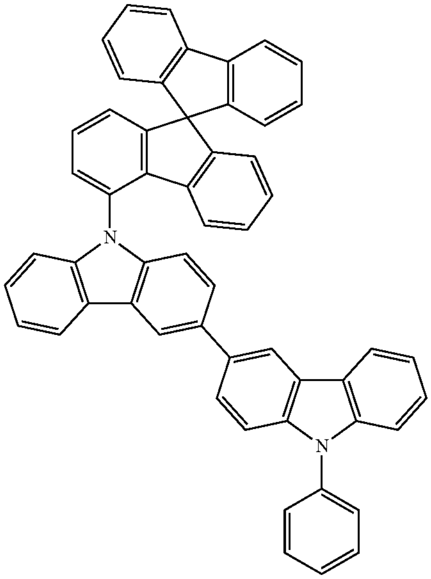
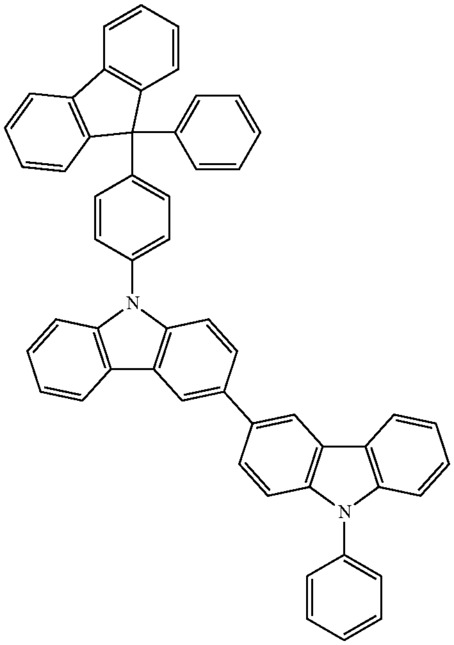
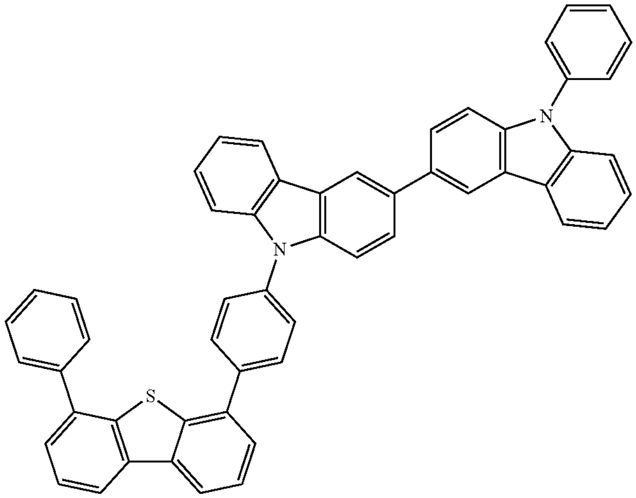
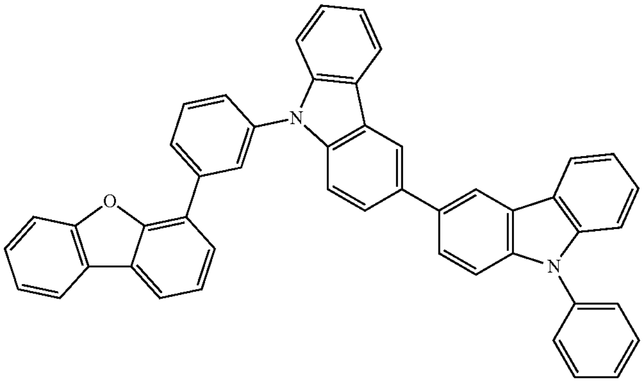

-continued
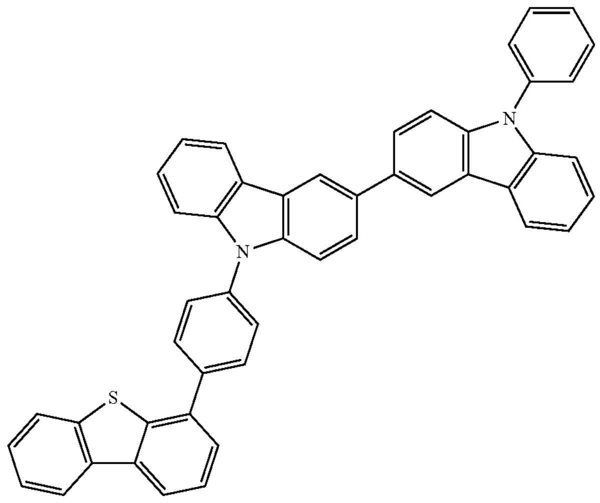
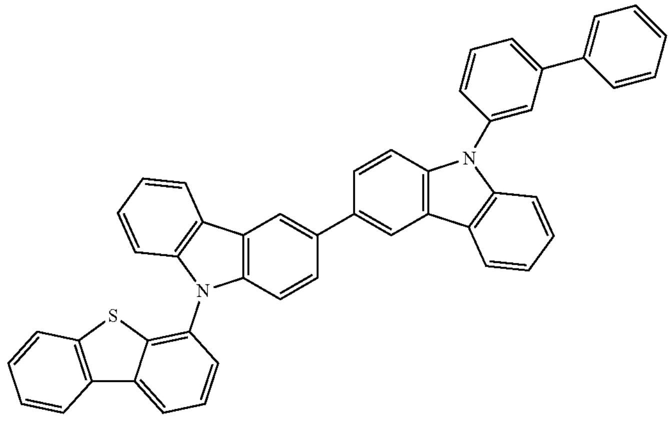
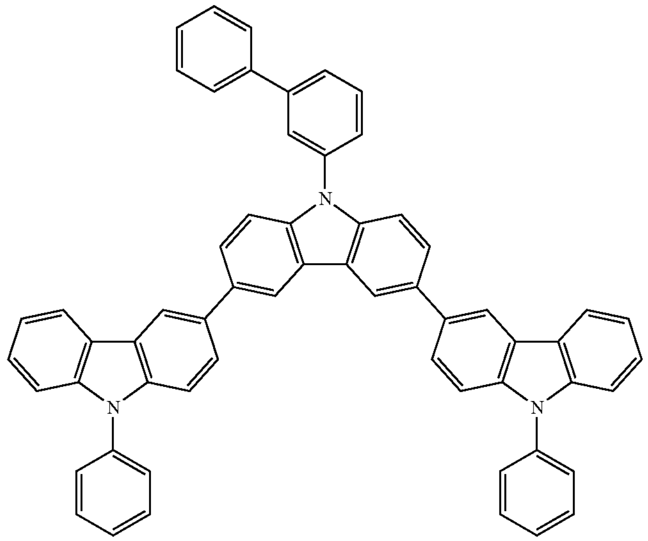
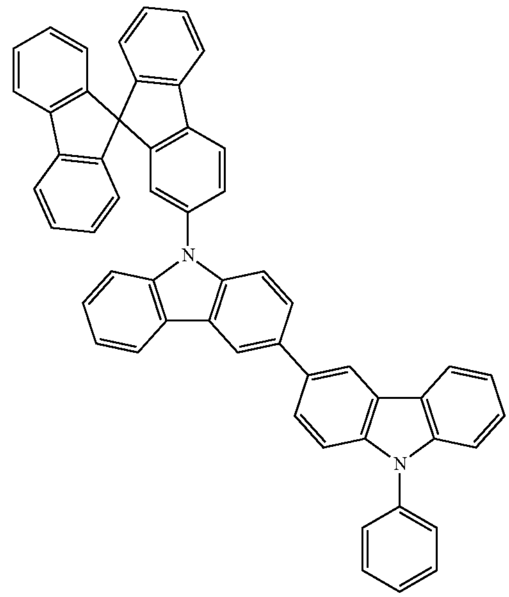

-continued
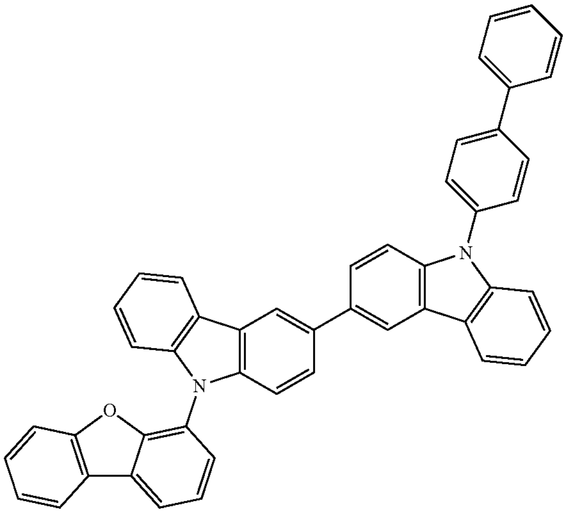
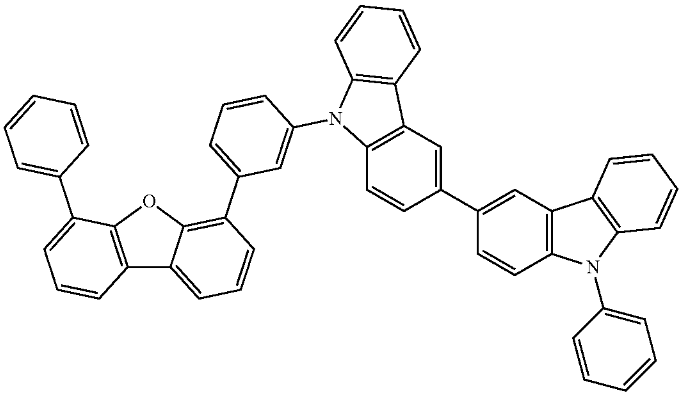
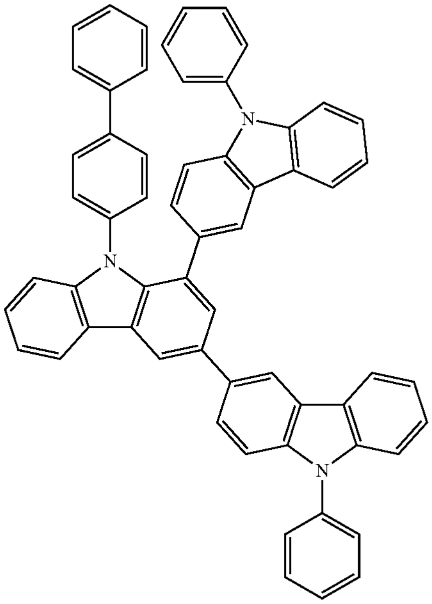
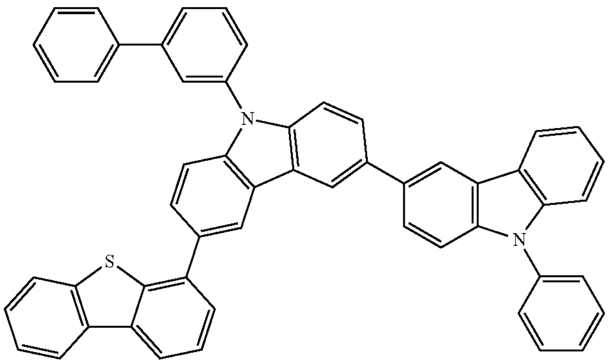

-continued
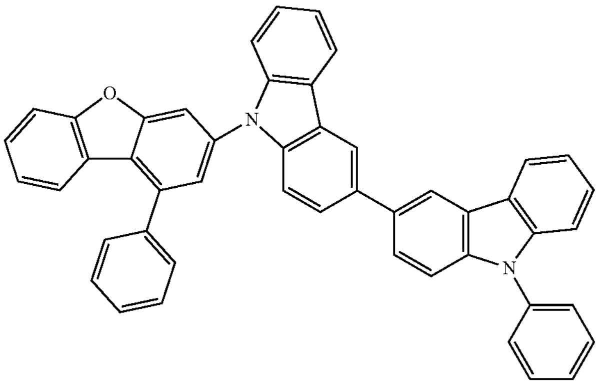
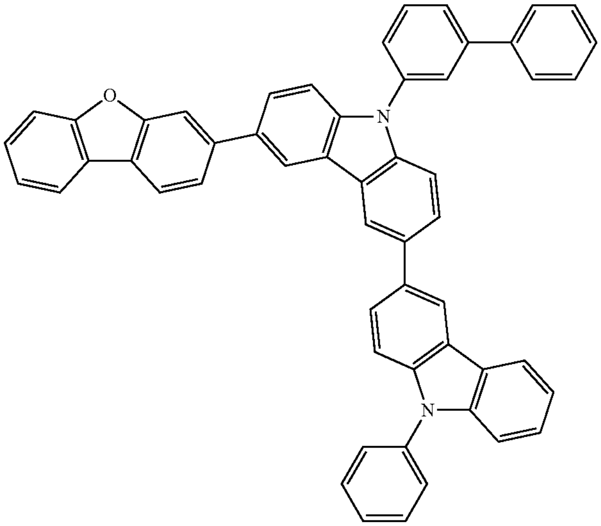
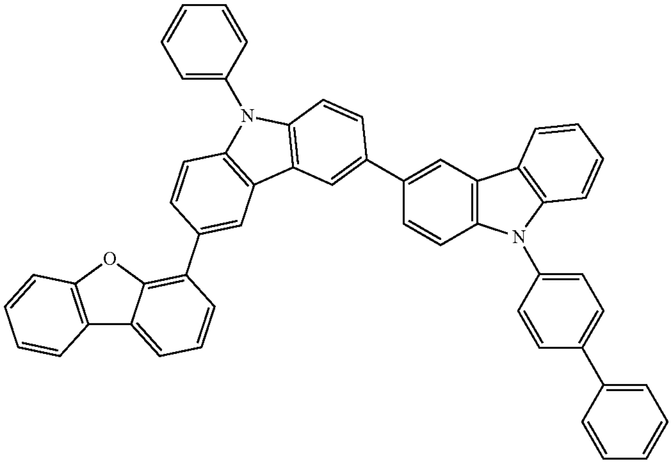
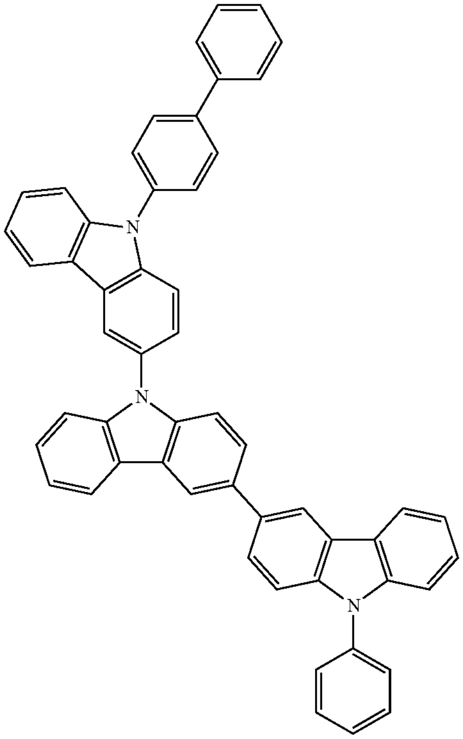

-continued
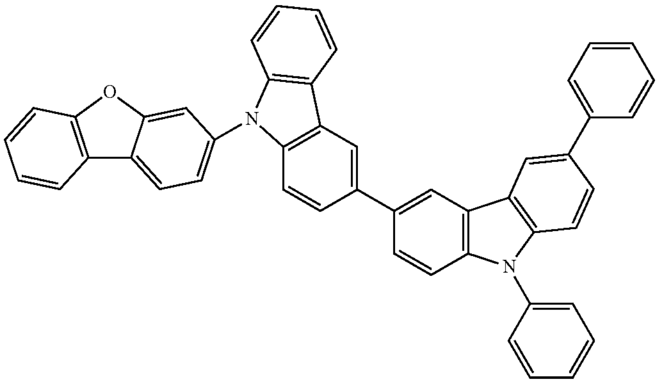
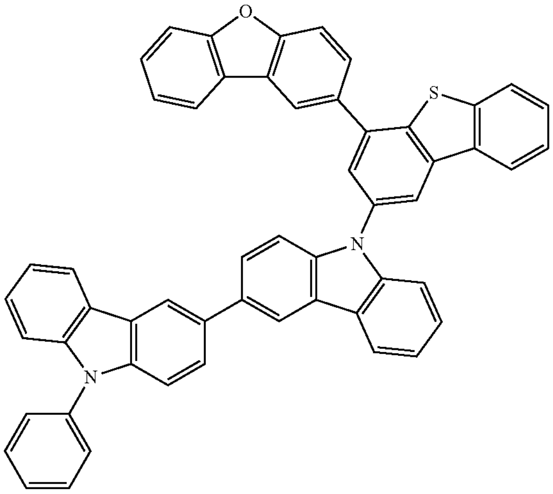
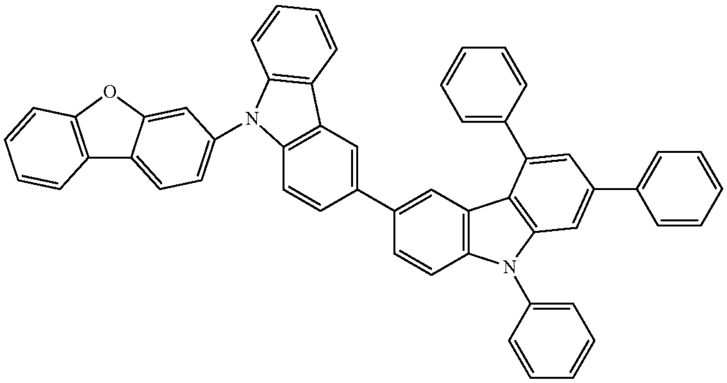

-continued
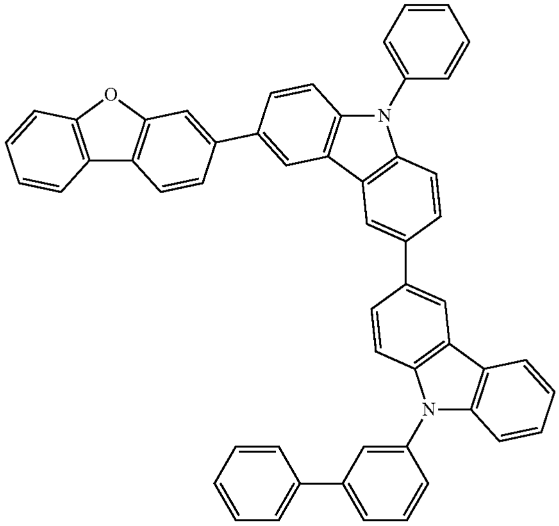
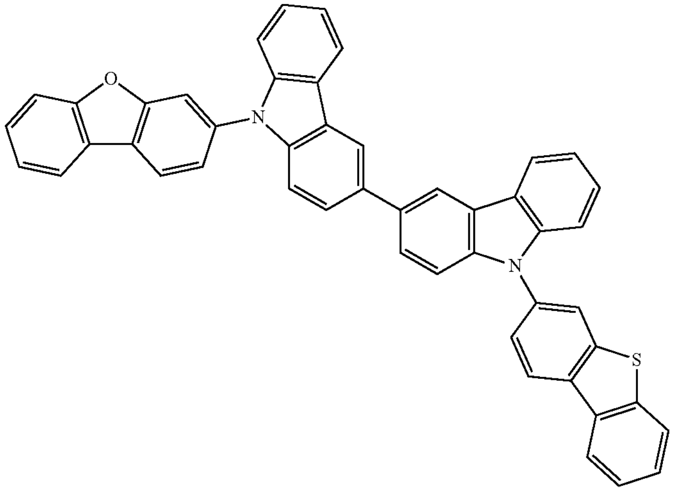
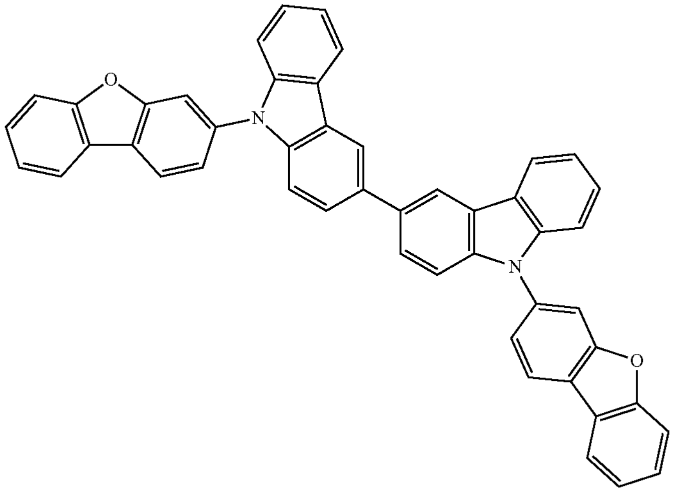

-continued
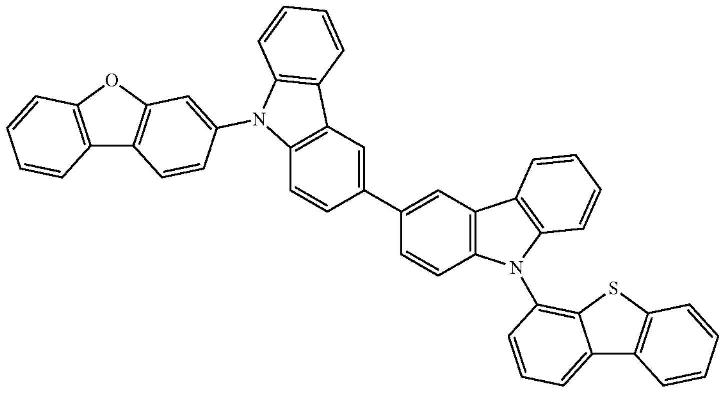
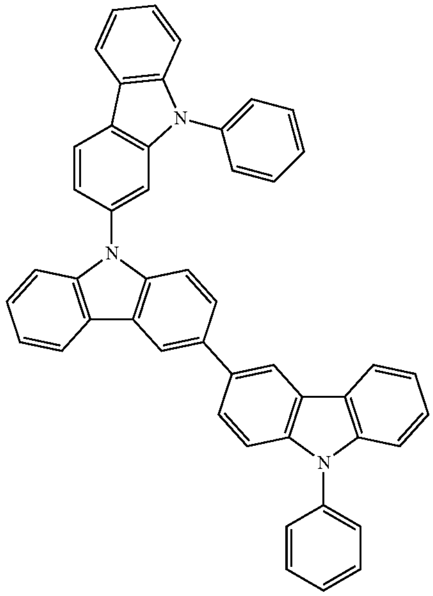
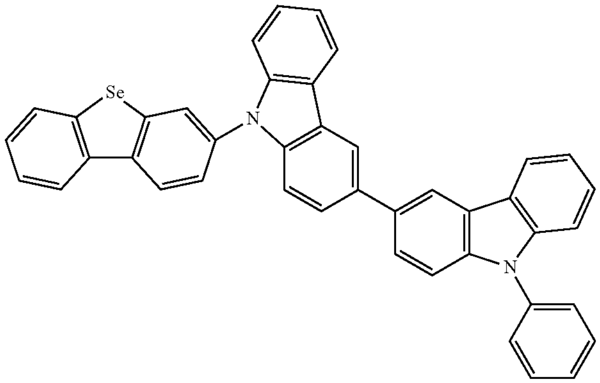
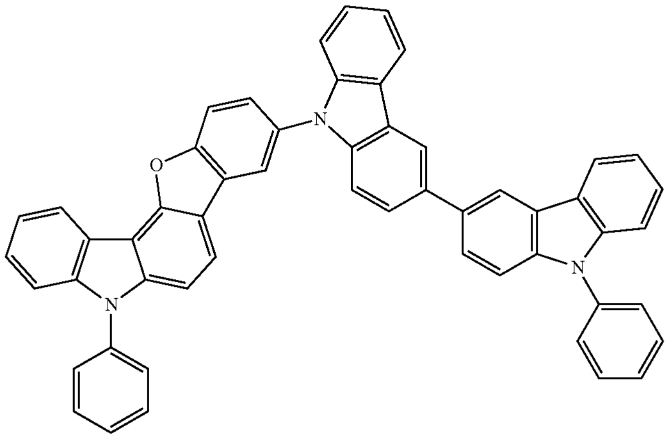
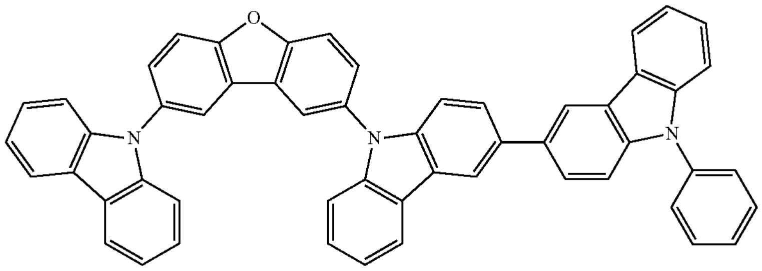

-continued
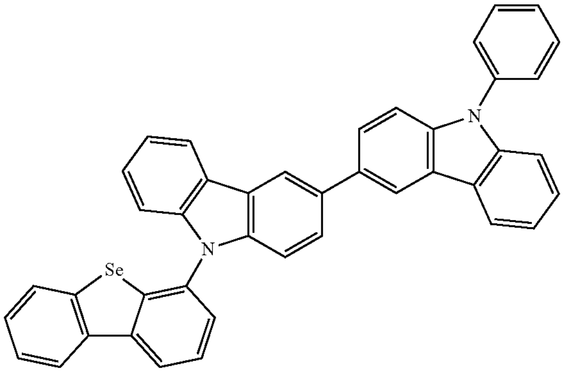
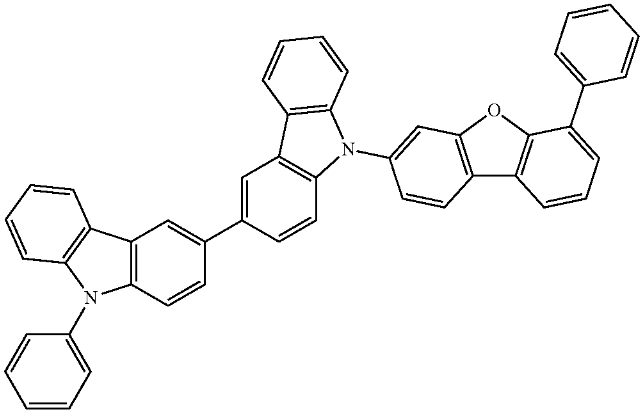
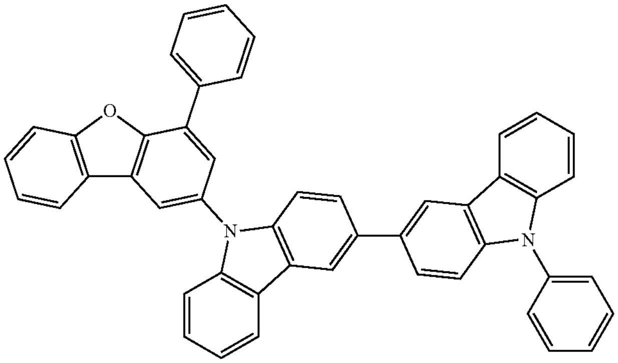
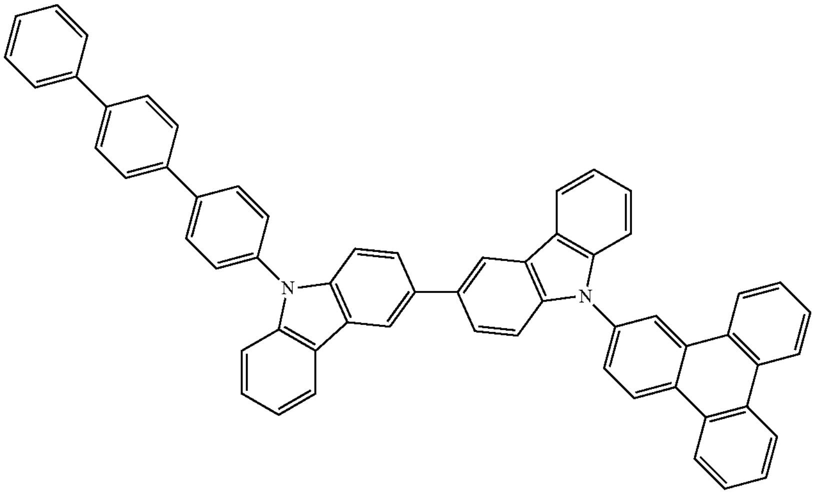

-continued
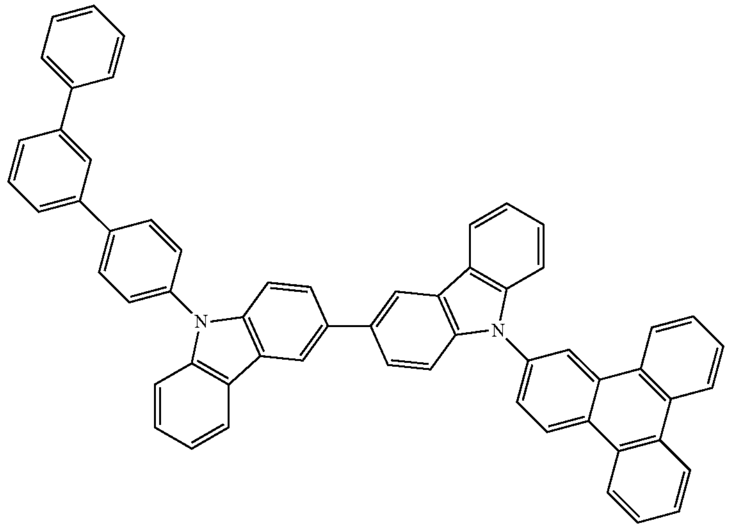
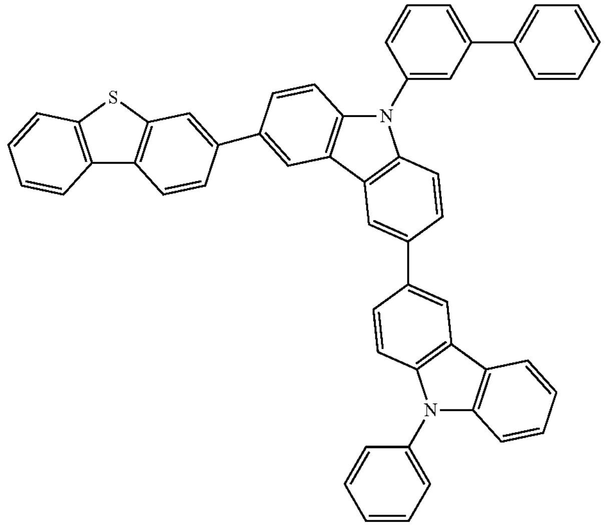
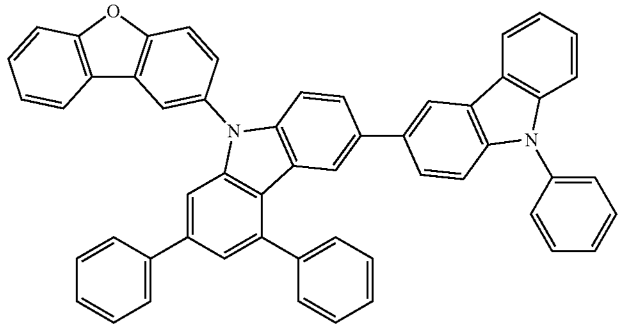

-continued
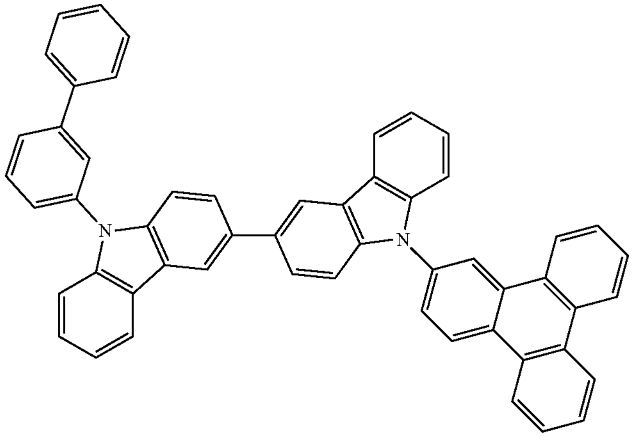
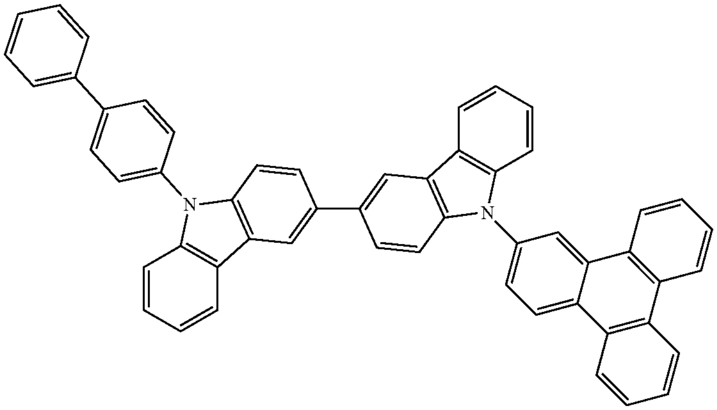
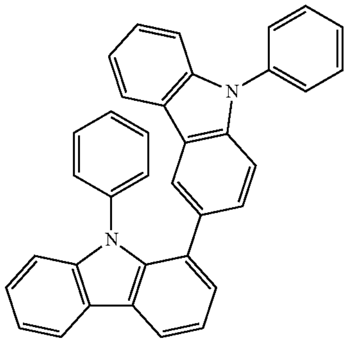
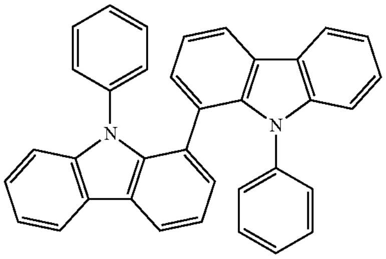
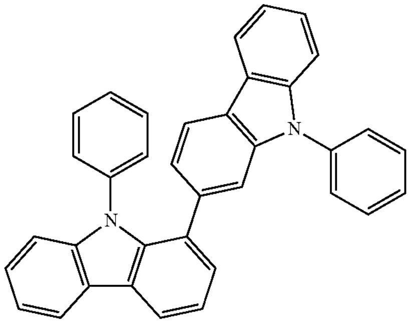
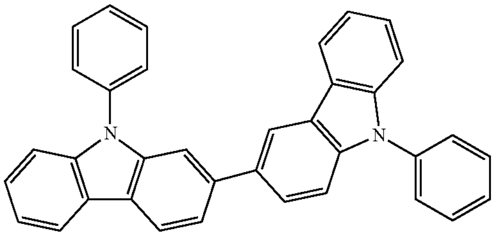
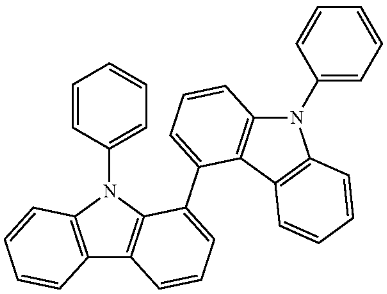

-continued
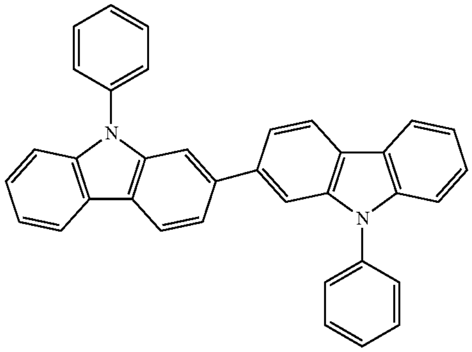
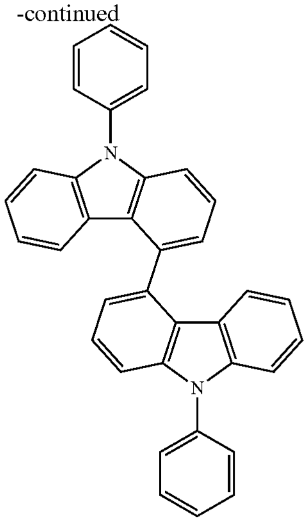
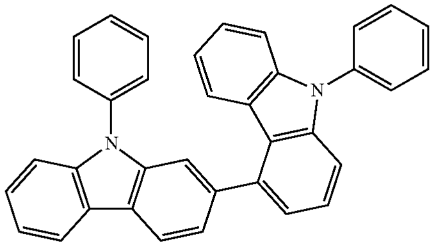
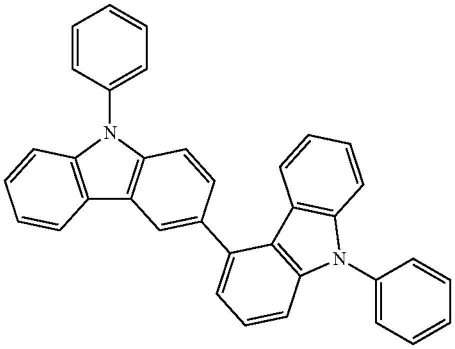
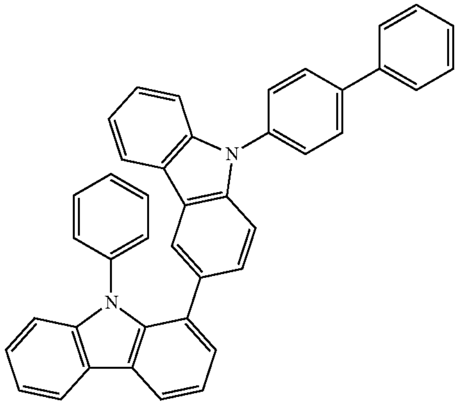
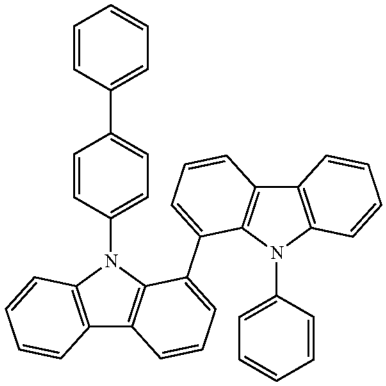

-continued
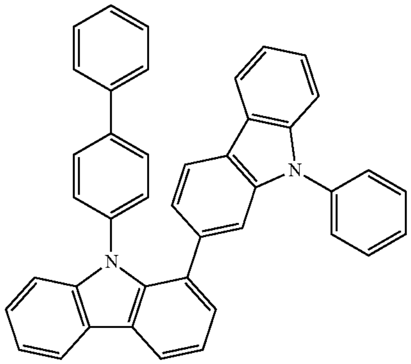
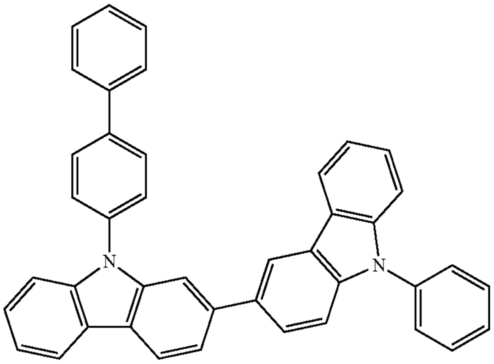
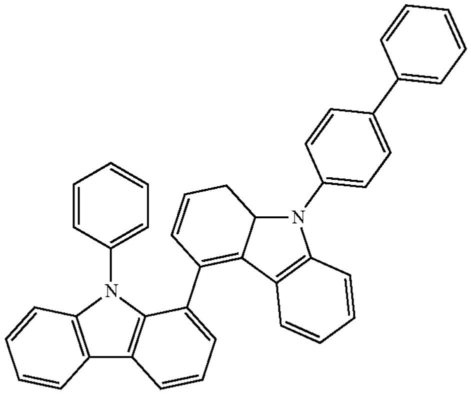
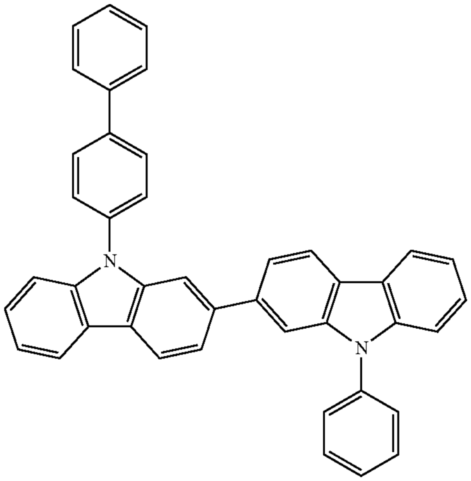
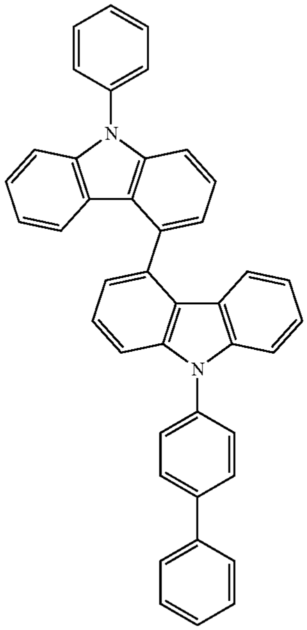
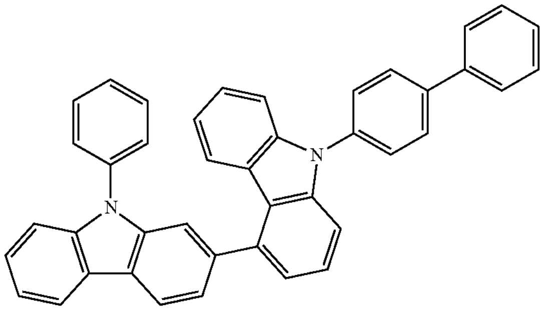

-continued
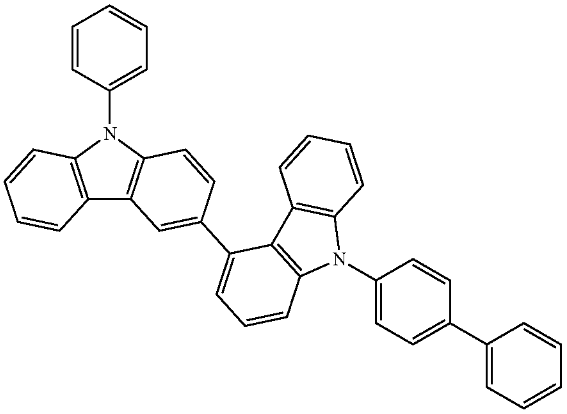
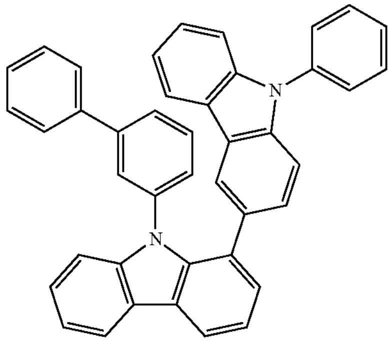
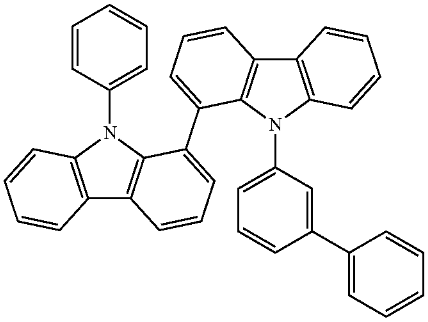
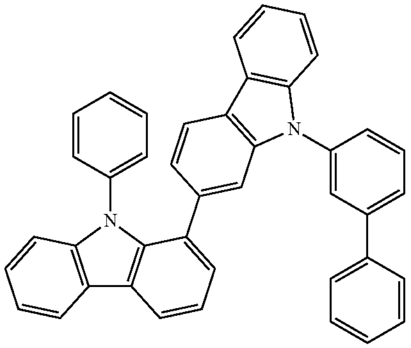
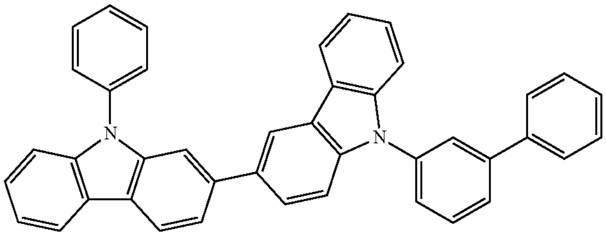
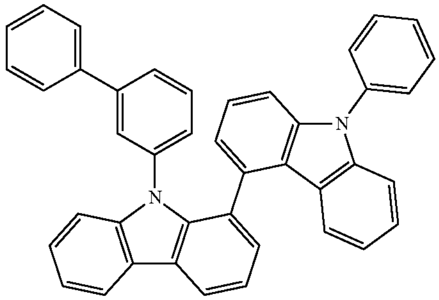
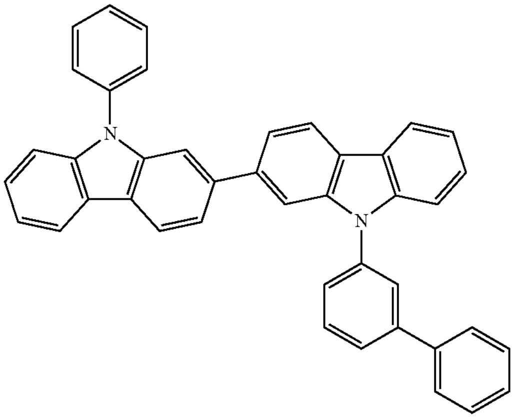
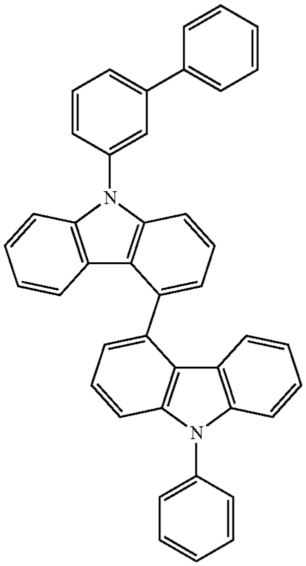

-continued
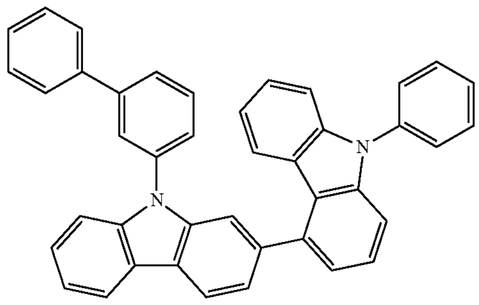
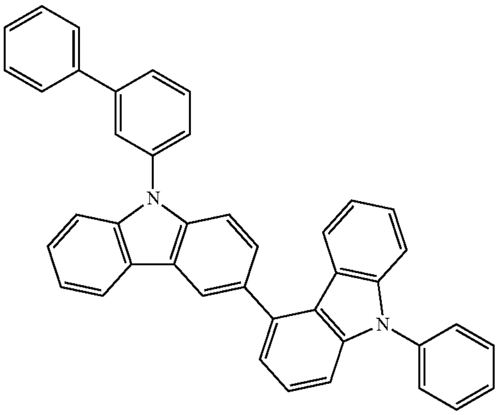
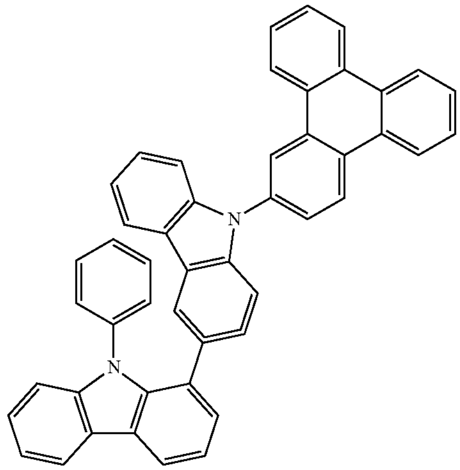
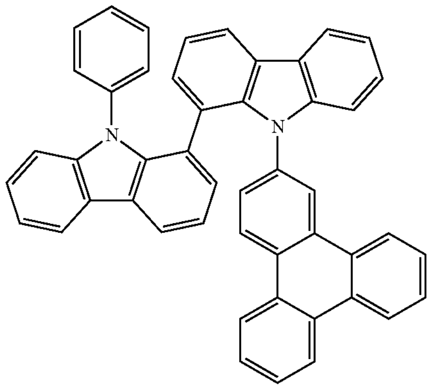
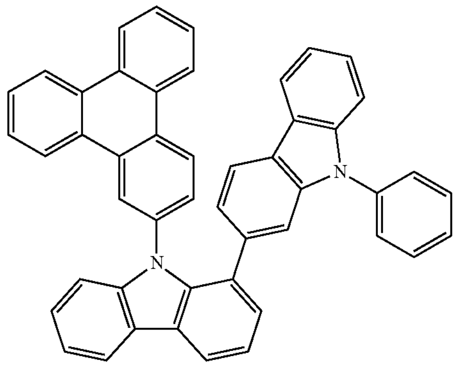
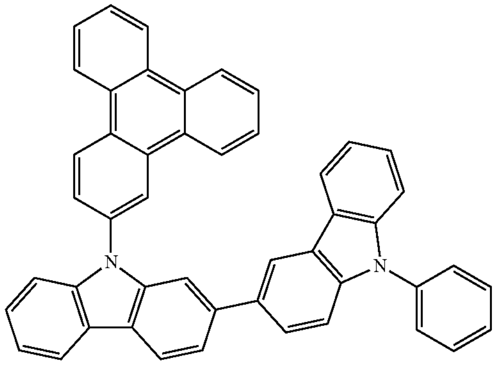

-continued
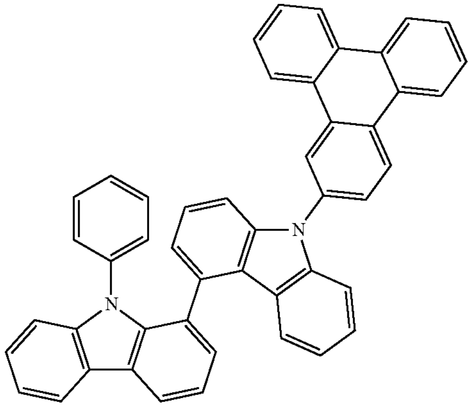
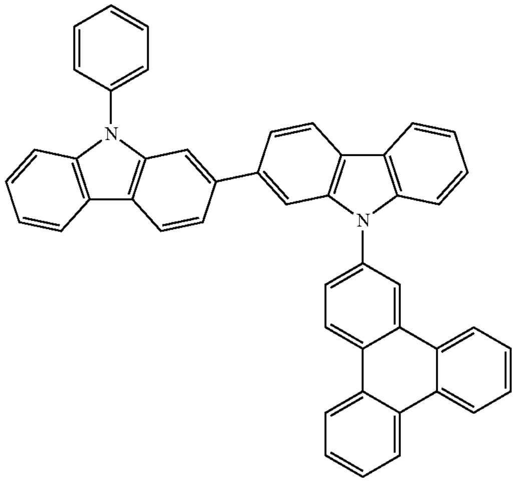
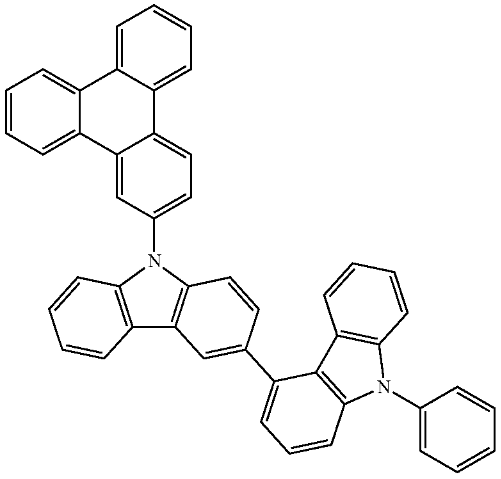
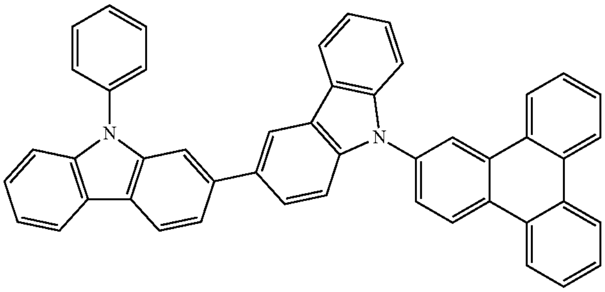
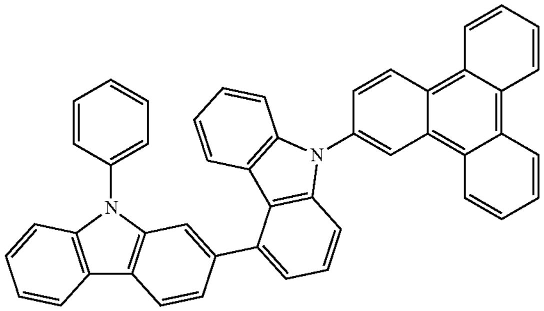
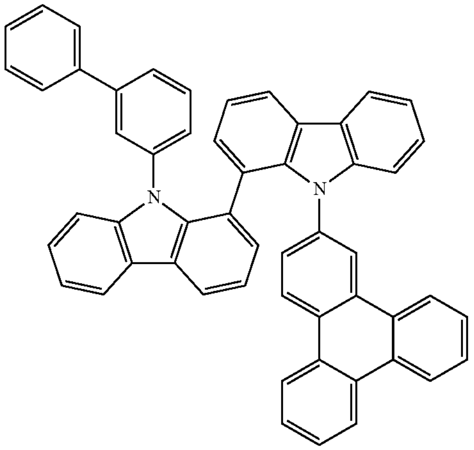

-continued
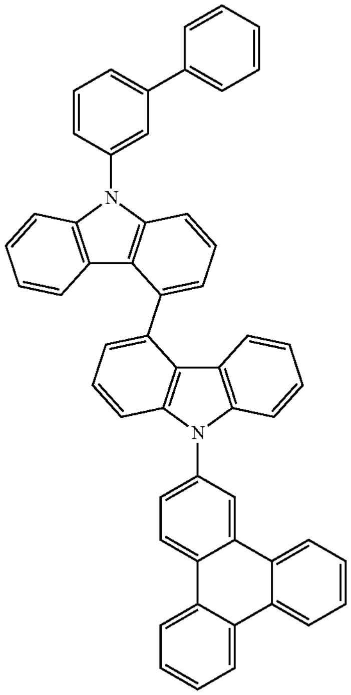
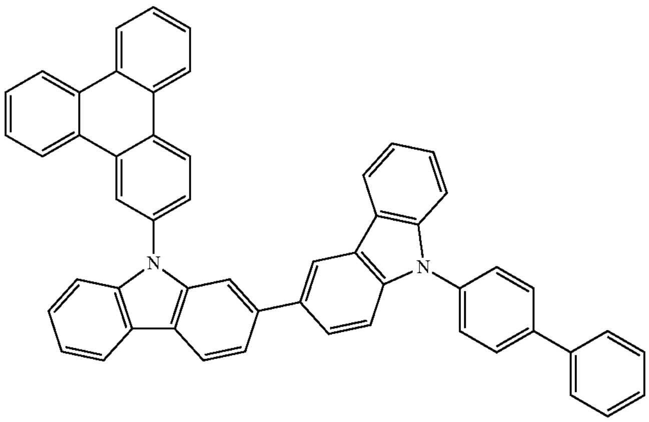
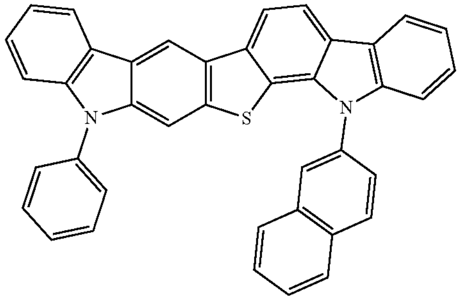
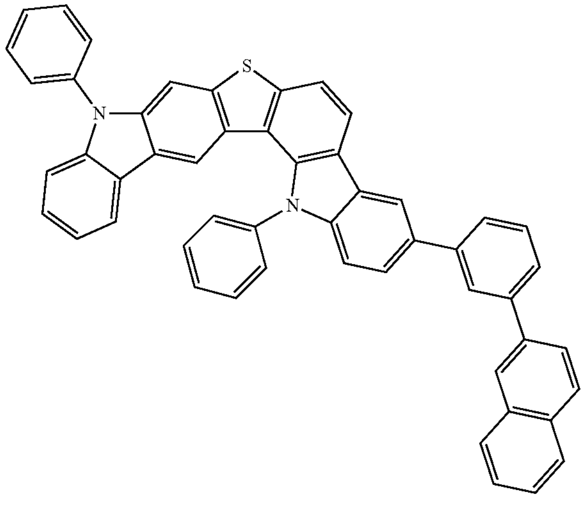

-continued
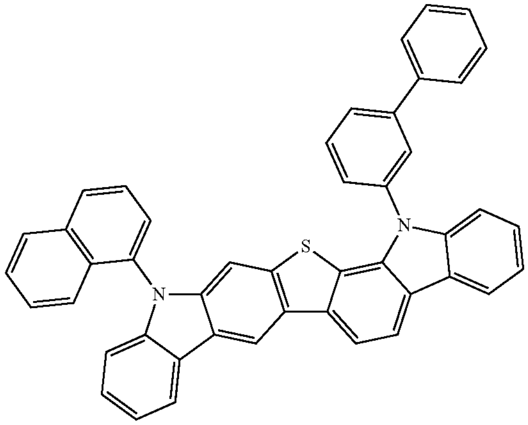
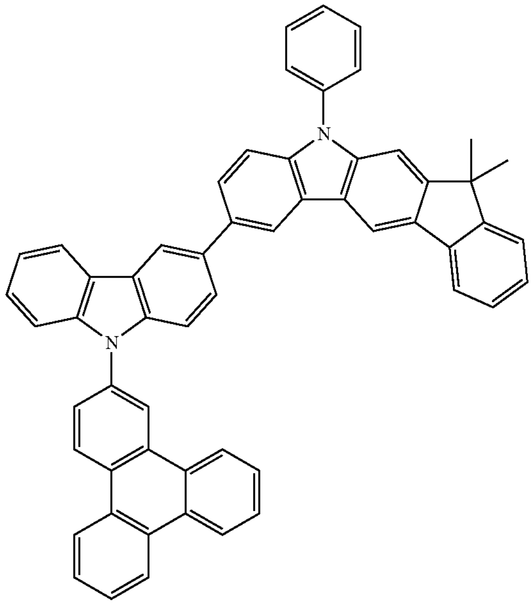
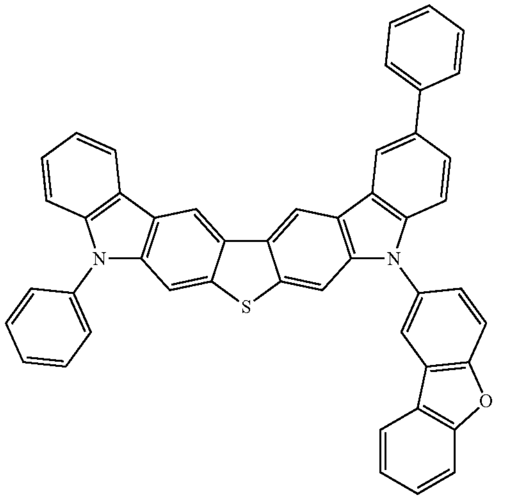
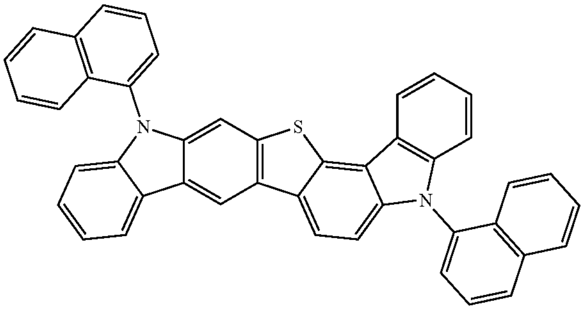
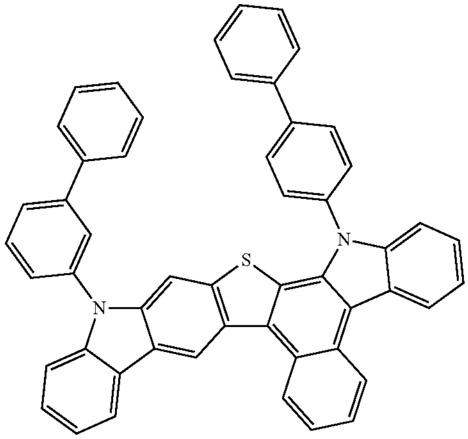
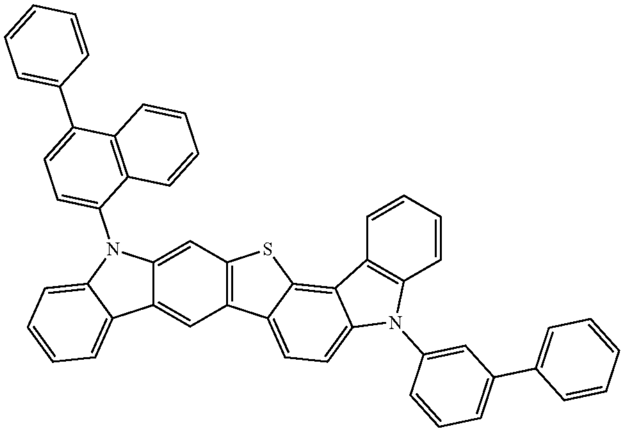

-continued
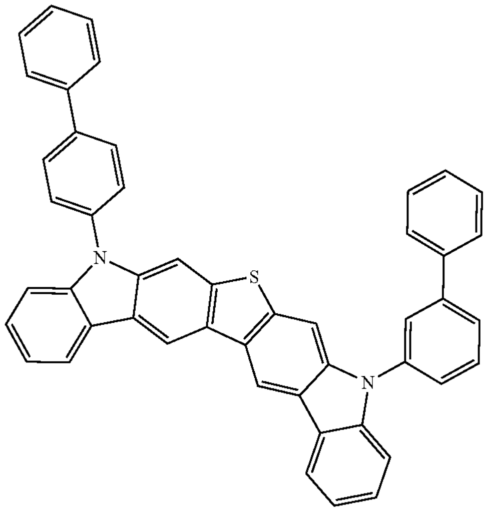
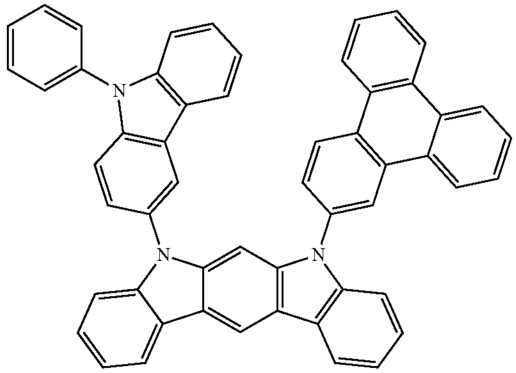
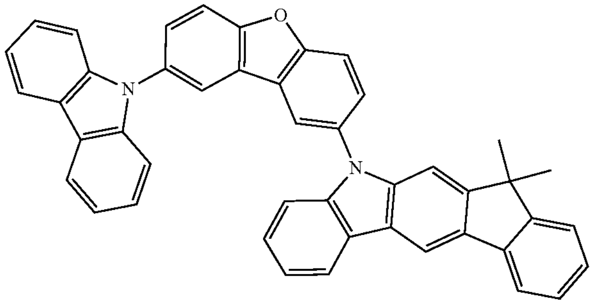
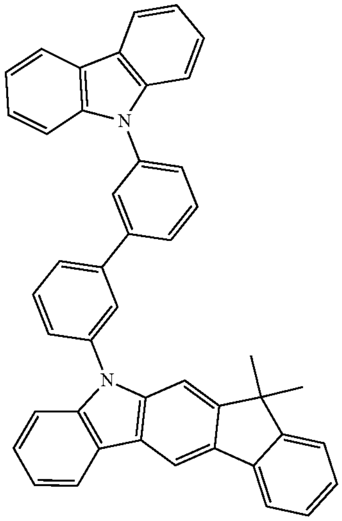
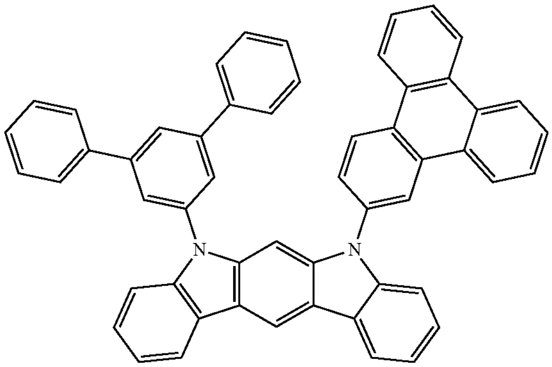

-continued
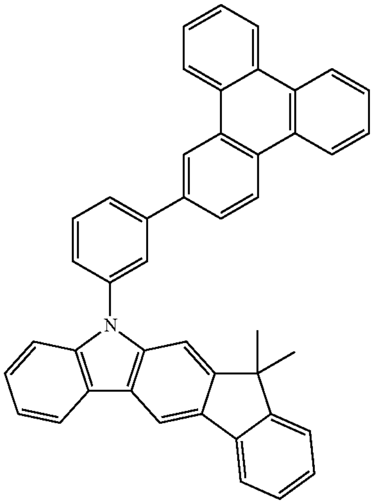
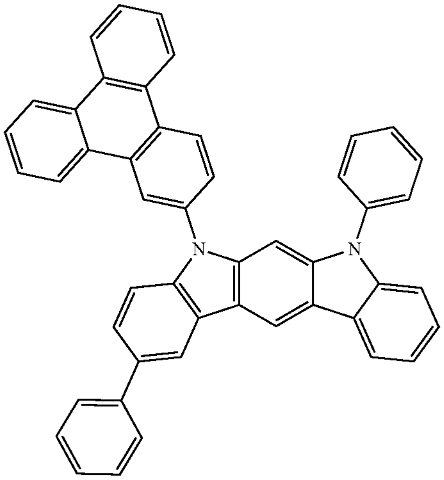
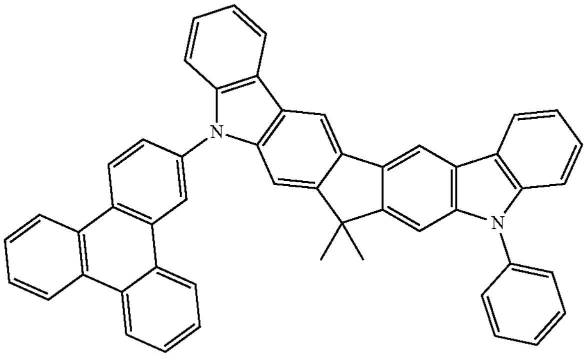
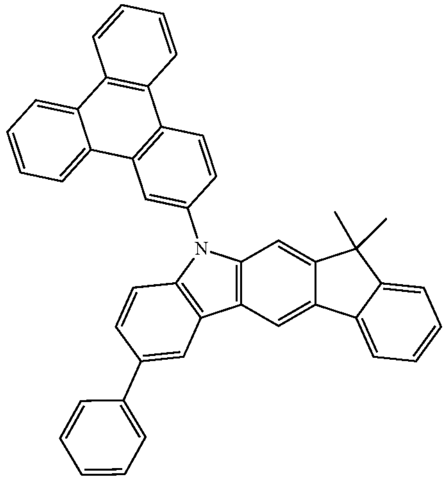
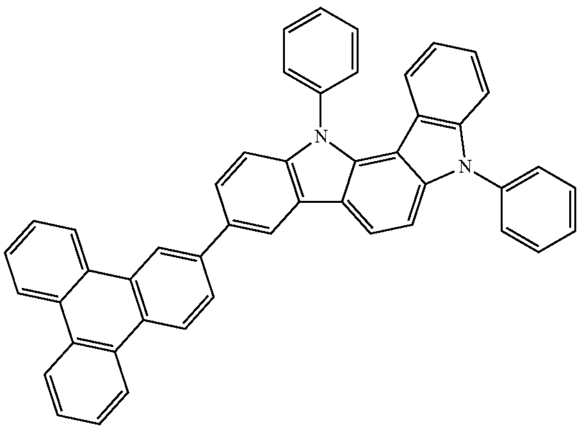
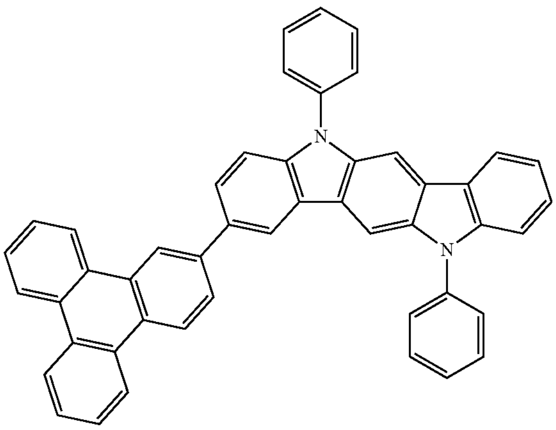

-continued
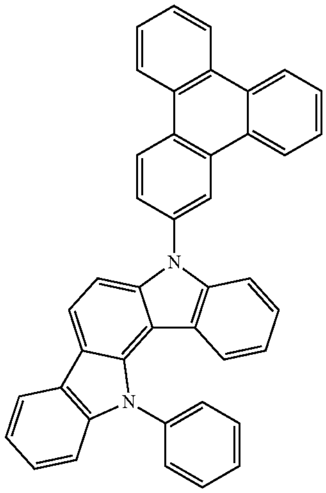
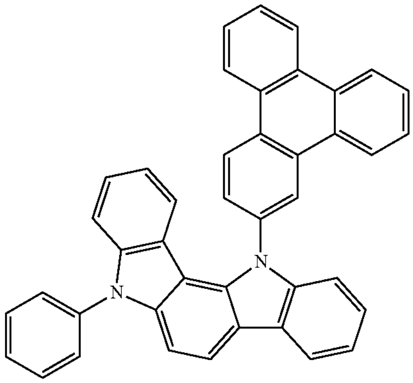
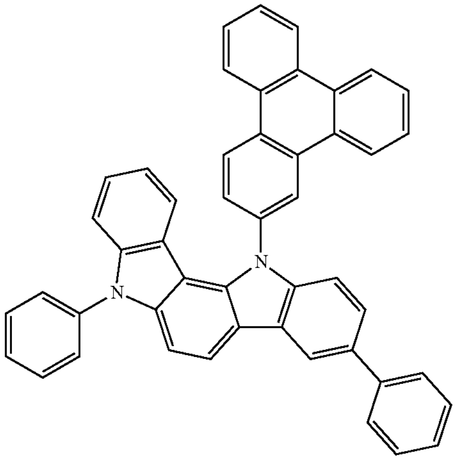
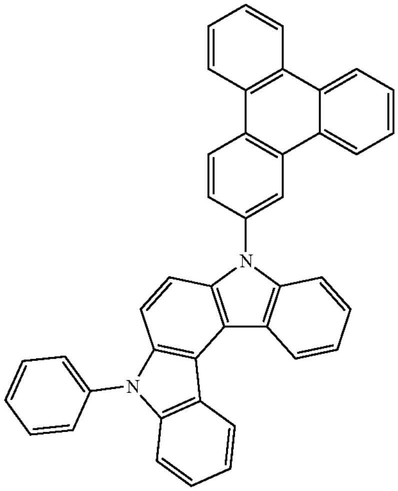
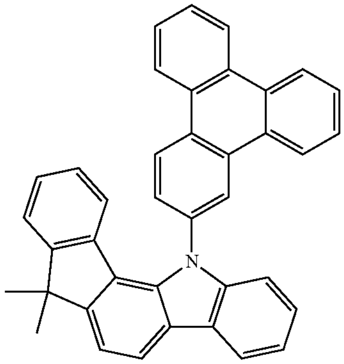
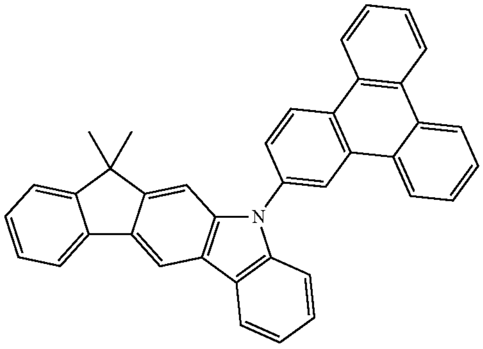
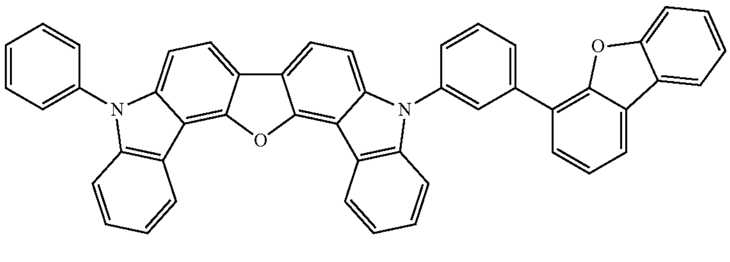
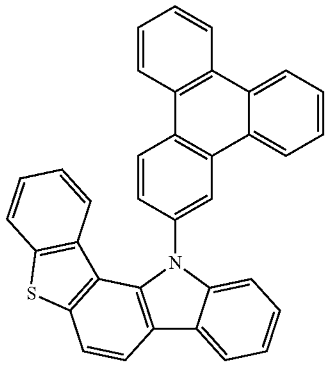

-continued
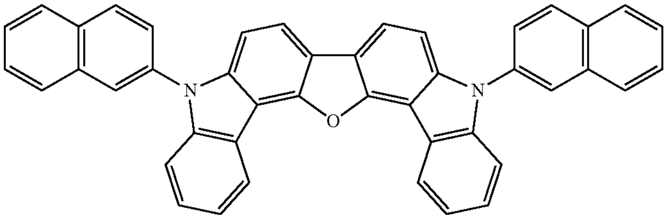
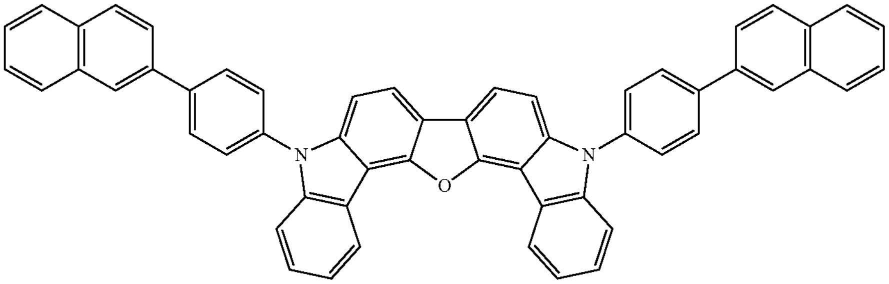
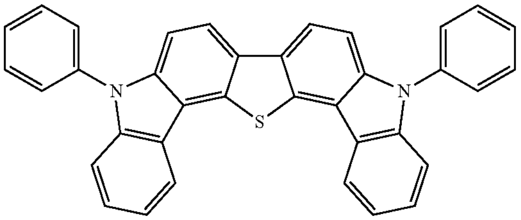
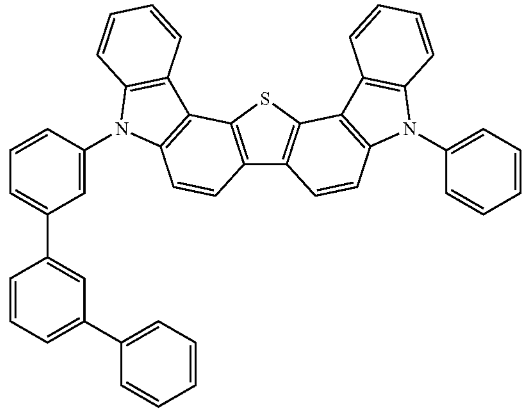
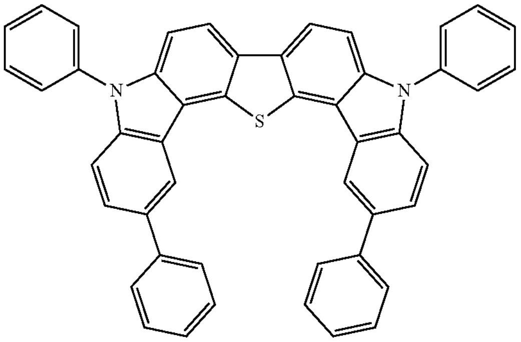
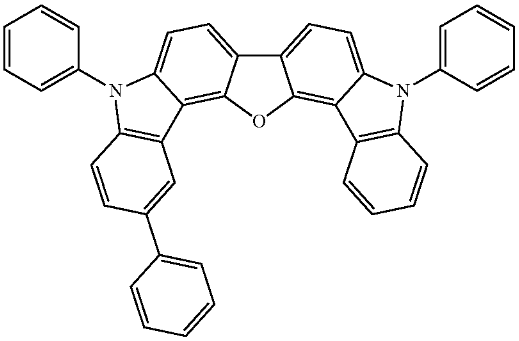
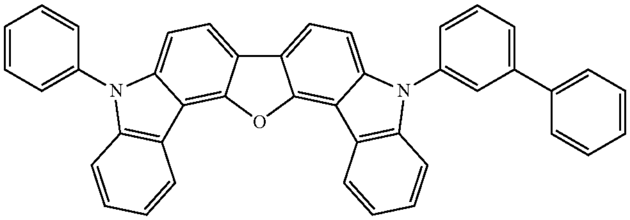

-continued
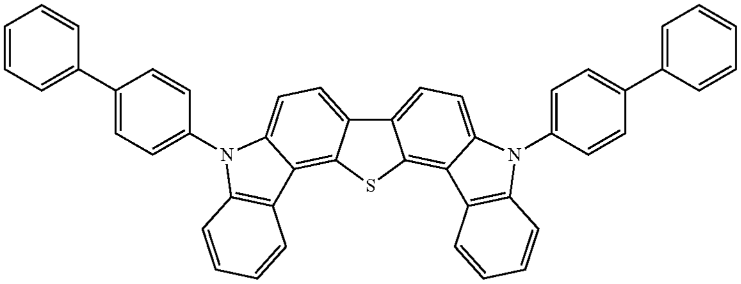
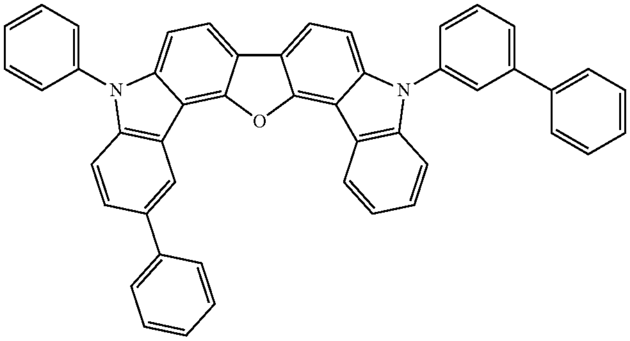
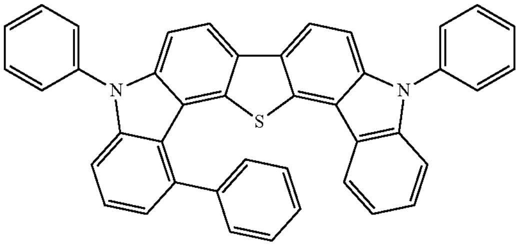
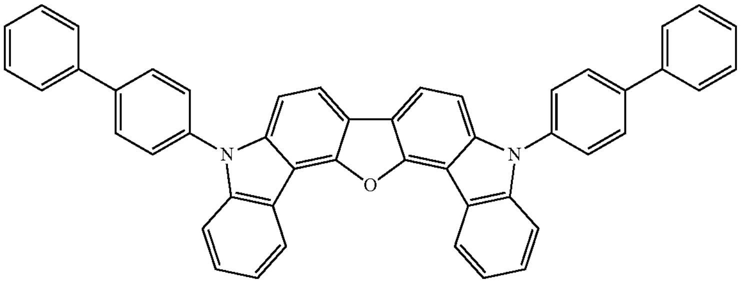
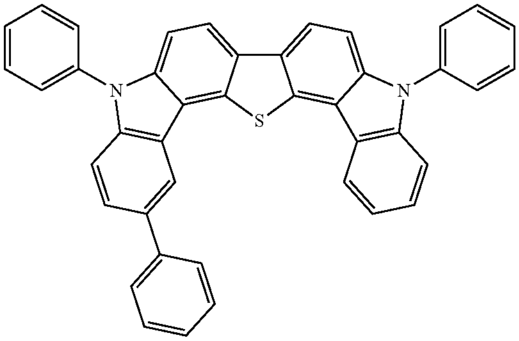
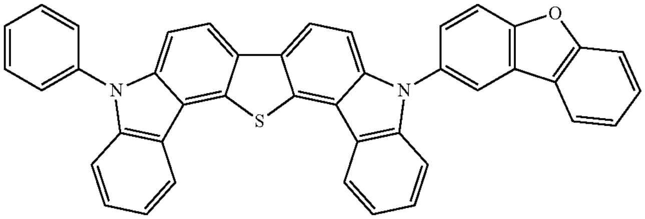

-continued
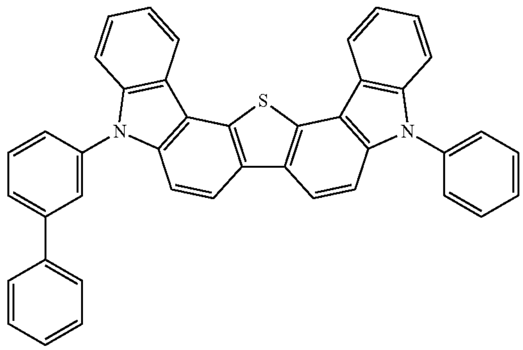
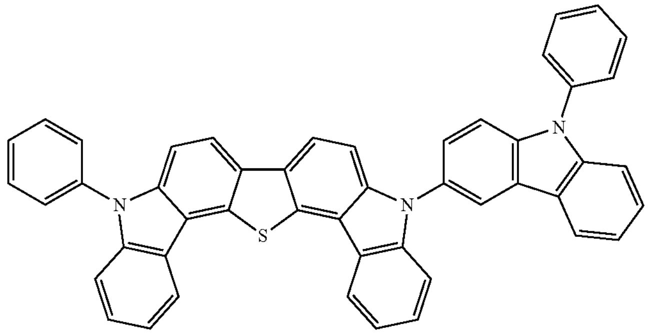
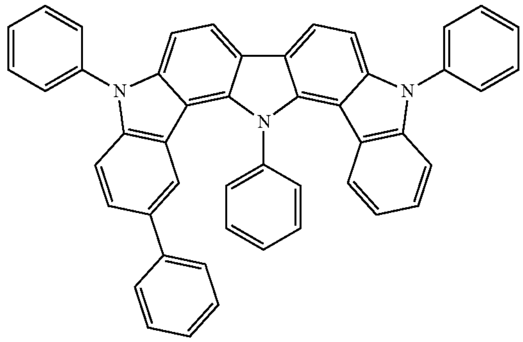
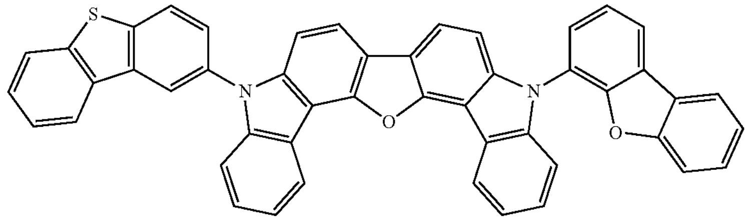
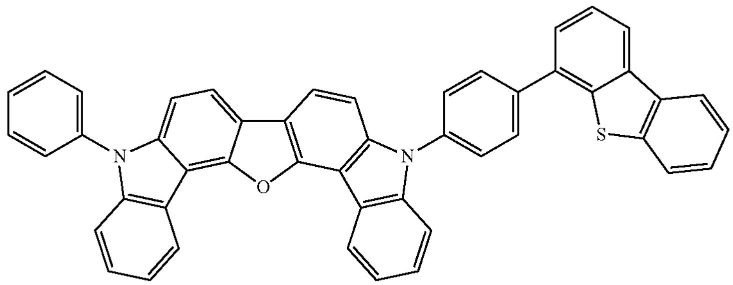

-continued
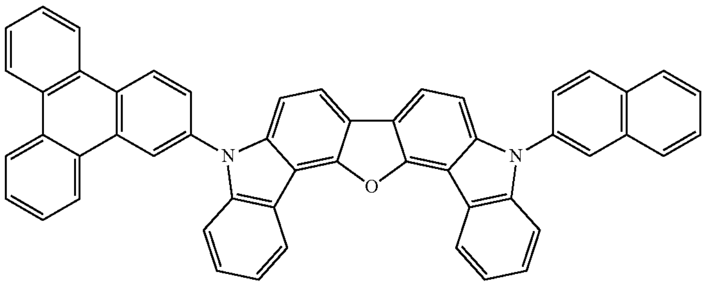
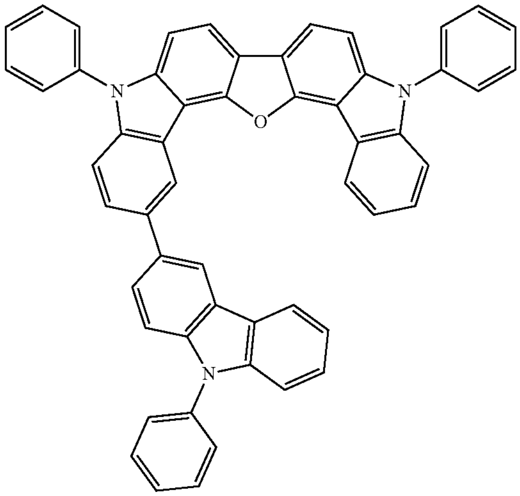
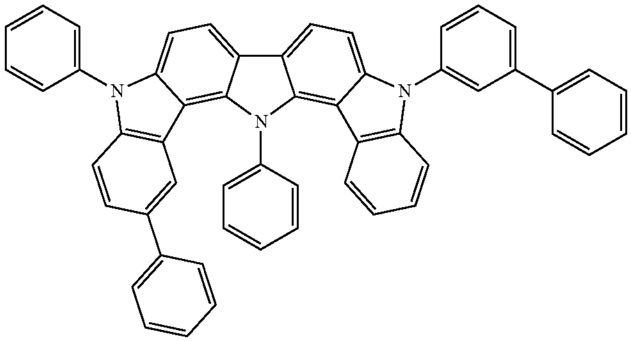
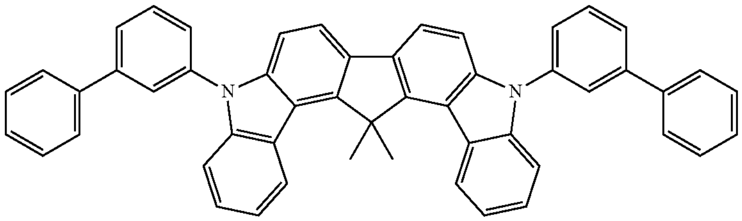

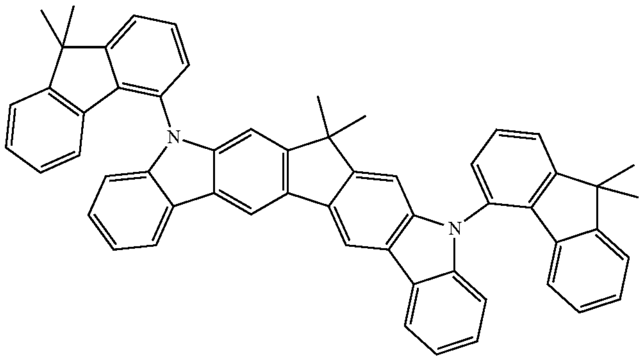
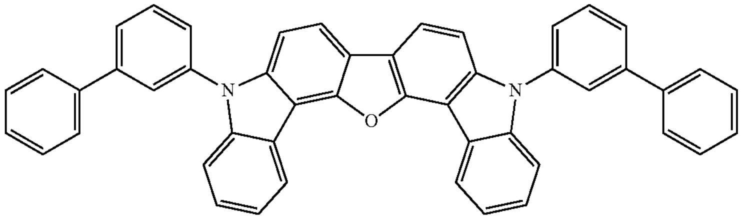
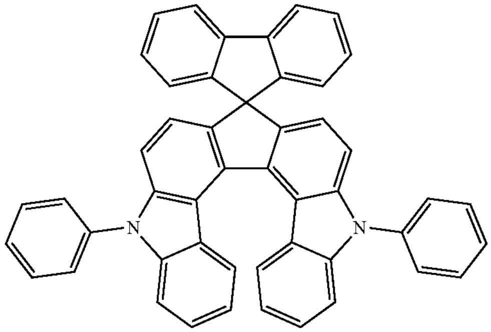
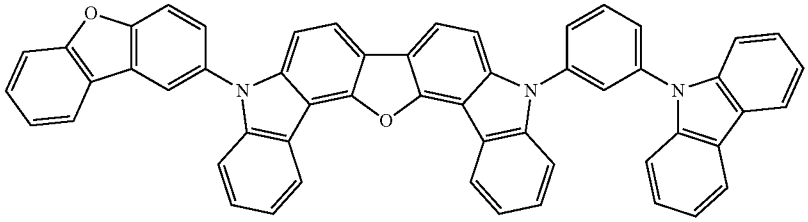
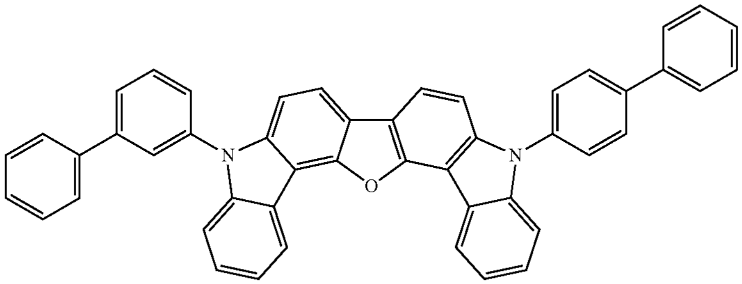
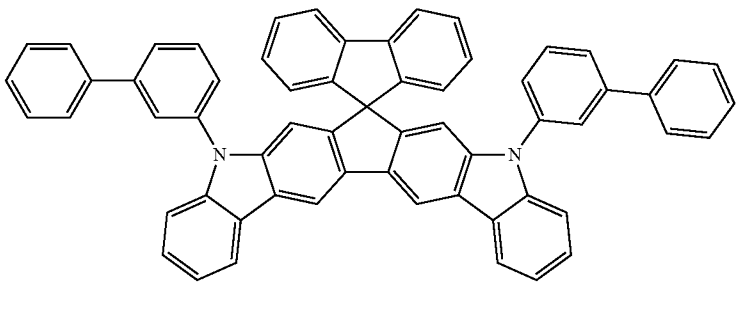

-continued
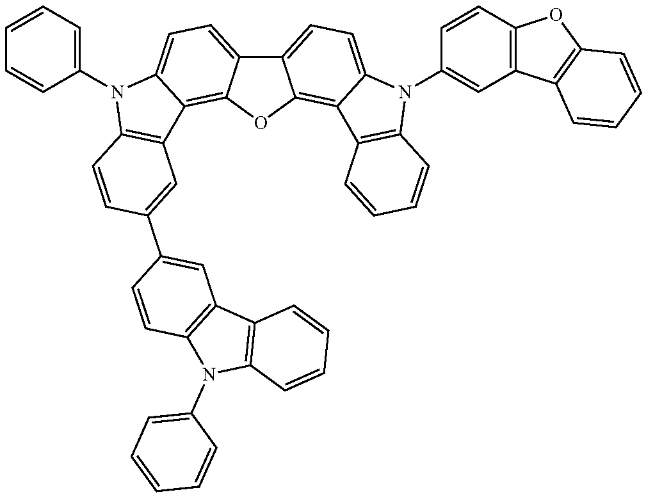
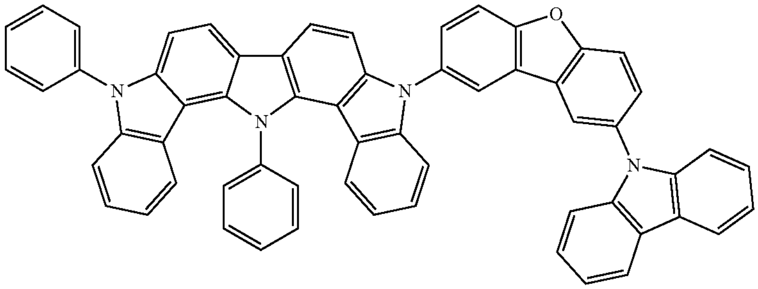
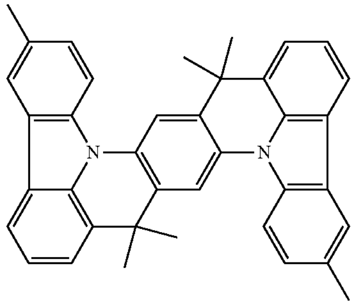
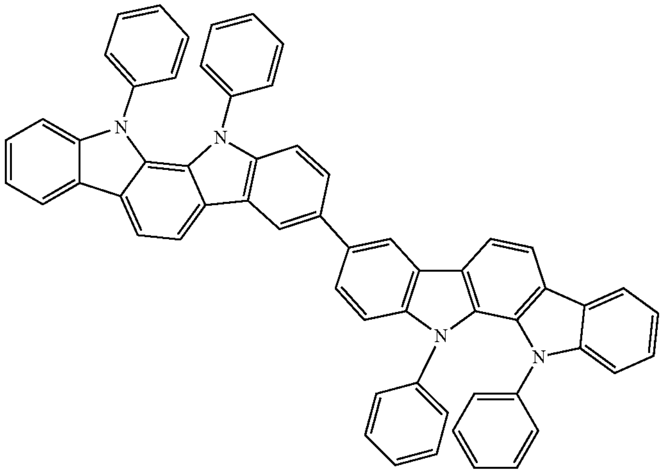
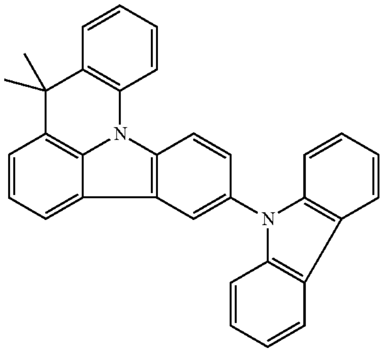

-continued
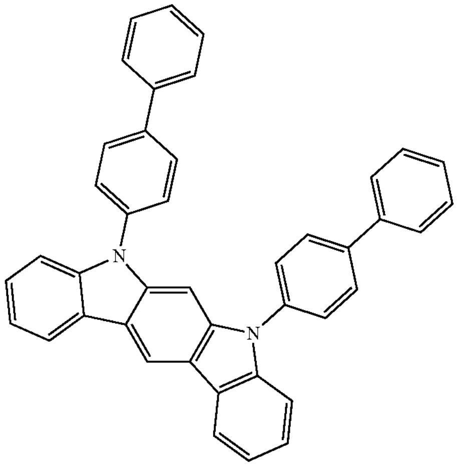
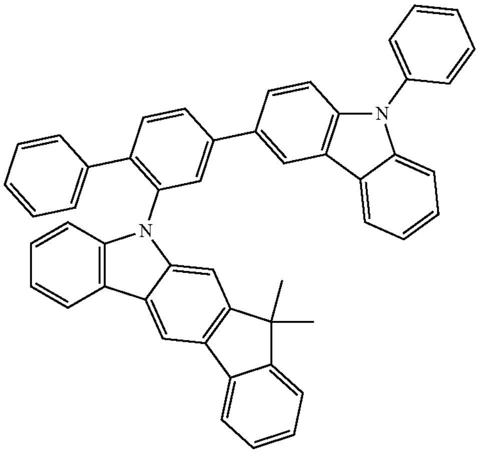
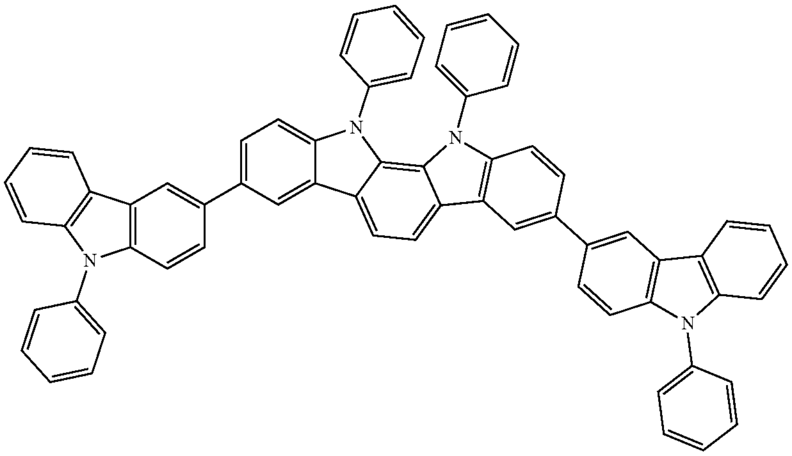
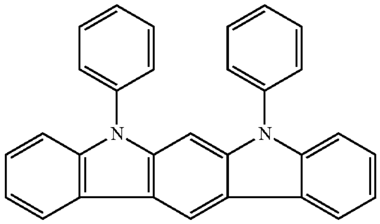
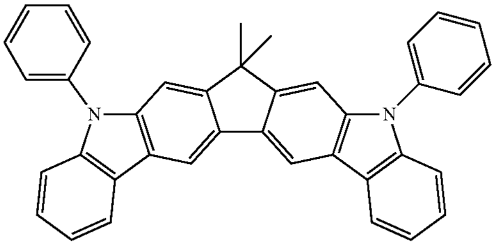
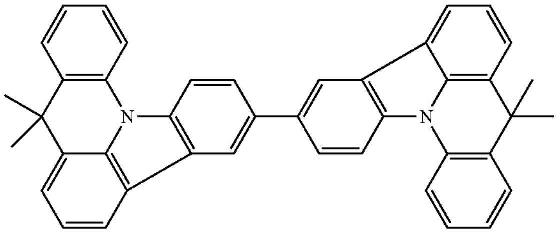
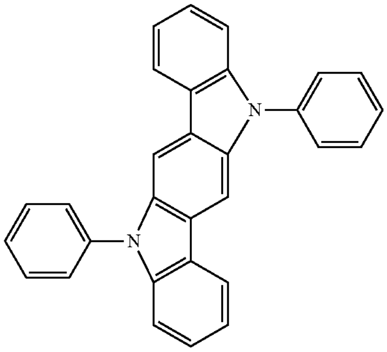

-continued
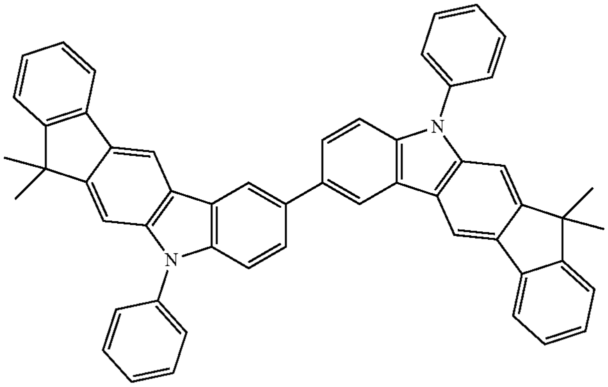
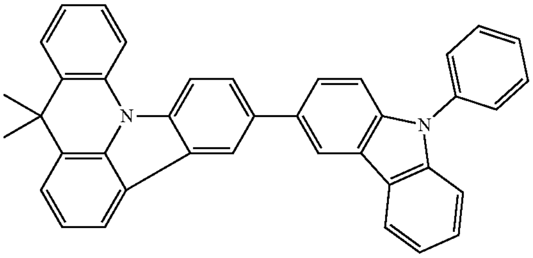
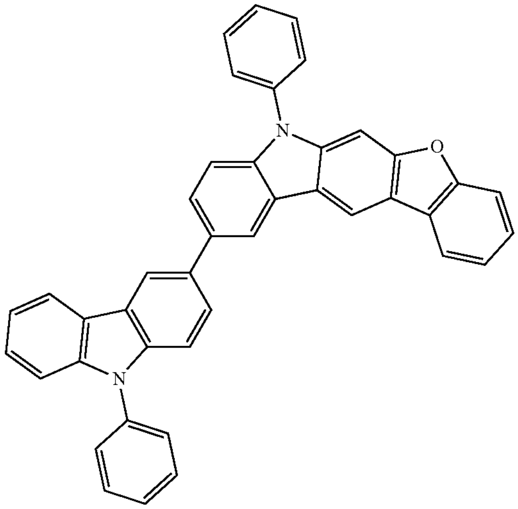
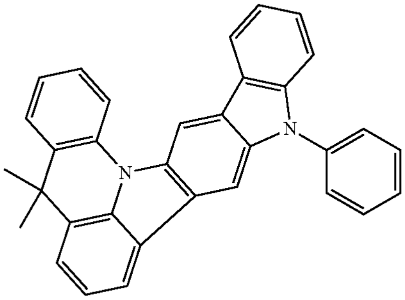
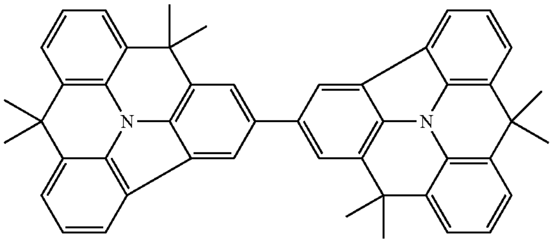
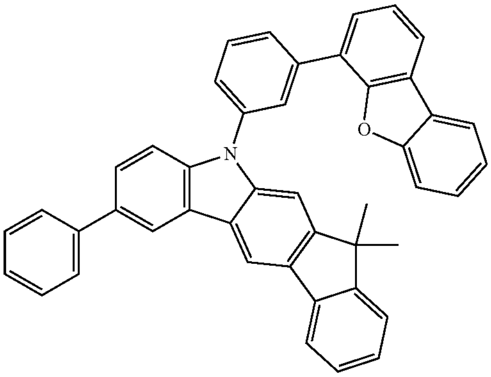
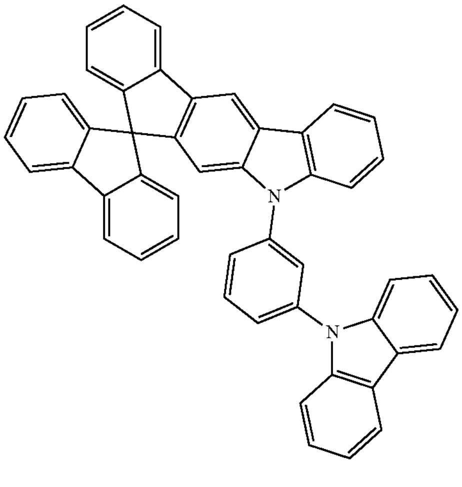
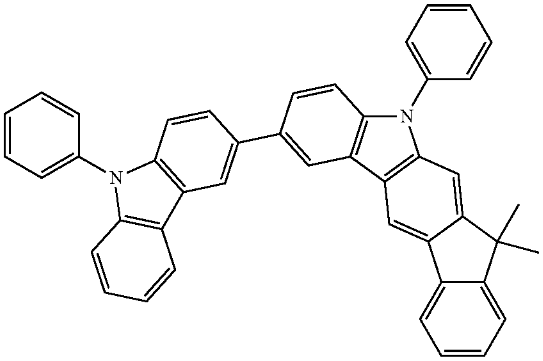

-continued
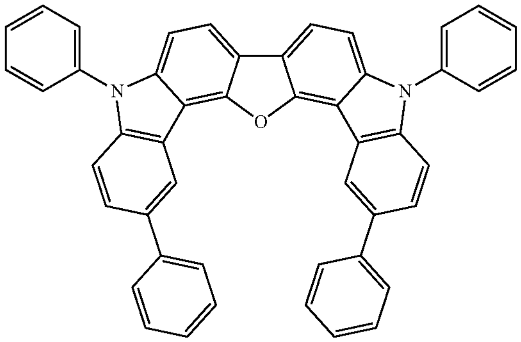
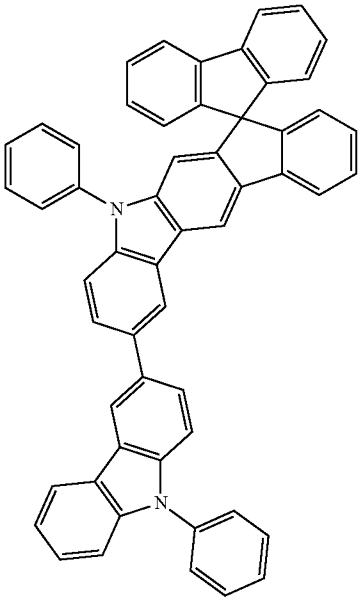
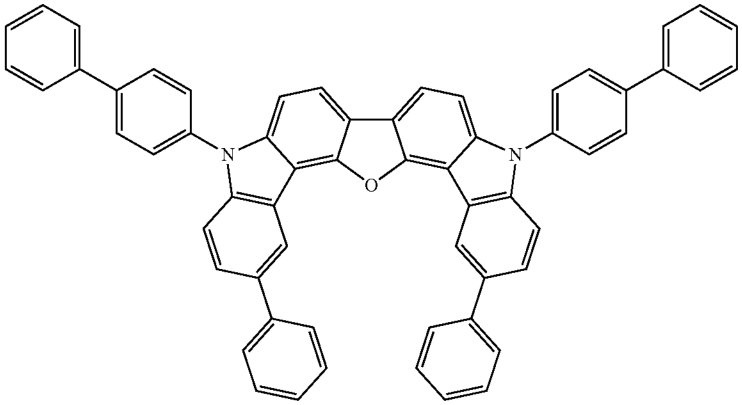
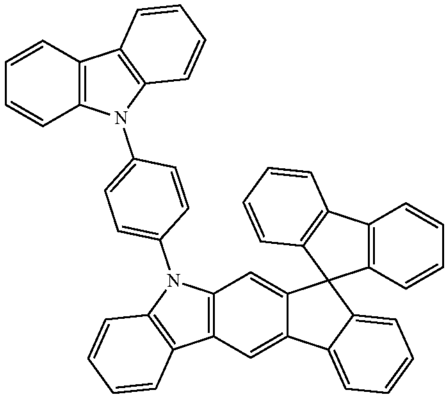
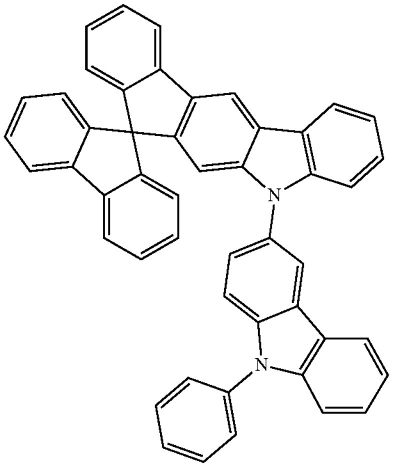

-continued
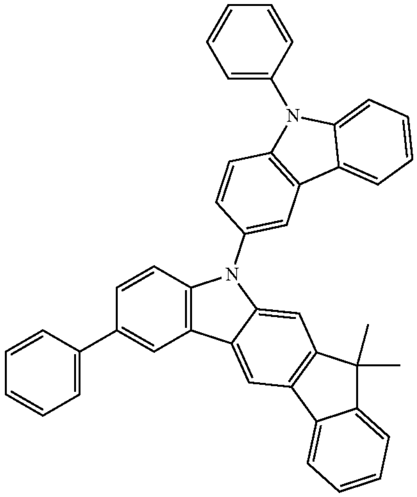
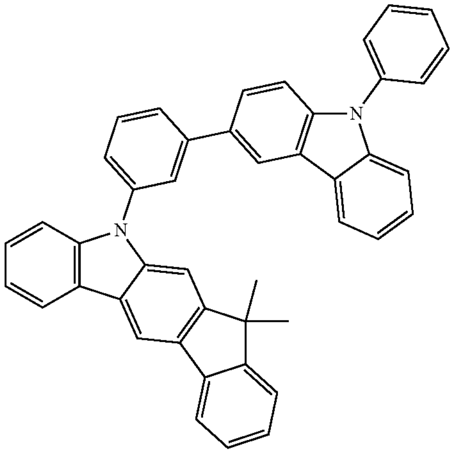
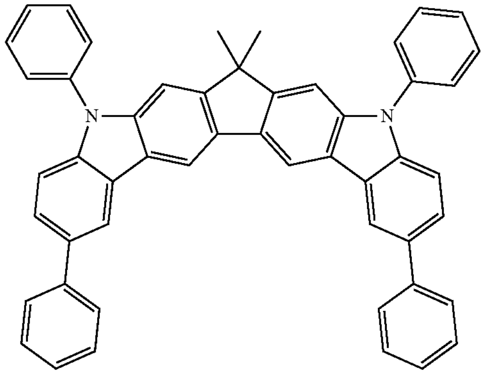
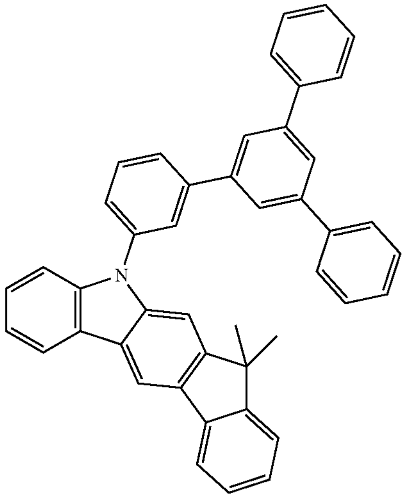
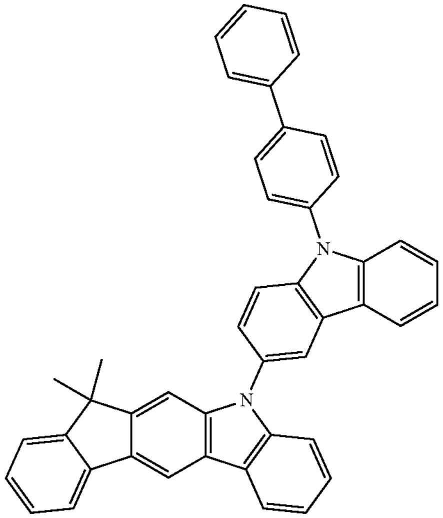
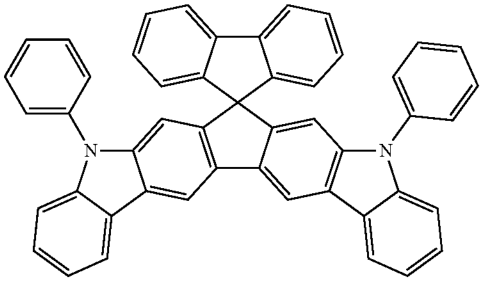

-continued
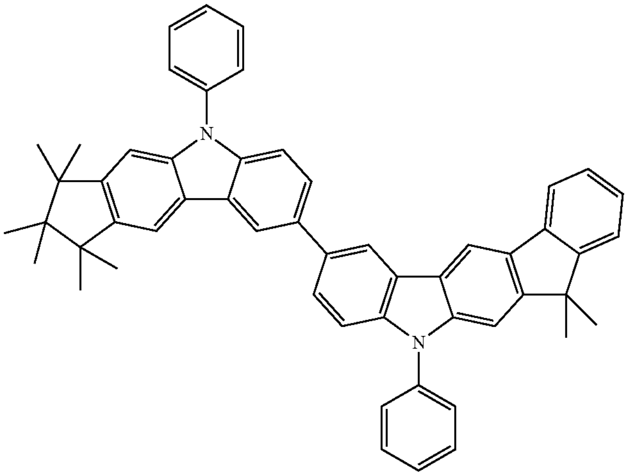
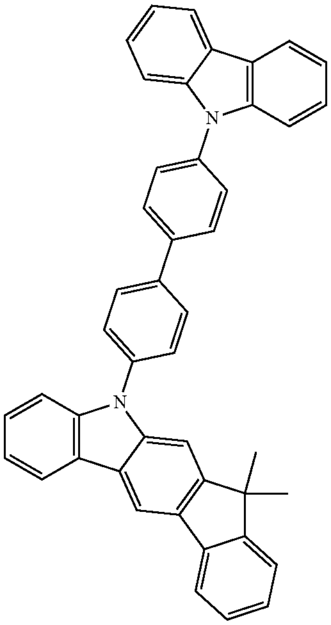
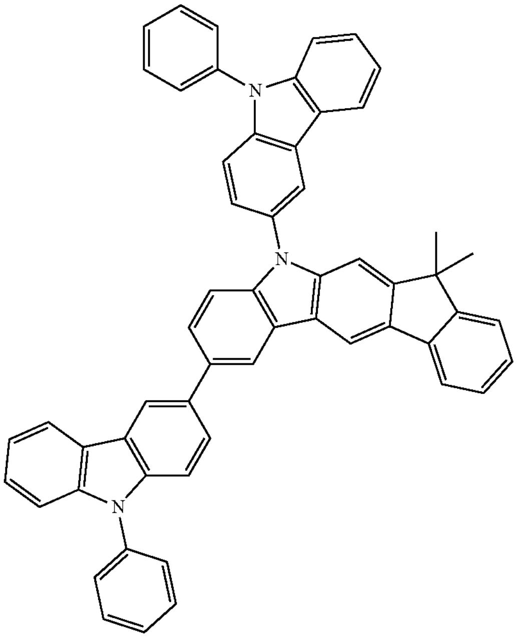
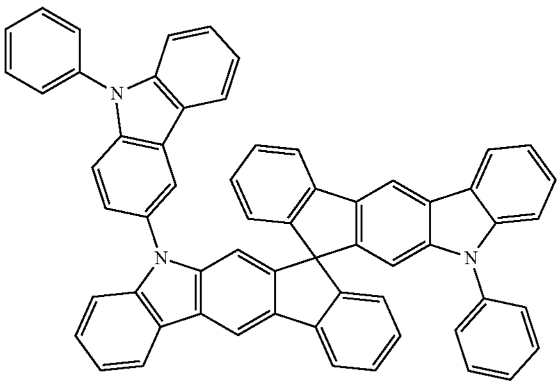

-continued
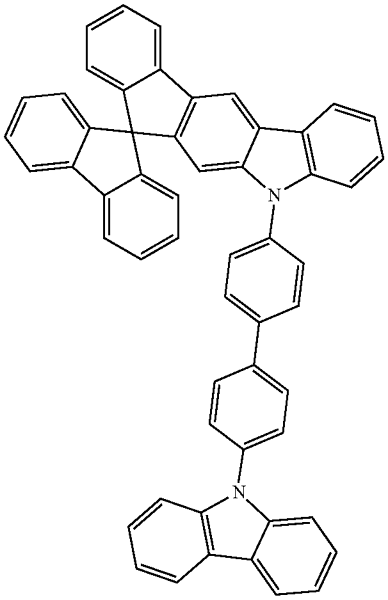
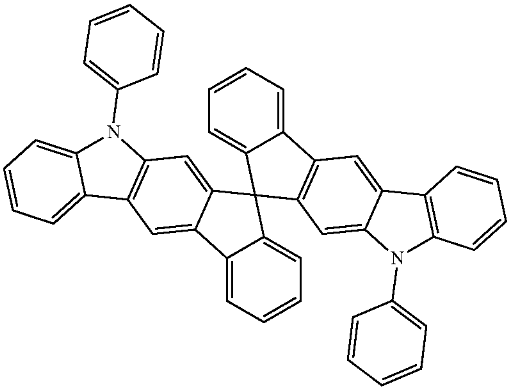
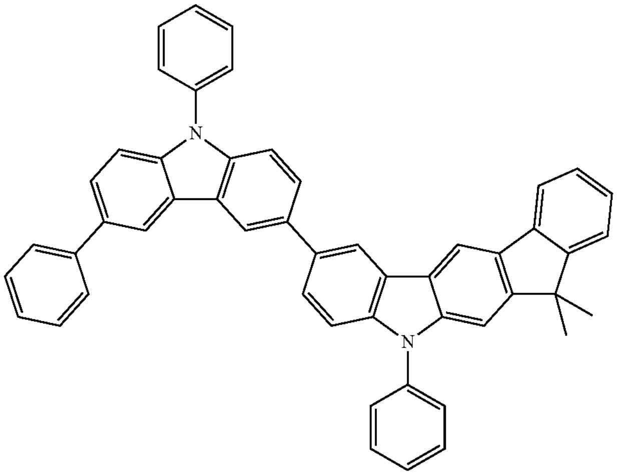
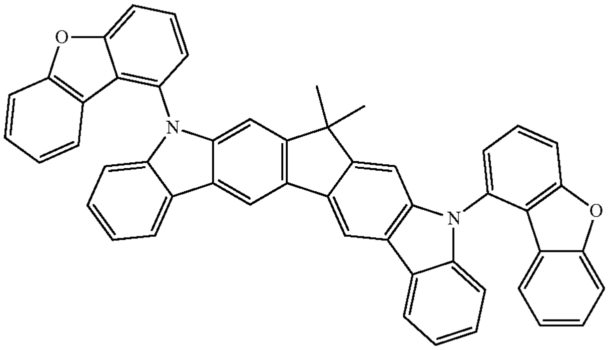
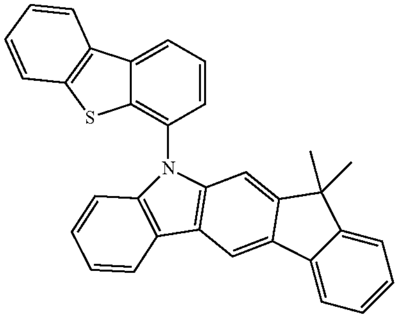

-continued
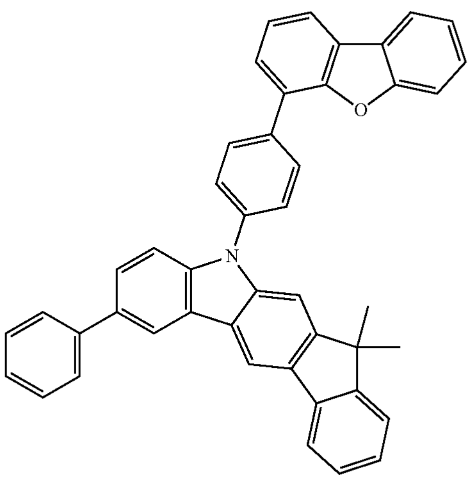
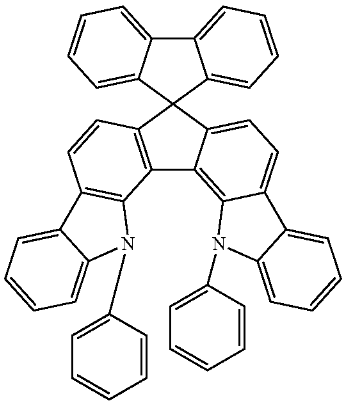
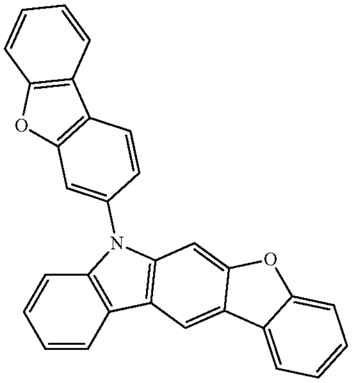
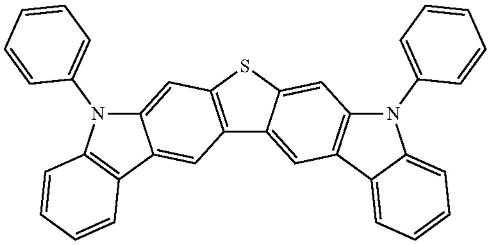
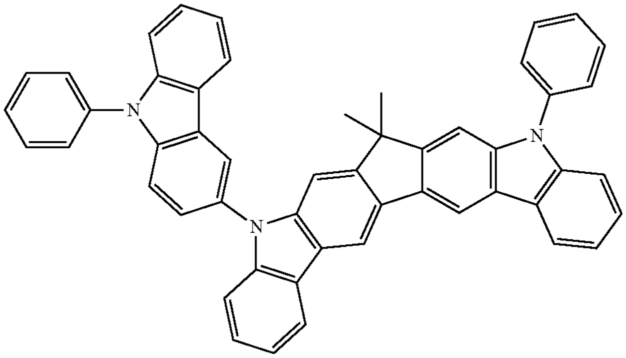
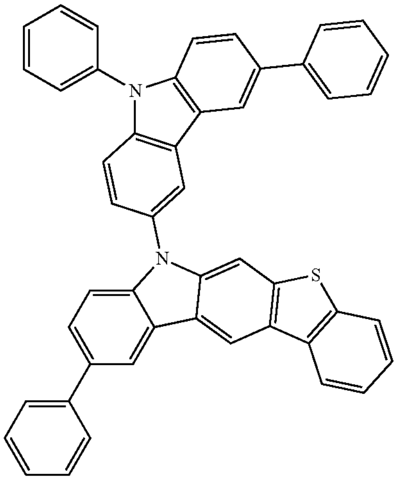
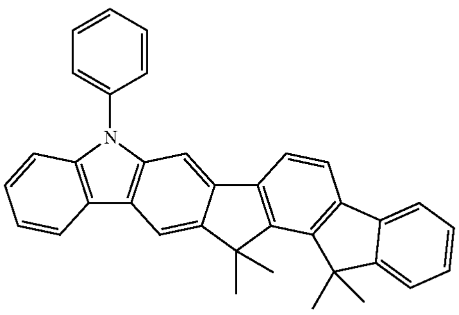
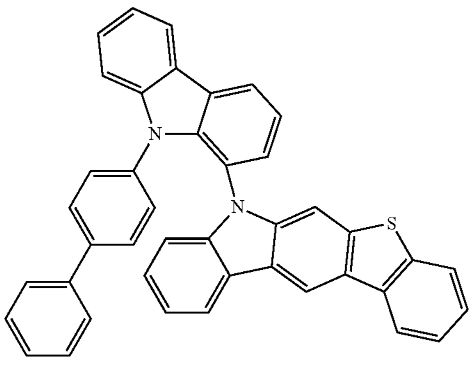

-continued
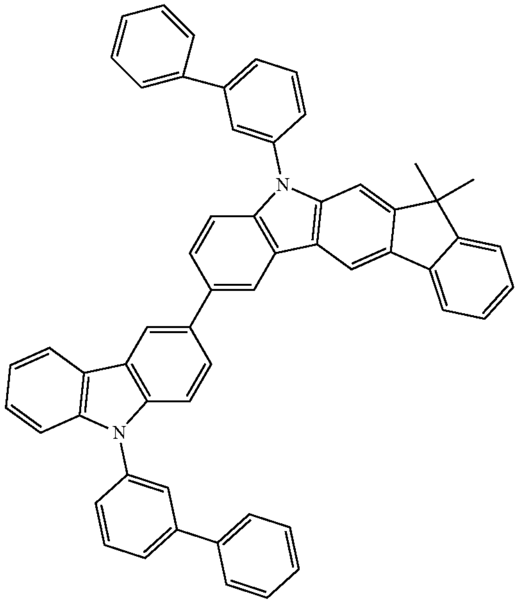
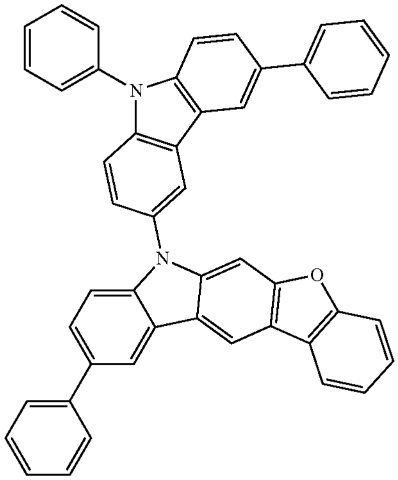
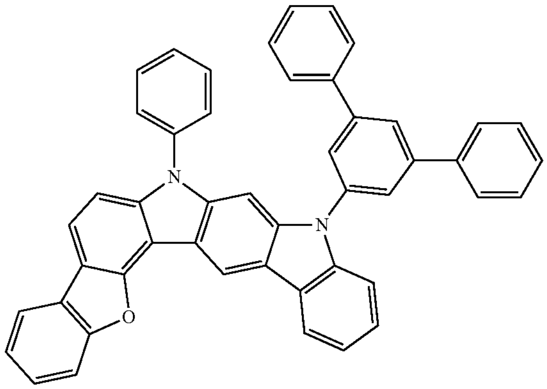
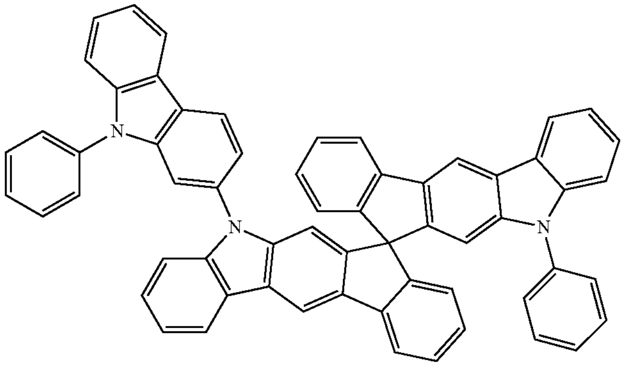

-continued
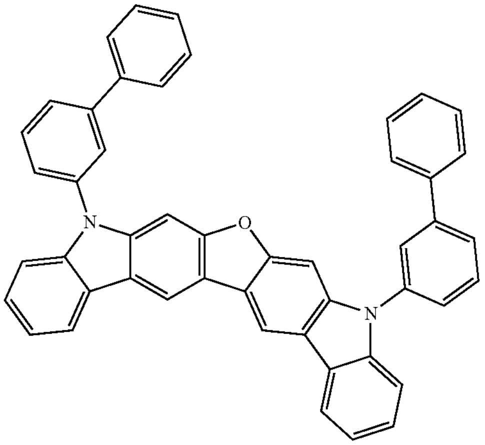
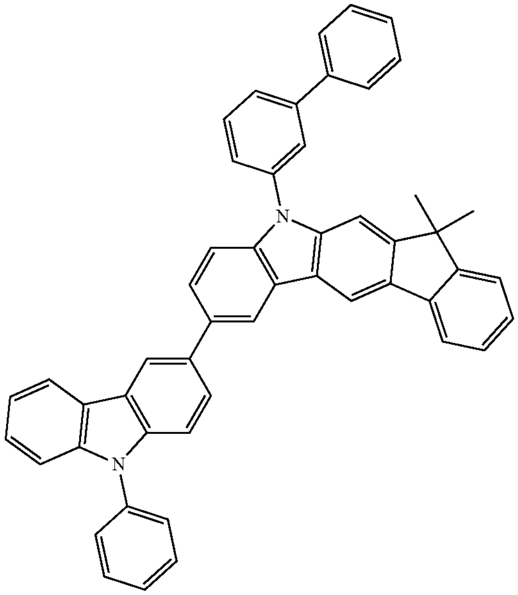
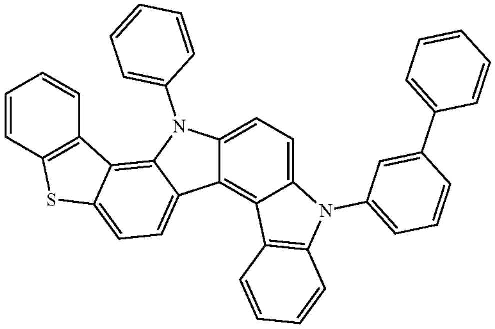
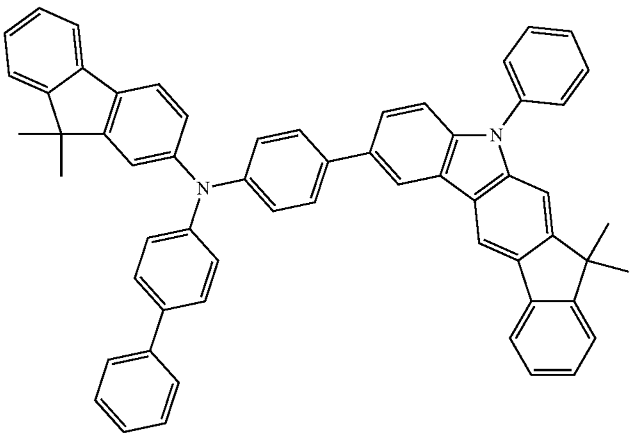
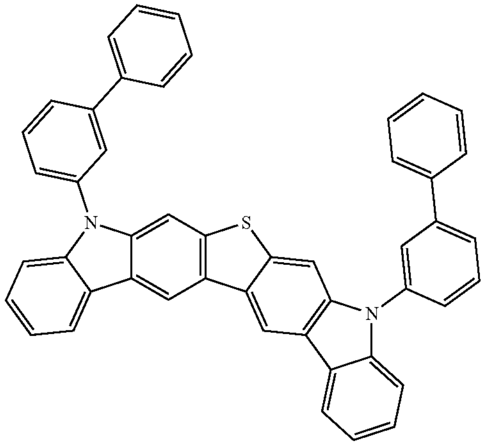
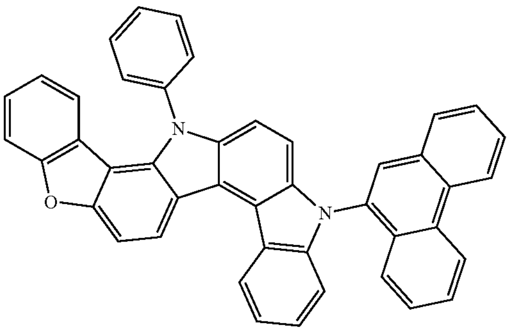

-continued
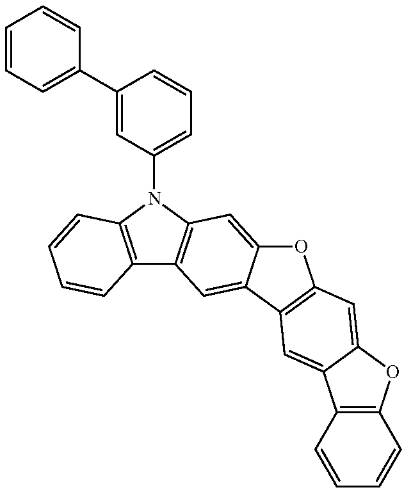
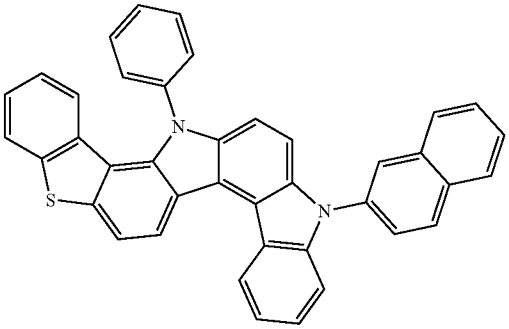
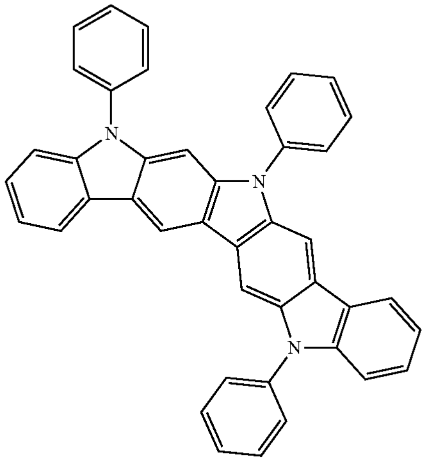
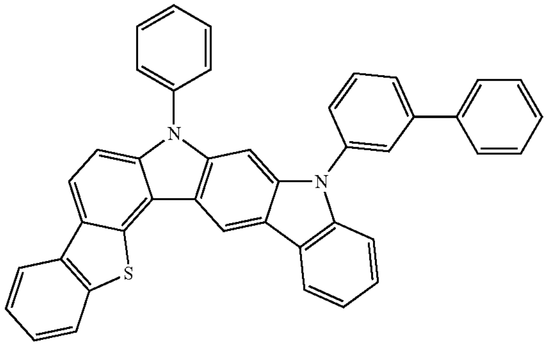
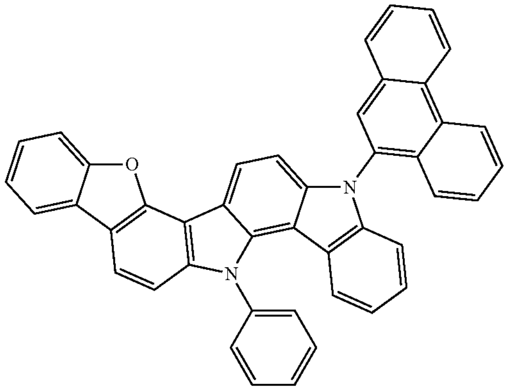
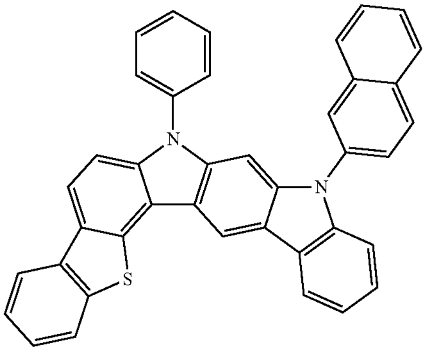

-continued
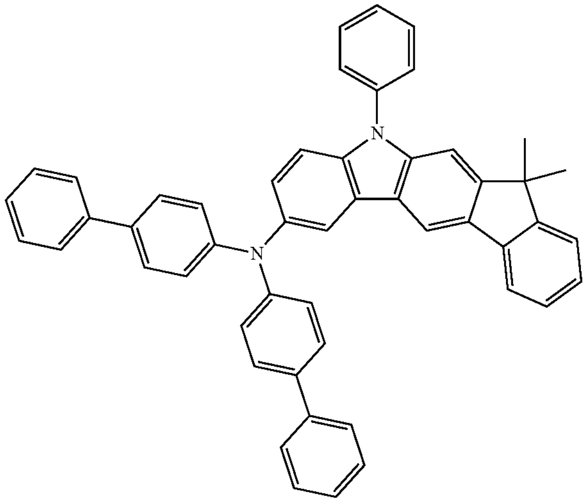
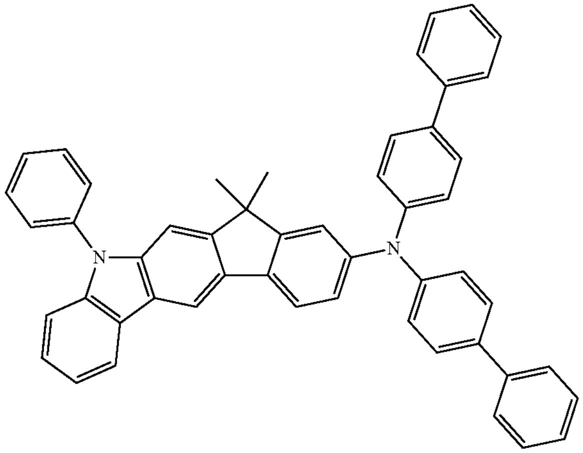
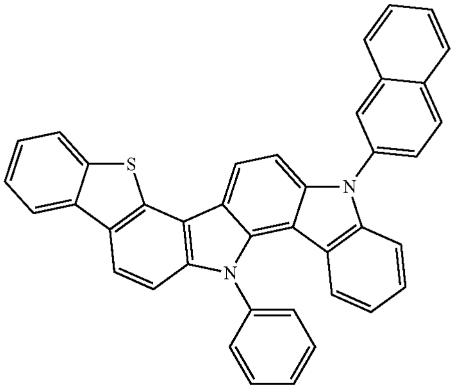
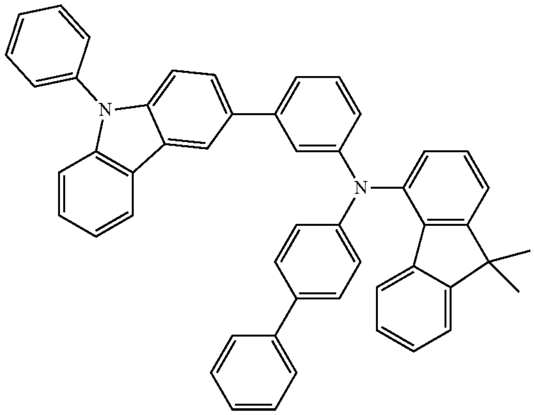
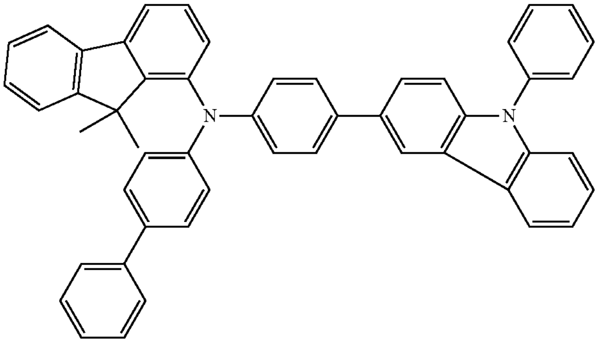

-continued
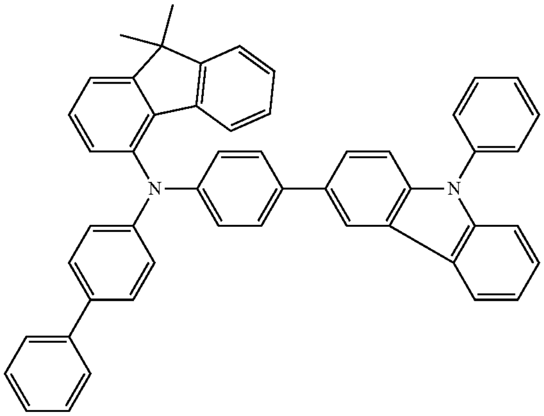
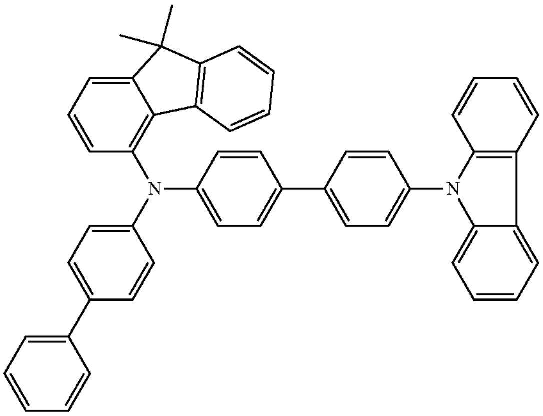
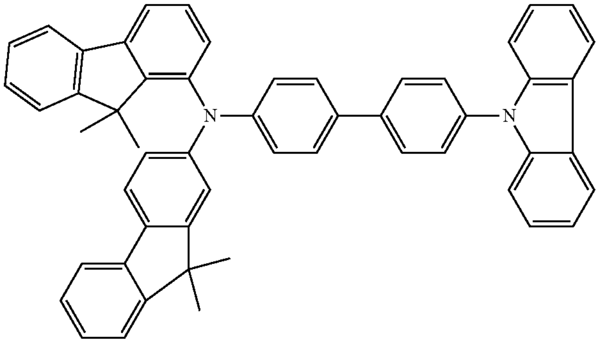
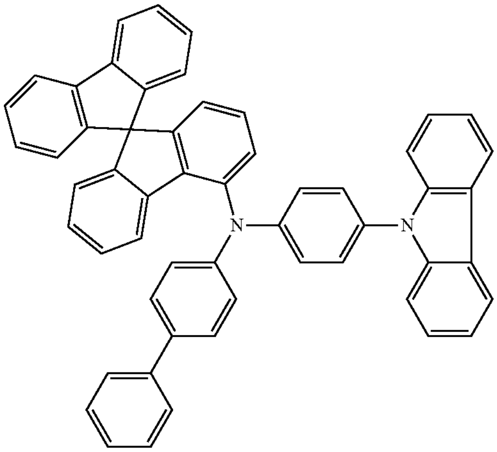
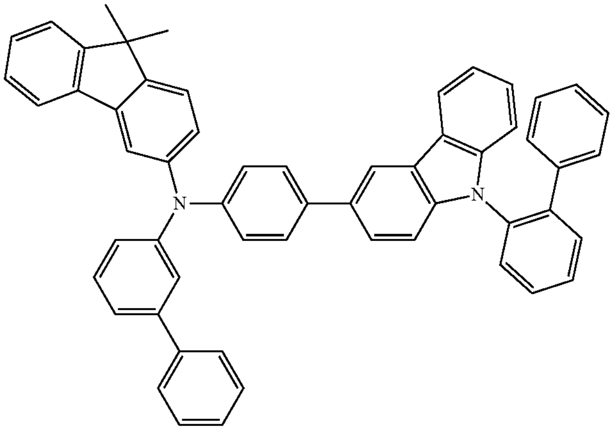

-continued
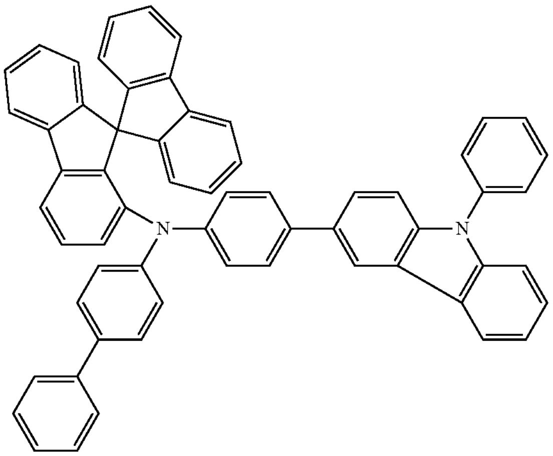
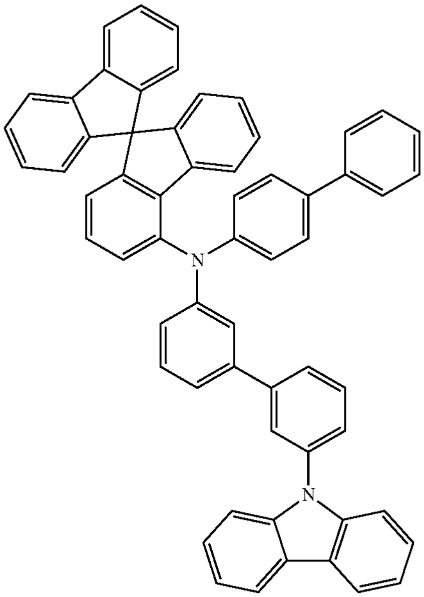
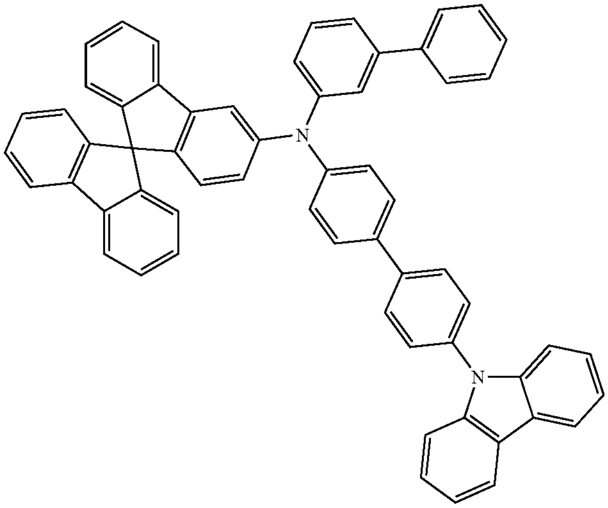
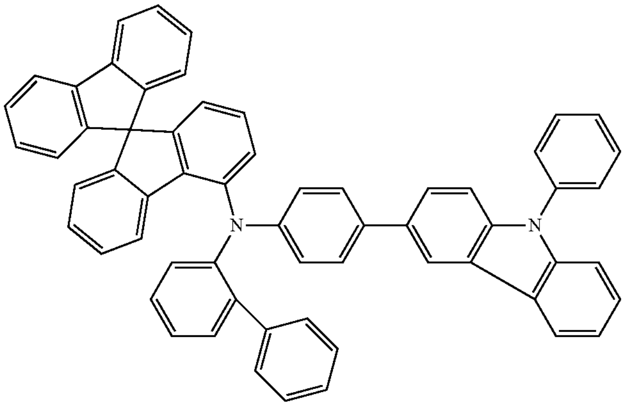

-continued
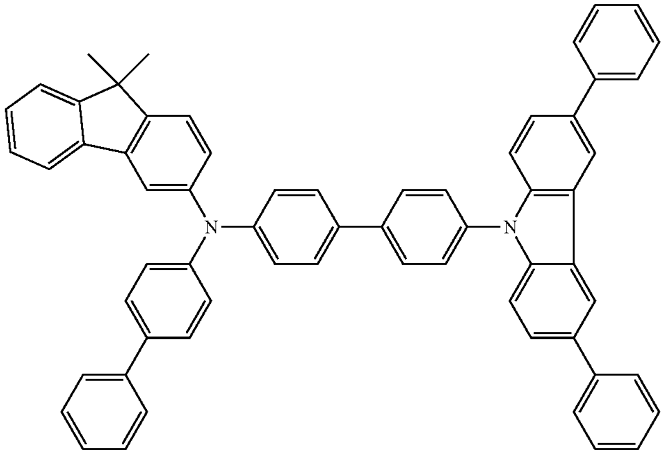
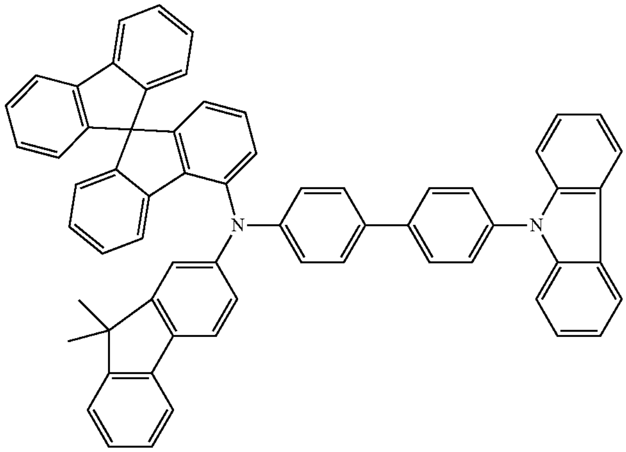
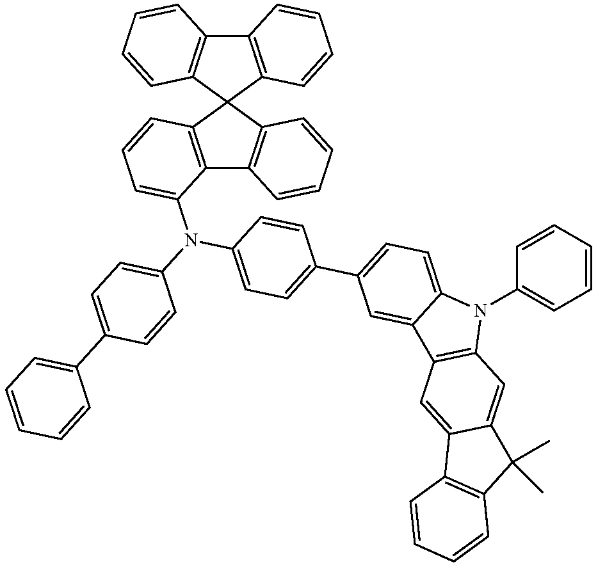
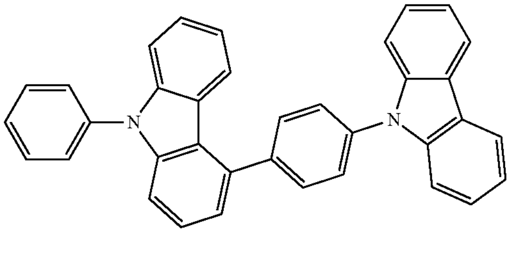

-continued
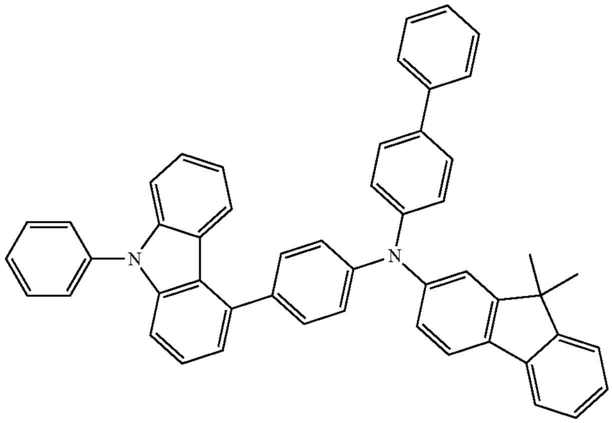
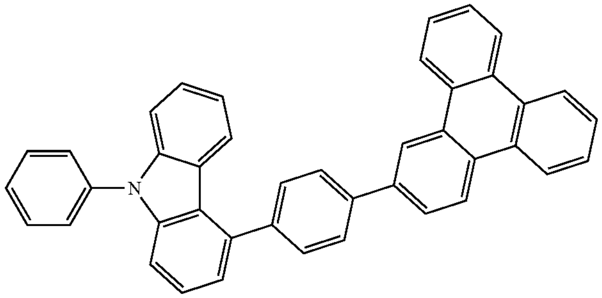
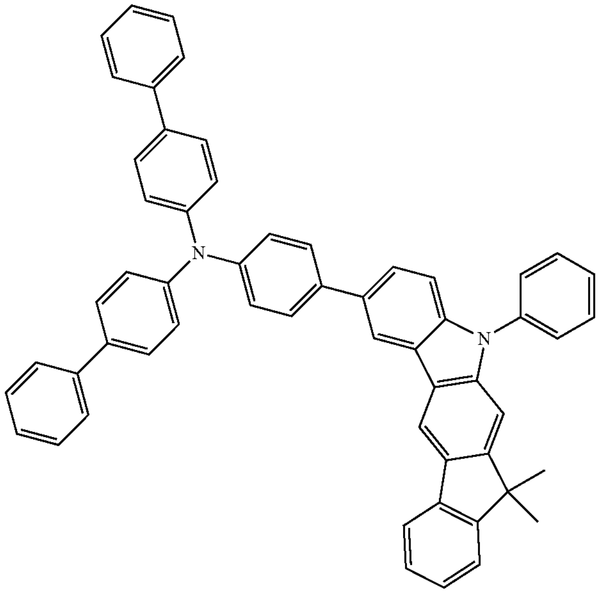

-continued
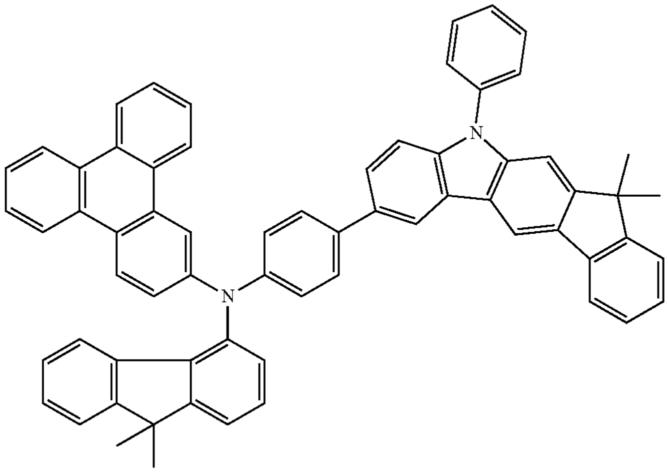
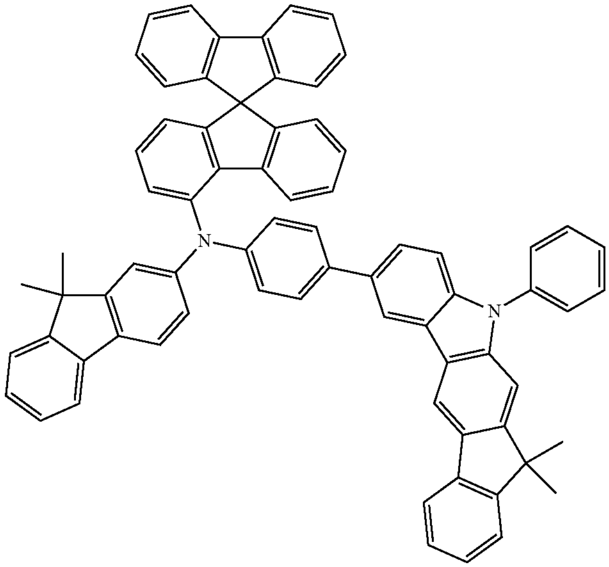
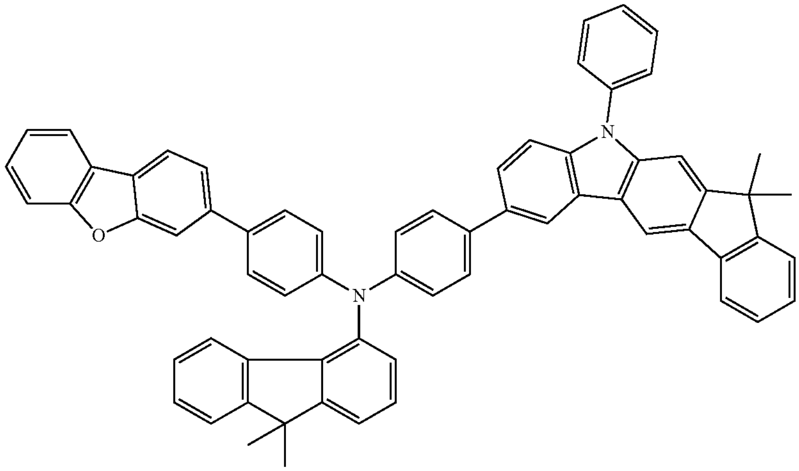

-continued
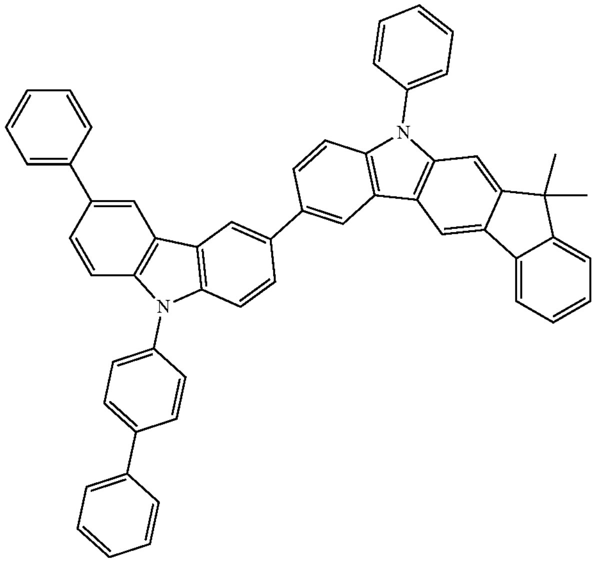
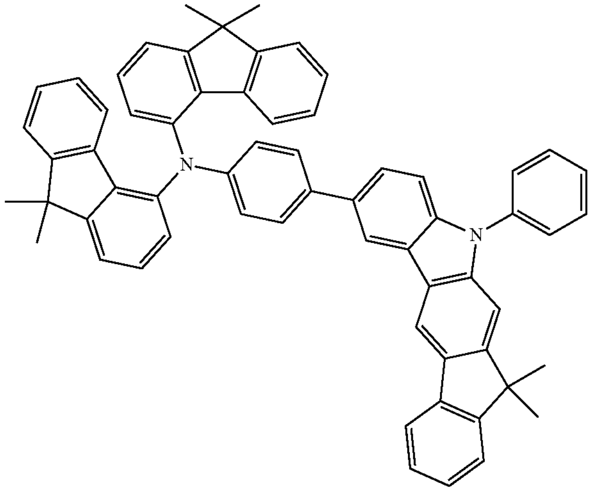
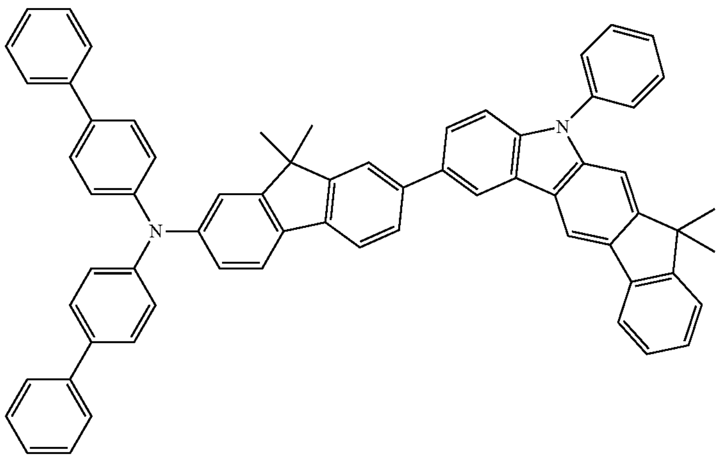

-continued
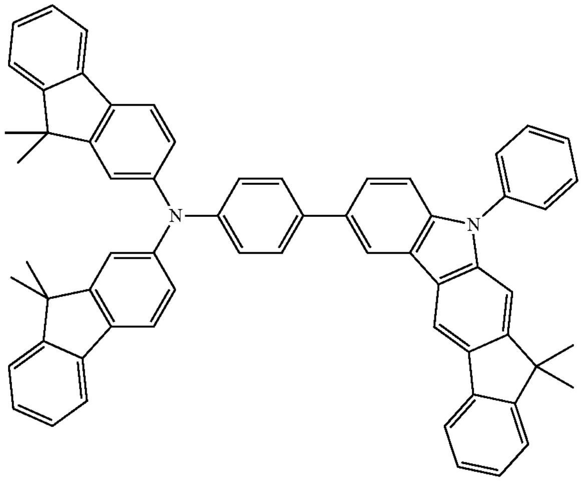
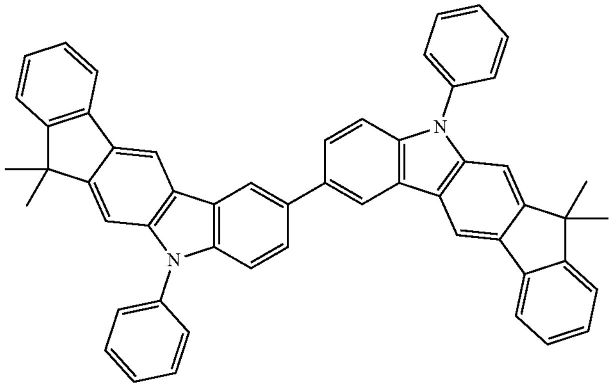
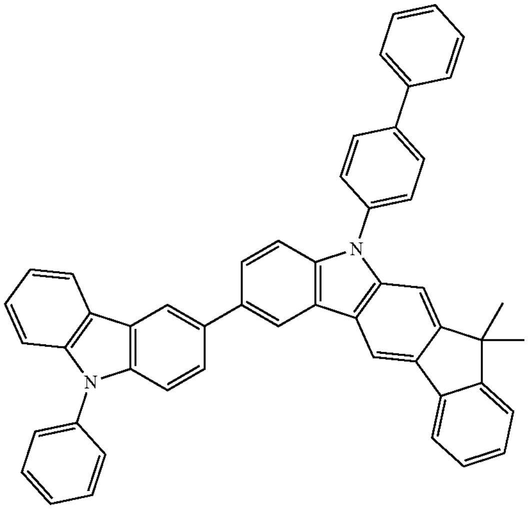
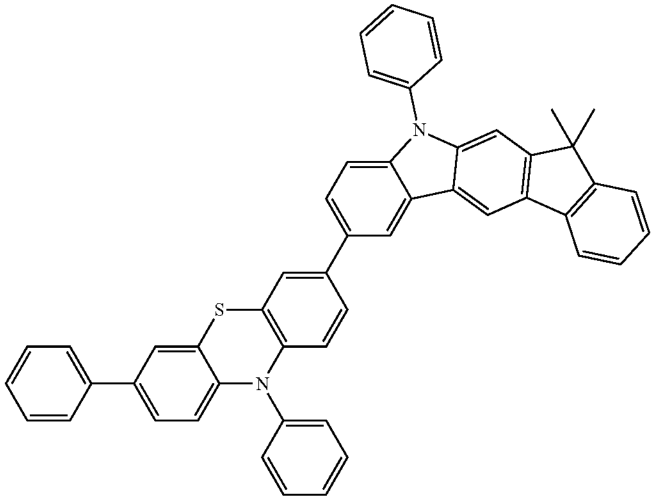

-continued
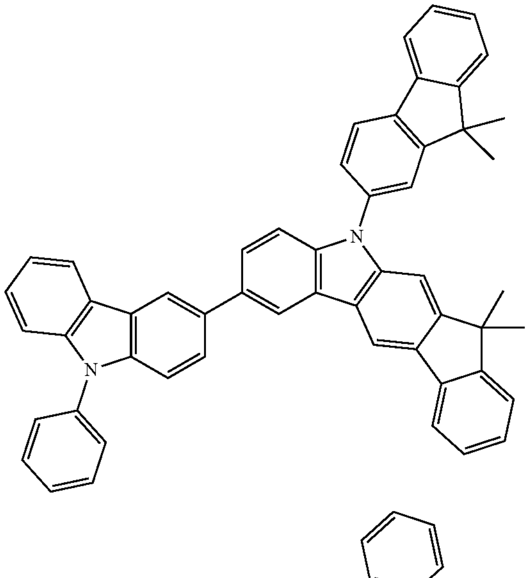
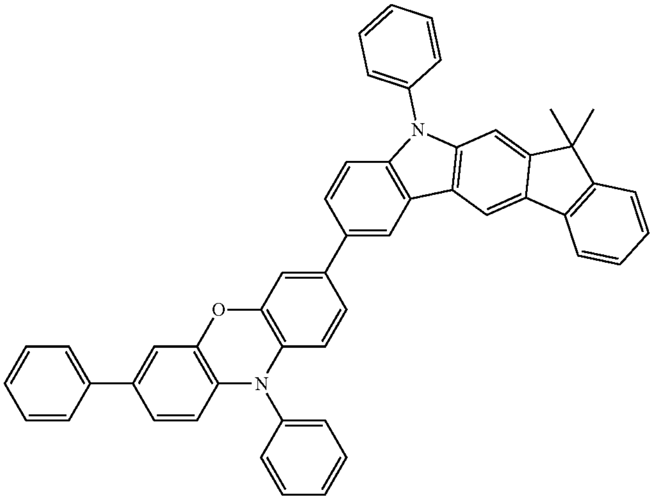
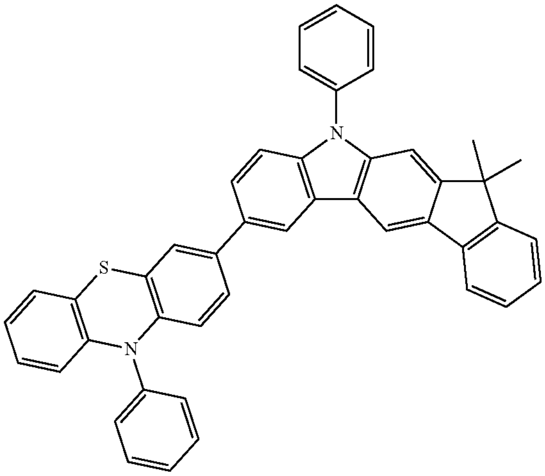
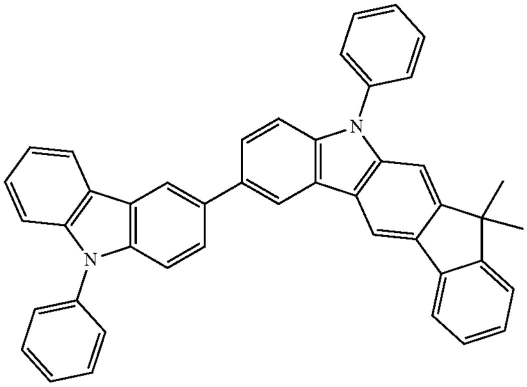

-continued
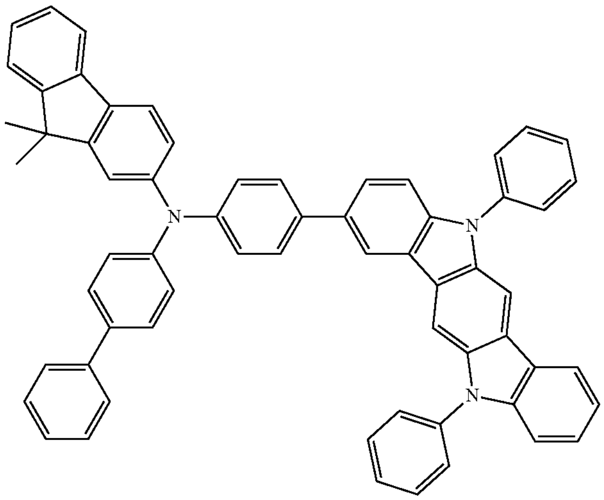
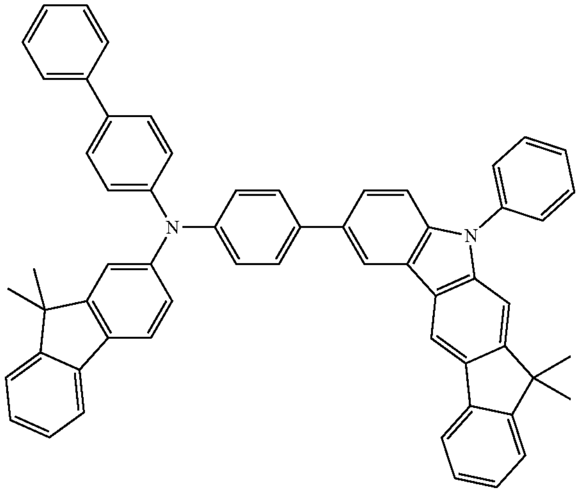
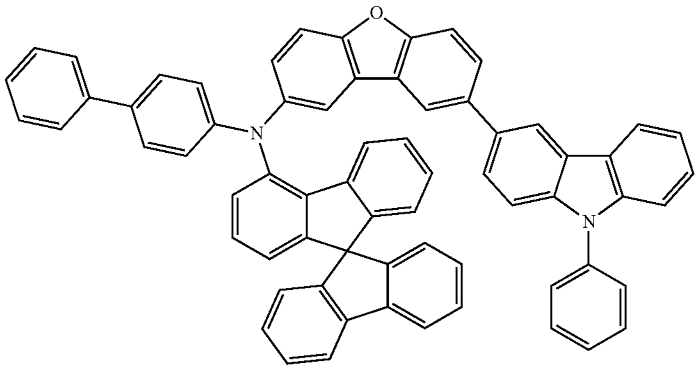
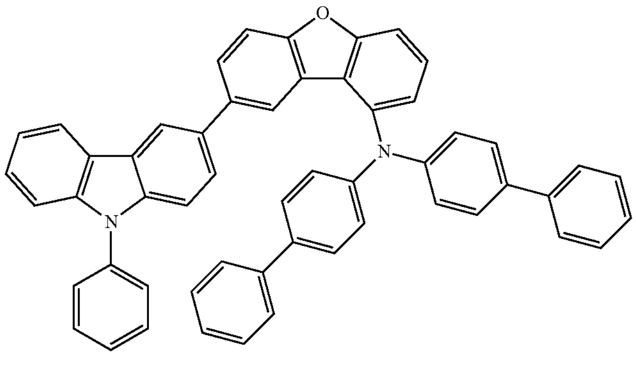

-continued
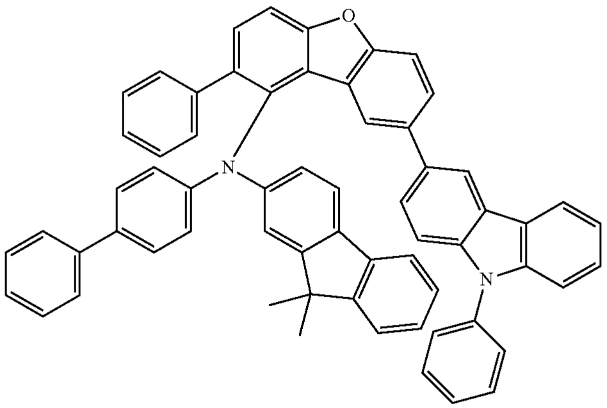
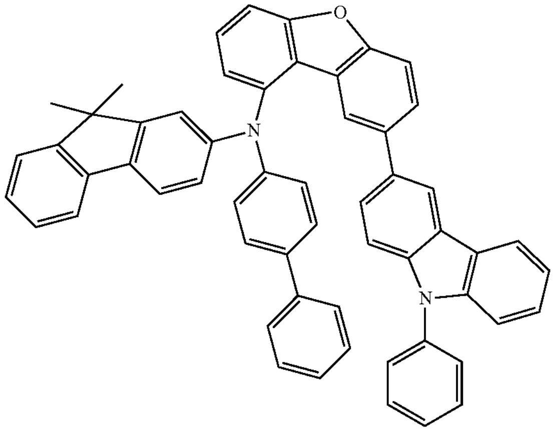
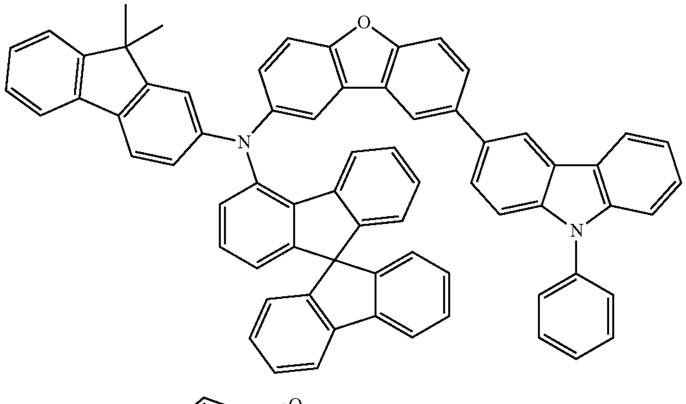
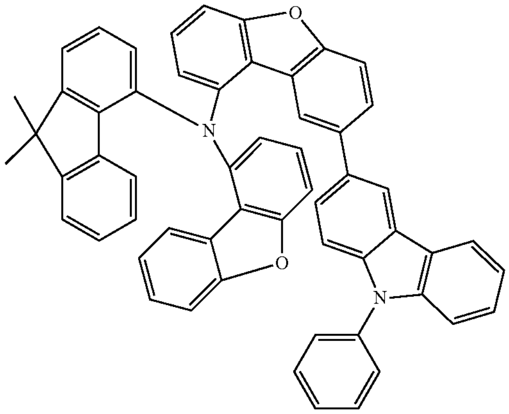
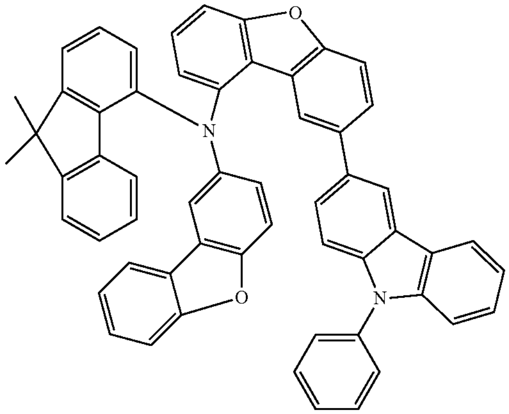

-continued
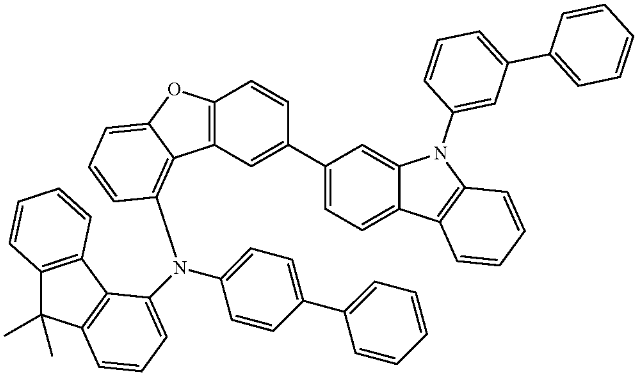
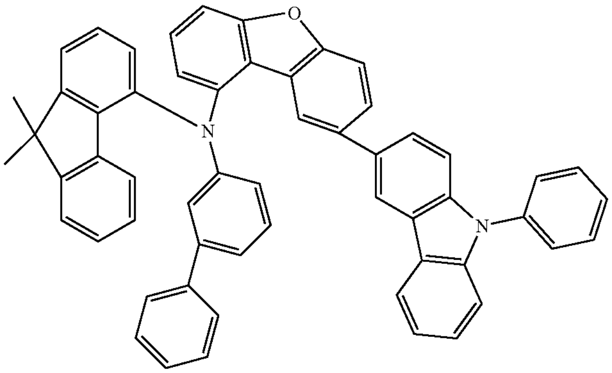
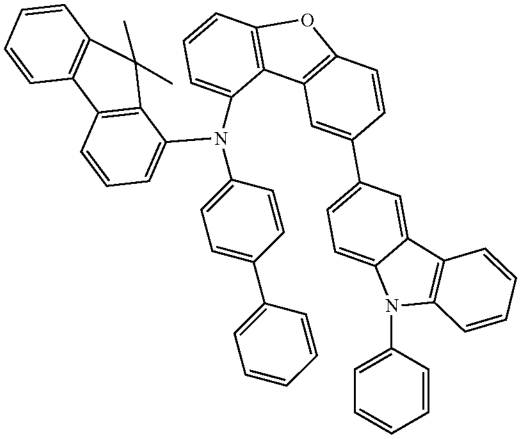
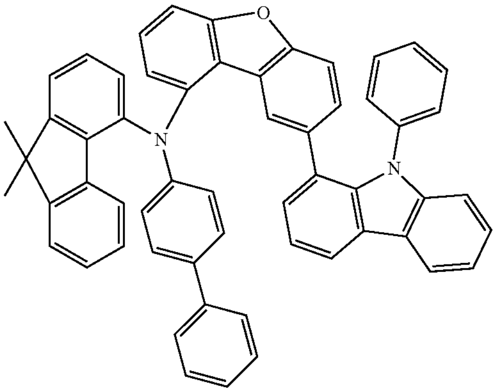
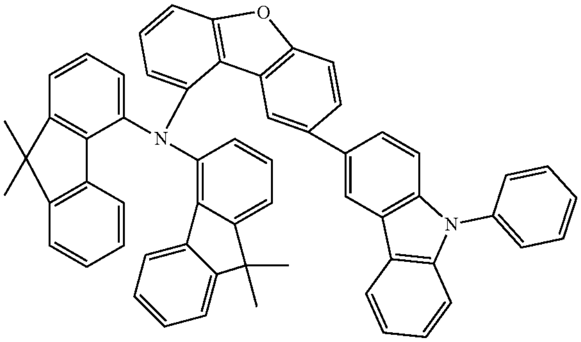
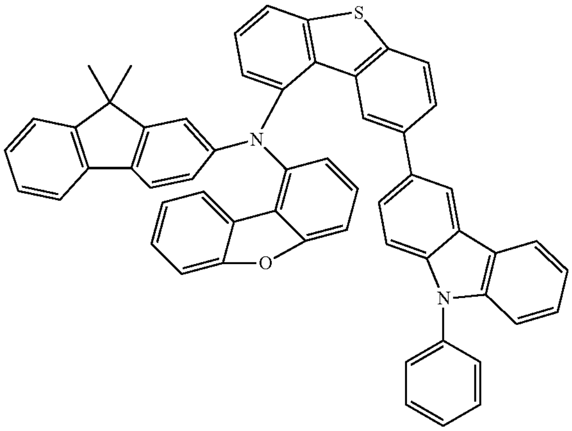

-continued
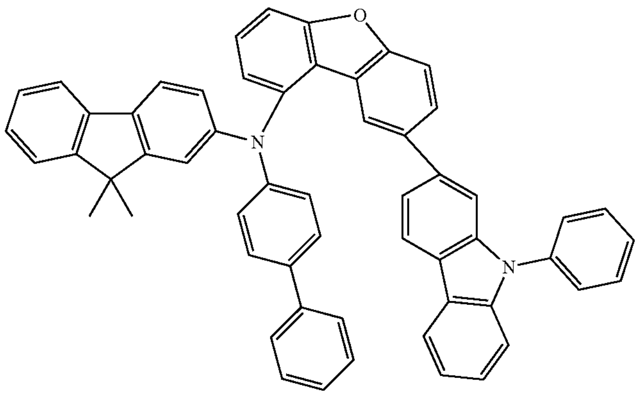
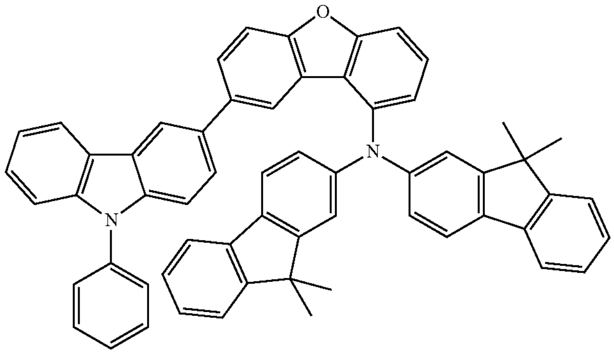
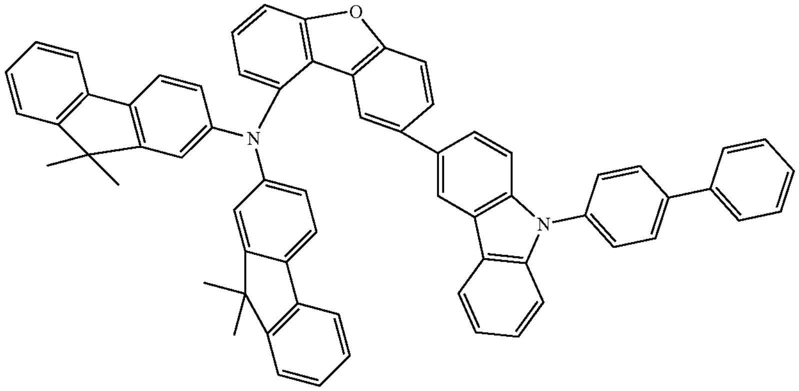
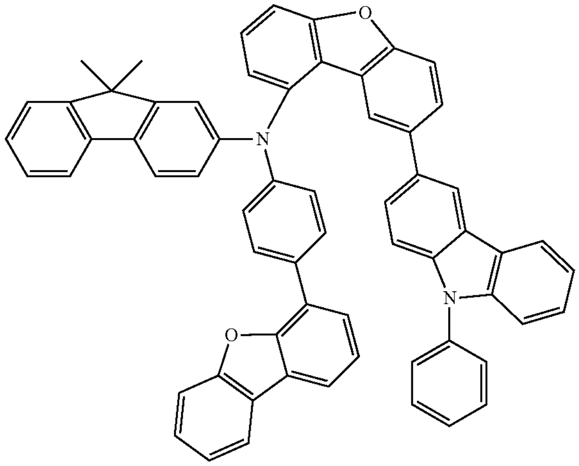

-continued
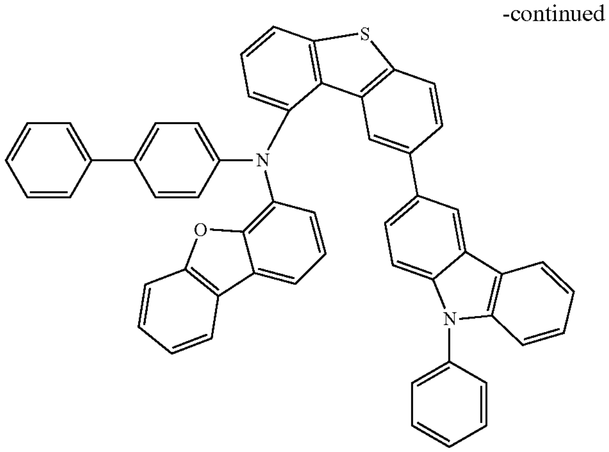
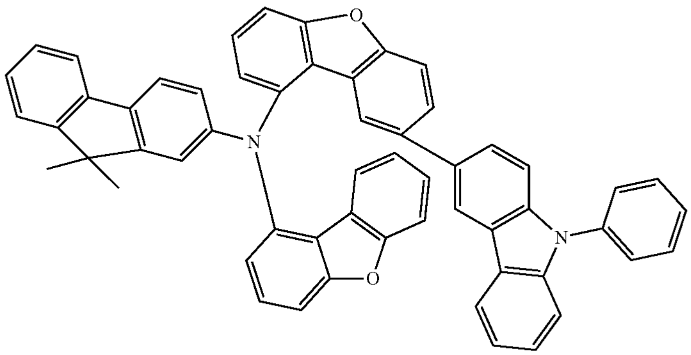
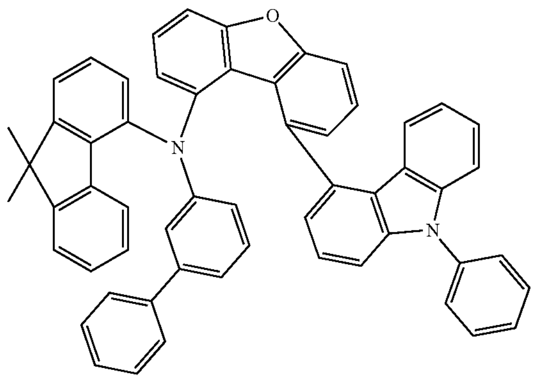
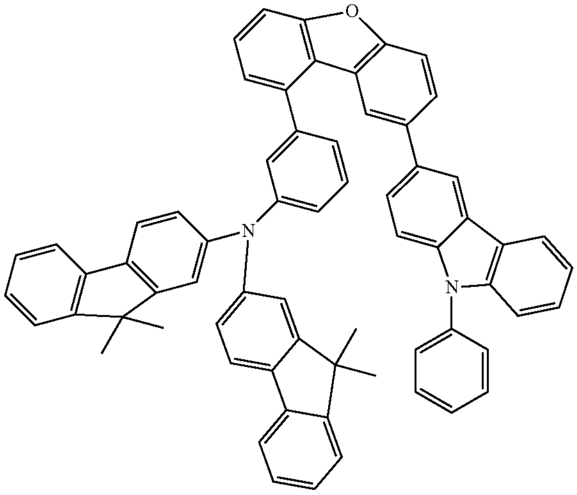

-continued
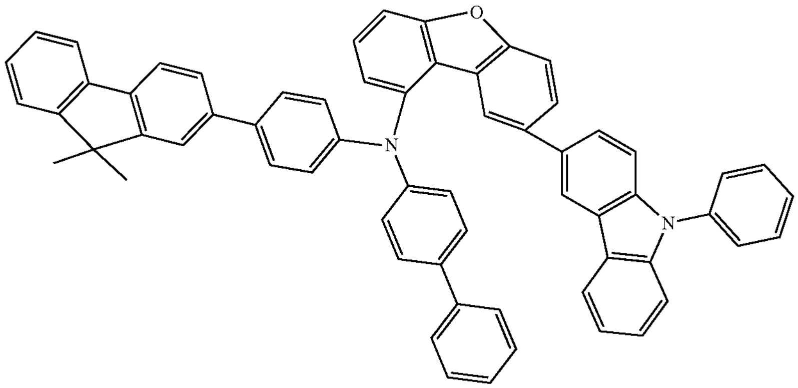
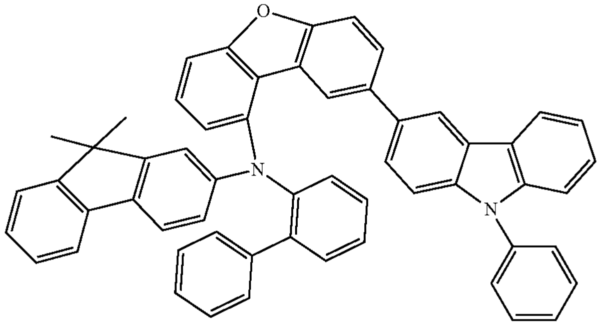
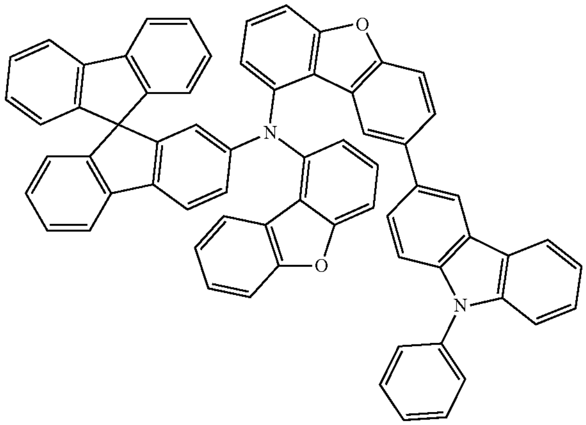
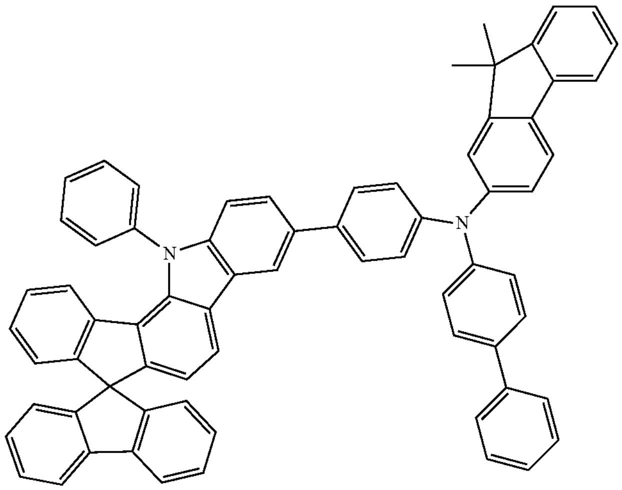

-continued
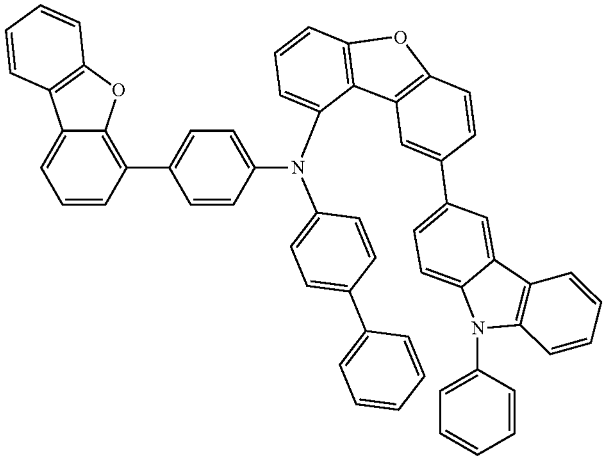
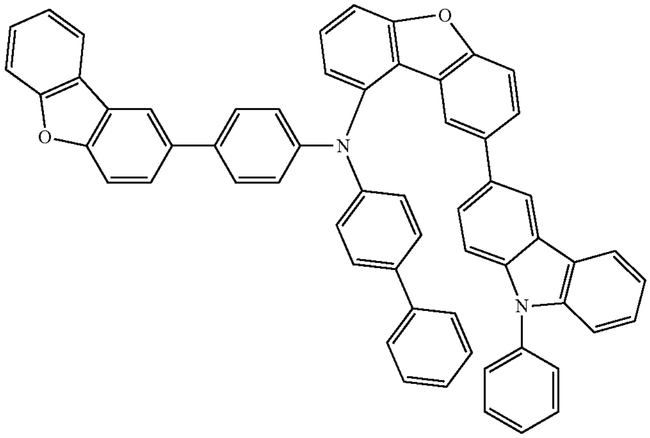
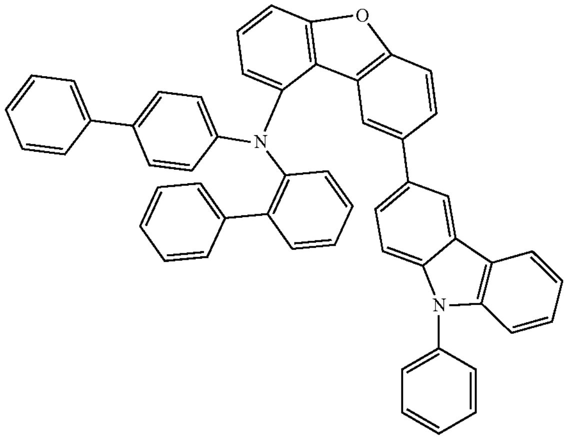
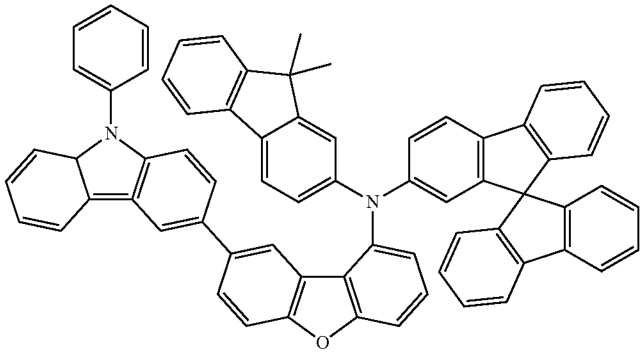

-continued
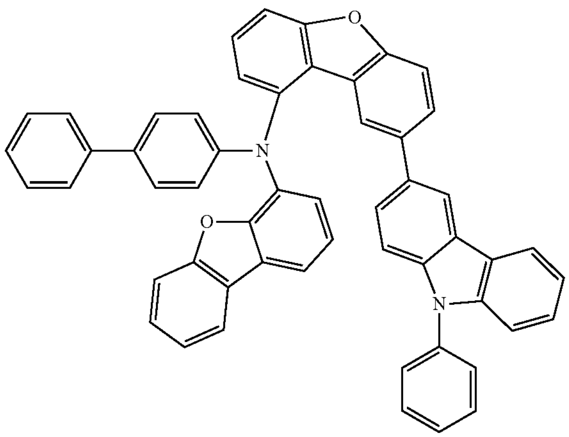
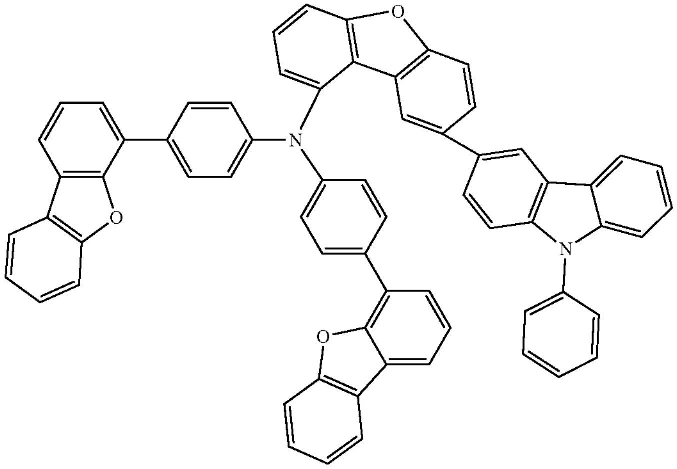
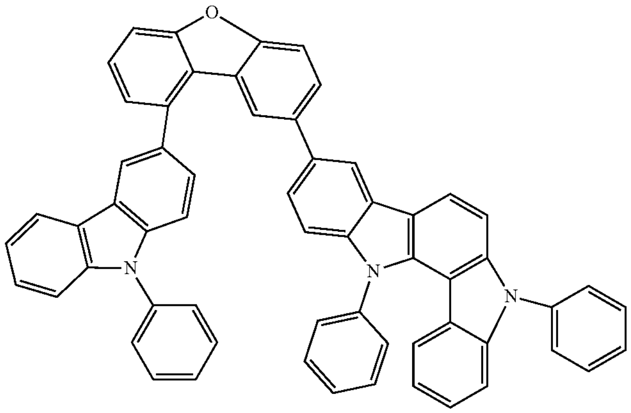
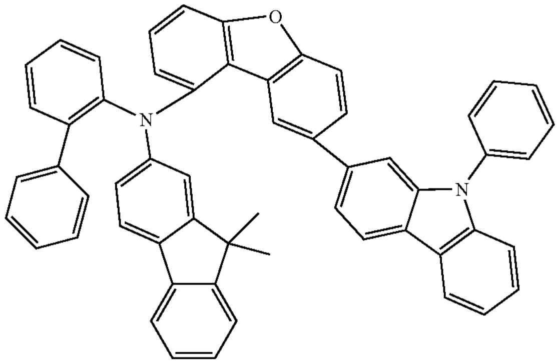

-continued
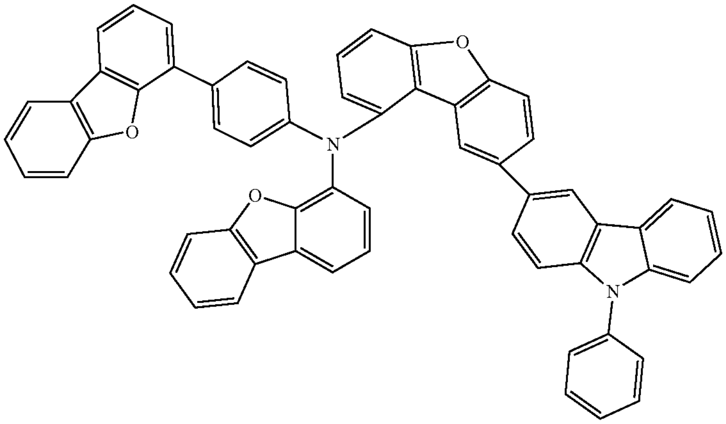
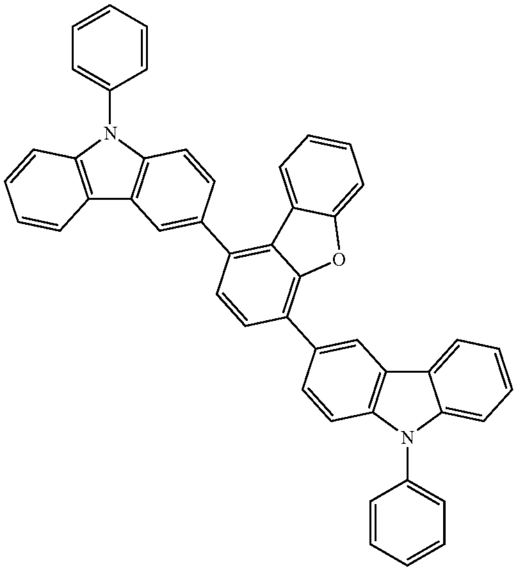
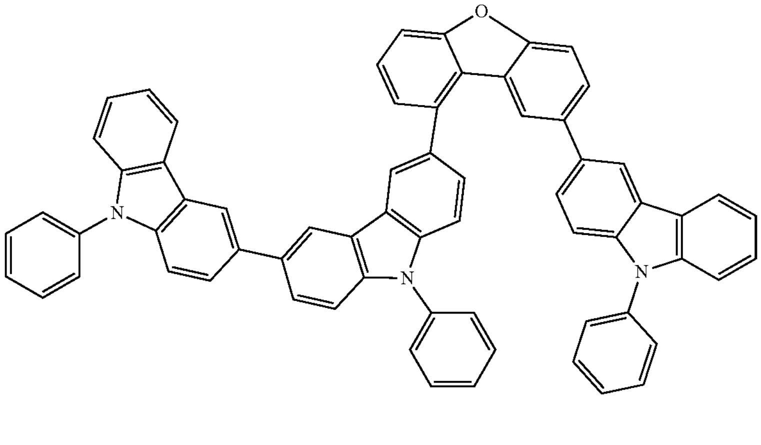

-continued
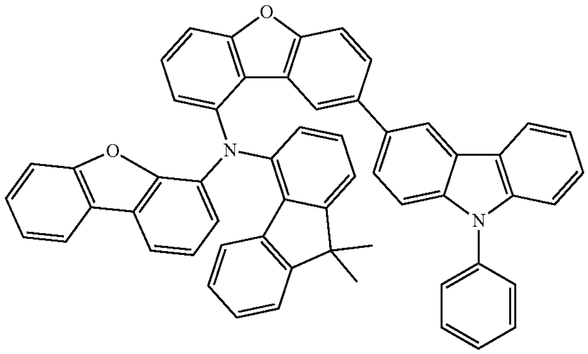
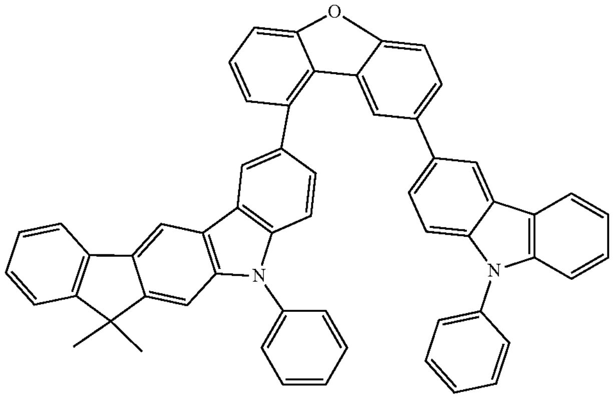
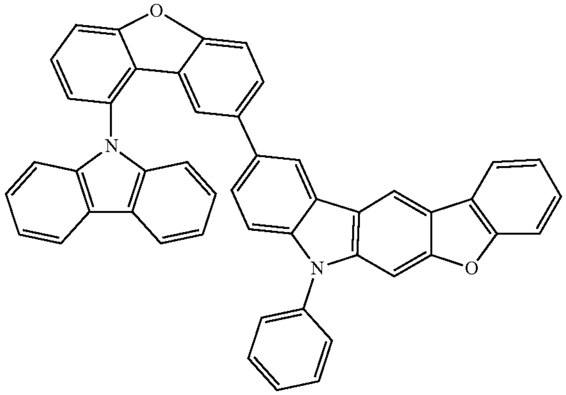
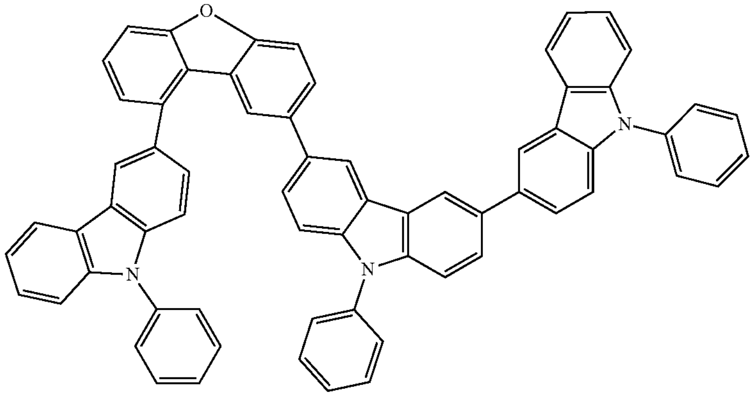

-continued
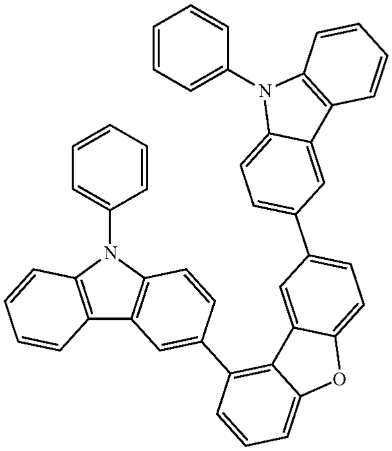
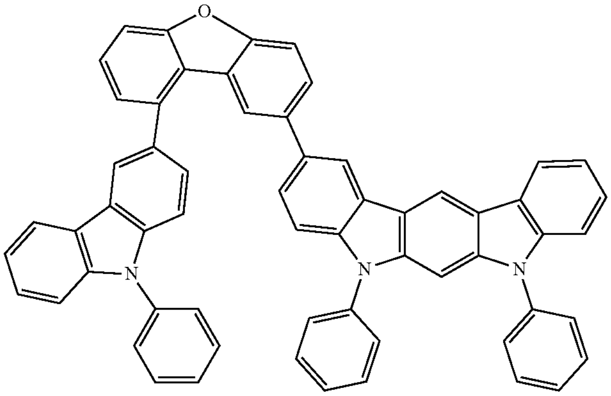
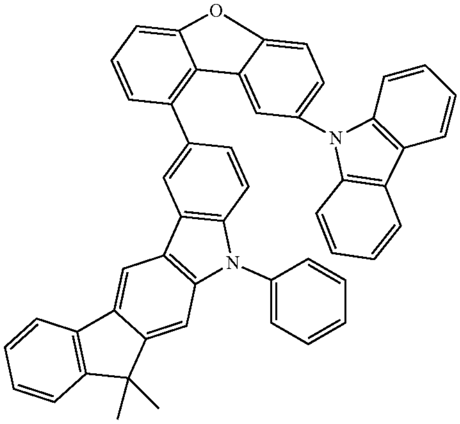
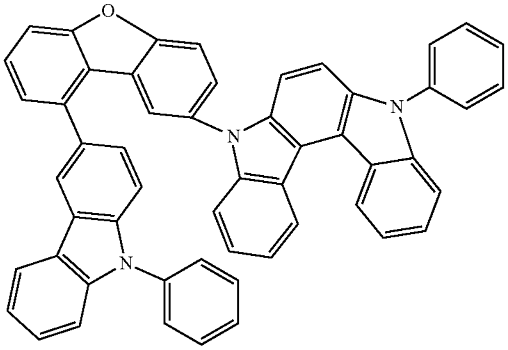
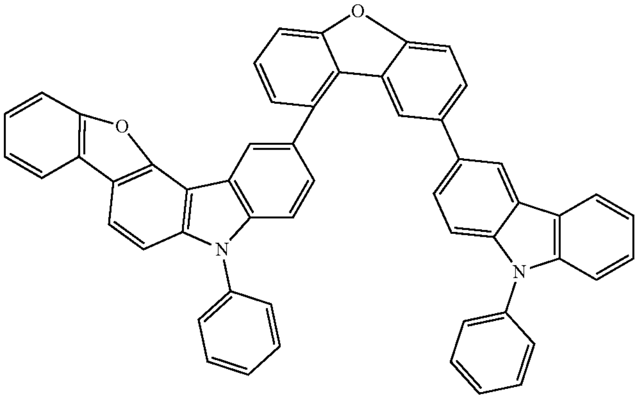
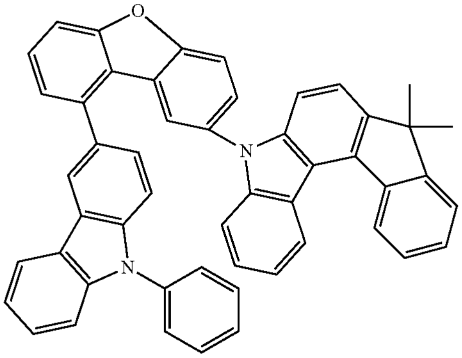
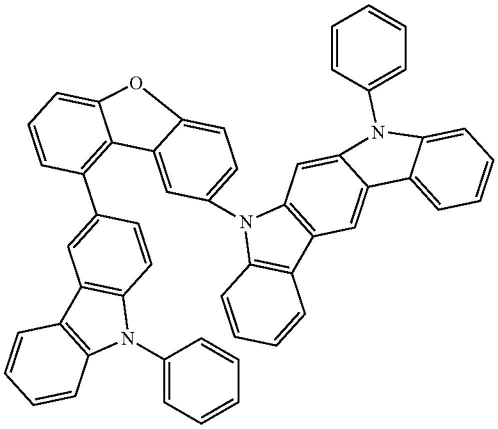

-continued
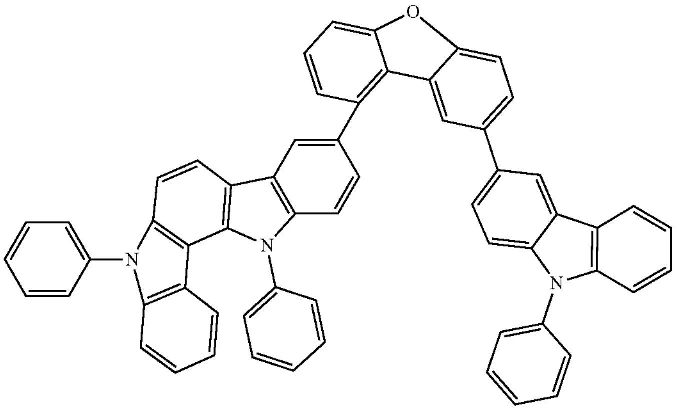
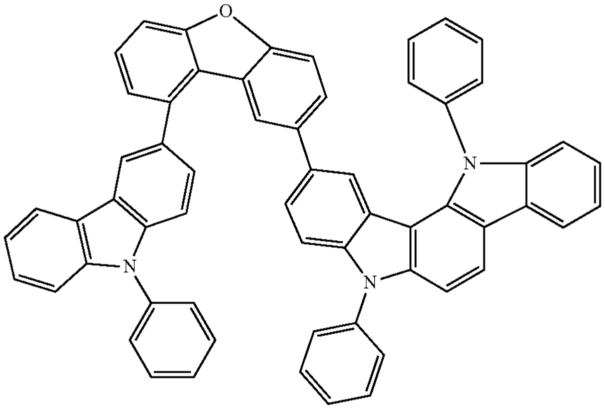
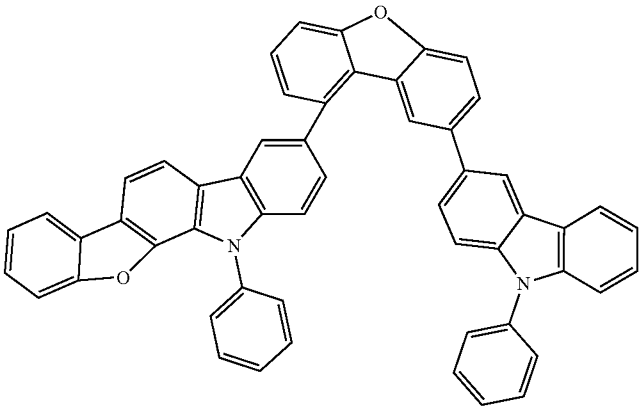
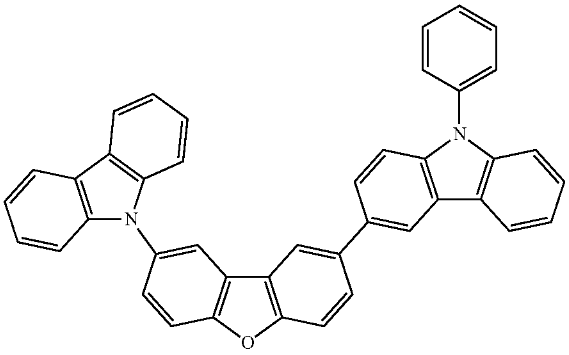

-continued
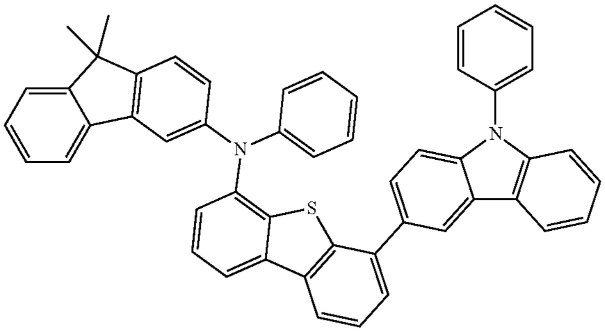
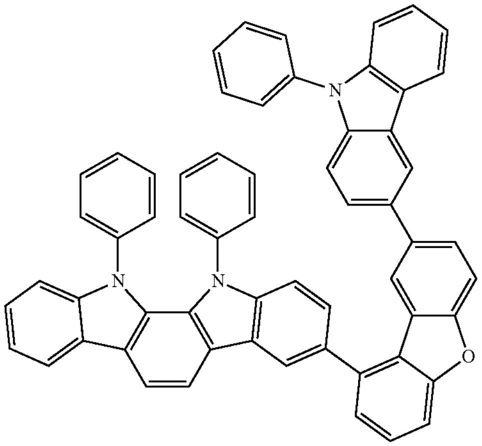
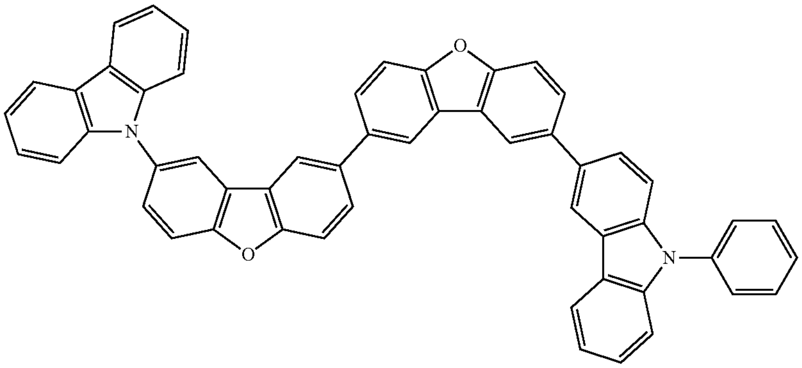
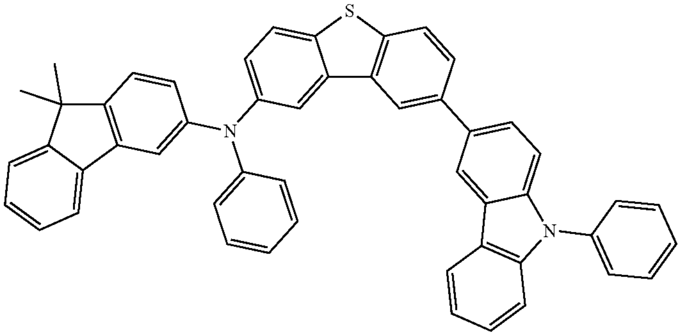
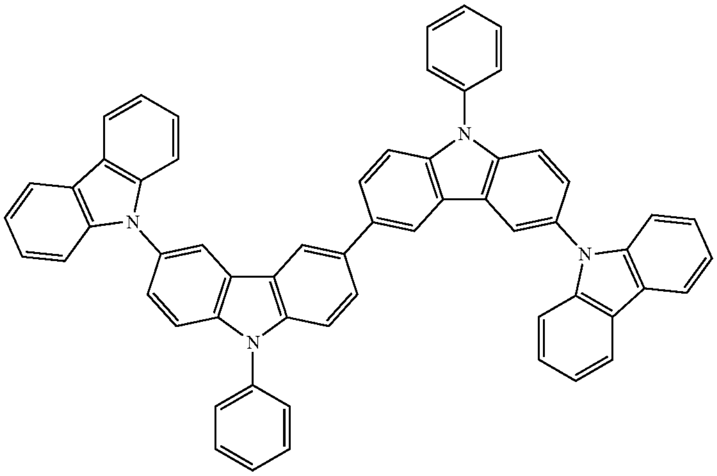

-continued
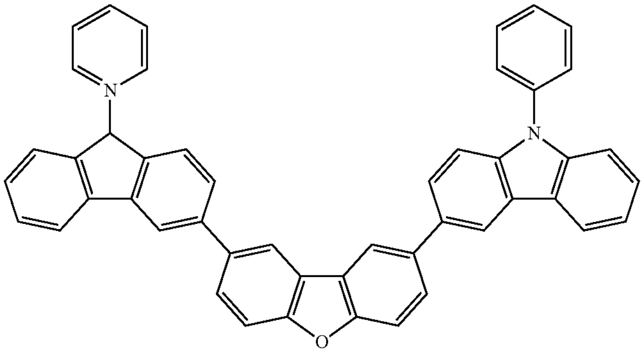
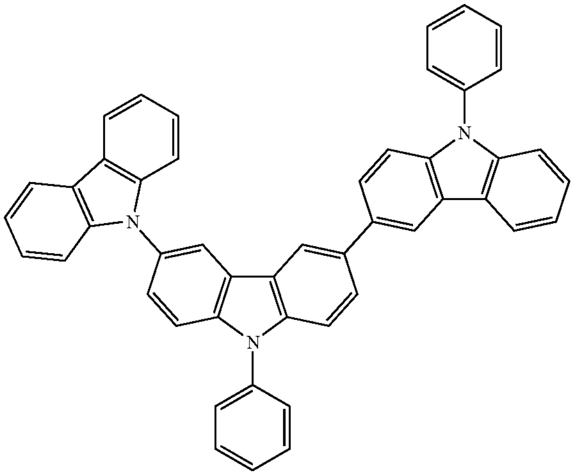
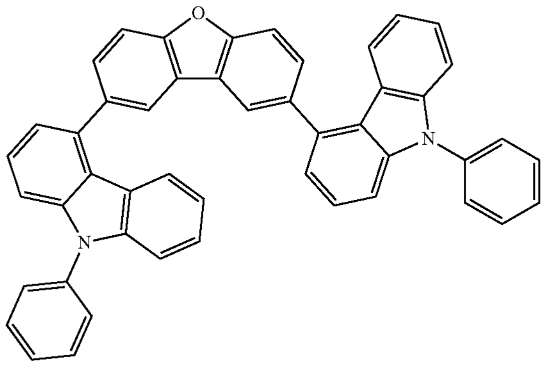
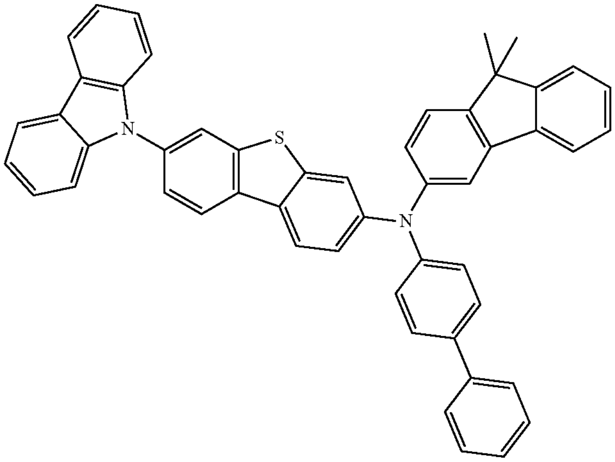
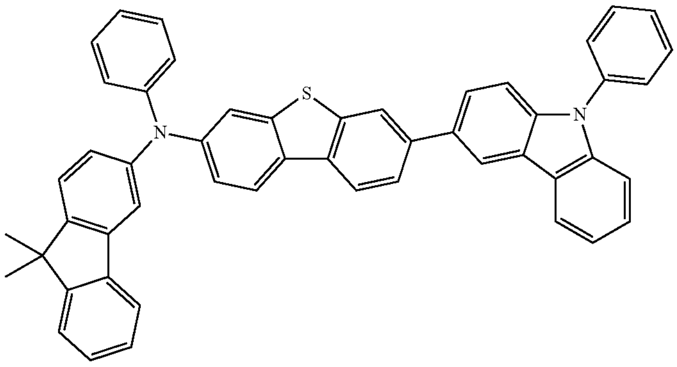

-continued
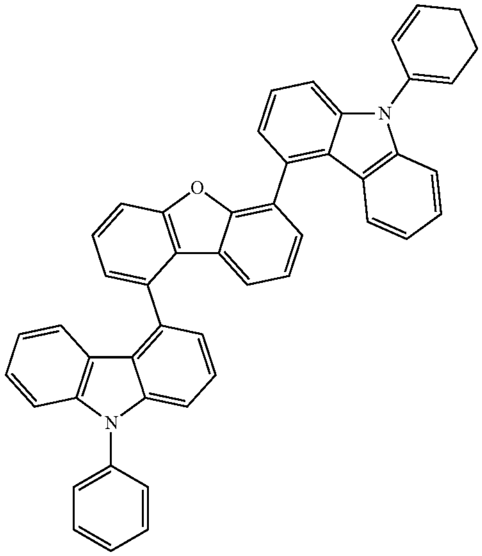
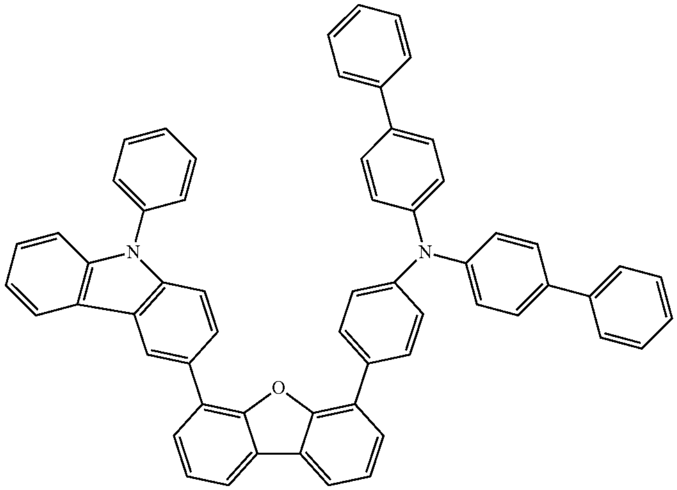
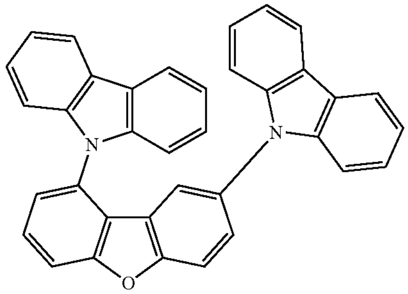
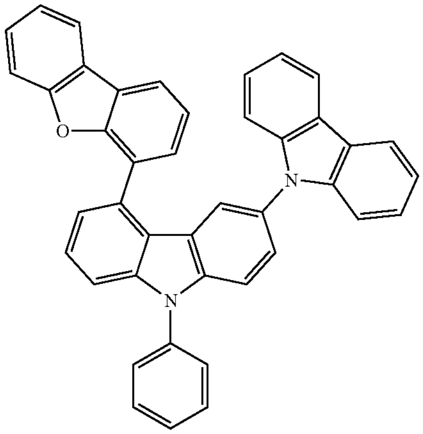
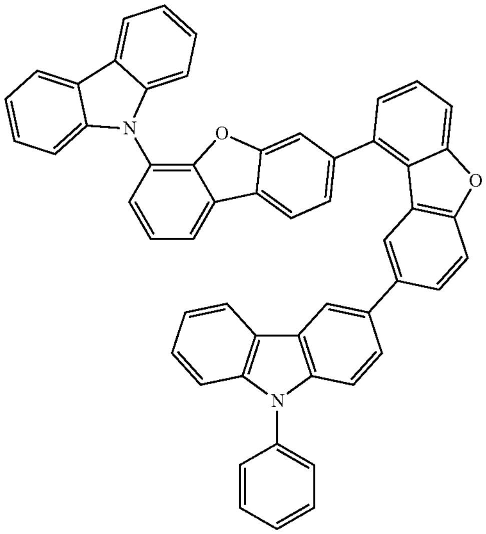

-continued
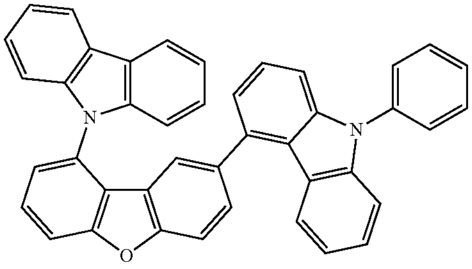
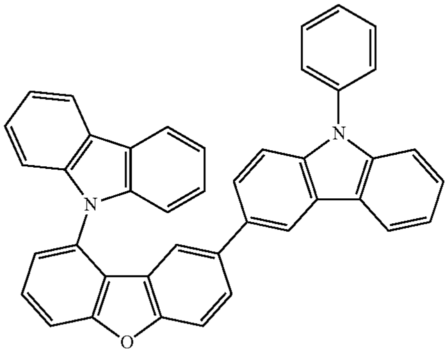
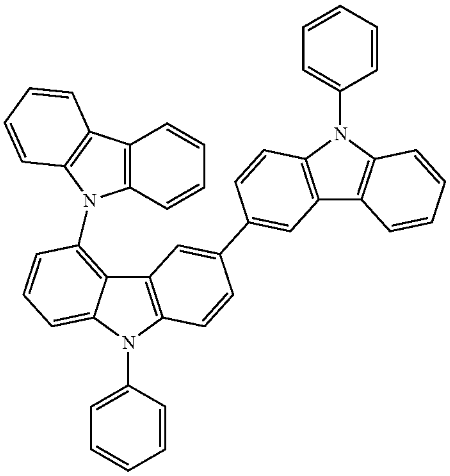
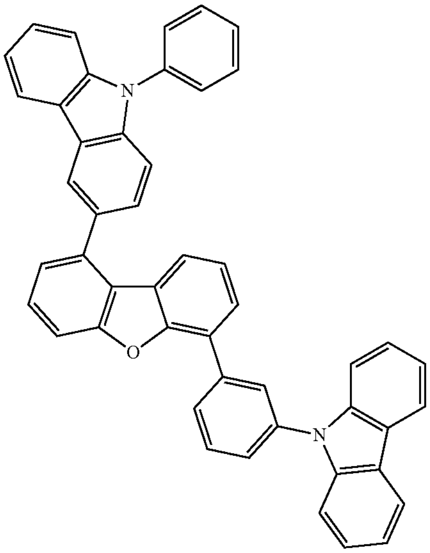
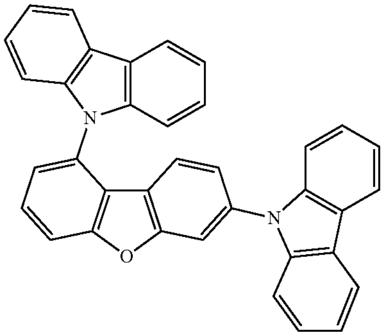
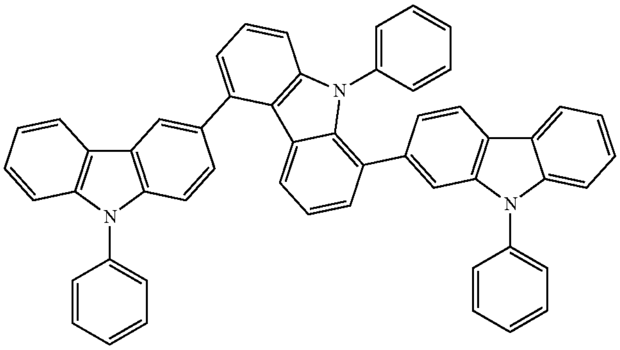

-continued
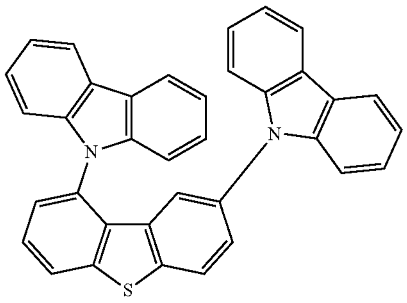
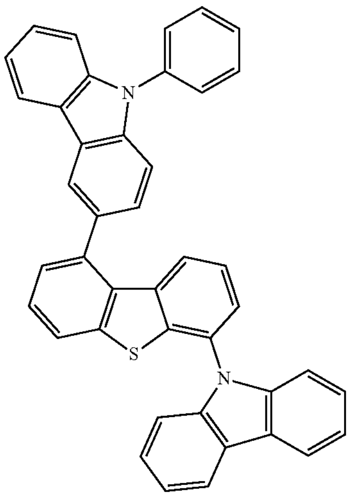
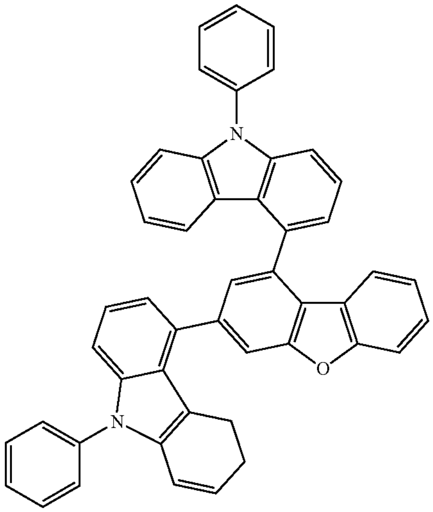
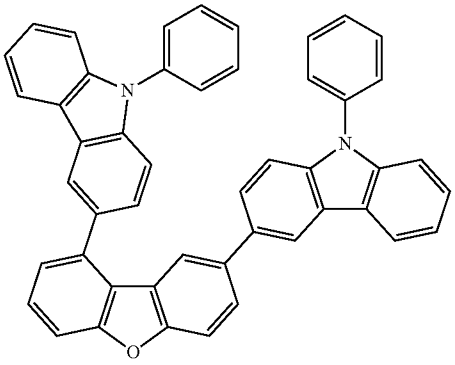
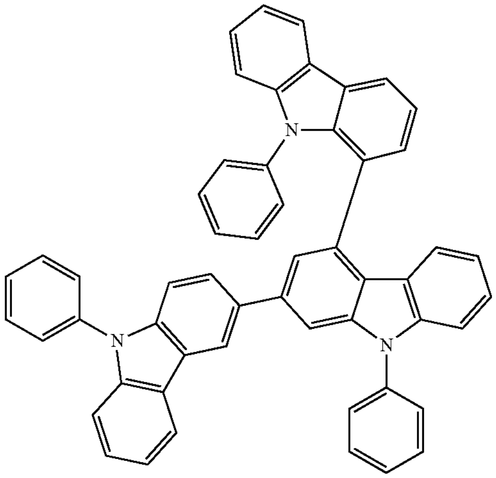
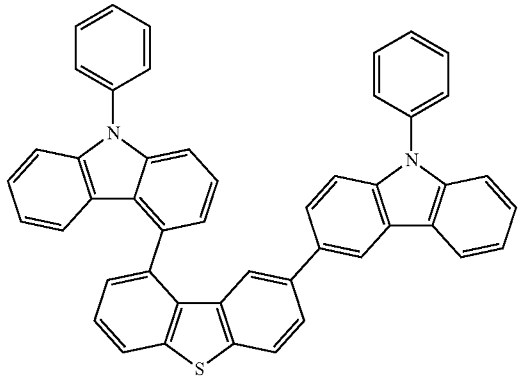

-continued
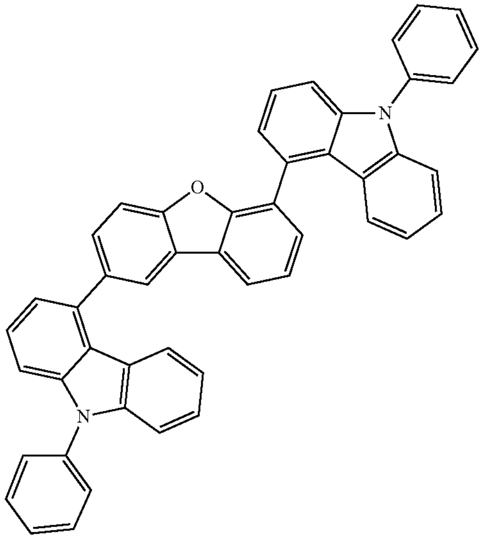
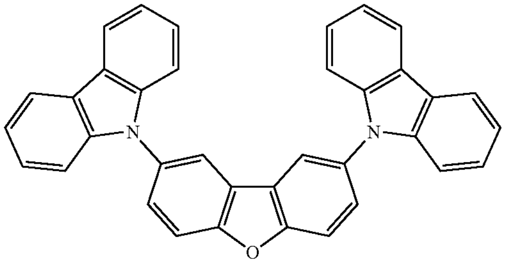
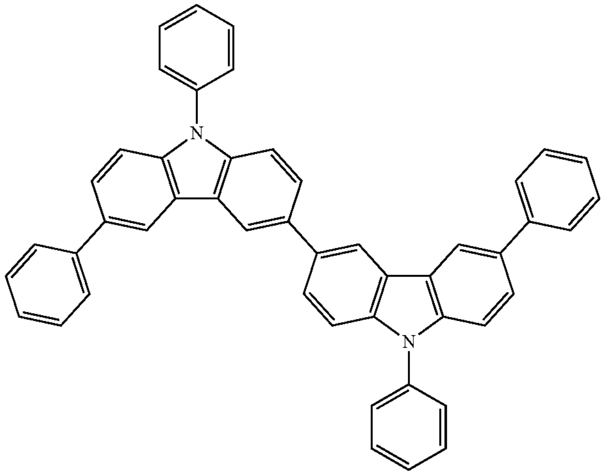
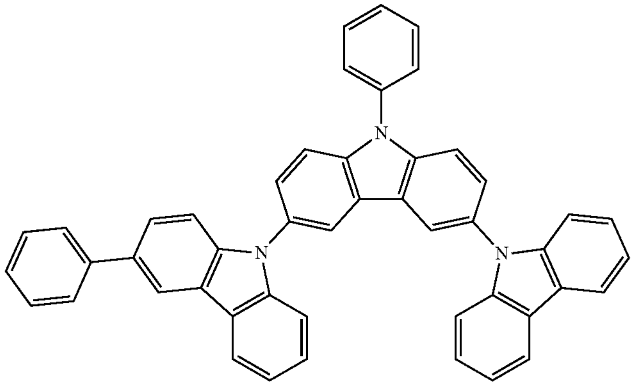
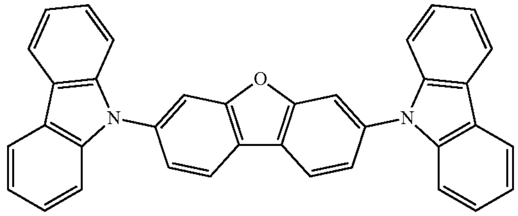
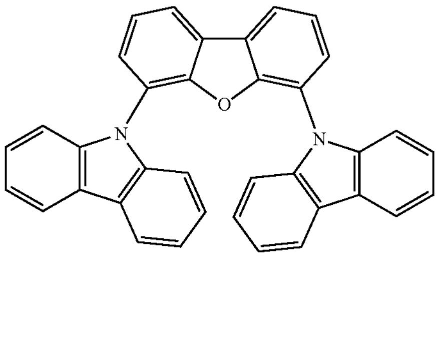
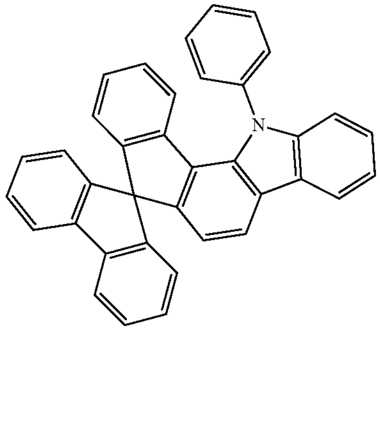

-continued
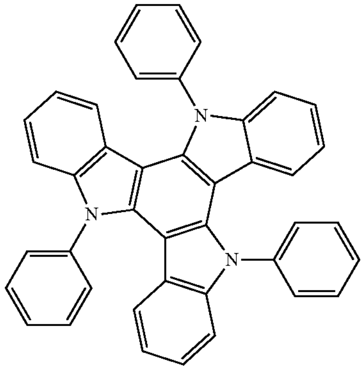
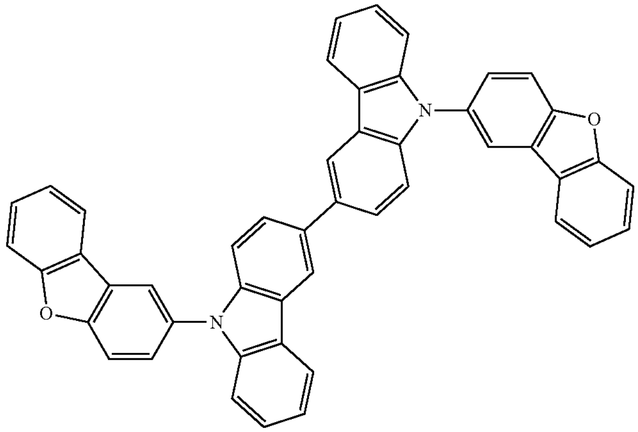
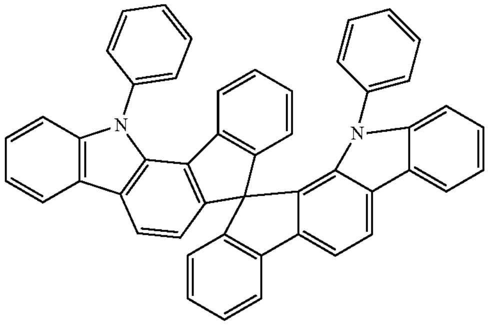
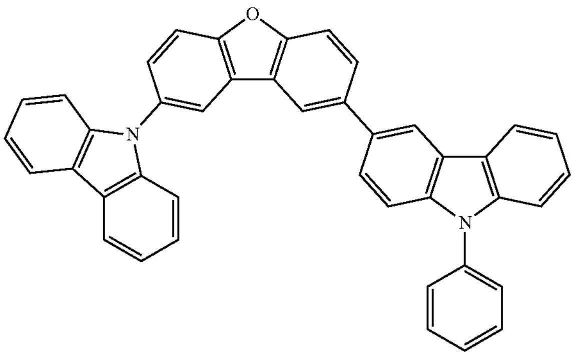
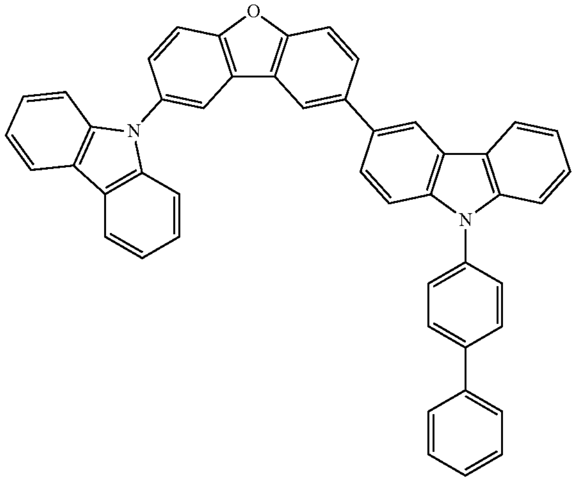
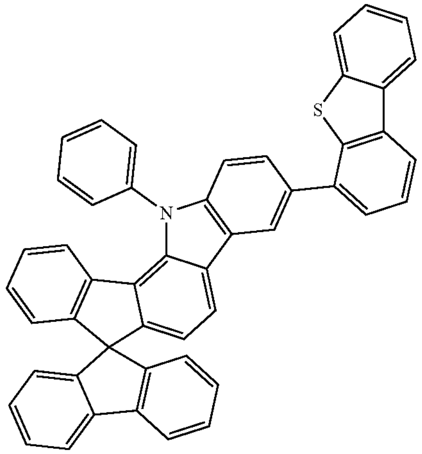
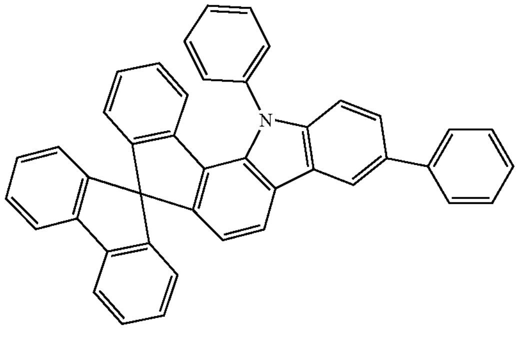
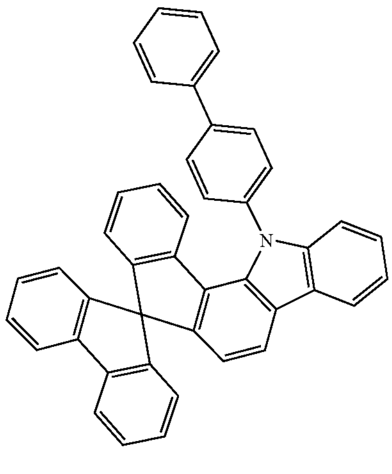

-continued
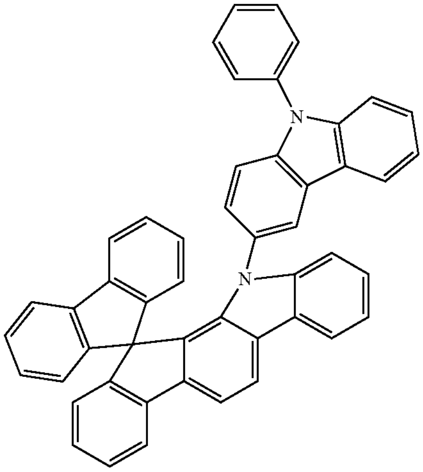
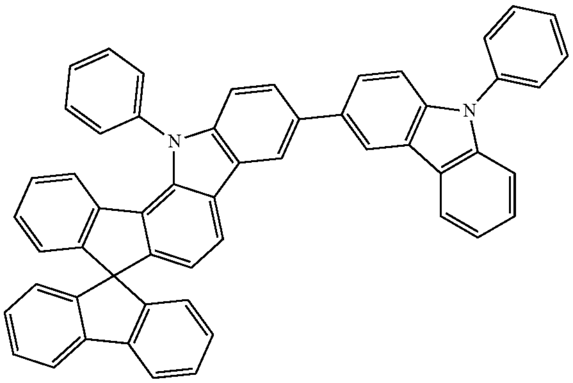
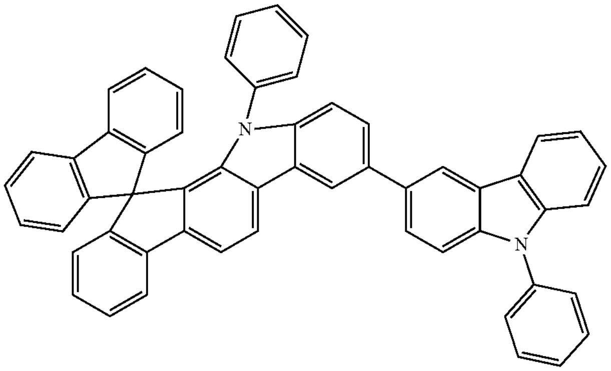
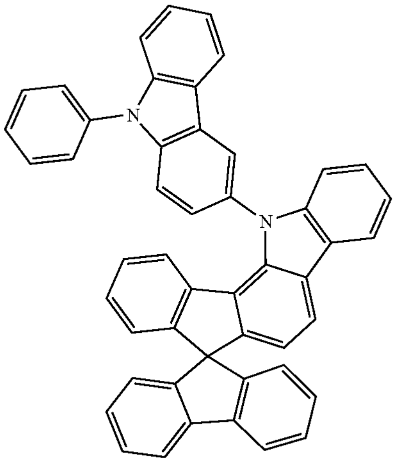
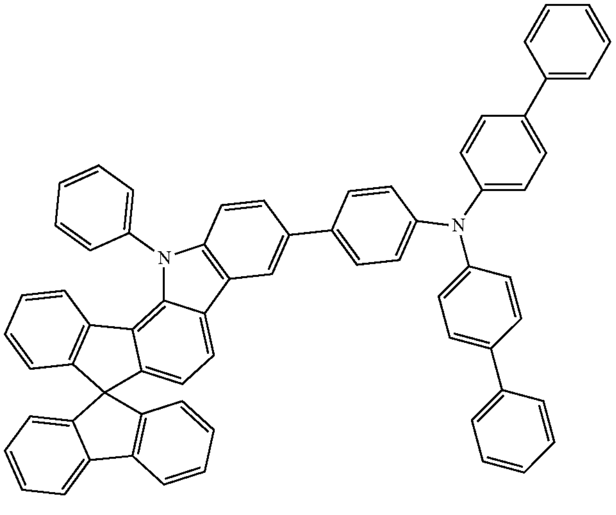

-continued
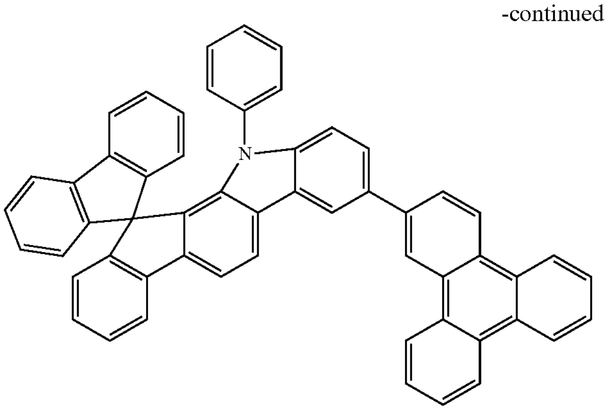
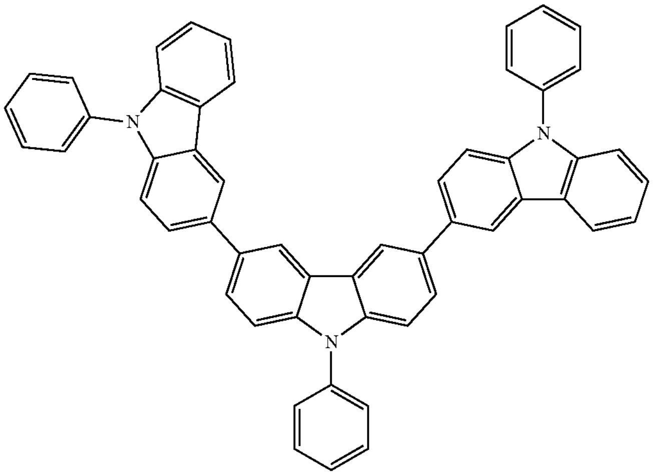
Particularly suitable examples of compounds of the formulae (9), (9a), (9b), (9c), (9d), (9e), (9f), (9g), (9h) and (9i) that are selected in accordance with the invention are the compounds H1-H27 depicted below:
H1
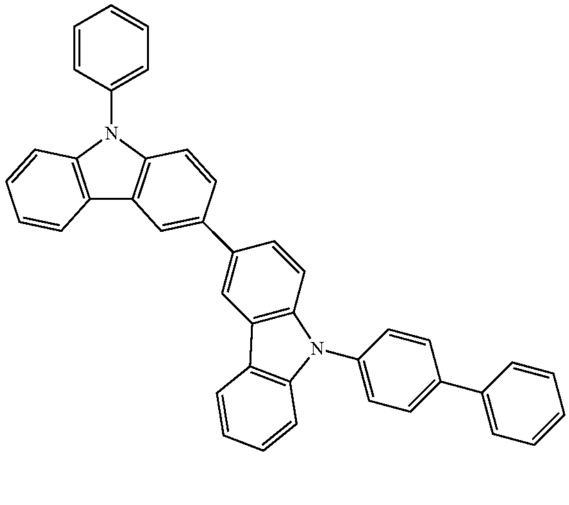
-continued
H2
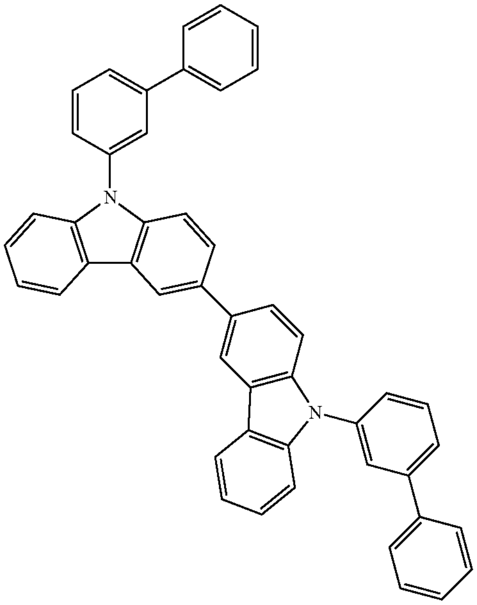

-continued
H3
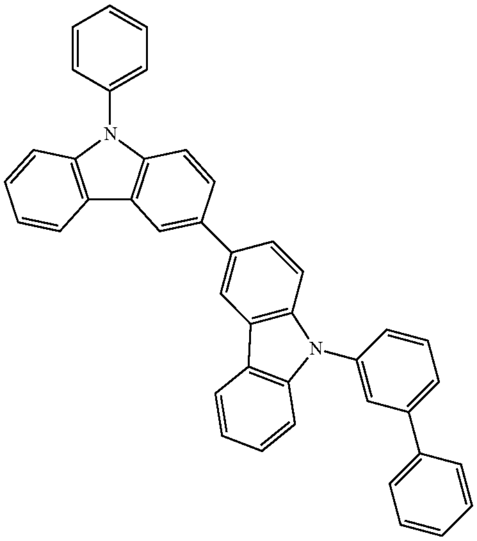
-continued
H5
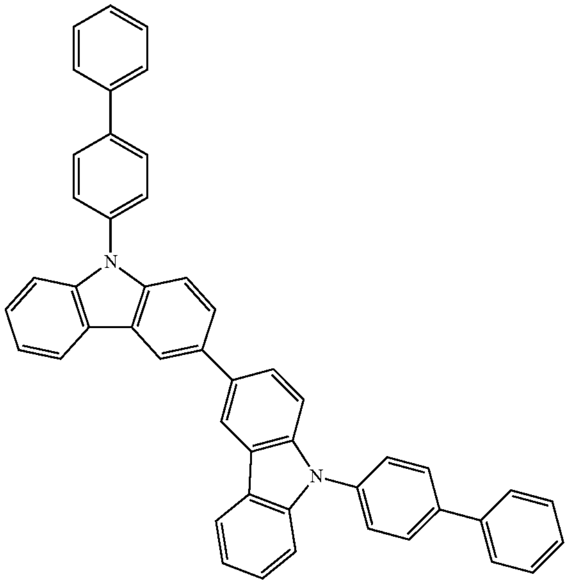
H4
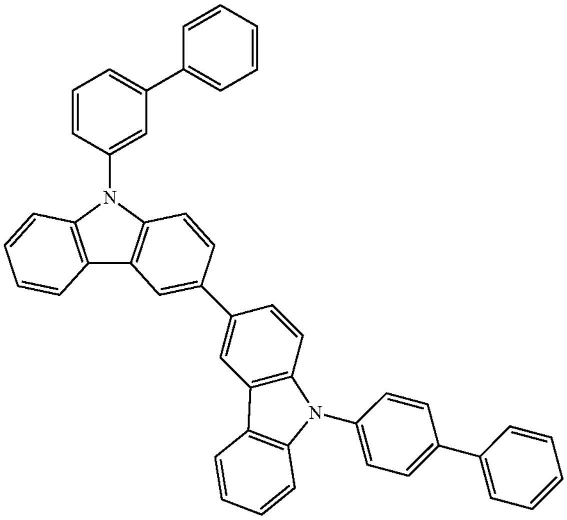
H6
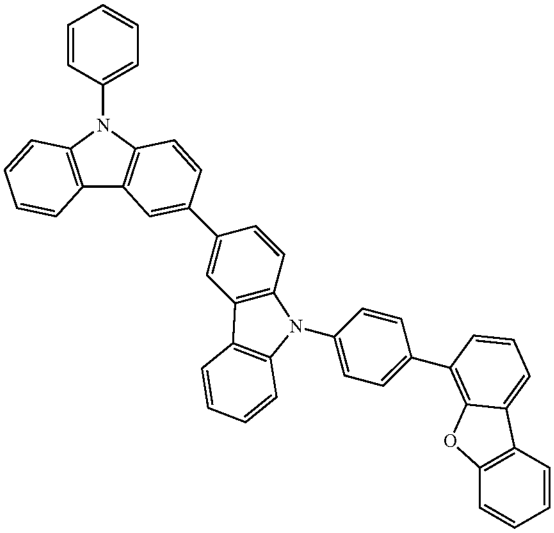

-continued
H7
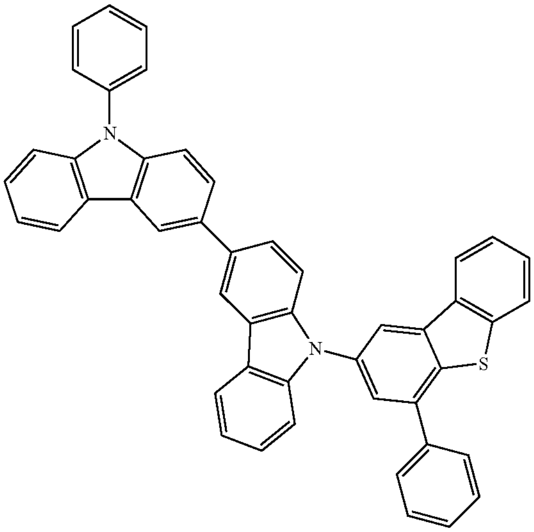
H8
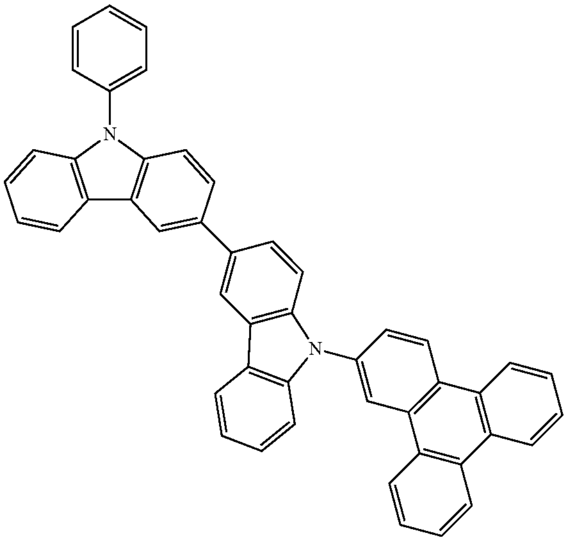
H9
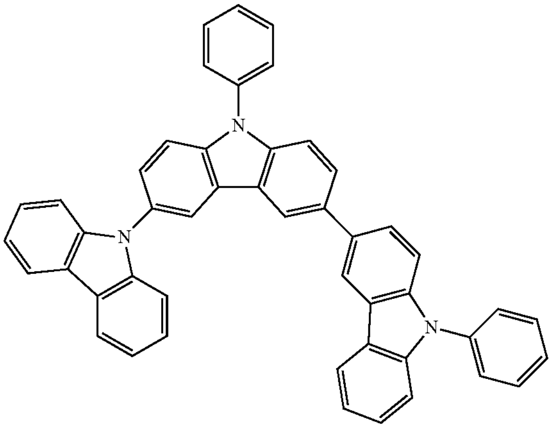
-continued
H10
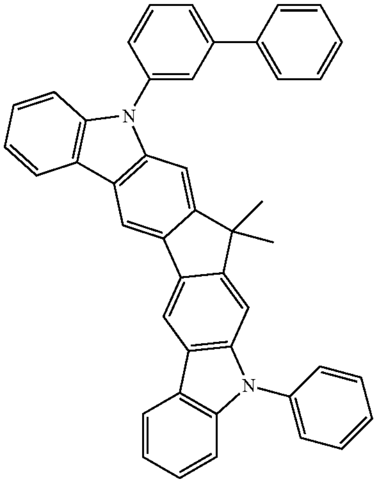
H11
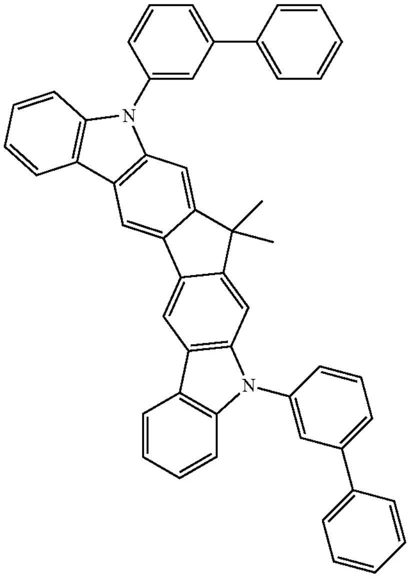
H12
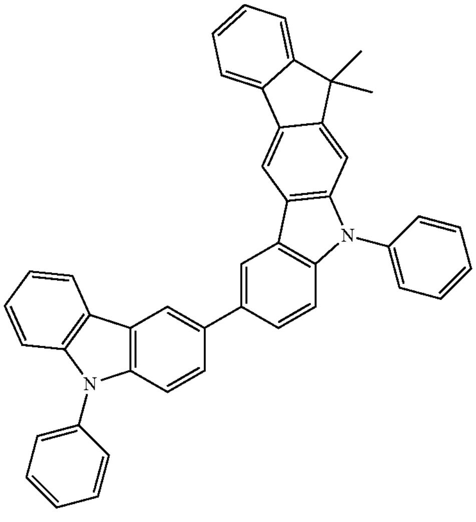

-continued
H13
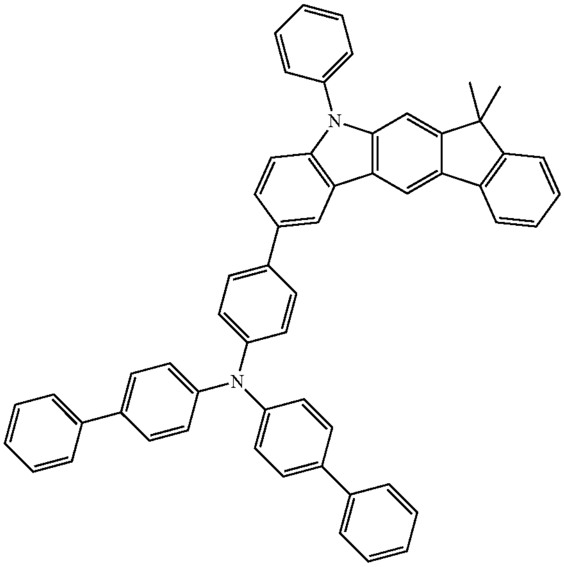
H14
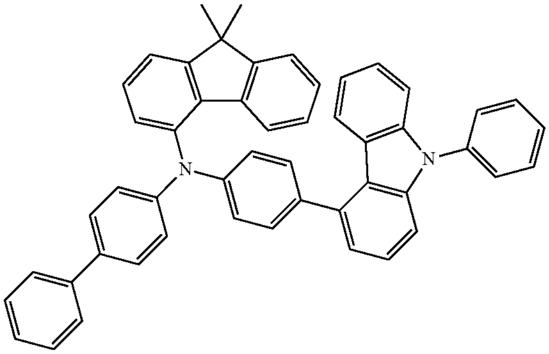
H15
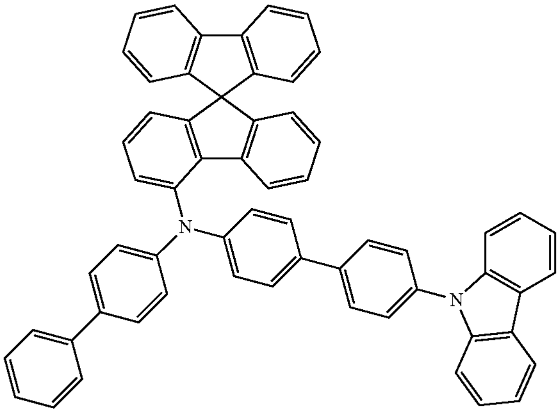
-continued
H16
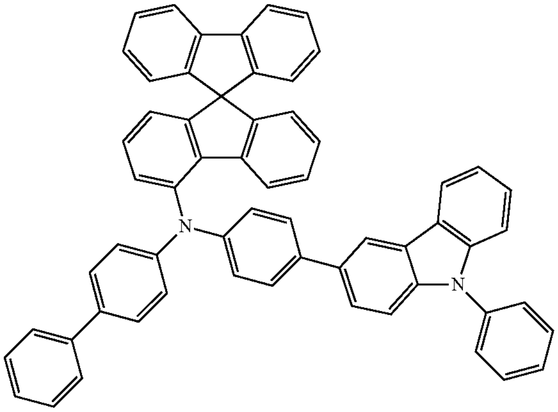
H17
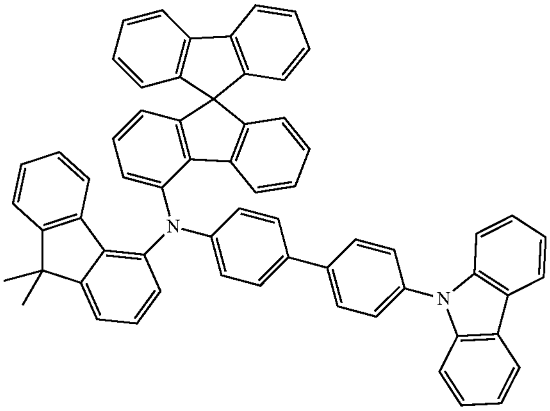
H18
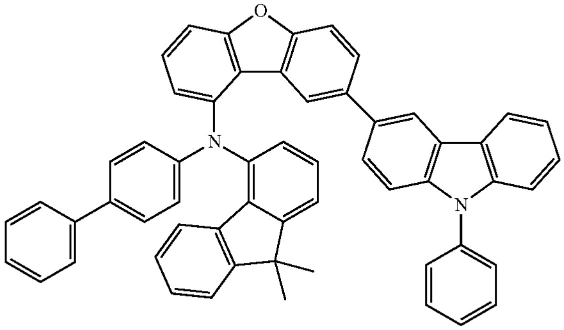
H19
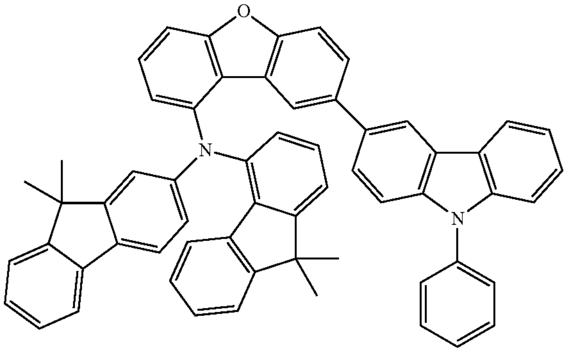

-continued
H20
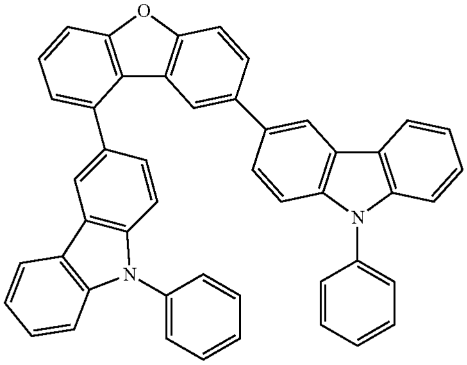
H21
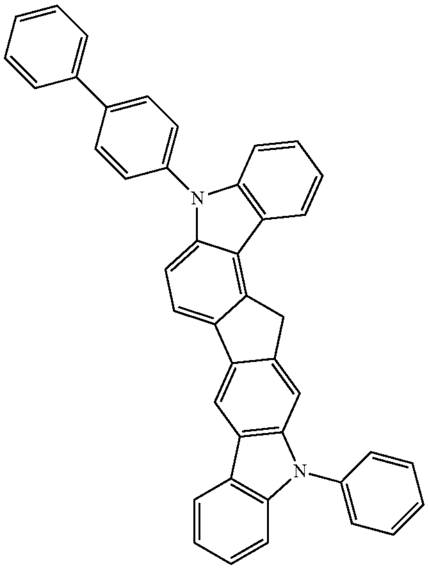
H22
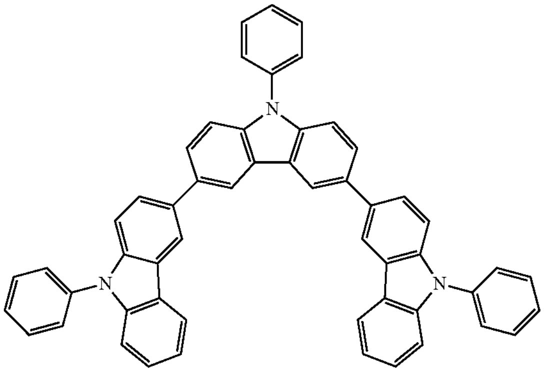
-continued
H23
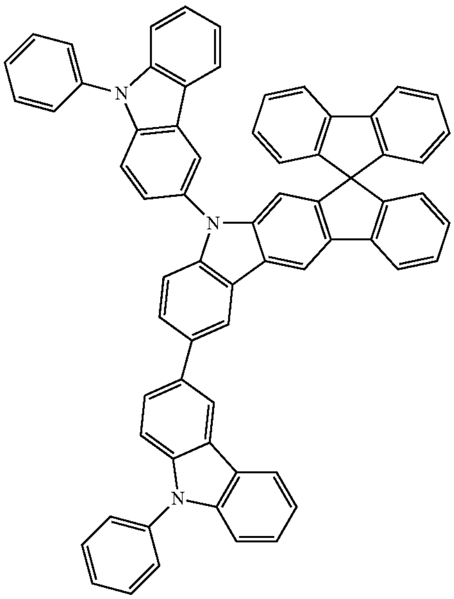
H24
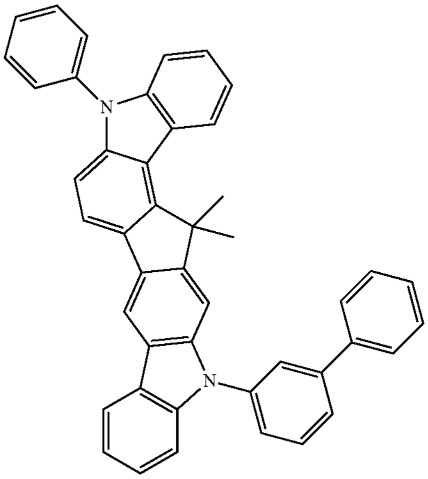
H25
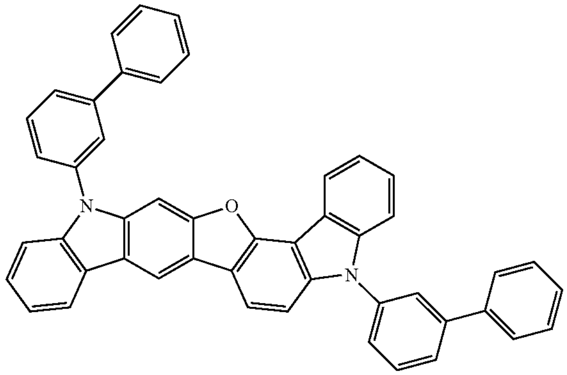

-continued
H26
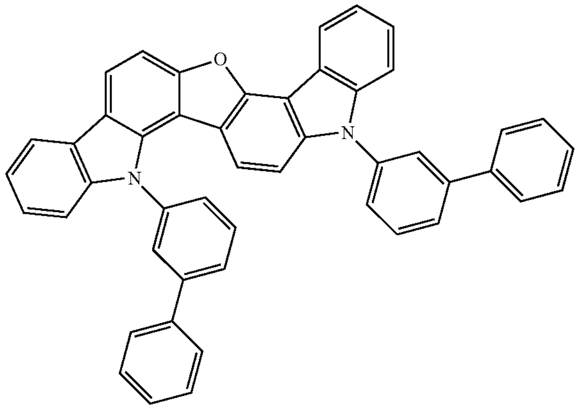
H27
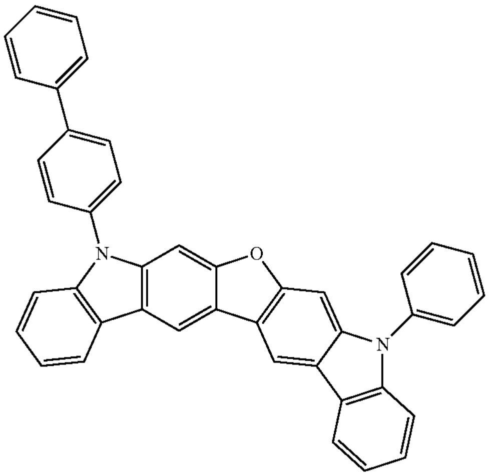
H28
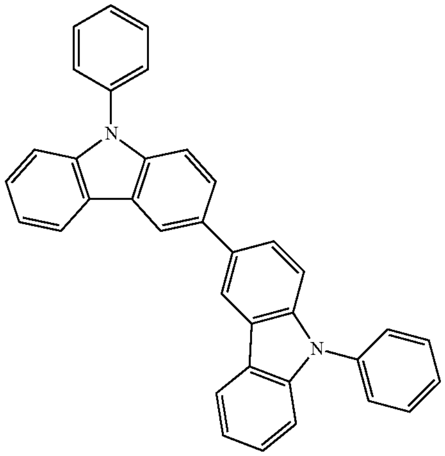
-continued
H29
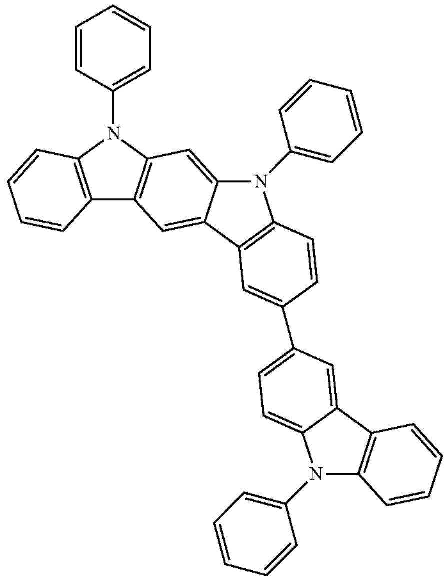
H30
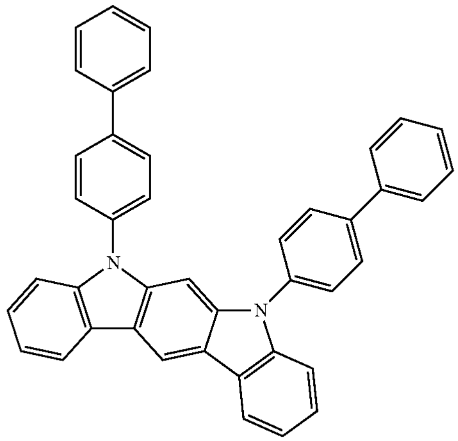
H31
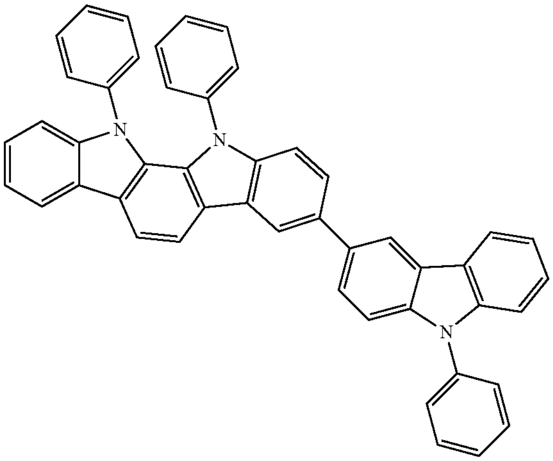

-continued

H32

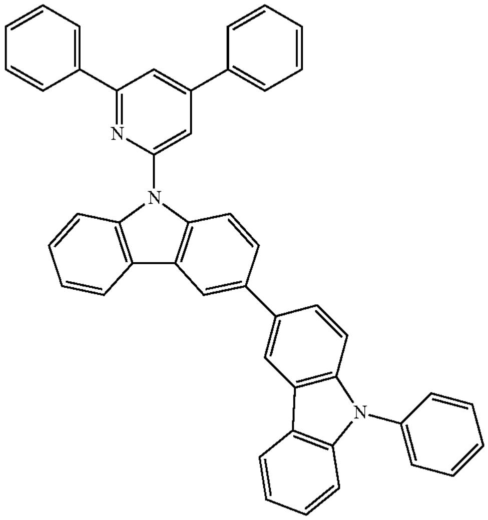

H33

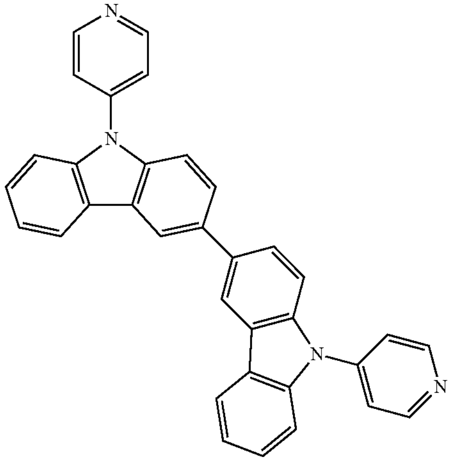

H34

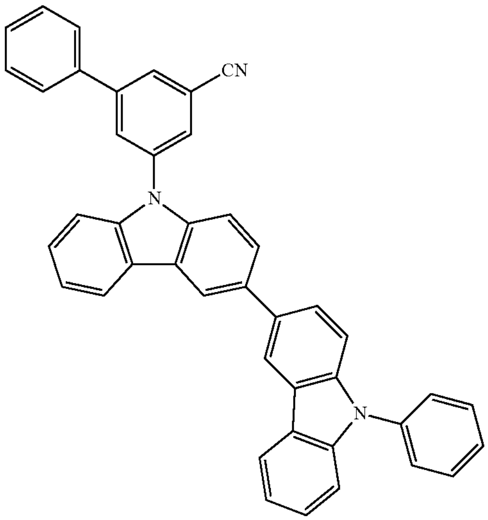

-continued

H35

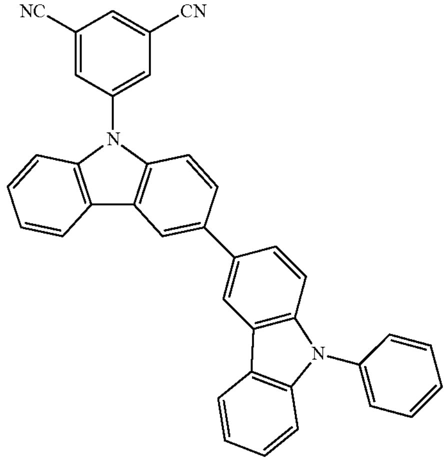

H36

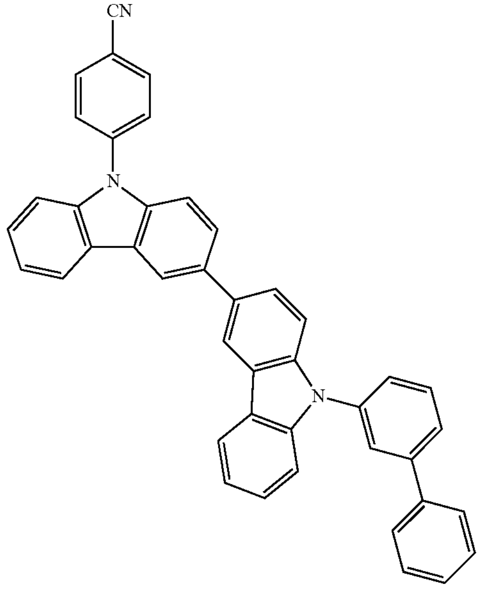

In addition, it is possible to use the compounds of the invention in a hole blocker and/or electron transport layer.

In the further layers of the organic electroluminescent device of the invention, it is possible to use any materials as typically used according to the prior art. The person skilled in the art is therefore able, without exercising inventive skill, to use any materials known for organic electroluminescent devices in combination with the inventive compounds of formula (1) or according to the preferred embodiments.

Additionally preferred is an organic electroluminescent device, characterized in that one or more layers are applied by a sublimation process. In this case, the materials are applied by vapour deposition in vacuum sublimation systems at an initial pressure of less than $10^{-5}$ mbar, preferably less than $10^{-6}$ mbar. It is also possible that the initial pressure is even lower or higher, for example less than $10^{-7}$ mbar.

Preference is likewise given to an organic electroluminescent device, characterized in that one or more layers are applied by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example M. S. Arnold et al., *Appl. Phys. Lett.* 2008, 92, 053301).

Preference is additionally given to an organic electroluminescent device, characterized in that one or more layers are produced from solution, for example by spin-coating, or by any printing method, for example inkjet printing, LITI (light-induced thermal imaging, thermal transfer printing), screen printing, flexographic printing, offset printing or nozzle printing. For this purpose, soluble compounds are needed, which are obtained, for example, through suitable substitution.

In addition, hybrid methods are possible, in which, for example, one or more layers are applied from solution and one or more further layers are applied by vapour deposition. For example, it is possible to apply the emitting layer from solution and to apply the electron transport layer by vapour deposition.

These methods are known in general terms to those skilled in the art and can be applied by those skilled in the art without exercising inventive skill to organic electroluminescent devices comprising the compounds of the invention.

The compounds of the invention generally have very good properties on use in organic electroluminescent devices. Especially in the case of use of the compounds of the invention in organic electroluminescent devices, the lifetime is better compared to similar compounds according to the prior art. At the same time, the further properties of the organic electroluminescent device, especially the efficiency and voltage, are comparable or better.

The invention is now illustrated in detail by the examples which follow, without any intention of restricting it thereby.

EXAMPLES

The syntheses which follow, unless stated otherwise, are conducted under a protective gas atmosphere in dried solvents. The solvents and reagents can be purchased, for example, from Sigma-ALDRICH or ABCR. The respective figures in square brackets or the numbers quoted for individual compounds relate to the CAS numbers of the compounds known from the literature.

Preparation of the Synthons:

S1:

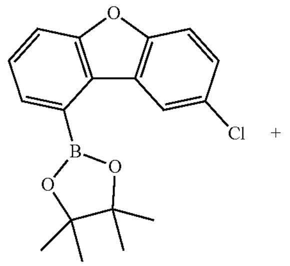

-continued

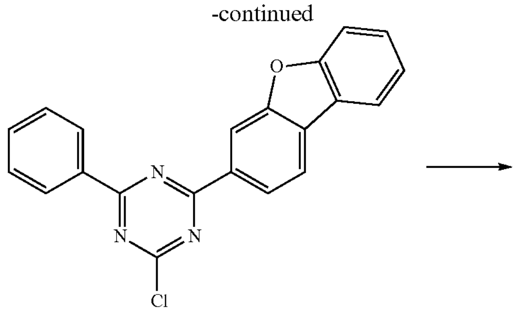

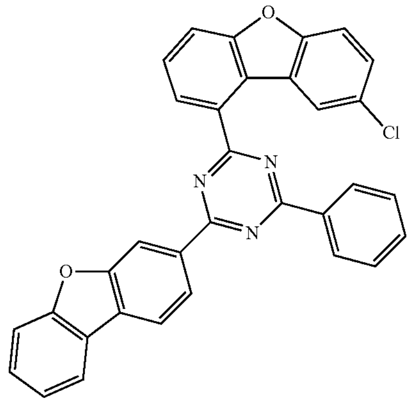

2-(8-Chlorodibenzofuran-1-yl)-4,4,5,5-tetramethyl-1,3,2-dioxaborolane [2140871-51-6] (32.86 g, 100.0 mmol), 2-chloro-4-dibenzofuran-3-yl-6-phenyl-1,3,5-triazine [2142681-84-1] (37.57 g, 105.0 mmol) and sodium carbonate (22.26 g, 210.0 mmol) are suspended in 600 ml of ethylene glycol dimethyl ether and 300 ml of water and inertized for 30 min. Subsequently, tri-o-tolylphosphine (913 mg, 3.0 mmol) and then palladium(II) acetate (112 mg, 0.5 mmol) are added, and the reaction mixture is heated under reflux for 20 h. After cooling, the precipitated solids are filtered off with suction and washed with ethanol. The crude product is recrystallized from m-xylene. Yield: 46.11 g (88 mmol, 88%) of solids, 98% by HPLC.

In an analogous manner, it is possible to prepare the compounds below. Purification can be effected using column chromatography, or recrystallization can be effected using standard solvents such as ethanol, butanol, acetone, ethyl acetate, acetonitrile, toluene, xylene, dichloromethane, methanol, tetrahydrofuran, n-butyl acetate, 1,4-dioxane, dimethyl sulfoxide, N,N-dimethylformamide, N,N-dimethylacetamide, N-methylpyrrolidone etc.

| Reactant 1 | Reactant 2 |
| --- | --- |
| 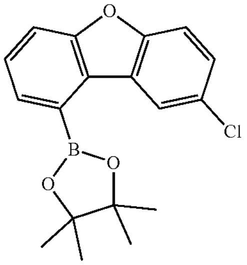 CAS-2140871-51-6 | 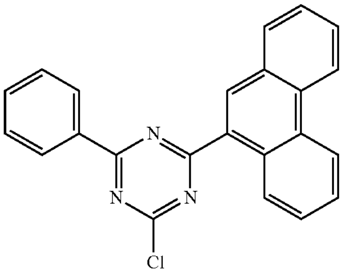 CAS-1821147-80-1 |
| 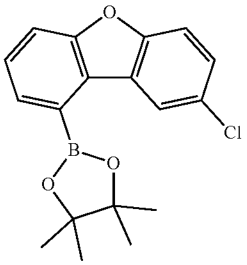 CAS-2140871-51-6 | 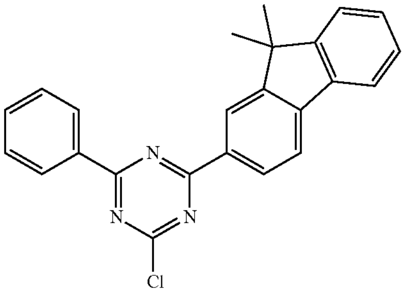 CAS-1618106-98-1 |
| 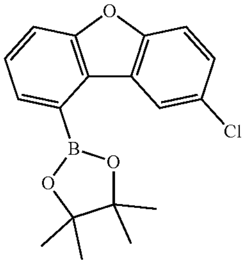 CAS-2140871-51-6 | 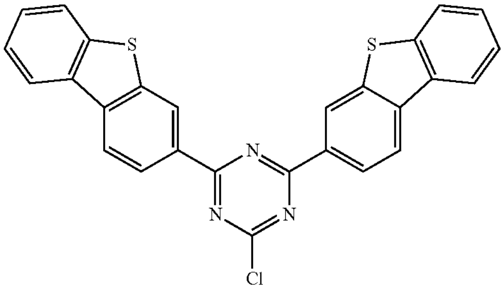 CAS-2172944-02-2 |
| 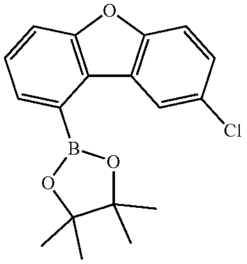 CAS-2140871-51-6 | 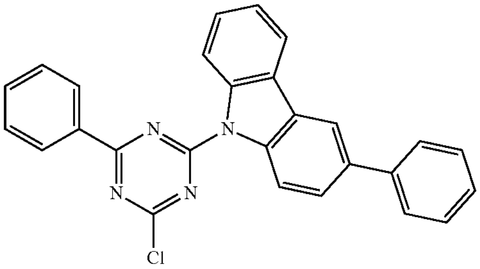 CAS-2260688-83-1 |
| 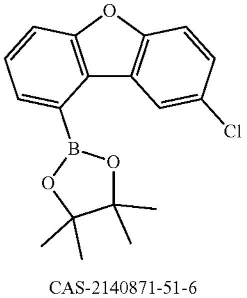 [SMILES: CC1(C)OB(c2cccc3oc4ccc(Cl)cc4c23)OC1(C)C] CAS-2140871-51-6 | 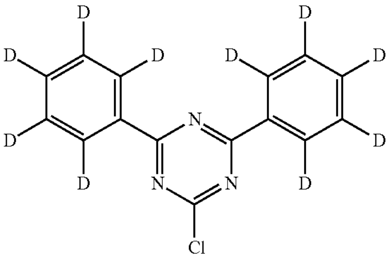 CAS-1300115-09-6 |

-continued
| | |
|---|---|
| 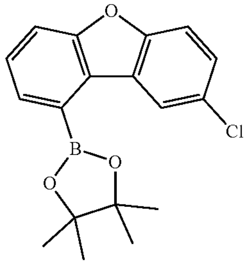<br>CAS-2140871-51-6 | 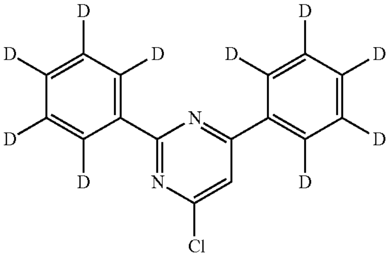<br>CAS-1852466-09-1 |
| Product | Yield |
|---|---|
| 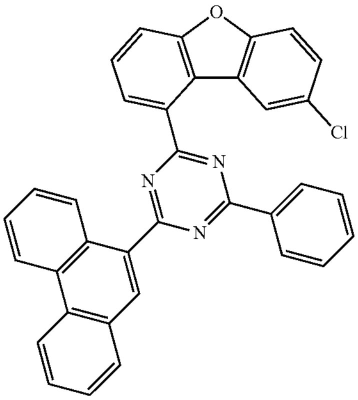<br>S2 | 85% |
| 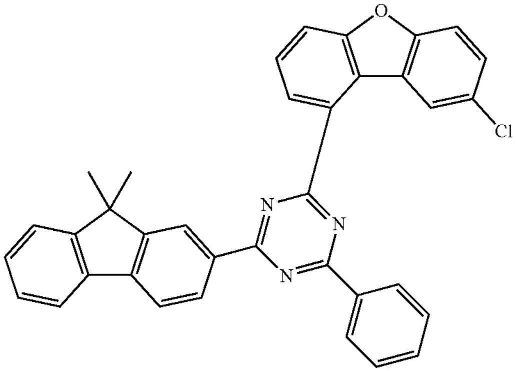<br>S3 | 82% |
| 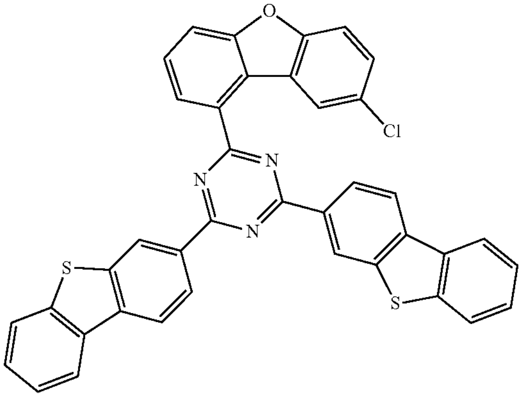<br>S4 | 91% |

-continued
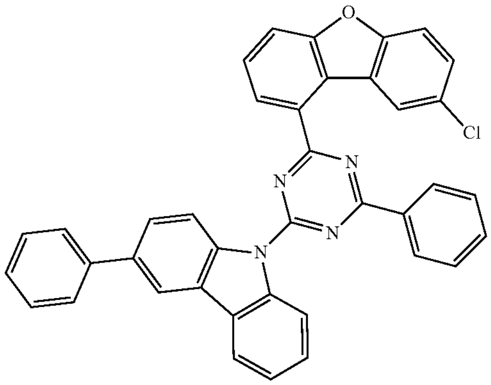
88%
S5
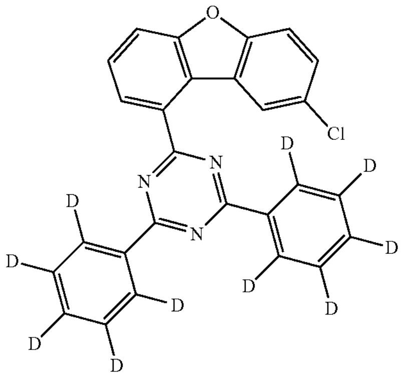
78%
S6
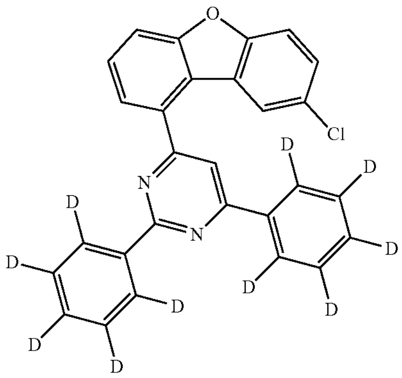
81%
S7

S50:

-continued

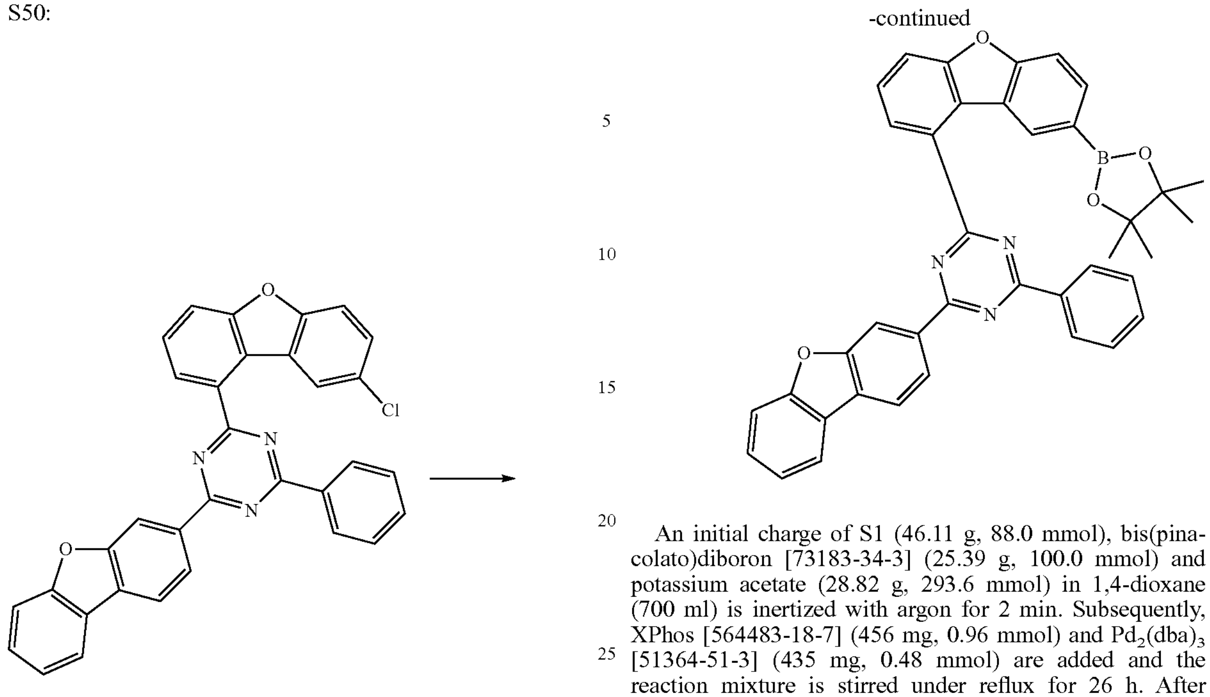

An initial charge of S1 (46.11 g, 88.0 mmol), bis(pinacolato)diboron [73183-34-3] (25.39 g, 100.0 mmol) and potassium acetate (28.82 g, 293.6 mmol) in 1,4-dioxane (700 ml) is inertized with argon for 2 min. Subsequently, XPhos [564483-18-7] (456 mg, 0.96 mmol) and $Pd_2(dba)_3$ [51364-51-3] (435 mg, 0.48 mmol) are added and the reaction mixture is stirred under reflux for 26 h. After cooling, the solvent is removed by rotary evaporation and the residue is worked up by extraction with toluene/water. The organic phase is dried over $Na_2SO_4$ and concentrated to dryness by rotary evaporation. The residue is boiled under reflux with ethyl acetate for 2 h, and the solids are filtered off with suction and washed with ethyl acetate. Yield: 49.4 g (80.2 mmol, 91%) of solids; 97% by $^1H$ NMR.

In an analogous manner, it is possible to prepare the compounds below. Purification can be effected using column chromatography, or recrystallization can be effected using standard solvents such as ethanol, butanol, acetone, ethyl acetate, acetonitrile, toluene, xylene, dichloromethane, methanol, tetrahydrofuran, n-butyl acetate, 1,4-dioxane, dimethyl sulfoxide, N,N-dimethylformamide, N,N-dimethylacetamide, N-methylpyrrolidone etc.

| Reactant | Product | Yield |
|---|---|---|
| 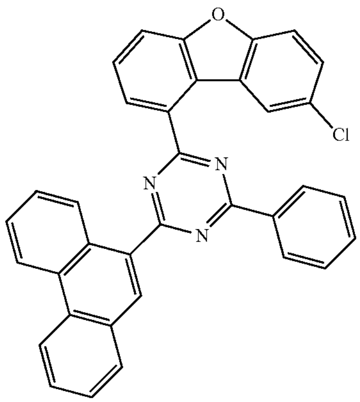 S2 | 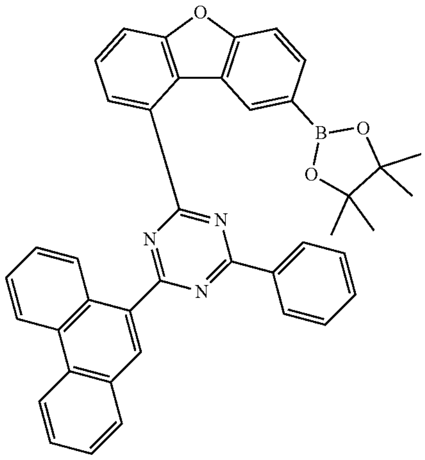 S51 | 90% |

-continued
| Reactant | Product | Yield |
|---|---|---|
| 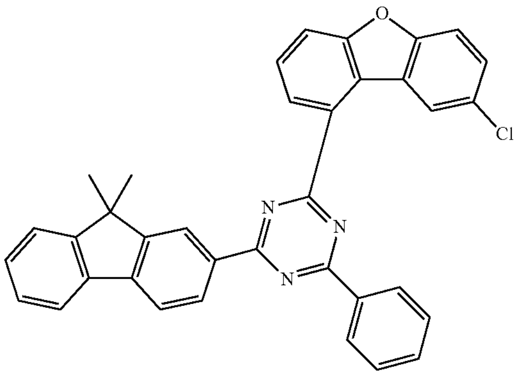 S3 | 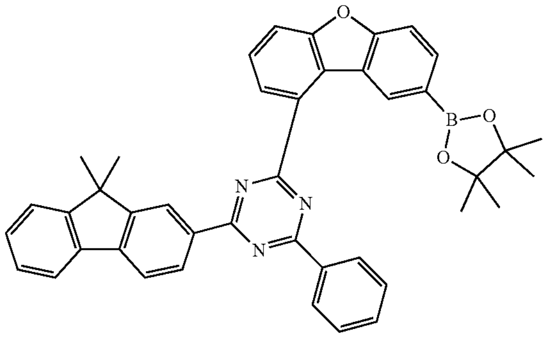 S52 | 88% |
| 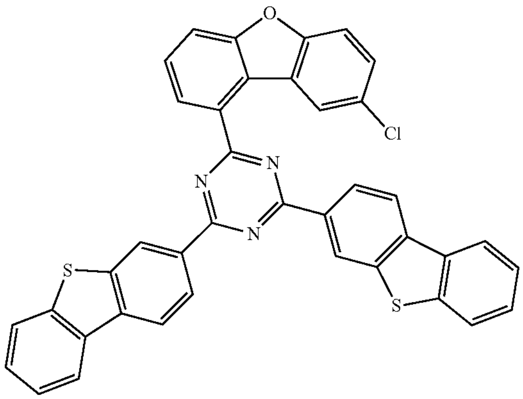 S4 | 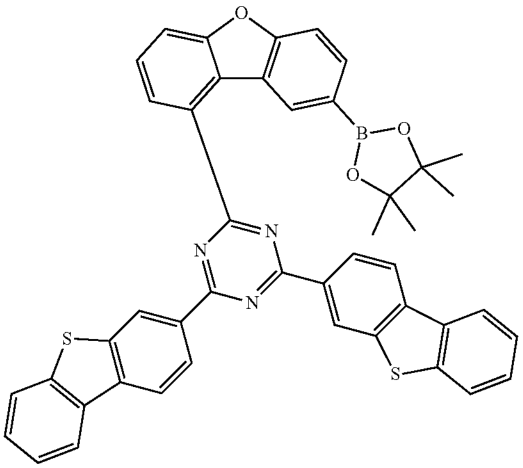 S53 | 84% |
| 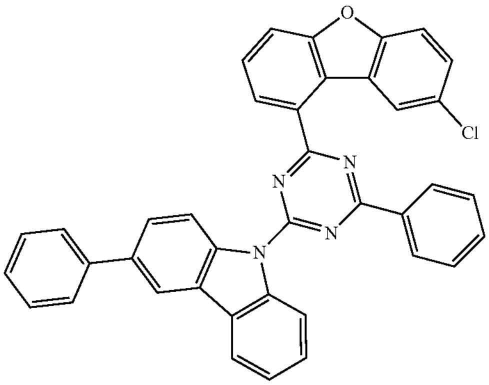 S5 | 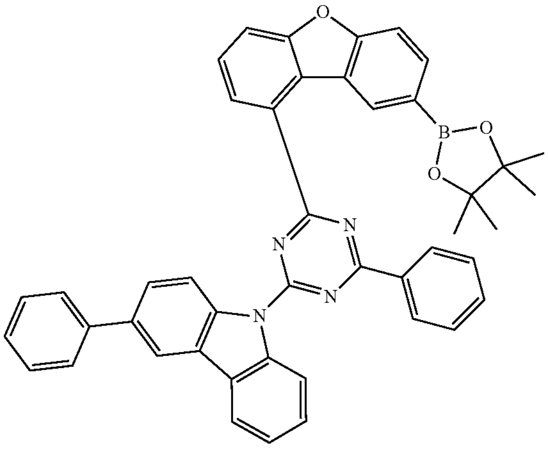 S54 | 80% |

-continued

| Reactant | Product | Yield |
| --- | --- | --- |
| 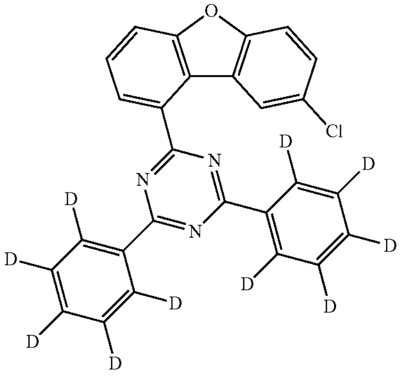 S6 | 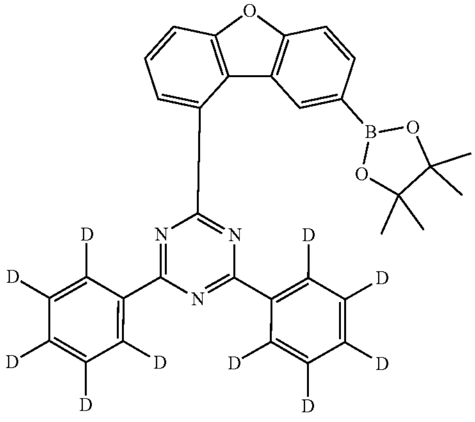 S55 | 82% |
| 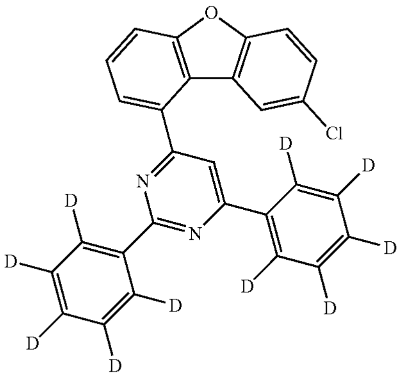 S7 | 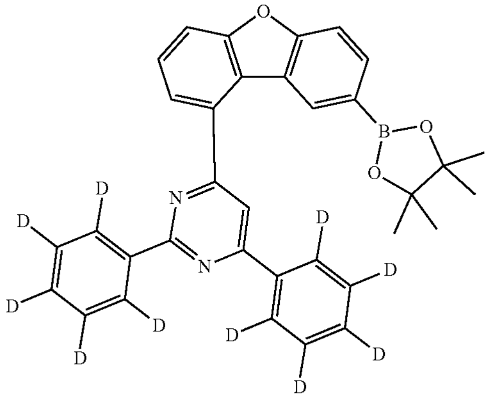 S56 | 79% |

S100:

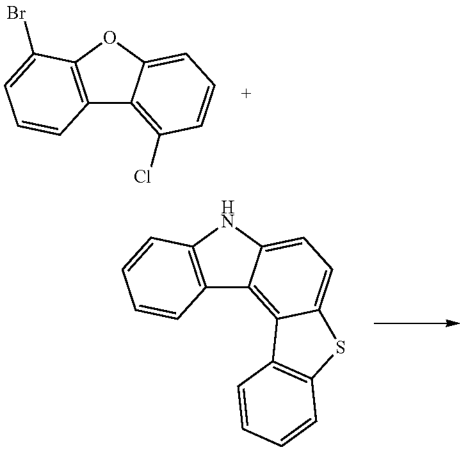

-continued

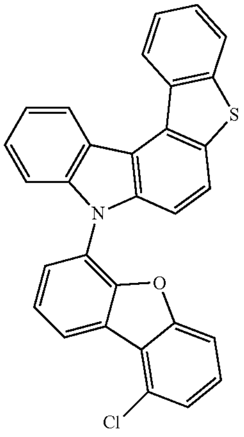

Under inert atmosphere, 6-bromo-1-chlorodibenzofuran [2144800-21-3] (28.15 g, 100 mmol), 8H-[1]benzothieno-[2,3-c]carbazole [1255309-17-1] (28.70 g, 105 mmol) and sodium tert-butoxide (19.21 g, 200 mmol) were initially charged in 1000 ml of ortho-xylene. Subsequently, tri-tert-butylphosphine [13716-12-6] (1 mol/l solution in toluene, 5.0 ml, 5.0 mmol) and tris(dibenzylideneacetone)dipalladium [51364-51-3] (1.14 g, 1.25 mmol) are added one after the other, and the reaction mixture is heated under reflux for 16 h. The reaction mixture is cooled down to room temperature and worked up by extraction with toluene/water. The organic phases are combined and dried over $Na_2SO_4$, and the solvent is removed under reduced pressure on a rotary evaporator. The resultant solids are suspended in 300 ml of ethanol, stirred under reflux for 1 h and filtered off with suction. The crude product is recrystallized from ethyl acetate. Yield: 32.2 g (68 mmol, 68%) of solids, 97% by $^1H$ NMR.

In an analogous manner, it is possible to prepare the compounds below. Purification can be effected using column chromatography, or recrystallization can be effected using standard solvents such as ethanol, butanol, acetone, ethyl acetate, acetonitrile, toluene, xylene, dichloromethane, methanol, tetrahydrofuran, n-butyl acetate, 1,4-dioxane, dimethyl sulfoxide, N,N-dimethylformamide, N,N-dimethylacetamide, N-methylpyrrolidone etc.

S150:

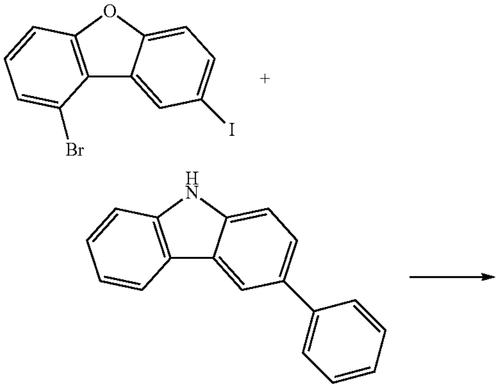

| Reactant 1 | Reactant 2 | Product | Yield |
| --- | --- | --- | --- |
| 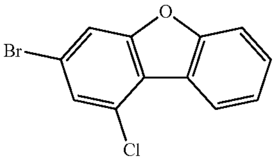 [SMILES: Clc1cc(Br)cc2oc3ccccc3c12] | 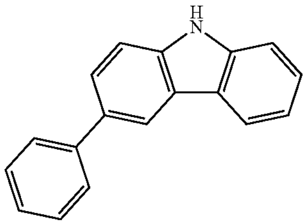 CAS-103012-26-6 | 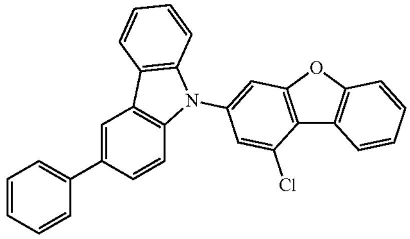 S101 | 71% |
| 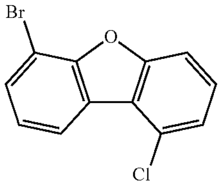 [SMILES: Clc1cccc2oc3c(Br)cccc3c12] | 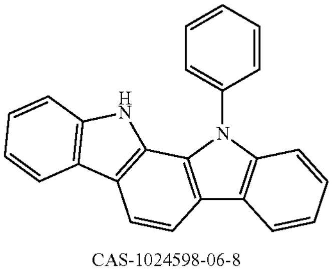 [SMILES: c1ccc(-n2c3ccccc3c3ccc4c5ccccc5[nH]c4c32)cc1] CAS-1024598-06-8 | 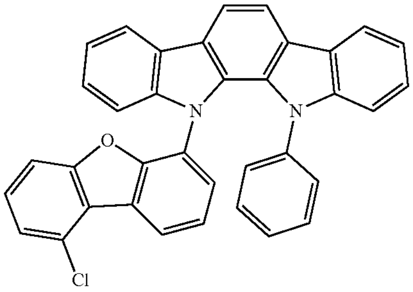 S102 | 34% |
| 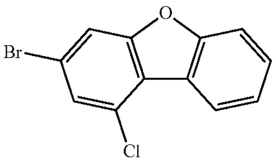 [SMILES: Clc1cc(Br)cc2oc3ccccc3c12] | 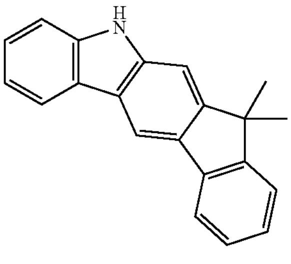 CAS-1257220-47-5 | 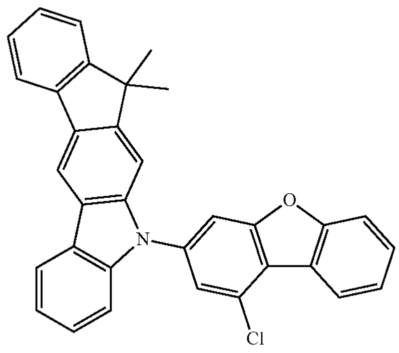 S103 | 59% |

-continued

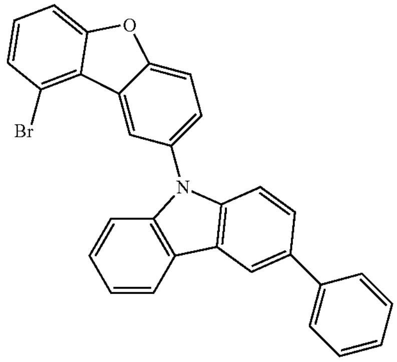

Under an inert atmosphere, an initial charge of 1-bromo-8-iododibenzofuran [1822311-11-4] (37.28 g, 100 mmol), 3-phenyl-9H-carbazole [103012-26-6] (16.71 g, 100 mmol) of potassium carbonate (34.55 g, 250 mmol), copper iodide (3.81 g, 20.0 mmol) and 1,3-di(2-pyridinyl)propane-1,3-dione (4.52 g, 20.0 mmol) in DMF (350 ml) are inertized with argon for a further 15 min and then stirred at 115° C. for 32 h.

The mixture is left to cool down to room temperature, filtered through a Celite bed and washed through twice with 200 ml of DMF, and the filtrate is concentrated to dryness on a rotary evaporator. The residue is worked up by extraction with dichloromethane/water, and the organic phase is washed twice with water and once with saturated NaCl solution and dried over $Na_2SO_4$. 150 ml of ethanol are added, dichloromethane is drawn off on a rotary evaporator down to 500 mbar, and the precipitated solids are filtered off with suction and washed with ethanol. Yield: 24.71 g (50.6 mmol, 51%) of grey solid; 95% by $^1$H NMR.

In an analogous manner, it is possible to prepare the compounds below. Purification can be effected using column chromatography, or recrystallization can be effected using standard solvents such as ethanol, butanol, acetone, ethyl acetate, acetonitrile, toluene, xylene, dichloromethane, methanol, tetrahydrofuran, n-butyl acetate, 1,4-dioxane, dimethyl sulfoxide, N,N-dimethylformamide, N,N-dimethylacetamide, N-methylpyrrolidone etc.

| Reactant 1 | Reactant 2 | Product | Yield |
|---|---|---|---|
| 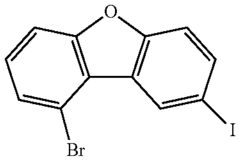 CAS-1822311-11-4 | 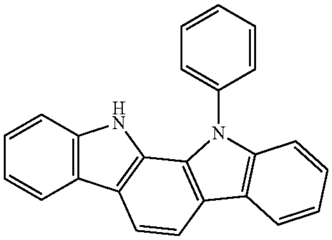 CAS-1024598-06-8 | 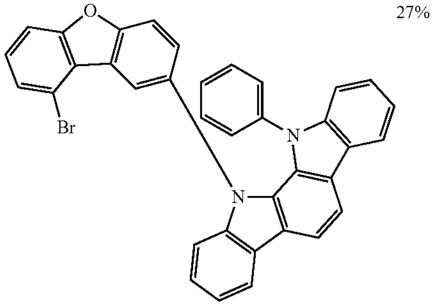 S151 | 27% |
| 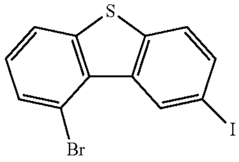 CAS-1822311-12-5 | 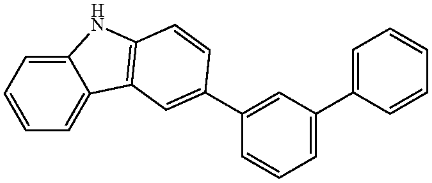 CAS-1643526-99-1 | 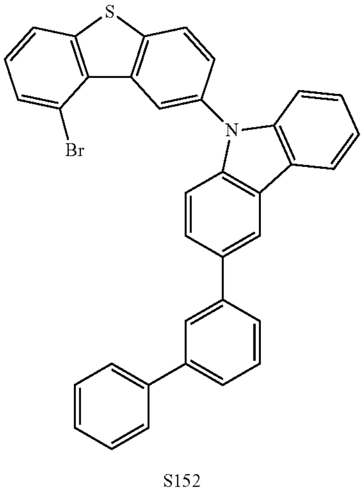 S152 | 57% |

-continued
| Reactant 1 | Reactant 2 | Product | Yield |
| --- | --- | --- | --- |
| 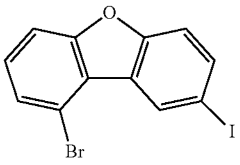 CAS-1822311-11-4 | 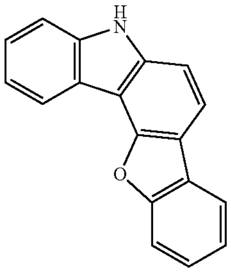 CAS-1199616-66-4 | 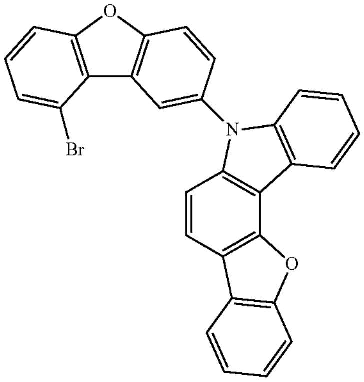 S153 | 49% |
| 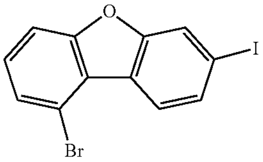 CAS-2244710-46-9 | 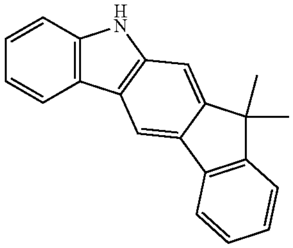 CAS-1257220-47-5 | 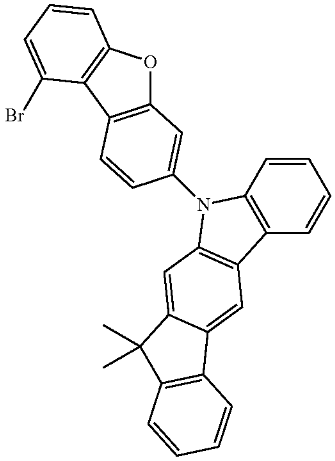 S154 | 51% |
| 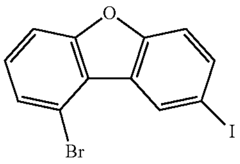 CAS-1822311-11-4 | 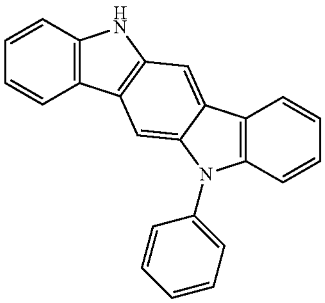 CAS-1316311-27-9 | 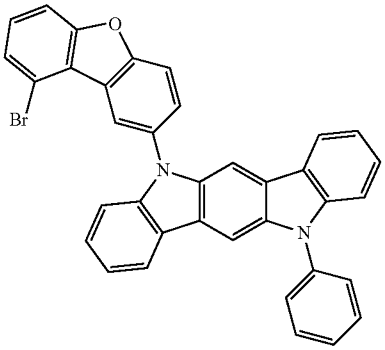 S155 | 50% |

-continued
| Reactant 1 | Reactant 2 | Product | Yield |
|---|---|---|---|
| 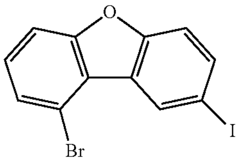 CAS-1822311-11-4 | 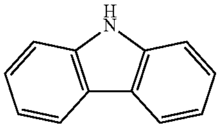 CAS-86-74-8 | 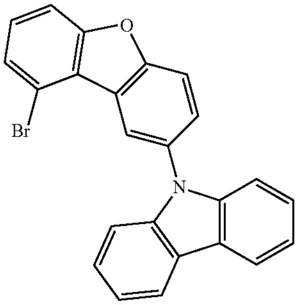 S156 | 61% |
| 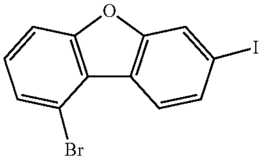 CAS-2244710-46-9 | 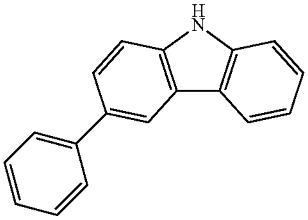 CAS-103012-26-6 | 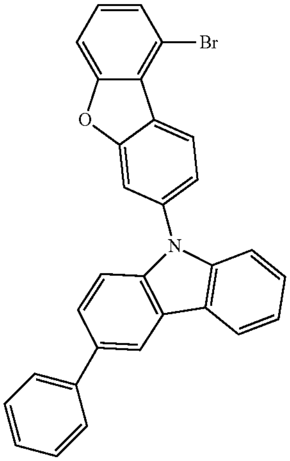 S157 | 54% |
| 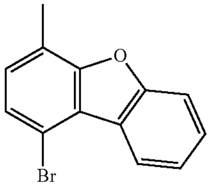 CAS-1923736-35-9 | 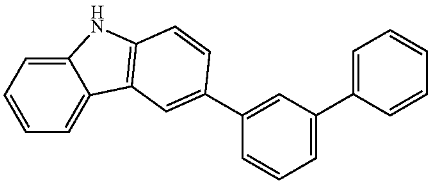 CAS-1643526-99-1 | 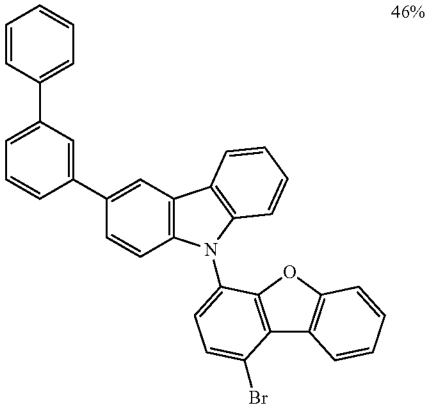 S158 | 46% |

S200:

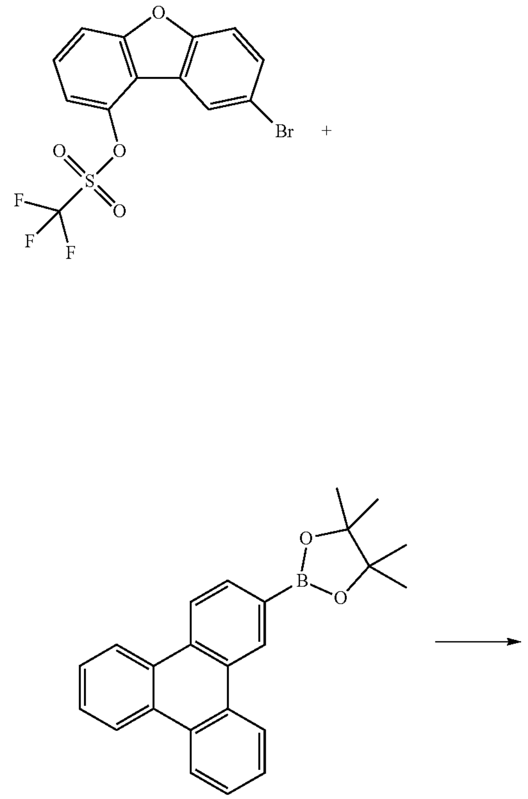

-continued

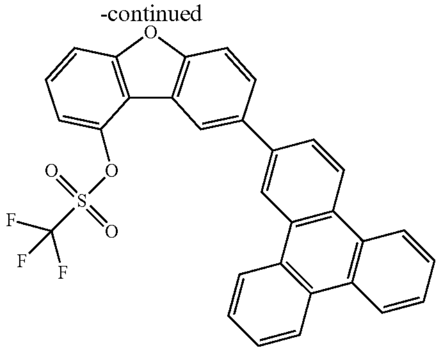

To an initial charge of 8-bromodibenzofuran-1-yl trifluoromethanesulfonate [2247123-46-0] (47.00 g, 118.9 mmol), 4,4,5,5-tetramethyl-2-(2-triphenylenyl)-1,3,2-dioxaborolane (49.72 g, 140.4 mmol) and $K_2CO_3$ (32.88 g, 237.9 mmol) in a flask are added toluene (500 ml) and water (150 ml), and the mixture is inertized with argon for 30 min. Subsequently, $Pd_2(dba)_3$ (545 mg, 0.59 mmol) and tri-ortho-tolylphosphine [6163-58-2] (724 mg, 2.38 mmol) are added and the mixture is heated under reflux for 24 h. After cooling, the precipitated solids are filtered off with suction and washed twice with ethanol. The crude product is extracted by stirring under reflux in ethanol for 2 h, and the solids are filtered off with suction after cooling. Yield: 58.8 g (108 mmol, 91%) of solids; purity 98% by $^1H$ NMR.

In an analogous manner, it is possible to prepare the compounds below. Purification can be effected using column chromatography, or recrystallization can be effected using standard solvents such as ethanol, butanol, acetone, ethyl acetate, acetonitrile, toluene, xylene, dichloromethane, methanol, tetrahydrofuran, n-butyl acetate, 1,4-dioxane, dimethyl sulfoxide, N,N-dimethylformamide, N,N-dimethylacetamide, N-methylpyrrolidone etc.

| Reactant 1 | Reactant 2 | Product | Yield |
|---|---|---|---|
| 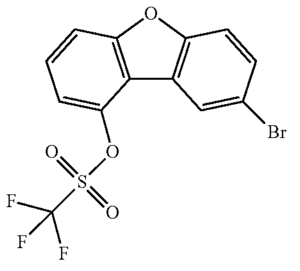 CAS-2247123-46-0 | 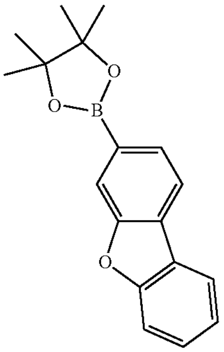 CAS-1056113-50-8 | 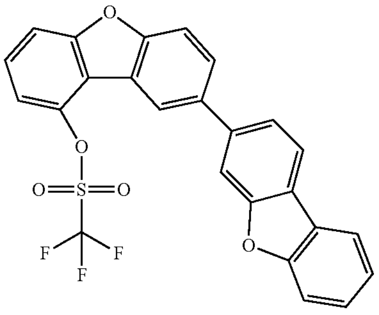 S201 | 89% |

-continued
| Reactant 1 | Reactant 2 | Product | Yield |
| --- | --- | --- | --- |
| 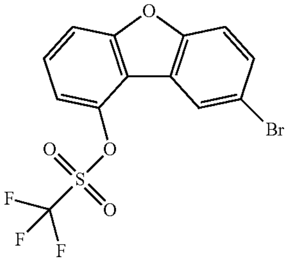<br>CAS-2247123-46-0 | 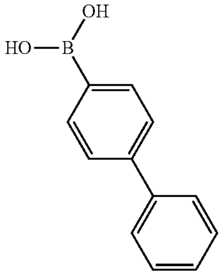<br>CAS-5122-94-1 | 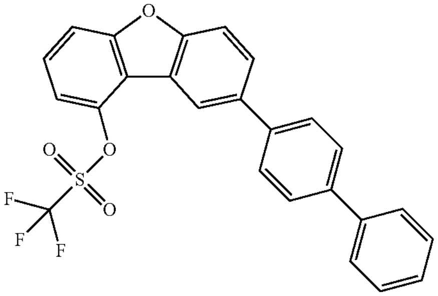<br>S202 | 92% |
| 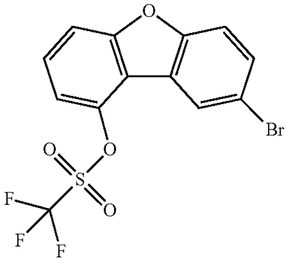<br>CAS-2247123-46-0 | 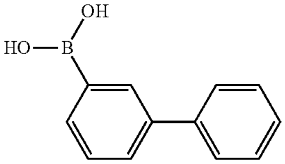<br>CAS-5122-95-2 | 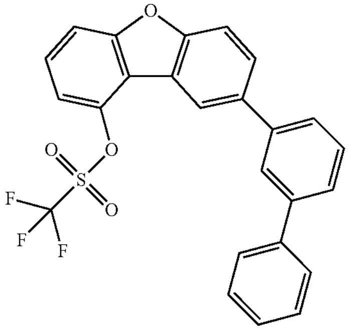<br>S203 | 83% |
| 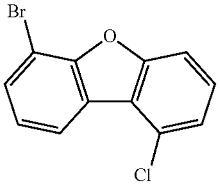<br>CAS-2144800-21-3 | 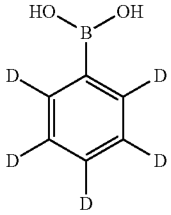<br>CAS-215527-70-1 | 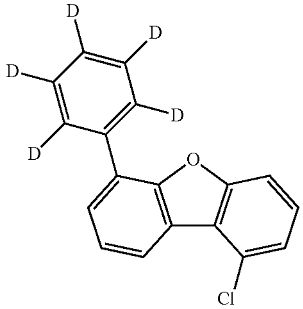<br>S204 | 91% |
| 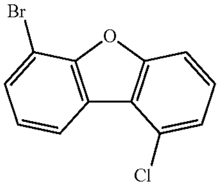<br>CAS-2144800-21-3 | 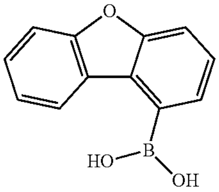<br>CAS-162607-19-4 | 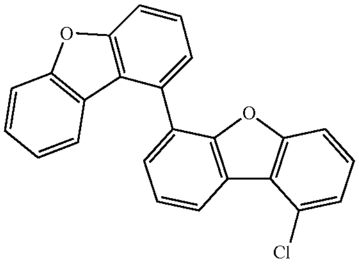<br>S205 | 80% |

-continued
| Reactant 1 | Reactant 2 | Product | Yield |
|---|---|---|---|
| 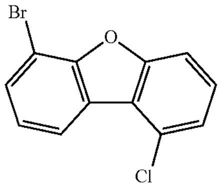 CAS-2144800-21-3 | 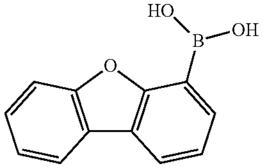 CAS-100124-06-9 | 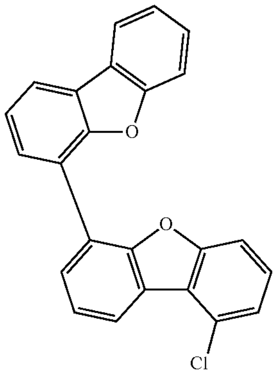 S206 | 82% |
| 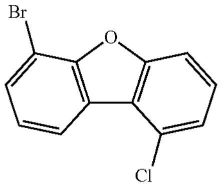 CAS-2144800-21-3 | 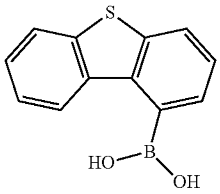 CAS-1245943-60-5 | 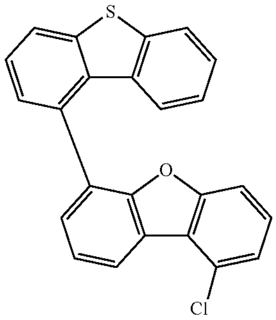 S207 | 85% |
| 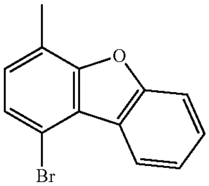 CAS-1923736-35-9 | 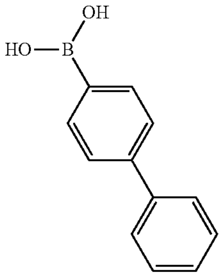 CAS-5122-94-1 | 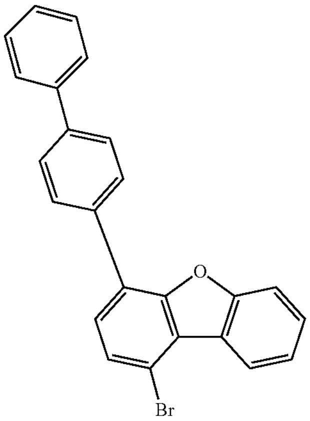 S208 | 77% |

-continued

| Reactant 1 | Reactant 2 | Product | Yield |
| --- | --- | --- | --- |
| 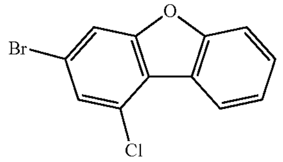 [SMILES: Clc1cc(Br)cc2oc3ccccc3c12] | 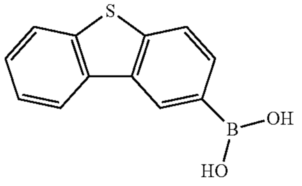 CAS-668983-97-9 | 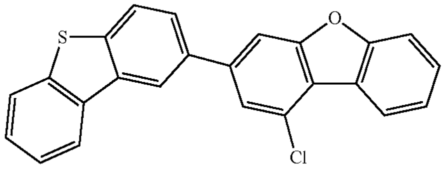 S209 | 90% |

Preparation of the Compounds of the Invention:

Synthesis of P1:

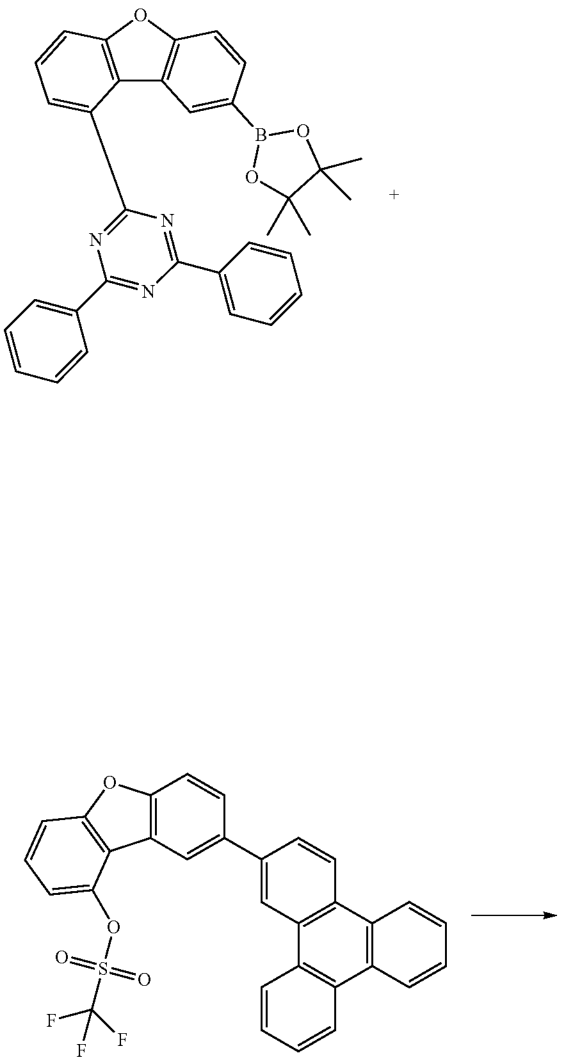

-continued

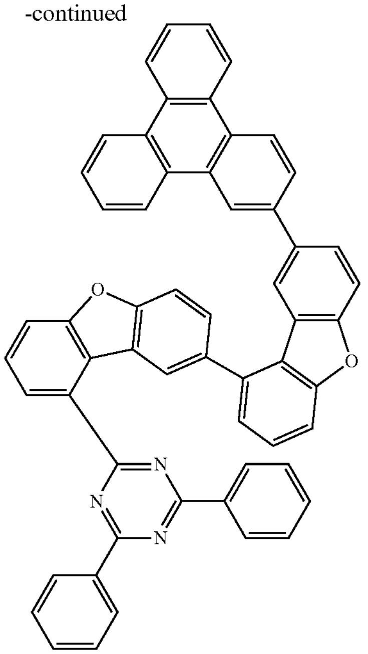

To an initial charge of 2,4-diphenyl-6-[8-(4,4,5,5-tetramethyl-1,3,2-dioxaborolan-2-yl)-1-dibenzofuranyl]-1,3,5-triazine [2138490-96-5] (15.31 g, 29.1 mmol), S200 (15.06 g, 27.8 mmol) and $K_3PO_4$ (12.17 g, 57.3 mmol) in a flask are added tetrahydrofuran (200 ml) and water (50 ml), and the mixture is inertized with argon for 30 min. Subsequently, $Pd(OAc)_2$ (124 mg, 0.55 mmol) and XPhos [564483-18-7] (556 mg, 1.11 mmol) are added and the mixture is heated under reflux for 24 h. After cooling, the precipitated solids are filtered off with suction and washed twice with water and twice with ethanol. The crude product is subjected to hot extraction with toluene/heptane (1:1) three times, then recrystallized three times from toluene and finally sublimed under high vacuum. Yield: 14.8 g (18.7 mmol, 67%); purity: >99.9% by HPLC In an analogous manner, it is possible to prepare the compounds below. The catalyst system used here (palladium source and ligand) may also be $Pd_2(dba)_3$ with SPhos [657408-07-6] or bis(triphenylphosphine)palladium(II) chloride [13965-03-2]. Purification can also be effected using column chromatography, or recrystallization or hot extraction using other standard solvents such as ethanol, butanol, acetone, ethyl acetate, acetonitrile, toluene, xylene, dichloromethane, methanol, tetrahydrofuran, n-butyl acetate, 1,4-dioxane, or recrystallization using high boilers such as dimethyl sulfoxide, N,N-dimethylformamide, N,N-dimethylacetamide, N-methylpyrrolidone, etc.

| Reactant 1 | Reactant 2 | Product | Yield |
|---|---|---|---|
| 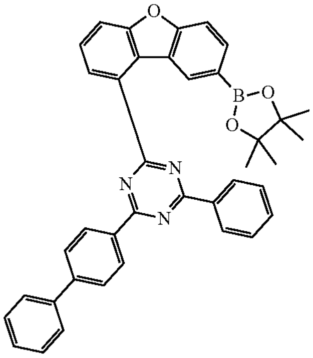 CAS-2173554-87-3 | 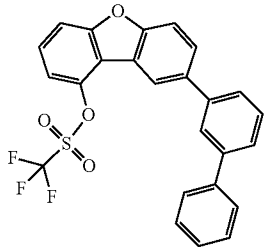 S203 | 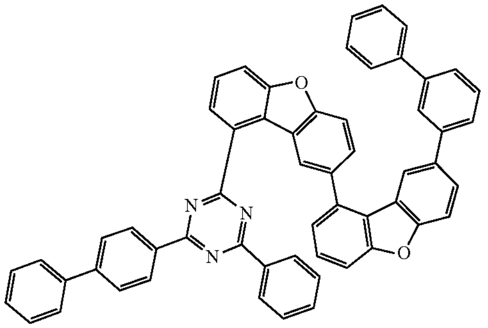 P2 | 50% |
| 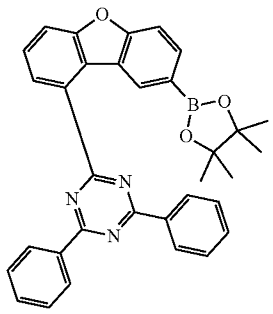 CAS-2138490-96-5 | 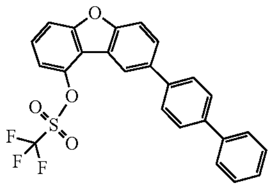 S202 | 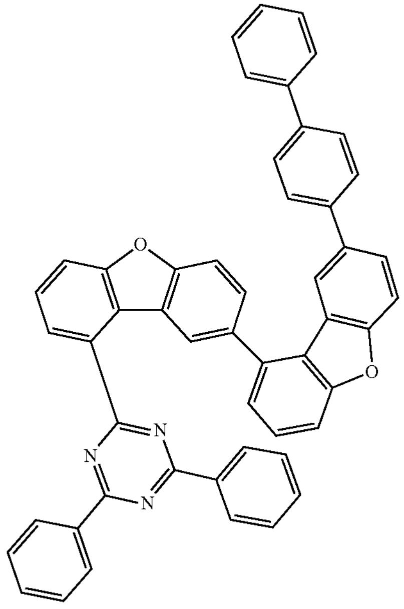 P3 | 48% |
| 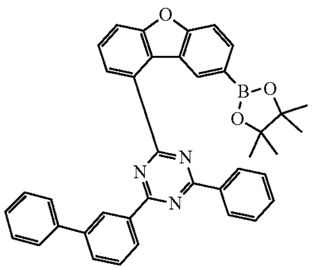 CAS-2173554-91-9 | 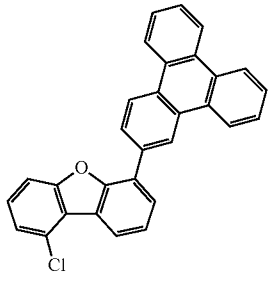 CAS-2173555-60-5 | 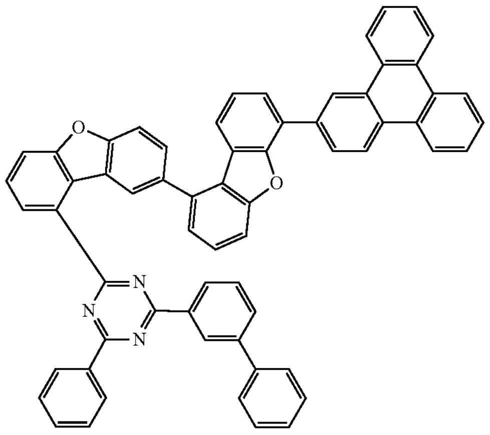 P4 | 55% |

-continued
| Reactant 1 | Reactant 2 | Product | Yield |
| --- | --- | --- | --- |
| 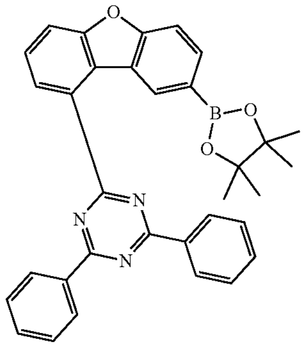 CAS-2138490-96-5 | 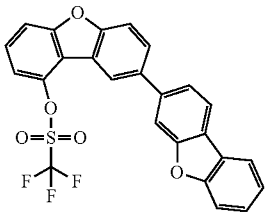 S201 | 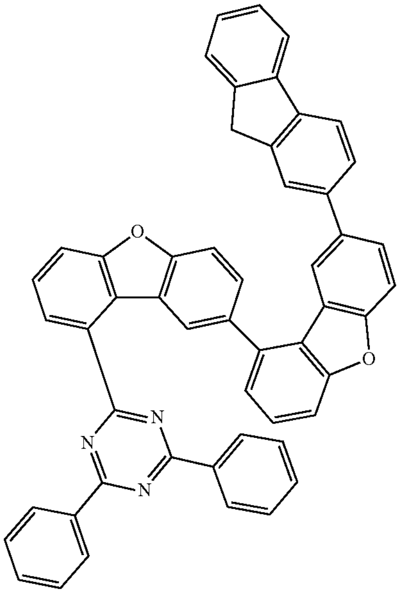 P5 | 57% |
| 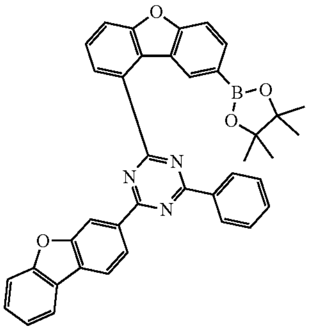 S50 | 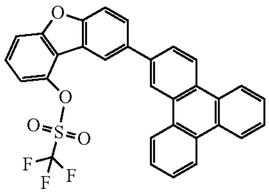 S200 | 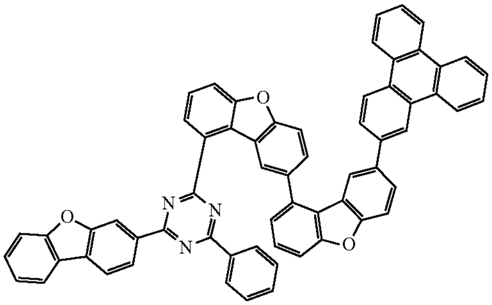 P6 | 56% |
| 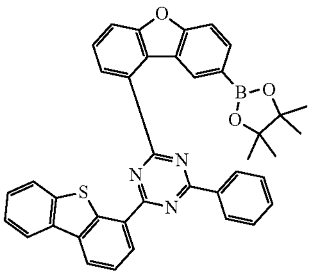 CAS-2268673-84-1 | 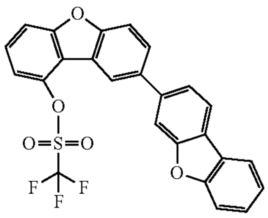 S201 | 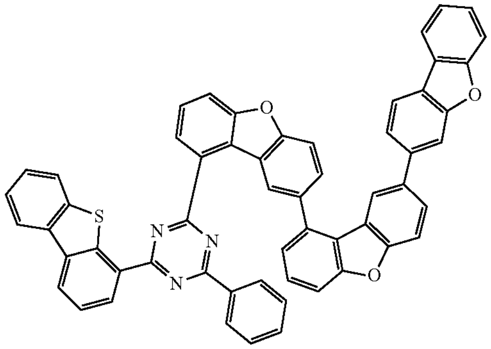 P7 | 63% |

-continued
| Reactant 1 | Reactant 2 | Product | Yield |
|---|---|---|---|
| 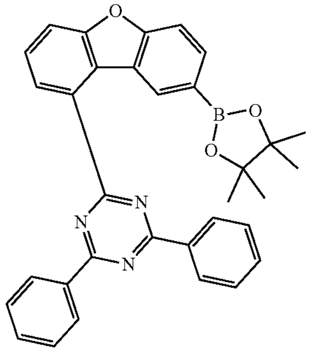 CAS-2140928-39-6 | 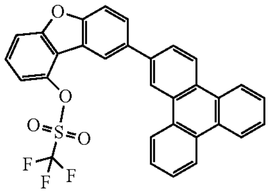 S200 | 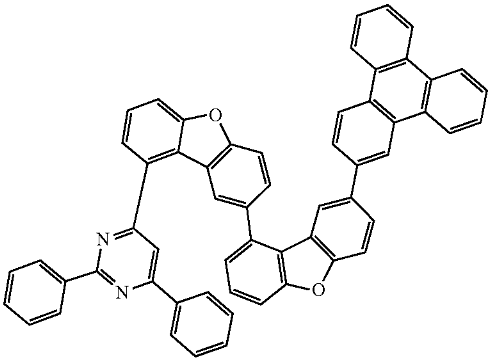 P8 | 52% |
| 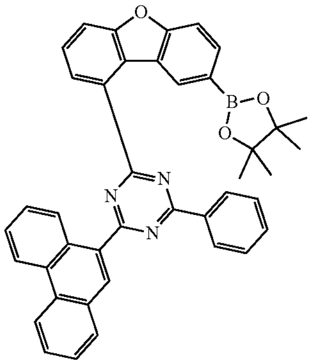 S51 | 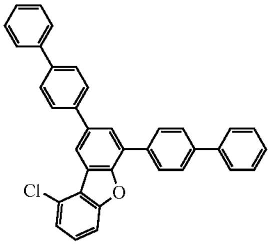 CAS-2299272-10-7 | 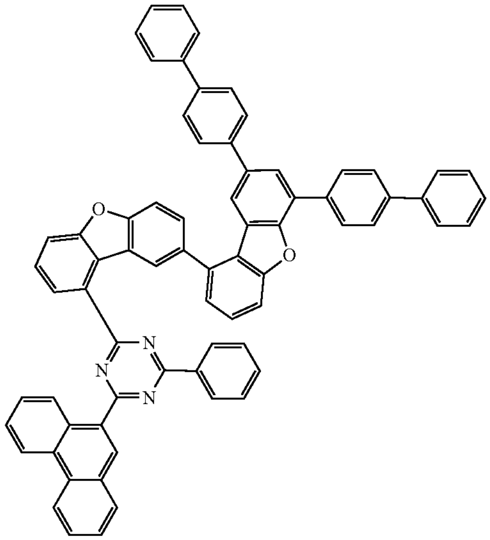 P9 | 55% |
| 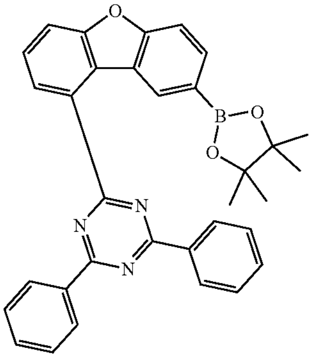 CAS-2138490-96-5 | 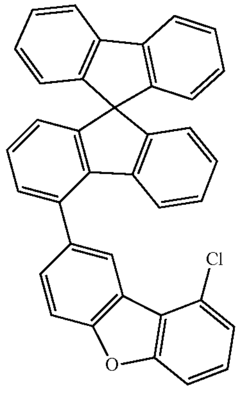 CAS-2055863-76-6 | 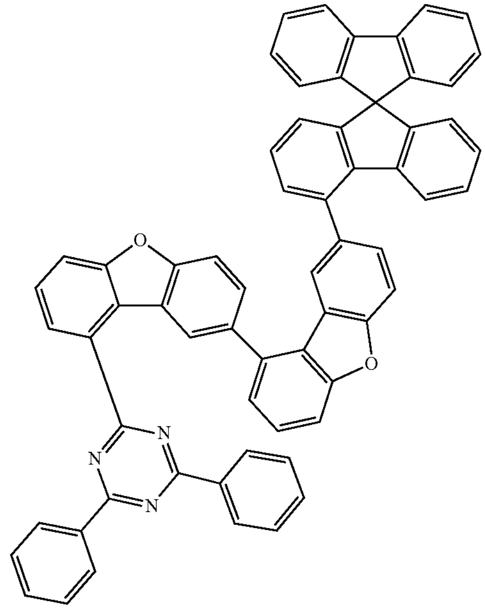 P10 | 62% |

-continued
| Reactant 1 | Reactant 2 | Product | Yield |
|---|---|---|---|
| 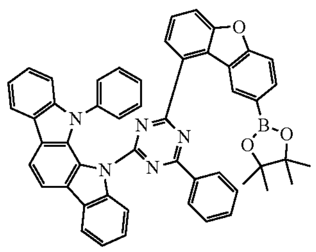 CAS-1311268-20-8 | 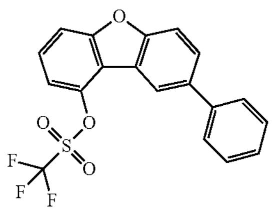 CAS-2033132-91-9 | 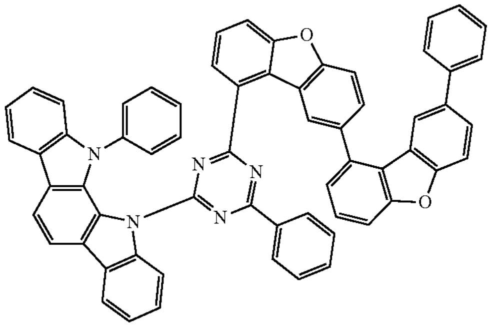 P11 | 49% |
| 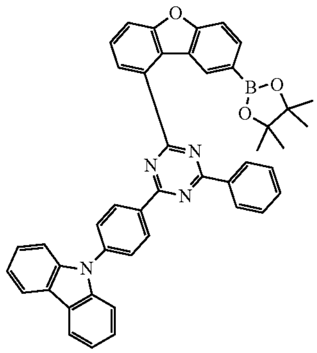 CAS-2268673-81-8 | 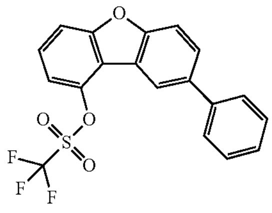 CAS-2033132-91-9 | 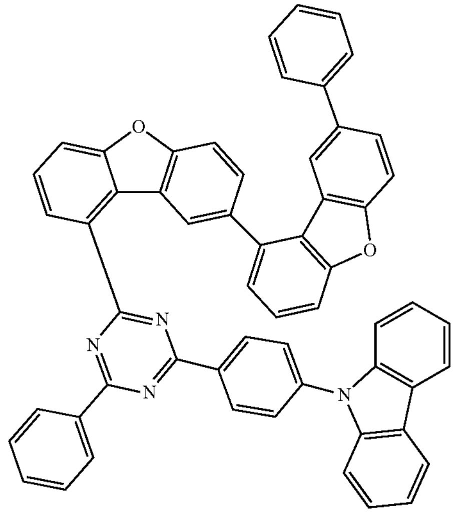 P12 | 50% |
| 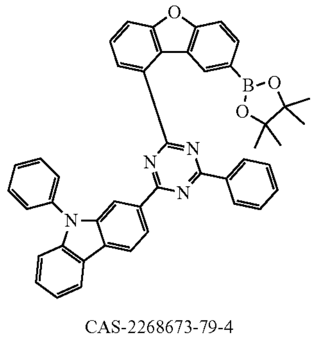 [SMILES: CC1(C)OB(c2ccc3oc4cccc(-c5nc(-c6ccccc6)nc(-c6ccc7c8ccccc8n(-c8ccccc8)c7c6)n5)c4c3c2)OC1(C)C] CAS-2268673-79-4 | 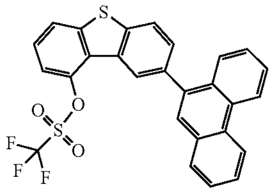 CAS-2096512-63-7 | 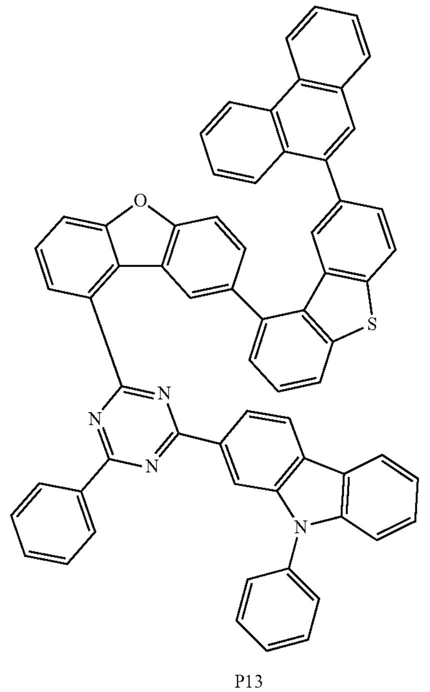 P13 | 60% |

-continued
| Reactant 1 | Reactant 2 | Product | Yield |
|---|---|---|---|
| 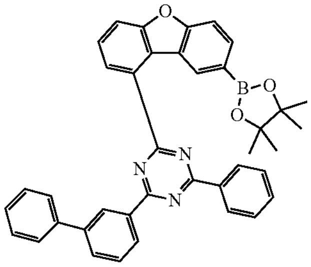 CAS-2173554-91-9 | 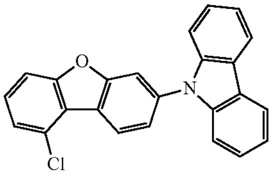 CAS-2245035-71-4 | 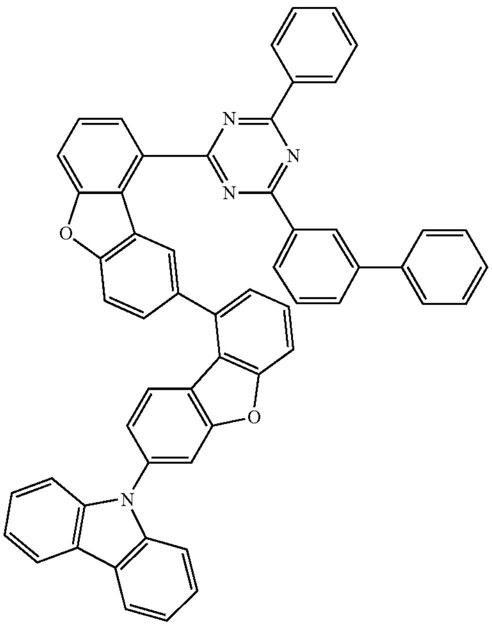 P14 | 57% |
| 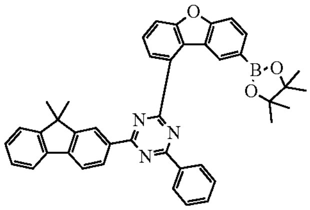 S52 | 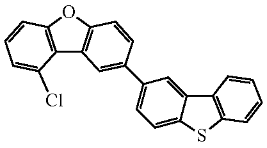 CAS-2055863-73-3 | 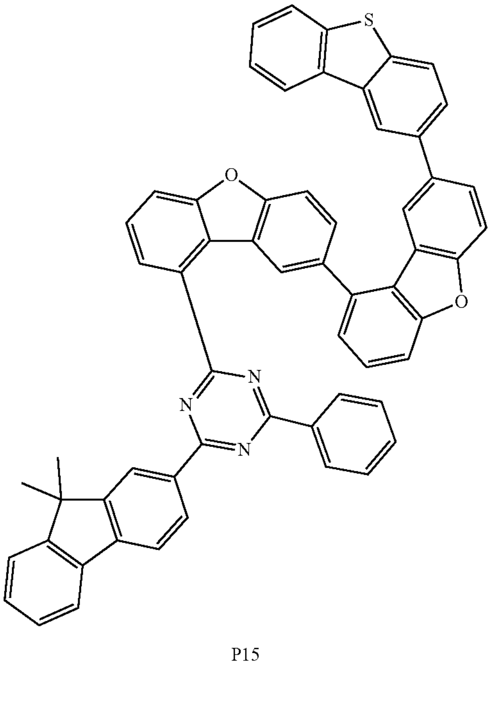 P15 | 45% |

-continued
| Reactant 1 | Reactant 2 | Product | Yield |
| --- | --- | --- | --- |
| 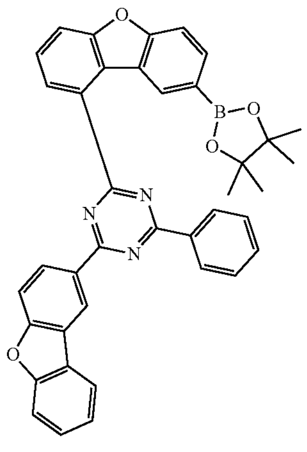 CAS-2178073-73-7 | 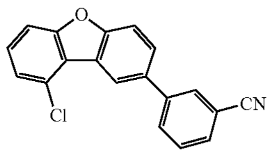 CAS-2225909-72-6 | 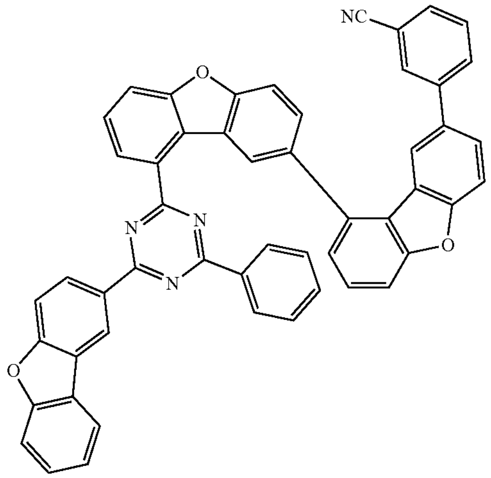 P16 | 39% |
| 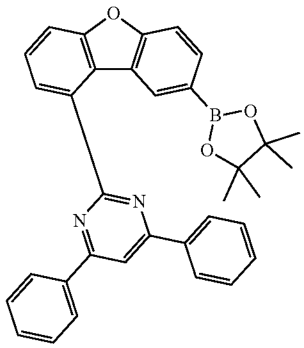 CAS-2140928-38-5 | 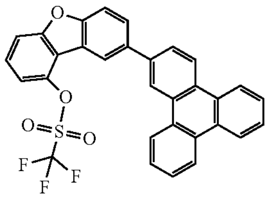 S200 | 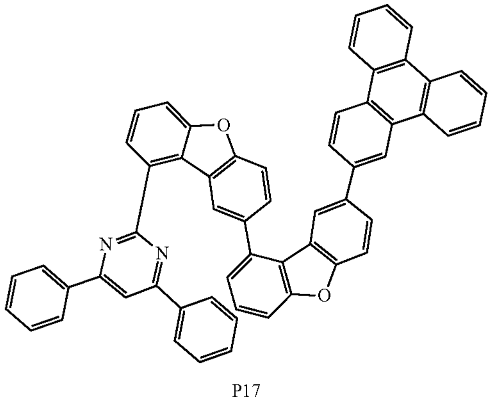 P17 | 60% |

-continued
| Reactant 1 | Reactant 2 | Product | Yield |
| --- | --- | --- | --- |
| 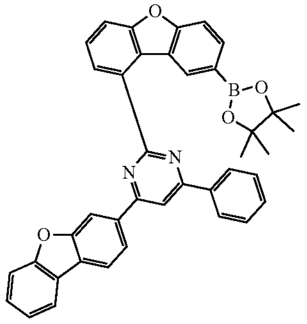 S50 | 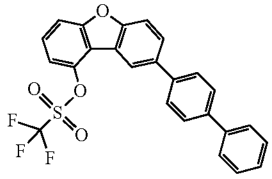 S202 | 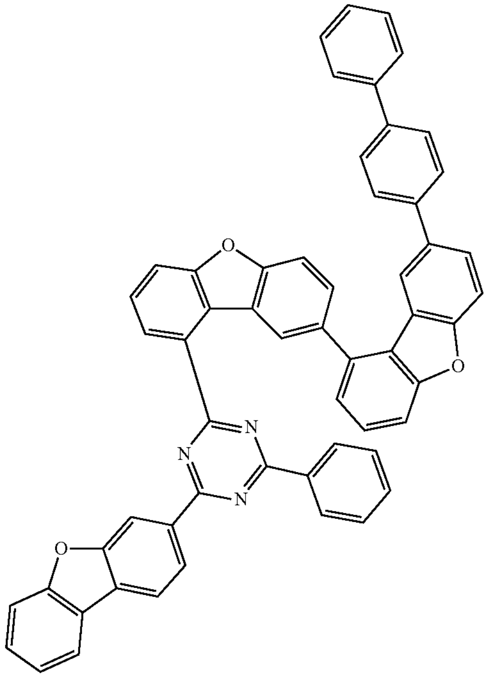 P18 | 51% |
| 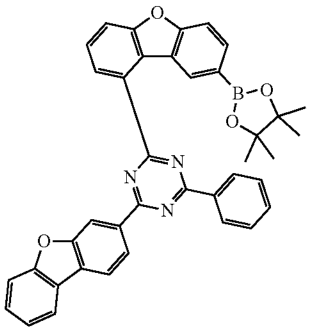 S50 | 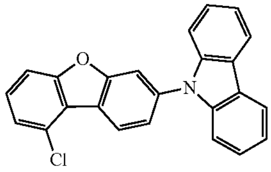 CAS-2245035-71-4 | 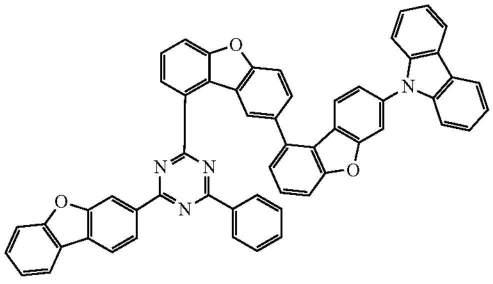 P19 | 55% |
| 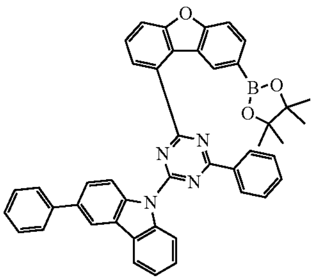 S54 | 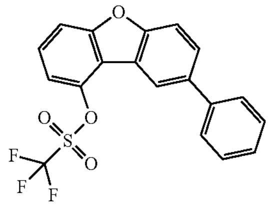 CAS-2033132-91-9 | 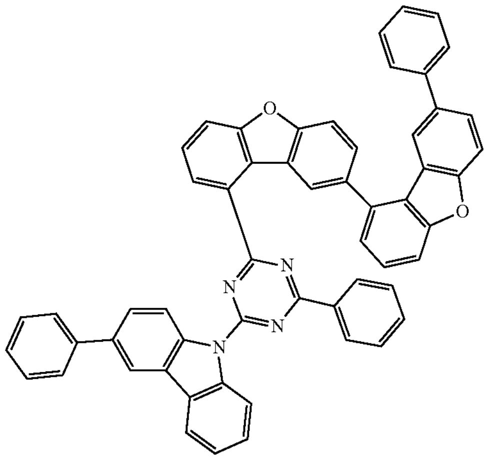 P20 | 48% |

-continued
| Reactant 1 | Reactant 2 | Product | Yield |
| --- | --- | --- | --- |
| 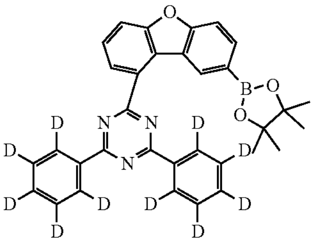 S55 | 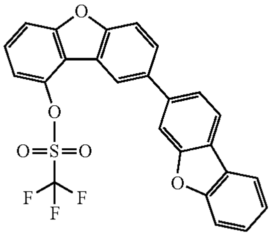 S201 | 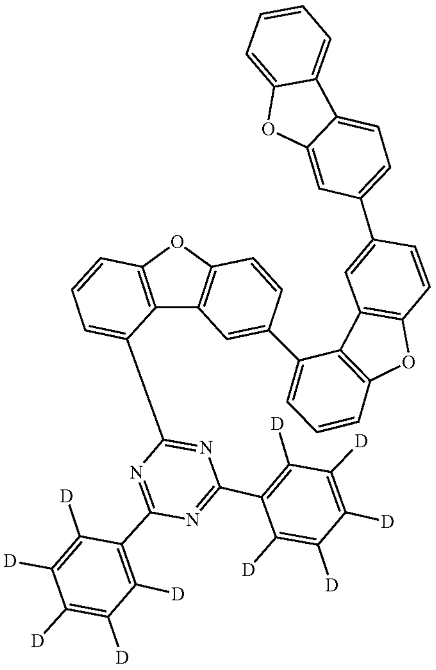 P21 | 51% |
| 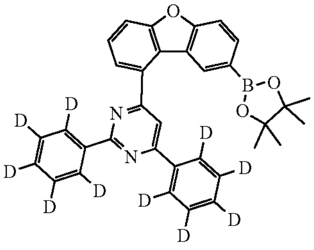 S56 | 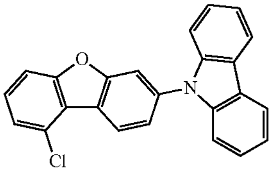 CAS-2245035-71-4 | 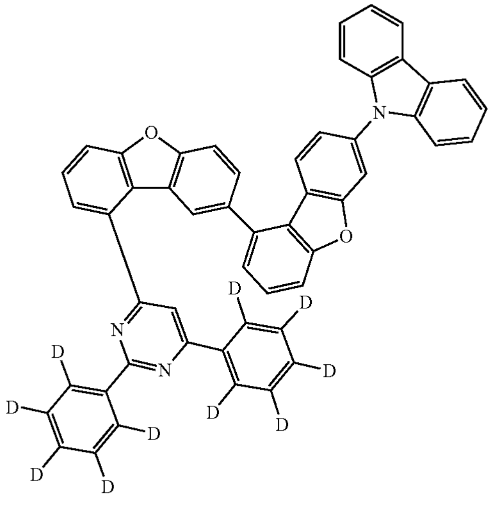 P22 | 44% |

-continued
| Reactant 1 | Reactant 2 | Product | Yield |
| --- | --- | --- | --- |
| 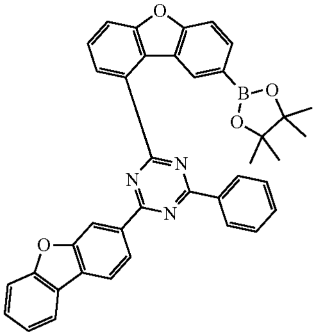 S50 | 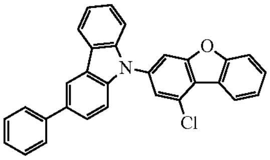 S101 | 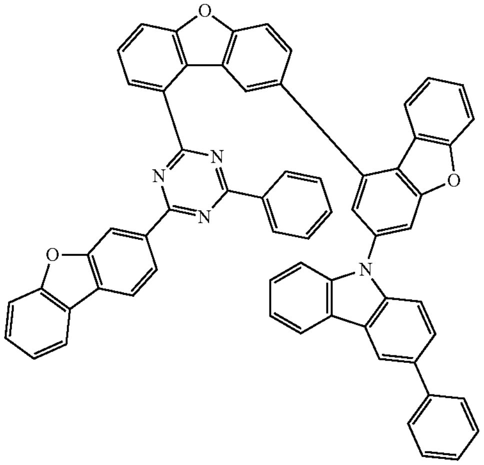 P23 | 44% |
| 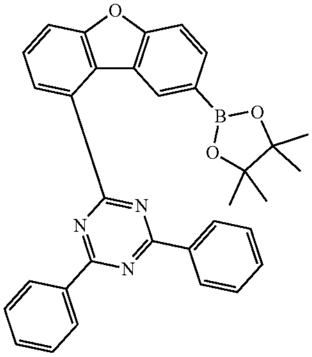 CAS-2138490-96-5 | 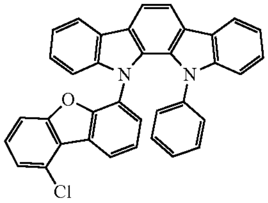 S102 | 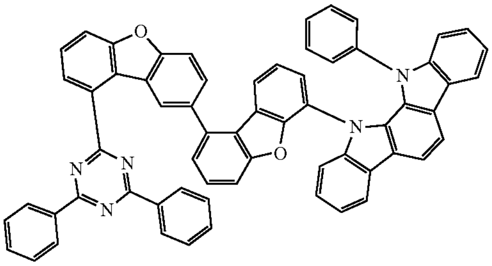 P24 | 60% |
| 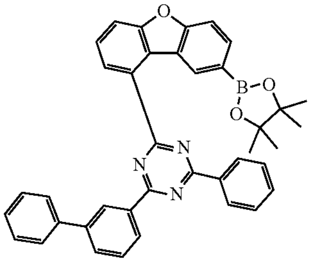 CAS-2173554-91-9 | 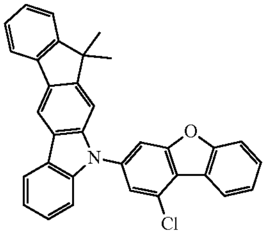 S103 | 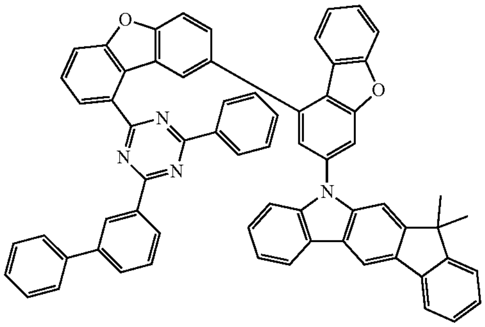 P25 | 53% |

-continued
| Reactant 1 | Reactant 2 | Product | Yield |
|---|---|---|---|
| 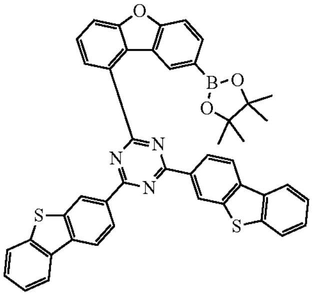 S53 | 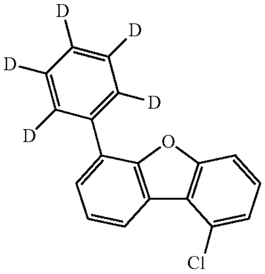 S204 | 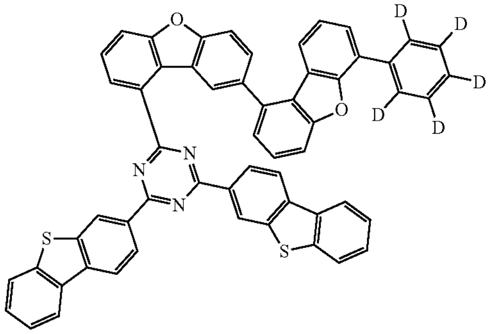 P26 | 41% |
| 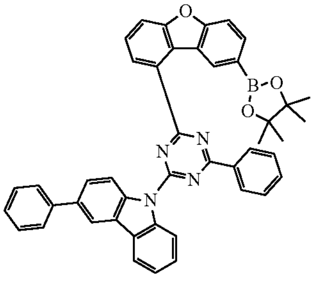 S54 | 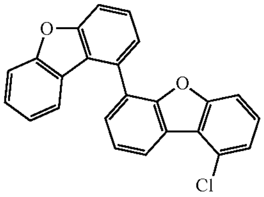 S205 | 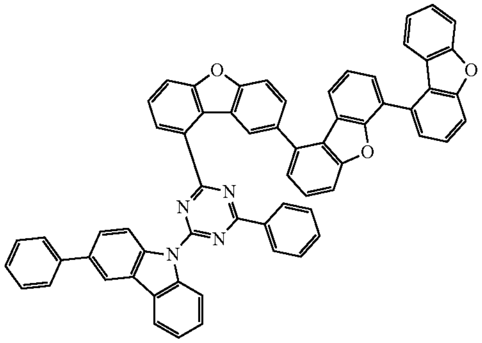 P27 | 42% |
| 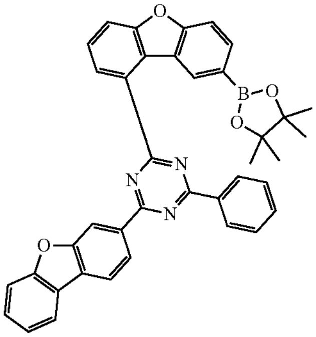 S50 | 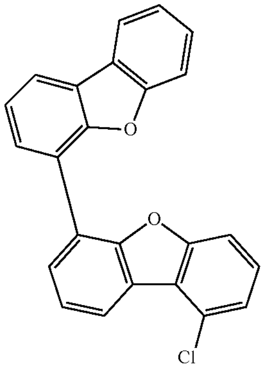 S206 | 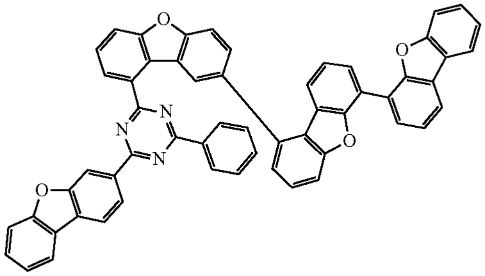 P28 | 56% |
| 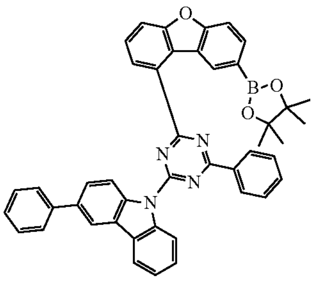 S54 | 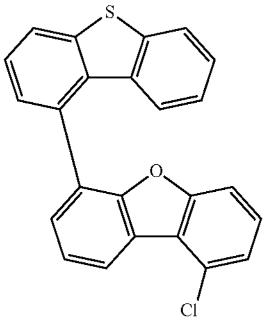 S207 | 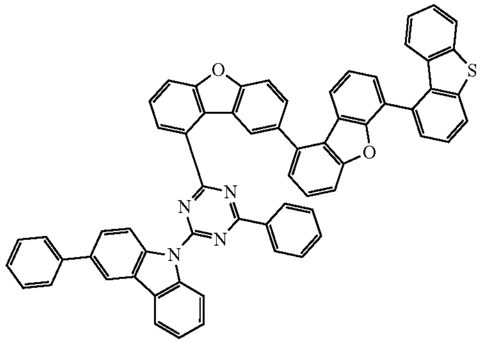 P29 | 45% |

-continued
| Reactant 1 | Reactant 2 | Product | Yield |
| --- | --- | --- | --- |
| 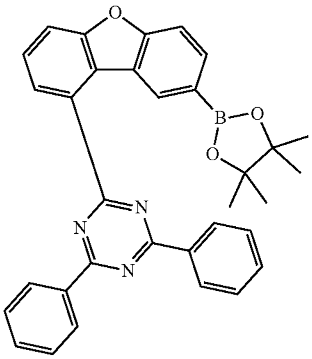 CAS-2138490-96-5 | 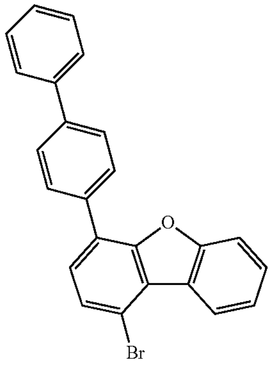 S208 | 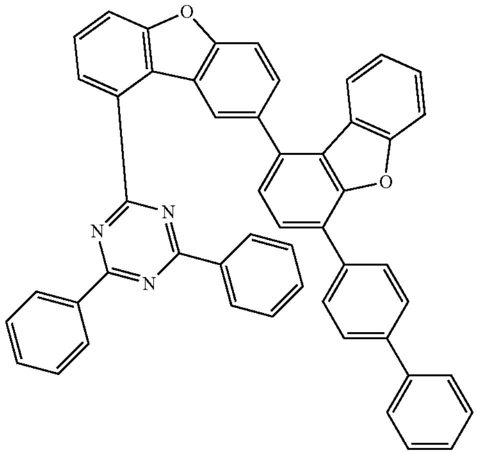 P30 | 58% |
| 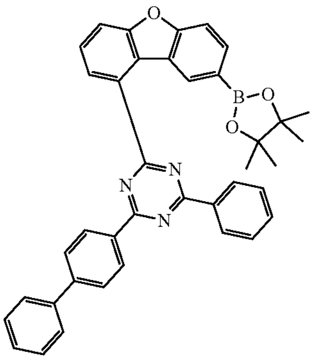 CAS-2173554-87-3 | 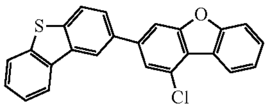 S209 | 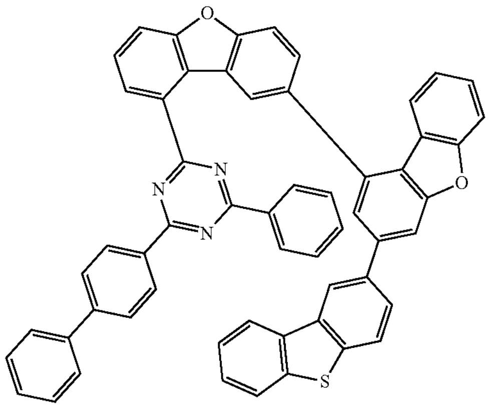 P31 | 50% |
| 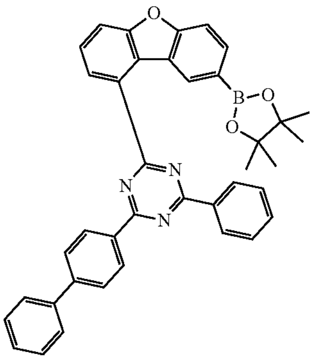 CAS-2173554-87-3 | 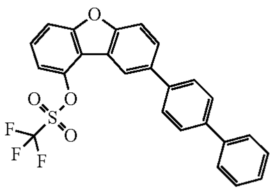 S202 | 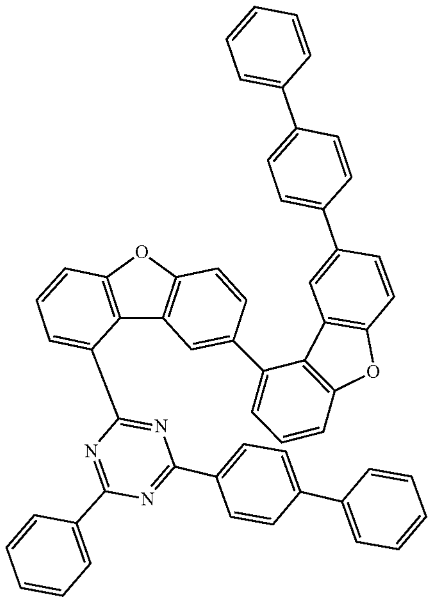 P32 | 47% |

-continued
| Reactant 1 | Reactant 2 | Product | Yield |
|---|---|---|---|
| 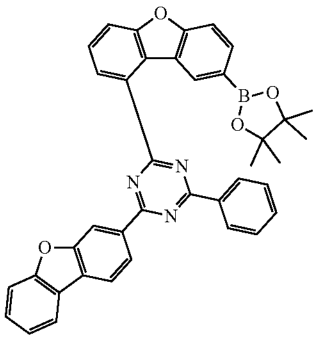 S50 | 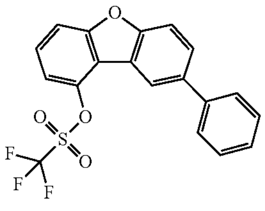 CAS-2033132-91-9 | 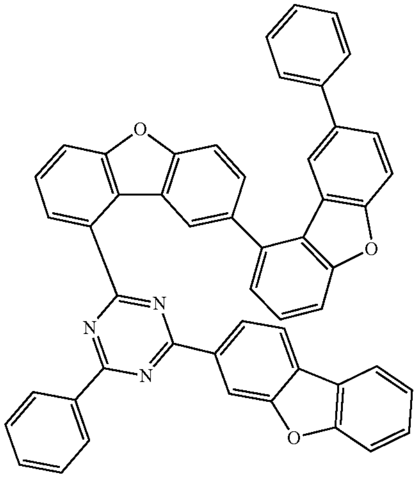 P33 | 50% |
| 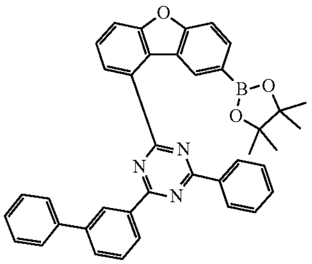 CAS-2173554-91-9 | 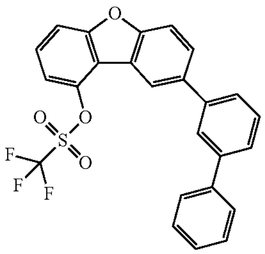 S203 | 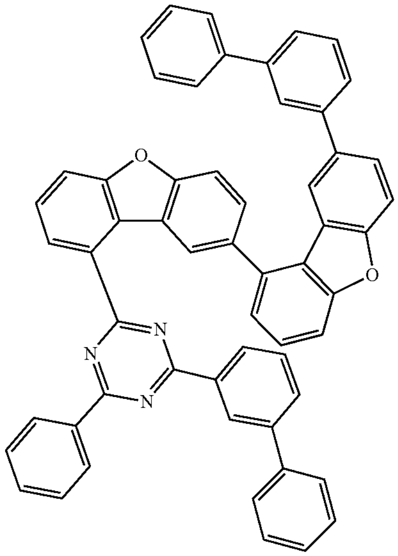 P34 | 46% |

-continued
| Reactant 1 | Reactant 2 | Product | Yield |
|---|---|---|---|
| 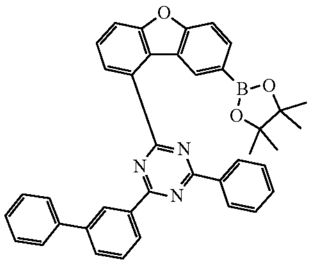 CAS-2173554-91-9 | 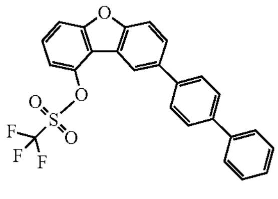 S202 | 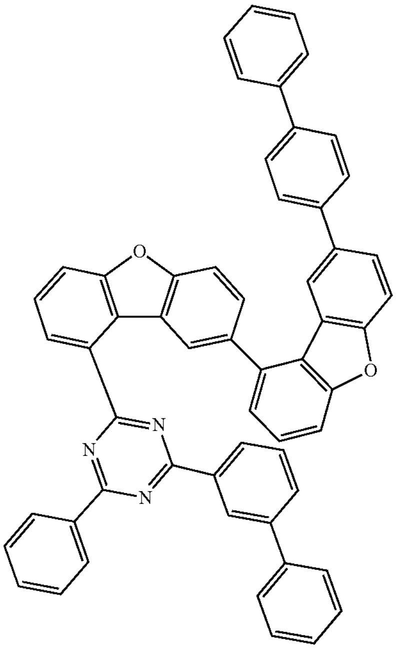 P35 | 44% |
P100:
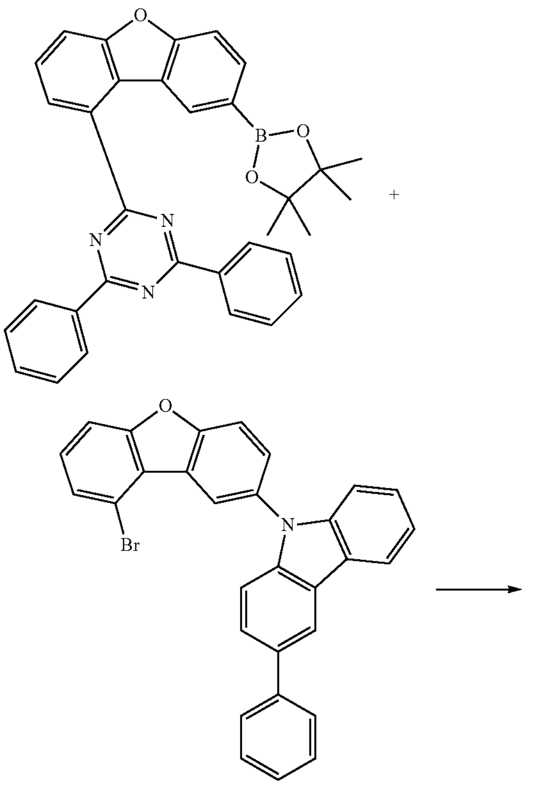
-continued
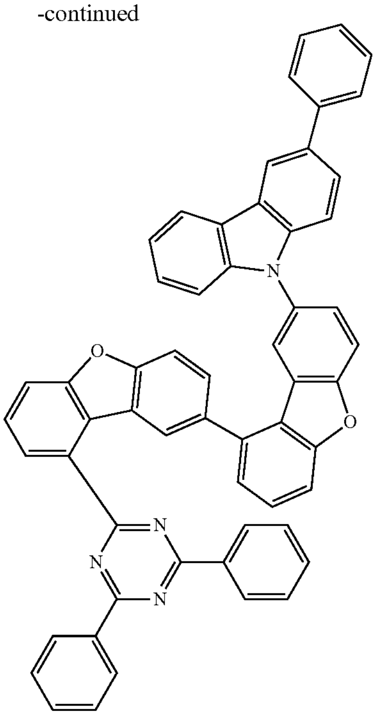
To an initial charge of 2,4-diphenyl-6-[8-(4,4,5,5-tetramethyl-1,3,2-dioxaborolan-2-yl)-1-dibenzofuranyl]-1,3,5-triazine [2138490-96-5] (15.31 g, 29.1 mmol), S150 (14.41 g, 29.5 mmol) and $Na_2CO_3$ (6.17 g, 58.2 mmol) in a flask are added toluene (300 ml) and water (100 ml), and the mixture is inertized with argon for 30 min. Subsequently, tetrakis (triphenylphosphine)palladium(0) [14221-01-3] (1.00 g, 0.87 mmol) is added and the mixture is heated under reflux for 36 h. After cooling, the reaction mixture is worked up by extraction with toluene and water, the combined organic phases are dried over $Na_2SO_4$, and the filtrate is concentrated to dryness by rotary evaporation. The residue is suspended in 350 ml of hot EtOH and stirred under reflux for 1 h, and the solids are filtered off with suction after cooling. The crude product is subjected to hot extraction with toluene/heptane (1:1) twice, then recrystallized three times from n-butyl acetate and finally sublimed under high vacuum. Yield: 14.8 g (18.7 mmol, 67%); purity: >99.9% by HPLC In an analogous manner, it is possible to prepare the compounds below. The catalyst system used here, rather than tetrakis(triphenylphosphine)palladium(0), may also be $Pd_2(dba)_3$ with SPhos [657408-07-6] (palladium source and ligand) or bis(triphenylphosphine)palladium(II) chloride [13965-03-2]. Purification can also be effected using column chromatography, or recrystallization or hot extraction using other standard solvents such as ethanol, butanol, acetone, ethyl acetate, acetonitrile, toluene, xylene, dichloromethane, methanol, tetrahydrofuran, n-butyl acetate, 1,4-dioxane, or recrystallization using high boilers such as dimethyl sulfoxide, N,N-dimethylformamide, N,N-dimethylacetamide, N-methylpyrrolidone, etc.

| Reactant 1 | Reactant 2 | Product | Yield |
| --- | --- | --- | --- |
| 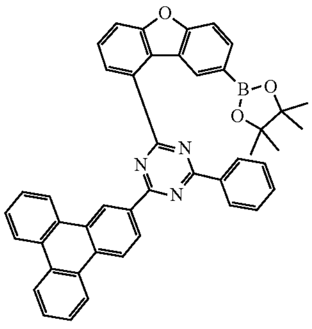 CAS-2268673-77-2 | 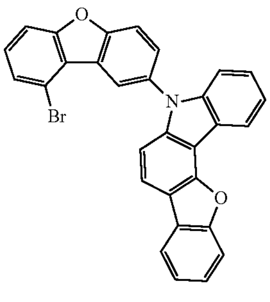 S153 | 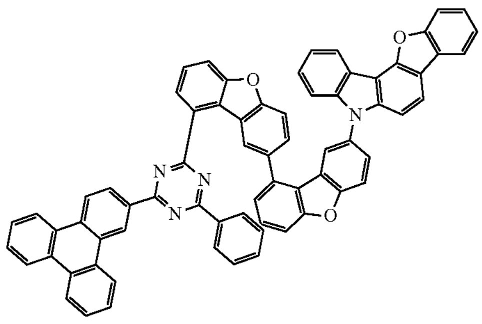 P101 | 60% |
| 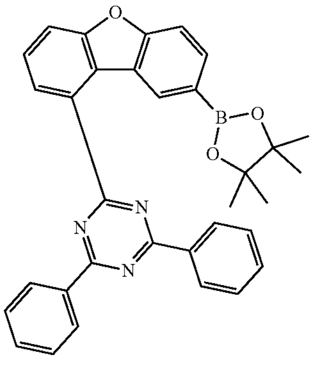 CAS-2138490-96-5 | 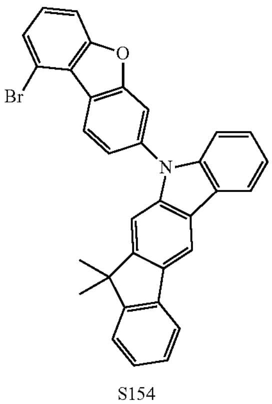 S154 | 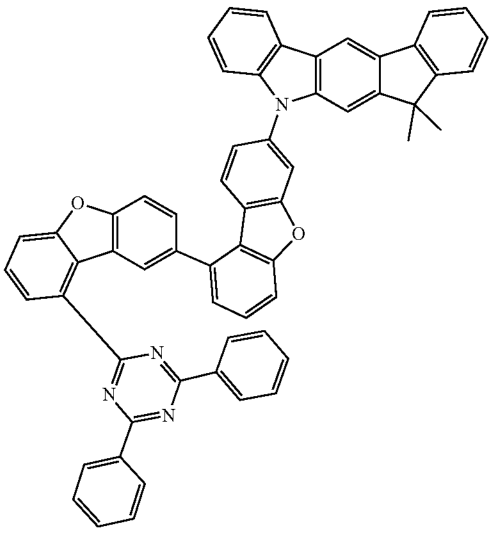 P102 | 57% |

-continued
| Reactant 1 | Reactant 2 | Product | Yield |
| --- | --- | --- | --- |
| 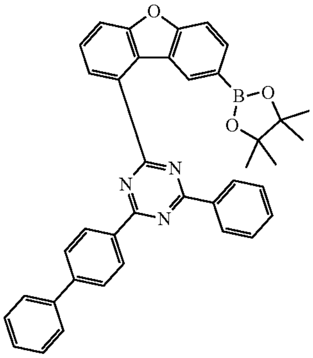 CAS-2173554-87-3 | 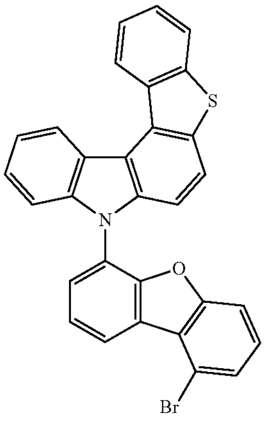 S100 | 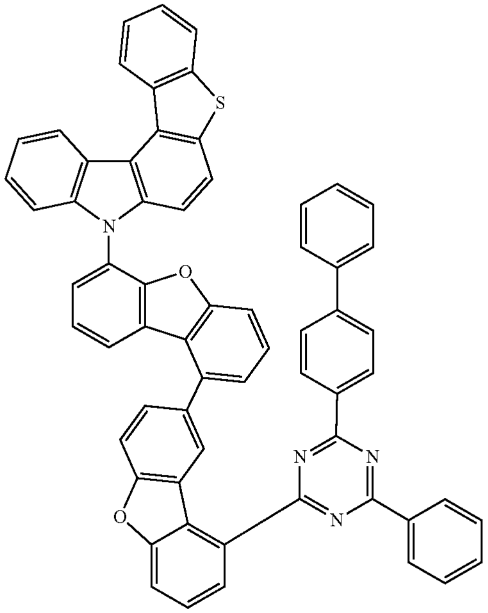 P103 | 62% |
| 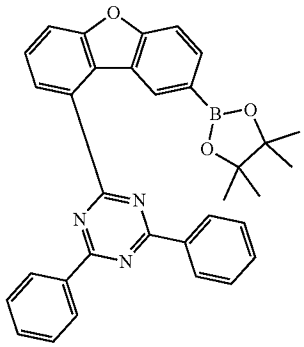 CAS-2138490-96-5 | 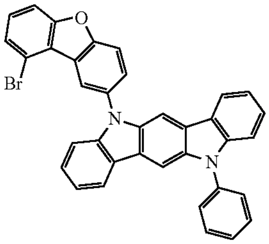 S155 | 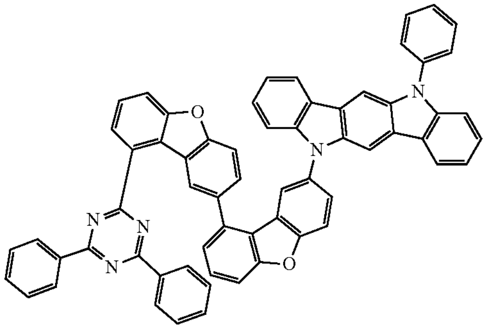 P104 | 51% |
| 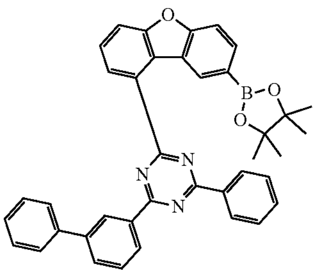 CAS-2173554-91-9 | 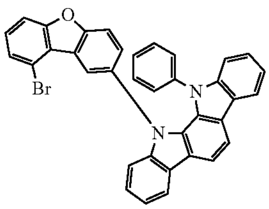 S151 | 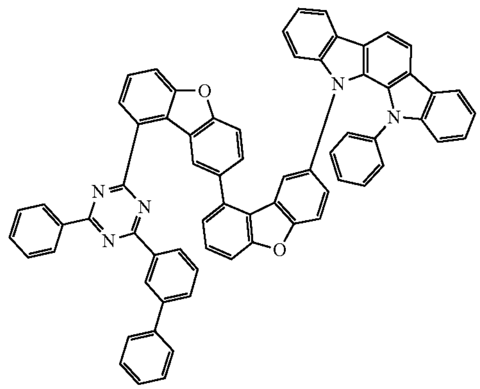 P105 | 52% |

-continued
| Reactant 1 | Reactant 2 | Product | Yield |
|---|---|---|---|
| 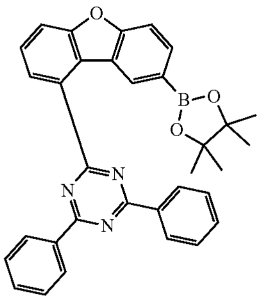 CAS-2138490-96-5 | 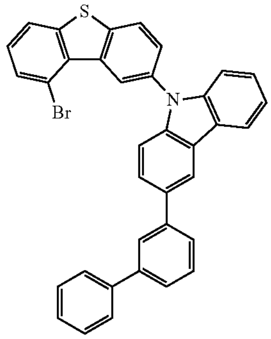 S152 | 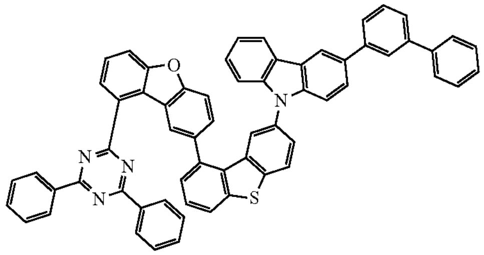 P106 | 49% |
| 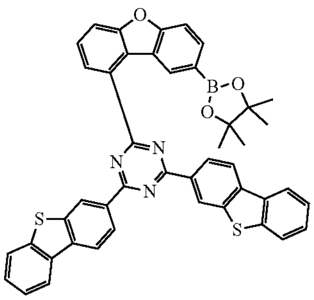 S53 | 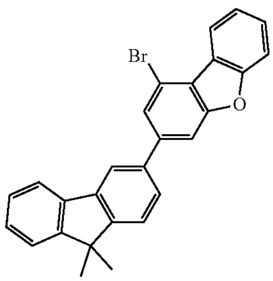 CAS-1821235-72-6 | 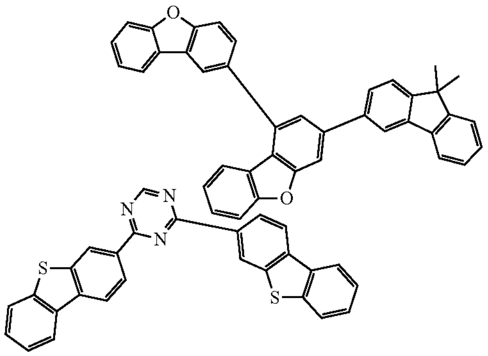 P107 | 52% |
| 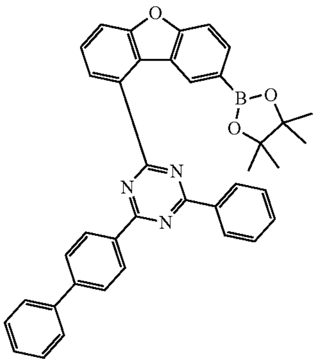 CAS-2173554-87-3 | 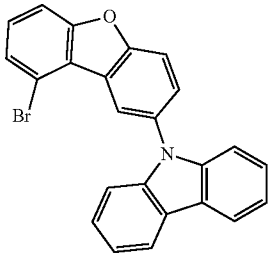 S156 | 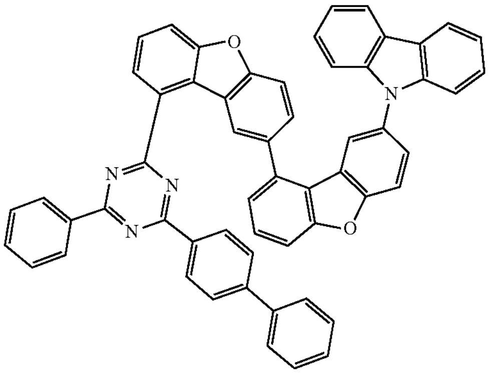 P108 | 40% |

-continued

| Reactant 1 | Reactant 2 | Product | Yield |
|---|---|---|---|
| 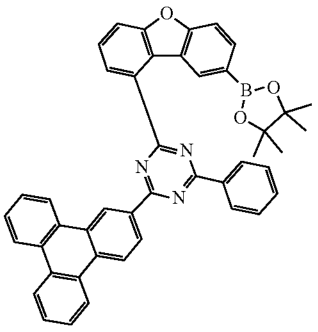 CAS-2268673-77-2 | 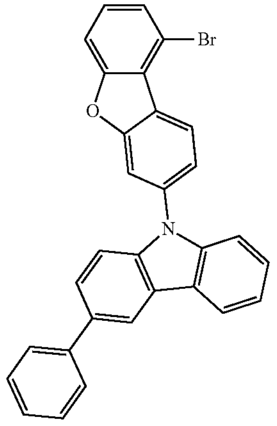 S157 | 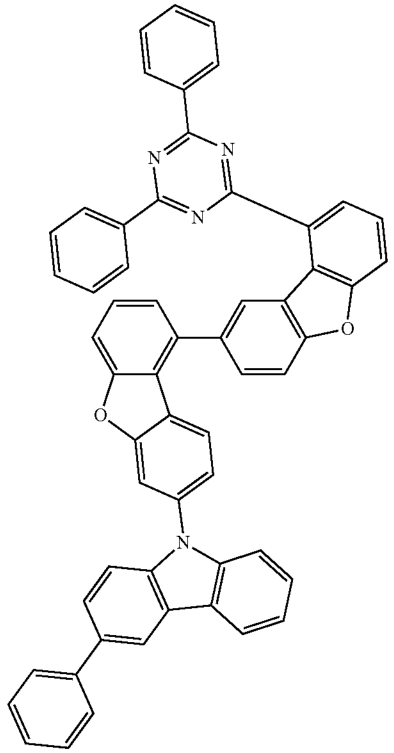 P109 | 37% |
| 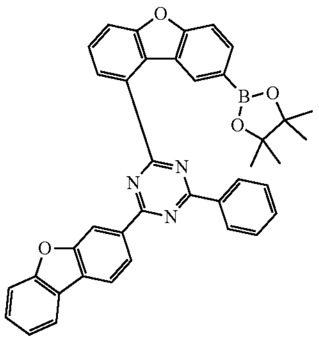 S50 | 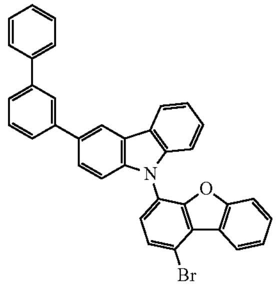 S158 | 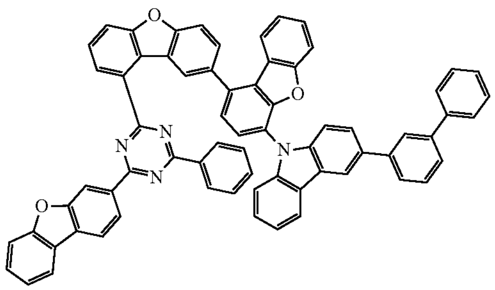 P110 | 42% |

Device Examples

Pretreatment for Examples V1-V5, E1-E28 and B1 to B54

Glass plaques coated with structured ITO (indium tin oxide) of thickness 50 nm are treated prior to coating, first with an oxygen plasma, followed by an argon plasma. These plasma-treated glass plaques form the substrates to which the OLEDs are applied.

The OLEDs basically have the following layer structure: substrate/hole injection layer (HIL)/hole transport layer (HTL)/electron blocker layer (EBL)/emission layer (EML)/optional hole blocker layer (HBL)/electron transport layer (ETL)/optional electron injection layer (EIL) and finally a cathode. The cathode is formed by an aluminium layer of thickness 100 nm. The exact structure of the OLEDs can be found in table 1. The materials required for production of the OLEDs are shown in Table 3. The data of the OLEDs are listed in table 2.

All materials are applied by thermal vapour deposition in a vacuum chamber. In this case, the emission layer always consists of at least one matrix material (host material) and an emitting dopant (emitter) which is added to the matrix material(s) in a particular proportion by volume by co-evaporation. Details given in such a form as IV1:H4:TEG2 (44%:44%:12%) mean here that the materials IV1 and 42 are each present in the layer in a proportion by volume of 44%, and TEG1 in a proportion by volume of 12%. Analogously, the electron transport layer may also consist of a mixture of two materials.

The OLEDs are characterized in a standard manner. For this purpose, the electroluminescence spectra, the current efficiency (CE, measured in cd/A) and the external quantum efficiency (EQE, measured in %) are determined as a function of luminance, calculated from current-voltage-luminance characteristics assuming Lambertian emission characteristics, as is the lifetime. The electroluminescence spectra are determined at a luminance of 1000 cd/m$^2$, and the CIE 1931 x and y colour coordinates are calculated therefrom. The parameter U1000 in table 2 refers to the voltage which is required fora luminance of 1000 cd/m$^2$. CE1000 and EQE1000 respectively denote the current efficiency and external quantum efficiency that are attained at 1000 cd/m$^2$. The parameter U10 in table 2 refers to the voltage which is required for a current density of 10 mA/cm$^2$. CE10 and EQE10 respectively denote the current efficiency and external quantum efficiency that are attained at 10 mA/m$^2$.

The lifetime LT is defined as the time after which the luminance drops from the starting luminance to a certain proportion L1 in the course of operation with constant current density $j_0$. A figure of L1=80% in table 2 means that the lifetime reported in the LT column corresponds to the time after which the luminance falls to 80% of its starting value.

Use of Materials of the Invention in the Emission Layer of Phosphorescent OLEDs

The inventive materials IV1 to IV31 are used in Examples E1 to E28 and B1 to B54 as matrix material in the emission layer of green-phosphorescing OLEDs. With otherwise comparable performance data of the OLEDs, the use of the compounds of the invention achieves distinctly higher lifetimes compared to PA1 (see table 2). E1-E3 can be compared here directly with V1, E4-E7 directly with V2, E8-E12 directly with V3, E13-E17 directly with V4, and E18-E28 directly with V5, and each comparison shows the improvement in lifetime relative to PA1.

TABLE 1

| Structure of the OLEDs | | | | | | | |
|---|---|---|---|---|---|---|---|
| Ex. | HIL thickness | HTL thickness | EBL thickness | EML thickness | HBL thickness | ETL thickness | EIL thickness |
| V1 | SpMA1:PD1 (95%:5%) 20 nm | SpMA1 215 nm | SpMA2 20 nm | PA1:H12:TEG1 (44%:44%:12%) 30 nm | ST2 10 nm | ST2:LiQ (50%:50%) 30 nm | LiQ 1 nm |
| E1 | PA2:PD1 (95%:5%) 20 nm | SpMA1 215 nm | SpMA2 20 nm | IV1:H12:TEG1 (44%:44%:12%) 30 nm | ST2 10 nm | PA6:LiQ (50%:50%) 30 nm | LiQ 1 nm |
| E2 | SpMA1:PD1 (95%:5%) 20 nm | SpMA1 215 nm | SpMA2 20 nm | IV2:H12:TEG1 (44%:44%:12%) 30 nm | ST2 10 nm | ST2:LiQ (50%:50%) 30 nm | LiQ 1 nm |
| E3 | SpMA1:PD1 (95%:5%) 20 nm | SpMA1 215 nm | SpMA2 20 nm | IV3:H12:TEG1 (44%:44%:12%) 30 nm | ST2 10 nm | ST2:LiQ (50%:50%) 30 nm | LiQ 1 nm |
| V2 | SpMA1:PD1 (95%:5%) 20 nm | SpMA1 200 nm | SpMA2 20 nm | PA1:H4:TEG2 (44%:44%:12%) 40 nm | ST2 5 nm | ST2:LiQ (50%:50%) 30 nm | LiQ 1 nm |
| E4 | SpMA1:PD1 (95%:5%) 20 nm | SpMA1 200 nm | SpMA2 20 nm | IV1:H4:TEG2 (44%:44%:12%) 40 nm | ST2 5 nm | ST2:LiQ (50%:50%) 30 nm | LiQ 1 nm |
| E5 | SpMA1:PD1 (95%:5%) 20 nm | SpMA1 200 nm | SpMA2 20 nm | IV5:H4:TEG2 (44%:44%:12%) 40 nm | ST2 5 nm | ST2:LiQ (50%:50%) 30 nm | LiQ 1 nm |
| E6 | SpMA1:PD1 (95%:5%) 20 nm | SpMA1 200 nm | SpMA2 20 nm | IV10:H4:TEG2 (44%:44%:12%) 40 nm | ST2 5 nm | ST2:LiQ (50%:50%) 30 nm | LiQ 1 nm |
| E7 | SpMA1:PD1 (95%:5%) 20 nm | SpMA1 200 nm | SpMA2 20 nm | IV3:H4:TEG2 (44%:44%:12%) 40 nm | ST2 5 nm | ST2:LiQ (50%:50%) 30 nm | LiQ 1 nm |
| V3 | SpMA1:PD1 (95%:5%) 20 nm | SpMA1 200 nm | SpMA2 20 nm | PA1:H4:TEG2 (23%:70%:7%) 40 nm | ST2 5 nm | ST2:LiQ (50%:50%) 30 nm | LiQ 1 nm |
| E8 | SpMA1:PD1 (95%:5%) 20 nm | SpMA1 200 nm | SpMA2 20 nm | IV1:H4:TEG2 (23%:70%:7%) 40 nm | ST2 5 nm | ST2:LiQ (50%:50%) 30 nm | LiQ 1 nm |
| E9 | SpMA1:PD1 (95%:5%) 20 nm | SpMA1 200 nm | SpMA2 20 nm | IV5:H4:TEG2 (23%:70%:7%) 40 nm | ST2 5 nm | ST2:LiQ (50%:50%) 30 nm | LiQ 1 nm |
| E10 | SpMA1:PD1 (95%:5%) 20 nm | SpMA1 200 nm | SpMA2 20 nm | IV10:H4:TEG2 (23%:70%:7%) 40 nm | ST2 5 nm | ST2:LiQ (50%:50%) 30 nm | LiQ 1 nm |
| E11 | SpMA1:PD1 (95%:5%) 20 nm | SpMA1 200 nm | SpMA2 20 nm | IV11:H4:TEG2 (23%:70%:7%) 40 nm | ST2 5 nm | ST2:LiQ (50%:50%) 30 nm | LiQ 1 nm |
| E12 | SpMA1:PD1 (95%:5%) 20 nm | SpMA1 200 nm | SpMA2 20 nm | IV3:H4:TEG2 (23%:70%:7%) 40 nm | ST2 5 nm | ST2:LiQ (50%:50%) 30 nm | LiQ 1 nm |
| V4 | SpMA1:PD1 (95%:5%) 20 nm | SpMA1 200 nm | SpMA2 20 nm | PA1:H8:TEG3 (23%:70%:7%) 40 nm | ST2 5 nm | ST2:LiQ (50%:50%) 30 nm | LiQ 1 nm |
| E13 | SpMA1:PD1 (95%:5%) 20 nm | SpMA1 200 nm | SpMA2 20 nm | IV1:H8:TEG3 (23%:70%:7%) 40 nm | ST2 5 nm | ST2:LiQ (50%:50%) 30 nm | LiQ 1 nm |

TABLE 1-continued

Structure of the OLEDs

| Ex. | HIL thickness | HTL thickness | EBL thickness | EML thickness | HBL thickness | ETL thickness | EIL thickness |
|---|---|---|---|---|---|---|---|
| E14 | SpMA1:PD1 (95%:5%) 20 nm | SpMA1 200 nm | SpMA2 20 nm | IV5:H8:TEG3 (23%:70%:7%) 40 nm | ST2 5 nm | ST2:LiQ (50%:50%) 30 nm | LiQ 1 nm |
| E15 | SpMA1:PD1 (95%:5%) 20 nm | SpMA1 200 nm | SpMA2 20 nm | IV10:H8:TEG3 (23%:70%:7%) 40 nm | ST2 5 nm | ST2:LiQ (50%:50%) 30 nm | LiQ 1 nm |
| E16 | SpMA1:PD1 (95%:5%) 20 nm | SpMA1 200 nm | SpMA2 20 nm | IV11:H8:TEG3 (23%:70%:7%) 40 nm | ST2 5 nm | ST2:LiQ (50%:50%) 30 nm | LiQ 1 nm |
| E17 | SpMA1:PD1 (95%:5%) 20 nm | SpMA1 200 nm | SpMA2 20 nm | IV3:H8:TEG3 (23%:70%:7%) 40 nm | ST2 5 nm | ST2:LiQ (50%:50%) 30 nm | LiQ 1 nm |
| V5 | SpMA1:PD1 (95%:5%) 20 nm | SpMA1 200 nm | SpMA2 20 nm | PA1:H26:TEG3 (22%:70%:8%) 40 nm | ST2 5 nm | ST2:LiQ (50%:50%) 30 nm | LiQ 1 nm |
| E18 | SpMA1:PD1 (95%:5%) 20 nm | SpMA1 200 nm | SpMA2 20 nm | IV1:H26:TEG3 (22%:70%:8%) 40 nm | ST2 5 nm | ST2:LiQ (50%:50%) 30 nm | LiQ 1 nm |
| E19 | SpMA1:PD1 (95%:5%) 20 nm | SpMA1 200 nm | SpMA2 20 nm | IV2:H26:TEG3 (22%:70%:8%) 40 nm | ST2 5 nm | ST2:LiQ (50%:50%) 30 nm | LiQ 1 nm |
| E20 | SpMA1:PD1 (95%:5%) 20 nm | SpMA1 200 nm | SpMA2 20 nm | IV8:H26:TEG3 (22%:70%:8%) 40 nm | ST2 5 nm | ST2:LiQ (50%:50%) 30 nm | LiQ 1 nm |
| E21 | SpMA1:PD1 (95%:5%) 20 nm | SpMA1 200 nm | SpMA2 20 nm | IV14:H26:TEG3 (22%:70%:8%) 40 nm | ST2 5 nm | ST2:LiQ (50%:50%) 30 nm | LiQ 1 nm |
| E22 | SpMA1:PD1 (95%:5%) 20 nm | SpMA1 200 nm | SpMA2 20 nm | IV15:H26:TEG3 (22%:70%:8%) 40 nm | ST2 5 nm | ST2:LiQ (50%:50%) 30 nm | LiQ 1 nm |
| E23 | SpMA1:PD1 (95%:5%) 20 nm | SpMA1 200 nm | SpMA2 20 nm | IV16:H26:TEG3 (22%:70%:8%) 40 nm | ST2 5 nm | ST2:LiQ (50%:50%) 30 nm | LiQ 1 nm |
| E24 | SpMA1:PD1 (95%:5%) 20 nm | SpMA1 200 nm | SpMA2 20 nm | IV18:H26:TEG3 (22%:70%:8%) 40 nm | ST2 5 nm | ST2:LiQ (50%:50%) 30 nm | LiQ 1 nm |
| E25 | SpMA1:PD1 (95%:5%) 20 nm | SpMA1 200 nm | SpMA2 20 nm | IV21:H26:TEG3 (22%:70%:8%) 40 nm | ST2 5 nm | ST2:LiQ (50%:50%) 30 nm | LiQ 1 nm |
| E26 | SpMA1:PD1 (95%:5%) 20 nm | SpMA1 200 nm | SpMA2 20 nm | IV22:H26:TEG3 (22%:70%:8%) 40 nm | ST2 5 nm | ST2:LiQ (50%:50%) 30 nm | LiQ 1 nm |
| E27 | SpMA1:PD1 (95%:5%) 20 nm | SpMA1 200 nm | SpMA2 20 nm | IV25:H26:TEG3 (22%:70%:8%) 40 nm | ST2 5 nm | ST2:LiQ (50%:50%) 30 nm | LiQ 1 nm |
| E28 | SpMA1:PD1 (95%:5%) 20 nm | SpMA1 200 nm | SpMA2 20 nm | IV26:H26:TEG3 (22%:70%:8%) 40 nm | ST2 5 nm | ST2:LiQ (50%:50%) 30 nm | LiQ 1 nm |
| B1 | SpMA1:PD1 (95%:5%) 20 nm | SpMA1 200 nm | SpMA2 20 nm | IV1:H4:TEG3 (44%:44%:12%) 40 nm | ST2 5 nm | ST2:LiQ (50%:50%) 30 nm | LiQ 1 nm |
| B2 | SpMA1:PD1 (95%:5%) 20 nm | SpMA1 200 nm | SpMA2 20 nm | IV1: H19:TEG2 (44%:44%:12%) 40 nm | ST2 5 nm | ST2:LiQ (50%:50%) 30 nm | LiQ 1 nm |
| B3 | SpMA1:PD1 (95%:5%) 20 nm | SpMA1 200 nm | SpMA2 20 nm | IV5:H8:TEG3 (44%:44%:12%) 40 nm | ST2 5 nm | ST2:LiQ (50%:50%) 30 nm | LiQ 1 nm |
| B4 | SpMA1:PD1 (95%:5%) 20 nm | SpMA1 200 nm | SpMA2 20 nm | IV7:H17:TEG2 (44%:44%:12%) 40 nm | ST2 5 nm | ST2:LiQ (50%:50%) 30 nm | LiQ 1 nm |
| B5 | SpMA1:PD1 (95%:5%) 20 nm | SpMA1 200 nm | SpMA2 20 nm | IV7:H1:TEG3 (44%:44%:12%) 40 nm | ST2 5 nm | ST2:LiQ (50%:50%) 30 nm | LiQ 1 nm |
| B6 | SpMA1:PD1 (95%:5%) 20 nm | SpMA1 200 nm | SpMA2 20 nm | IV8:H5:TEG2 (44%:44%:12%) 40 nm | ST2 5 nm | ST2:LiQ (50%:50%) 30 nm | LiQ 1 nm |
| B7 | SpMA1:PD1 (95%:5%) 20 nm | SpMA1 200 nm | SpMA2 20 nm | IV9:H23:TEG3 (44%:44%:12%) 40 nm | ST2 5 nm | ST2:LiQ (50%:50%) 30 nm | LiQ 1 nm |
| B8 | SpMA1:PD1 (95%:5%) 20 nm | SpMA1 200 nm | SpMA2 20 nm | IV10:H2:TEG3 (44%:44%:12%) 40 nm | ST2 5 nm | ST2:LiQ (50%:50%) 30 nm | LiQ 1 nm |
| B9 | SpMA1:PD1 (95%:5%) 20 nm | SpMA1 200 nm | SpMA2 20 nm | IV10:H8:TEG3 (44%:44%:12%) 40 nm | ST2 5 nm | ST2:LiQ (50%:50%) 30 nm | LiQ 1 nm |

TABLE 1-continued

| Structure of the OLEDs | | | | | | | |
|---|---|---|---|---|---|---|---|
| Ex. | HIL thickness | HTL thickness | EBL thickness | EML thickness | HBL thickness | ETL thickness | EIL thickness |
| B10 | SpMA1:PD1<br>(95%:5%)<br>20 nm | SpMA1<br>200 nm | SpMA2<br>20 nm | IV12:H5:TEG3<br>(44%:44%:12%)<br>40 nm | ST2<br>5 nm | ST2:LiQ<br>(50%:50%)<br>30 nm | LiQ<br>1 nm |
| B11 | SpMA1:PD1<br>(95%:5%)<br>20 nm | SpMA1<br>200 nm | SpMA2<br>20 nm | IV13:H4:TEG3<br>(44%:44%:12%)<br>40 nm | ST2<br>5 nm | ST2:LiQ<br>(50%:50%)<br>30 nm | LiQ<br>1 nm |
| B12 | SpMA1:PD1<br>(95%:5%)<br>20 nm | SpMA1<br>200 nm | SpMA2<br>20 nm | IV13:H26:TEG2<br>(44%:44%:12%)<br>40 nm | ST2<br>5 nm | ST2:LiQ<br>(50%:50%)<br>30 nm | LiQ<br>1 nm |
| B13 | SpMA1:PD1<br>(95%:5%)<br>20 nm | SpMA1<br>200 nm | SpMA2<br>20 nm | IV9:H11:TEG3<br>(44%:22%:12%)<br>40 nm | ST2<br>5 nm | ST2:LiQ<br>(50%:50%)<br>30 nm | LiQ<br>1 nm |
| B14 | SpMA1:PD1<br>(95%:5%)<br>20 nm | SpMA1<br>200 nm | SpMA2<br>20 nm | IV4:H8:TEG2<br>(44%:44%:12%)<br>40 nm | ST2<br>5 nm | ST2:LiQ<br>(50%:50%)<br>30 nm | LiQ<br>1 nm |
| B15 | SpMA1:PD1<br>(95%:5%)<br>20 nm | SpMA1<br>200 nm | SpMA2<br>20 nm | IV9:H14:TEG3<br>(44%:44%:12%)<br>40 nm | ST2<br>5 nm | ST2:LiQ<br>(50%:50%)<br>30 nm | LiQ<br>1 nm |
| B16 | SpMA1:PD1<br>(95%:5%)<br>20 nm | SpMA1<br>200 nm | SpMA2<br>20 nm | IV1:H1:TEG3<br>(44%:44%:12%)<br>40 nm | ST2<br>5 nm | ST2:LiQ<br>(50%:50%)<br>30 nm | LiQ<br>1 nm |
| B17 | SpMA1:PD1<br>(95%:5%)<br>20 nm | SpMA1<br>200 nm<br>40 nm | SpMA2<br>20 nm | IV3:H8:TEG2<br>(44%:44%:12%)<br>30 nm | ST2<br>5 nm | ST2:LiQ<br>(50%:50%) | LiQ<br>1 nm |
| B18 | SpMA1:PD1<br>(95%:5%)<br>20 nm | SpMA1<br>200 nm | SpMA2<br>20 nm | IV1:H34:TEG2<br>(23%:70%:7%)<br>40 nm | ST2<br>5 nm | ST2:LiQ<br>(50%:50%)<br>30 nm | LiQ<br>1 nm |
| B19 | SpMA1:PD1<br>(95%:5%)<br>20 nm | SpMA1<br>200 nm | SpMA2<br>20 nm | IV19:H2:TEG2<br>(23%:70%:7%)<br>40 nm | ST2<br>5 nm | ST2:LiQ<br>(50%:50%)<br>30 nm | LiQ<br>1 nm |
| B20 | SpMA1:PD1<br>(95%:5%)<br>20 nm | SpMA1<br>200 nm | SpMA2<br>20 nm | IV2:H7:TEG3<br>(22%:70%:8%)<br>40 nm | ST2<br>5 nm | ST2:LiQ<br>(50%:50%)<br>30 nm | LiQ<br>1 nm |
| B21 | SpMA1:PD1<br>(95%:5%)<br>20 nm | SpMA1<br>200 nm | SpMA2<br>20 nm | IV20:H1:TEG2<br>(44%:44%:12%)<br>40 nm | ST2<br>5 nm | ST2:LiQ<br>(50%:50%)<br>30 nm | LiQ<br>1 nm |
| B22 | SpMA1:PD1<br>(95%:5%)<br>20 nm | SpMA1<br>200 nm | SpMA2<br>20 nm | IV22:H5:TEG3<br>(22%:70%:8%)<br>40 nm | ST2<br>5 nm | ST2:LiQ<br>(50%:50%)<br>30 nm | LiQ<br>1 nm |
| B23 | SpMA1:PD1<br>(95%:5%)<br>20 nm | SpMA1<br>200 nm | SpMA2<br>20 nm | IV1:H9:TEG3<br>(22%:70%:8%)<br>40 nm | ST2<br>5 nm | ST2:LiQ<br>(50%:50%)<br>30 nm | LiQ<br>1 nm |
| B24 | SpMA1:PD1<br>(95%:5%)<br>20 nm | SpMA1<br>200 nm | SpMA2<br>20 nm | IV1:H14:TEG3<br>(22%:70%:8%)<br>40 nm | ST2<br>5 nm | ST2:LiQ<br>(50%:50%)<br>30 nm | LiQ<br>1 nm |
| B25 | SpMA1:PD1<br>(95%:5%)<br>20 nm | SpMA1<br>200 nm | SpMA2<br>20 nm | IV23:H4:TEG2<br>(23%:70%:7%)<br>40 nm | ST2<br>5 nm | ST2:LiQ<br>(50%:50%)<br>30 nm | LiQ<br>1 nm |
| B26 | SpMA1:PD1<br>(95%:5%)<br>20 nm | SpMA1<br>200 nm | SpMA2<br>20 nm | IV24:H9:TEG3<br>(44%:44%:12%)<br>40 nm | ST2<br>5 nm | ST2:LiQ<br>(50%:50%)<br>30 nm | LiQ<br>1 nm |
| B27 | SpMA1:PD1<br>(95%:5%)<br>20 nm | SpMA1<br>200 nm | SpMA2<br>20 nm | IV10:H32:TEG2<br>(23%:70%:7%)<br>40 nm | ST2<br>5 nm | ST2:LiQ<br>(50%:50%)<br>30 nm | LiQ<br>1 nm |
| B28 | SpMA1:PD1<br>(95%:5%)<br>20 nm | SpMA1<br>215 nm | SpMA2<br>20 nm | IV2:H19:TEG1<br>(44%:44%:12%)<br>30 nm | ST2<br>10 nm | ST2:LiQ<br>(50%:50%)<br>30 nm | LiQ<br>1 nm |
| B29 | SpMA1:PD1<br>(95%:5%)<br>20 nm | SpMA1<br>200 nm | SpMA2<br>20 nm | IV11:H29:TEG2<br>(23%:70%:7%)<br>40 nm | ST2<br>5 nm | ST2:LiQ<br>(50%:50%)<br>30 nm | LiQ<br>1 nm |
| B30 | SpMA1:PD1<br>(95%:5%)<br>20 nm | SpMA1<br>200 nm | SpMA2<br>20 nm | IV1:H1:TEG3<br>(44%:44%:12%)<br>40 nm | ST2<br>5 nm | ST2:LiQ<br>(50%:50%)<br>30 nm | LiQ<br>1 nm |
| B31 | SpMA1:PD1<br>(95%:5%)<br>20 nm | SpMA1<br>200 nm | SpMA2<br>20 nm | IV16:H2:TEG2<br>(44%:44%:12%)<br>40 nm | ST2<br>5 nm | ST2:LiQ<br>(50%:50%)<br>30 nm | LiQ<br>1 nm |
| B32 | SpMA1:PD1<br>(95%:5%)<br>20 nm | SpMA1<br>200 nm | SpMA2<br>20 nm | IV18:H4:TEG2<br>(44%:44%:12%)<br>40 nm | ST2<br>5 nm | ST2:LiQ<br>(50%:50%)<br>30 nm | LiQ<br>1 nm |
| B33 | SpMA1:PD1<br>(95%:5%)<br>20 nm | SpMA1<br>200 nm | SpMA2<br>20 nm | IV15:H5:TEG3<br>(22%:70%:8%)<br>40 nm | ST2<br>5 nm | ST2:LiQ<br>(50%:50%)<br>30 nm | LiQ<br>1 nm |
| B34 | SpMA1:PD1<br>(95%:5%)<br>20 nm | SpMA1<br>200 nm | SpMA2<br>20 nm | IV23:H19:TEG2<br>(23%:70%:7%)<br>40 nm | ST2<br>5 nm | ST2:LiQ<br>(50%:50%)<br>30 nm | LiQ<br>1 nm |

TABLE 1-continued

| Ex. | HIL thickness | HTL thickness | EBL thickness | EML thickness | HBL thickness | ETL thickness | EIL thickness |
|---|---|---|---|---|---|---|---|
| | Structure of the OLEDs | | | | | | |
| B35 | SpMA1:PD1 (95%:5%) 20 nm | SpMA1 200 nm | SpMA2 20 nm | IV22:H8:TEG3 (30%:60%:8%) 40 nm | ST2 5 nm | ST2:LiQ (50%:50%) 30 nm | LiQ 1 nm |
| B36 | SpMA1:PD1 (95%:5%) 20 nm | SpMA1 200 nm | SpMA2 20 nm | IV20:H11:TEG2 (68%:20%:12%) 40 nm | ST2 5 nm | ST2:LiQ (50%:50%) 30 nm | LiQ 1 nm |
| B37 | SpMA1:PD1 (95%:5%) 20 nm | SpMA1 200 nm | SpMA2 20 nm | IV26:H8:TEG3 (22%:70%:8%) 40 nm | ST2 5 nm | ST2:LiQ (50%:50%) 30 nm | LiQ 1 nm |
| B38 | SpMA1:PD1 (95%:5%) 20 nm | SpMA1 200 nm | SpMA2 20 nm | IV14:H5:TEG2 (32%:61%:7%) 40 nm | ST2 5 nm | ST2:LiQ (50%:50%) 30 nm | LiQ 1 nm |
| B39 | SpMA1:PD1 (95%:5%) 20 nm | SpMA1 200 nm | SpMA2 20 nm | IV12:H8:TEG3 (44%:44%:12%) 40 nm | ST2 5 nm | ST2:LiQ (50%:50%) 30 nm | LiQ 1 nm |
| B40 | SpMA1:PD1 (95%:5%) 20 nm | SpMA1 200 nm | SpMA2 20 nm | IV5:H6:TEG3 (44%:44%:12%) 40 nm | ST2 5 nm | ST2:LiQ (50%:50%) 30 nm | LiQ 1 nm |
| B41 | SpMA1:PD1 (95%:5%) 20 nm | SpMA1 200 nm | SpMA2 20 nm | IV24:H7:TEG3 (44%:44%:12%) 40 nm | ST2 5 nm | ST2:LiQ (50%:50%) 30 nm | LiQ 1 nm |
| B42 | SpMA1:PD1 (95%:5%) 20 nm | SpMA1 200 nm | SpMA2 20 nm | IV27:H2:TEG2 (44%:44%:12%) 40 nm | ST2 5 nm | ST2:LiQ (50%:50%) 30 nm | LiQ 1 nm |
| B43 | SpMA1:PD1 (95%:5%) 20 nm | SpMA1 200 nm | SpMA2 20 nm | IV27:H4:TEG2 (44%:44%:12%) 40 nm | ST2 5 nm | ST2:LiQ (50%:50%) 30 nm | LiQ 1 nm |
| B44 | SpMA1:PD1 (95%:5%) 20 nm | SpMA1 200 nm | SpMA2 20 nm | IV27:H5:TEG2 (44%:44%:12%) 40 nm | ST2 5 nm | ST2:LiQ (50%:50%) 30 nm | LiQ 1 nm |
| B45 | SpMA1:PD1 (95%:5%) 20 nm | SpMA1 200 nm | SpMA2 20 nm | IV28:H1:TEG2 (44%:44%:12%) 40 nm | ST2 5 nm | ST2:LiQ (50%:50%) 30 nm | LiQ 1 nm |
| B46 | SpMA1:PD1 (95%:5%) 20 nm | SpMA1 200 nm | SpMA2 20 nm | IV29:H2:TEG2 (44%:44%:7%) 40 nm | ST2 5 nm | ST2:LiQ (50%:50%) 30 nm | LiQ 1 nm |
| B47 | SpMA1:PD1 (95%:5%) 20 nm | SpMA1 200 nm | SpMA2 20 nm | IV29:H4:TEG2 (44%:44%:7%) 40 nm | ST2 5 nm | ST2:LiQ (50%:50%) 30 nm | LiQ 1 nm |
| B48 | SpMA1:PD1 (95%:5%) 20 nm | SpMA1 200 nm | SpMA2 20 nm | IV29:H5:TEG2 (44%:44%:7%) 40 nm | ST2 5 nm | ST2:LiQ (50%:50%) 30 nm | LiQ 1 nm |
| B49 | SpMA1:PD1 (95%:5%) 20 nm | SpMA1 200 nm | SpMA2 20 nm | IV30:H2:TEG2 (44%:44%:7%) 40 nm | ST2 5 nm | ST2:LiQ (50%:50%) 30 nm | LiQ 1 nm |
| B50 | SpMA1:PD1 (95%:5%) 20 nm | SpMA1 200 nm | SpMA2 20 nm | IV30:H4:TEG2 (44%:44%:7%) 40 nm | ST2 5 nm | ST2:LiQ (50%:50%) 30 nm | LiQ 1 nm |
| B51 | SpMA1:PD1 (95%:5%) 20 nm | SpMA1 200 nm | SpMA2 20 nm | IV30:H5:TEG2 (44%:44%:7%) 40 nm | ST2 5 nm | ST2:LiQ (50%:50%) 30 nm | LiQ 1 nm |
| B52 | SpMA1:PD1 (95%:5%) 20 nm | SpMA1 200 nm | SpMA2 20 nm | IV31:H2:TEG2 (44%:44%:7%) 40 nm | ST2 5 nm | ST2:LiQ (50%:50%) 30 nm | LiQ 1 nm |
| B53 | SpMA1:PD1 (95%:5%) 20 nm | SpMA1 200 nm | SpMA2 20 nm | IV31:H4:TEG2 (44%:44%:7%) 40 nm | ST2 5 nm | ST2:LiQ (50%:50%) 30 nm | LiQ 1 nm |
| B54 | SpMA1:PD1 (95%:5%) 20 nm | SpMA1 200 nm | SpMA2 20 nm | IV31:H5:TEG2 (44%:44%:7%) 40 nm | ST2 5 nm | ST2:LiQ (50%:50%) 30 nm | LiQ 1 nm |

TABLE 2

Data of the OLEDs

| Ex. | U1000 (V) | CE1000 (cd/A) | EQE1000 (%) | CIE x/y at 1000 cd/m2 | j0 (mA/cm$^2$) | L1 (%) | LT (h) |
|---|---|---|---|---|---|---|---|
| V1 | 3.3 | 68 | 19 | 0.32/0.63 | 20 | 80 | 990 |
| E1 | 3.3 | 70 | 19 | 0.35/0.61 | 20 | 80 | 1170 |
| E2 | 3.3 | 73 | 20 | 0.35/0.61 | 20 | 80 | 1270 |
| E3 | 3.4 | 71 | 19 | 0.34/0.62 | 20 | 80 | 1330 |

TABLE 2-continued

Data of the OLEDs

| Ex. | U10 (V) | CE10 (cd/A) | EQE10 (%) | CIE x/y at 1000 cd/m2 | j0 (mA/cm$^2$) | L1 (%) | LT (h) |
|---|---|---|---|---|---|---|---|
| V2 | 4.9 | 64 | 17 | 0.34/0.62 | 40 | 80 | 1210 |
| E4 | 4.7 | 63 | 17 | 0.34/0.62 | 40 | 80 | 1420 |
| E5 | 4.8 | 62 | 17 | 0.34/0.62 | 40 | 80 | 1350 |

TABLE 2-continued
| Data of the OLEDs | | | | | | | |
|---|---|---|---|---|---|---|---|
| E6 | 4.7 | 62 | 17 | 0.34/0.62 | 40 | 80 | 1310 |
| E7 | 4.8 | 62 | 17 | 0.34/0.62 | 40 | 80 | 1490 |
| V3 | 5.4 | 68 | 18 | 0.34/0.62 | 40 | 80 | 600 |
| E8 | 5.3 | 71 | 19 | 0.34/0.62 | 40 | 80 | 710 |
| E9 | 5.4 | 70 | 19 | 0.34/0.62 | 40 | 80 | 670 |
| E10 | 5.3 | 70 | 19 | 0.34/0.62 | 40 | 80 | 650 |
| E11 | 5.4 | 68 | 18 | 0.34/0.62 | 40 | 80 | 630 |
| E12 | 5.4 | 70 | 19 | 0.34/0.62 | 40 | 80 | 750 |
| V4 | 4.3 | 86 | 22 | 0.35/0.63 | 40 | 80 | 630 |
| E13 | 4.4 | 89 | 23 | 0.35/0.63 | 40 | 80 | 810 |
| E14 | 4.4 | 89 | 23 | 0.35/0.63 | 40 | 80 | 1030 |
| E15 | 4.5 | 92 | 24 | 0.35/0.63 | 40 | 80 | 790 |
| E16 | 4.5 | 87 | 23 | 0.35/0.63 | 40 | 80 | 770 |
| E17 | 4.8 | 86 | 22 | 0.35/0.63 | 40 | 80 | 850 |
| V5 | 4.6 | 85 | 22 | 0.35/0.63 | 40 | 80 | 550 |
| E18 | 4.5 | 88 | 23 | 0.35/0.63 | 40 | 80 | 700 |
| E19 | 4.4 | 92 | 24 | 0.35/0.63 | 40 | 80 | 640 |
| E20 | 4.8 | 86 | 22 | 0.35/0.63 | 40 | 80 | 720 |
| E21 | 4.4 | 87 | 23 | 0.35/0.63 | 40 | 80 | 790 |
| E22 | 4.4 | 93 | 24 | 0.35/0.63 | 40 | 80 | 630 |
| E23 | 4.5 | 88 | 23 | 0.35/0.63 | 40 | 80 | 730 |
| E24 | 4.4 | 87 | 23 | 0.35/0.63 | 40 | 80 | 650 |
| E25 | 4.4 | 85 | 22 | 0.35/0.63 | 40 | 80 | 840 |
| E26 | 4.1 | 86 | 22 | 0.35/0.63 | 40 | 80 | 785 |
| E27 | 4.1 | 84 | 22 | 0.35/0.63 | 40 | 80 | 900 |
| E28 | 4.3 | 87 | 23 | 0.35/0.63 | 40 | 80 | 640 |
| B1 | 4.3 | 79 | 21 | 0.35/0.63 | 40 | 80 | 1170 |
| B2 | 4.8 | 60 | 16 | 0.34/0.62 | 40 | 80 | 1010 |
| B3 | 4.4 | 77 | 20 | 0.35/0.63 | 40 | 80 | 1130 |
| B4 | 4.6 | 64 | 18 | 0.34/0.62 | 40 | 80 | 1150 |
| B5 | 4.4 | 77 | 20 | 0.35/0.63 | 40 | 80 | 1010 |
| B6 | 4.7 | 63 | 17 | 0.34/0.62 | 40 | 80 | 1340 |
| B7 | 4.3 | 75 | 20 | 0.35/0.63 | 40 | 80 | 1050 |
| B8 | 4.3 | 78 | 21 | 0.35/0.63 | 40 | 80 | 1080 |
| B9 | 4.4 | 77 | 20 | 0.35/0.63 | 40 | 80 | 1080 |
| B10 | 4.5 | 78 | 21 | 0.35/0.63 | 40 | 80 | 1130 |
| B11 | 4.3 | 78 | 21 | 0.35/0.63 | 40 | 80 | 1020 |
| B12 | 4.8 | 58 | 16 | 0.34/0.62 | 40 | 80 | 1260 |
| B13 | 3.9 | 69 | 18 | 0.35/0.63 | 40 | 80 | 910 |
| B14 | 4.4 | 64 | 17 | 0.34/0.62 | 40 | 80 | 1390 |
| B15 | 4.3 | 80 | 21 | 0.35/0.63 | 40 | 80 | 1010 |
TABLE 2-continued
| Data of the OLEDs | | | | | | | |
|---|---|---|---|---|---|---|---|
| B16 | 4.2 | 80 | 21 | 0.35/0.63 | 40 | 80 | 1150 |
| B17 | 4.7 | 63 | 17 | 0.34/0.62 | 40 | 80 | 1540 |
| B18 | 5.2 | 72 | 19 | 0.34/0.62 | 40 | 80 | 750 |
| B19 | 5.5 | 71 | 19 | 0.34/0.62 | 40 | 80 | 860 |
| B20 | 4.2 | 88 | 23 | 0.35/0.63 | 40 | 80 | 940 |
| B21 | 4.6 | 64 | 18 | 0.34/0.62 | 40 | 80 | 1030 |
| B22 | 4.3 | 86 | 22 | 0.35/0.63 | 40 | 80 | 1010 |
| B23 | 4.4 | 90 | 24 | 0.35/0.63 | 40 | 80 | 870 |
| B24 | 4.1 | 92 | 24 | 0.35/0.63 | 40 | 80 | 670 |
| B25 | 5.3 | 70 | 19 | 0.34/0.62 | 40 | 80 | 870 |
| B26 | 4.4 | 77 | 20 | 0.35/0.63 | 40 | 80 | 850 |
| B27 | 5.1 | 67 | 18 | 0.34/0.62 | 40 | 80 | 740 |
| B28 | 3.4 | 71 | 19 | 0.35/0.61 | 20 | 80 | 1250 |
| B29 | 5.0 | 67 | 18 | 0.34/0.62 | 40 | 80 | 680 |
| B30 | 4.3 | 82 | 21 | 0.35/0.63 | 40 | 80 | 990 |
| B31 | 4.7 | 66 | 18 | 0.34/0.62 | 40 | 80 | 1230 |
| B32 | 4.7 | 63 | 17 | 0.34/0.62 | 40 | 80 | 1450 |
| B33 | 4.0 | 87 | 22 | 0.35/0.63 | 40 | 80 | 890 |
| B34 | 5.0 | 74 | 20 | 0.34/0.62 | 40 | 80 | 610 |
| B35 | 4.2 | 85 | 22 | 0.35/0.63 | 40 | 80 | 1040 |
| B36 | 4.2 | 60 | 16 | 0.34/0.62 | 40 | 80 | 1210 |
| B37 | 4.3 | 85 | 22 | 0.35/0.63 | 40 | 80 | 910 |
| B38 | 5.4 | 72 | 19 | 0.34/0.62 | 40 | 80 | 890 |
| B39 | 4.6 | 77 | 20 | 0.35/0.63 | 40 | 80 | 1170 |
| B40 | 4.4 | 77 | 20 | 0.35/0.63 | 40 | 80 | 1410 |
| B41 | 4.6 | 75 | 20 | 0.35/0.63 | 40 | 80 | 1080 |
| B42 | 4.5 | 67 | 18 | 0.34/0.62 | 40 | 80 | 1120 |
| B43 | 4.6 | 66 | 18 | 0.34/0.62 | 40 | 80 | 1170 |
| B44 | 4.4 | 66 | 18 | 0.34/0.62 | 40 | 80 | 1090 |
| B45 | 4.4 | 68 | 19 | 0.34/0.62 | 40 | 80 | 1290 |
| B46 | 5.4 | 71 | 19 | 0.34/0.62 | 40 | 80 | 860 |
| B47 | 5.3 | 71 | 19 | 0.34/0.62 | 40 | 80 | 830 |
| B48 | 5.2 | 72 | 19 | 0.34/0.62 | 40 | 80 | 850 |
| B49 | 5.5 | 70 | 19 | 0.34/0.62 | 40 | 80 | 890 |
| B50 | 5.5 | 72 | 19 | 0.34/0.62 | 40 | 80 | 860 |
| B51 | 5.3 | 72 | 19 | 0.34/0.62 | 40 | 80 | 860 |
| B52 | 5.5 | 69 | 19 | 0.34/0.62 | 40 | 80 | 830 |
| B53 | 5.5 | 71 | 19 | 0.34/0.62 | 40 | 80 | 820 |
| B54 | 5.3 | 74 | 20 | 0.34/0.62 | 40 | 80 | 790 |
TABLE 3
Structural formulae of the materials for the OLEDs
PD1
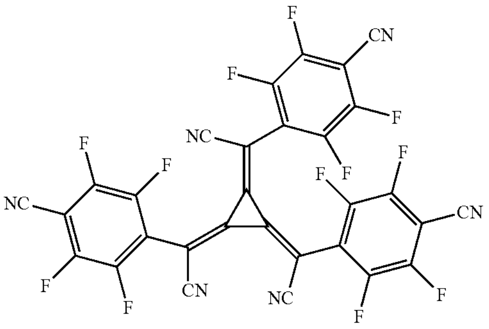
(CAS Reg. No. 1224447-88-4)

TABLE 3-continued
| Structural formulae of the materials for the OLEDs |
| --- |
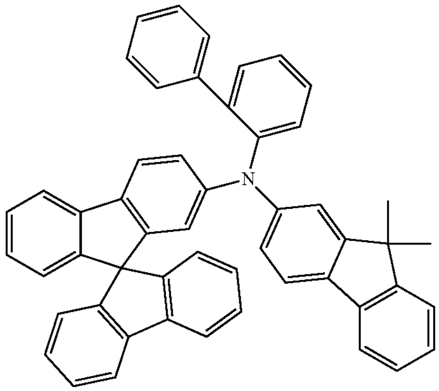 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
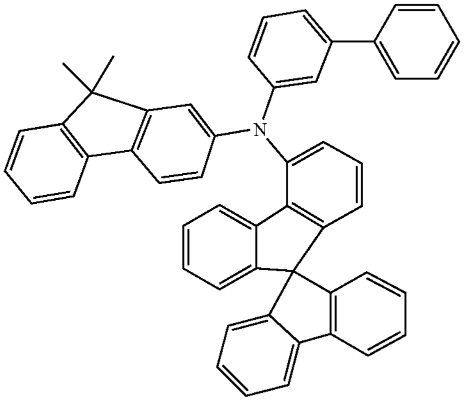 [SMILES: CC1(C)c2ccccc2-c2ccc(N(c3cccc(-c4ccccc4)c3)c3cccc4c3-c3ccccc3C43c4ccccc4-c4ccccc43)cc21]
SpMA2
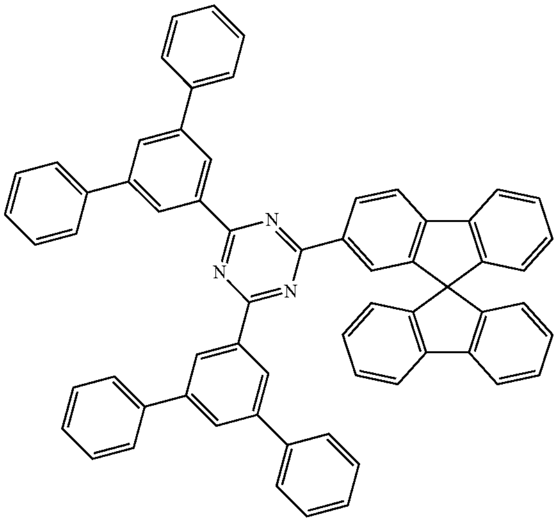 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2
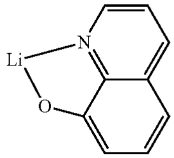
LiQ TABLE 3-continued
| Structural formulae of the materials for the OLEDs |
| --- |
| 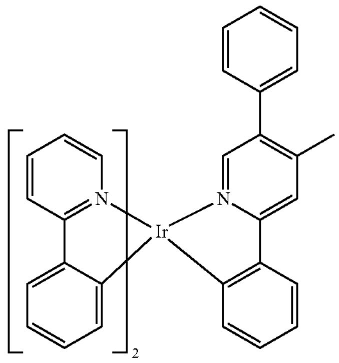 TEG1 |
| 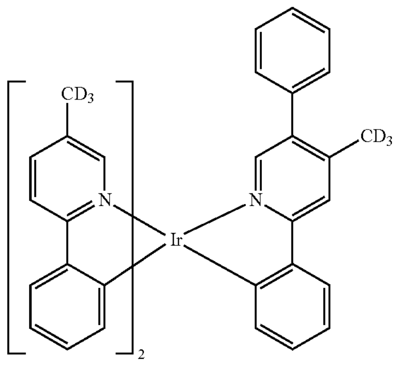 TEG-2 |
| 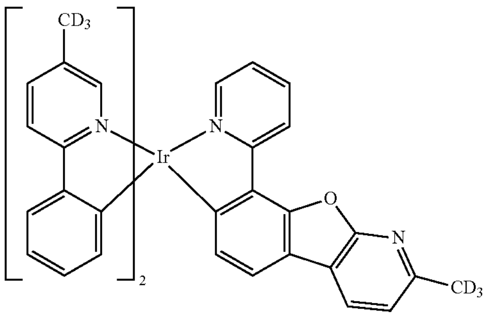 TEG3 |
| 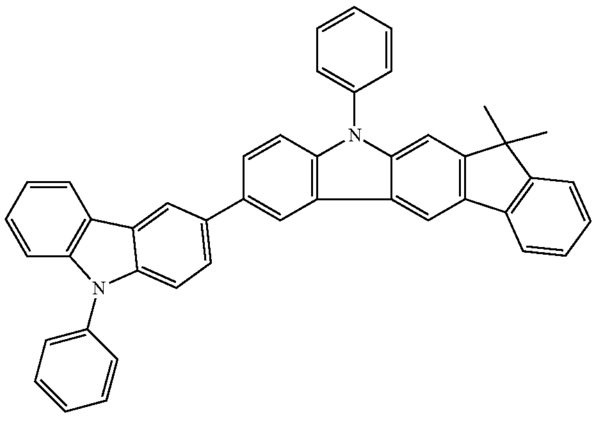 H12 |

TABLE 3-continued
| Structural formulae of the materials for the OLEDs |
| --- |
| 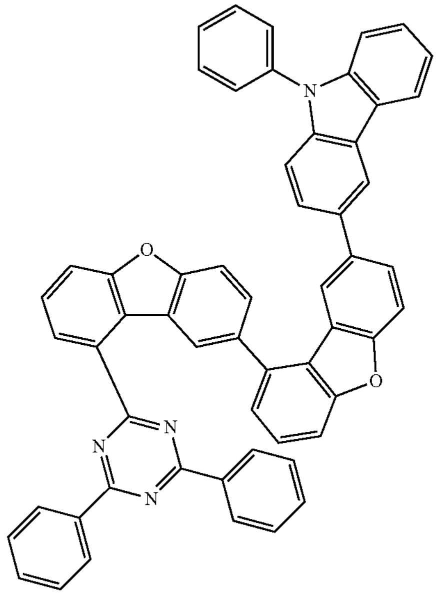 PA1 (according to WO 2015/169412) |
| 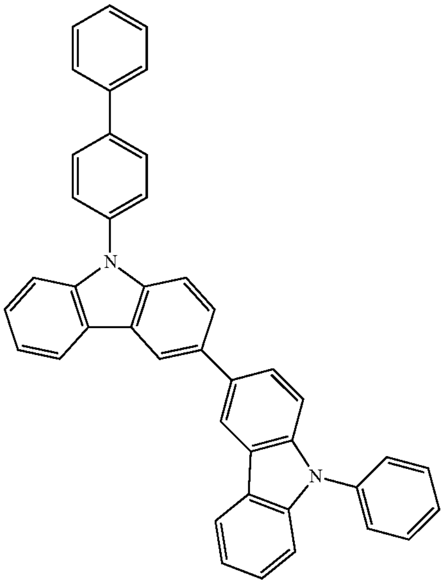 [SMILES: c1ccc(-c2ccc(-n3c4ccccc4c4cc(-c5ccc6c(c5)c5ccccc5n6-c5ccccc5)ccc43)cc2)cc1] H1 |

TABLE 3-continued
| Structural formulae of the materials for the OLEDs |
| --- |
| 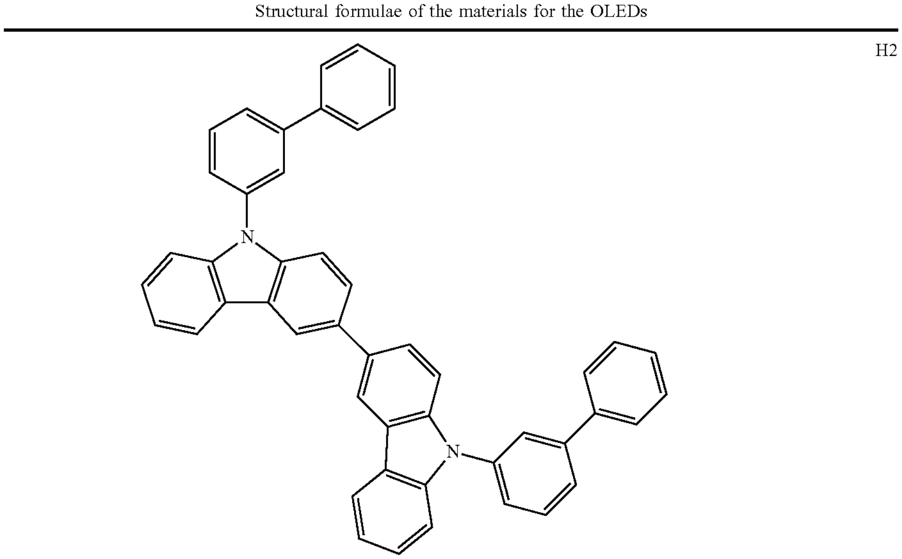 H2 |
| 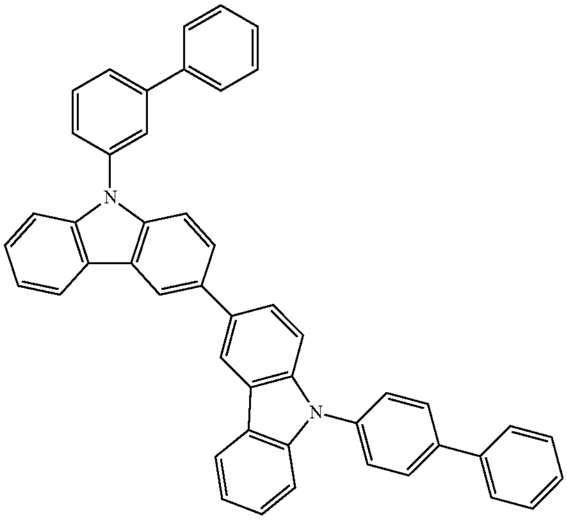 H4 |
| 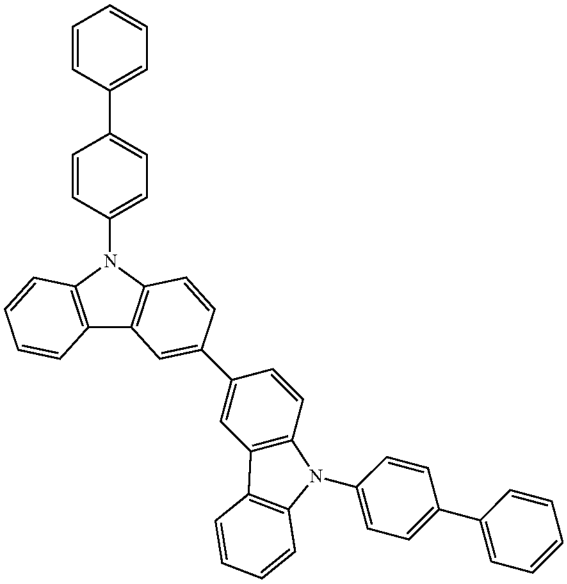 H5 |

TABLE 3-continued
| Structural formulae of the materials for the OLEDs |
| --- |
| 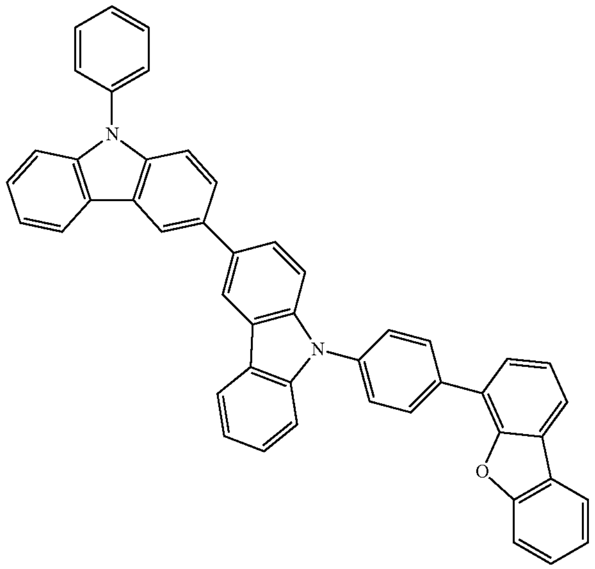 H6 |
| 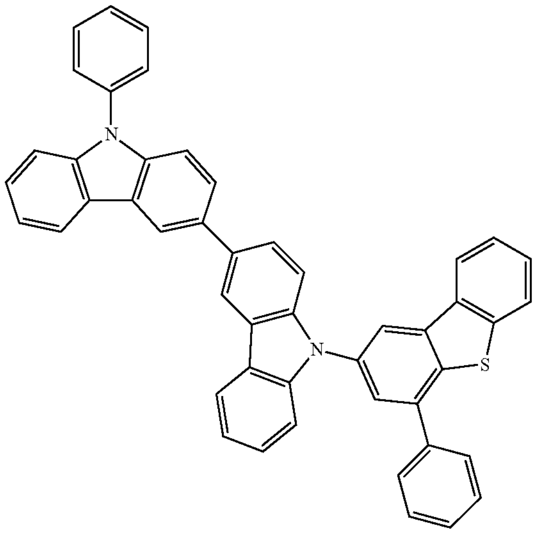 H7 |

TABLE 3-continued
| Structural formulae of the materials for the OLEDs |
| --- |
| 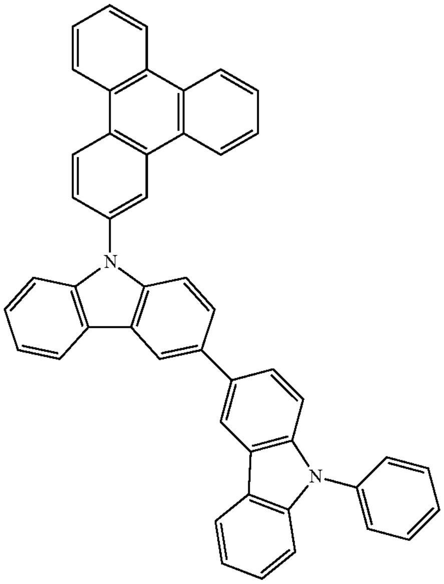 H8 |
| 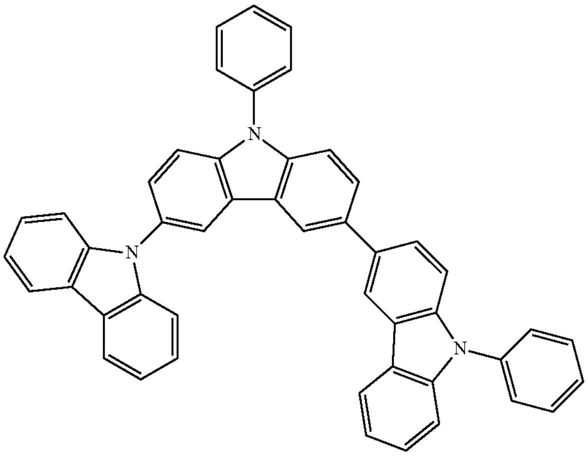 H9 |
| 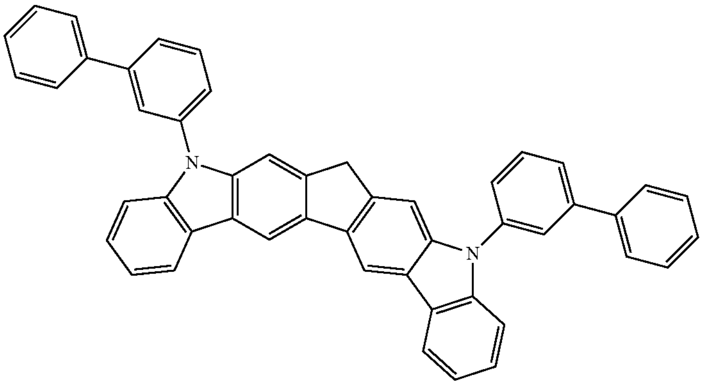 H11 |

TABLE 3-continued
| Structural formulae of the materials for the OLEDs |
|---|
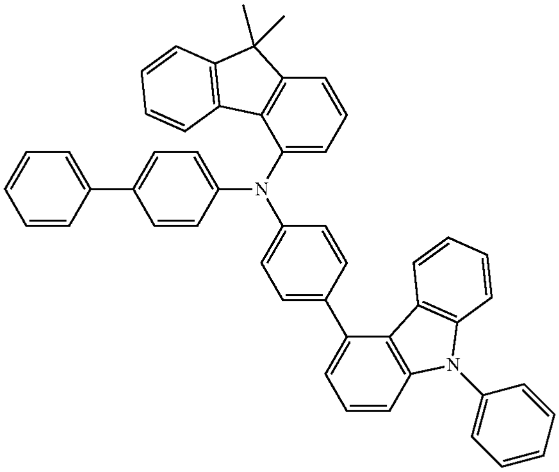 [SMILES: CC1(C)c2ccccc2-c2c(N(c3ccc(-c4ccccc4)cc3)c3ccc(-c4cccc5c4c4ccccc4n5-c4ccccc4)cc3)cccc21]
H14
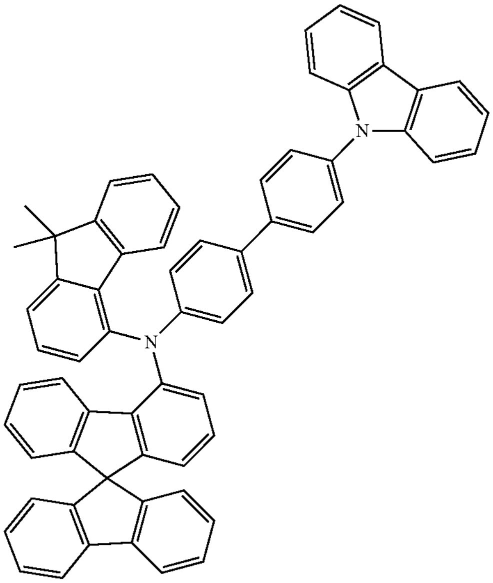 [SMILES: CC1(C)c2ccccc2-c2c(N(c3ccc(-c4ccc(-n5c6ccccc6c6ccccc65)cc4)cc3)c3cccc4c3-c3ccccc3C43c4ccccc4-c4ccccc43)cccc21]
H17
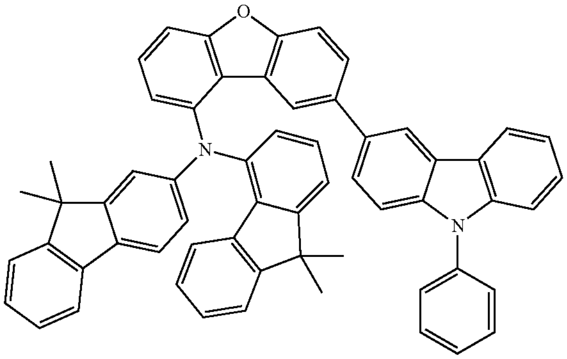 [SMILES: CC1(C)c2ccccc2-c2ccc(N(c3cccc4c3-c3ccccc3C4(C)C)c3cccc4oc5ccc(-c6ccc7c(c6)c6ccccc6n7-c6ccccc6)cc5c34)cc21]
H19

TABLE 3-continued
| Structural formulae of the materials for the OLEDs |
| --- |
| H23 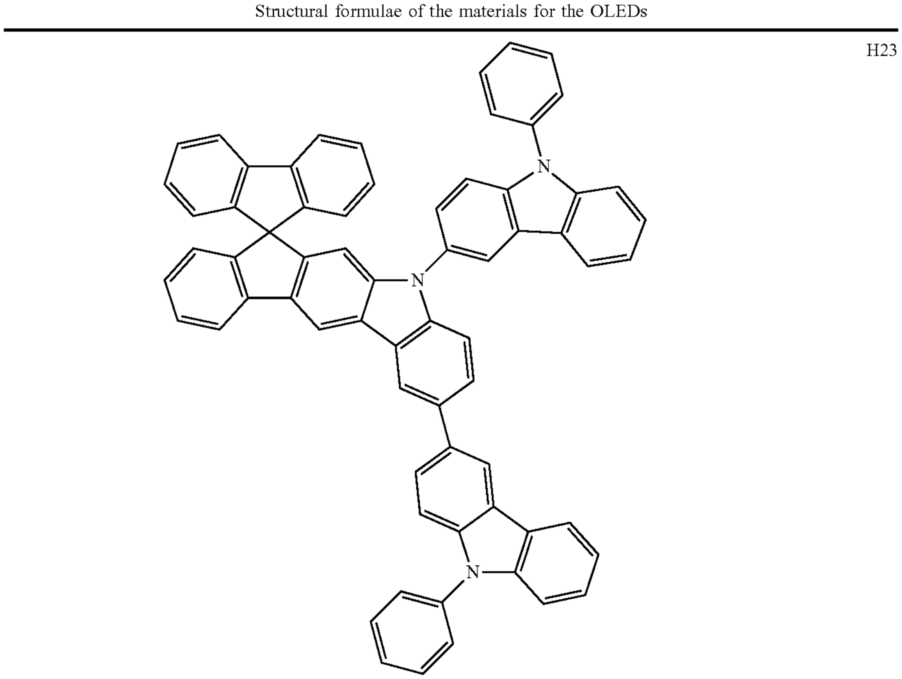 |
| H26 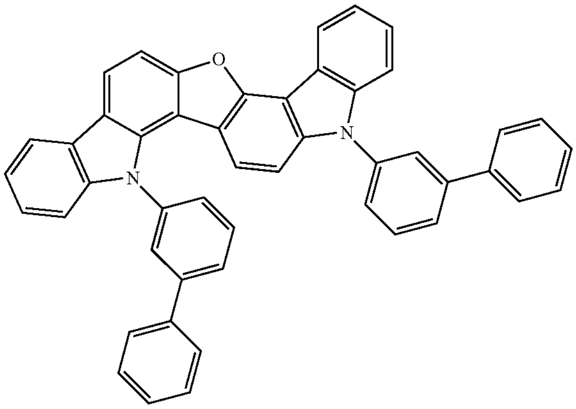 |
| H29 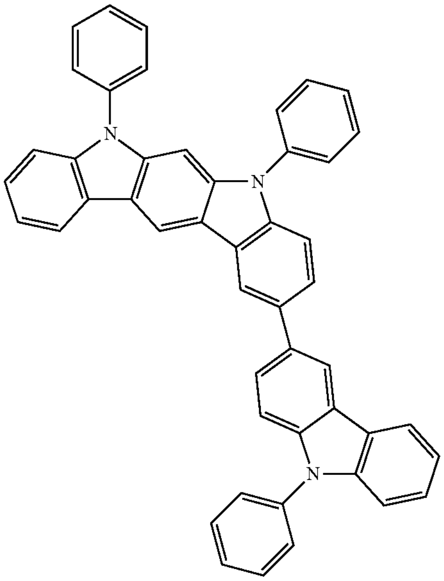 |

TABLE 3-continued
| Structural formulae of the materials for the OLEDs |
|---|
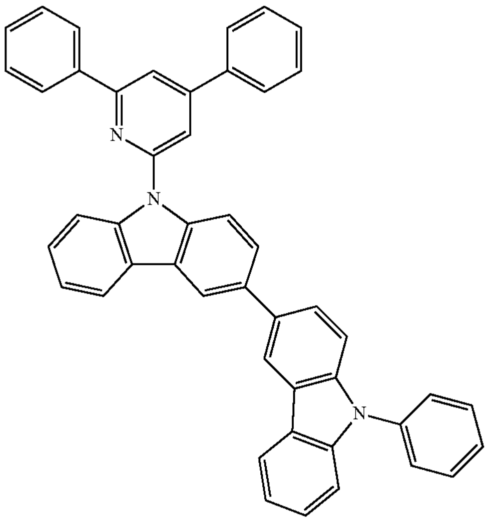 [SMILES: c1ccc(-c2cc(-c3ccccc3)nc(-n3c4ccccc4c4cc(-c5ccc6c(c5)c5ccccc5n6-c5ccccc5)ccc43)c2)cc1]
H32
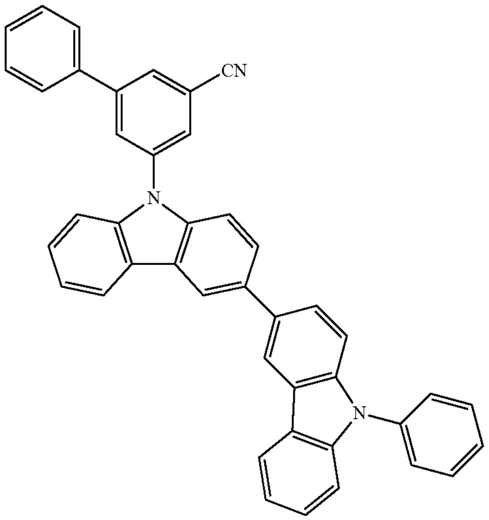 [SMILES: N#Cc1cc(-c2ccccc2)cc(-n2c3ccccc3c3cc(-c4ccc5c(c4)c4ccccc4n5-c4ccccc4)ccc32)c1]
H34

TABLE 3-continued
| Structural formulae of the materials for the OLEDs |
| --- |
| 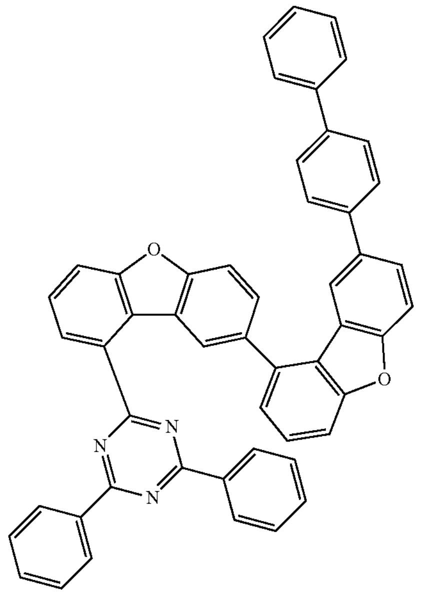 P3/IV1 |
| 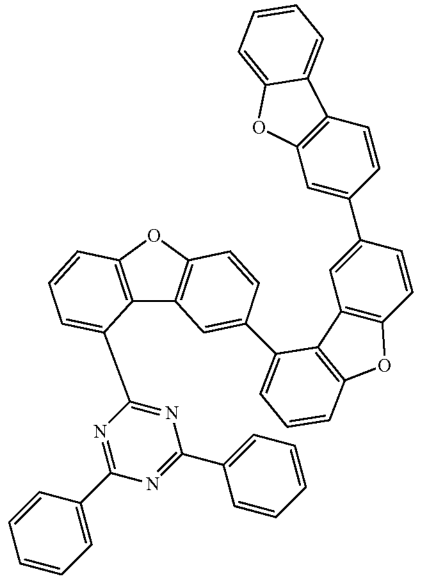 P5/IV2 |

TABLE 3-continued
| Structural formulae of the materials for the OLEDs |
|---|
| 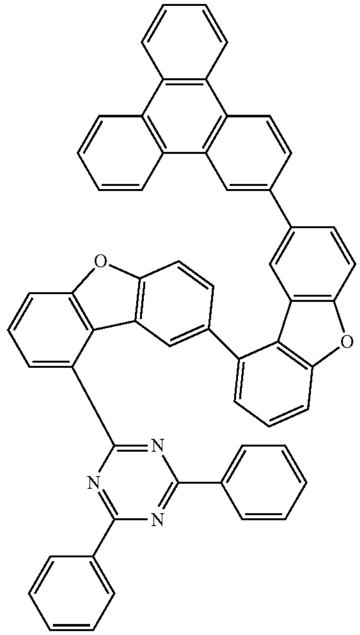 P1/IV3 |
| 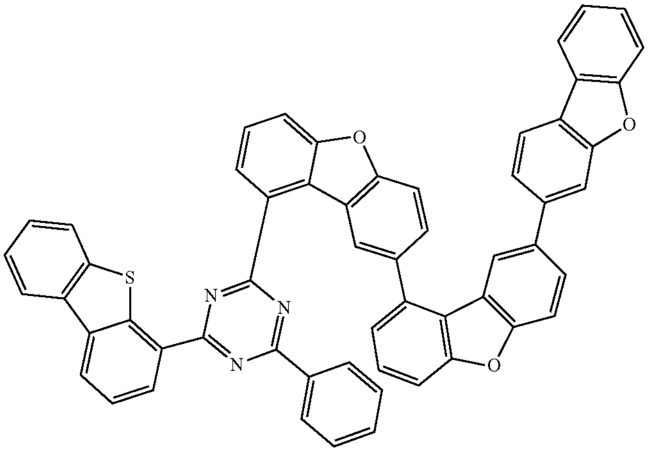 P7/IV4 |

TABLE 3-continued
| Structural formulae of the materials for the OLEDs |
| --- |
| P105/IV5 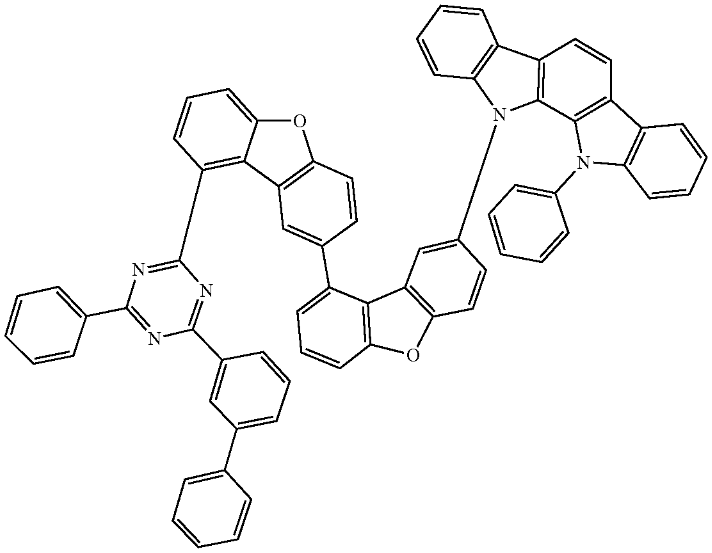 |
| P107/IV7 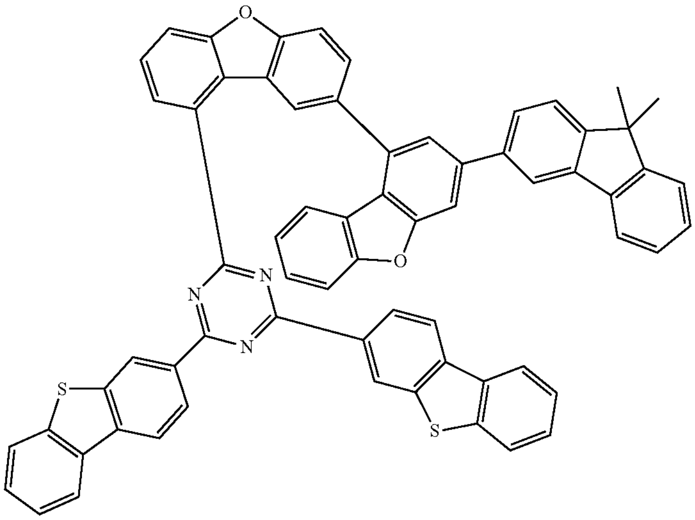 |

TABLE 3-continued
| Structural formulae of the materials for the OLEDs |
| --- |
| 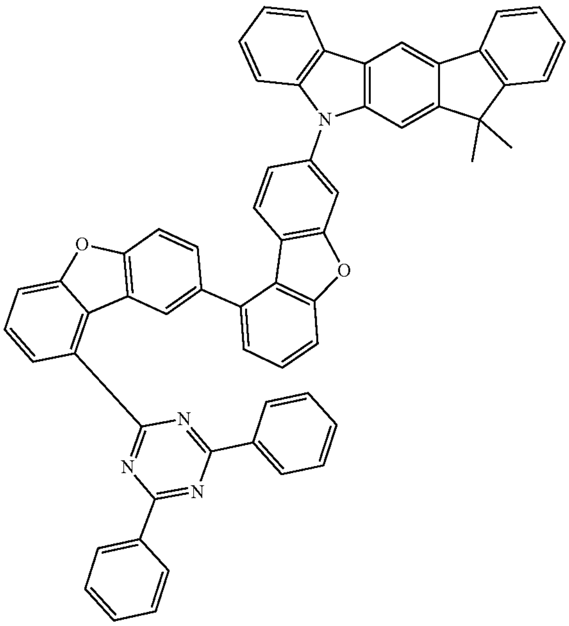 P102/IV8 |
| 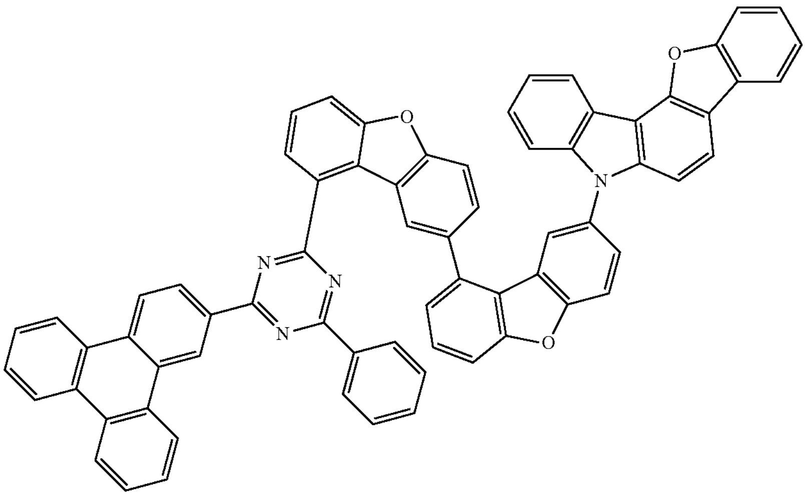 P101/IV9 |

TABLE 3-continued
| Structural formulae of the materials for the OLEDs |
| --- |
| 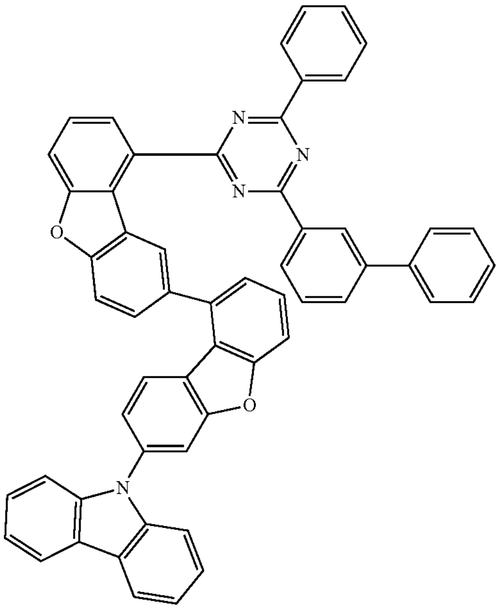 P14/IV10 |
| 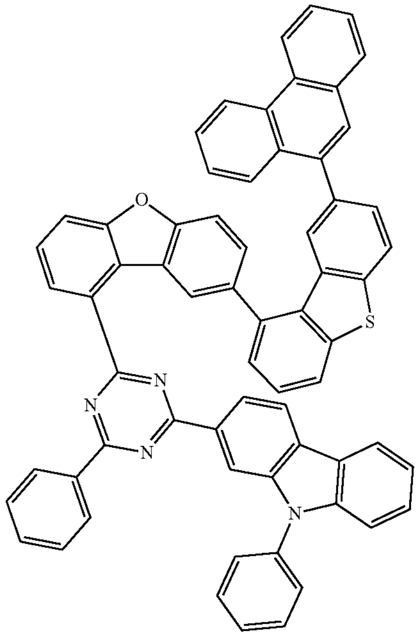 P13/IV11 |

TABLE 3-continued
| Structural formulae of the materials for the OLEDs |
| --- |
| 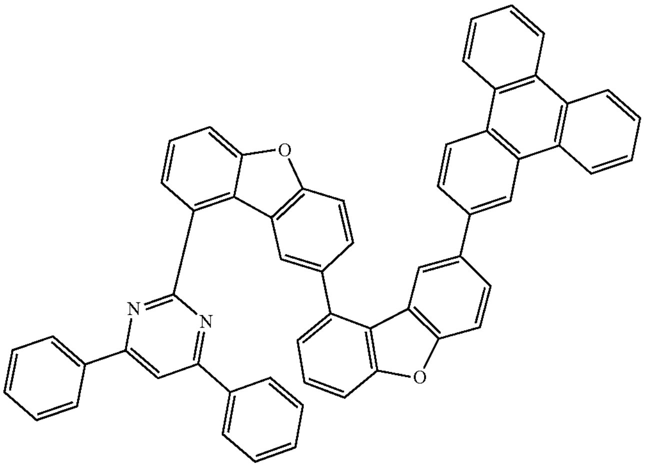 P17/IV12 |
| 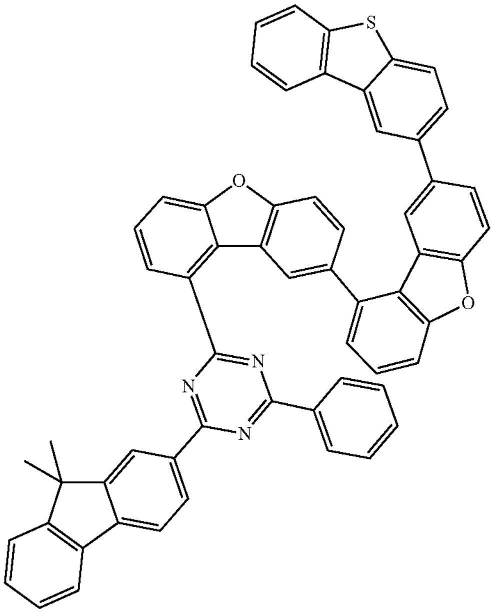 P15/IV13 |

TABLE 3-continued
| Structural formulae of the materials for the OLEDs |
| --- |
| P18/IV14 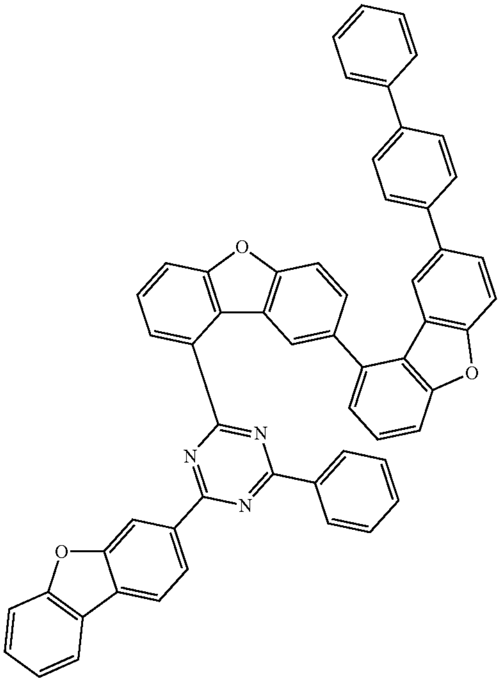 |
| P20/IV15 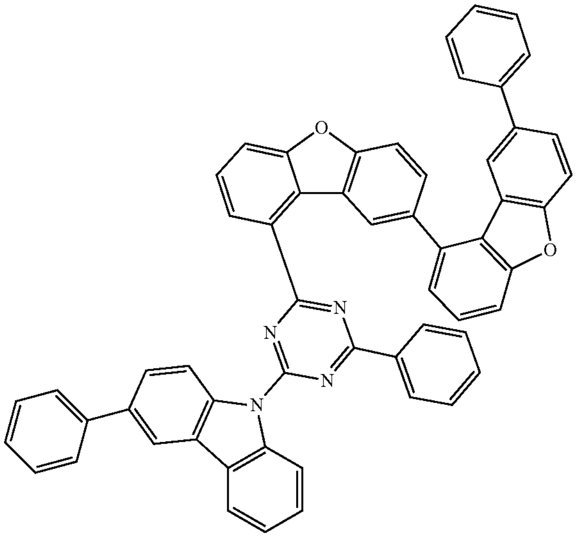 |

TABLE 3-continued
| Structural formulae of the materials for the OLEDs |
| --- |
| 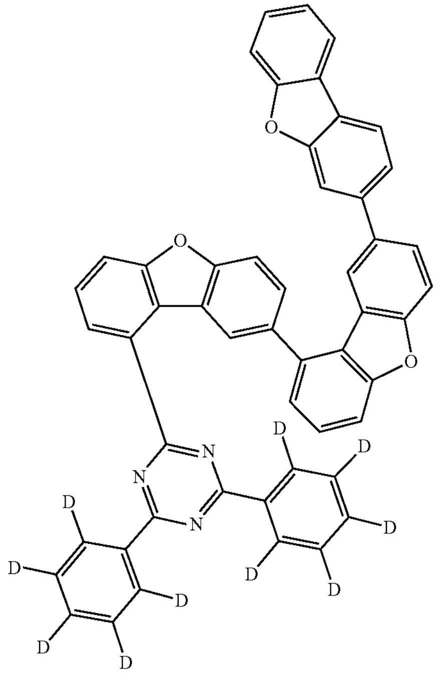 P21/IV16 |
| 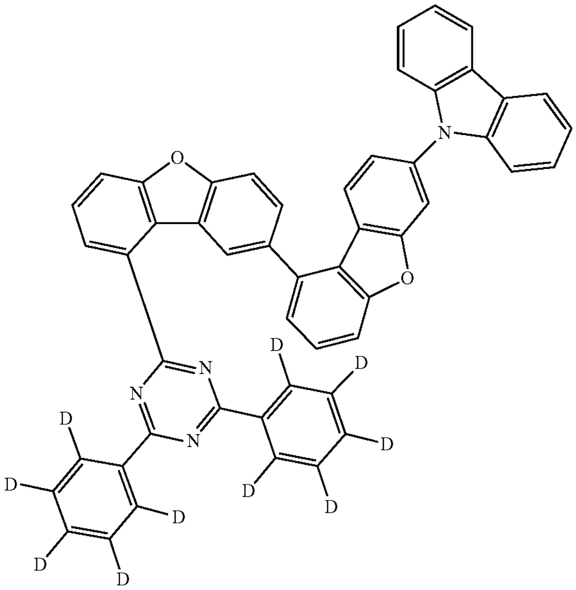 P22/IV17 |

TABLE 3-continued
| Structural formulae of the materials for the OLEDs |
| --- |
| 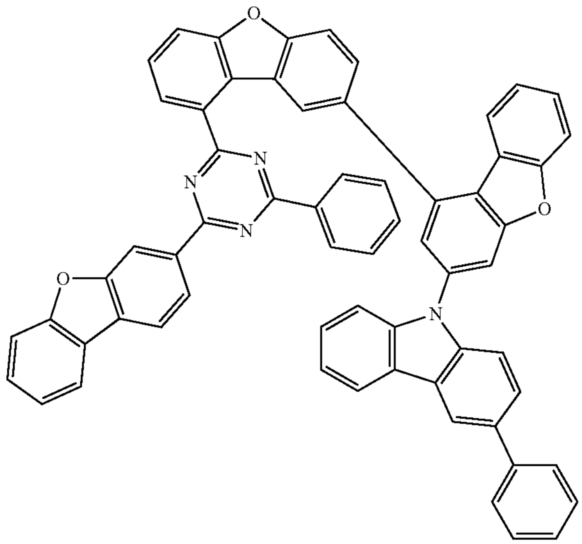 P23/IV18 |
| 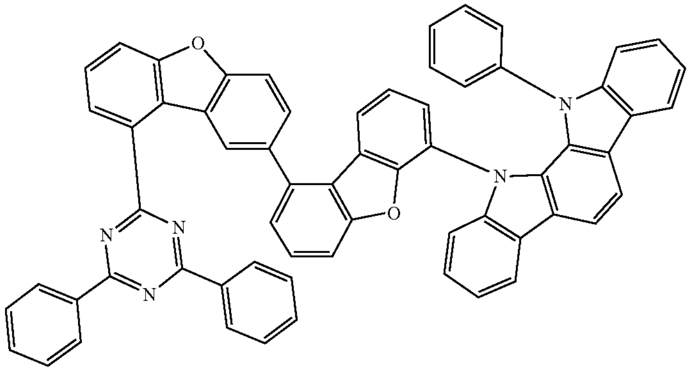 P24/IV19 |
| 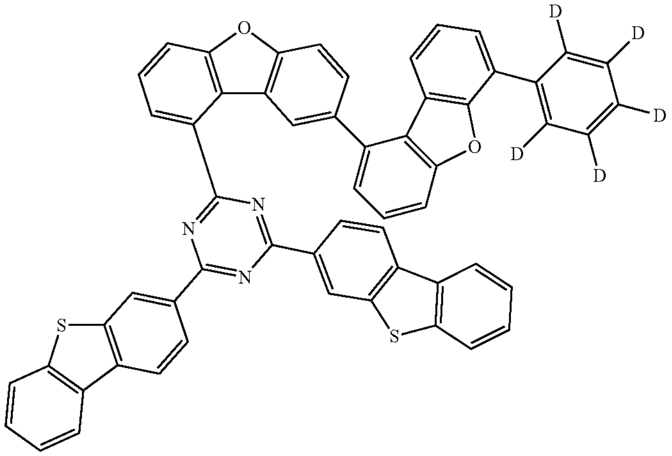 P26/IV20 |

TABLE 3-continued
| Structural formulae of the materials for the OLEDs |
|---|
| 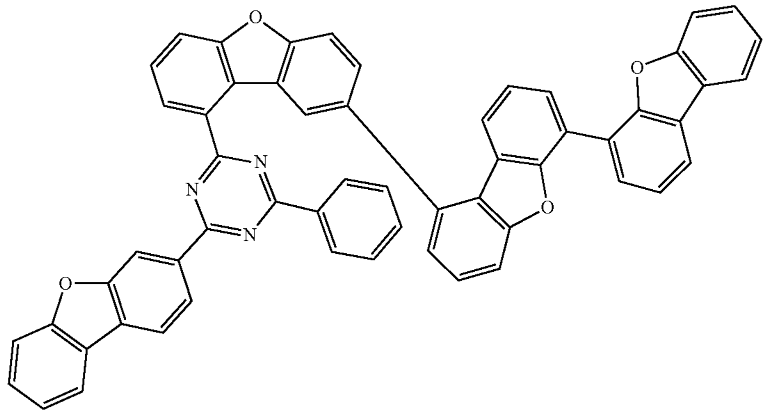 P28/IV21 |
| 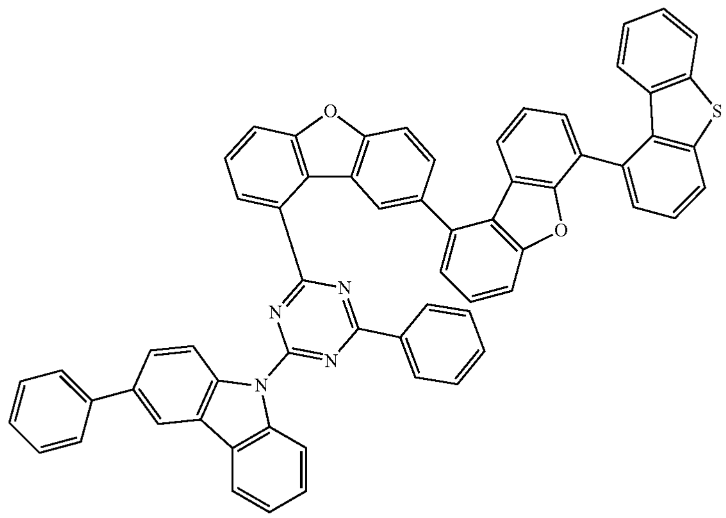 P29/IV22 |
| 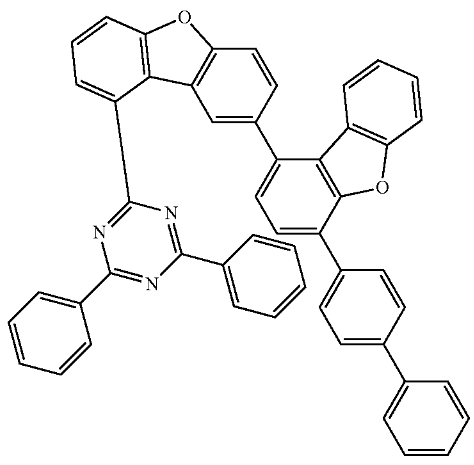 P30/IV23 |

TABLE 3-continued
| Structural formulae of the materials for the OLEDs |
| --- |
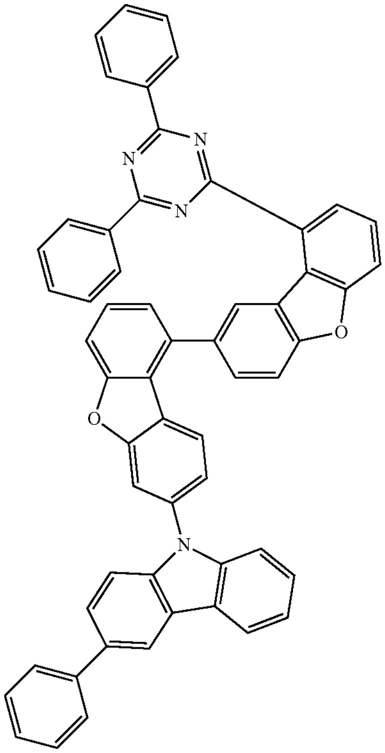 [SMILES: c1ccc(-c2ccc3c(c2)c2ccccc2n3-c2ccc3c(c2)oc2cccc(-c4ccc5oc6cccc(-c7nc(-c8ccccc8)nc(-c8ccccc8)n7)c6c5c4)c23)cc1]
P109/IV24
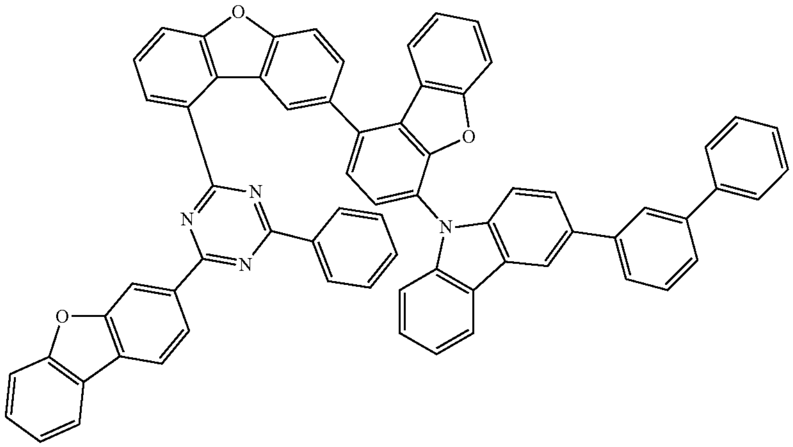 [SMILES: c1ccc(-c2cccc(-c3ccc4c(c3)c3ccccc3n4-c3ccc(-c4ccc5oc6cccc(-c7nc(-c8ccccc8)nc(-c8ccc9c(c8)oc8ccccc89)n7)c6c5c4)c4c3oc3ccccc34)c2)cc1]
P110/IV25

TABLE 3-continued
| Structural formulae of the materials for the OLEDs |
| --- |
| P100/IV26 |
| 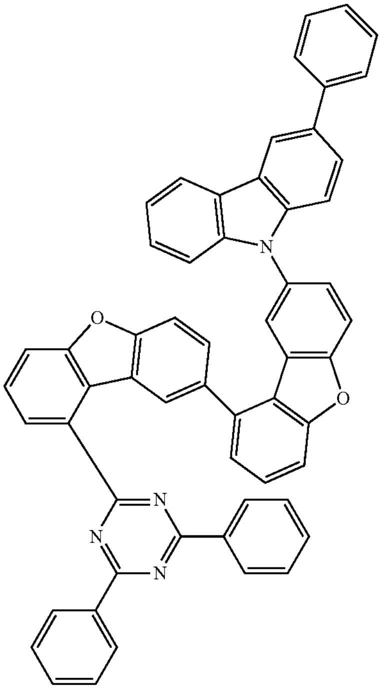 |
| P32/IV27 |
| 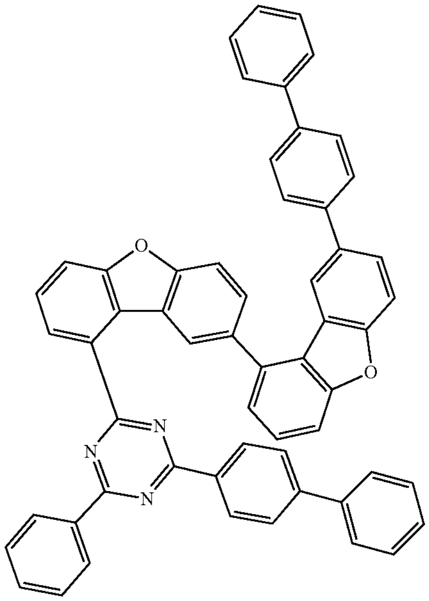 |

TABLE 3-continued
| Structural formulae of the materials for the OLEDs |
| --- |
P33/IV28
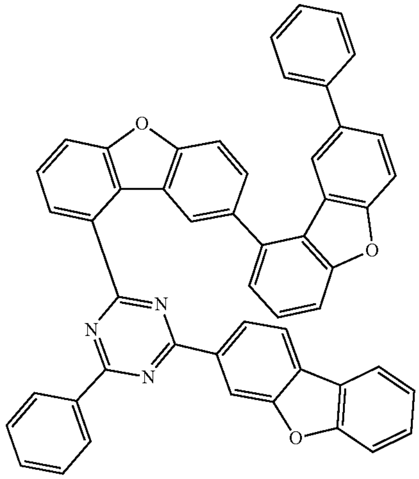 [SMILES: c1ccc(-c2ccc3oc4cccc(-c5ccc6oc7cccc(-c8nc(-c9ccccc9)nc(-c9ccc%10c(c9)oc9ccccc9%10)n8)c7c6c5)c4c3c2)cc1]
P2/IV29
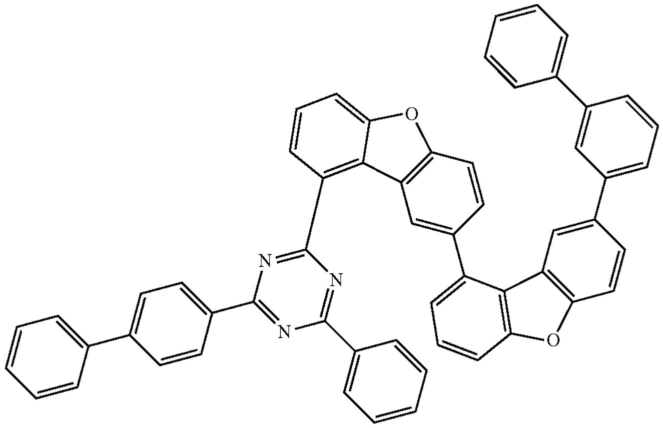 [SMILES: c1ccc(-c2ccc(-c3nc(-c4ccccc4)nc(-c4cccc5oc6ccc(-c7cccc8oc9ccc(-c%10cccc(-c%11ccccc%11)c%10)cc9c78)cc6c45)n3)cc2)cc1]
P34/IV30
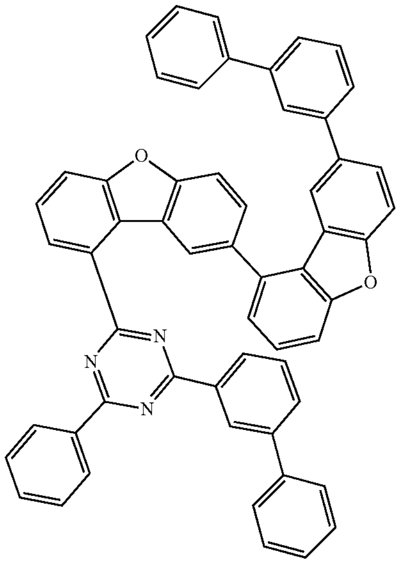 [SMILES: c1ccc(-c2cccc(-c3ccc4oc5cccc(-c6ccc7oc8cccc(-c9nc(-c%10ccccc%10)nc(-c%10cccc(-c%11ccccc%11)c%10)n9)c8c7c6)c5c4c3)c2)cc1]

TABLE 3-continued

| Structural formulae of the materials for the OLEDs |
|---|
| 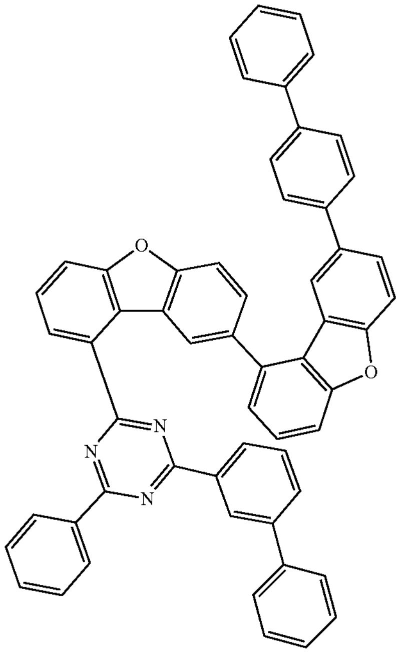 P35/IV31 |

The invention claimed is:

1. A compound of formula (1)

Formula (1)

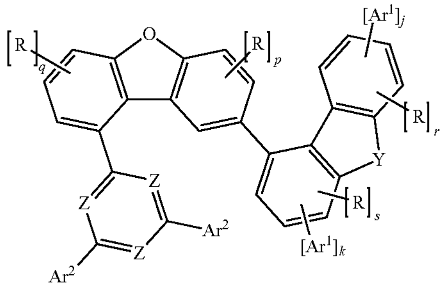

where the symbols used are as follows:

Y is O or S;

Z is the same or different at each instance and is CR or N, with the proviso that at least two Z are N;

$Ar^1$ is the same or different at each instance and is an aromatic ring system which has 6 to 40 aromatic ring atoms and may be substituted by one or more R radicals, or a heteroaromatic ring system containing at least one nitrogen atom which has 5 to 40 aromatic ring atoms and which is bonded to the dibenzofuran or dibenzothiophene via the at least one nitrogen atom and which may be substituted by one or more R radicals, or a dibenzofuran or dibenzothiophene group which may be substituted by one or more R radicals;

$Ar^2$ is the same or different at each instance and is an aromatic or heteroaromatic ring system which has 5 to 40 aromatic ring atoms and may be substituted by one or more R radicals;

R is the same or different at each instance and is H, D, F, Cl, Br, I, $N(Ar')_2$, $N(R^1)_2$, OAr', SAr', CN, $NO_2$, $OR^1$, $SR^1$, $COOR^1$, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^1$ radicals, where one or more nonadjacent $CH_2$ groups may be replaced by $Si(R^1)_2$, C↑O, $NR^1$, O, S or $CONR^1$, or an aromatic or heteroaromatic ring system which has 5 to 60 aromatic ring atoms, preferably 5 to 40 aromatic ring atoms, and may be substituted in each case by one or more $R^1$ radicals; at the same time, two R radicals together may also form a ring system;

Ar' is the same or different at each instance and is an aromatic or heteroaromatic ring system which has 5 to 40 aromatic ring atoms and may be substituted by one or more $R^1$ radicals; at the same time, two Ar' radicals bonded to the same nitrogen atom may also be bridged to one another by a single bond or a bridge selected from $N(R^1)$, $C(R^1)_2$, O and S;

R is the same or different at each instance and is H, D, F, Cl, Br, I, $N(R^2)_2$, CN, $NO_2$, $OR^2$, $SR^2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may each be substituted by one or more $R^2$ radicals, where one or more non-adjacent $CH_2$ groups may be replaced by $Si(R^2)_2$, C=O, $NR^2$, O, S or $CONR^2$ and where one or more hydrogen atoms in the alkyl, alkenyl or alkynyl group may be replaced by D, F, Cl, Br, I or CN, or an aromatic or heteroaromatic ring system which has 5 to 40 aromatic ring atoms and may be substituted in each case by one or more $R^2$ radicals; at the same time, two or more $R^1$ radicals together may form an aliphatic ring system;

$R^2$ is the same or different at each instance and is H, D, F, CN or an aliphatic, aromatic or heteroaromatic organic radical, especially a hydrocarbyl radical, having 1 to 20 carbon atoms, in which one or more hydrogen atoms may also be replaced by F;

p, q are the same or different at each instance and are 0, 1, 2 or 3;

r is 0, 1, 2, 3 or 4, with the proviso that r is not more than (4-j);

S is 0, 1, 2 or 3, with the proviso that s is not more than (3-k);

j, k are the same or different at each instance and are 0, 1, 2 or 3, with the proviso that j+k≥1.

2. The compound according to claim 1, wherein all three Z groups are N, or in that two Z groups are N and the third Z group is CH.

3. The compound according to claim 1, wherein the compound is selected from the compounds of the formula (4)

Formula (4)

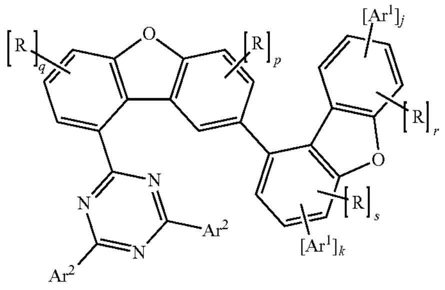

where the symbols and indices used have the definitions given in claim 1.

4. The compound according to claim 1, wherein the compound is compounds of the formula (5)

Formula (5)

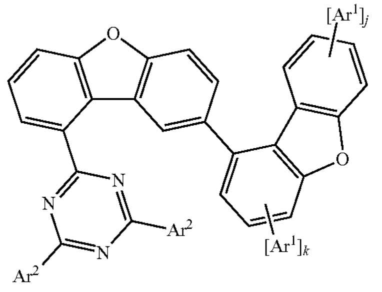

where the symbols and indices used have the definitions given in claim 1.

5. The compound according to claim 1, wherein the compound is selected from the compounds of the formulae (6a) and (6b)

Formula (6a)

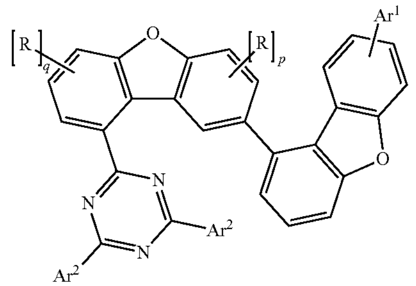

Formula (6b)

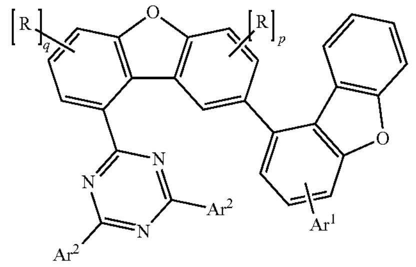

where the symbols and indices used have the definitions given above.

6. The compound according to claim 1, wherein the compound is selected from the compounds of the formulae (7a) and (7b)

Formula (7a)

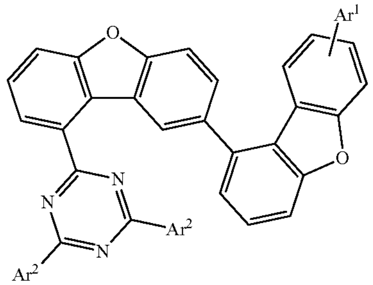

Formula (7b)

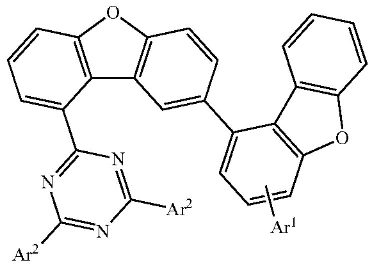

where the symbols used have the definitions given in claim 1.

7. The compound according to claim 1, wherein, when j=1, the $Ar^1$ group is bonded in the 7 or 8 position of the dibenzofuran or dibenzothiophene, and in that, when k=1, the $Ar^1$ group is bonded in the 3 or 4 position of the dibenzofuran or dibenzothiophene.

8. The compound according to claim 1, wherein $Ar^2$ is the same or different at each instance and represents an aromatic or heteroaromatic ring system which has 6 to 30 aromatic ring atoms and may be substituted by one or more nonaromatic R radicals.

9. The compound according to claim 1, wherein $Ar^1$ is an aromatic ring system which has 6 to 30 aromatic ring atoms and may be substituted by one or more nonaromatic R radicals, or N-carbazolyl which may be substituted by one or more R radicals, or dibenzofuran or dibenzothiophene, each of which may be substituted by one or more R radicals.

10. A formulation comprising at least one compound according to claim 1 and at least one further compound and/or solvent.

11. An electronic device comprising at least one compound according to claim 1.

12. An organic electroluminescent device (OLED) comprising the compound according to claim 1 is used as matrix material for a phosphorescent emitter in an emitting layer.

13. An organic electroluminescent device (OLED) comprising the compound according to claim 1 is used in combination with a further matrix material for a phosphorescent emitter in an emitting layer, where the further matrix material is a compound of formula (9)

Formula (9)

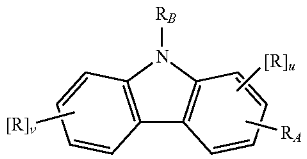

where $R^1$, $R^2$ and Ar' have the definitions detailed in claim 1 and the further symbols and indices used are as follows:

$R_A$ is H, $-L^3-Ar^5$ or $-L^1-N(Ar')_2$;

$R_B$ is $Ar^4$ or $-L^2-N(Ar')_2$;

$L^1$, $L^2$ are the same or different at each instance and are a single bond or an aromatic or heteroaromatic ring system which has 5 to 30 aromatic ring atoms and may be substituted by one or more $R^1$ radicals;

$L^3$ is a single bond or an aromatic or heteroaromatic ring system which has 5 to 30 aromatic ring atoms and may be substituted by one or more $R^2$ radicals, where one substituent $R^1$ may form a ring with a substituent R on the carbazole;

$Ar^4$ is an aromatic ring system having 6 to 40 aromatic ring atoms or a heteroaromatic ring system having 5 to 40 aromatic ring atoms, which may be substituted by one or more $R^1$ radicals;

$Ar^5$ is the same or different at each instance and is an unsubstituted or substituted 9-arylcarbazolyl or unsubstituted or substituted carbazol-9-yl, which may be substituted by one or more $R^1$ radicals, and where one or more instances each of two $R^1$ radicals or one $R^1$ radical together with one R radical may independently form a monocyclic or polycyclic, aliphatic, aromatic or heteroaromatic ring, where aryl is an aromatic or heteroaromatic ring system which has 5 to 30 aromatic ring atoms and may be substituted by $R^1$;

u at each instance is independently 0, 1, 2 or 3;

v at each instance is independently 0, 1, 2, 3 or 4.

* * * * *